(12) United States Patent
He et al.

(10) Patent No.: US 10,981,860 B2
(45) Date of Patent: Apr. 20, 2021

(54) CASPASE INHIBITOR AND PHARMACEUTICAL COMPOSITION, USE AND THERAPEUTIC METHOD THEREOF

(71) Applicants: Chia Tai Tianqing Pharmaceutical Group Co., Ltd., Lianyungang (CN); Medshine Discovery Inc., Nanjing (CN)

(72) Inventors: Haiying He, Nanjing (CN); Songliang Wu, Nanjing (CN); Zhi Luo, Nanjing (CN); Jianfeng Mou, Nanjing (CN); Fengying Guo, Nanjing (CN); Chuan Wang, Nanjing (CN); Guoqing Li, Nanjing (CN); Minggao Zeng, Nanjing (CN); Shuhui Chen, Nanjing (CN)

(73) Assignees: Chia Tai Tianqing Pharmaceutical Group Co., Ltd., Lianyungang (CN); Medshine Discovery Inc., Nanjing (CN)

( * ) Notice: Subject to any disclaimer, the term of this patent is extended or adjusted under 35 U.S.C. 154(b) by 60 days.

(21) Appl. No.: 16/099,989

(22) PCT Filed: May 11, 2017

(86) PCT No.: PCT/CN2017/083909
§ 371 (c)(1),
(2) Date: Nov. 8, 2018

(87) PCT Pub. No.: WO2017/193951
PCT Pub. Date: Nov. 16, 2017

(65) Prior Publication Data
US 2019/0135733 A1    May 9, 2019

(30) Foreign Application Priority Data

May 11, 2016  (CN) .......................... 201610310917.0
Jan. 23, 2017  (CN) .......................... 201710058653.9

(51) Int. Cl.
*C07C 225/22*    (2006.01)
*C07C 225/10*    (2006.01)
*C07C 225/18*    (2006.01)
*C07D 205/04*    (2006.01)
*C07D 207/04*    (2006.01)
*C07D 221/22*    (2006.01)
*C07D 221/20*    (2006.01)
*C07D 221/04*    (2006.01)
*C07D 223/04*    (2006.01)
*C07D 265/30*    (2006.01)
*C07D 267/12*    (2006.01)
*C07D 401/06*    (2006.01)
*A61P 43/00*    (2006.01)
*C07D 409/06*    (2006.01)
(Continued)

(52) U.S. Cl.
CPC .......... *C07C 225/22* (2013.01); *A61K 31/445* (2013.01); *A61K 31/46* (2013.01); *A61P 43/00* (2018.01); *C07C 237/12* (2013.01); *C07D 205/04* (2013.01); *C07D 207/06* (2013.01); *C07D 211/60* (2013.01); *C07D 211/62* (2013.01); *C07D 221/04* (2013.01); *C07D 221/22* (2013.01); *C07D 223/04* (2013.01); *C07D 227/04* (2013.01); *C07D 239/26* (2013.01); *C07D 265/30* (2013.01); *C07D 333/10* (2013.01); *C07D 333/72* (2013.01); *C07D 401/06* (2013.01); *C07D 409/06* (2013.01); *C07D 413/06* (2013.01); *C07D 451/02* (2013.01)

(58) Field of Classification Search
CPC ... C07C 225/10; C07C 225/18; C07C 225/22; C07D 205/04; C07D 207/04; C07D 221/04; C07D 221/20; C07D 221/22; C07D 223/04; C07D 265/30; C07D 267/12
See application file for complete search history.

(56) References Cited

U.S. PATENT DOCUMENTS

2003/0096737 A1    5/2003  Diu-Hercend et al.

FOREIGN PATENT DOCUMENTS

WO    WO 00/23421 A1    4/2000
WO    WO 01/90070 A2    11/2001
(Continued)

OTHER PUBLICATIONS

Ueno, Hirokazu et al., "Synthesis and structure—activity relationships of oxamyl dipeptide caspase inhibitors developed for the treatment of liver disease" Bioorganic & Medicinal Chemistry Letters, 2009, pp. 199-202, vol. 19.

(Continued)

*Primary Examiner* — Emily A Bernhardt
*Assistant Examiner* — Laura M Daniel
(74) *Attorney, Agent, or Firm* — Knobbe Martens Olson & Bear LLP

(57) ABSTRACT

Disclosed are a class of compounds as a caspase inhibitor, and in particular the compound as shown in formula (I) or a pharmaceutically acceptable salt thereof, and the use of the compound in treating caspase-related diseases.

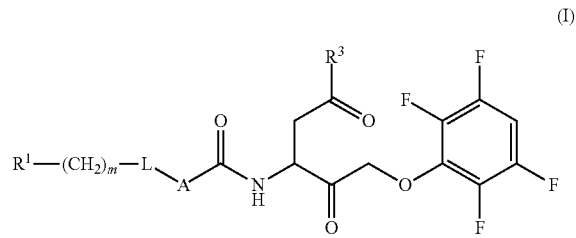

18 Claims, No Drawings

(51) Int. Cl.
    *C07D 211/62*     (2006.01)
    *C07D 451/02*     (2006.01)
    *A61K 31/46*     (2006.01)
    *A61K 31/445*     (2006.01)
    *C07C 237/12*     (2006.01)
    *C07D 211/60*     (2006.01)
    *C07D 207/06*     (2006.01)
    *C07D 227/04*     (2006.01)
    *C07D 239/26*     (2006.01)
    *C07D 333/10*     (2006.01)
    *C07D 333/72*     (2006.01)
    *C07D 413/06*     (2006.01)

(56)     References Cited

FOREIGN PATENT DOCUMENTS

| WO | WO 2007/007162 A1 | 1/2007 |
| WO | WO 2012/021800 A2 | 2/2012 |
| WO | WO 2015/175381 A1 | 11/2015 |

OTHER PUBLICATIONS

International Search Report for PCT/CN2017/083909 dated Aug. 15, 2017.
Supplementary European Search Report for EP 17795569 dated Sep. 3, 2019.

CASPASE INHIBITOR AND PHARMACEUTICAL COMPOSITION, USE AND THERAPEUTIC METHOD THEREOF

CROSS REFERENCE TO RELATED APPLICATIONS

This application is a U.S. National Phase Application of PCT International Application Number PCT/CN2017/083909, filed on May 11, 2017, designating the United States of America and published in the Chinese language, which is an International Application of and claims the benefit of priority to Chinese Patent Application No. 201610310917.0, filed on May 11, 2016, and Chinese Patent Application No. 201710058653.9, filed on Jan. 23, 2017. The disclosures of the above-referenced applications are hereby expressly incorporated by reference in their entireties.

FIELD OF THE INVENTION

The present application relates to a class of novel compounds and pharmaceutically acceptable salts thereof as a caspase inhibitor, and to pharmaceutical compositions containing these compounds and methods using such pharmaceutical compositions.

BACKGROUND OF THE INVENTION

The control of the number of mammalian cells depends on the balance between reproduction and death of the cells to some extent. Necrotic cell death is one of the forms of cell death, characterized by pathological cell death caused by trauma or cell damage. Necrotic cell death is harmful to tissues, such as, by leading to inflammation. In contrast, another physiological form of cell death occurs in an orderly, controlled manner. This orderly, controlled form of cell death is called as apoptotic cell death (Barr, et al., Bio/Technology, 12: 487-497, 1994; Steller, et al., 267: 1445-1449, 1995). Through this programmed manner of apoptotic cell death, organisms eliminate unwanted cells (activity and presence of the cells that are no longer needed) without damaging other tissues. Therefore, apoptotic cell death is an extremely important physiological process to maintain the normal development and dynamic equilibrium of an organism.

There are many factors that can cause apoptotic cell death. Among them, the most important factor is a class of proteases called caspase (cysteine aspartate-specific protease, 14 caspase proteases are known). Capase is a type of cysteine protease, and many important proteins in cells are its substrate. The process of apoptotic cell death includes decomposing cells by action of caspase enzymes to form cell debris, and absorbing the cell debris by other cells or eliminating them by macrophages and the like, without inflammation, etc.

SUMMARY OF THE INVENTION

The present application provides a compound represented by formula (I), a pharmaceutically acceptable salt or tautomer thereof,

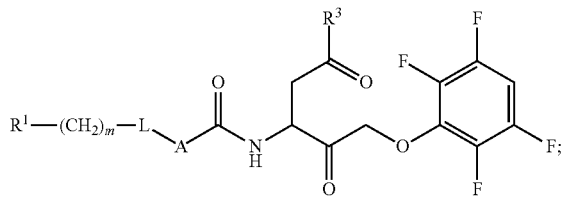

wherein, $R^1$ is selected from $C_{1-6}$ alkyl, $C_{3-12}$ cycloalkyl, 3- to 12-membered heterocycloalkyl, 6- to 12-membered aryl, or 5- to 12-membered heteroaryl, which is optionally substituted with 1, 2 or 3 R;

m is 0, 1, 2 or 3;

L is selected from a bond; C(=O); S(=O); S(=O)$_2$;

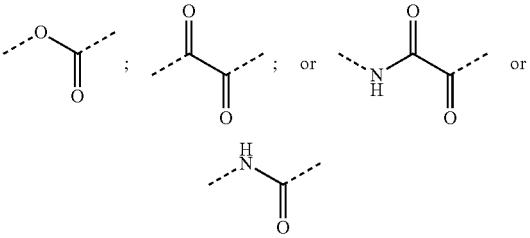

which is optionally substituted with R;

A is selected from the following groups optionally substituted with R: —NHR²—, wherein $R^2$ is selected from $(CH_2)_{2-4}$, phenylene, cyclohexylidene;

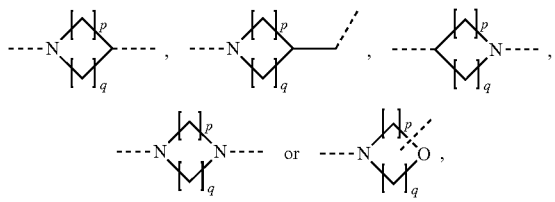

wherein p, q are independently selected from 1, 2, 3, 4 or 5;

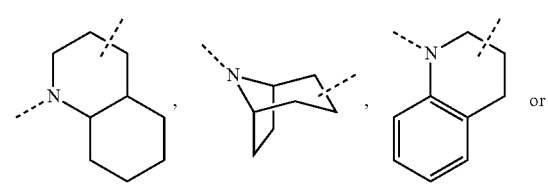

$R^3$ is selected from OH, $OR^7$ or

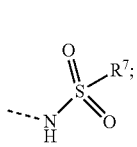

$R^7$ is selected from $C_{1-6}$ alkyl or $C_{3-6}$ cycloalkyl, which is optionally substituted with 1, 2 or 3 R;
R is selected from halogen; CN; OH; $NH_2$; COOH; or $C_{1-6}$ alkyl, $C_{1-6}$ alkoxy, $C_{3-6}$ cycloalkyl, 3- to 6-membered heterocycloalkyl, phenyl, or 5- to 6-membered heteroaryl, which is optionally substituted with 1, 2 or 3 R';
R' is selected from halogen, OH, CN, $NH_2$, COOH, Me, Et, $CF_3$, $CHF_2$, $CH_2F$, $NHCH_3$ or $N(CH_3)_2$.

In some embodiments of the present application, the above R is selected from halogen; CN; OH; $NH_2$; COOH; or $C_{1-4}$ alkyl, $C_{1-4}$ alkoxy, or phenyl, which is optionally substituted with 1, 2 or 3 R'.

In some embodiments of the present application, the above R is selected from F; Cl; CN; OH; $NH_2$; COOH; or methyl, ethyl, propyl, isopropyl, tert-butyl, methoxy, ethoxy or phenyl, which is optionally substituted with 1, 2 or 3 R'.

In some embodiments of the present application, the above R is selected from F, Cl, CN, OH, $NH_2$, COOH, Me, MeO, Et, $CF_3$, $CHF_2$, $CH_2F$,

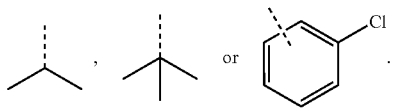

In some embodiments of the present application, the above R is selected from F, Cl, CN, OH, $NH_2$, COOH, Me, MeO, Et, $CF_3$, $CHF_2$, $CH_2F$,

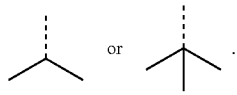

In some embodiments of the present application, the above R' is selected from F or Cl.

In some embodiments of the present application, the above $R^1$ is selected from $C_{1-6}$ alkyl, $C_{3-10}$ cycloalkyl, 4- to 7-membered heterocycloalkyl, phenyl, naphthyl, or 5- to 12-membered heteroaryl containing 1, 2 or 3 atoms independently selected from N, O, S, which is optionally substituted with 1, 2 or 3 R.

In some embodiments of the present application, the above $R^1$ is selected from $C_{1-5}$ alkyl, $C_{3-10}$ cycloalkyl, azetidinyl, pyrrolidinyl, piperidinyl, tetrahydropyranyl, morpholinyl, oxazolyl, isoxazolyl, thiazolyl, isothiazolyl, thienyl, furyl, imidazolyl, pyrazolyl, pyrrolyl, phenyl, pyridyl, pyrimidinyl, pyrazinyl, naphthyl, quinolyl, isoquinolyl, indolyl, benzimidazolyl, benzothiazolyl, benzisothiazolyl, benzoxazolyl, benzisoxazolyl, benzothienyl or quinazolinyl, which is optionally substituted with 1, 2 or 3 R.

In some embodiments of the present application, the above $R^1$ is selected from Me, Et,

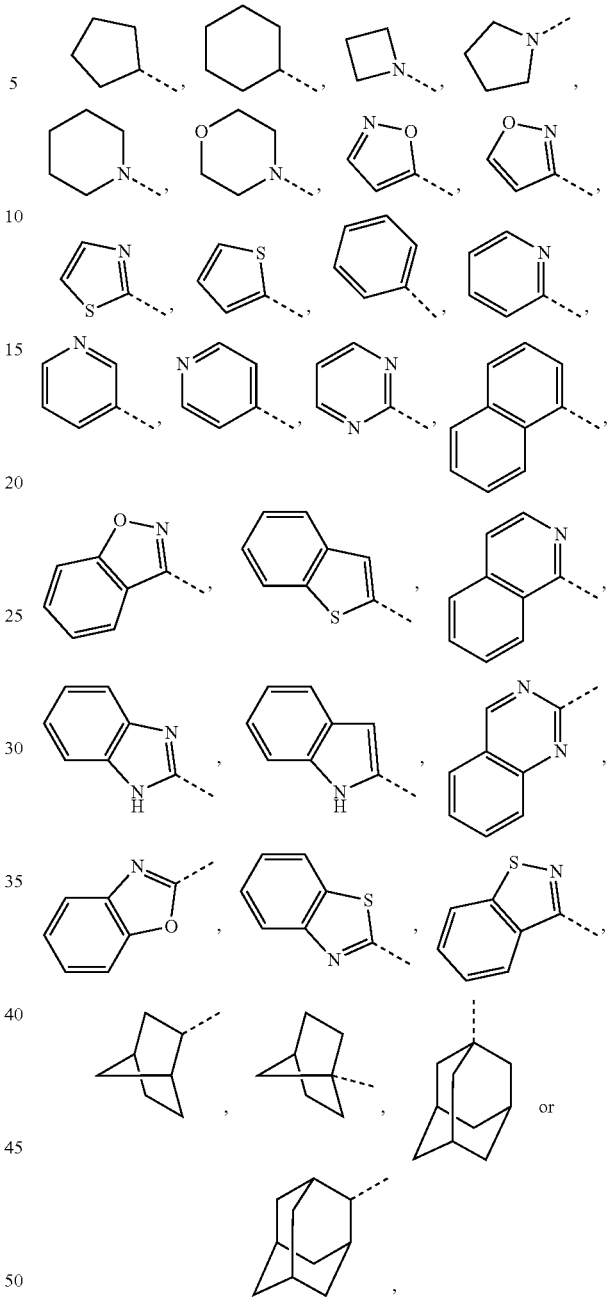

which is optionally substituted with 1, 2 or 3 R.

In some embodiments of the present application, the above $R^1$ is selected from Me,

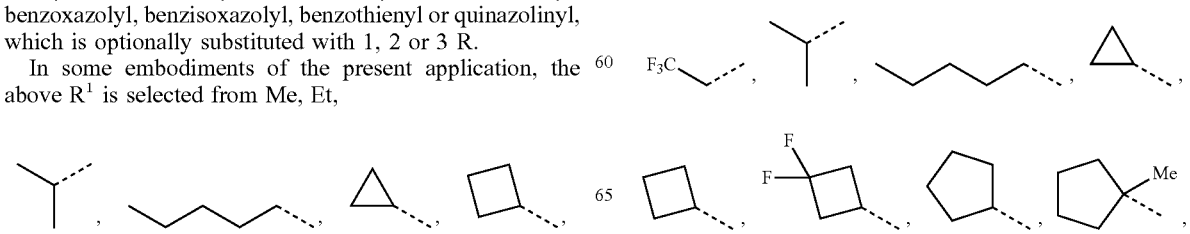

-continued
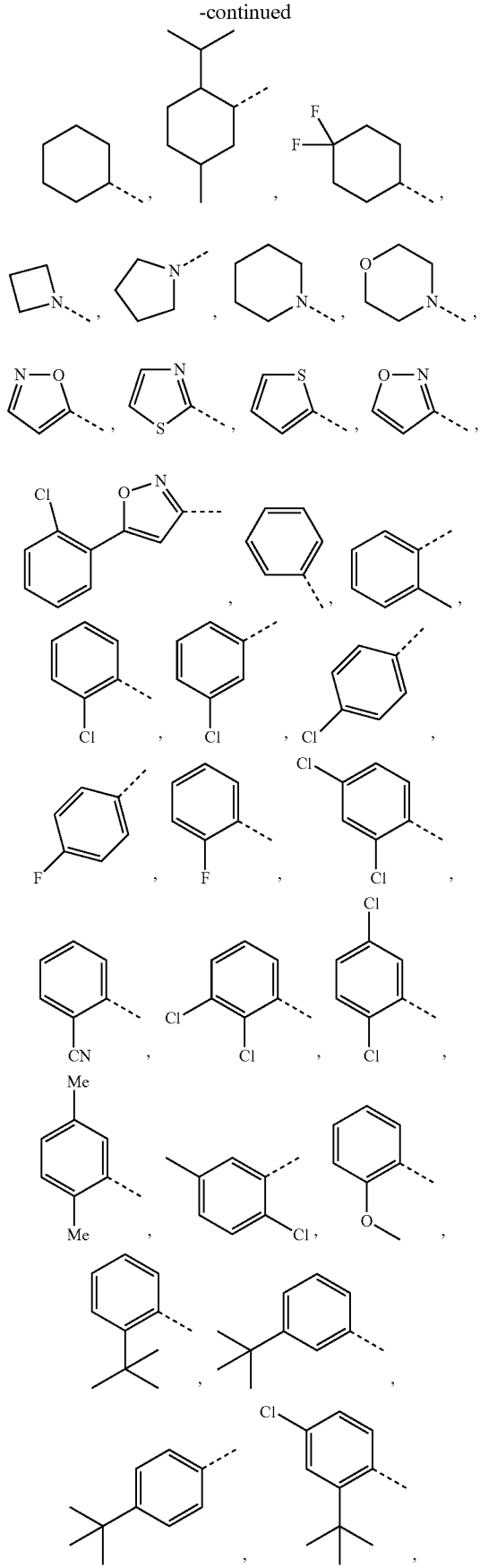
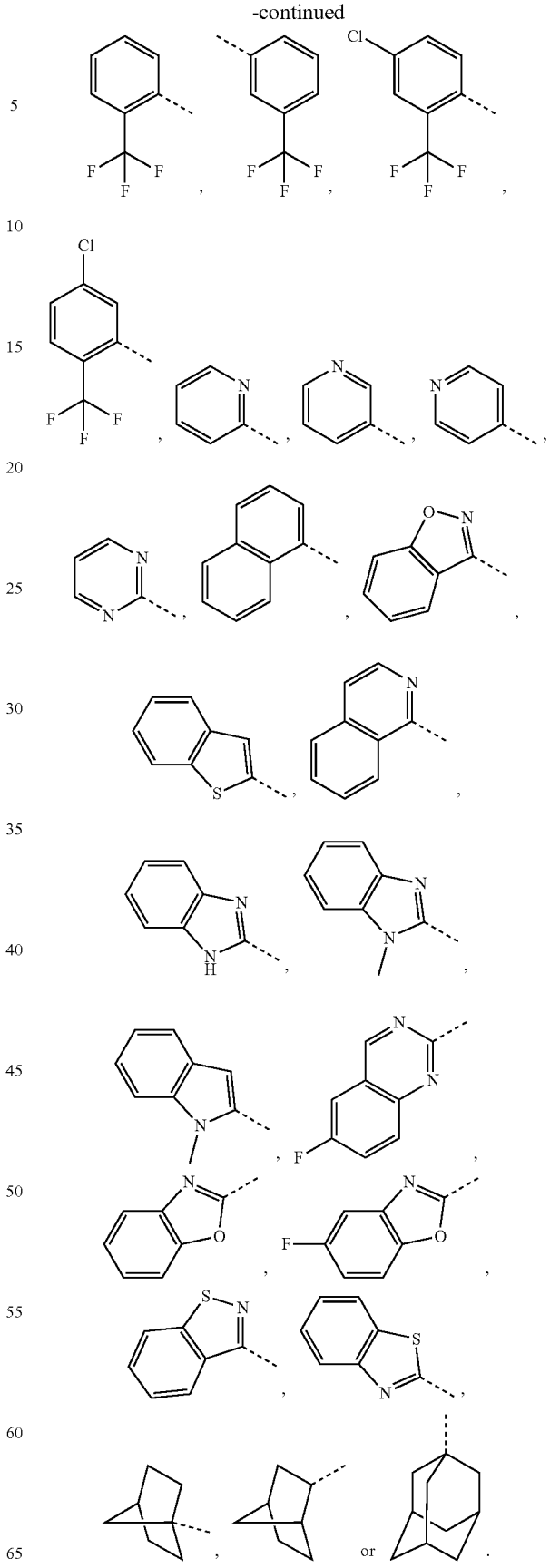

In some embodiments of the present application, the above L is selected from a bond, C(=O), S(=O)$_2$,

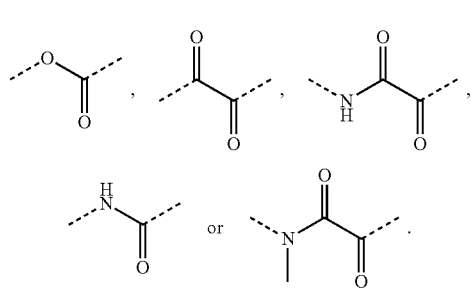

In some embodiments of the present application, A is selected from the following groups optionally substituted with R:

—NHR$^2$—, wherein R$^2$ is selected from (CH$_2$)$_2$, phenylene, or cyclohexylidene;

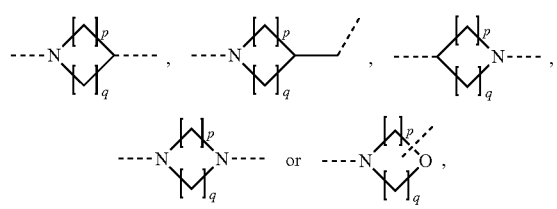

wherein p, q are independently selected from 1, 2, 3, 4, or 5;

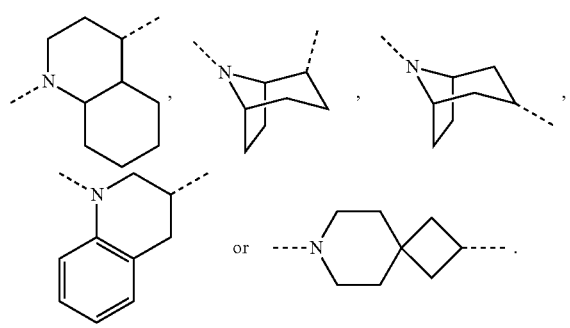

In some embodiments of the present application, A is selected from the following groups optionally substituted with R:

—NHR$^2$—, wherein R$^2$ is selected from (CH$_2$)$_2$, phenylene, or cyclohexylidene;

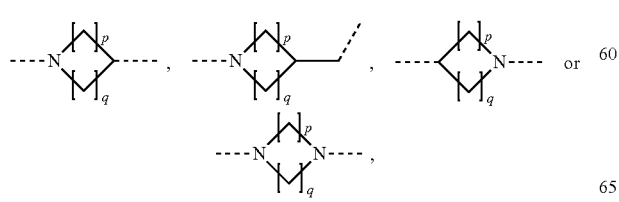

wherein p, q are independently selected from 1, 2, 3 or 4;

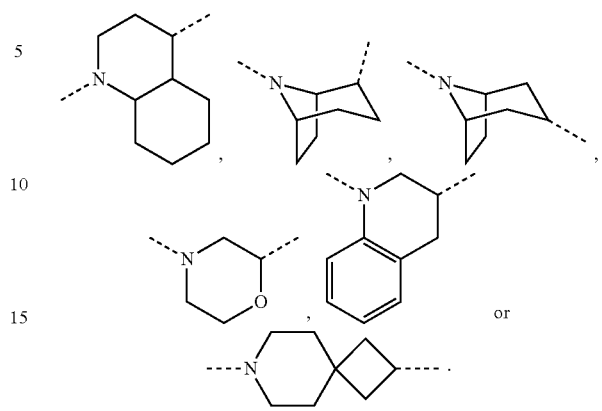

In some embodiments of the present application, A is selected from the following groups optionally substituted with

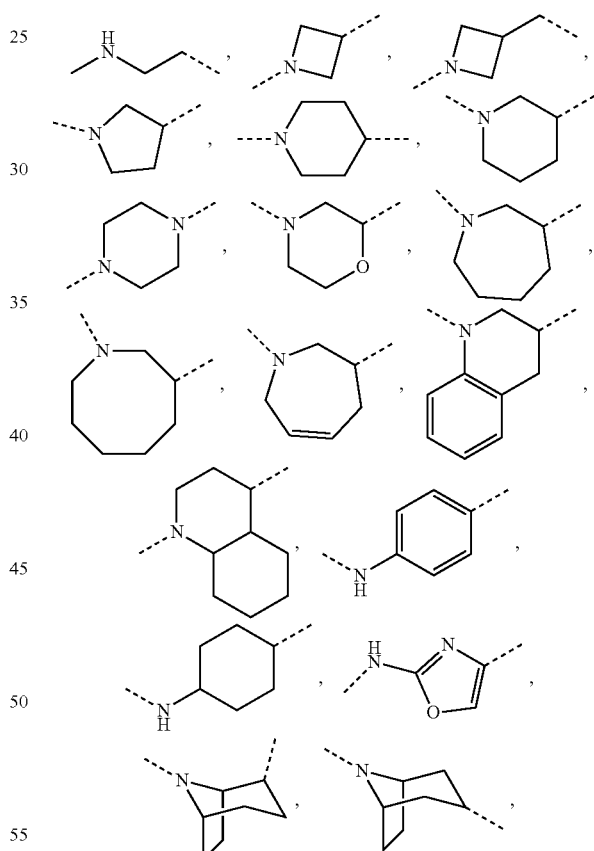

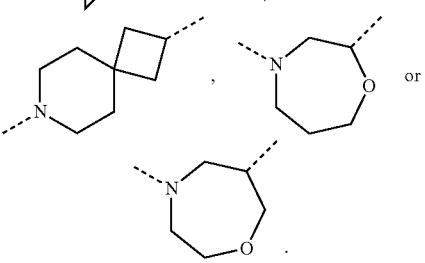

In some embodiments of the present application, A is selected from:
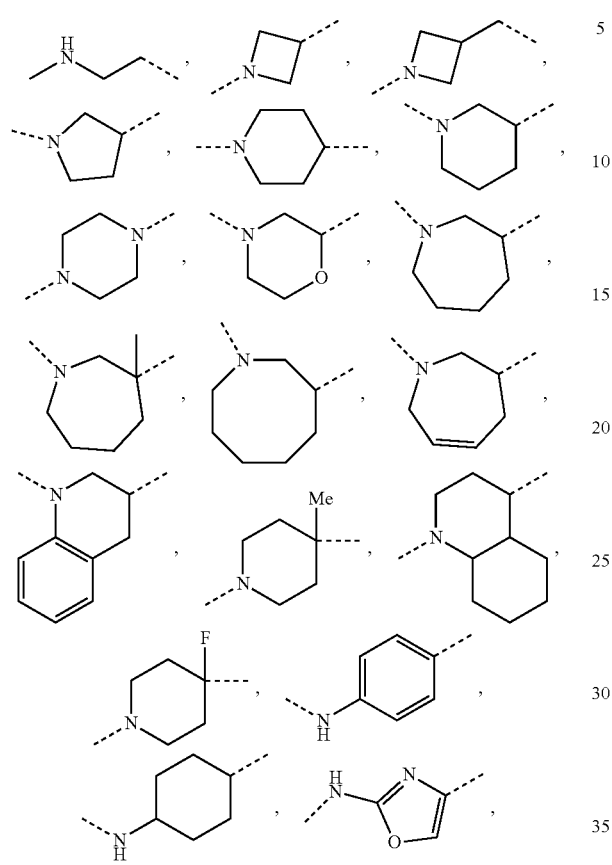
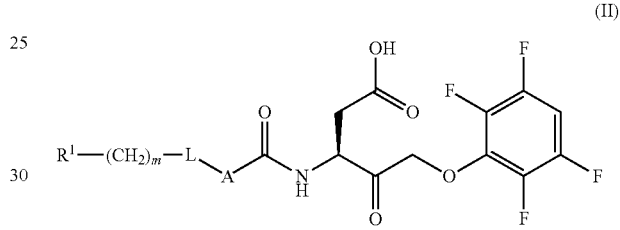
In some embodiments, $R^3$ is OH.
The present application provides a compound represented by formula (II), a pharmaceutically acceptable salt or tautomer thereof,
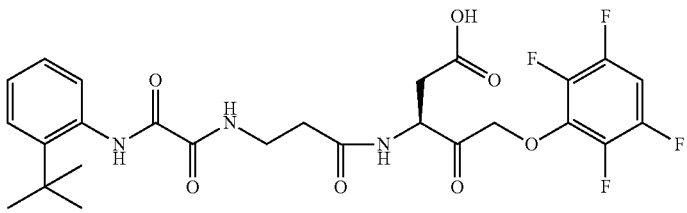
(II)
wherein $R^1$, m, L, A are as defined in the compound of formula (I).
In some embodiments, the compound of formula (I) is selected from:
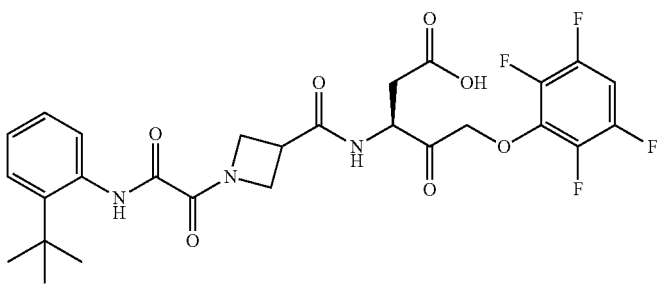

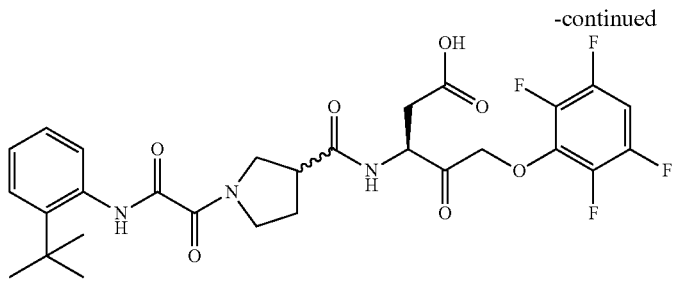
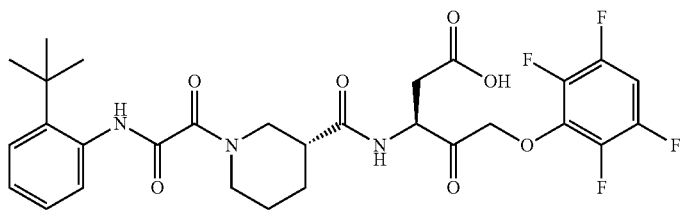
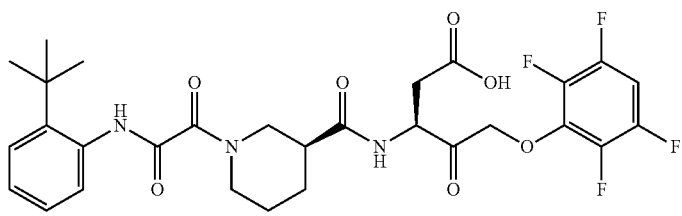
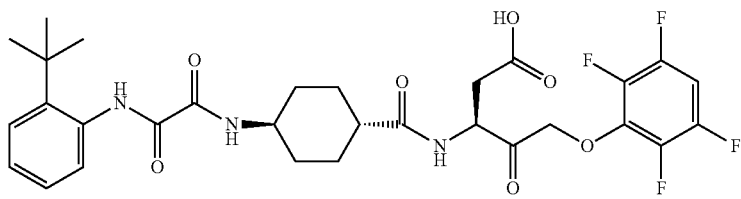
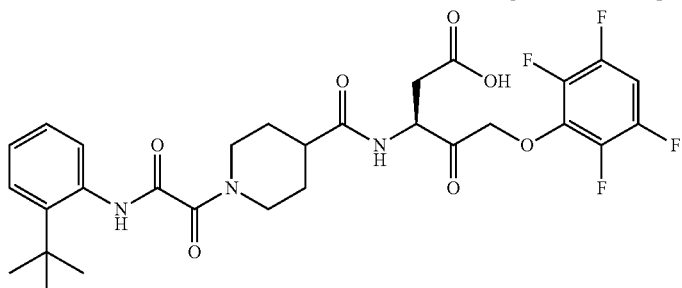
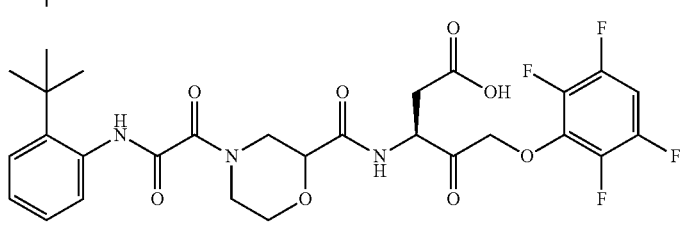
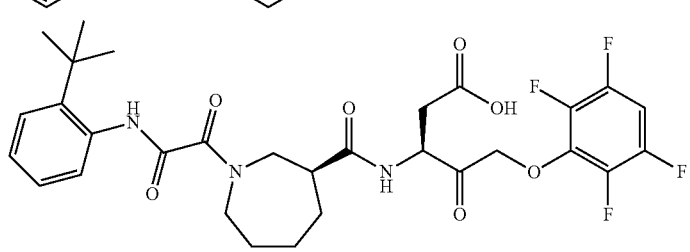

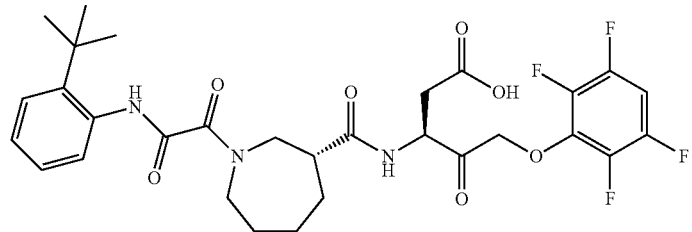
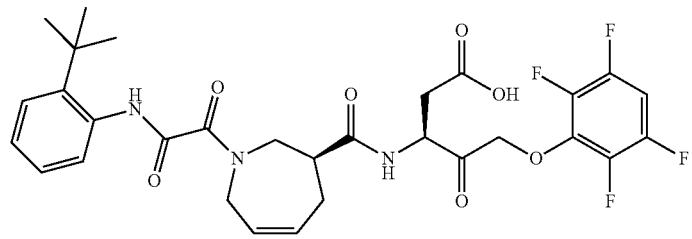
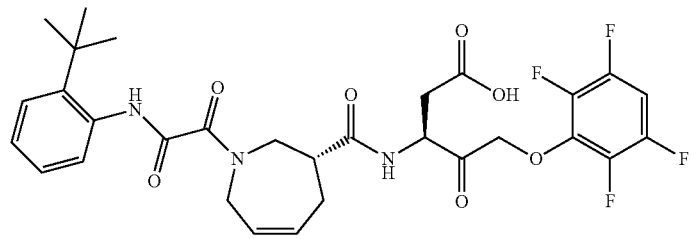
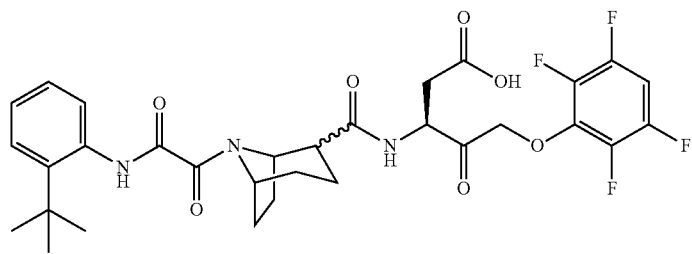
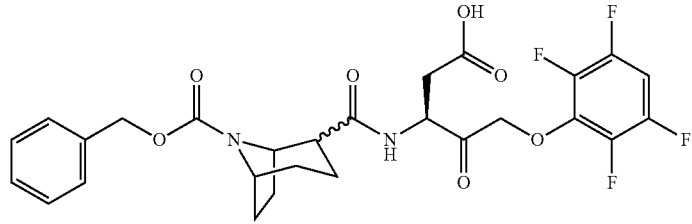
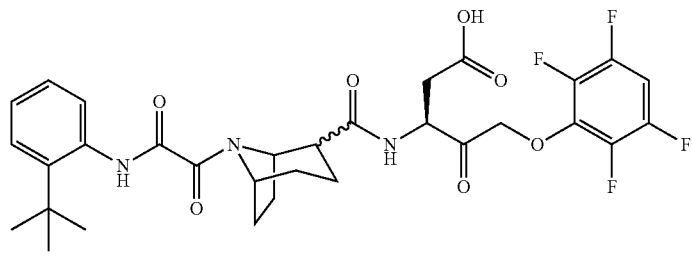
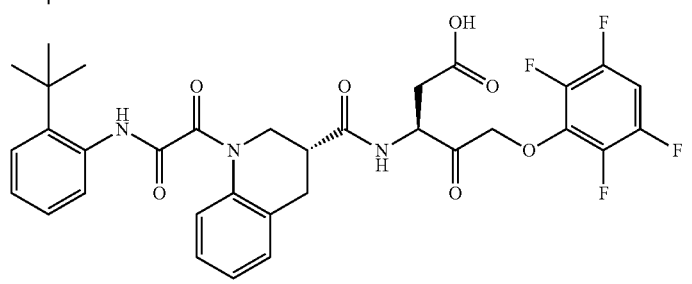

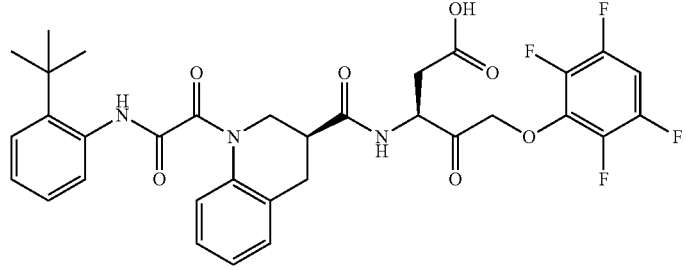
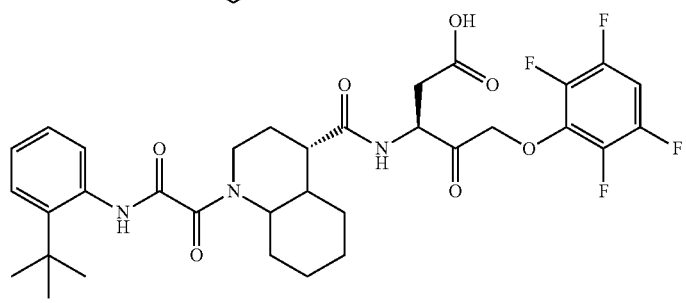
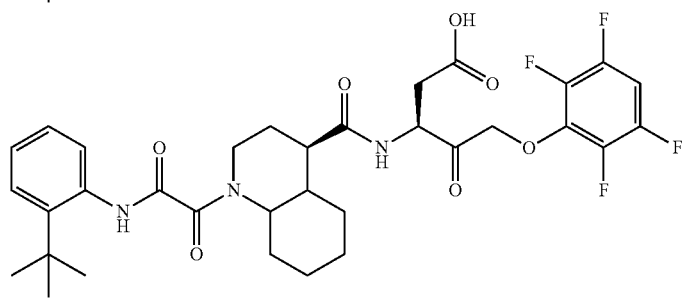
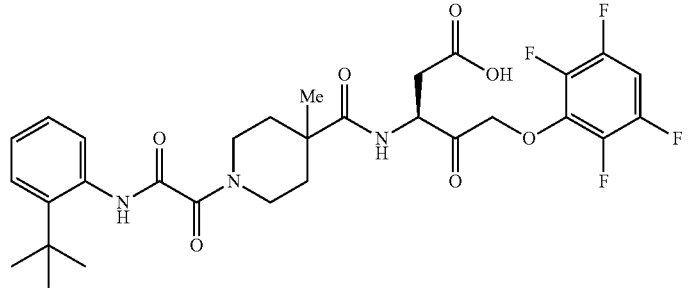
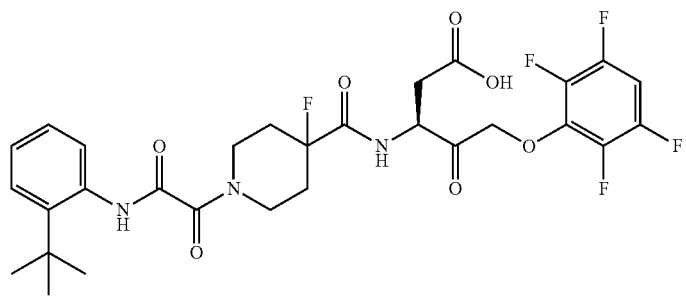
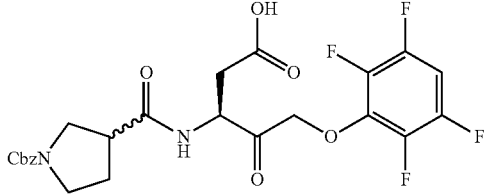
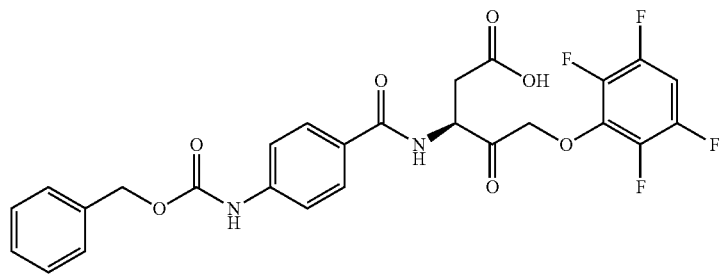

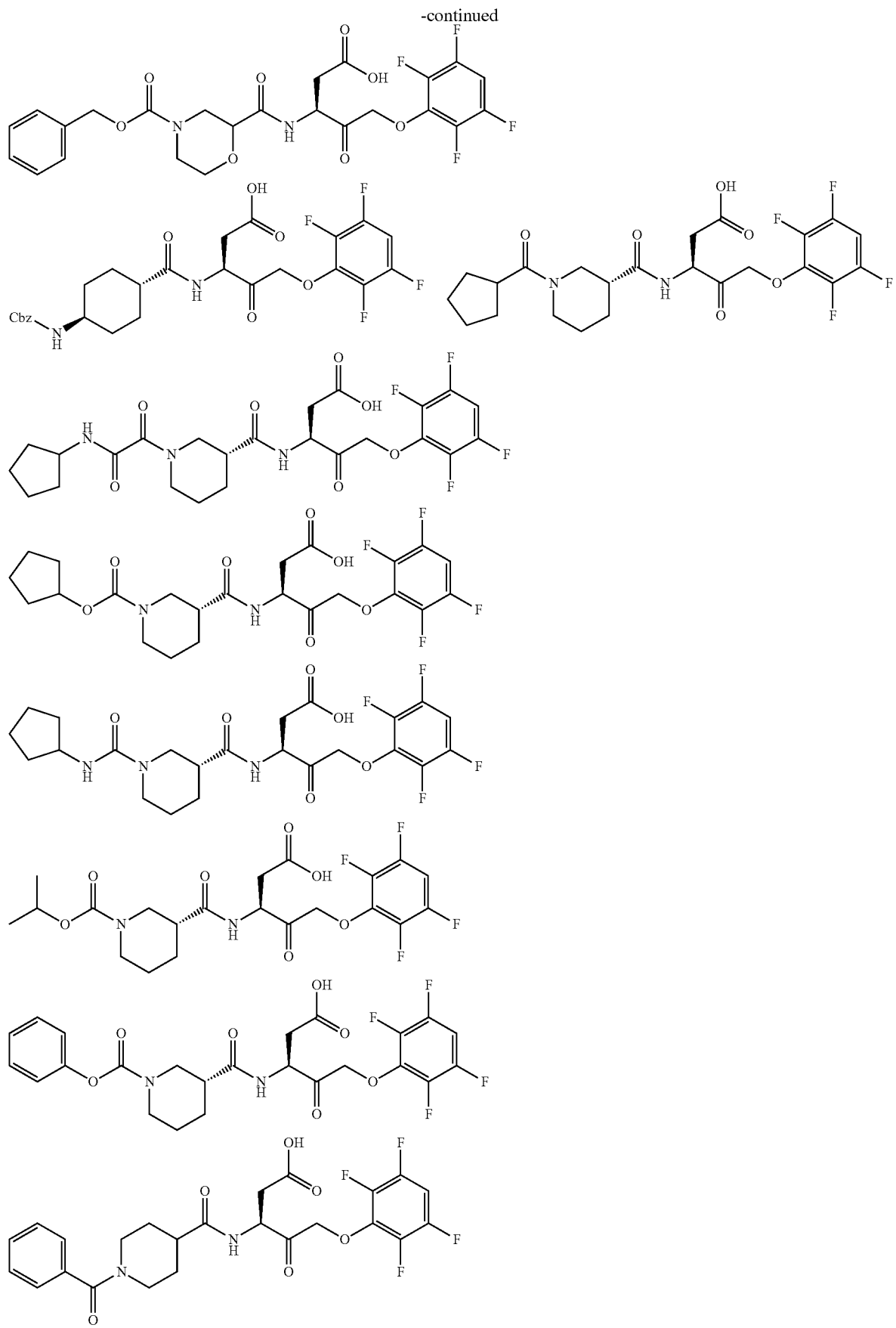

-continued
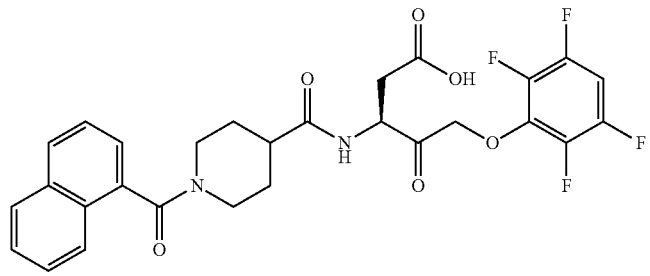
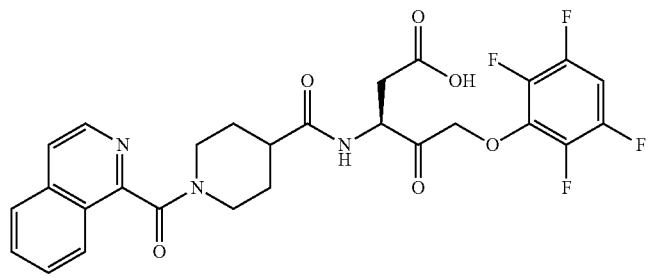
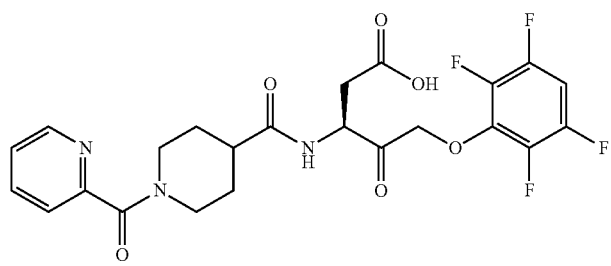
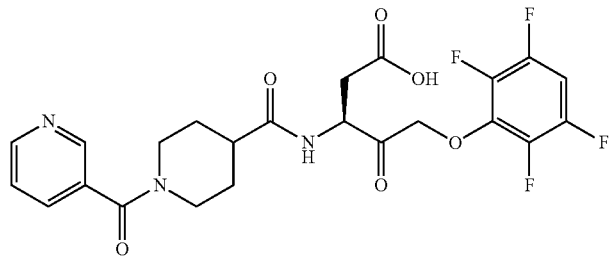
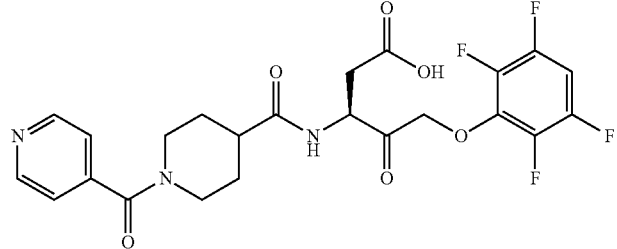
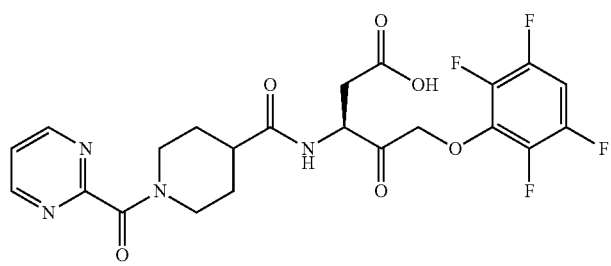

-continued
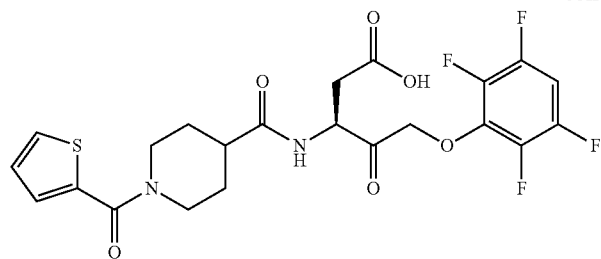
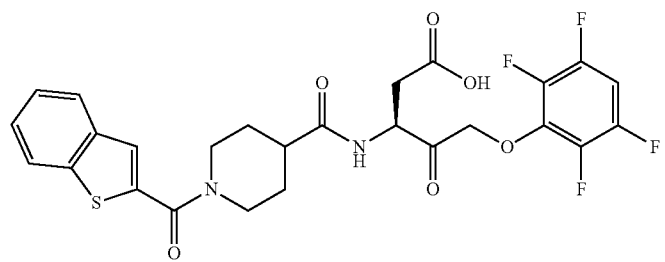
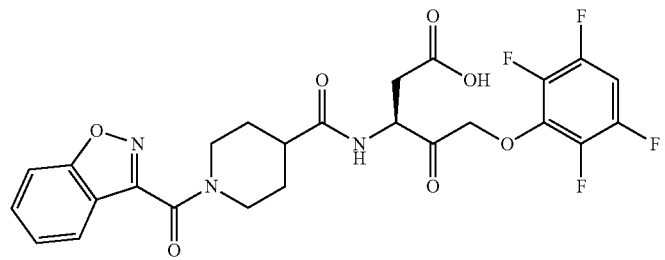
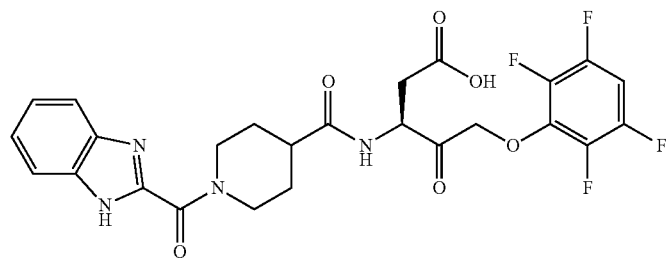
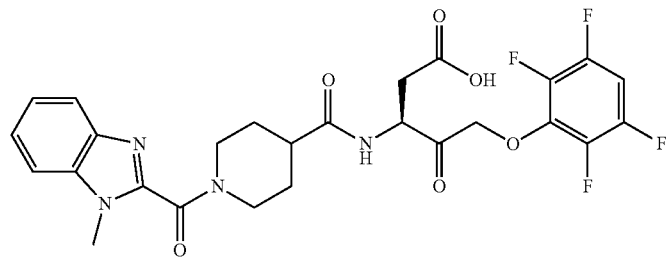
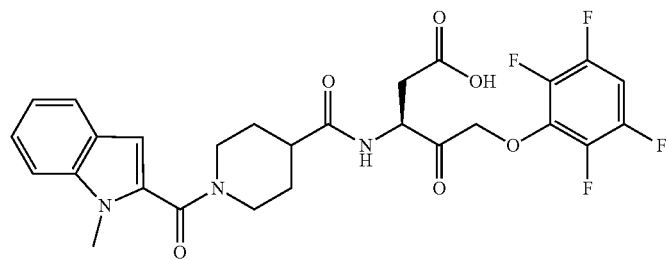

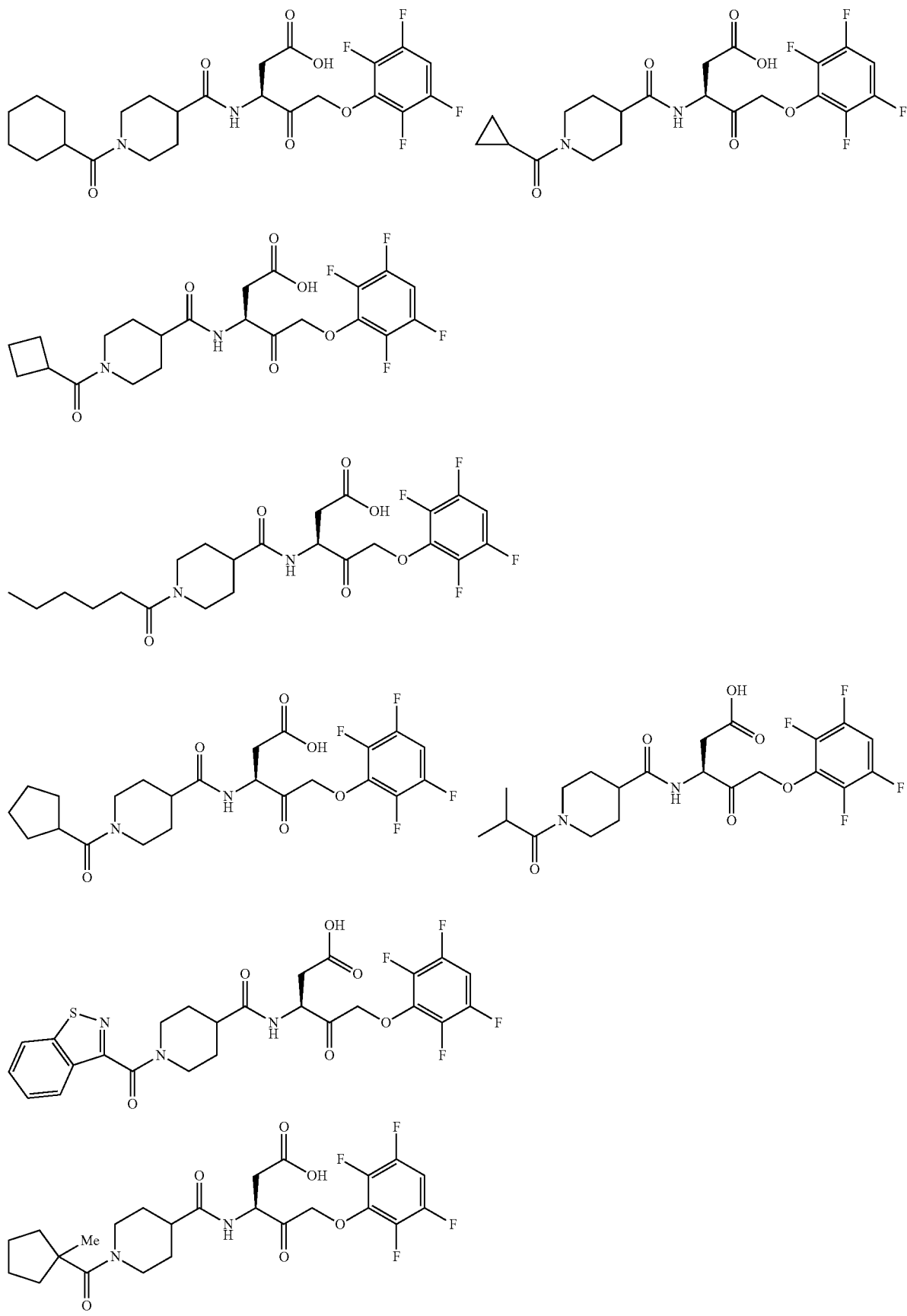

-continued
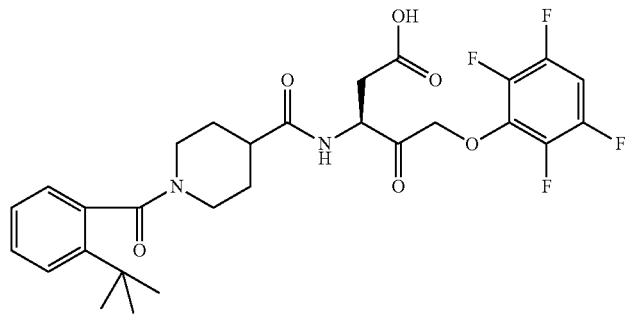
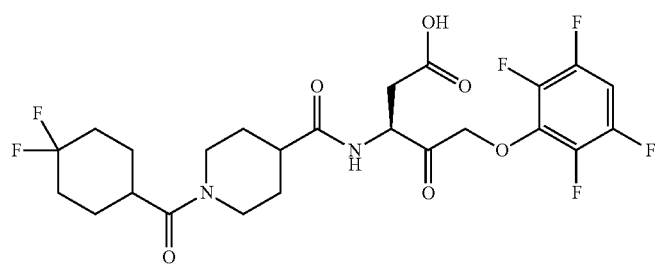
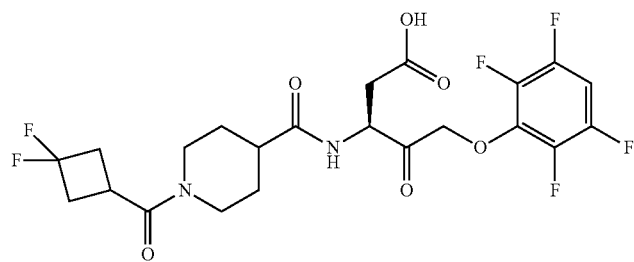
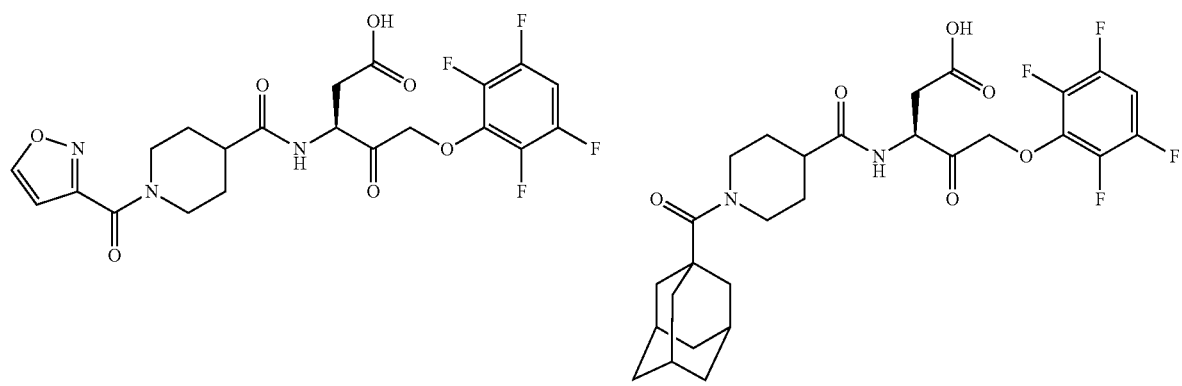
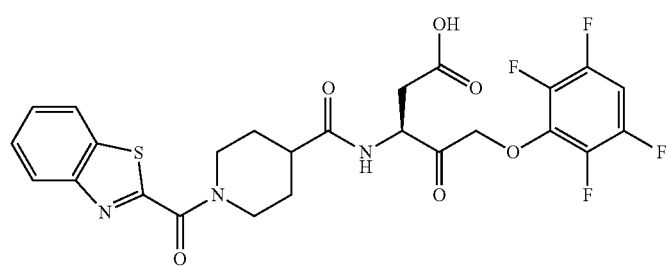

-continued
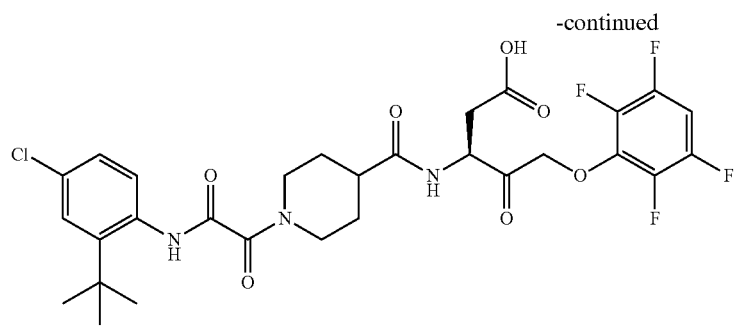
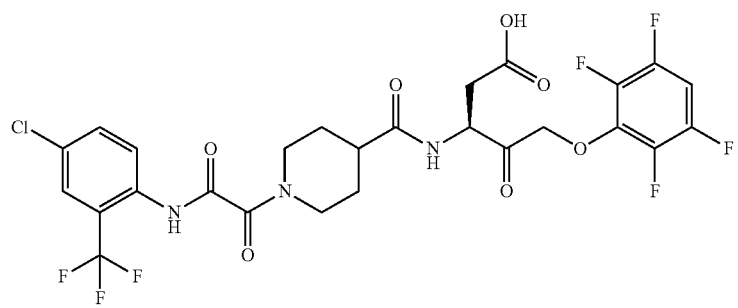
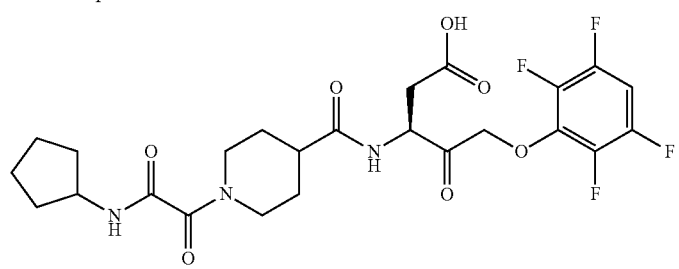
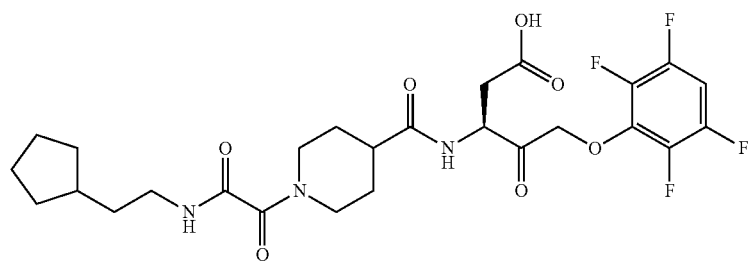
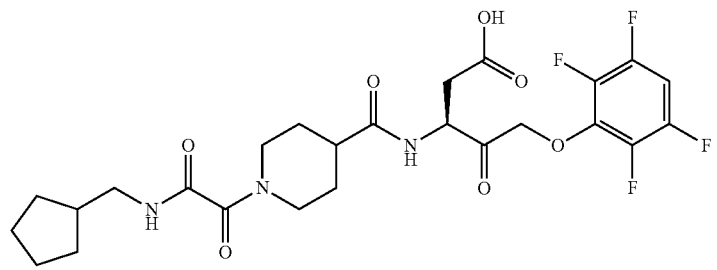
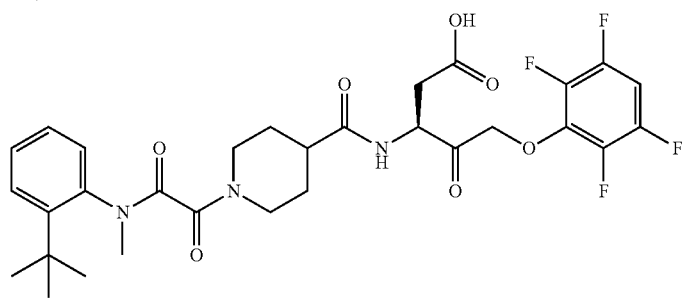

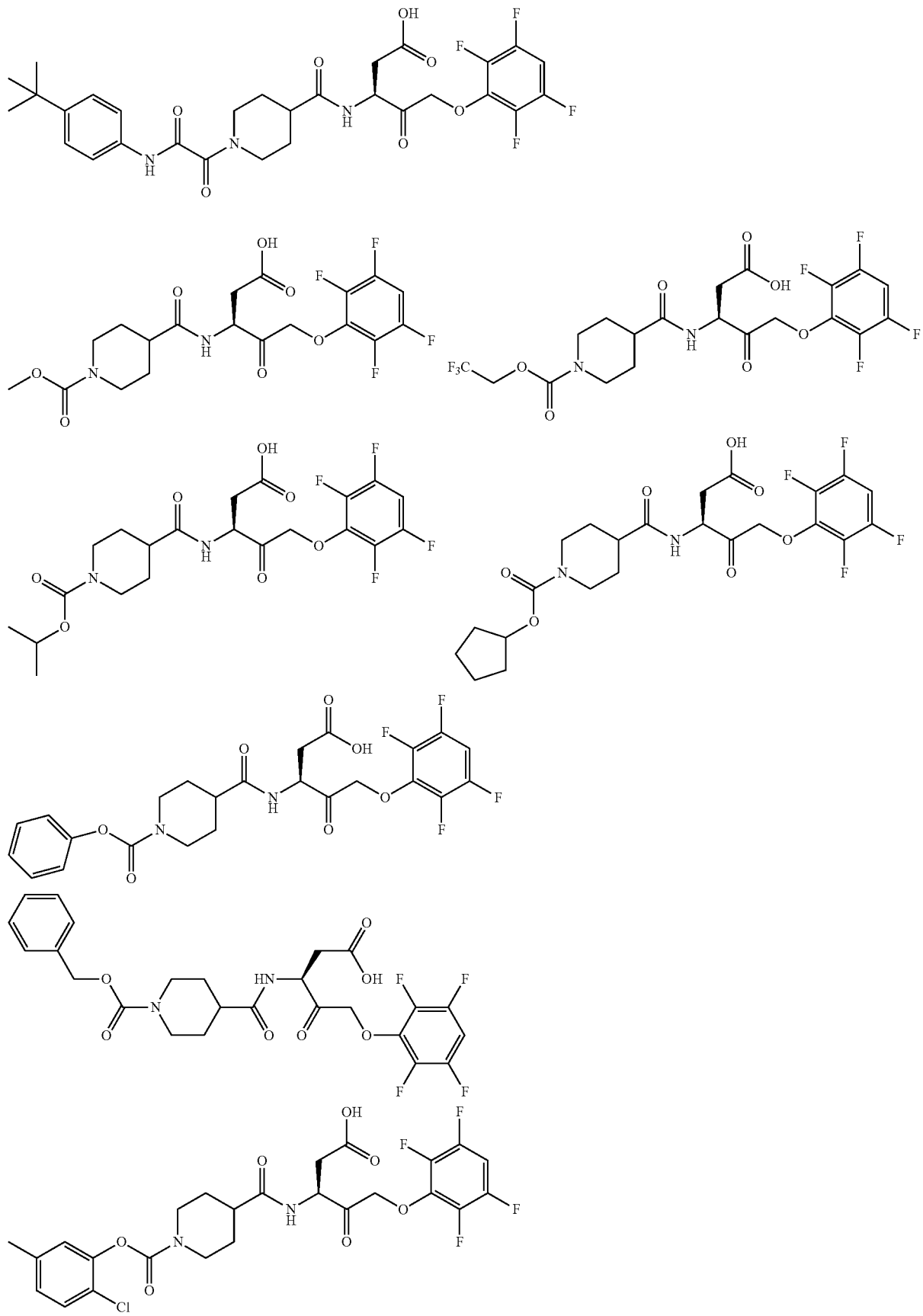

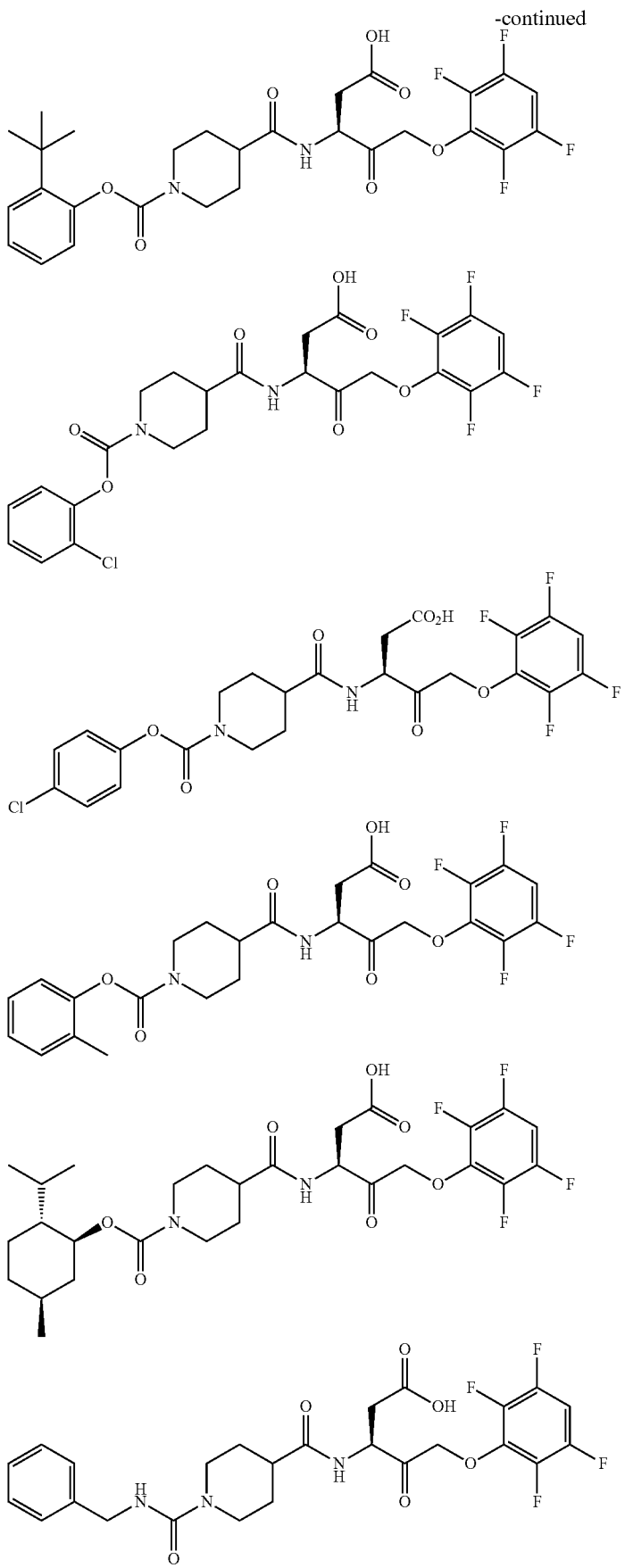

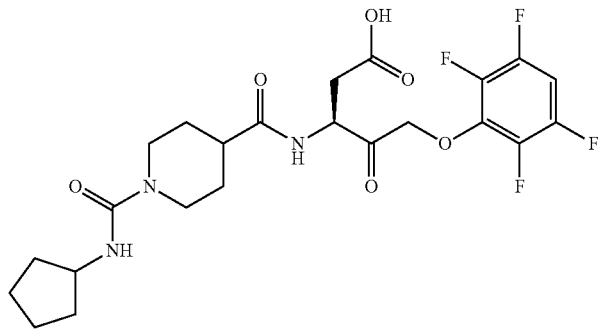
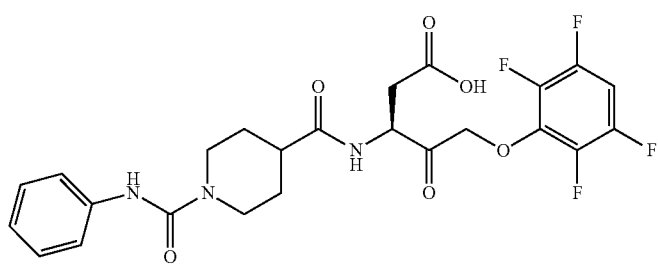
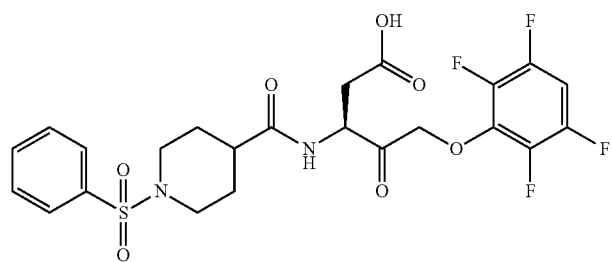
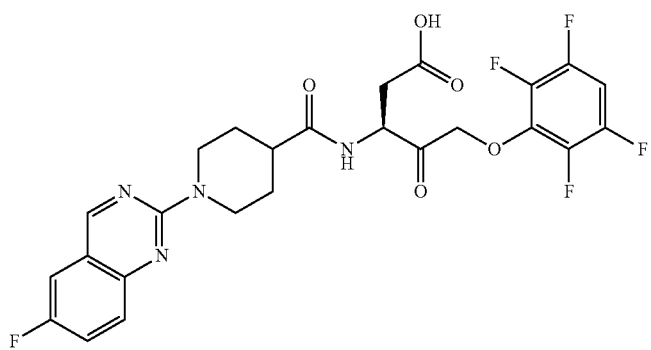
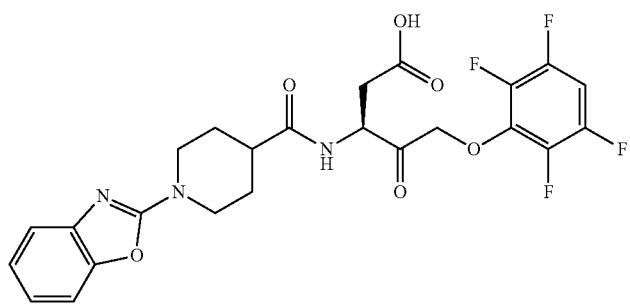

-continued
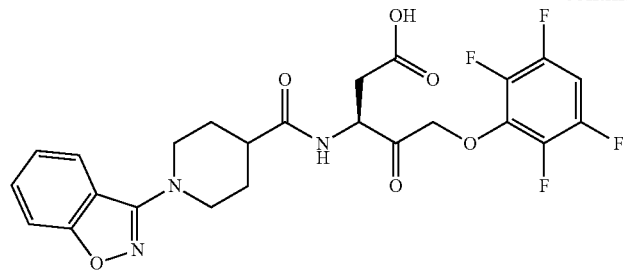
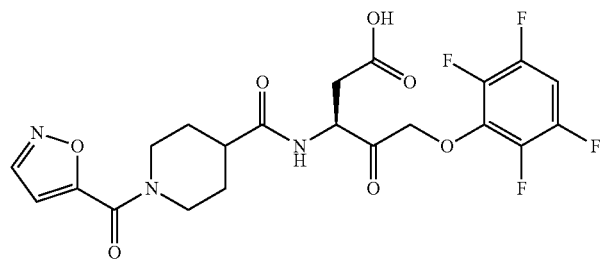
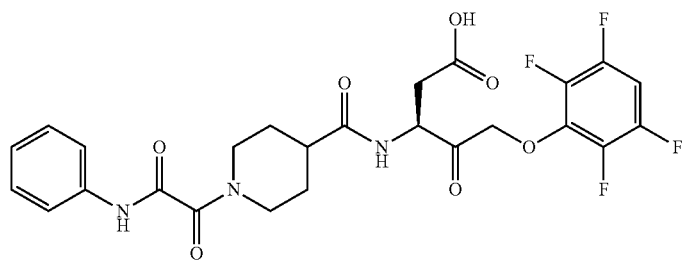
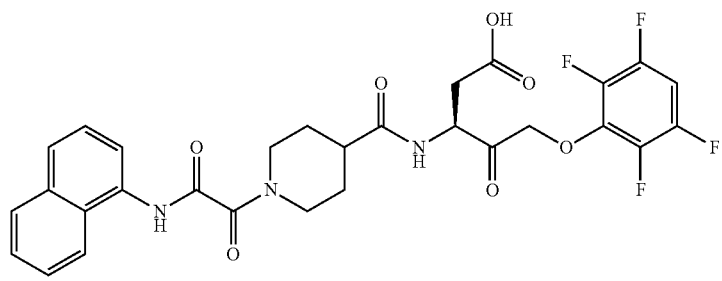
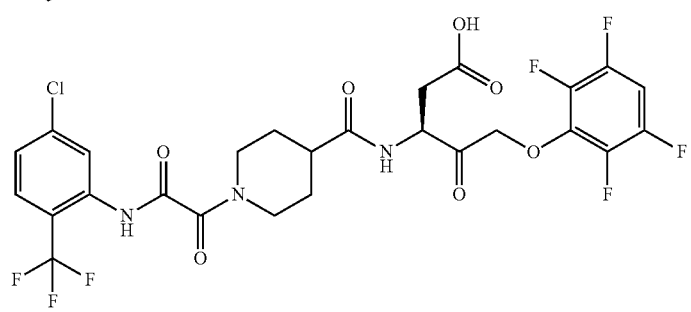
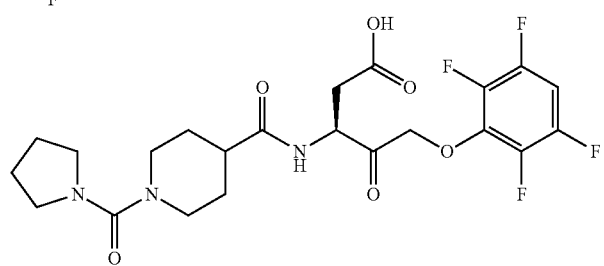

-continued
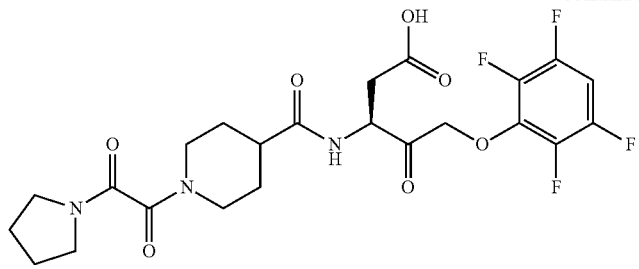
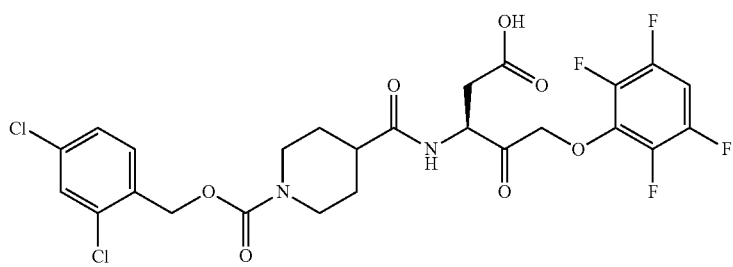
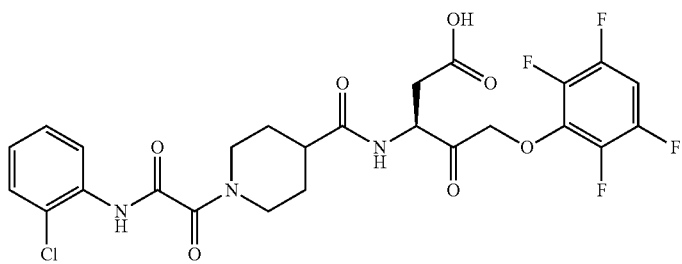
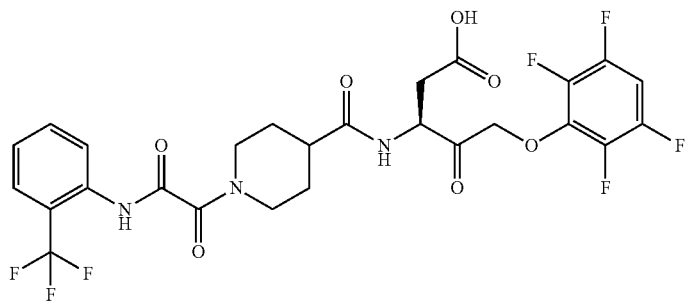
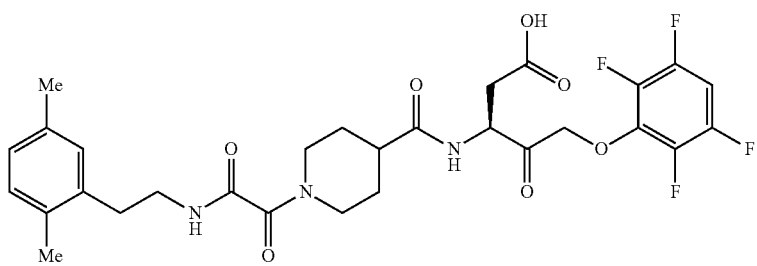
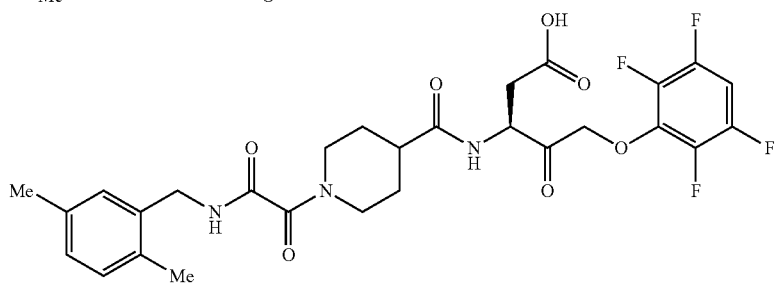

-continued
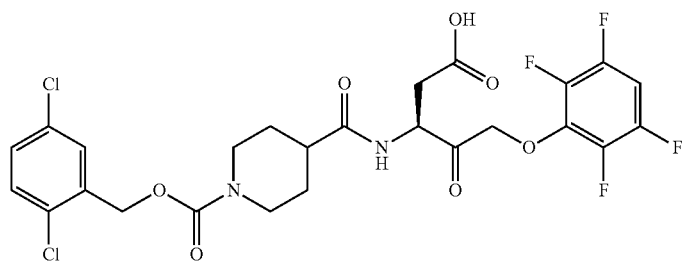
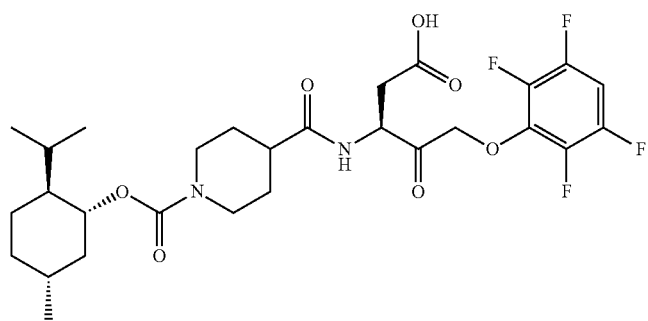
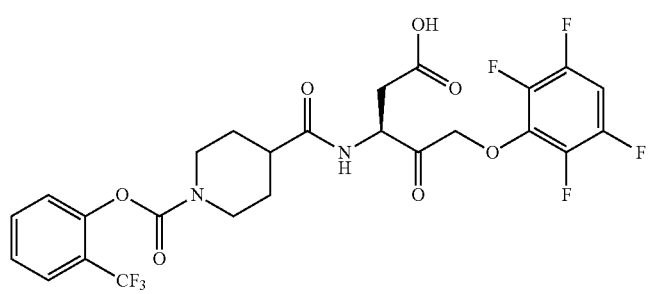
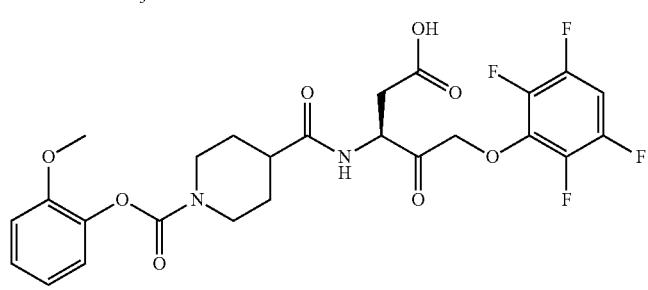
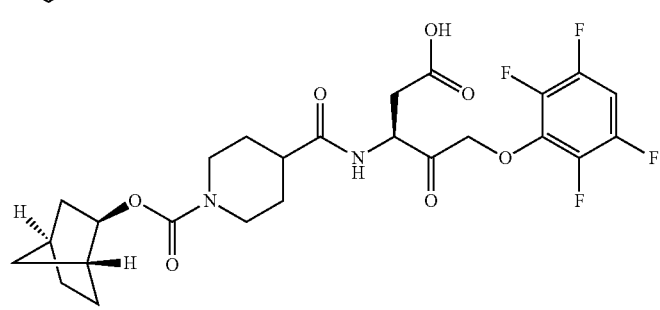
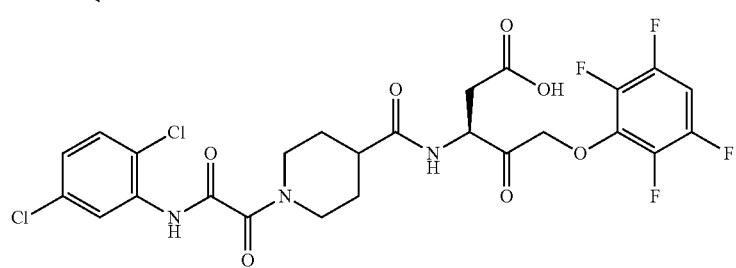

-continued
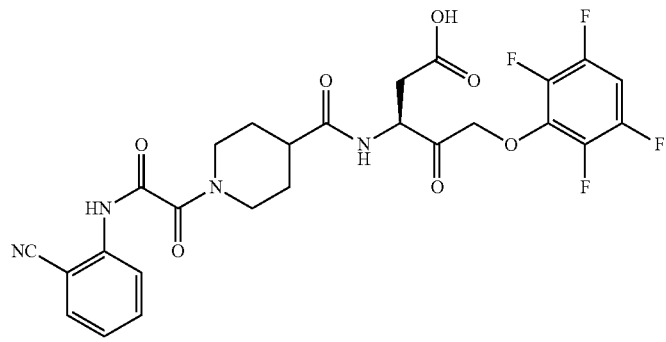
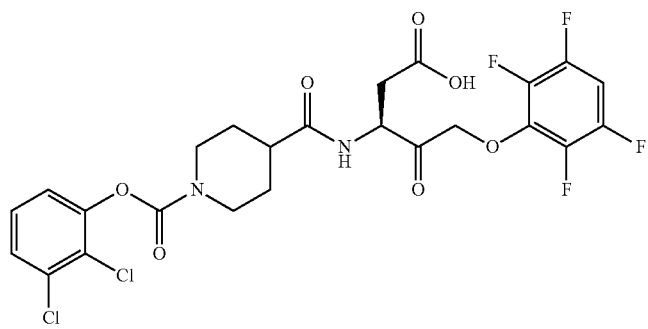
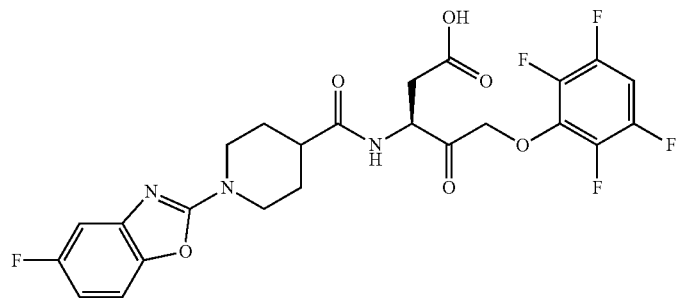
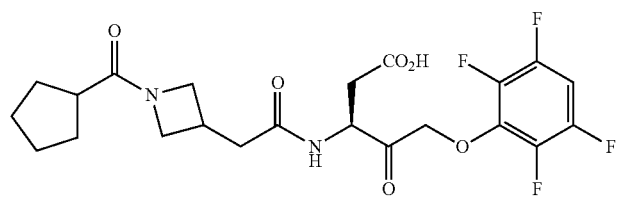
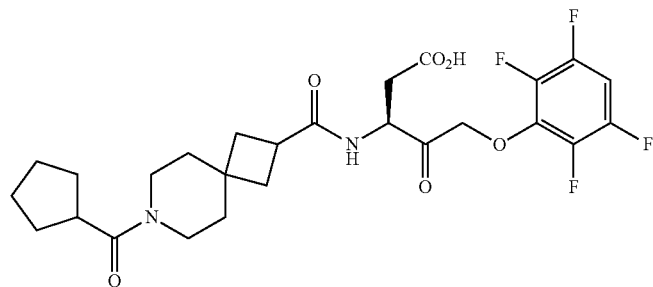
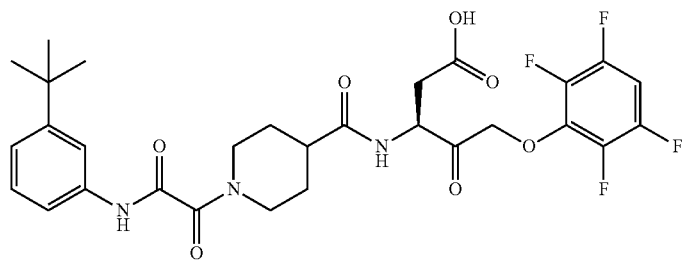

-continued
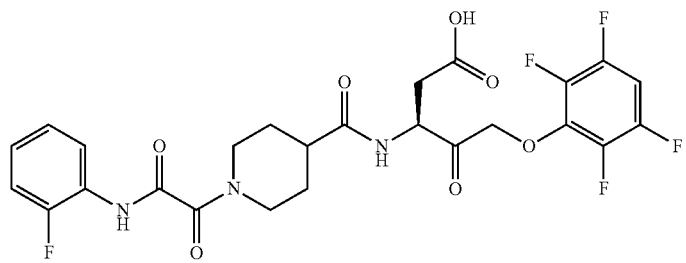
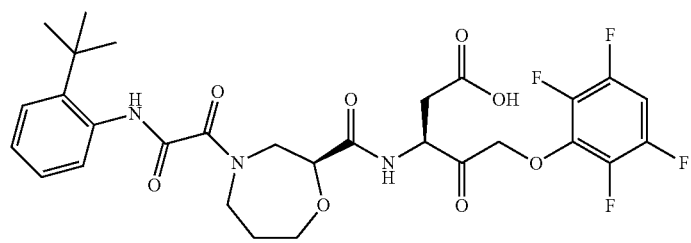
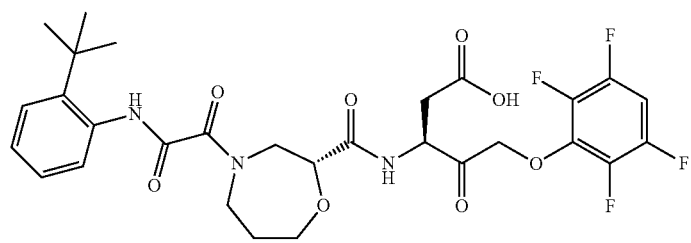
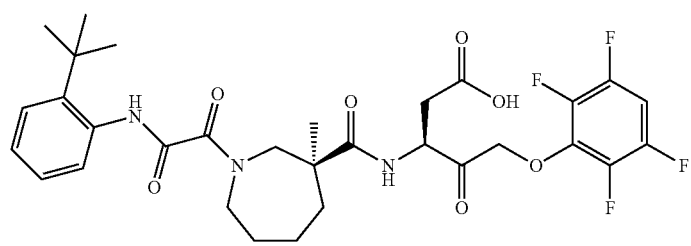
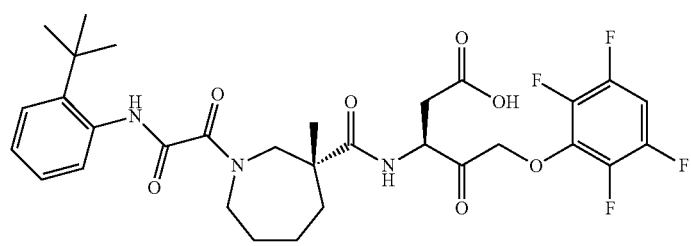
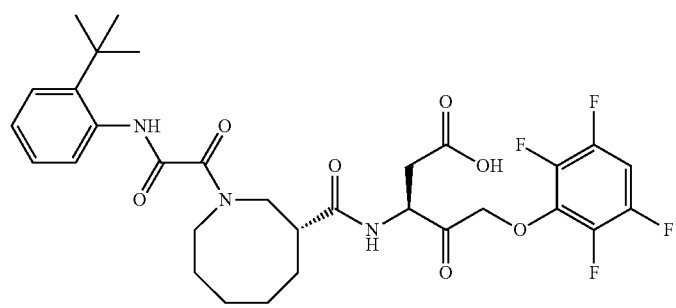

-continued
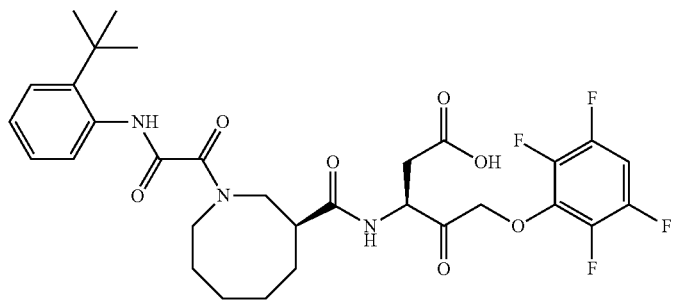
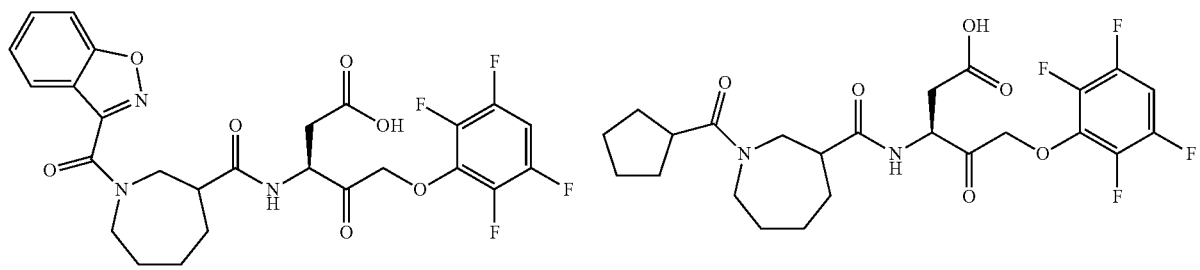
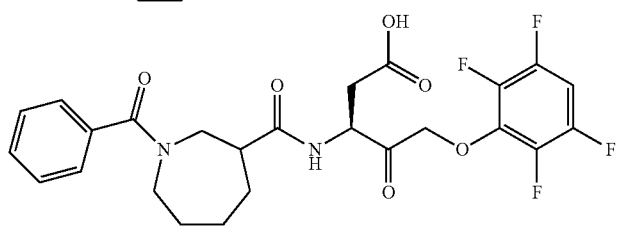
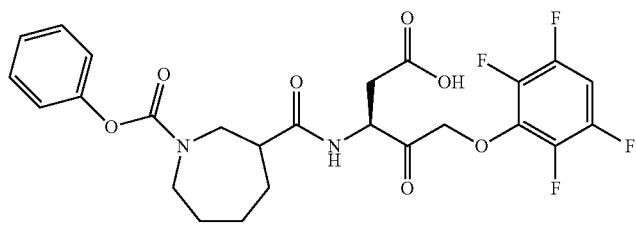
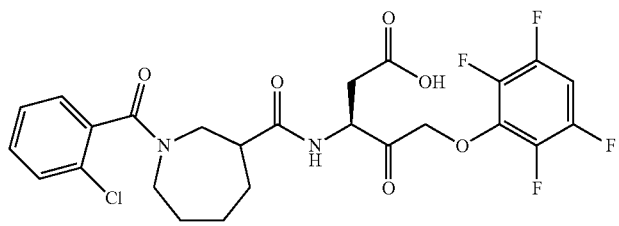
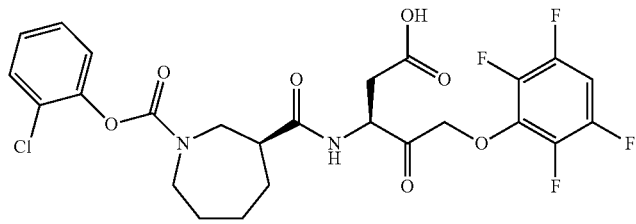
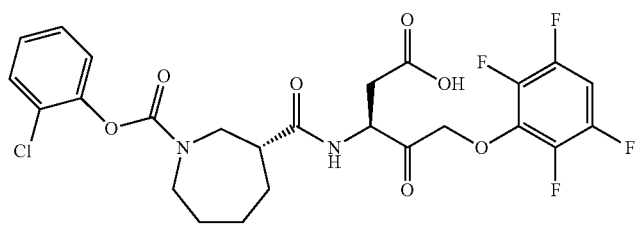

-continued
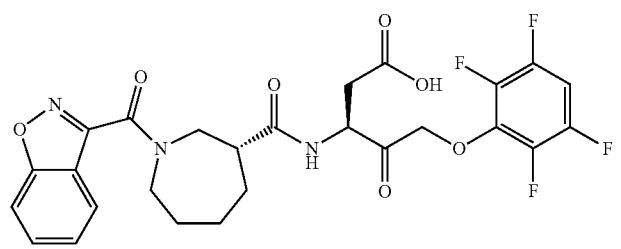
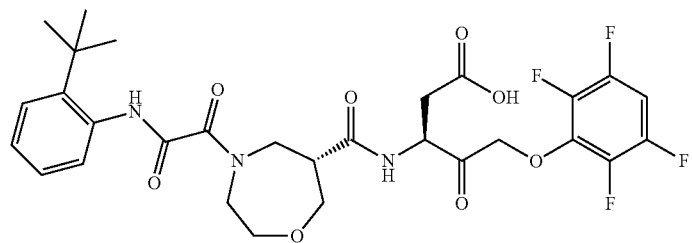
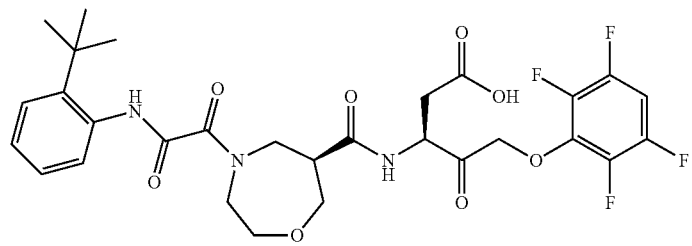
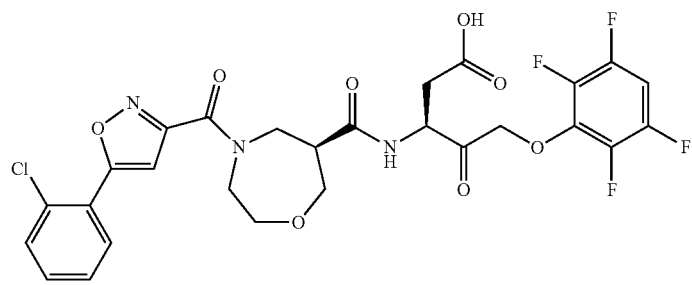
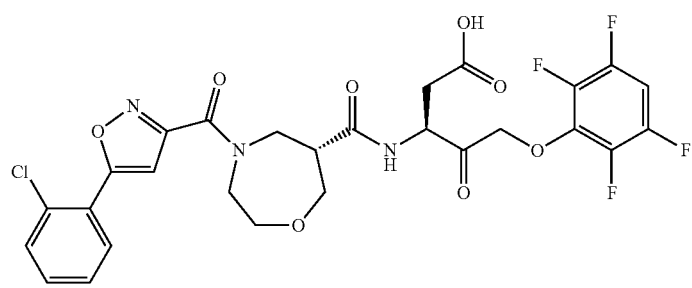
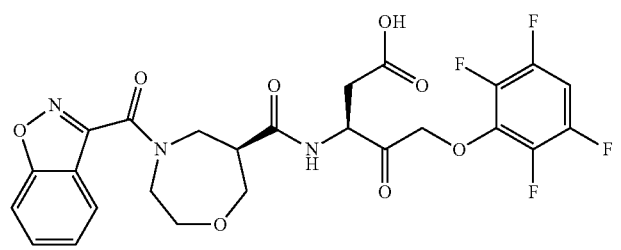

-continued
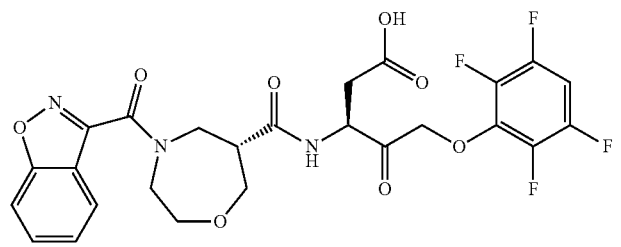
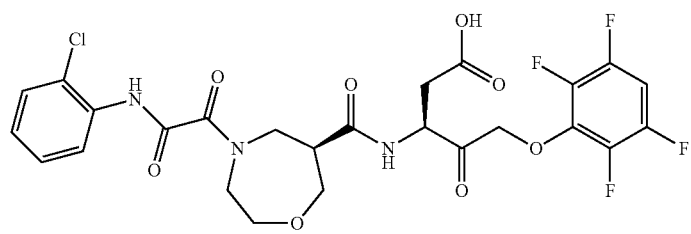
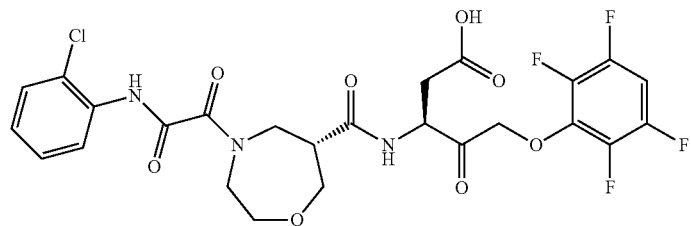
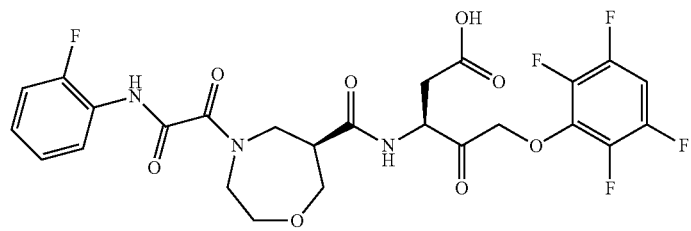
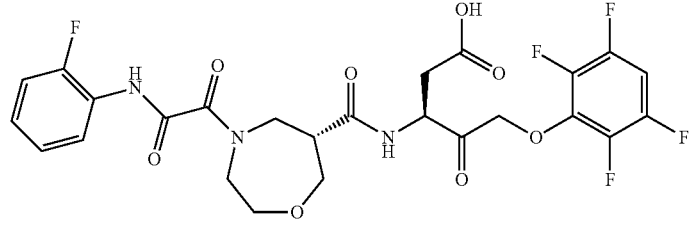
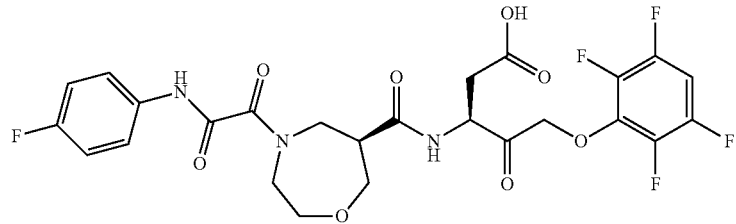
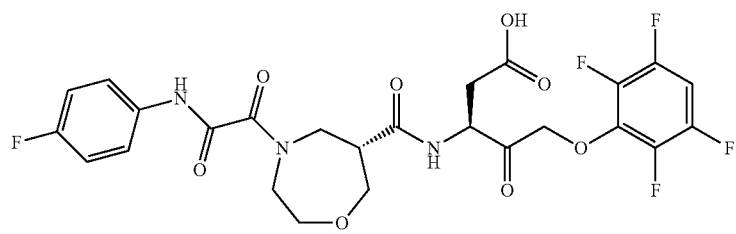

-continued

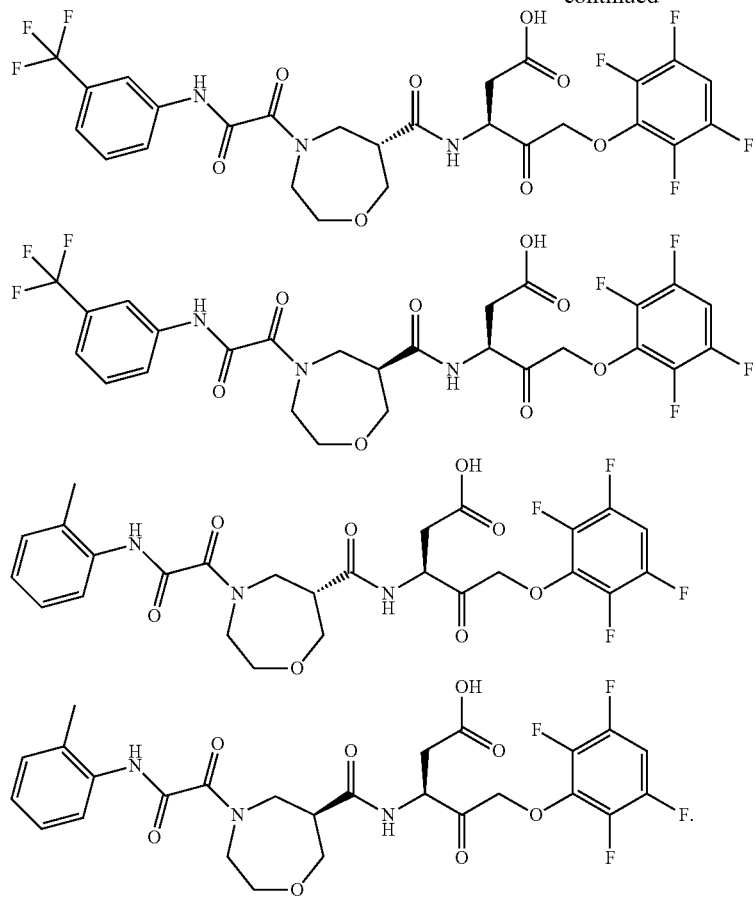

Another aspect of the present application provides a pharmaceutical composition comprising a therapeutically effective amount of the compound of formula (I) or the pharmaceutically acceptable salt thereof, and a pharmaceutically acceptable carrier or excipient. The pharmaceutical composition of the present application can further comprise one or more additional therapeutic agents.

The pharmaceutical composition of the present invention can be prepared by combining a compound of the present invention, or the pharmaceutically acceptable salt or tautomer thereof with suitable pharmaceutically acceptable carrier(s). For example, it can be formulated into solid, semi-solid, liquid or gaseous preparations, such as tablets, pills, capsules, powders, granules, ointments, emulsions, suspensions, solutions, suppositories, injections, inhalants, gels, microspheres, aerosols and the like.

Typical administration routes of the compounds of the present invention, or the pharmaceutically acceptable salts or tautomers thereof, or the pharmaceutical compositions thereof includes, but not limited to, oral, rectal, transmucosal, intestinal administration, or topical, transdermal, inhalation, parenteral, sublingual, intravaginal, intranasal, intraocular, intraperitoneal, intramuscular, subcutaneous, and intravenous administration.

The pharmaceutical composition of the present invention may be manufactured by methods well-known in the art, such as a conventional mixing method, a dissolution method, a granulation method, a method for preparing sugar-coated pills, a grinding method, an emulsification method, a freeze-drying method and the like.

For oral administration, the pharmaceutical composition can be formulated by mixing an active compound with a pharmaceutically acceptable carrier well-known in the art. These carriers can allow the compounds of the present invention to be formulated into tablets, pills, troches, dragees, capsules, liquids, gels, slurries, suspensions and the like, for oral administration to patients. A solid oral composition can be prepared by conventional mixing, filling or tableting methods. For example, it can be obtained by the following methods: mixing the active compound with solid excipients, optionally milling the resultant mixture, adding additional suitable adjuvants if necessary, and then processing the mixture into granules, to produce tablet cores or dragee cores. Suitable adjuvants include, but not limited to, adhesives, diluents, disintegrants, lubricants, glidants, sweeteners, flavoring agents or the like, such as, microcrystalline cellulose, glucose solution, arabic gum slurry, gelatin solution, sucrose and starch paste; talcum, starch, magnesium stearate, calcium stearate or stearic acid; lactose, sucrose, starch, mannitol, sorbitol or dicalcium phosphate; silicon dioxide; croscarmellose sodium, pregelatinized starch, sodium starch glycolate, alginic acid, corn starch, potato starch, methylcellulose, agar, carboxymethyl cellulose, crosslinked polyvinylpyrrolidone and the like. The dragee core can be optionally coated, especially with an enteric coating, according to methods recognized in common practice for drugs.

The pharmaceutical composition can also be suitable for parenteral administration, such as sterile solutions, suspensions or freeze-dried products in a suitable unit dosage form. An appropriate excipient such as a bulking agent, a buffer agent, or surfactant can be used.

The compound of formula (I) or the pharmaceutically acceptable salt, solvate or hydrate thereof in the present invention can be administered by any suitable routes and methods, for example orally or parenterally (e.g., intravenously) administration. The therapeutically effective amount of the compound of formula (I) ranges from about 0.0001 mg/Kg of body weight to 20 mg/Kg of body weight per day, for example from 0.001 mg/Kg of body weight to 10 mg/Kg of body weight per day.

The dosing frequency of the compound of formula (I) depends on needs of individual patients, for example, once or twice every day or more times every day. Administration can be intermittent, for example, where during a period of several days, patients receives a daily dose of the compound of formula (I), and during a period of next several or more days, they do not receive a daily dose of said compound.

Another object of the present application is to provide use of the compound of formula (I), or the pharmaceutically acceptable salt or tautomer thereof, or the above pharmaceutical composition in the preparation of a medicament for treating diseases related to caspase receptors.

Another aspect of the present application provides a method of treating diseases related to caspase receptors, the method comprising administering a therapeutically effective amount of the compound of formula (I), the pharmaceutically acceptable salt or tautomer thereof, or the above pharmaceutical composition.

In some embodiments, diseases related to caspase receptors are selected from non-alcoholic fatty liver disease, hepatitis or liver fibrosis.

Definition and Description

Unless otherwise specified, the following terms and phrases as used herein have the following meanings ascribed to them. A particular term or phrase should not be considered to be indefinite or unclear in the absence of a specific definition, but should be interpreted as its ordinary meanings. When a trade name appears herein, it is intended to refer to the corresponding commodity or active ingredient thereof.

The numerical ranges herein refer to each integer within the given range. For example, "$C_{1-12}$" refers to $C_1$, $C_2$, $C_3$, $C_4$, $C_5$, $C_6$, $C_7$, $C_8$, $C_9$, $C_{10}$, $C_{11}$ and $C_{12}$; "$C_{3-12}$" refers to $C_3$, $C_4$, $C_5$, $C_6$, $C_7$, $C_8$, $C_9$, $C_{10}$, $C_{11}$ and $C_{12}$.

As used herein, $C_m$ refers to that said moiety has m carbon atoms. "$C_4$ alkyl" means that said alkyl group has 4 carbon atoms. Where alkylene groups have 0 carbon atom, this group is a bond.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to the salt of the compound of the present application, which is prepared from the compound with specific substituents found in the present application and a relatively nontoxic acid or base. When the compound of the present invention contains relatively acidic functional groups, the base addition salts thereof can be obtained by contacting the neutral form of such compound with a sufficient amount of base in a pure solution or suitable inert solvent. Pharmaceutically acceptable base addition salts include sodium, potassium, calcium, ammonium, organic ammonia or magnesium salts. When the compound of the present invention contains relatively basic functional groups, the acid addition salts thereof can be obtained by contacting the neutral form of such compound with a sufficient amount of acid in a pure solution or suitable inert solvent. Examples of pharmaceutically acceptable acid addition salts include, inorganic acid salts, the inorganic acid including, for example, hydrochloric acid, hydrobromic acid, nitric acid, carbonic acid, hydrogen carbonate, phosphoric acid, monohydrogen phosphate, dihydrogen phosphate, sulfuric acid, hydrogen sulfate, hydroiodic acid, phosphorous acid, etc.; and organic acid salts, the organic acid including, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid and the like; also include salts of amino acids (such as arginine, etc.) and salts of organic acids such as glucuronic acid, etc. (see Berge et al, "Pharmaceutical Salts", Journal of Pharmaceutical Science 66: 1-19 (1977)). Certain specific compounds of the present application contain basic and acidic functional groups, and thus can be converted to base or acid addition salts.

In addition to the form of salts, the compounds provided by the present application also include the form of prodrugs. Prodrugs of the compounds described herein readily occur chemical changes under physiological conditions, to be converted to the compounds of the present application. In addition, prodrugs can be converted to the compounds of the present application by chemical or biochemical methods in vivo.

Certain compounds of the present application may exist in unsolvated or solvated forms, including hydrated forms. In general, solvated forms are equivalent to unsolvated forms, and are intended to be encompassed within the scope of the present application.

Certain compounds of the present application may have asymmetric carbon atoms (optical centers) or double bonds. Racemates, diastereomers, geometric isomers, and individual isomers are all included within the scope of the present application. For example,

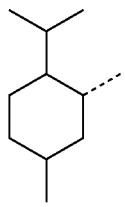

can be

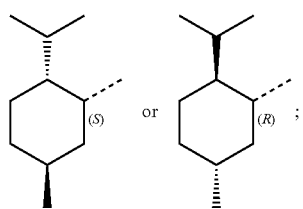

for example,

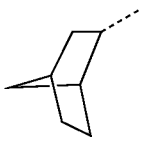

can be

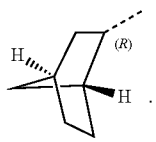

The graphic representations of racemic, ambiscalemic and scalemic or enantiomerically pure compounds herein are from Maehr, J. Chem. Ed. 1985, 62: 114-120. When the compounds described herein contain olefinic double bonds or other geometric asymmetrical centers, unless otherwise specified, they include E, Z geometric isomers. Likewise, all tautomeric forms are included within the scope of the present application.

The compounds of the present application may exist in specific geometric or stereoisomeric forms. All such compounds envisaged by the present application include cis and trans isomers, (−)- and (+)-enantiomer pairs, (R)- and (S)-enantiomers, diastereomers, (D)-isomers, (L)-isomers, and racemic mixtures and other mixtures thereof, such as enantiomers or diastereomers enriched mixtures, all of which fall within the scope of the present application. Other asymmetric carbon atoms may be present in the substituents such as alkyl. All these isomers and their mixtures are included in the scope of the present application.

The optically active (R)- and (S)-isomers as well as the D and L isomers can be prepared by chiral synthesis or chiral reagents or other conventional techniques. If an enantiomer of a certain compound of the present application is desired, it may be prepared by asymmetric synthesis, or by derivatization with a chiral auxiliary, wherein the resulting diastereomeric mixture is separated and the ancillary group is cleaved to provide the pure desired enantiomers. Alternatively, when a molecule contains a basic functional group (such as an amino) or an acidic functional group (such as a carboxyl), it forms a salt of diastereomer with a suitable optically active acid or base, and then a diastereomer resolution is performed by methods well known in the art, followed by recovering to give pure enantiomers. In addition, the separation of the enantiomers and diastereomers is generally accomplished by the use of chromatography adopting a chiral stationary phase, and optionally in combination with chemical derivatization method (e.g., forming carbamates from amines).

The compounds of the present application may contain non-natural proportions of atomic isotopes on one or more atoms which constitute the compound. For example, the compound may be labeled with a radioisotope, such as tritium ($^3H$), iodine-125 ($^{125}I$) or C-14 ($^{14}C$). Any isotopic composition transformations of the compounds of the present application, whether are radioactive or not, are included in the scope of the present application.

The term "pharmaceutically acceptable carrier" refers to any formulation or carrier medium capable of delivering an effective amount of the active substance of the present application, without interfering with the biological activity of the active substance and having no toxic side effects on the host or patient. Representative carriers include water, oils, vegetables and minerals, cream bases, lotion bases, ointment bases, etc. These bases include suspensions, tackifiers, transdermal enhancers, etc. Their formulations are well known to the skilled in the cosmetic field or topical drug field. Other information about carriers can refer to Remington: The Science and Practice of Pharmacy, 21$^{st}$ Ed., Lippincott, Williams & Wilkins (2005), the contents of which are incorporated herein by reference.

The term "excipient" generally refers to the carrier, diluent and/or medium which is required to formulate an effective pharmaceutical composition.

The term "effective amount" or "therapeutically effective amount" refers to a sufficient amount of a drug or agent that can achieve the desired effect. The determination of the effective amount varies with each individual, depending on the age and general condition of the subject, as well as the specific active substance. The appropriate effective amount in each case can be determined by the skilled in the art according to routine experiments.

The term "active ingredient", "therapeutic agent", "active substance" or "active agent" refers to a chemical entity that can effectively treat target disorders, diseases or conditions.

The term "substituted" means that any one or more hydrogens on the designated atom is replaced with a substituent, including heavy hydrogen and variants of hydrogen, provided that the valence of the designated atom is normal and the substitution results in a stable compound. When the substituent is a ketone group (i.e., =O), it means that two hydrogen atoms are substituted, and the ketone substitution will not occur on an aromatic group. The term "optionally substituted" means that it may be substituted or not, and unless otherwise specified, the species and numbers of substituents may be arbitrary provided that it is chemically achievable.

When any variable (eg, R) occurs more than one time in constituent or structure of a compound, its definition is independent in each occurrence. Thus, for example, if a group is showed to be substituted with 0-2 R, said group may optionally be substituted with up to two R, and R at each occurrence is selected independently from the definition of R. In addition, combinations of substituents and/or variables thereof are permissible only if such combinations result in stable compounds.

When the number of a linking group is 0, such as —(CH$_2$)$_0$—, it means that said linking group is a bond.

When one of the variables is selected from a bond, it means that the two groups to which they are attached are directly linked to each other. For example, when L represents a single bond in A-L-Z, the structure is actually A-Z.

When a substituent is vacant, it means that the substituent does not exist. For example, when X is vacant in A-X, the structure is actually A. When a bond of one substituent can cross-link to two atoms on one ring, this substituent may be bonded to any atom on the ring. When it does not specify through which atom the listed substituent is linked to a compound included but not specifically mentioned in a chemical structure formula, this substituent may be bonded through any of its atoms. The combination of substituents and/or variants thereof is allowable only if such combination will result in stable compounds. For example, the structural unit

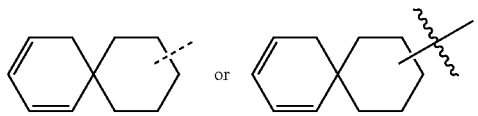

indicates that a substitution may occur at any position on cyclohexyl or cyclohexadiene.

The term "halo" or "halogen" refers to fluorine, chlorine, bromine and iodine.

The term "alkyl" refers to a straight- or branched-chain saturated aliphatic hydrocarbon group consisting of carbon and hydrogen atoms, which links to the rest of the molecule by a single bond. For example, said alkyl may have 1 to 6 carbon atoms (represented by $C_{1-6}$ alkyl), preferably 1 to 4 carbon atoms. Non-limiting examples of alkyl include, but not limited to, methyl (Me), ethyl (Et), propyl, 2-propyl, n-butyl, isobutyl, tert-butyl, n-pentyl, 2-methylbutyl, neopentyl, n-hexyl.

Unless otherwise specified, the term "hetero" refers to a heteroatom or a heteroatom radical (i.e., a radical containing a heteroatom), including an atom other than carbon (C) and hydrogen (H), and a radical containing these heteroatoms, for example including oxygen (O), nitrogen (N), sulfur (S), silicon (Si), boron (B), —O—, —S—, —C(=O)O—, —C(=O)—, —C(=S)—, —S(=O)—, —S(=O)$_2$—, and —C(=O)N(H)—, —N(H)—, —C(=NH)—, —S(=O)$_2$N(H)— or —S(=O)N(H)— which is optionally substituted.

Unless otherwise specified, a "ring" refers to a substituted or unsubstituted cycloalkyl, heterocycloalkyl, cycloalkenyl, heterocycloalkenyl, cycloalkynyl, heterocycloalkynyl, aryl, or heteroaryl. The ring includes a monocyclic ring, a bicyclic ring, a spiro ring, a fused ring, or a bridged ring. The number of atoms in a ring is typically defined by the number of members in the rings. For example, a "5- to 7-membered ring" refers to 5 to 7 atoms arranged in a circle. For example, the term "5- to 7-membered heterocycloalkyl" includes azetidinyl, tetrahydropyrrolyl, piperidinyl etc.

The term "cycloalkyl" refers to a saturated or unsaturated, non-aromatic cyclic hydrocarbon group. Non-limiting examples of cycloalkyl include, but not limited to, cyclopropyl, cyclobutyl, cyclopentyl, cyclohexyl, cycloheptyl and adamantane etc.

Unless otherwise specified, the term "heterocycle" or "heterocyclyl" refers to a stable mono-, bi-, or tri-cyclic ring containing a heteroatom or heteroatom radical, which may be saturated, partially unsaturated, or aromatic, and they contain carbon atoms and 1, 2, 3, or 4 cyclic heteroatoms independently selected from N, O, and S. The nitrogen and sulfur heteroatoms may be optionally oxidized (i.e., NO and $S(O)_p$, p is 1 or 2). The nitrogen atom may be substituted or unsubstituted (i.e., N or NR, wherein R is H or other substituents as already defined herein). The heterocyclic rings described herein may be substituted on carbon or on nitrogen atoms if the resulting compound is stable. N atom in the heterocycle is optionally quaternized. It is preferred that when the total number of S and O atoms in the heterocycle exceeds 1, these heteroatoms are not adjacent to each another. It is preferred that the total number of S and O atoms in the heterocycle is not more than 1. As used herein, the term "aromatic heterocyclic group" or "heteroaryl" refers to a stable 5-, 6- or 7-membered monocyclic or bicyclic, or 7-, 8-, 9- or 10-membered bicyclic aromatic heterocycle radical, which contains carbon atoms and 1, 2, 3, or 4 cyclic heteroatoms independently selected from N, O, and S. The nitrogen atom may be substituted or unsubstituted (i.e., N or NR, wherein R is H or other substituents as already defined herein). The nitrogen and sulfur heteroatoms may be optionally oxidized (i.e., NO and $S(O)_p$, and p is 1 or 2). It is to be noted that the total number of S and O atoms in the aromatic heterocycle is not more than 1. Bridged rings are also included in the definition of heterocycles. A bridged ring occurs when one or more atoms (i.e., C, O, N, or S) link two non-adjacent carbon or nitrogen atoms. Preferred bridged rings include, but not limited to, one carbon atom, two carbon atoms, one nitrogen atom, two nitrogen atoms, and a carbon-nitrogen group. It is noted that a bridge always converts a monocyclic ring into a tricyclic ring. In a bridged ring, substituents recited for the ring may also be present on the bridge.

Examples of heterocyclic compounds include, but not limited to, acridinyl, azocinyl, benzimidazolyl, benzofuranyl, benzomercaptofuranyl, benzomercaptophenyl, benzoxazolyl, benzooxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnoline decahydroquinolinyl, 2H,6H-1,5,2-dithiazinyl, dihydrofuro[2,3-b]tetrahydrofuranyl, furyl, furastanyl, imidazolidinyl, imidazolinyl, imidazolyl, 1H-indazolyl, indole alkenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidinyl, phenanthridinyl, phenanthrolinyl, phenazine, phenothiazine, benzoxanthinyl, phenoxazinyl, phthalazinyl, piperazinyl, piperidinyl, piperidone, 4-piperidone, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4 thiadiazolyl, thianthrenyl, thiazolyl, isothiazolylthiophenyl, thienooxazolyl, thienothiazolyl, thienoimidazolyl, thienyl, triazinyl, 1,2,3-triazolyl, 1,2,4-triazolyl, 1,2,5-triazolyl, 1,3,4-triazolyl, and xanthenyl. Fused rings and spiro compounds are also included.

The terms "alkoxy", "alkylamino" and "alkylthio" (or thioalkoxy) belong to idiomatic expressions and refer to those alkyl groups which are linked to the remainder of the molecule respectively through an oxygen atom, an amino group or a sulfur atom.

Unless otherwise stated, the term "aryl" means all-carbon monocyclic or fused polycyclic aromatic ring groups having a conjugated π-electron system, which may be mono-, di-, or poly-substituted, or may be monovalent, divalent, or polyvalent, or which may be a single ring or multiple rings (such as 1 to 3 rings; at least one of which is aromatic). The term "heteroaryl" refers to an aryl group containing one to four heteroatoms. In some embodiments, the heteroatom is selected from N, O, and S. A heteroaryl group can be attached to the remainder of the molecule through a heteroatom. Non-limiting examples of aryl or heteroaryl groups include phenyl, 1-naphthyl, 2-naphthyl, 4-biphenyl, 1-pyrrolyl, 2-pyrrolyl, 3-pyrrolyl, 3-pyrazole, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl, and 6-quinolinyl.

For example, "—NHR$^2$—, wherein, R$^2$ is selected from phenylene" refers to

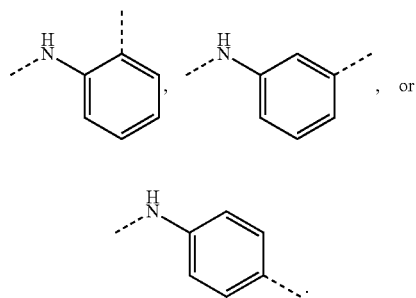

For example, in R$^1$—(CH$_2$)$_m$-L-A-, when L is selected from a bond, C(=O), S(=O)$_2$,

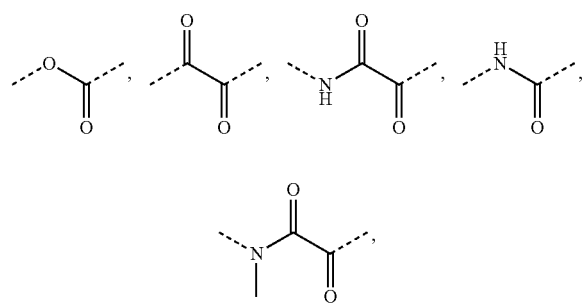

it respectively refers to R$_1$—(CH$_2$)$_m$-A-, R$_1$—(CH$_2$)$_m$—C(=O)-A-, R$_1$—(CH$_2$)$_m$—S(=O)$_2$-A-,

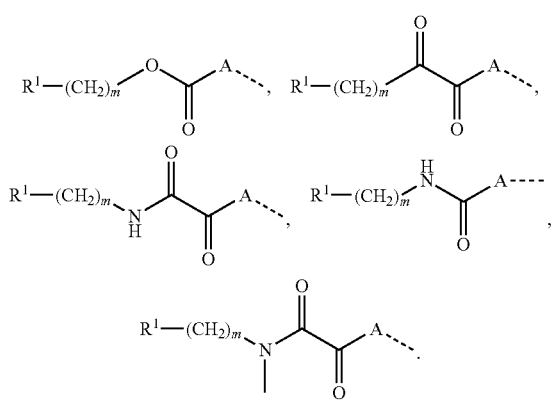

For example, when A is selected from

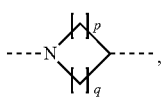

wherein p and q are 2, it may represent (but is not limited thereto) the following groups having unsaturated bonds or not:

The term "leaving group" refers to a functional group or atom which can be substituted with anther functional group or atom through a substitution reaction, such as a nucleophilic substitution reaction. By way of example, representative leaving groups include trifluoromethanesulfonate; chloro, bromo and iodo; sulfonic acid ester groups, such as mesylate, tosylate, brosylate, p-toluenesulfonate and the like; and acyloxy groups, such as acetoxy, trifluoroacetoxy and the like.

The term "protecting groups" includes, but not limited to "amino protecting group", "hydroxyl protecting group", or "thiol protecting group". The term "amino protecting group" refers to a protecting group suitable for preventing undesired reactions at N position of an amino group. Representative amino protecting groups include, but not limited to: formyl; acyl, for example, alkane acyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), trityl (Tr), 1,1-di(4'-methoxyphenyl) methyl; silyl, such as trimethylsilyl (TMS), tert-butyldimethylsilyl (TBS), and the like. The term "hydroxyl protecting group" refers to a protecting group suitable for preventing undesired reactions at a hydroxyl group. Representative hydroxyl protecting groups include, but not limited to: alkyl, such as methyl, ethyl, and tert-butyl; acyl, for example, alkane acyl (such as acetyl); aryl methyl, such as benzyl (Bn), p-methoxybenzyl (PMB), 9-fluroenylmethyl (Fm), benzhydryl (diphenylmethyl, DPM); silyl, such as trimethylsilyl (TMS), tert-butyldimethylsilyl (TBS), and the like.

The compounds of the present application may be prepared by various synthesis methods well known to the skilled in the art, including the specific embodiments listed below, the embodiments formed by combining the specific embodiments with other chemical synthesis methods, and equivalent replacements well known to the skilled in the art, and the preferred embodiments include, but not limited to, the Examples of the present application.

Solvents used in the present application are commercially available. The following abbreviations are used in the present application: eq represents equivalent; EDCl represents N-(3-dimethylaminopropyl)-N'-ethylcarbodiimide hydrochloride; HOBt represents 1-hydroxybenzotriazole; NMM represents N-methylmorpholine; DMF represents N,N-dimethylformamide; PIDA represents phenyliodonium diacetate; TEMPO represents 2,2,6,6-tetramethylpiperidine-N-oxide; TFA represents trifluoroacetic acid; DCM represents dichloromethane; t-BuOK represents potassium tert-butoxide; THF represents tetrahydrofuran; EtOAc represents ethyl acetate; CbzCl represents benzyl chloroformate; NaCNBH$_3$ represents sodium cyanoborohydride; DIEA represents N,N-diisopropylethylamine; HATU represents 2-(7-azabenzotriazolyl)-N,N,N',N'-tetramethyluronium hexafluorophosphate; LDA represents lithium diisopropylamide; NFSI represents N-fluoro-N-(phenylsulfonyl)benzenesulfonamide; CDI represents carbonyldiimidazole; DMP represents dimethyl phthalate; T₃P represents propylphosphonic anhydride; DMSO represents dimethyl sulfoxide; Dess-Martin periodinane represents Dess-Martin oxidant, specifically 1,1,1-triacetoxy-1,1-dihydro-1,2-benziodoxol-3-(1H)-one; EtOH represents ethanol; mp represents melting point; aq represents water; m-CPBA represents 3-chloroperoxybenzoic acid; DIAD represents diisopropyl azodicarboxylate; Cbz represents benzyloxycarbonyl; Boc represents t-butyloxycarbonyl; HOAc represents acetic acid; r.t. represents room temperature; O/N represents reacting overnight; DIPEA represents diisopropylethylamine; SOCl₂ represents thionyl chloride; CS₂ represents carbon disulfide; TsOH represents p-toluenesulfonic acid; NCS represents 1-chloropyrrolidine-2,5-dione; n-Bu₄NF represents tetrabutylammonium fluoride; iPrOH represents 2-propanol; PE represents petroleum ether.

The compounds are named manually or the ChemDraw® software, and the supplier's catalog names are used for the commercially available compounds.

EXAMPLES

The present application is described in detail below by way of examples, but is not intended to be construed as limitation. The present application has been described in detail herein, and the specific embodiments thereof are disclosed. Various changes and modifications made to the embodiments of the present application will be apparent to persons skilled in the art, without departing from the spirit and scope of the present application.

Example 1: Compound 1

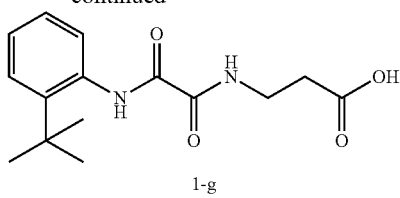

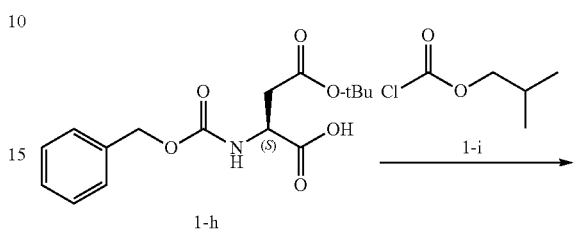

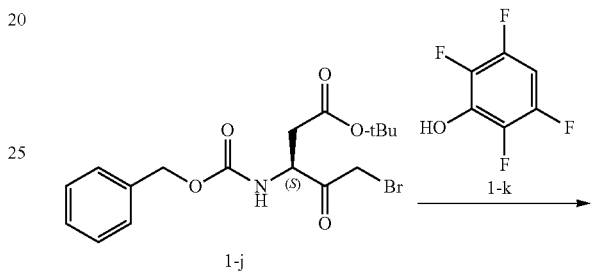

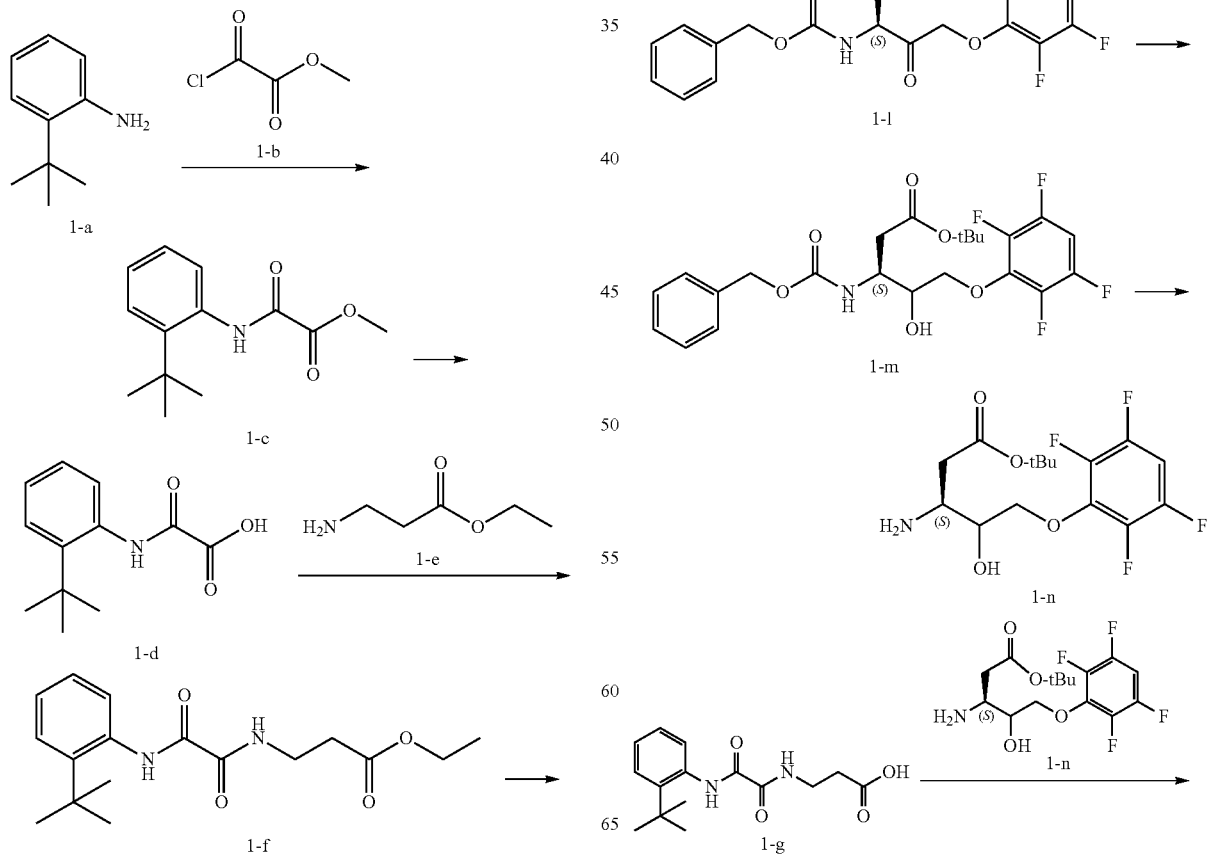

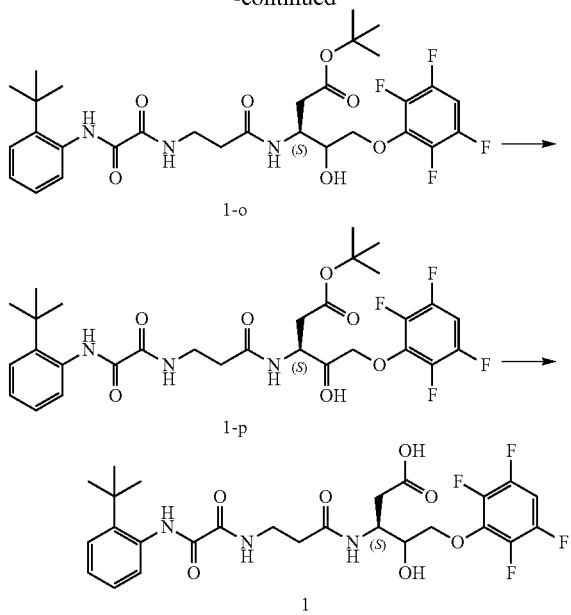

1-o 1-p

1

Step 1: Synthesis of Compound 1-c

Compound 1-a (10.00 g, 67.01 mmol, 1.00 eq) and triethylamine (7.46 g, 73.71 mmol, 1.10 eq) were added to dichloromethane (100 mL) and stirred at 0-5° C. for 15 min. Compound 1-b (9.03 g, 73.71 mmol, 1.10 eq) was then added to the above solution, and stirred at 10-20° C. for 16 hours. After the reaction was completed, 100 mL of water was added thereto and then separated. The aqueous phase was further extracted with dichloromethane (200 mL×2). The organic phases were combined, and washed with dilute hydrochloric acid (0.1 M, 150 mL) and water (100 mL). The organic phases were dried over anhydrous sodium sulfate, filtered and concentrated, to give the product of compound 1-c (14.0 g, yield: 88.8%). $^1$H NMR (400 MHz, CHLOROFORM-d)·δ=9.04-9.31 (m, 1H), 7.97 (d, J=8.03 Hz, 1H), 7.43 (d, J=7.53 Hz, 1H), 7.25-7.32 (m, 1H), 7.15-7.22 (m, 1H), 4.00 (s, 3H), 1.47 (s, 9H).

Step 2: Synthesis of Compound 1-d

Compound 1-c (12.50 g, 53.13 mmol, 1.00 eq) was dissolved in 1,4-dioxane, an aqueous solution (63.00 mL) formulated with LiOH.H$_2$O (2.23 g, 53.13 mmol, 1.00 eq) was added thereto, and after completion of the addition, the mixture was stirred at room temperature for 16 hours. After the reaction was completed, 200 mL of water was added to the reaction mixture, stirred, and washed with 200 mL of ethyl acetate. The aqueous phase was adjusted to pH=2 with hydrochloric acid, and then extracted with ethyl acetate (200 mL×2). The organic phases were combined, washed with 200 mL of water, dried over anhydrous sodium sulfate, filtered and concentrated, to give compound 1-d (11.00 g, yield: 93.58%). $^1$H NMR (400 MHz, CHLOROFORM-d) δ=9.38 (br. s., 1H), 7.92 (dd, J=3.01, 7.53 Hz, 1H), 7.46 (d, J=7.53 Hz, 1H), 7.19-7.34, (m, 2H), 1.47 (s, 9H).

Step 3: Synthesis of Compound 1-f

Compound 1-d (1.00 g, 4.52 mmol, 1.00 eq) and compound 1-e (694.28 mg, 4.52 mmol, 1.00 eq) were dissolved in dichloromethane (20.00 mL), and EDCl (866.44 mg, 4.52 mmol, 1.00 eq), HOBt (610.71 mg, 4.52 mmol, 1.00 eq) and NMM (1.83 g, 18.08 mmol, 1.99 mL, 4.00 eq) were added thereto. After completion of the addition, the reaction was purged with nitrogen gas three times and stirred at 25° C. for 12 hours. After the reaction was completed, the reaction mixture was concentrated, then directly purified with flash column machine (petroleum ether:ethyl acetate=1:0~1:1), and concentrated, to give compound 1-f (900.00 mg, yield: 62.15%) as a yellow oil. $^1$H NMR (400 MHz, CHLOROFORM-d) δ=9.65-9.55 (m, 1H), 8.02-8.00 (m, 2H), 7.49-7.38 (m, 1H), 7.27-7.26 (m, 1H), 7.22-7.13 (m, 1H), 4.19 (d, J=7.0 Hz, 2H), 3.76-3.62 (m, 2H), 2.64 (s, 2H), 1.47 (s, 9H), 1.29 (t, J=7.3 Hz, 3H).

Step 4: Synthesis of Compound 1-g

Compound 1-f (600.00 mg, 1.87 mmol, 1.00 eq) was dissolved in a mixed solvent of tetrahydrofuran (10.00 mL) and water (10.00 mL), and LiOH.H$_2$O (314.33 mg, 7.49 mmol, 4.00 eq) was added thereto. The mixture was stirred at 25° C. for 1 hour. After the reaction was completed, the reaction mixture was added to 50 mL of water, and adjusted to pH of about 2 with dilute hydrochloric acid. The aqueous phase was extracted with ethyl acetate (50 mL×3). The organic phases were combined, washed with water (50 mL) and brine (50 mL), dried, filtered and concentrated, to give compound 1-g (450.00 mg, yield: 82.32%). $^1$H NMR (400 MHz, DMSO-d$_6$) δ=10.02-9.82 (m, 1H), 9.25-8.84 (m, 1H), 7.64-7.36 (m, 2H), 7.36-7.13 (m, 2H), 4.18-3.96 (m, 1H), 3.49-3.39 (m, 2H), 2.59-2.52 (m, 2H), 1.36 (s, 9H).

Step 5: Synthesis of Compound 1-j

Compound 1-h (30.00 g, 92.78 mmol, 1.00 eq) and 4-methylmorpholine (15.02 g, 148.45 mmol, 16.33 mL, 1.60 eq) were dissolved in tetrahydrofuran (468 mL) at −10° C. under the protection of nitrogen gas. Compound 1-i (19.01 g, 139.17 mmol, 18.28 mL, 1.50 eq) was slowly added dropwise, and stirred for 40 min at −10° C. The reaction mixture was filtered, and the filter cake was washed with tetrahydrofuran (200 mL). The combined filtrate was poured into a three-necked flask, and the temperature was maintained at 0° C. A CH$_2$N$_2$-diethyl ether solution (370 mL) was added into the flask under the protection of nitrogen gas, stirred at 0° C. for 20 min, warmed up to 20° C. and stirred for another 2 hours. The reaction mixture was then cooled down to 0° C. and treated with HBr (30 mL, 35% acetic acid solution). The mixture was stirred at 0° C. for 15 min, warmed up to 20° C. and stirred for another 45 min. After the reaction was completed, the reaction mixture was extracted with ethyl acetate (500 mL) and water (400 mL), and separated. The organic phase was further washed successively with water (400 mL), saturated sodium hydrogen carbonate solution (400 mL) and saturated brine (400 mL), dried over anhydrous sodium sulfate and concentrated to give a crude product. The crude product was purified with column chromatography, to give compound 1-j (30.00 g, yield: 76%) as a colorless oil.

Step 6: Synthesis of Compound 1-l

Compounds 1-j (25.00 g, 62.46 mmol, 1.00 eq) and 1-k (12.45 g, 74.95 mmol, 1.20 eq) were dissolved in DMF (350.00 mL), and KF (14.52 g, 249.84 mmol, 5.85 mL, 4.00 eq) was added thereto under the protection of nitrogen gas. The reaction was stirred at 20° C. for 15 hours. After the reaction was completed, it was added with 500 mL of ethyl acetate, and washed successively with saturated sodium hydrogen carbonate solution (350 mL), water (350 mL) and saturated brine (350 mL). The organic phase was dried over anhydrous sodium sulfate and concentrated to give a crude product. The crude product was purified by column chromatography (petroleum ether:ethyl acetate=1:0~3:1) to give compound 1-l (18.00 g, yield: 56%).

Step 7: Synthesis of Compound 1-m

Compound 1-l (9.50 g, 19.57 mmol, 1.00 eq) was added to a mixed solvent of methanol (30.00 mL) and tetrahydrofuran (30.00 mL), and sodium borohydride (2.96 g, 78.28 mmol, 4.00 eq) was added thereto at 0° C. After the addition was completed, the reaction mixture was stirred at 25° C. for 1 hour. After the reaction was completed, the reaction mixture was added to water (200 mL), added with $NH_4Cl$ (200 mL, aq, 10%), and then extracted with ethyl acetate (500 mL×3). The combined organic phases were washed with water (500 mL) and brine (500 mL), dried over anhydrous sodium sulfate and filtered, to give compound 1-m (9.00 g, crude) as a colorless oil, which was used directly in the next step without purification.

Step 8: Synthesis of Compound 1-n

Compound 1-m (9.00 g, 18.46 mmol, 1.00 eq) was dissolved in methanol (500.00 mL), and Pd—C (10%, 2.5 g) was added thereto. The mixture was purged with hydrogen gas three times, maintained at a pressure of 15 psi and stirred at 25° C. for 4 hours. After the reaction was completed, the reaction mixture was filtered and concentrated to give compound 1-n (6.10 g, crude) as a yellow oil, which was used directly in the next step without purification.

Step 9: Synthesis of Compound 1-o

Compounds 1-g (400.00 mg, 1.37 mmol, 1.00 eq) and 1-n (483.44 mg, 1.37 mmol, 1.00 eq) were dissolved in dichloromethane (10.00 mL), and EDCl (359.36 mg, 1.87 mmol, 1.37 eq), HOBt (253.30 mg, 1.87 mmol, 1.37 eq) and NMM (415.22 mg, 4.10 mmol, 451.32 μL, 3.00 eq) were added thereto. The reaction mixture was purged with nitrogen gas three times, and stirred at 25° C. for 10 hours. After the reaction was completed, the reaction mixture was directly concentrated and purified by column chromatography (petroleum ether:ethyl acetate=1:0~1:1), to give compound 1-o (400.00 mg, yield: 47%). $^1$H NMR (400 MHz, CHLOROFORM-d) δ=9.69-9.55 (m, 1H), 8.21-8.09 (m, 1H), 8.06-7.96 (m, 1H), 7.52-7.39 (m, 1H), 7.22-7.06 (m, 1H), 6.90-6.63 (m, 2H), 4.50-4.35 (m, 1H), 4.14 (d, J=7.0 Hz, 4H), 3.72 (d, J=6.3 Hz, 2H), 2.56 (s, 4H), 1.47 (d, J=7.5 Hz, 17H).

Step 10: Synthesis of Compound 1-p

Compound 1-o (300.00 mg, 478.00 μmol, 1.00 eq) was dissolved in dichloromethane (5.00 mL), and PIDA (615.85 mg, 1.91 mmol, 4.00 eq) and TEMPO (15.03 mg, 95.60 μmol, 0.20 eq) were added thereto. The mixture was stirred at 25° C. for 12 hours. After the reaction was completed, the reaction mixture was directly concentrated to give a crude product. The crude product was purified by column chromatography (petroleum ether:ethyl acetate=1:0~1:1), to give compound 1-p (200.00 mg, yield: 67%). $^1$H NMR (400 MHz, CHLOROFORM-d) δ=9.66-9.52 (m, 1H), 8.16-7.93 (m, 2H), 7.46-7.38 (m, 1H), 7.21-7.06 (m, 1H), 6.84-6.68 (m, 2H), 5.21-4.95 (m, 3H), 3.84-3.63 (m, 2H), 3.06-2.92 (m, 1H), 2.83-2.70 (m, 1H), 2.61 (s, 2H), 2.21 (s, 1H), 1.50-1.38 (m, 17H).

Step 11: Synthesis of Compound 1

Compound 1-p (200.00 mg, 319.69 μmol, 1.00 eq) was dissolved in dichloromethane (2.00 mL), and TFA (1.00 mL) was added thereto. The mixture was stirred at 25° C. for 2 hours. The reaction mixture was directly concentrated and purified by preparative HPLC, to give compound 1 (30.00 mg, yield: 16%). $^1$H NMR (400 MHz, DMSO-$d_6$) δ=9.96-9.89 (m, 1H), 9.09-8.96 (m, 1H), 8.58-8.45 (m, 1H), 7.62-7.48 (m, 2H), 7.47-7.38 (m, 1H), 7.30-7.18 (m, 2H), 5.39-5.07 (m, 2H), 4.74-4.59 (m, 1H), 2.78-2.63 (m, 2H), 2.46 (br. s., 2H), 1.35 (s, 9H).

Example 2: Compound 2

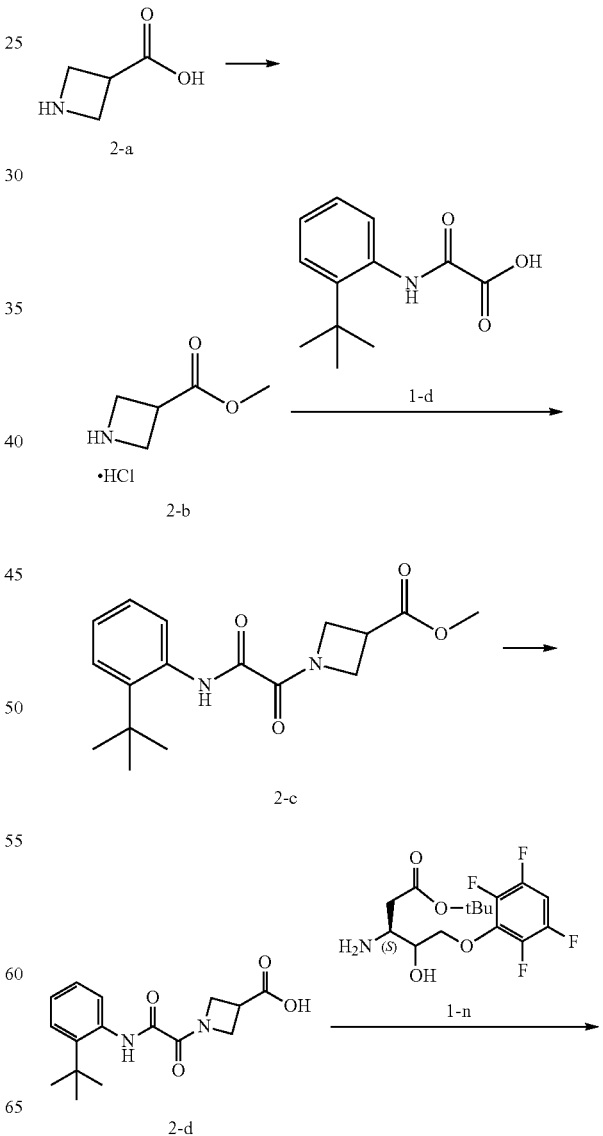

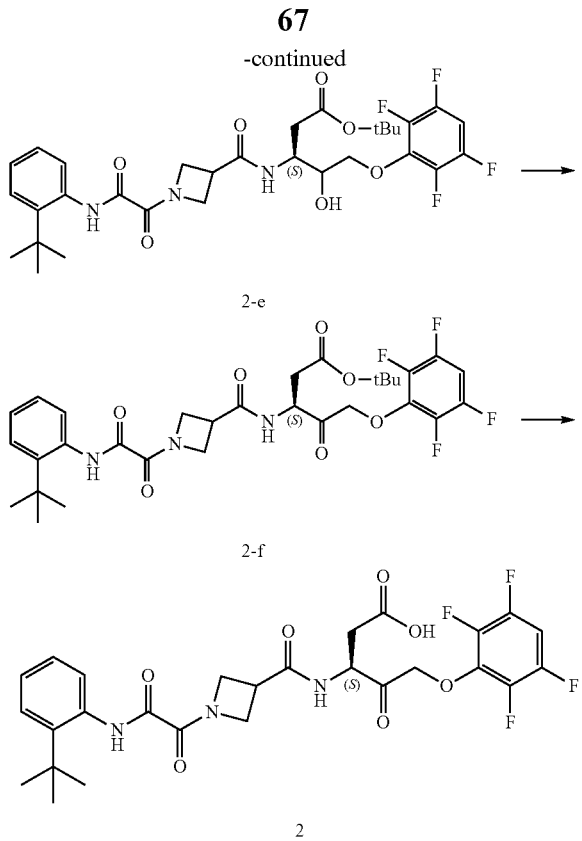

Step 1: Synthesis of Compound 2-b

Compound 2-a (1.00 g, 9.89 mmol, 1.00 eq) was dissolved in methanol (50.00 mL), and thionyl chloride (2.44 g, 20.54 mmol, 1.49 mL, 2.08 eq) was added dropwise thereto at 0° C., maintained at 0° C. and stirred for 15 min, followed by stirring at 25° C. for 2 hours. After the reaction was completed, the reaction solution was spin-dried, added with toluene, and further spin-dried, to give the pale yellow product of compound 2-b (1.40 g, crude), which was used directly in the next step without purification. $^1$H NMR (400 MHz, DMSO-$d_6$) δ=9.71 (br. s., 1H), 9.39 (br. s., 1H), 4.05 (d, J=10.54 Hz, 4H), 3.69-3.76 (m, 1H), 3.67 (s, 3H).

Step 2: Synthesis of Compound 2-c

Compound 1-d (1.90 g, 8.59 mmol, 1.00 eq) was dissolved in dichloromethane (80.00 mL), and HOBt (1.59 g, 11.77 mmol, 1.37 eq), EDCl (2.26 g, 11.77 mmol, 1.37 eq), compound 2-b (1.30 g, 8.59 mmol, 1.00 eq, HCl) and NMM (3.48 g, 34.36 mmol, 3.78 mL, 4.00 eq) were added thereto. The reaction solution was stirred at 25° C. for 15 hours. After the reaction was completed, 150 mL of water was added to the reaction solution, and extracted with dichloromethane (150 mL×3). The organic phase was dried over anhydrous sodium sulfate, filtered and concentrated to give a crude product. The crude product was subjected to column chromatography (petroleum ether:ethyl acetate=1:0~3:1) to give the product of compound 2-c (1.65 g, yield: 57%) as a colorless oil. $^1$H NMR (400 MHz, CHLOROFORM-d) δ=9.58 (br. s., 1H), 7.95 (dd, J=0.88, 7.91 Hz, 1H), 7.42 (dd, J=1.13, 7.91 Hz, 1H), 7.23-7.26 (m, 1H), 7.13-7.19 (m, 1H), 4.86-4.98 (m, 2H), 4.38 (d, J=7.53 Hz, 2H), 3.79 (s, 3H), 3.50-3.62 (m, 1H), 1.46 (s, 9H).

Step 3: Synthesis of Compound 2-d

Compound 2-c (1.65 g, 5.18 mmol, 1.00 eq) was dissolved in tetrahydrofuran (40.00 mL), and a solution of LiOH.H$_2$O (260.96 mg, 6.22 mmol, 1.20 eq) dissolved in water (40.00 mL) was added into the above solution at 0° C. The reaction solution was maintained at 0° C. and stirred for 30 min. After the reaction was completed, the reaction solution was adjusted to pH=6 with 2N dilute hydrochloric acid, added with 150 mL of water, and extracted with dichloromethane (150 mL×3). The organic phase was dried over anhydrous sodium sulfate, filtered and concentrated to give the product of compound 2-d (1.50 g, crude) as a colorless oil, which was used directly in the next step without purification. $^1$H NMR (400 MHz, CHLOROFORM-d) δ=9.57 (s, 1H), 7.88-7.94 (m, 1H), 7.39-7.46 (m, 1H), 7.22-7.26 (m, 1H), 7.14-7.20 (m, 1H), 4.87-5.02 (m, 2H), 4.41 (d, J=7.53 Hz, 2H), 3.58 (quin, J=7.53 Hz, 1H), 1.45 (s, 9H).

Step 4: Synthesis of Compound 2-e

Compound 1-n (400.00 mg, 1.13 mmol, 1.00 eq) was dissolved in dichloromethane (40.00 mL), and compound 2-d (343.90 mg, 1.13 mmol, 1.00 eq), EDCl (296.77 mg, 1.55 mmol, 1.37 eq), HOBt (209.18 mg, 1.55 mmol, 1.37 eq) and NMM (342.90 mg, 3.39 mmol, 372.72 μL, 3.00 eq) were added thereto. The reaction solution was stirred at 27° C. for 15 hours under the protection of nitrogen gas. After the reaction was completed, the reaction solution was added with 100 mL of water and extracted with dichloromethane (100 mL×3). After combining, the organic phases were dried over anhydrous sodium sulfate, filtered and concentrated to give a crude product. The crude product was subjected to column chromatography (petroleum ether:ethyl acetate=10:1~1:1) to give the product of compound 2-e (400.00 mg, yield: 54%) as a colorless oil. $^1$H NMR (400 MHz, CHLOROFORM-d) δ=9.57 (s, 1H), 7.93 (dd, J=1.76, 7.78 Hz, 1H), 7.41 (d, J=8.03 Hz, 1H), 7.22-7.26 (m, 1H), 7.12-7.18 (m, 1H), 6.77-6.88 (m, 1H), 6.72 (d, J=8.53 Hz, 1H), 4.83-4.95 (m, 2H), 4.16-4.47 (m, 5H), 4.05-4.11 (m, 0.5H), 3.36-3.44 (m, 1.5H), 2.56-2.81 (m, 2H), 1.46 (d, J=3.01 Hz, 18H).

Step 5: Synthesis of Compound 2-f

Compound 2-e (400.00 mg, 625.36 μmol, 1.00 eq) was dissolved in dichloromethane (40.00 mL), and PIDA (779.53 mg, 2.42 mmol, 3.87 eq) and TEMPO (19.67 mg, 125.07 μmol, 0.20 eq) were added thereto. The reaction solution was stirred at 27° C. for 15 hours under the protection of nitrogen gas. After the reaction was completed, 150 mL of ethyl acetate was added to the reaction solution. The reaction solution was washed successively with saturated sodium hydrogen carbonate (70 mL), saturated brine (70 mL) and water (70 mL). The organic phase was dried over anhydrous sodium sulfate, filtered and concentrated to give a crude product. The crude product was subjected to column chromatography (petroleum ether:ethyl acetate=1:0~2:1) to give the product of compound 2-f (350.00 mg, yield: 83%) as a colorless oil. $^1$H NMR (CHLOROFORM-d, 400 MHz) δ=9.57 (s, 1H), 7.90-7.97 (m, 1H), 7.42 (d, J=7.8 Hz, 1H), 7.22-7.26 (m, 1H), 7.12-7.19 (m, 1H), 6.77-6.86 (m, 2H), 4.83-5.16 (m, 5H), 4.30-4.46 (m, 2H), 3.42-3.52 (m, 1H), 3.03 (dd, J=17.1, 4.5 Hz, 1H), 2.82 (dd, J=17.1, 5.0 Hz, 1H), 1.45 ppm (d, J=8.5 Hz, 18H).

Step 6: Synthesis of Compound 2

Compound 2-f (300.00 mg, 470.50 μmol, 1.00 eq) was dissolved in dichloromethane (12.00 mL), and trifluoroacetic acid (9.65 g, 84.60 mmol, 6.27 mL, 179.81 eq) was added thereto. The reaction solution was stirred at 27° C. for 1 hour under the protection of nitrogen gas. After the reaction was completed, the reaction solution was spin-dried to give a crude product. The crude product was purified by preparative HPLC (under a condition of formic acid) and lyophilized to give the product of compound 2 (125.00 mg, yield: 46%). $^1$H NMR (400 MHz, DMSO-$d_6$) δ=9.87 (s, 1H), 8.62 (br. s., 1H), 7.58 (d, J=7.53 Hz, 1H), 7.37-7.48 (m, 2H), 7.17-7.28 (m, 2H), 5.26 (br. s., 1H), 4.67 (dt, J=4.02, 9.54 Hz, 2H), 4.51 (dd, J=5.77, 10.29 Hz, 1H), 4.13-4.23 (m, 1H), 4.01-4.10 (m, 1H), 3.45-3.55 (m, 1H), 2.57-2.86 (m, 2H), 1.34 (s, 9H); LCMS m/z=582.2[M+H]+.

Example 3: Compound 3

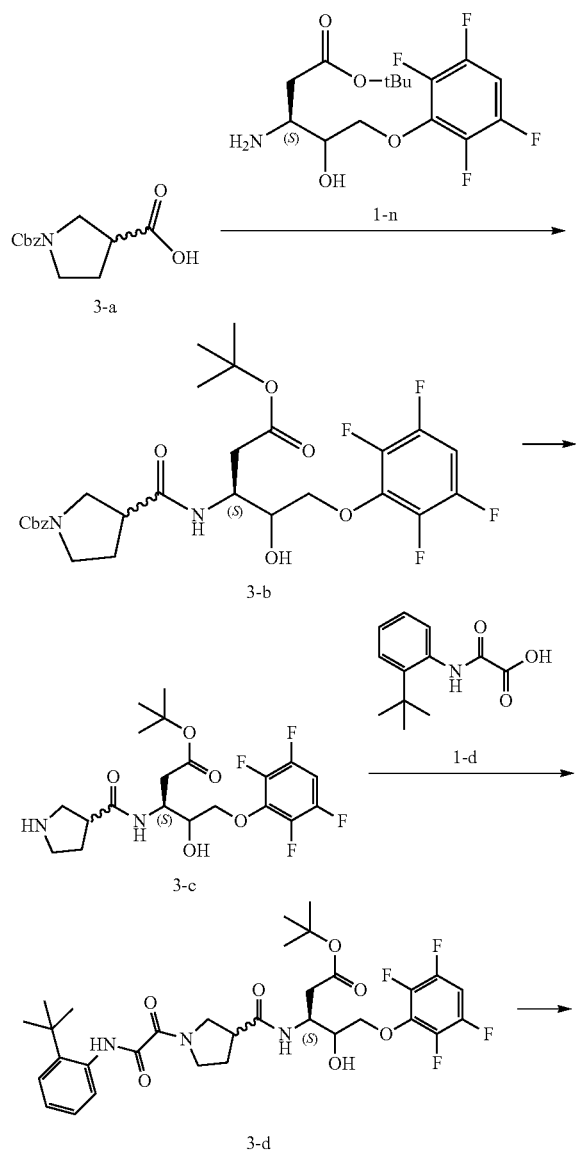

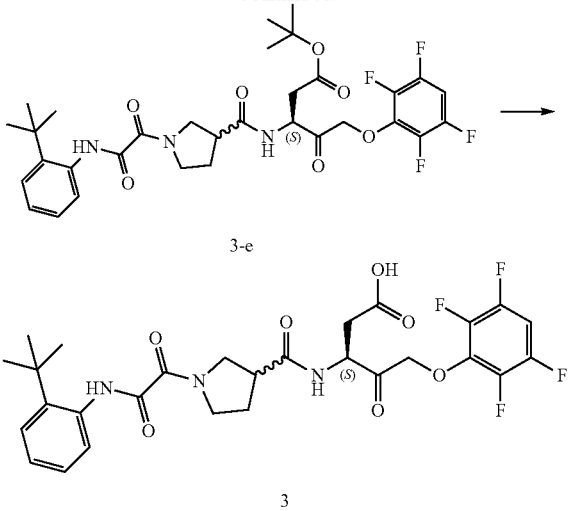

Step 1: Synthesis of Compound 3-b

Compounds 1-n (311.84 mg, 882.61 μmol, 1.10 eq) and 3-a (200.00 mg, 802.38 μmol, 1.00 eq) were dissolved in dichloromethane (5 mL), and EDCl (210.73 mg, 1.10 mmol, 1.37 eq), HOBt (148.53 mg, 1.10 mmol, 1.37 eq) and NMM (243.48 mg, 2.41 mmol, 264.65 μL, 3.00 eq) were added to the solution. After the addition was completed, the reaction was purged with nitrogen gas three times, and stirred at 25° C. for 12 hours. After the reaction was completed, the reaction mixture was directly concentrated and purified by column chromatography (petroleum ether:ethyl acetate=1:0~1:1) to give compound 3-b (450.00 mg, yield: 88%) as a colorless oil.

Step 2: Synthesis of Compound 3-c

Compound 3-b (200.00 mg, 342.14 μmol, 1.00 eq) was dissolved in methanol (250.00 mL), and Pd—C (10%, 100 mg) was added thereto. The mixture was purged with hydrogen three times, and stirred at 25° C. for 2 hours under the pressure of 15 psi. After filtration, the filtrate was concentrated to give compound 3-c (70.00 mg, yield: 45%) as a yellow oil.

Step 3: Synthesis of Compound 3-d

Compounds 1-d (24.56 mg, 111.01 μmol, 1.00 eq) and 3-c (50.00 mg, 111.01 μmol, 1.00 eq) were dissolved in dichloromethane (10 mL), and EDCl (28.94 mg, 150.97 μmol, 1.36 eq), HOBt (20.40 mg, 150.97 μmol, 1.36 eq) and NMM (33.69 mg, 333.02 μmol, 36.61 μL, 3.00 eq) were added thereto, purged with nitrogen gas three times, and stirred at 25° C. for 12 hours. After the reaction was completed, the reaction solution was directly concentrated to give a crude product, which was purified by column chromatography (petroleum ether:ethyl acetate=1:0~1:1) to give compound 3-d (40.00 mg, yield: 55%) as a yellow oil.

Step 4: Synthesis of Compound 3-e

Compound 3-d (30.00 mg, 45.90 μmol, 1.00 eq) was dissolved in dichloromethane (5.00 mL), and PIDA (59.13 mg, 183.58 μmol, 4.00 eq) and TEMPO (1.44 mg, 9.18

μmol, 0.20 eq) were added thereto. The mixture was stirred at 25° C. for 5 hours. After the reaction was completed, the reaction solution was directly concentrated, and purified and separated by preparative silica gel plates (petroleum ether: ethyl acetate=2:1), to give compound 3-e (20.00 mg, yield: 67%) as a yellow oil.

Step 5: Synthesis of Compound 3

Compound 3-e (40.00 mg, 61.38 μmol, 1.00 eq) was dissolved in dichloromethane (2.00 mL), and TFA (1.00 mL) was added thereto. The mixture was stirred at 25° C. for 0.8 hour. After the reaction was completed, the reaction solution was directly concentrated, purified by preparative HPLC, and lyophilized to give the product of compound 3 (10.00 mg, yield: 25%). $^1$H NMR (400 MHz, DMSO-$d_6$) δ=10.00-9.89 (m, 1H), 8.71-8.59 (m, 1H), 7.65-7.48 (m, 1H), 7.44-7.33 (m, 2H), 7.26-7.17 (m, 2H), 5.25 (br. s., 2H), 4.70-4.58 (m, 1H), 4.09-3.76 (m, 3H), 3.16-3.00 (m, 2H), 2.81-2.56 (m, 3H), 2.24-1.78 (m, 2H), 1.33 (s, 9H).

Example 4: Compound 4

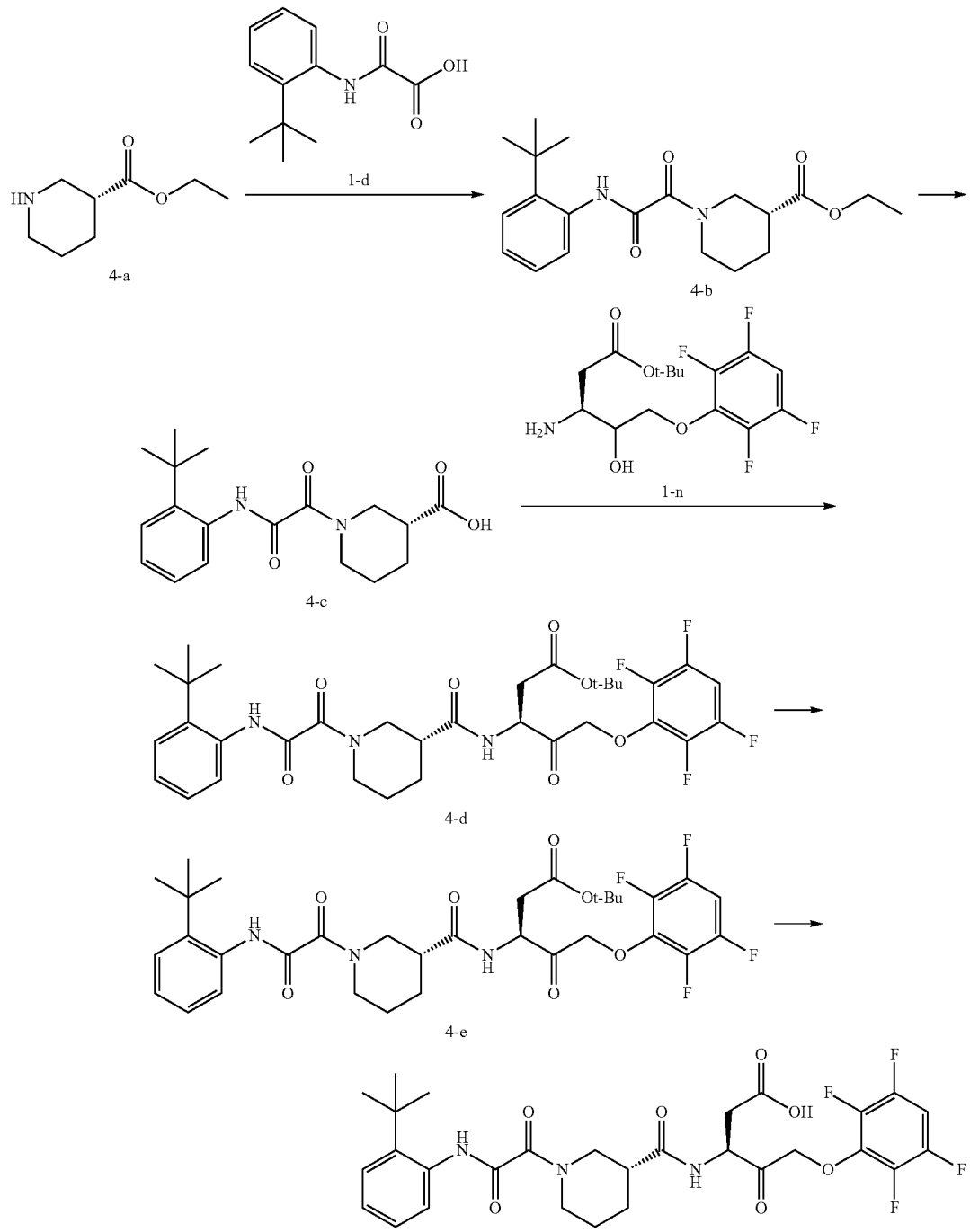

Step 1: Synthesis of Compound 4-b

Compound 1-d (2.81 g, 12.72 mmol, 1.00 eq) was dissolved in dichloromethane (100.00 mL), and HOBt (2.35 g, 17.43 mmol, 1.37 eq), EDCl (3.34 g, 17.43 mmol, 1.37 eq), compound 4-a (2.00 g, 12.72 mmol, 1.00 eq) and NMM (3.86 g, 38.16 mmol, 4.20 mL, 3.00 eq) were added thereto. The reaction solution was stirred at 25° C. for 15 hours. After the reaction was completed, the reaction solution was added with 150 mL of water, and extracted with dichloromethane (150 mL×3). The organic phase was dried over anhydrous sodium sulfate, filtered and concentrated to give a crude product. The crude product was subjected to column chromatography (petroleum ether:ethyl acetate=1:0~5:1) to give the product of compound 4-b (3.80 g, yield: 83%) as a colorless oil. $^1$H NMR (400 MHz, CHLOROFORM-d) δ=9.45 (d, J=18.57 Hz, 1H), 7.86 (t, J=7.03 Hz, 1H), 7.39-7.46 (m, 1H), 7.23-7.27 (m, 1H), 7.14-7.21 (m, 1H), 4.91-5.09 (m, 1H), 4.13-4.60 (m, 3H), 3.08-3.89 (m, 2H), 2.54-2.73 (m, 1H), 2.06-2.21 (m, 1H), 1.66-1.94 (m, 3H), 1.46 (d, J=1.51 Hz, 9H), 1.25-1.30 (m, 3H).

Step 2: Synthesis of Compound 4-c

Compound 4-b (3.80 g, 10.54 mmol, 1.00 eq) was dissolved in tetrahydrofuran (30.00 mL), and a solution of LiOH.H$_2$O (1.33 g, 31.62 mmol, 3.00 eq) dissolved in water (30.00 mL) was added to the above solution. The reaction solution was maintained at 25° C. and stirred for 40 min. After the reaction was completed, the reaction solution was adjusted to pH=6 with 2 N dilute hydrochloric acid, added with 200 mL of water, and extracted with dichloromethane (200 mL×3). The organic phase was dried over anhydrous sodium sulfate, filtered and concentrated to give the product of compound 4-c (3.50 g, crude) as a colorless oil, which was used directly in the next step without purification. $^1$H NMR (400 MHz, CHLOROFORM-d) δ=9.32-9.49 (m, 1H), 7.73-7.93 (m, 1H), 7.39-7.47 (m, 1H), 7.13-7.27 (m, 2H), 4.58-5.04 (m, 1H), 3.94-4.04 (m, 1H), 3.77 (t, J=6.40 Hz, 2H), 3.31-3.41 (m, 1H), 2.59-2.78 (m, 1H), 2.10-2.23 (m, 1H), 1.88-1.98 (m, 1H), 1.59-1.85 (m, 2H), 1.41-1.49 (m, 9H).

Step 3: Synthesis of Compound 4-d

Compound 4-c (471.99 mg, 1.42 mmol, 1.00 eq) was dissolved in dichloromethane (30.00 mL), and compound 1-n (500.00 mg, 1.42 mmol, 1.00 eq), EDCl (372.93 mg, 1.95 mmol, 1.37 eq), HOBt (262.86 mg, 1.95 mmol, 1.37 eq) and NMM (430.90 mg, 4.26 mmol, 468.37 μL, 3.00 eq) were added thereto. The reaction solution was stirred at 27° C. for 16 hours under the protection of nitrogen gas. After the reaction was completed, the reaction solution was added with 80 mL of water, and extracted with dichloromethane (80 mL×3). The organic phase was combined, dried over anhydrous sodium sulfate, filtered and concentrated to give a crude product. The crude product was subjected to column chromatography (petroleum ether:ethyl acetate=1:0~2:1) to give the product of compound 4-d (507.00 mg, yield: 49%) as a colorless oil. $^1$H NMR (400 MHz, CHLOROFORM-d) δ=9.45 (d, J=5.52 Hz, 1H), 7.83 (dd, J=5.40, 7.40 Hz, 1H), 7.43 (d, J=8.03 Hz, 1H), 7.14-7.26 (m, 2H), 6.73-6.86 (m, 1H), 4.70-5.03 (m, 1H), 4.10-4.47 (m, 4H), 3.66-3.93 (m, 1H), 3.18-3.53 (m, 2H), 2.40-2.81 (m, 3H), 1.76-2.05 (m, 3H), 1.57-1.65 (m, 1H), 1.41-1.52 (m, 18H).

Step 4: Synthesis of Compound 4-e

Compound 4-d (507.00 mg, 759.33 μmol, 1.00 eq) was dissolved in dichloromethane (26.00 mL), and PIDA (946.53 mg, 2.94 mmol, 3.87 eq) and TEMPO (23.88 mg, 151.87 μmol, 0.20 eq) were added thereto. The reaction solution was stirred at 27° C. for 18 hours under the protection of nitrogen gas. After the reaction was completed, 100 mL of ethyl acetate was added to the reaction solution. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was subjected to column chromatography (petroleum ether:ethyl acetate=1:0~2:1) to give the product of compound 4-e (420.00 mg, yield: 78%) as a colorless oil. LCMS m/z=666.3 [M+H]$^+$.

Step 5: Synthesis of Compound 4

Compound 4-e (500.00 mg, 751.12 μmol, 1.00 eq) was dissolved in dichloromethane (16.00 mL), and trifluoroacetic acid (12.32 g, 108.05 mmol, 8.00 mL, 143.85 eq) was added thereto. The reaction solution was stirred at 27° C. for 1 hour under the protection of nitrogen gas. After the reaction was completed, the reaction solution was spin-dried to give a crude product. The crude product was purified by preparative HPLC (under a condition of trifluoroacetic acid), and lyophilized to give a solid product. The solid was dissolved in acetonitrile (20 mL), added with hydrochloric acid solution (0.1 M, 20 mL), mixed uniformly, and lyophilized to give the product of compound 4 (300.80 mg, yield: 66%). $^1$H NMR (400 MHz, DMSO-d$_6$) δ=10.02 (d, J=3.01 Hz, 1H), 8.60 (t, J=8.03 Hz, 1H), 7.50-7.69 (m, 1H), 7.43 (dd, J=3.51, 6.02 Hz, 1H), 7.18-7.31 (m, 2H), 7.04-7.14 (m, 1H), 5.15-5.34 (m, 2H), 4.64 (q, J=6.69 Hz, 1H), 4.12-4.43 (m, 1H), 3.96 (d, J=13.05 Hz, 1H), 3.08-3.31 (m, 1H), 2.55-2.98 (m, 4H), 2.28-2.46 (m, 1H), 1.90-2.05 (m, 1H), 1.78 (d, J=12.55 Hz, 1H), 1.63 (q, J=12.05 Hz, 1H), 1.39-1.54 (m, 1H), 1.33 (d, J=5.52 Hz, 9H); LCMS m/z=610.1 [M+H]+.

Example 5: Compound 5
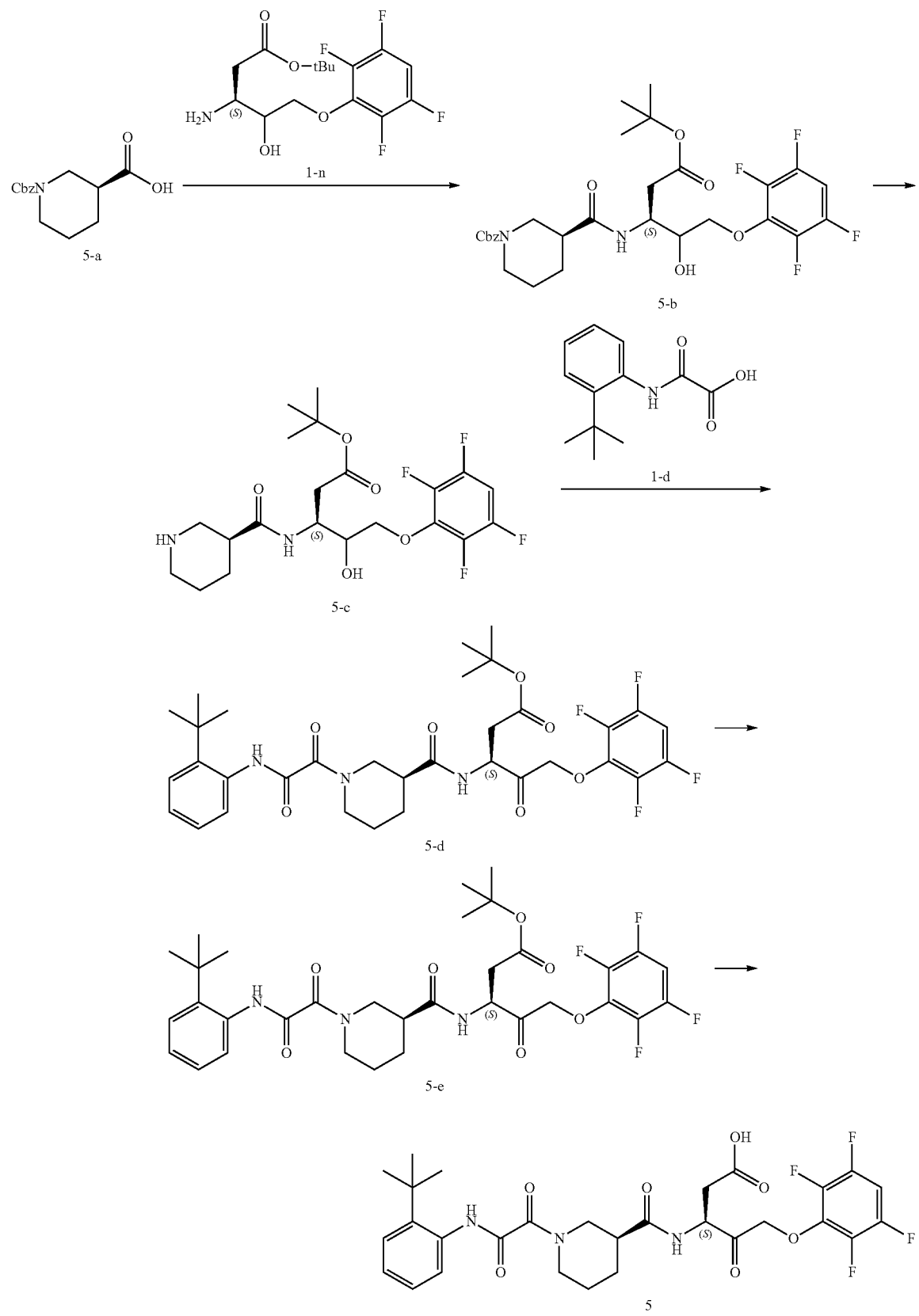

Step 1: Synthesis of Compound 5-b

Compound 1-n (320.00 mg, 905.72 μmol, 1.00 eq) was dissolved in dichloromethane (5.00 mL), and HOBt (167.66 mg, 1.24 mmol, 1.37 eq), EDCl (237.87 mg, 1.24 mmol, 1.37 eq), compound 5-a (238.47 mg, 905.72 μmol, 1.00 eq) and NMM (274.84 mg, 2.72 mmol, 298.74 μL, 3.00 eq) were added thereto. The reaction solution was stirred at 25° C. for 12 hours. After the reaction was completed, the reaction solution was added with 20 mL of water, and extracted with dichloromethane (20 mL×3). The organic phase was dried over anhydrous sodium sulfate, filtered and concentrated to give a crude product. The crude product was subjected to column chromatography (petroleum ether:ethyl acetate=1: 0~1:1) to give the product of compound 5-b (350.00 mg, crude) as a colorless oil.

Step 2: Synthesis of Compound 5-c

Compound 5-b (400.00 mg, 668.25 μmol, 1.00 eq) was dissolved in methanol (50.00 mL), and Pd—C (10%, 100 mg) was added thereto. The reaction mixture was purged with hydrogen gas three times, maintained at a hydrogen pressure of 15 psi, and stirred at 25° C. for 2 hours. After the reaction was completed, the filtrate was concentrated to give compound 5-c (250.00 mg, crude) as a colorless oil.

Step 3: Synthesis of Compound 5-d

Compounds 1-d (119.09 mg, 538.27 μmol, 1.00 eq) and 5-c (250.00 mg, 538.27 μmol, 1.00 eq) were dissolved in dichloromethane (10.00 mL), and EDCl (140.33 mg, 732.05 μmol, 1.36 eq), HOBt (98.91 mg, 732.05 μmol, 1.36 eq) and NMM (163.34 mg, 1.61 mmol, 177.54 μL, 3.00 eq) were added thereto. After the addition was completed, the reaction was purged with nitrogen gas three times, and stirred at 25° C. for 12 hours. After the reaction was completed, the reaction solution was directly concentrated and purified by column chromatography (petroleum ether:ethyl acetate=1: 0~1:1) to give compound 5-d (200.00 mg, yield: 56%) as a yellow oil.

Step 4: Synthesis of Compound 5-e

Compound 5-d (180.00 mg, 269.59 μmol, 1.00 eq) was dissolved in dichloromethane (5.00 mL), and PIDA (347.33 mg, 1.08 mmol, 4.00 eq) and TEMPO (8.48 mg, 53.92 μmol, 0.20 eq) were added thereto. The mixture was stirred at 25° C. for 5 hours. After the reaction was completed, the reaction mixture was directly concentrated and purified by preparative silica gel plates (petroleum ether:ethyl acetate=2:1) to give compound 5-e (90.00 mg, yield: 50%) as a yellow oil. $^1$H NMR (400 MHz, CHLOROFORM-d) δ=9.50-9.41 (m, 1H), 7.89-7.85 (m, 1H), 7.84-7.79 (m, 1H), 7.48-7.42 (m, 1H), 7.24-7.09 (m, 2H), 6.83-6.74 (m, 1H), 5.22-5.17 (m, 1H), 5.15 (s, 1H), 5.11-5.07 (m, 1H), 5.07-5.02 (m, 1H), 5.00-4.75 (m, 3H), 4.38-4.29 (m, 1H), 4.17-4.06 (m, 1H), 3.96-3.86 (m, 1H), 3.65-3.56 (m, 1H), 3.51-3.42 (m, 1H), 3.34-3.26 (m, 1H), 3.01-2.90 (m, 1H), 2.84-2.76 (m, 1H), 2.70-2.51 (m, 2H), 1.49-1.43 (m, 10H).

Step 5: Synthesis of Compound 5

Compound 5-e (80.00 mg, 120.18 μmol, 1.00 eq) was dissolved in dichloromethane (2.00 mL), and TFA (1.00 mL) was added thereto. The mixture was stirred at 25° C. for 1 hour. After the reaction was completed, the reaction solution was directly concentrated, purified by preparative HPLC, and lyophilized to give the product of compound 5 (10.00 mg, yield: 11%). $^1$H NMR (400 MHz, DMSO-$d_6$) δ=10.02 (s, 1H), 8.67-8.40 (m, 1H), 7.69-7.50 (m, 1H), 7.47-7.39 (m, 1H), 7.31-7.17 (m, 2H), 7.15-7.06 (m, 1H), 5.31-5.03 (m, 1H), 4.73-4.58 (m, 1H), 4.41-4.30 (m, 1H), 4.26-4.16 (m, 1H), 4.06-3.91 (m, 1H), 3.20-3.10 (m, 2H), 2.88-2.59 (m, 4H), 2.44-2.32 (m, 1H), 2.05-1.87 (m, 1H), 1.84-1.71 (m, 1H), 1.69-1.54 (m, 1H), 1.34 (s, 9H).

Example 6: Compound 6

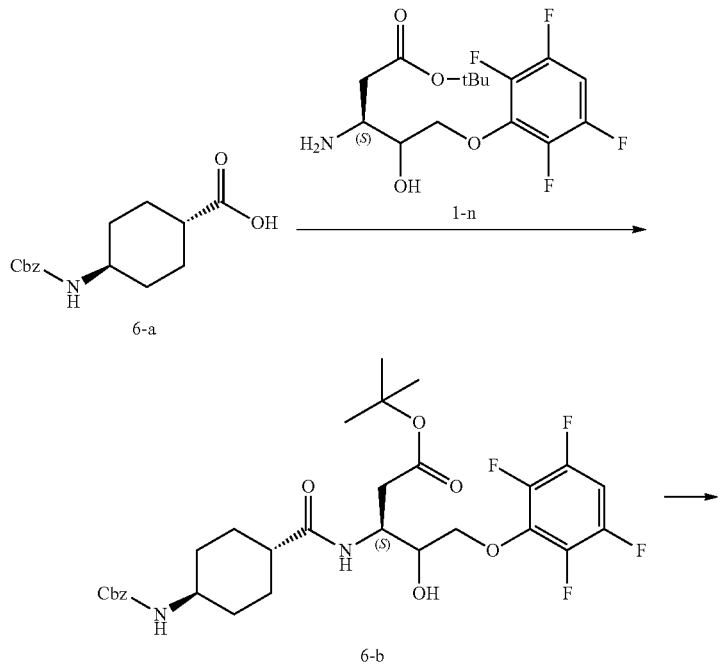

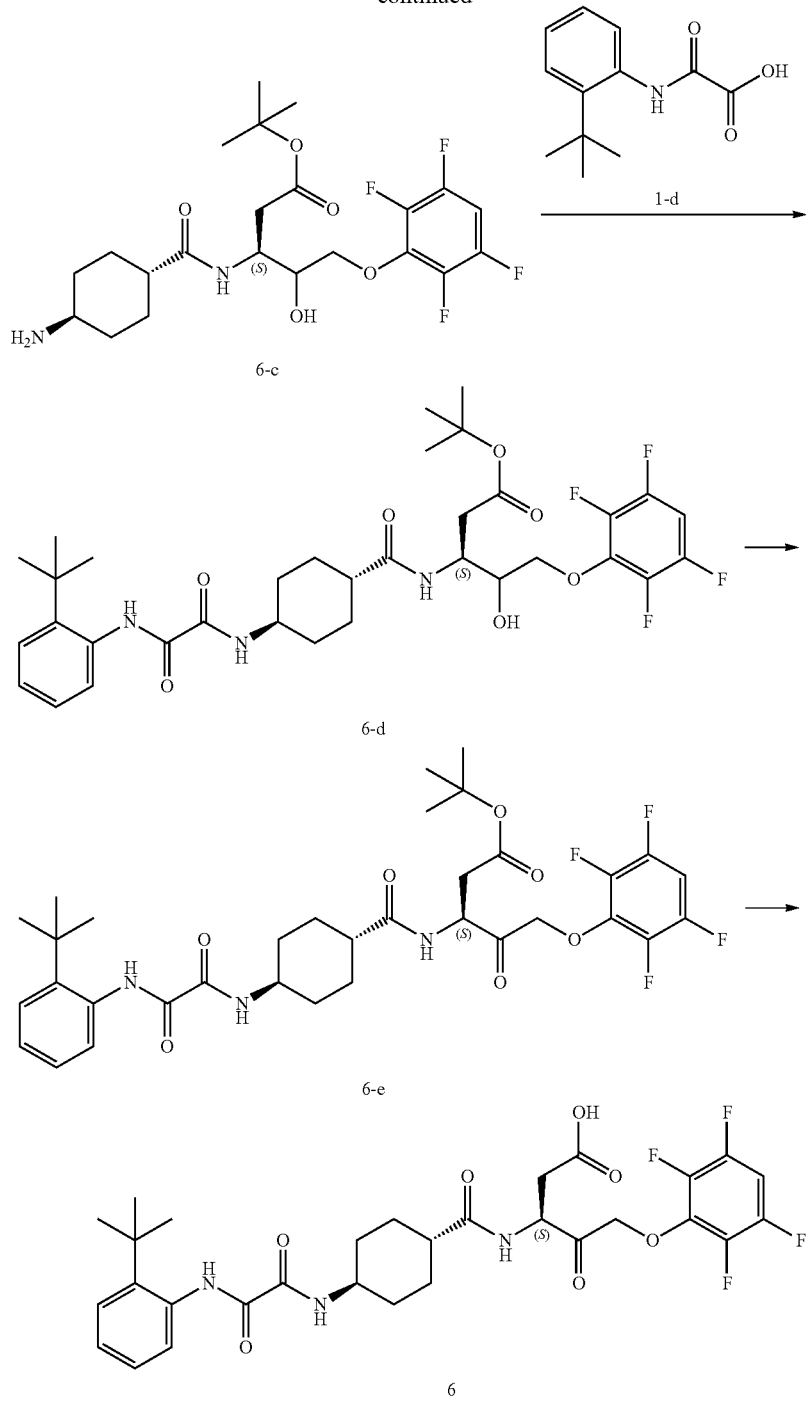

Step 1: Synthesis of Compound 6-b

Compound 1-n (504.53 mg, 1.43 mmol, 1.10 eq) was dissolved in dichloromethane (5.00 mL), and compound 6-a (360.00 mg, 1.30 mmol, 1.00 eq), HOBt (240.31 mg, 1.78 mmol, 1.37 eq), EDCl (340.94 mg, 1.78 mmol, 1.37 eq) and NMM (393.93 mg, 3.89 mmol, 428.19 µL, 3.00 eq) were added thereto. The reaction solution was stirred at 25° C. for 12 hours. After the reaction was completed, the reaction solution was added with 20 mL of water, and extracted with dichloromethane (20 mL×3). The organic phase was dried over anhydrous sodium sulfate, filtered and concentrated to give a crude product. The crude product was subjected to column chromatography (petroleum ether:ethyl acetate=1: 0~1:1) to give the product of compound 6-b (500.00 mg, yield: 63%) as a colorless oil.

Step 2: Synthesis of Compound 6-c

Compound 6-b (300.00 mg, 489.71 µmol, 1.00 eq) was dissolved in methanol (100.00 mL), and Pd—C (10%, 100 mg) was added thereto. The reaction mixture was purged with hydrogen gas three times, maintained at a hydrogen pressure of 15 psi, and stirred at 25° C. for 2 hours. After the reaction was completed, the reaction solution was filtered. The filtrate was concentrated to give compound 6-c (170.00 mg, crude). $^1$H NMR (400 MHz, CHLOROFORM-d) δ=6.91-6.75 (m, 1H), 6.60-6.49 (m, 1H), 4.38-4.19 (m, 2H), 2.85-2.54 (m, 3H), 2.14-1.85 (m, 6H), 1.82-1.59 (m, 4H), 1.41 (s, 9H) 1.19-1.04 (m, 1H).

Step 3: Synthesis of Compound 6-d

Compounds 1-d (89.05 mg, 402.49 μmol, 1.00 eq) and 6-c (170.00 mg, 402.49 μmol, 1.00 eq) were dissolved in dichloromethane (5.00 mL), and EDCl (104.93 mg, 547.39 μmol, 1.36 eq), HOBt (73.96 mg, 547.39 μmol, 1.36 eq) and NMM (122.14 mg, 1.21 mmol, 132.76 μL, 3.00 eq) were added thereto. After the addition was completed, the reaction was purged with nitrogen gas three times, and stirred at 25° C. for 12 hours. After the reaction was completed, the reaction solution was poured into 50 mL of water, and extracted with ethyl acetate (50 mL×3). The organic phases were combined, and washed with water (50 mL) and saturated brine (50 mL), dried over anhydrous sodium sulfate, filtered and concentrated to give compound 6-d (170.00 mg, crude), which was used directly in the next step.

Step 4: Synthesis of Compound 6-e

Compound 6-d (100.00 mg, 146.69 μmol, 1.00 eq) was dissolved in dichloromethane (5.00 mL), and PIDA (189.00 mg, 586.76 μmol, 4.00 eq) and TEMPO (4.61 mg, 29.34 μmol, 0.20 eq) were added thereto. The mixture was stirred at 25° C. for 12 hours. After the reaction was completed, the reaction mixture was directly concentrated and purified by preparative silica gel plates (petroleum ether:ethyl acetate=2:1) to give compound 6-e (60.00 mg, yield: 35%).

Step 5: Synthesis of Compound 6

Compound 6-e (60.00 mg, 88.27 μmol, 1.00 eq) was dissolved in dichloromethane (8.00 mL) and TFA (4.00 mL) was added thereto. The mixture was stirred at 25° C. for 0.8 hour. After the reaction was completed, the reaction solution was directly concentrated, purified by preparative HPLC, and lyophilized to give the product of compound 6 (16.00 mg, yield: 27%). $^1$H NMR (400 MHz, DMSO-d$_6$) δ=9.99-9.88 (m, 1H), 8.99-8.85 (m, 1H), 8.49-8.35 (m, 1H), 7.62-7.49 (m, 2H), 7.48-7.14 (m, 3H), 5.33-5.13 (m, 2H), 4.67-4.51 (m, 1H), 3.73-3.56 (m, 1H), 2.82-2.65 (m, 1H), 2.65-2.54 (m, 2H), 2.24-2.06 (m, 1H), 1.88-1.68 (m, 4H), 1.56-1.39 (m, 4H), 1.36 (s, 9H).

Example 7: Compound 7

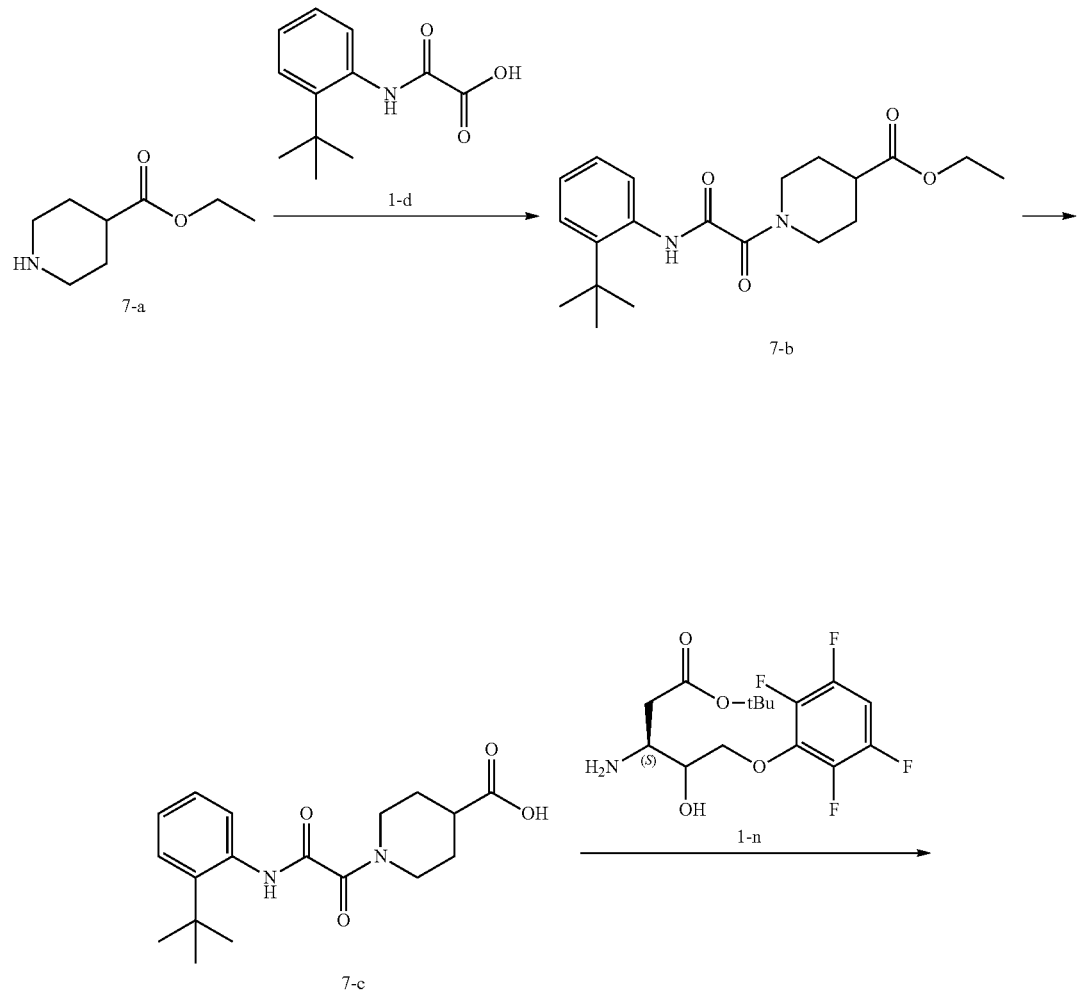

-continued

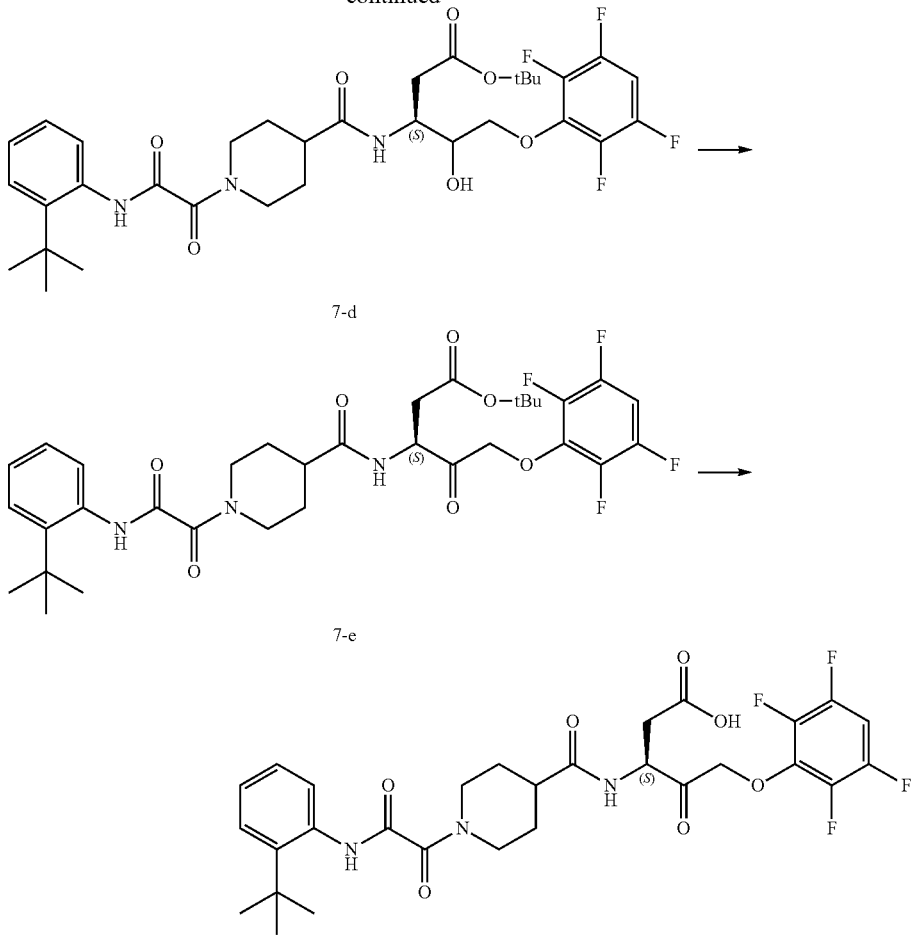

Step 1: Synthesis of Compound 7-b

Compound 1-d (4.14 g, 18.70 mmol, 1.05 eq) and HOBt (3.61 g, 26.72 mmol, 1.50 eq) were dissolved in dichloromethane (100 mL), and EDCl (5.12 g, 26.72 mmol, 1.50 eq) were added thereto and stirred at room temperature for 15 min. Compound 7-a (2.80 g, 17.81 mmol, 2.75 mL, 1.00 eq) and N,N-diisopropylethylamine (4.60 g, 35.62 mmol, 6.22 mL, 2.00 eq) were then dissolved in dichloromethane, added to the above solution, and stirred at room temperature for 16 hours. After the reaction was completed, the reaction solution was added with 100 mL of water, and separated. The aqueous phase was extracted with dichloromethane (200 mL×2). The organic phases were combined and washed with saturated sodium hydrogen carbonate solution (150 mL) and saturated brine (100 mL). The organic phase was dried over anhydrous sodium sulfate, filtered, concentrated, and separated by column chromatography (petroleum ether:ethyl acetate=1:0~5:1) to give the product of compound 7-b (560.00 mg, yield: 9%). LCMS m/z=361.1 [M+H]$^+$.

Step 2: Synthesis of Compound 7-c

Compound 7-b (790.00 mg, 2.19 mmol, 1.00 eq) was dissolved in tetrahydrofuran (20.00 mL), and a solution of LiOH.H$_2$O (183.93 mg, 4.38 mmol, 2.00 eq) dissolved in water (20.00 mL) was added to the above solution. The reaction solution was maintained at 25° C. and stirred for 2 hours. After the reaction was completed, the reaction solution was adjusted to pH of 6 with 2 N dilute hydrochloric acid, added with 200 mL of water, and extracted with dichloromethane (200 mL×3). The organic phase was dried over anhydrous sodium sulfate, filtered and concentrated to give the product of compound 7-c (0.65 g, crude) as a pale yellow oil, which was used directly in the next step without purification. LCMS m/z=355.1 [M+Na]$^+$.

Step 3: Synthesis of Compound 7-d

Compound 7-c (900.00 mg, 2.71 mmol, 1.05 eq) and HOBt (488.23 mg, 3.61 mmol, 1.40 eq) were dissolved in dichloromethane (10 mL), and EDCl (692.68 mg, 3.61 mmol, 1.40 eq) was added thereto and stirred at room temperature for 15 min. Compound 1-n (911.00 mg, 2.58 mmol, 1.00 eq) and NMM (783.19 mg, 7.74 mmol, 851.29 µL, 3.00 eq) were then dissolved in dichloromethane, added to the above solution, and stirred at room temperature for 60 hours. After the reaction was completed, the reaction solution was added with 80 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 7-d (1.24 g, yield: 66%) as a yellow oil. LCMS m/z=690.4 [M+Na]⁺.

Step 4: Synthesis of Compound 7-e

Compound 7-d (1.24 g, 1.86 mmol, 1.00 eq) was dissolved in dichloromethane (50.00 mL), and PIDA (2.40 g, 7.44 mmol, 4.00 eq) and TEMPO (58.50 mg, 372.00 μmol, 0.20 eq) were added thereto. The reaction solution was stirred at room temperature for 24 hours. After the reaction was completed, the reaction solution was added with saturated sodium hydrogen carbonate solution (50 mL) and saturated sodium sulfite solution (50 mL), extracted with dichloromethane (80 mL×3) and washed with saturated brine (100 mL). The organic phase was dried over anhydrous sodium sulfate, filtered and concentrated to give a crude product. The crude product was subjected to column chromatography (petroleum ether:ethyl acetate=1:0~5:2), to give the product of compound 7-e (738.00 mg, yield: 48%) as a yellow oil. LCMS m/z=688.3 [M+Na]⁺.

Step 5: Synthesis of Compound 7

Compound 7-e (700.00 mg, 1.05 mmol, 1.00 eq) was dissolved in dichloromethane (6.00 mL), and trifluoroacetic acid (4.62 g, 40.52 mmol, 3.00 mL) was added thereto. The reaction solution was stirred at room temperature for 2 hours. After the reaction was completed, the reaction solution was spin-dried to give a crude product. The crude product was purified by preparative HPLC (under trifluoroacetic acid condition), to give the product of compound 7 (484.00 mg, yield: 75%). ¹H NMR (400 MHz, DMSO-d₆) δ=8.52 (d, J=7.6 Hz, 1H), 7.54 (br. s, 1H), 7.45 (d, J=7.6 Hz, 1H), 7.30-7.21 (m, 2H), 7.13 (d, J=6.0 Hz, 1H), 5.25 (dd, J=14.8, 7.6 Hz, 2H), 4.63 (d, J=4.8 Hz, 1H), 4.38-4.26 (m, 1H), 4.03 (d, J=7.6 Hz, 1H), 3.22 (t, J=7.6 Hz, 1H), 2.89-2.71 (m, 2H), 2.68-2.55 (m, 2H), 1.86-1.75 (m, 2H), 1.62-1.49 (m, 2H), 1.35 (s, 9H); LCMS m/z=610.3 [M+H]⁺, 632.3 [M+Na]⁺.

Example 8: Compound 8

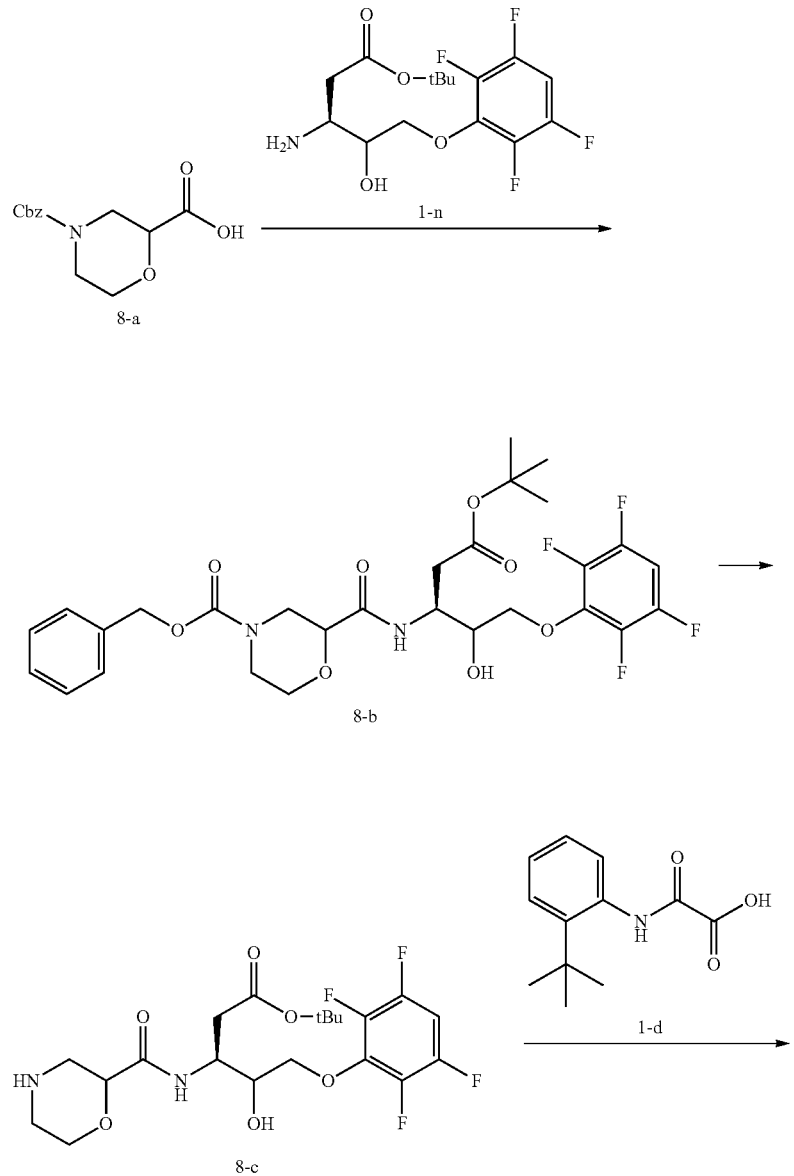

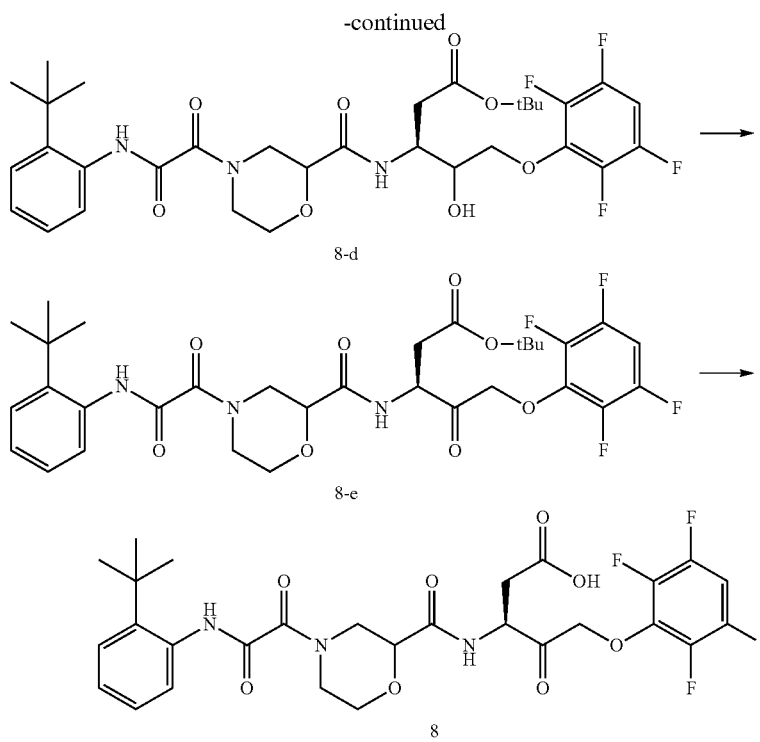

8-d 8-e

8

Step 1: Synthesis of Compound 8-b

Compound 1-n (400.00 mg, 1.13 mmol, 1.00 eq) was dissolved in dichloromethane (12.00 mL), and compound 8-a (299.74 mg, 1.13 mmol, 1.00 eq), EDCl (296.77 mg, 1.55 mmol, 1.37 eq), HOBt (209.18 mg, 1.55 mmol, 1.37 eq) and NMM (342.90 mg, 3.39 mmol, 372.72 μL, 3.00 eq) were added thereto. The reaction solution was stirred at 27° C. for 16 hours. After the reaction was completed, the reaction solution was added with 150 mL of water, and extracted with dichloromethane (150 mL×3). The organic phase was dried over anhydrous sodium sulfate, filtered and concentrated to give a crude product. The crude product was subjected to column chromatography (petroleum ether:ethyl acetate=1:0~2:1) to give the product of compound 8-b (417.00 mg, yield: 58%) as a colorless oil. $^1$H NMR (400 MHz, CHLOROFORM-d) δ=7.29-7.45 (m, 5H), 6.75-6.87 (m, 1H), 5.10-5.21 (m, 2H), 4.10-4.53 (m, 5H), 3.88-4.04 (m, 3H), 3.59 (t, J=11.04 Hz, 1H), 2.57-2.89 (m, 3H), 1.43-1.51 (m, 9H).

Step 2: Synthesis of Compound 8-c

Compound 8-b (300.00 mg, 499.54 μmol, 1.00 eq) was dissolved in methanol (15.00 mL), and Pd/C (40.00 mg, purity of 10%) was added to the solution. The reaction solution was stirred at 27° C. for 2 hours in hydrogen atmosphere (hydrogen balloon). After the reaction was completed, the reaction solution was filtered through diatomaceous earth, and the filter cake was washed with methanol (100 mL). The resulting filtrate was concentrated to give the product of compound 8-c (240.00 mg, crude) as a colorless oil, which was used directly in the next step without purification. LCMS m/z=467.2 [M+H]$^+$.

Step 3: Synthesis of Compound 8-d

Compound 1-d (94.87 mg, 428.80 μmol, 1.00 eq) was dissolved in dichloromethane (5.00 mL), and compound 8-c (200.00 mg, 428.80 μmol, 1.00 eq), EDCl (112.61 mg, 587.46 μmol, 1.37 eq), HOBt (79.38 mg, 587.46 μmol, 1.37 eq) and NMM (130.12 mg, 1.29 mmol, 141.43 μL, 3.00 eq) were added thereto. The reaction solution was stirred at 27° C. for 18 hours under the protection of nitrogen gas. After the reaction was completed, the reaction solution was added with 100 mL of water, and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~1:2) to give the product of compound 8-d (120.00 mg, yield: 41%) as a colorless oil. LCMS m/z=670.3 [M+H]$^+$.

Step 4: Synthesis of Compound 8-e

Compound 8-d (120.00 mg, 179.20 μmol, 1.00 eq) was dissolved in dichloromethane (6.00 mL), and PIDA (223.37 mg, 693.50 μmol, 3.87 eq) and TEMPO (5.64 mg, 35.84 μmol, 0.20 eq) were added thereto. The reaction solution was stirred at 27° C. for 16 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was subjected to column chromatography (petroleum ether:ethyl acetate=1:0~2:1) to give the product of compound 8-e (110.00 mg, yield: 85%) as a colorless oil. LCMS m/z=668.3 [M+H]$^+$.

Step 5: Synthesis of Compound 8

Compound 8-e (110.00 mg, 164.76 μmol, 1.00 eq) was dissolved in dichloromethane (4.00 mL), and trifluoroacetic acid (2.70 g, 23.70 mmol, 1.75 mL, 143.85 eq) was added thereto. The reaction solution was stirred at 27° C. for 1 hour under the protection of nitrogen gas. After the reaction was completed, the reaction solution was spin-dried to give a crude product. The crude product was purified by preparative HPLC (under trifluoroacetic acid condition), and lyophilized to give the product of compound 8 (55.10 mg, yield: 55%). $^1$H NMR (400 MHz, DMSO-$d_6$) δ=10.05-10.14 (m, 1H), 8.38-8.47 (m, 1H), 7.52-7.68 (m, 1H), 7.40-7.48 (m, 1H), 7.21-7.31 (m, 2H), 7.08-7.20 (m, 1H), 5.16-5.33 (m, 2H), 4.73-4.83 (m, 1H), 3.97-4.49 (m, 5H), 3.55-3.70 (m, 1H), 3.27-3.45 (m, 1H), 2.76-3.12 (m, 2H), 2.60-2.71 (m, 1H), 1.34 (s, 9H); LCMS m/z=612.1 [M+H]$^+$.

Example 9: Compound 9

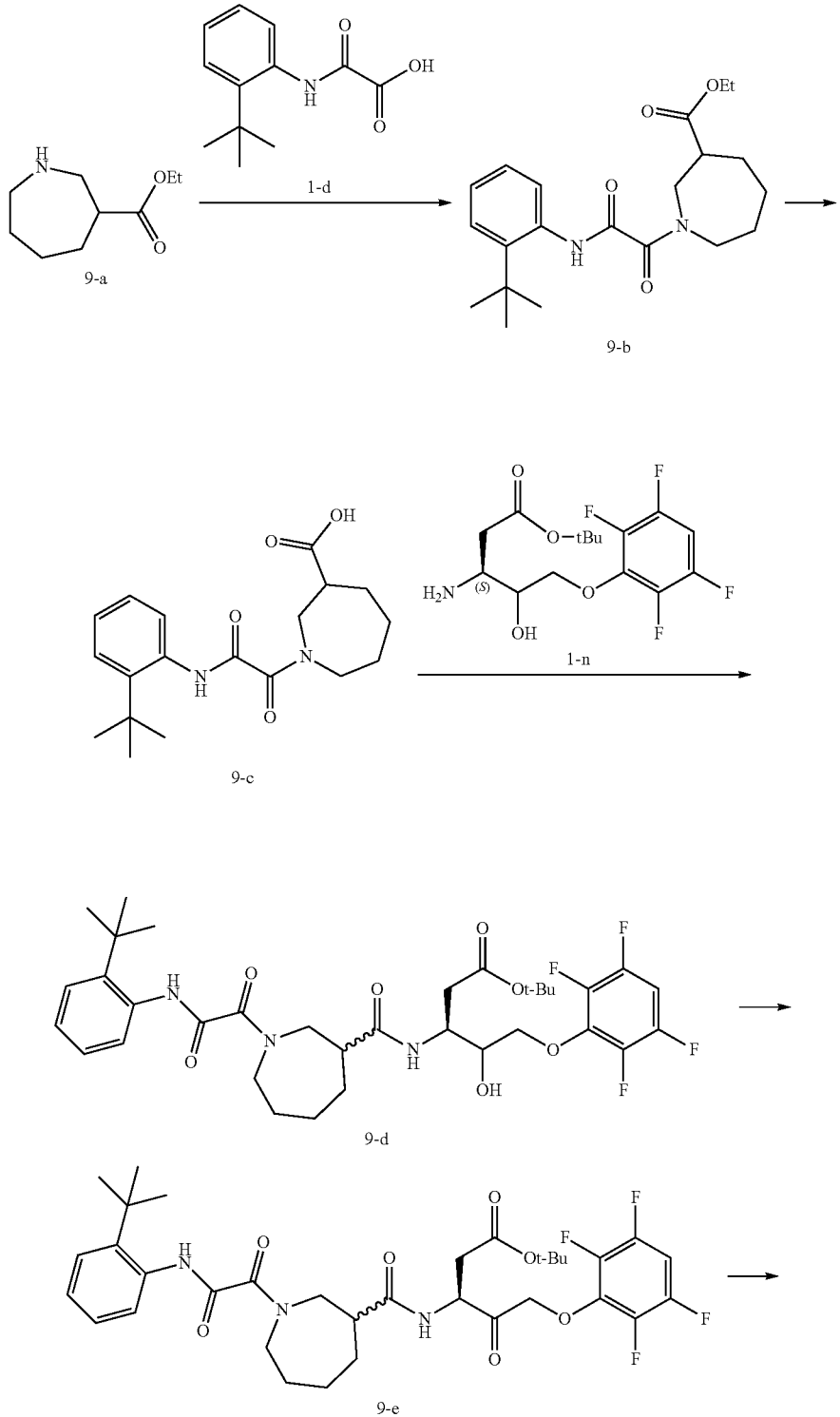

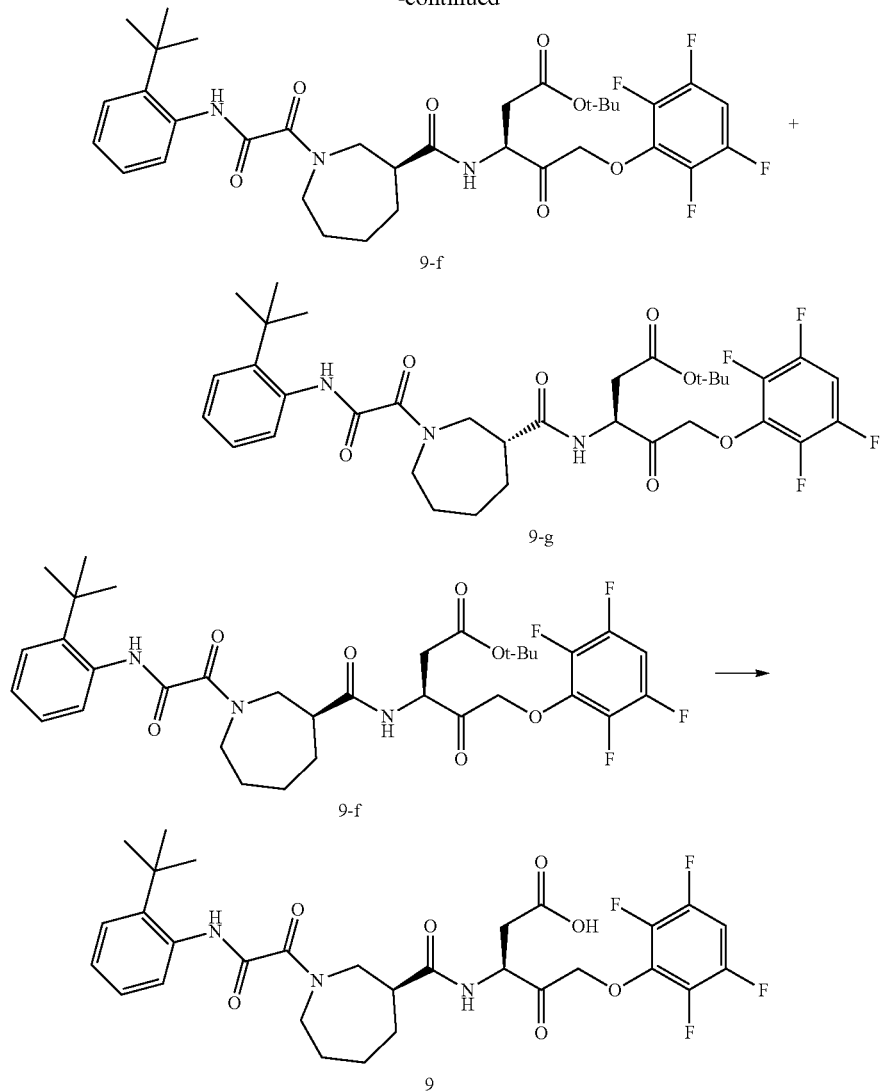

Step 1: Synthesis of Compound 9-b

Compound 1-d (1.15 g, 5.19 mmol, 1.40 eq) and HOBt (751.94 mg, 5.57 mmol, 1.50 eq) were dissolved in dichloromethane (70 mL), added with EDCl (1.07 g, 5.57 mmol, 1.50 eq), and stirred at room temperature for 15 min. Then, compound 9-a (635.30 mg, 3.71 mmol, 1.00 eq) and N,N-diisopropylethylamine (958.96 mg, 7.42 mmol, 1.30 mL, 2.00 eq) were dissolved in dichloromethane, added to the above solution, and stirred at room temperature for 18 hours. After the reaction was completed, the reaction solution was added with 100 mL of water and separated, and the aqueous phase was further extracted with dichloromethane (200 mL×2). The organic phases were combined, and washed with saturated sodium hydrogen carbonate solution (150 mL) and saturated brine (100 mL). The organic phase was dried over anhydrous sodium sulfate, filtered, concentrated, and separated by column chromatography (petroleum ether: ethyl acetate=1:0~10:1) to give the product of compound 9-b (386.00 mg, yield: 23%). LCMS m/z=397.2 [M+Na]$^+$.

Step 2: Synthesis of Compound 9-c

Compound 9-b (350.00 mg, 934.65 μmol, 1.00 eq) was dissolved in tetrahydrofuran (10.00 mL), and a solution of LiOH.H$_2$O (78.44 mg, 1.87 mmol, 2.00 eq) dissolved in water (20.00 mL) was added to the above solution. The reaction solution was maintained at 25° C. and stirred for 2 hours. After the reaction was completed, the reaction solution was adjusted to pH of 6 with 2 N dilute hydrochloric acid, added with 200 mL of water, and extracted with dichloromethane (200 mL×3). The organic phase was dried over anhydrous sodium sulfate, filtered and concentrated to give the product of compound 9-c (0.65 g, crude) as a pale yellow oil, which was used directly in the next step without purification. LCMS m/z=347.1[M+H]$^+$, 369.1 [M+Na]$^+$.

Step 3: Synthesis of Compound 9-d

Compound 9-c (323.56 mg, 933.90 μmol, 1.10 eq) and HOBt (160.60 mg, 1.19 mmol, 1.40 eq) were dissolved in dichloromethane (50 mL), added with EDCl (227.85 mg, 1.19 mmol, 1.40 eq), and stirred at room temperature for 15 min. Then, compound 1-n (299.96 mg, 849.00 µmol, 1.00 eq) and NMM (257.63 mg, 2.55 mmol, 280.03 µL, 3.00 eq) were dissolved in dichloromethane, added to the above solution, and stirred at room temperature for 62 hours. After the reaction was completed, the reaction solution was added with 80 mL of water, and extracted with dichloromethane (80 mL×3). The organic phases were combined, dried over anhydrous sodium sulfate, filtered, and concentrated to give a crude product. The crude product was subjected to column chromatography (petroleum ether:ethyl acetate=1:0~3:1) to give the product of compound 9-d (448.00 mg, yield: 75%) as a yellow oil. LCMS m/z=704.4 [M+Na]$^+$.

Step 4: Synthesis of Compounds 9-e, 9-f and 9-g

Compound 9-d (440.00 mg, 645.44 µmol, 1.00 eq) was dissolved in dichloromethane (50.00 mL), and PIDA (831.58 mg, 2.58 mmol, 4.00 eq) and TEMPO (20.30 mg, 129.09 µmol, 0.20 eq) were added thereto. The reaction solution was stirred at room temperature for 54 hours. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was subjected to column chromatography (petroleum ether:ethyl acetate=1:0~3:1) to give the product of compound 9-e (415.00 mg, yield: 94%) as yellow oil. LCMS m/z=702.3 [M+Na]$^+$. Compound 9-e was isolated via SFC (Column: Lux Cellulose-2 150×4.6 mm I.D., 3 µm; Mobile phase: A:$CO_2$, B: methanol (0.05% diethylamine); Gradient: 5%~40% of mobile phase B (0-5.5 min), hold 40% of mobile phase B for 3 min, and 5% of mobile phase B for 1.5 min; Flow rate: 2.5 mL/min; Column temp.: 40° C.), to give compounds 9-f (Retention time: 4.18 min, 80% ee) and 9-g (Retention time: 4.47 min, 99% ee).;

Step 5: Synthesis of Compound 9

Compound 9-f (72.00 mg, 105.93 µmol, 1.00 eq) was dissolved in dichloromethane (6.00 mL), and trifluoroacetic acid (4.62 g, 40.52 mmol, 1.5 mL) was added thereto. The reaction solution was stirred at room temperature for 2 hours. After the reaction was completed, the reaction solution was spin-dried to give a crude product. The crude product was purified by preparative HPLC (under trifluoroacetic acid condition), and lyophilized to give the product of compound 9 (59.00 mg, yield: 88%). $^1$H NMR (400 MHz, DMSO-$d_6$) δ=10.06 (s, 1H), 8.64-8.50 (m, 1H), 7.62-7.52 (m, 1H), 7.47-7.38 (m, 1H), 7.30-7.08 (m, 3H), 5.29-5.21 (m, 2H), 4.59-4.65 (m, 1H), 3.95-3.89 (m, 1H), 3.75-3.65 (m, 3H), 3.42-3.31 (m, 1H), 2.83-2.62 (m, 1H), 2.62-2.53 (m, 1H), 1.90-1.56 (m, 5H), 1.52-1.38 (m, 1H), 1.34 (s, 9H); LCMS m/z=624.1 [M+H]$^+$, 646.1 [M+Na]$^+$.

Example 10: Compound 10

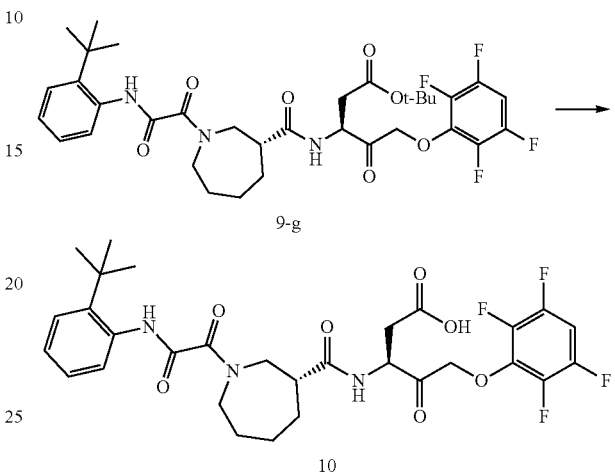

Step 1: Synthesis of Compound 10

Compound 9-g (53.00 mg, 77.98 µmol, 1.00 eq) was dissolved in dichloromethane (5.00 mL), and trifluoroacetic acid (4.62 g, 40.52 mmol, 1.50 mL) was added thereto. The reaction solution was stirred at room temperature for 2 hours. After the reaction was completed, the reaction solution was spin-dried to give a crude product. The crude product was purified by preparative HPLC (under trifluoroacetic acid condition), and lyophilized to give the product of compound 10 (59.00 mg, yield: 88%). $^1$H NMR (400 MHz, DMSO-$d_6$) δ=10.03 (s, 1H), 8.58 (dd, J=7.4, 11.2 Hz, 1H), 7.62-7.42 (m, 1H), 7.46-7.40 (m, 1H), 7.29-7.18 (m, 2H), 7.16-7.08 (m, 1H), 5.34-5.15 (m, 2H), 4.62 (t, J=6.8 Hz, 1H), 3.95 (dt, J=5.0, 13.2 Hz, 1H), 3.85-3.68 (m, 1H), 3.59 (dd, J=9.9, 14.4 Hz, 1H), 3.30-3.22 (m, 1H), 2.83-2.69 (m, 2H), 2.67-2.55 (m, 1H), 1.89-1.57 (m, 4H), 1.52-1.38 (m, 1H), 1.34 (s, 9H); LCMS m/z=624.1 [M+H]$^+$, 646.2 [M+Na]$^+$.

Example 11: Compound 11

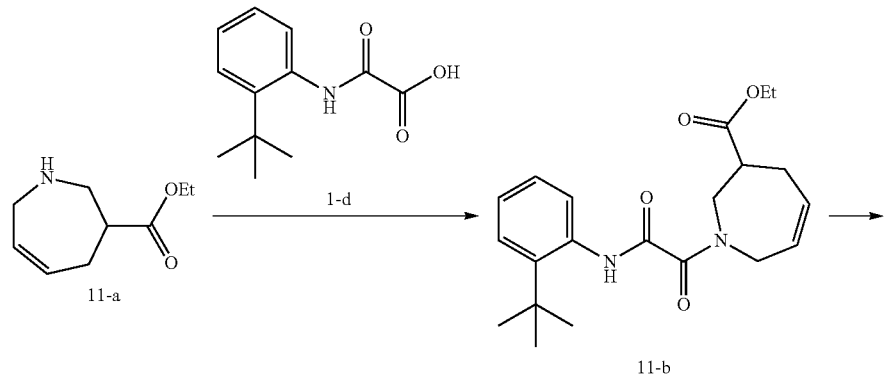

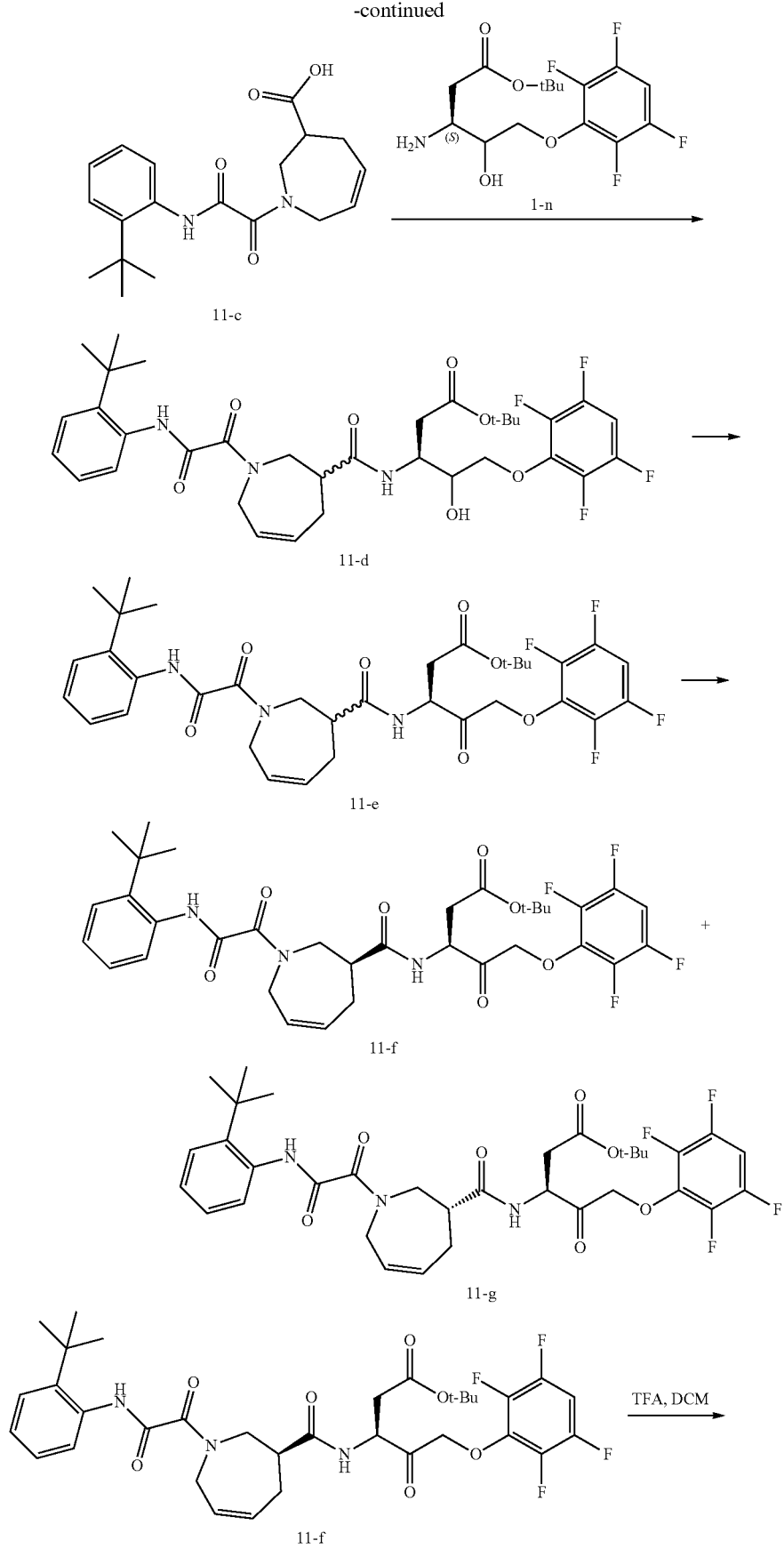

-continued

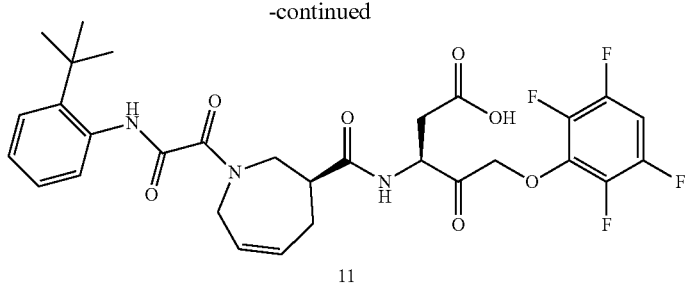

11

Step 1: Synthesis of Compound 11-b

Compound 1-d (1.15 g, 5.19 mmol, 1.40 eq) and HOBt (751.94 mg, 5.57 mmol, 1.50 eq) were dissolved in dichloromethane (80 mL), added with EDCl (1.07 g, 5.57 mmol, 1.50 eq), and stirred at room temperature for 15 min. Compound 11-a (627.33 mg, 3.71 mmol, 1.00 eq) and N,N-diisopropylethylamine (958.96 mg, 7.42 mmol, 1.30 mL, 2.00 eq) were then dissolved in dichloromethane, added to the above solution, and stirred at room temperature for 65 hours. After the reaction was completed, the reaction solution was added with 150 mL of water and separated, and the aqueous phase was further extracted with dichloromethane (200 mL×2). The organic phases were combined, and washed with saturated sodium hydrogen carbonate solution (150 mL) and saturated brine (100 mL). The organic phase was dried over anhydrous sodium sulfate, filtered, concentrated, and separated by column chromatography (petroleum ether:ethyl acetate=1:0~5:1) to give the product of compound 11-b (430.00 mg, yield: 27%). LCMS m/z=395.1 [M+Na]$^+$.

Step 2: Synthesis of Compound 11-c

Compound 11-b (430.00 mg, 1.15 mmol, 1.00 eq) was dissolved in tetrahydrofuran (10.00 mL), and a solution of LiOH.H$_2$O (96.88 mg, 2.31 mmol, 2.00 eq) dissolved in water (10.00 mL) was added to the above solution. The reaction solution was maintained at 25° C. and stirred for 2 hours. After the reaction was completed, the reaction solution was adjusted to pH of 6 with 2N dilute hydrochloric acid, added with 200 mL of water, and extracted with dichloromethane (200 mL×3). The organic phase was dried over anhydrous sodium sulfate, filtered and concentrated to give the product of compound 11-c (408.00 mg, crude) as a pale yellow oil, which was used directly in the next step without purification. LCMS m/z=367.1 [M+Na]$^+$.

Step 3: Synthesis of Compound 11-d

Compound 11-c (396.06 mg, 1.15 mmol, 1.15 eq) and HOBt (189.17 mg, 1.40 mmol, 1.40 eq) were dissolved in dichloromethane (10 mL), added with EDCl (268.38 mg, 1.40 mmol, 1.40 eq), and stirred at room temperature for 15 min. Compound 1-n (353.31 mg, 1.00 mmol, 1.00 eq) and NMM (303.45 mg, 3.00 mmol, 329.84 μL, 3.00 eq) were then dissolved in dichloromethane, added to the above solution, and stirred at room temperature for 18 hours. After the reaction was completed, the reaction solution was added with 80 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 11-d (500.00 mg, yield: 72%) as a yellow oil. LCMS m/z=702.3 [M+Na]$^+$.

Step 4: Synthesis of Compounds 11-e, 11-f and 11-g

Compound 11-d (500.00 mg, 735.62 μmol, 1.00 eq) was dissolved in dichloromethane (10.00 mL), and PIDA (947.77 mg, 2.94 mmol, 4.00 eq) and TEMPO (23.14 mg, 147.12 μmol, 0.20 eq) were added thereto. The reaction solution was stirred at room temperature for 54 hours. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was subjected to column chromatography (petroleum ether:ethyl acetate=1:0~3:1) to give the product of compound 11-e (325.00 mg, yield: 63%) as yellow oil. LCMS m/z=702.2 [M+Na]$^+$. Compound 11-e was separated via SFC (Column: Chiralpak AD-3 100×4.6 mm I.D., 3 um; Mobile phase: A: CO$_2$, B: isopropanol (0.05% diethylamine); Gradient: 5%~40% of mobile phase B (0-4.5 min), hold 40% of mobile phase B for 2.5 min, and 5% of mobile phase B for 1.0 min; Flow rate: 2.8 mL/min; Column temp.: 40° C.), to give compounds 11-f (Retention time: 2.90 min, 95% ee) and 11-g (Retention time: 3.08 min, 95% ee).

Step 5: Synthesis of Compound 11

Compound 11-f (65.00 mg, 95.92 μmol, 1.00 eq) was dissolved in dichloromethane (3.00 mL), and trifluoroacetic acid (4.62 g, 40.52 mmol, 1.5 mL) was added thereto. The reaction solution was stirred at room temperature for 2 hours. After the reaction was completed, the reaction solution was spin-dried to give a crude product. The crude product was purified by preparative HPLC (under trifluoroacetic acid condition), and lyophilized to give the product of compound 11 (58.00 mg, yield: 95%). $^1$H NMR (400 MHz, DMSO-d$_6$) δ=10.14-10.02 (m, 1H), 8.65 (t, J=12.0 Hz, 1H), 7.64-7.52 (m, 1H), 7.46-7.40 (m, 1H), 7.30-7.19 (m, 3H), 7.17-7.10 (m, 1H), 5.80-5.68 (m, 2H), 5.35-5.17 (m, 2H), 4.65 (q, J=5.9 Hz, 1H), 4.42-4.25 (m, 1H), 4.22-4.04 (m, 2H), 3.96-3.84 (m, 2H), 3.07-2.86 (m, 1H), 2.83-2.72 (m, 1H), 2.70-2.58 (m, 1H), 2.42-2.33 (m, 1H), 1.34 (s, 9H); LCMS m/z=622.1 [M+H]$^+$, 644.1 [M+Na]$^+$.

Example 12: Compound 12

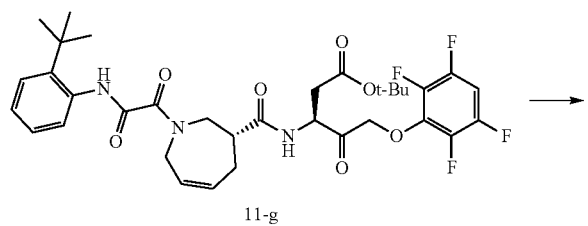

Step 1: Synthesis of Compound 12

Compound 11-g (56.00 mg, 82.63 μmol, 1.00 eq) was dissolved in dichloromethane (3.00 mL), and trifluoroacetic acid (4.62 g, 40.52 mmol, 1.5 mL) was added thereto. The reaction solution was stirred at room temperature for 2 hours. After the reaction was completed, the reaction solution was spin-dried to give a crude product. The crude product was purified by preparative HPLC (under trifluoroacetic acid condition), and lyophilized to give the product of compound 12 (49.00 mg, yield: 93%). $^1$H NMR (400 MHz, DMSO-$d_6$) δ=10.13-10.00 (m, 1H), 8.62 (dd, J=7.5, 19.1 Hz, 1H), 7.66-7.52 (m, 1H), 7.47-7.39 (m, 1H), 7.31-7.20 (m, 2H), 7.16-7.09 (m, 1H), 5.75 (br. s., 2H), 5.35-5.16 (m, 2H), 4.70-4.59 (m, 1H), 4.35-4.13 (m, 1H), 4.09 (br. s., 1H), 3.95-3.87 (m, 2H), 3.73-3.67 (m, 1H), 3.06-2.88 (m, 1H), 2.84-2.72 (m, 1H), 2.68-2.58 (m, 1H), 2.39-2.32 (m, 1H), 1.34 (s, 9H); LCMS m/z=622.1 [M+H]$^+$, 644.3 [M+Na]$^+$.

Example 13: Compound 13

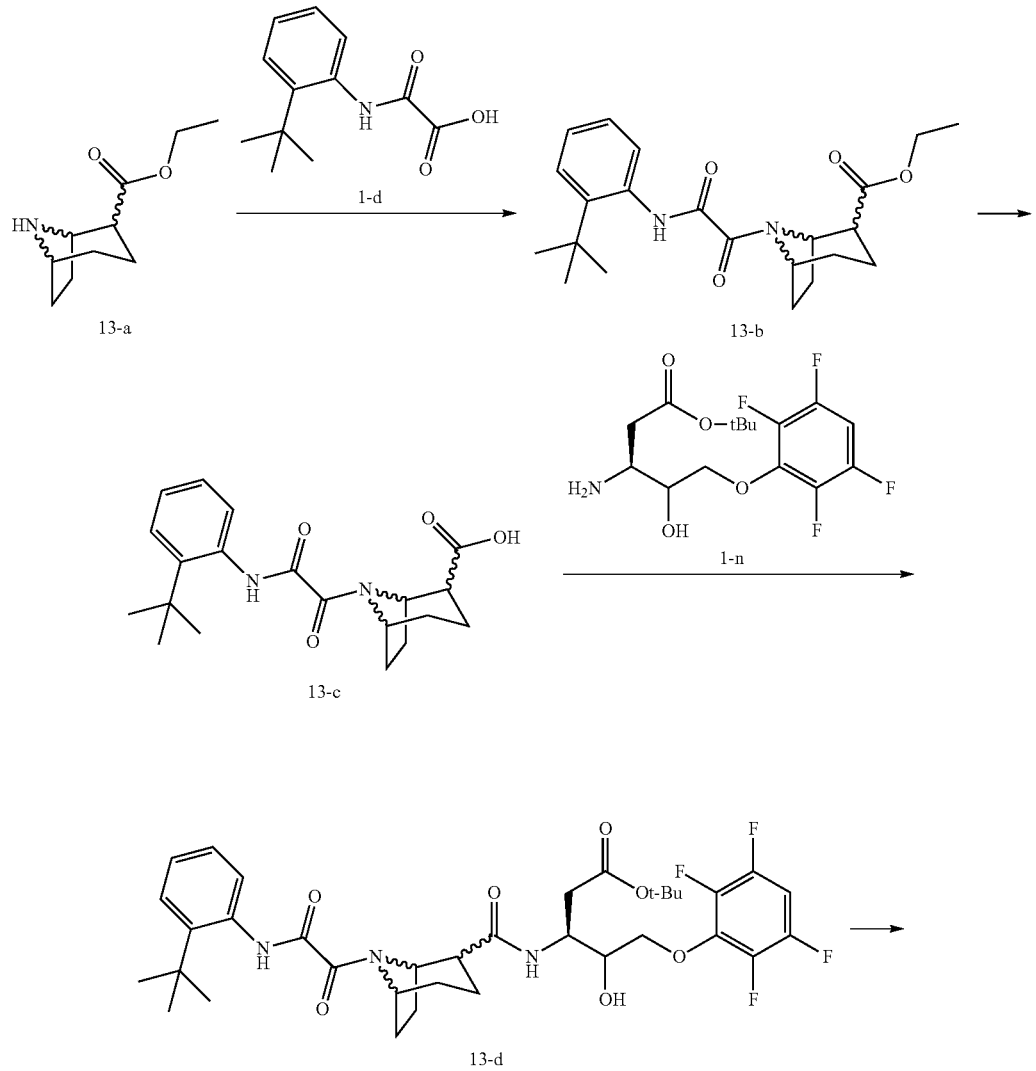

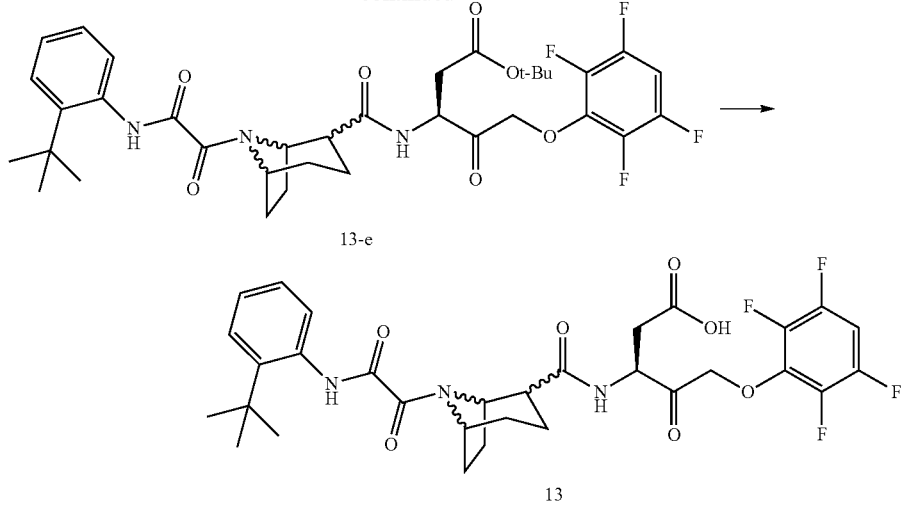

Step 1: Synthesis of Compound 13-b

Compound 1-d (1.00 g, 4.52 mmol, 1.00 eq) was dissolved in dichloromethane (8.00 mL), and HOBt (836.68 mg, 6.19 mmol, 1.37 eq) and EDCl (1.19 g, 6.19 mmol, 1.37 eq) were added thereto at 0° C. The above solution was stirred at 0° C. for 10 min, and then added with compound 13-a (993.04 mg, 4.52 mmol, 1.00 eq, HCl) and NMM (1.37 g, 13.56 mmol, 3.00 eq). The reaction solution was stirred at 20° C. for 39 hours. After the reaction was completed, the reaction solution was added with 50 mL of water, and extracted with dichloromethane (50 mL×3). The organic phase was dried over anhydrous sodium sulfate, filtered and concentrated to give a crude product. The crude product was subjected to column chromatography (petroleum ether:ethyl acetate=1:0~3:1) to give the product of compound 13-b (1.00 g, yield: 56%) as a colorless oil. $^1$H NMR (400 MHz, CHLOROFORM-d) δ=9.71-9.84 (m, 1H), 7.93-8.06 (m, 1H), 7.41 (d, J=7.28 Hz, 1H), 7.21-7.26 (m, 1H), 7.10-7.19 (m, 1H), 5.67-6.11 (m, 1H), 4.77-5.20 (m, 1H), 3.92-4.16 (m, 2H), 2.61 (dd, J=5.77, 19.07 Hz, 1H), 2.22-2.45 (m, 1H), 1.73-2.18 (m, 5H), 1.47 (d, J=12.30 Hz, 9H), 1.18-1.30 (m, 3H).

Step 2: Synthesis of Compound 13-c

Compound 13-b (1.00 g, 2.59 mmol, 1.00 eq) was dissolved in methanol (10.00 mL), and a solution of LiOH.H$_2$O (325.71 mg, 7.77 mmol, 3.00 eq) dissolved in water (15.00 mL) was added to the above solution. The reaction solution was maintained at 20° C. and stirred for 15 hours. After the reaction was completed, the reaction solution was adjusted to pH of 6 with 2 N dilute hydrochloric acid, added with 50 mL of water, and extracted with ethyl acetate (60 mL×3). The organic phase was dried over anhydrous sodium sulfate, filtered and concentrated to give compound 13-c (940.00 mg, crude) as a colorless solid, which was used directly in the next step without purification. $^1$H NMR (400 MHz, CHLOROFORM-d) δ=9.66-9.79 (m, 1H), 7.76-8.05 (m, 1H), 7.37-7.46 (m, 1H), 7.09-7.26 (m, 2H), 5.62-6.07 (m, 1H), 4.74-5.20 (m, 1H), 2.55 (dd, J=5.52, 16.06 Hz, 1H), 2.06-2.37 (m, 2H), 1.62-2.02 (m, 6H), 1.43-1.48 (m, 9H).

Step 3: Synthesis of Compound 13-d

Compound 1-n (200.00 mg, 566.08 μmol, 1.00 eq) was dissolved in dichloromethane (12.00 mL), and compound 13-c (202.90 mg, 566.08 μmol, 1.00 eq), EDCl (148.67 mg, 775.53 μmol, 1.37 eq), HOBt (104.79 mg, 775.53 μmol, 1.37 eq) and NMM (171.78 mg, 1.70 mmol, 186.72 μL, 3.00 eq) were added thereto. The reaction solution was stirred at 27° C. for 16 hours under the protection of nitrogen gas. After the reaction was completed, the reaction solution was added with 80 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 13-d (220.00 mg, yield: 55%) as a colorless oil. $^1$H NMR (400 MHz, CHLOROFORM-d) δ=9.53-10.11 (m, 1H), 7.84-8.03 (m, 1H), 7.34-7.48 (m, 1H), 6.94-7.26 (m, 2H), 6.68-6.85 (m, 1H), 5.66-6.05 (m, 1H), 5.33-5.56 (m, 1H), 4.77-5.09 (m, 1H), 4.16-4.47 (m, 2H), 3.74-4.09 (m, 1H), 2.07-2.90 (m, 5H), 1.72-2.03 (m, 5H), 1.52-1.64 (m, 1H), 1.35-1.51 (m, 18H).

Step 4: Synthesis of Compound 13-e

Compound 13-d (270.00 mg, 389.21 μmol, 1.00 eq) was dissolved in dichloromethane (10.00 mL), and PIDA (485.16 mg, 1.51 mmol, 3.87 eq) and TEMPO (12.24 mg, 77.84 μmol, 0.20 eq) were added thereto. The reaction solution was stirred at 27° C. for 16 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was subjected to column chromatography (petroleum ether:ethyl acetate=1:0~2:1) to give the product of compound 13-e (220.00 mg, yield: 76%) as a pale yellow oil. $^1$H NMR (400 MHz, CHLOROFORM-d) δ=9.56-9.95 (m, 1H), 7.81-8.11 (m, 1H), 7.38-7.51 (m, 1H), 7.09-7.26 (m, 2H), 6.65-6.83 (m, 1H), 5.49-6.05 (m, 1H), 4.65-5.29 (m, 4H), 2.07-3.04 (m, 5H), 1.63-2.04 (m, 5H), 1.59 (br. s., 1H), 1.39-1.49 (m, 18H).

Step 5: Synthesis of Compound 13

Compound 13-e (200.00 mg, 289.14 μmol, 1.00 eq) was dissolved in dichloromethane (6.00 mL), and trifluoroacetic acid (4.74 g, 41.59 mmol, 3.08 mL, 143.85 eq) was added thereto. The reaction solution was stirred at 27° C. for 1 hour under the protection of nitrogen gas. After the reaction was completed, the reaction solution was spin-dried to give a crude product. The crude product was purified by preparative HPLC (under trifluoroacetic acid condition), and lyophilized to give a solid product. The solid was dissolved in acetonitrile (20 mL), added with hydrochloric acid solution (0.1 M, 20 mL), mixed uniformly, and lyophilized to give compound 13 (128.50 mg, yield: 70%). $^1$HNMR (400 MHz, DMSO-$d_6$) δ=9.59-10.05 (m, 1H), 8.37-8.61 (m, 1H), 6.97-7.68 (m, 5H), 4.80-5.68 (m, 3H), 4.40-4.68 (m, 2H), 2.55-2.84 (m, 3H), 1.39-2.34 (m, 9H), 1.27-1.38 (m, 9H); LCMS m/z=636.1 [M+H]$^+$.

Example 14: Compound 14

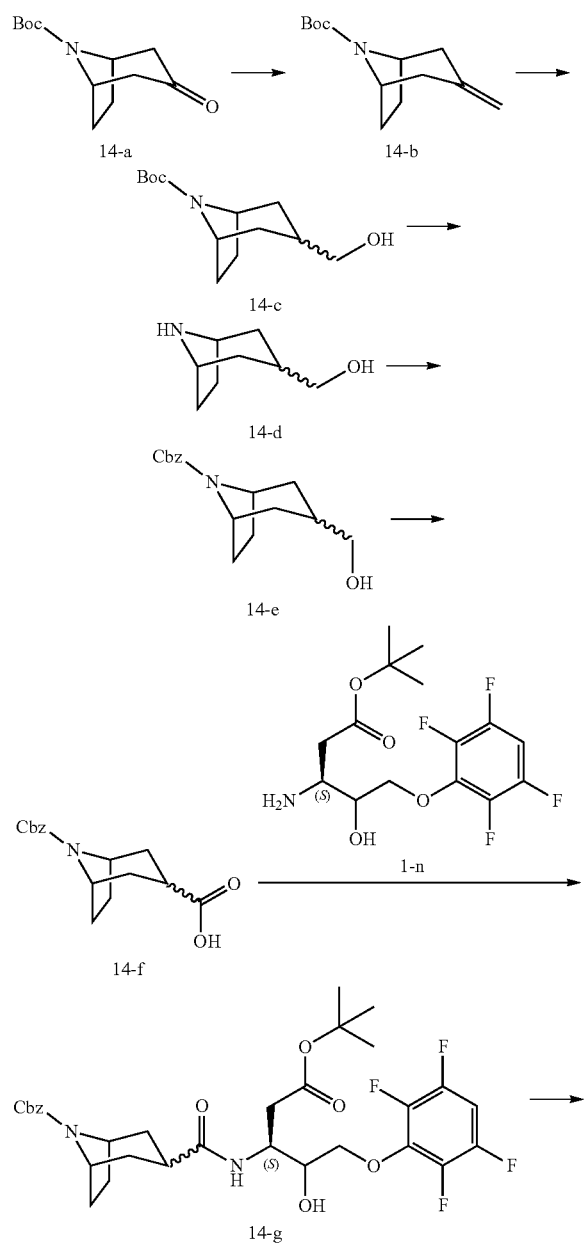

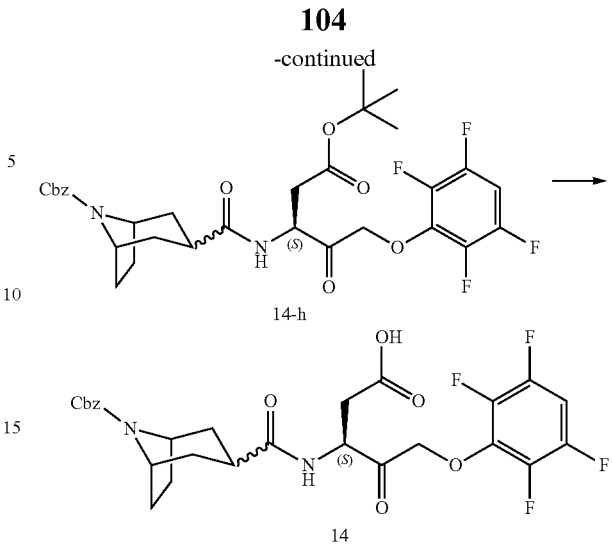

Step 1: Synthesis of Compound 14-b

A mixed solution of t-BuOK (6.97 g, 62.14 mmol, 1.40 eq) and anhydrous tetrahydrofuran (260 mL) was cooled with an ice bath, and then added with methyltriphenylphosphonium bromide (23.15 g, 64.81 mmol, 1.46 eq) with stirring under the protection of nitrogen gas. After the addition was completed, the above mixed solution was stirred in the ice bath for 15 min, followed by heating to 70° C. for 45 min. After cooling down to 15° C., a solution of compound 14-a (10.00 g, 44.39 mmol, 1.00 eq) dissolved in anhydrous tetrahydrofuran (50 mL) was added dropwise thereto. After the dropwise addition was completed, the reaction solution was maintained at 15° C. and stirred for 2 hours. After the reaction was completed, the reaction solution was added with acetone (44 mL) for quenching, and the solid was removed by filtering. The filtrate was evaporated to remove the solvent therein, added with water (200 mL), and extracted with ethyl acetate (300 mL×3). The organic phase was dried over anhydrous sodium sulfate, filtered and concentrated to give a crude product. The crude product was subjected to column chromatography (petroleum ether:ethyl acetate=1:0~10:1) to give the product of compound 14-b (10.00 g, yield: 93%) as a colorless oil. $^1$H NMR (400 MHz, CHLOROFORM-d) δ=4.84 (s, 2H), 4.15-4.33 (m, 2H), 2.34-2.59 (m, 2H), 2.08 (s, 2H), 1.82-1.90 (m, 2H), 1.53-1.61 (m, 2H), 1.47 (s, 9H).

Step 2: Synthesis of Compound 14-c

Compound 14-b (10.62 g, 47.56 mmol, 1.00 eq) was dissolved in tetrahydrofuran (1.10 L), and BH$_3$.THF (1 M, 95.11 mL, 2.00 eq) was added to the above solution at 0° C. After the addition was completed, the reaction solution was slowly warmed up to 15° C., and stirred at this temperature for 16 hours. The reaction solution was then cooled down to 0° C., and sodium hydroxide solution (2 M, 53.03 mL, 2.23 eq) and H$_2$O$_2$ (30% aqueous solution, 26 mL) were successively added. After the addition was completed, the reaction solution was warmed up to 15° C., and stirred for 2 hours. After the reaction was completed, the reaction solution was quenched with saturated sodium hydrogen carbonate (500 mL), and added with water (500 mL) and ethyl acetate (800 mL) for extraction. The organic phase was washed respectively with saturated NaHSO$_3$ (500 mL×2) and saturated brine (500 mL), then dried over anhydrous sodium sulfate, filtered and concentrated to give a crude product. The crude product was subjected to column chromatography (petroleum ether:ethyl acetate=5:1~1:1) to give the product of compound 14-c (9.70 g, yield: 67%) as a colorless oil. $^1$H NMR (400 MHz, CHLOROFORM-d) δ=4.11-4.27 (m, 2H), 3.63 (d, J=8.03 Hz, 2H), 2.04-2.26 (m, 2H), 1.96 (d, J=4.52 Hz, 2H), 1.81-1.89 (m, 2H), 1.53-1.64 (m, 2H), 1.45 (s, 9H), 1.41 (br. s., 1H).

Step 3: Synthesis of Compound 14-d

Compound 14-c (8.00 g, 33.15 mmol, 1.00 eq) was dissolved in dichloromethane (60.00 mL), and HCl/EtOAc (4 M, 100.03 mL, 12.07 eq) was added thereto at 0° C. The reaction solution was stirred at 0° C. for 10 min, and further stirred at 20° C. for 50 min. After the reaction was completed, the reaction solution was concentrated to give the product of compound 14-d (4.50 g, crude), which was used directly in the next step without purification. $^1$H NMR (400 MHz, DMSO-$d_6$) δ=3.85 (br. s., 2H), 3.39 (br. s., 2H), 2.02-2.12 (m, 2H), 1.91-2.01 (m, 2H), 1.72-1.86 (m, 3H), 1.67 (d, J=14.56 Hz, 2H).

Step 4: Synthesis of Compound 14-e

Compound 14-d (4.50 g, 25.33 mmol, 1.00 eq, HCl) was dissolved in acetonitrile (80.00 mL), and triethylamine (7.69 g, 75.99 mmol, 3.00 eq) was added thereto. The above solution was cooled down to 0° C., and added with CbzCl (6.48 g, 38.00 mmol, 1.50 eq). After the addition was completed, the reaction solution was warmed up to 20° C., and stirred for 16 hours. After the reaction was completed, the reaction solution was added with 100 mL of water, and extracted with dichloromethane (150 mL×3). The organic phases were combined, dried over anhydrous sodium sulfate, filtered and concentrated to give a crude product. The crude product was subjected to column chromatography (petroleum ether:ethyl acetate=5:1~1:1) to give the product of compound 14-e (5.00 g, yield: 70%) as a colorless oil. $^1$H NMR (400 MHz, CHLOROFORM-d) δ=7.28-7.41 (m, 5H), 5.15 (s, 2H), 4.29 (br. s., 2H), 3.65 (d, J=7.03 Hz, 2H), 2.06-2.27 (m, 2H), 1.94-2.04 (m, 2H), 1.81-1.92 (m, 1H), 1.63 (d, J=7.28 Hz, 2H), 1.49 (d, J=14.05 Hz, 2H).

Step 5: Synthesis of Compound 14-f

Compound 14-e (2.50 g, 9.08 mmol, 1.00 eq) was dissolved in a mixed solution of acetonitrile (8.30 mL), ethyl acetate (8.30 mL) and water (12.50 mL), and NaIO$_4$ (8.93 g, 41.77 mmol, 4.60 eq) and RuCl$_3$—H$_2$O (102.35 mg, 454.00 µmol, 0.05 eq) were added successively thereto. The reaction solution stirred at 20° C. for 16 hours. After the reaction was completed, the reaction solution was added with 150 mL of water, and extracted with dichloromethane (150 mL×3). The organic phases were combined, dried over anhydrous sodium sulfate, filtered and concentrated to give a crude product. The crude product was subjected to column chromatography (petroleum ether:ethyl acetate=5:1~1:2) to give the product of compound 14-f (1.82 g, yield: 64%). $^1$H NMR (400 MHz, CHLOROFORM-d) δ=7.29-7.40 (m, 5H), 5.16 (s, 2H), 4.30 (d, J=9.03 Hz, 2H), 2.67-2.76 (m, 1H), 2.30 (d, J=14.05 Hz, 2H), 2.13 (d, J=8.78 Hz, 1H), 2.04 (d, J=15.06 Hz, 1H), 1.87-1.96 (m, 2H), 1.78 (d, J=8.53 Hz, 2H).

Step 6: Synthesis of Compound 14-g

Compound 1-n (700.00 mg, 1.98 mmol, 1.00 eq) was dissolved in dichloromethane (36.00 mL), and compound 14-f (573.24 mg, 1.98 mmol, 1.00 eq), EDCl (520.34 mg, 2.71 mmol, 1.37 eq), HOBt (366.76 mg, 2.71 mmol, 1.37 eq) and NMM (601.21 mg, 5.94 mmol, 653.49 µL, 3.00 eq) were added thereto. The reaction solution was stirred at 27° C. for 16 hours under the protection of nitrogen gas. After the reaction was completed, the reaction solution was added with 150 mL of water, and extracted with dichloromethane (150 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 14-g (600.00 mg, yield: 44%) as a brownish yellow oil. $^1$H NMR (400 MHz, CHLOROFORM-d) δ=7.29-7.41 (m, 5H), 6.75-6.87 (m, 1H), 6.37-6.68 (m, 1H), 5.15 (s, 2H), 4.11-4.44 (m, 6H), 3.61 (br. s., 1H), 2.52-2.82 (m, 2H), 2.49 (br. s., 1H), 2.16-2.30 (m, 1H), 2.06-2.14 (m, 1H), 1.71-2.04 (m, 6H), 1.42-1.51 (m, 9H).

Step 7: Synthesis of Compound 14-h

Compound 14-g (250.00 mg, 400.24 µmol, 1.00 eq) was dissolved in dichloromethane (10.00 mL), and PIDA (498.91 mg, 1.55 mmol, 3.87 eq) and TEMPO (12.59 mg, 80.05 µmol, 0.20 eq) were added thereto. The reaction solution was stirred at 27° C. for 16 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was subjected to column chromatography (petroleum ether:ethyl acetate=1:0~2:1) to give the product of compound 14-h (200.00 mg, yield: 75%) as a pale yellow oil. $^1$H NMR (400 MHz, CHLOROFORM-d) δ=7.29-7.41 (m, 5H), 6.81 (tt, J=7.22, 9.85 Hz, 1H), 6.73 (d, J=7.28 Hz, 1H), 4.93-5.19 (m, 5H), 4.29 (br. s., 2H), 2.98 (dd, J=4.64, 16.69 Hz, 1H), 2.79 (dd, J=5.14, 16.69 Hz, 1H), 2.54 (br. s., 1H), 2.07-2.28 (m, 2H), 1.65-2.05 (m, 6H), 1.43 (s, 9H).

Step 8: Synthesis of Compound 14

Compound 14-h (180.00 mg, 289.11 µmol, 1.00 eq) was dissolved in dichloromethane (6.00 mL), and trifluoroacetic acid (4.74 g, 41.59 mmol, 3.08 mL, 143.85 eq) was added thereto. The reaction solution was stirred at 27° C. for 1 hour under the protection of nitrogen gas. After the reaction was completed, the reaction solution was spin-dried to give a crude product. The crude product was purified by preparative HPLC (under trifluoroacetic acid condition), and lyophilized to give a solid product. The solid was dissolved in acetonitrile (20 mL), added with hydrochloric acid solution (0.1 M, 20 mL), mixed uniformly, and lyophilized to give compound 14 (86.80 mg, yield: 53%). $^1$H NMR (400 MHz, DMSO-$d_6$) δ=8.32 (d, J=7.03 Hz, 1H), 7.50-7.65 (m, 1H), 7.27-7.41 (m, 5H), 5.23 (s, 2H), 5.08 (s, 2H), 4.64 (q, J=6.86 Hz, 1H), 4.08 (br. s., 2H), 2.73-2.87 (m, 1H), 2.52-2.61 (m, 2H), 1.84-2.10 (m, 4H), 1.71 (br. s., 4H); LCMS m/z=567.1 [M+H]$^+$.

Example 15: Compound 15

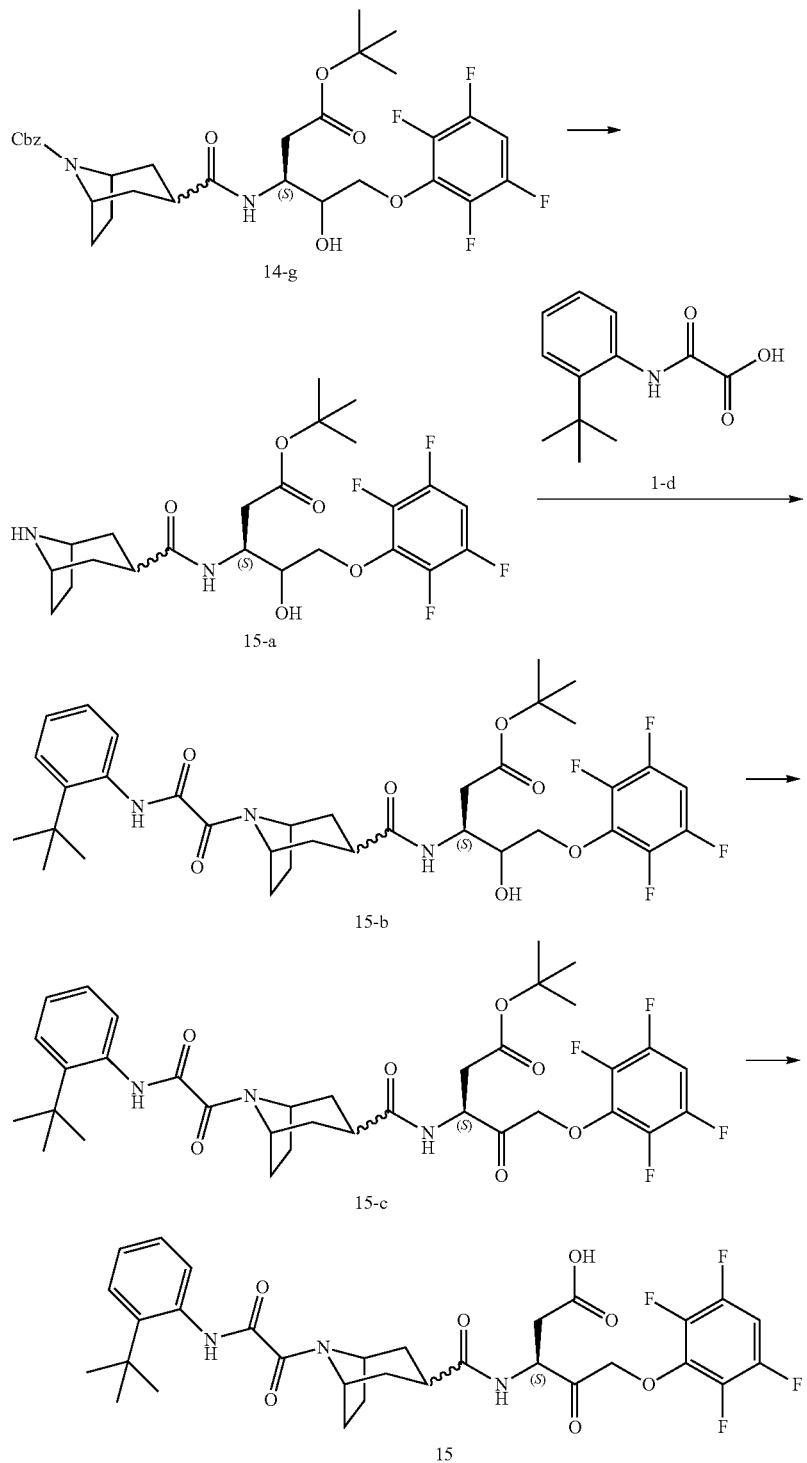

Step 1: Synthesis of Compound 15-a

Compound 14-g (350.00 mg, 560.34 μmol, 1.00 eq) was dissolved in methanol (15.00 mL), and Pd/C (80.00 mg, purity of 10%) was added to the solution. The reaction solution was stirred at 27° C. for 6 hours in a hydrogen atmosphere (hydrogen balloon). After the reaction was completed, the reaction solution was filtered through diatomaceous earth, and the filter cake was washed with methanol (100 mL). The resulting filtrate was concentrated to give the product of compound 15-a (250.00 mg, crude) as a pale yellow oil, which was used directly in the next step without purification. LCMS m/z=491.2 [M+H]$^+$.

Step 2: Synthesis of Compound 15-b

Compound 15-a (200.00 mg, 407.76 μmol, 1.00 eq) was dissolved in dichloromethane (8.00 mL), and compound 1-d (90.22 mg, 407.76 μmol, 1.00 eq), EDCl (107.09 mg, 558.63 μmol, 1.37 eq), HOBt (75.48 mg, 558.63 μmol, 1.37 eq) and NMM (123.73 mg, 1.22 mmol, 134.49 μL, 3.00 eq) were added thereto. The reaction solution was stirred at 27° C. for 16 hours under the protection of nitrogen gas. After the reaction was completed, the reaction solution was added with 100 mL of water, and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 15-b (112.00 mg, yield: 33%) as a colorless oil. $^1$H NMR (400 MHz, CHLOROFORM-d) δ=9.80 (br. s., 1H), 7.99 (d, J=8.03 Hz, 1H), 7.43 (d, J=8.03 Hz, 1H), 7.25 (s, 1H), 7.12-7.20 (m, 1H), 6.82 (tt, J=7.15, 9.91 Hz, 1H), 6.67 (dd, J=3.76, 8.03 Hz, 1H), 5.61 (br. s., 1H), 4.74-4.84 (m, 1H), 4.17-4.46 (m, 3H), 3.57 (d, J=3.26 Hz, 1H), 2.54-2.83 (m, 3H), 2.16-2.41 (m, 4H), 1.81-2.05 (m, 4H), 1.41-1.51 (m, 18H).

Step 3: Synthesis of Compound 15-c

Compound 15-b (112.00 mg, 161.45 μmol, 1.00 eq) was dissolved in dichloromethane (6.00 mL), and PIDA (201.25 mg, 624.81 μmol, 3.87 eq) and TEMPO (5.08 mg, 32.29 μmol, 0.20 eq) were added thereto. The reaction solution was stirred at 27° C. for 16 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was subjected to column chromatography (petroleum ether:ethyl acetate=1:0~2:1) to give the product of compound 15-c (88.00 mg, yield: 77%) as a colorless oil. $^1$H NMR (400 MHz, CHLOROFORM-d) δ=9.80 (br. s., 1H), 7.99 (dd, J=3.76, 7.03 Hz, 1H), 7.43 (d, J=7.28 Hz, 1H), 7.25-7.29 (m, 1H), 7.13-7.20 (m, 1H), 6.72-6.87 (m, 2H), 5.63 (br. s., 1H), 4.95-5.16 (m, 3H), 4.79 (br. s., 1H), 3.00 (dd, J=4.89, 16.69 Hz, 1H), 2.82 (ddd, J=1.88, 5.02, 16.69 Hz, 1H), 2.63 (t, J=7.78 Hz, 1H), 2.14-2.45 (m, 4H), 1.79-2.05 (m, 4H), 1.46 (d, J=17.32 Hz, 18H).

Step 4: Synthesis of Compound 15

Compound 15-c (110.00 mg, 159.03 μmol, 1.00 eq) was dissolved in dichloromethane (4.00 mL), and trifluoroacetic acid (2.61 g, 22.88 mmol, 1.69 mL, 143.85 eq) was added thereto. The reaction solution was stirred at 27° C. for 1 hour under the protection of nitrogen gas. After the reaction was completed, the reaction solution was spin-dried to give a crude product. The crude product was purified by preparative HPLC (under trifluoroacetic acid condition), and lyophilized to give the product of compound 15 (43.40 mg, yield: 43%). $^1$H NMR (400 MHz, DMSO-$d_6$) δ=10.00 (s, 1H), 8.38 (d, J=7.03 Hz, 1H), 7.50-7.69 (m, 1H), 7.38-7.46 (m, 1H), 7.28-7.34 (m, 1H), 7.19-7.27 (m, 2H), 5.25 (s, 2H), 4.77 (br. s., 1H), 4.66 (d, J=3.51 Hz, 1H), 4.50 (br. s., 1H), 2.74-2.88 (m, 1H), 2.54-2.69 (m, 2H), 1.96-2.23 (m, 4H), 1.62-1.89 (m, 4H), 1.35 (s, 9H); LCMS m/z=636.2 [M+H]$^+$.

Example 16: Compound 16

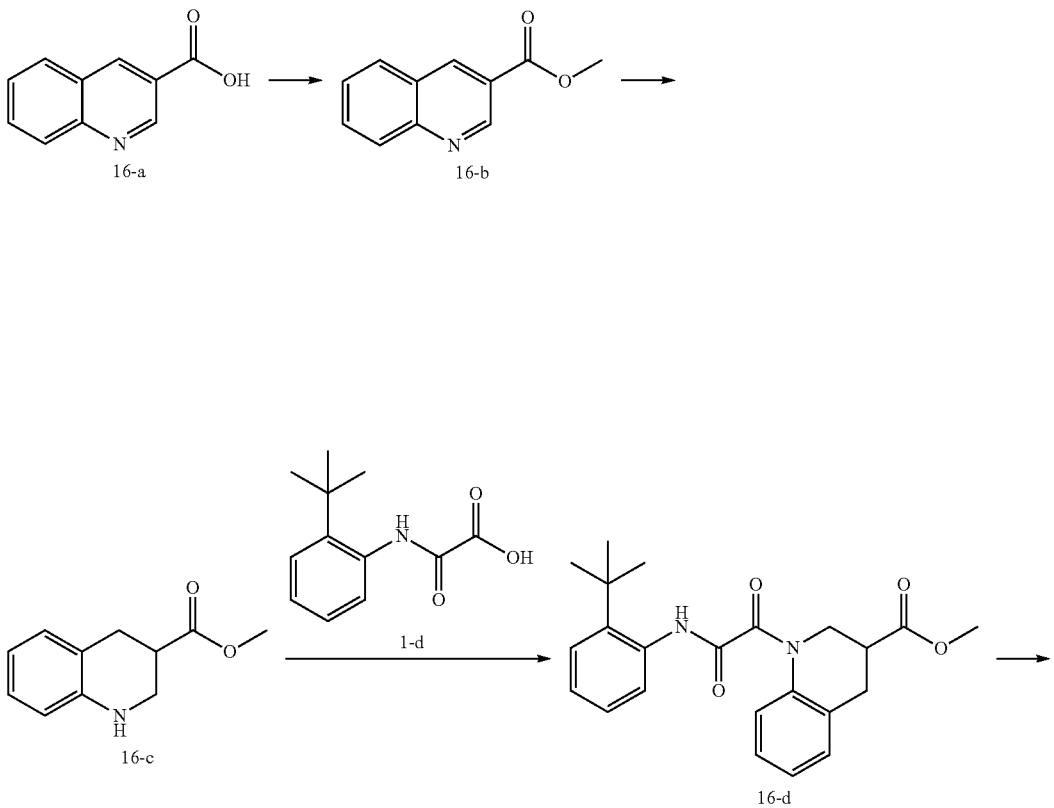

-continued
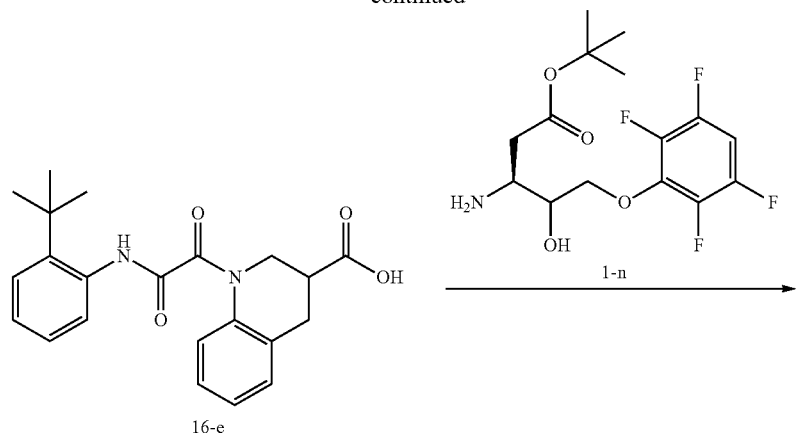
16-e
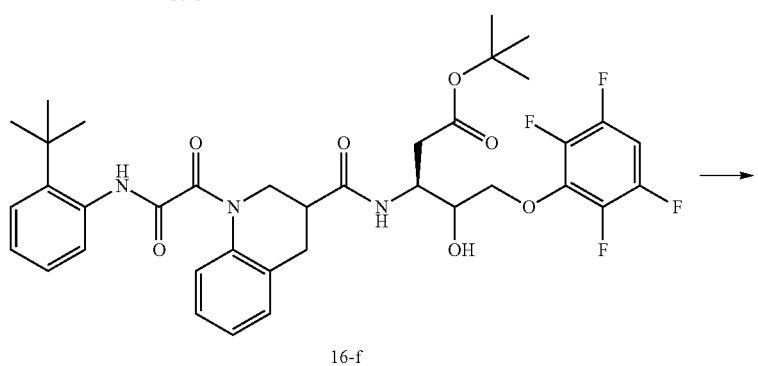
16-f
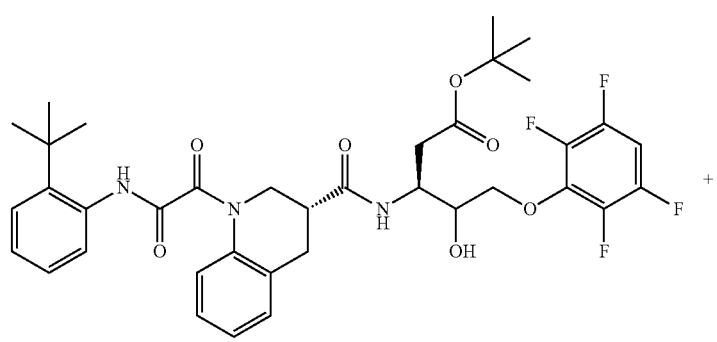
16-g
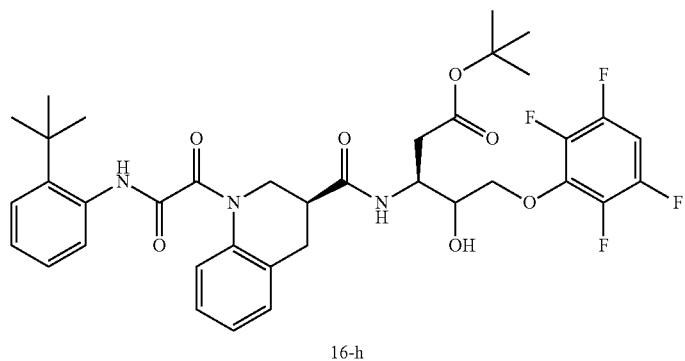
16-h

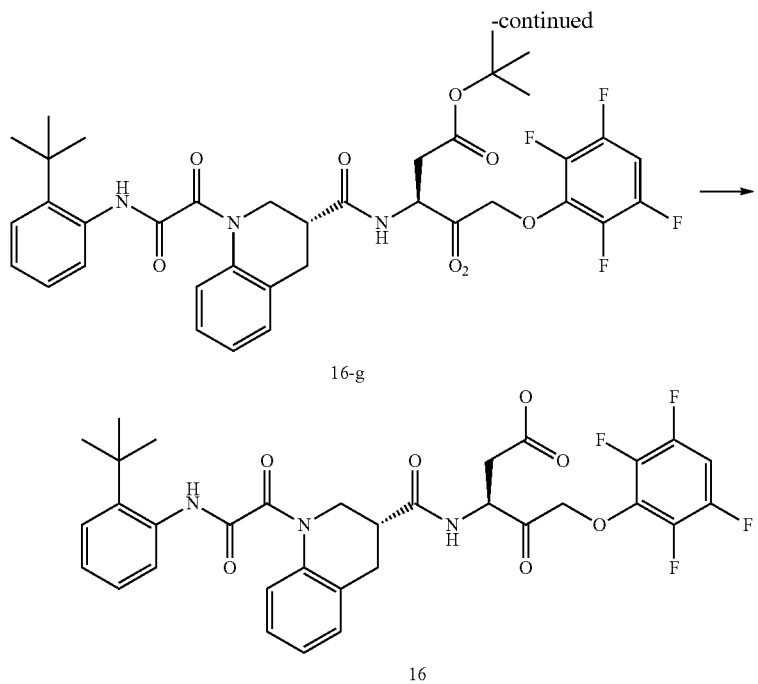

16-g

16

Step 1: Synthesis of Compound 16-b

Compound 16-a (1.00 g, 5.77 mmol, 1.00 eq) was dissolved in methanol (15.00 mL), and thionyl chloride (2.06 g, 17.31 mmol, 1.26 mL, 3.00 eq) was added thereto at 0° C. The above reaction solution was stirred at 80° C. for 14 hours. After the reaction was completed, the reaction solution was spin-dried, to give the product of compound 16-b (1.00 g, crude), which was used directly in the next step without purification. $^1$H NMR (400 MHz, methanol) δ=9.82 (s, 1H), 9.72 (s, 1H), 8.52-8.58 (m, 1H), 8.30-8.42 (m, 2H), 8.05-8.14 (m, 1H), 4.13 (s, 3H).

Step 2: Synthesis of Compound 16-c

Compound 16-b (1.00 g, 5.34 mmol, 1.00 eq) was dissolved in methanol (12.50 mL), and NaBH$_3$CN (1.68 g, 26.70 mmol, 5.00 eq) and HCl/dioxane (4 M, 8.00 mL, 5.99 eq) were added thereto. The reaction solution was stirred at 25° C. for 12 hours. After the reaction was completed, the reaction solution was added with 50 mL of water, and adjusted to pH of 7 with saturated sodium hydrogen carbonate solution. The above solution was extracted with ethyl acetate (100 mL×3). The organic phases were combined, washed successively with brine (100 mL) and water (100 mL), dried over anhydrous sodium sulfate, filtered and concentrated to give a crude product. The crude product was subjected to column chromatography (petroleum ether:ethyl acetate=1:0~1:1) to give the product of compound 16-c (800.00 mg, yield: 65%) as a yellow oil. LCMS m/z=192.0 [M+H]$^+$.

Step 3: Synthesis of Compound 16-d

Compounds 1-d (890.88 mg, 4.03 mmol, 1.10 eq), 16-c (700.00 mg, 3.66 mmol, 1.00 eq), DIEA (1.42 g, 10.98 mmol, 1.92 mL, 3.00 eq) and HATU (2.78 g, 7.32 mmol, 2.00 eq) were dissolved in dichloromethane (10.00 mL). The solution was stirred at 25° C. for 3 hours under the protection of nitrogen gas. After the reaction was completed, the reaction solution was directly concentrated to give a crude product. The crude product was subjected to column chromatography (petroleum ether:ethyl acetate=1:0~1:1) to give the product of compound 16-d (1.10 g, yield: 72%). LCMS m/z=395.3 [M+H]$^+$.

Step 4: Synthesis of Compound 16-e

Compound 16-d (900.00 mg, 2.28 mmol, 1.00 eq) was dissolved in tetrahydrofuran (15.00 mL), and a solution of LiOH.H$_2$O (143.60 mg, 3.42 mmol, 1.50 eq) dissolved in water (15.00 mL) was added to the above solution at 0° C. The reaction solution was maintained at 25° C. and stirred for 40 min. After the reaction was completed, the reaction solution was adjusted to pH of 6 with 2 N dilute hydrochloric acid, added with 200 mL of water, and extracted with dichloromethane (200 mL×3). The organic phase was dried over anhydrous sodium sulfate, filtered and concentrated to give the product of compound 16-e (900.00 mg, crude) as a pale yellow oil, which was used directly in the next step without purification. $^1$H NMR (400 MHz, DMSO-d$_6$) δ=9.93-10.20 (m, 1H), 7.09-7.54 (m, 7H), 6.86 (d, J=7.03 Hz, 1H), 4.20 (d, J=12.30 Hz, 1H), 3.78 (br. s., 1H), 3.60 (t, J=6.27 Hz, 2H), 2.96-3.15 (m, 1H), 1.28-1.39 (m, 9H).

Step 5: Synthesis of Compound 16-f

Compound 16-e (462.84 mg, 1.31 mmol, 1.00 eq) was dissolved in dichloromethane (50.00 mL), and compound 1-n (500.00 mg, 1.31 mmol, 1.00 eq), EDCl (344.04 mg, 1.79 mmol, 1.37 eq), HOBt (242.50 mg, 1.79 mmol, 1.37 eq) and NMM (397.52 mg, 3.93 mmol, 432.09 µL, 3.00 eq) were added thereto. The reaction solution was stirred at 25° C. for 15 hours under the protection of nitrogen gas. After the reaction was completed, the reaction solution was added with 150 mL of water, and extracted with dichloromethane (150 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 16-f (516.00 mg, yield: 45%) as a colorless oil. LCMS m/z=738.3 [M+Na]⁺.

Step 6: Synthesis of Compounds 16-g and 16-h

Compound 16-f (516.00 mg, 720.94 µmol, 1.00 eq) was dissolved in dichloromethane (20.00 mL), and PIDA (898.67 mg, 2.79 mmol, 3.87 eq) and TEMPO (34.01 mg, 216.28 µmol, 0.30 eq) were added thereto. The reaction solution was stirred at 25° C. for 16 hours under the protection of nitrogen gas. After the reaction was completed, the reaction solution was added with 200 mL of ethyl acetate. The solution was washed successively with saturated sodium hydrogen carbonate (100 mL), saturated brine (50 mL) and water (50 mL). The organic phase was dried over anhydrous sodium sulfate, filtered and concentrated to give a crude product. The crude product was separated by column chromatography (petroleum ether:ethyl acetate=1: 0~2:1) and SFC (Column: Chiralcel OD-3 150×4.6 mm I.D., 3 um; Mobile phase: A: $CO_2$ B: isopropanol (0.05% diethylamine); Gradient: 5-40% of B (0-5 min), 40% of B (2.5 min), 5% of B (2.5 min); Flow rate: 2.5 mL/min; Column temp.: 35° C.) to give the colorless solid product of compounds 16-g (Retention time: 4.55 min, 136.00 mg, yield: 25%) and 16-h (Retention time: 5.65 min, 120.00 mg, yield: 23%). 16-g: LCMS m/z=714.1 [M+H]; 16-h: LCMS m/z=714.2 [M+H]⁺.

Step 7: Synthesis of Compound 16

Compound 16-g (136.00 mg, 190.55 µmol, 1.00 eq) was dissolved in dichloromethane (4.00 mL), and trifluoroacetic acid (3.13 g, 27.41 mmol, 2.03 mL, 143.85 eq) was added thereto. The reaction solution was stirred at 25° C. for 1 hour under the protection of nitrogen gas. After the reaction was completed, the reaction solution was evaporated to remove the solvent and trifluoroacetic acid therein, and lyophilized to give the product of compound 16 (118.40 mg, yield: 94%). ¹H NMR (400 MHz, DMSO-d₆) δ=9.81 (br. s., 1H), 8.86 (d, J=6.53 Hz, 1H), 7.51-7.69 (m, 1H), 7.41 (br. s., 2H), 7.10-7.33 (m, 5H), 6.83 (d, J=6.53 Hz, 1H), 5.16-5.35 (m, 2H), 4.66 (br. s., 1H), 3.96-4.20 (m, 1H), 3.83-3.91 (m, 1H), 2.85-3.17 (m, 3H), 2.72-2.83 (m, 1H), 2.59-2.69 (m, 1H), 1.30 (br. s., 9H); LCMS m/z=658.1 [M+H]⁺.

Example 17: Compound 17

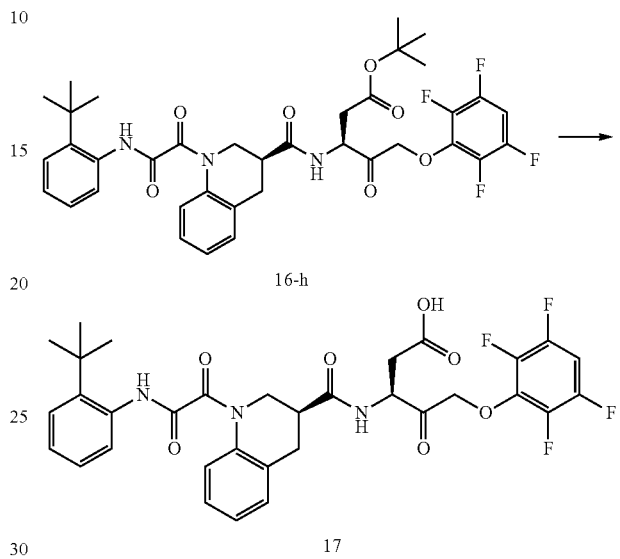

Step 1: Synthesis of Compound 17

Compound 16-h (120.00 mg, 168.13 µmol, 1.00 eq) was dissolved in dichloromethane (4.00 mL), and trifluoroacetic acid (2.76 g, 24.19 mmol, 1.79 mL, 143.85 eq) was added thereto. The reaction solution was stirred at 25° C. for 1 hour under the protection of nitrogen gas. After the reaction was completed, the reaction solution was evaporated to remove the solvent and trifluoroacetic acid therein, and lyophilized to give the product of compound 17 (83.80 mg, yield: 76%). ¹H NMR (400 MHz, DMSO-d₆) δ=9.81 (br. s., 1H), 8.83 (d, J=6.53 Hz, 1H), 7.52-7.70 (m, 1H), 7.41 (br. s., 2H), 7.09-7.34 (m, 5H), 6.83 (d, J=6.53 Hz, 1H), 5.12-5.36 (m, 2H), 4.68 (br. s., 1H), 3.93-4.18 (m, 1H), 3.80 (dd, J=8.03, 12.05 Hz, 1H), 2.86-3.20 (m, 3H), 2.72-2.82 (m, 1H), 2.60-2.70 (m, 1H), 1.30 (br. s., 9H); LCMS m/z=658.1 [M+H]⁺.

Example 18: Compound 18

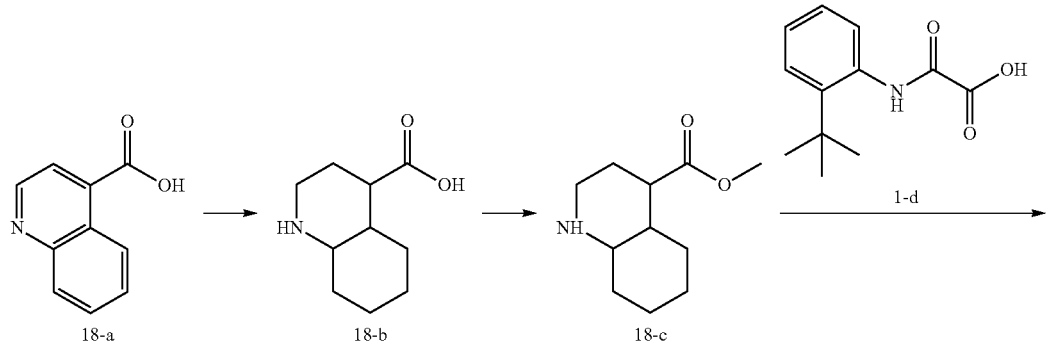

-continued
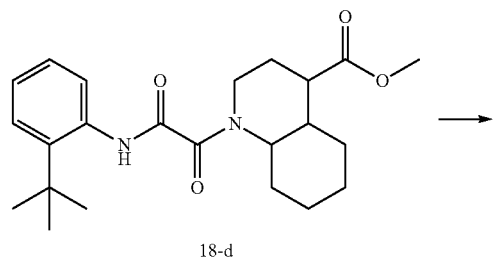
18-d
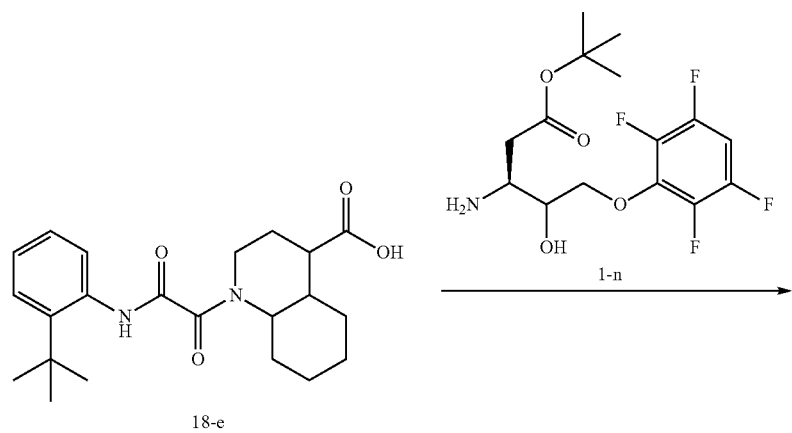
18-e  1-n
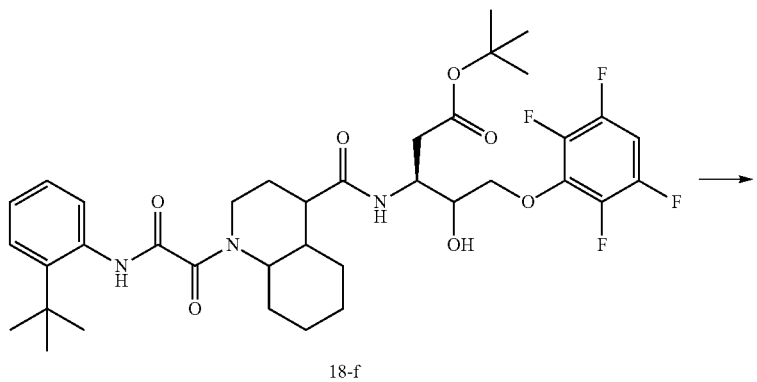
18-f
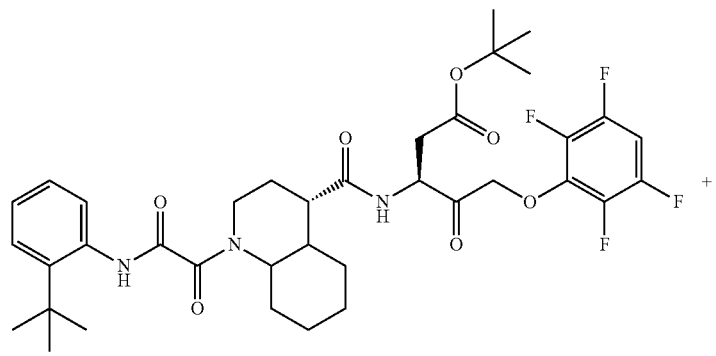
18-g

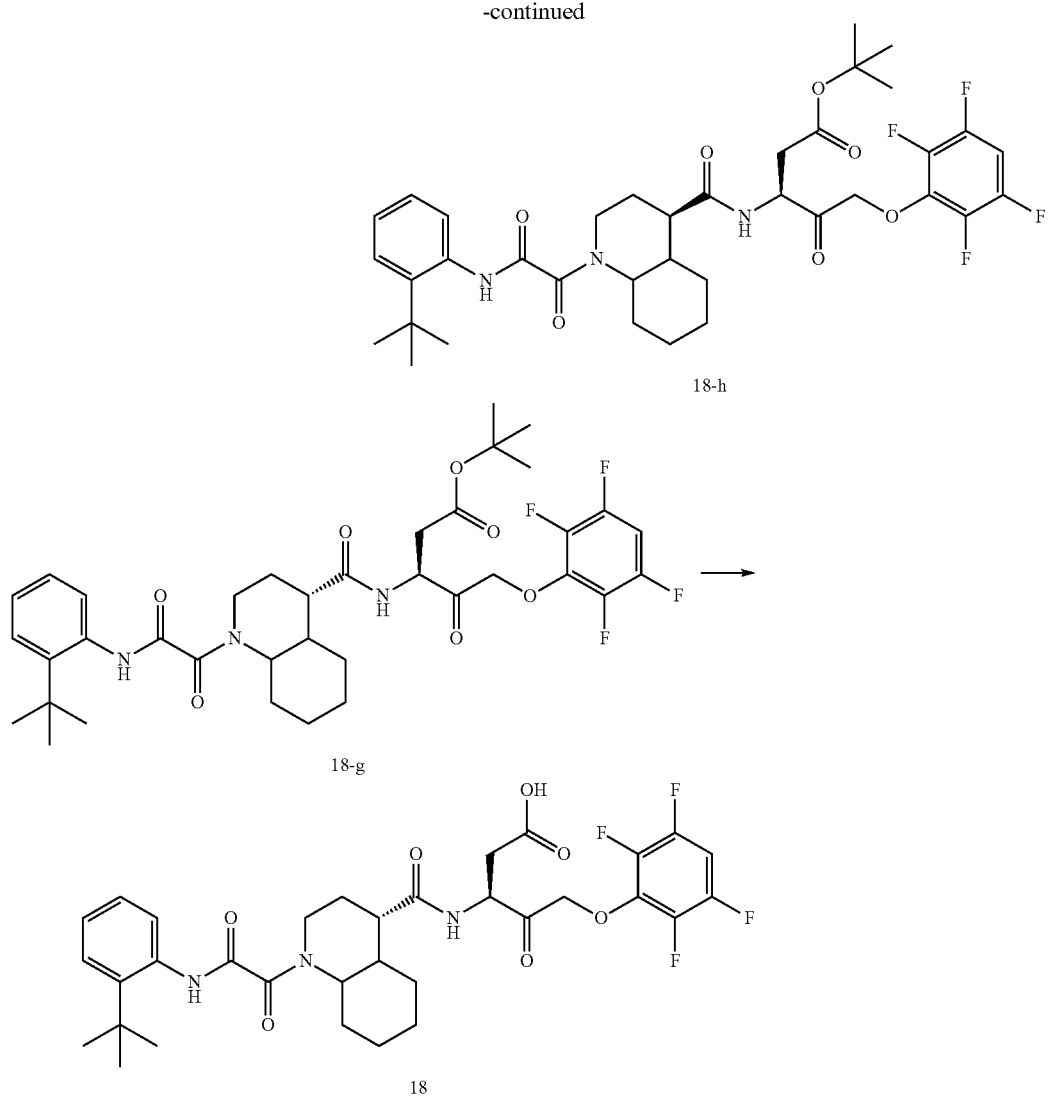

Step 1: Synthesis of Compound 18-b

Under the protection of nitrogen gas, PtO$_2$ (200.35 mg, 882.30 μmol, 0.51 eq) was added to a solution of compound 18-a (300.00 mg, 1.73 mmol, 1.00 eq) in acetic acid (4.00 mL). The reaction system was purged with hydrogen gas three times and then stirred in an hydrogen atmosphere (hydrogen balloon) at 25° C. for 42 hours. After the reaction was completed, the reaction solution was filtered. The filtrate was concentrated to give the product of compound 18-b (350.00 mg, crude), which was used directly in the next step without purification. LCMS m/z=183.9 [M+H]$^+$.

Step 2: Synthesis of Compound 18-c

Compound 18-b (300.00 mg, 1.64 mmol, 1.00 eq) was dissolved in methanol (12.00 mL), and thionyl chloride (292.67 mg, 2.46 mmol, 178.46 μL, 1.50 eq) was added thereto at 0° C. After the addition was completed, the reaction solution was stirred at 25° C. for 18 hours. After the reaction was completed, the reaction solution was spin-dried, to give the product of compound 18-c (350.00 mg, crude), which was used directly in the next step without purification.

Step 3: Synthesis of Compound 18-d

Compound 1-d (640.52 mg, 2.90 mmol, 1.50 eq) was dissolved in dichloromethane (20.00 mL), and compound 18-c (380.00 mg, 1.93 mmol, 1.00 eq), HATU (1.47 g, 3.86 mmol, 2.00 eq) and N,N-diisopropylethylamine (997.73 mg, 7.72 mmol, 1.35 mL, 4.00 eq) were added thereto. The reaction solution was stirred at 25° C. for 15 hours. After the reaction was completed, the reaction solution was added with 150 mL of water, and extracted with dichloromethane (150 mL×3). The organic phase was dried over anhydrous sodium sulfate, filtered and concentrated to give a crude product. The crude product was subjected to column chromatography (petroleum ether:ethyl acetate=1:0~5:1) to give the product of compound 18-d (555.00 mg, yield: 70%) as a colorless oil. $^1$H NMR (400 MHz, CHLOROFORM-d) δ=9.48 (br. s., 1H), 7.87 (d, J=8.03 Hz, 1H), 7.40-7.45 (m, 1H), 7.25-7.28 (m, 1H), 7.14-7.20 (m, 1H), 3.68-3.75 (m, 3H), 2.73 (dt, J=3.01, 6.02 Hz, 1H), 1.60-2.42 (m, 9H), 1.49-1.58 (m, 1H), 1.47 (s, 9H), 1.23-1.45 (m, 3H), 0.96-1.22 (m, 1H).

Step 4: Synthesis of Compound 18-e

Compound 18-d (555.00 mg, 1.39 mmol, 1.00 eq) was dissolved in tetrahydrofuran (15.00 mL), and a solution of LiOH.H$_2$O (174.97 mg, 4.17 mmol, 3.00 eq) dissolved in water (15.00 mL) was added to the above solution. The reaction solution was stirred at 25° C. for 16 hours. After the reaction was completed, the reaction solution was adjusted to pH of 6 with 2 N dilute hydrochloric acid, added with 150 mL of water, and extracted with dichloromethane (150 mL×3). The organic phase was dried over anhydrous sodium sulfate, filtered and concentrated to give the product of compound 18-e (550.00 mg, crude) as a colorless oil, which was used directly in the next step without purification. $^1$H NMR (400 MHz, CHLOROFORM-d) δ=9.30-9.63 (m, 1H), 7.81-7.93 (m, 1H), 7.40-7.48 (m, 1H), 7.25-7.33 (m, 1H), 7.14-7.21 (m, 1H), 3.72-3.81 (m, 1H), 2.72-2.81 (m, 1H), 1.49-2.44 (m, 9H), 1.47 (s, 9H), 1.12-1.44 (m, 4H).

Step 5: Synthesis of Compound 18-f

Compound 1-n (501.70 mg, 1.42 mmol, 1.00 eq) was dissolved in dichloromethane (27.00 mL), and compound 18-e (550.00 mg, 1.42 mmol, 1.00 eq), EDCl (372.93 mg, 1.95 mmol, 1.37 eq), HOBt (262.86 mg, 1.95 mmol, 1.37 eq) and NMM (430.90 mg, 4.26 mmol, 468.37 μL, 3.00 eq) were added thereto. The reaction solution was stirred at 25° C. for 18 hours under the protection of nitrogen gas. After the reaction was completed, the reaction solution was added with 150 mL of water, and extracted with dichloromethane (150 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 18-f (435.00 mg, yield: 42%) as a colorless solid. LCMS m/z=744.3 [M+Na]$^+$.

Step 6: Synthesis of Compounds 18-g and 18-h

Compound 18-f (435.00 mg, 602.68 μmol, 1.00 eq) was dissolved in dichloromethane (20.00 mL), and PIDA (751.25 mg, 2.33 mmol, 3.87 eq) and TEMPO (28.43 mg, 180.80 μmol, 0.30 eq) were added thereto. The reaction solution was stirred at 25° C. for 18 hours under the protection of nitrogen gas. After the reaction was completed, the reaction solution was added with 200 mL of ethyl acetate. The solution was washed successively with saturated sodium hydrogen carbonate (100 mL), saturated brine (50 mL) and water (50 mL). The organic phase was dried over anhydrous sodium sulfate, filtered and concentrated to give a crude product. The crude product was separated by column chromatography (petroleum ether:ethyl acetate=1: 0~2:1) and SFC (Column: Lux Cellulose-2 150×4.6 mm I.D., 3 μm; Mobile phase: A: CO$_2$, B: methanol (0.05% diethylamine); Gradient: 5%~40% of mobile phase B (0~5.5 min), hold 40% of mobile phase B for 3 min, and 5% of mobile phase B for 1.5 min; Flow rate: 2.5 mL/min; Column temp.: 40° C.) to give the product of compounds 18-g (Retention time: 4.84, 119.00 mg, yield: 27%) and 18-h (Retention time: 5.24, 72.00 mg, yield: 17%) as a colorless oil. 18-g: LCMS m/z=742.1 [M+Na]$^+$; 18-h: LCMS m/z=742.2 [M+Na]$^+$.

Step 7: Synthesis of Compound 18

Compound 18-g (119.00 mg, 165.33 μmol, 1.00 eq) was dissolved in dichloromethane (3.50 mL), and trifluoroacetic acid (2.71 g, 23.78 mmol, 1.76 mL, 143.85 eq) was added thereto. The reaction solution was stirred at 20° C. for 1 hour under the protection of nitrogen gas. After the reaction was completed, the reaction solution was evaporated to remove the solvent and trifluoroacetic acid therein, and lyophilized to give the product of compound 18 (100.60 mg, yield: 90%). $^1$H NMR (400 MHz, DMSO-d$_6$) δ=10.00 (s, 1H), 8.50-8.74 (m, 1H), 7.50-7.70 (m, 1H), 7.38-7.46 (m, 1H), 7.18-7.31 (m, 2H), 6.95-7.16 (m, 1H), 5.16-5.42 (m, 2H), 4.64-4.77 (m, 1H), 4.17 (br. s., 1H), 2.55-2.93 (m, 3H), 1.37-2.44 (m, 9H), 1.34 (s, 9H), 0.82-1.30 (m, 4H); LCMS m/z=664.1 [M+H]$^+$.

Example 19: Compound 19

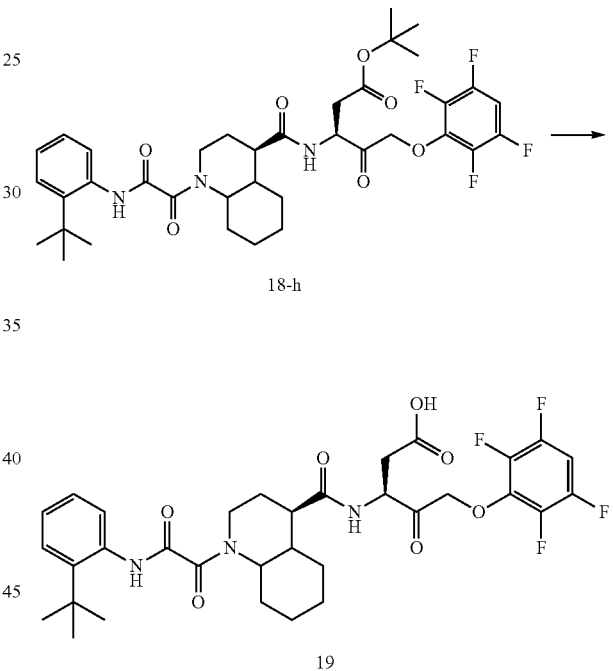

Step 1: Synthesis of Compound 19

Compound 18-h (72.00 mg, 100.03 μmol, 1.00 eq) was dissolved in dichloromethane (2.00 mL), and trifluoroacetic acid (1.64 g, 14.39 mmol, 1.07 mL, 143.85 eq) was added thereto. The reaction solution was stirred at 20° C. for 1 hour under the protection of nitrogen gas. After the reaction was completed, the reaction solution was evaporated to remove the solvent and trifluoroacetic acid therein, and lyophilized to give the product of compound 19 (51.80 mg, yield: 78%). $^1$H NMR (400 MHz, DMSO-d$_6$) δ=9.99 (br. s., 1H), 8.64-8.84 (m, 1H), 7.51-7.71 (m, 1H), 7.38-7.47 (m, 1H), 7.18-7.30 (m, 2H), 6.94-7.15 (m, 1H), 5.27 (s, 2H), 4.60 (q, J=6.53 Hz, 1H), 4.06-4.27 (m, 1H), 2.56-2.85 (m, 3H), 1.36-2.45 (m, 9H), 1.34 (s, 9H), 1.09-1.30 (m, 4H); LCMS m/z=664.1 [M+H]$^+$.

Example 20: Compound 20
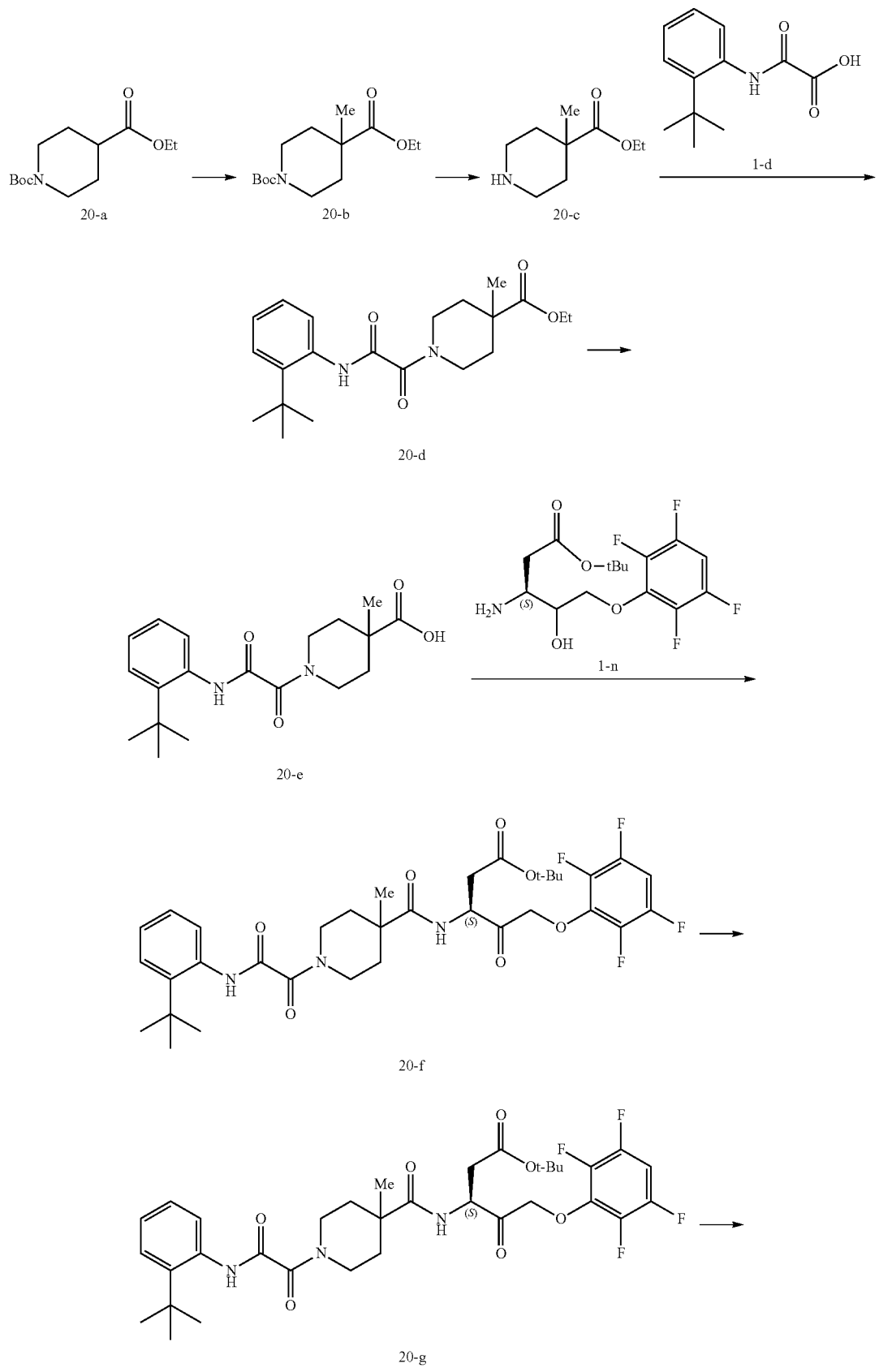

-continued

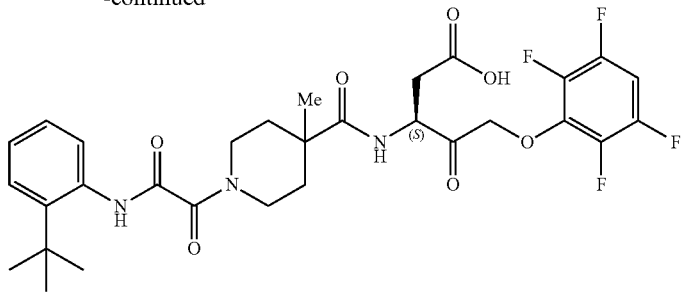

20

Step 1: Synthesis of Compound 20-b

Under the protection of nitrogen gas, compound 20-a (2.57 g, 10.00 mmol, 1.00 eq) was dissolved in tetrahydrofuran (100 mL). The system was cooled down to −78° C., added with LDA (2 M, 5.50 mL, 1.10 eq), and stirred at −78° C. for 1 hour. MeI (3.68 g, 25.93 mmol, 1.61 mL, 2.59 eq) was then added to the above solution, slowly brought back to room temperature from −78° C., and stirred for another 15 hours. After the reaction was completed, the reaction solution was added with 150 mL of saturated ammonium chloride solution for quenching, and extracted with ethyl acetate (200 mL×3). The organic phases were combined, and washed with saturated brine (100 mL). The organic phase was dried over anhydrous sodium sulfate, filtered, concentrated, and separated by column chromatography (petroleum ether:ethyl acetate=1:0~10:1) to give the product of compound 20-b (1.64 g, yield: 57%). $^1$H NMR (400 MHz, CHLOROFORM-d) δ=4.18 (q, J=7.2 Hz, 2H), 3.77 (br. s., 2H), 2.99 (t, J=11.2 Hz, 2H), 2.08 (d, J=13.6 Hz, 2H), 1.46 (s, 9H), 1.41-1.32 (m, 2H), 1.27 (t, J=7.0 Hz, 3H), 1.21 (s, 3H); LCMS m/z=171.8 [M-Boc+H]$^+$.

Step 2: Synthesis of Compound 20-c

Compound 20-b (1.60 g, 5.90 mmol, 1.00 eq) was dissolved in dichloromethane (15.00 mL), and trifluoroacetic acid (7 mL) was added to the above solution. The reaction solution was maintained at 25° C. and stirred for 1.5 hours. After the reaction was completed, the reaction solution was concentrated to give the product of compound 20-c (1.12 g, crude) as a yellow oil, which was used directly in the next step without purification. LCMS m/z=171.8 [M+H]$^+$.

Step 3: Synthesis of Compound 20-d

Compound 1-d (1.70 g, 7.67 mmol, 1.30 eq) and HATU (4.49 g, 11.80 mmol, 2.00 eq) were dissolved in dichloromethane (80 mL), and stirred at room temperature for 15 min. Compound 20-c (1.01 g, 5.90 mmol, 1.00 eq) and N,N-diisopropylethylamine (2.29 g, 17.70 mmol, 3.09 mL, 3.00 eq) were then added thereto, and stirred at room temperature for 65 hours. After the reaction was completed, the reaction solution was 150 mL of water and separated, and the aqueous phase was further extracted with dichloromethane (200 mL×2). The organic phases were combined, and washed with saturated sodium hydrogen carbonate solution (150 mL) and saturated brine (100 mL). The organic phase was dried over anhydrous sodium sulfate, filtered, concentrated, and separated by column chromatography (petroleum ether:ethyl acetate=1:0~12:1) to give the product of compound 20-d (2.17 g, yield: 90%). LCMS m/z=375.2 [M+H]$^+$.

Step 4: Synthesis of Compound 20-e

Compound 20-d (187.24 mg, 500.00 μmol, 1.00 eq) was dissolved in tetrahydrofuran (5.00 mL), and a solution of LiOH.H$_2$O (41.96 mg, 1.00 mmol, 2.00 eq) dissolved in water (5.00 mL) was added to the above solution. The reaction solution was maintained at 25° C. and stirred for 48 hours. After the reaction was completed, the reaction solution was adjusted to pH of 6 with 2 N dilute hydrochloric acid, added with 200 mL of water, and extracted with dichloromethane (200 mL×3). The organic phase was dried over anhydrous sodium sulfate, filtered and concentrated to give the product of compound 20-e (193.00 mg, crude) as a pale yellow oil, which was used directly in the next step without purification. LCMS m/z=347.1 [M+H]$^+$; 369.0 [M+Na]$^+$.

Step 5: Synthesis of Compound 20-f

Compound 20-e (173.21 mg, 500.00 μmol, 1.25 eq) and HOBt (75.67 mg, 560.00 μmol, 1.40 eq) were dissolved in dichloromethane (10 mL), added with EDCl (107.35 mg, 560.00 μmol, 1.40 eq), and stirred at room temperature for 15 min. Compound 1-n (141.32 mg, 400.00 μmol, 1.00 eq) and NMM (121.38 mg, 1.20 mmol, 131.93 μL, 3.00 eq) were then dissolved in dichloromethane, added to the above solution, and stirred at room temperature for 18 hours. After the reaction was completed, the reaction solution was added with 80 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 20-f (74.00 mg, yield: 26%) as a yellow oil. LCMS m/z=704.2 [M+Na]$^+$.

Step 6: Synthesis of Compound 20-g

Compound 20-f (74.00 mg, 108.55 μmol, 1.00 eq) was dissolved in dichloromethane (20.00 mL), and PIDA (139.85 mg, 434.20 μmol, 4.00 eq) and TEMPO (3.41 mg, 21.71 μmol, 0.20 eq) were added thereto. The reaction solution was stirred at room temperature for 72 hours. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was subjected to column chromatography (petroleum ether:ethyl acetate=1:0~5:2) to give the product of compound 20-g (25.00 mg, yield: 30%) as a yellow oil. LCMS m/z=702.2 [M+Na]$^+$.

Step 7: Synthesis of Compound 20

Compound 20-g (22.00 mg, 32.37 μmol, 1.00 eq) was dissolved in dichloromethane (3.00 mL), and trifluoroacetic acid (4.62 g, 40.52 mmol, 1.5 mL) was added thereto. The reaction solution was stirred at room temperature for 2 hours. After the reaction was completed, the reaction solution was spin-dried to give a crude product. The crude product was purified by preparative HPLC (under trifluoroacetic acid condition), and lyophilized to give the product of compound 20 (15.00 mg, yield: 74%). $^1$H NMR (400 MHz, CHLOROFORM-d) δ=9.44 (br. s., 1H), 7.82-7.64 (m, 1H), 7.43 (d, J=7.5 Hz, 1H), 7.29-7.22 (m, 1H), 7.21-7.14 (m, 1H), 6.83 (d, J=7.0 Hz, 1H), 5.10-4.81 (m, 2H), 4.60 (br. s., 1H), 4.45-4.27 (m, 1H), 4.17-3.96 (m, 1H), 3.96-3.63 (m, 1H), 3.51-3.25 (m, 1H), 3.11-2.63 (m, 2H), 2.28-2.06 (m, 2H), 1.73-1.50 (m, 2H), 1.44 (s, 9H), 1.28 (s, 3H); LCMS m/z=624.1 [M+H]$^+$.

Example 21: Compound 21

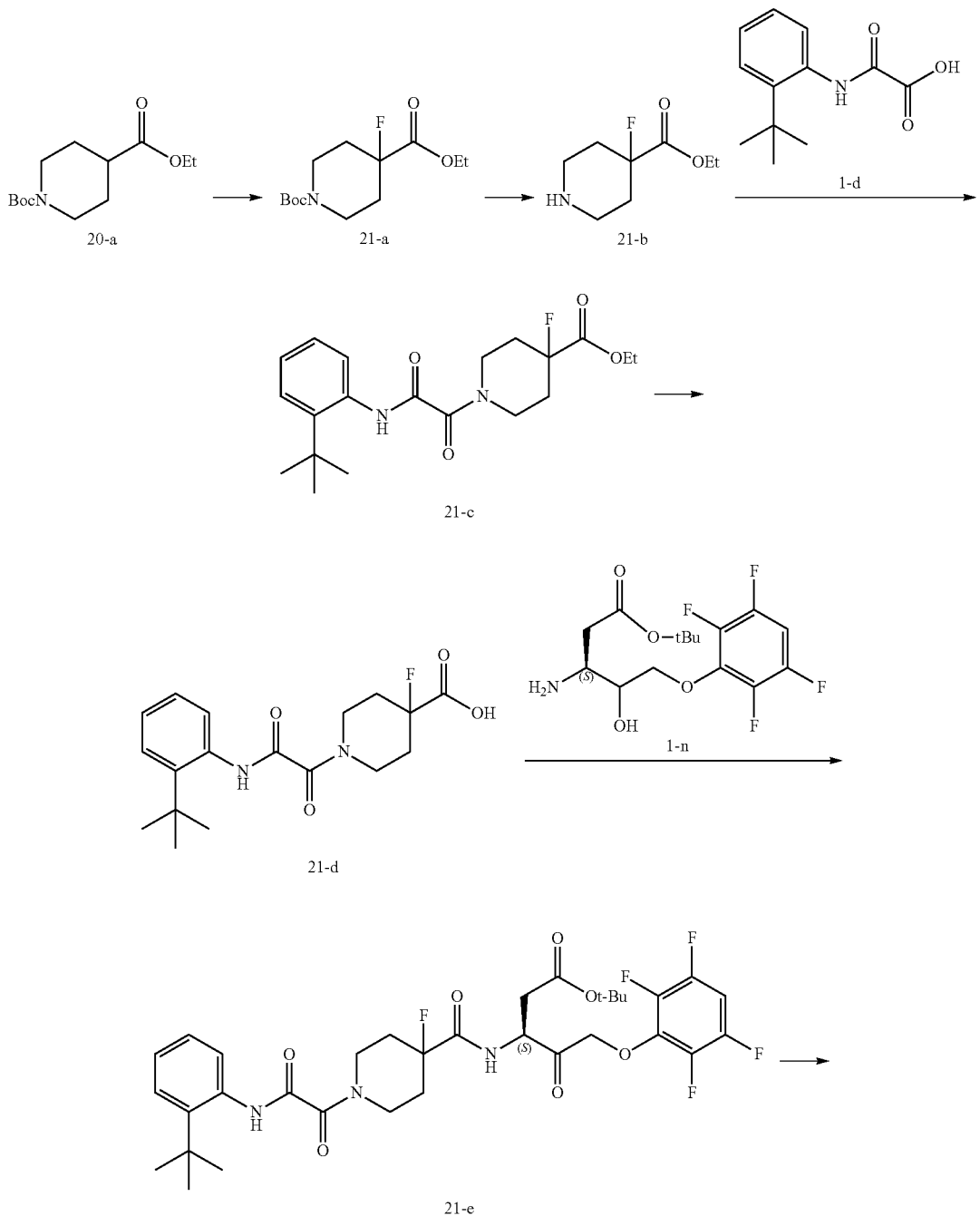

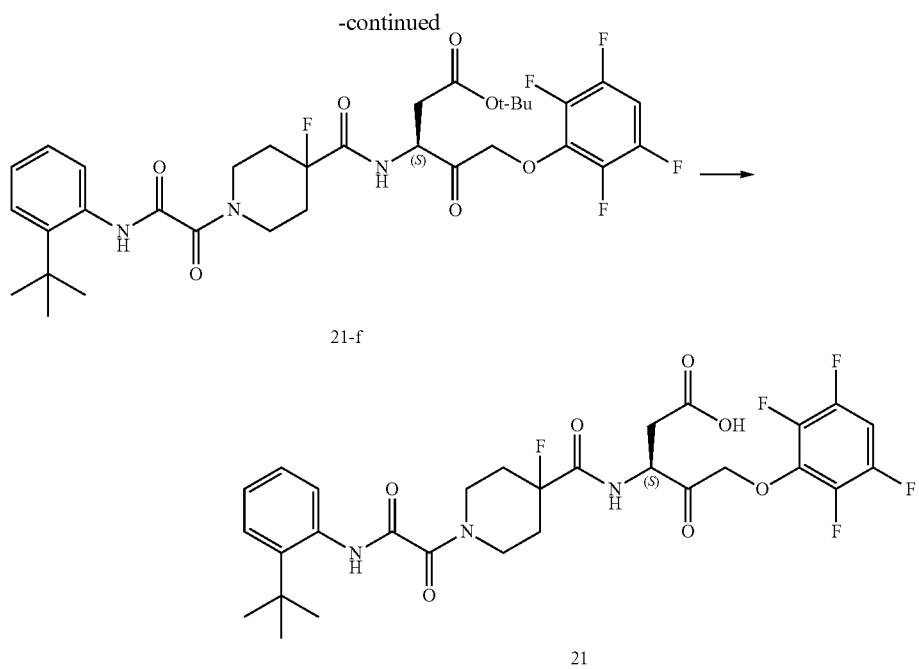

Step 1: Synthesis of Compound 21-a

Under the protection of nitrogen gas, compound 20-a (2.57 g, 10.00 mmol, 1.00 eq) was dissolved in tetrahydrofuran (100 mL). The system was cooled down to 0° C., added with LDA (2 M, 5.50 mL, 1.10 eq), and stirred at 0° C. for 1 hour. NFSI (3.94 g, 12.50 mmol, 1.25 eq) was then added to the above solution, slowly brought back to room temperature from 0° C., and stirred for 15 hours. After the reaction was completed, the solvent was spin-dried, following by adding ethyl acetate (150 mL) for dilution. The organic phase was washed successively with water (100 mL), 1 N hydrochloric acid (100 mL), saturated sodium hydrogen carbonate solution (100 mL) and saturated brine (100 mL). The organic phase was dried over anhydrous sodium sulfate, filtered, concentrated, and separated by column chromatography (petroleum ether:ethyl acetate=1: 0~10:1) to give the product of compound 21-a (1.00 g, yield: 24%). LCMS m/z=175.3 [M-Boc+H]$^+$.

Step 2: Synthesis of Compound 21-b

Compound 21-a (1.00 g, 3.63 mmol, 1.00 eq) was dissolved in dichloromethane (15.00 mL), and trifluoroacetic acid (7 mL) was added to the above solution. The reaction solution was maintained at 25° C. and stirred for 1.5 hours. After the reaction was completed, the reaction solution was concentrated to give the product of compound 21-b (0.712 g, crude) as a yellow oil, which was used directly in the next step without purification. LCMS m/z=175.9 [M+H]$^+$.

Step 3: Synthesis of Compound 21-c

Compound 1-d (1.04 g, 4.72 mmol, 1.30 eq) and HATU (2.76 g, 7.26 mmol, 2.00 eq) were dissolved in dichloromethane (80 mL), and stirred at room temperature for 15 min. Compound 21-b (635.98 mg, 3.63 mmol, 1.00 eq) and N,N-diisopropylethylamine (1.41 g, 10.89 mmol, 1.90 mL, 3.00 eq) were then added, and stirred at room temperature for 18 hours. After the reaction was completed, the reaction solution was added with 150 mL of water and separated, and the aqueous phase was further extracted with dichloromethane (200 mL×2). The organic phases were combined, and washed with saturated sodium hydrogen carbonate solution (150 mL) and saturated brine (100 mL). The organic phase was dried over anhydrous sodium sulfate, filtered, concentrated, and separated by column chromatography (petroleum ether:ethyl acetate=1:0~4:1) to give the product of compound 21-c (852.00 mg, yield: 61%). $^1$H NMR (400 MHz, CHLOROFORM-d) δ=9.54 (br. s., 1H), 7.88 (dd, J=1.0, 7.8 Hz, 1H), 7.45 (dd, J=1.1, 7.9 Hz, 1H), 7.32-7.25 (m, 1H), 7.24-7.15 (m, 1H), 5.39-5.31 (m, 1H), 4.58 (d, J=13.6 Hz, 1H), 4.29 (q, J=7.0 Hz, 2H), 3.65-3.53 (m, 1H), 3.28-3.17 (m, 1H), 2.36-2.06 (m, 4H), 1.49 (s, 9H), 1.34 (t, J=7.2 Hz, 3H); LCMS m/z=361.0 [M-F+H]$^+$.

Step 4: Synthesis of Compound 21-d

Compound 21-c (567.66 mg, 1.50 mmol, 1.00 eq) was dissolved in tetrahydrofuran (5.00 mL), and a solution of LiOH.H$_2$O (125.88 mg, 3.00 mmol, 2.00 eq) dissolved in water (5.00 mL) was added to the above solution. The reaction solution was maintained at 25° C. and stirred for 48 hours. After the reaction was completed, the reaction solution was adjusted to pH of 6 with 2 N dilute hydrochloric acid, added with 50 mL of water, and extracted with dichloromethane (50 mL×3). The organic phase was dried over anhydrous sodium sulfate, filtered and concentrated to give the product of compound 21-d (852.00 mg, crude) as a pale yellow oil, which was used directly in the next step without purification. LCMS m/z=351.1 [M+H]$^+$.

Step 5: Synthesis of Compound 21-e

Compound 21-d (315.34 mg, 900.00 μmol, 1.50 eq) and HATU (456.28 mg, 1.20 mmol, 2.00 eq) were dissolved in dichloromethane (10 mL), and stirred at room temperature for 15 min. Compound 1-n (211.99 mg, 600.00 μmol, 1.00 eq) and N,N-diisopropylethylamine (232.63 mg, 1.80 mmol, 314.37 μL, 3.00 eq) were then added, and stirred at room temperature for 18 hours. After the reaction was completed, the reaction solution was added with 80 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 21-e (190.00 mg, yield: 39%) as a yellow oil. LCMS m/z=708.2 [M+Na]+.

Step 6: Synthesis of Compound 21-f

Compound 21-e (190.00 mg, 278.71 μmol, 1.00 eq) was dissolved in dichloromethane (20.00 mL), and PIDA (359.09 mg, 1.11 mmol, 4.00 eq) and TEMPO (8.77 mg, 55.74 μmol, 0.20 eq) were added thereto. The reaction solution was stirred at room temperature for 72 hours. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was subjected to column chromatography (petroleum ether:ethyl acetate=1:0~3:1) to give the product of compound 21-f (127.00 mg, yield: 60%) as a yellow oil. LCMS m/z=706.2 [M+Na]+.

Step 7: Synthesis of Compound 21

Compound 21-f (120.00 mg, 175.53 μmol, 1.00 eq) was dissolved in dichloromethane (3.00 mL), and trifluoroacetic acid (4.62 g, 40.52 mmol, 1.5 mL) was added thereto. The reaction solution was stirred at room temperature for 2 hours. After the reaction was completed, the reaction solution was spin-dried to give a crude product. The crude product was purified by preparative HPLC (under trifluoroacetic acid condition), and lyophilized to give the product of compound 21 (108.00 mg, yield: 94%). $^1$H NMR (400 MHz, DMSO-$d_6$) δ=10.16 (s, 1H), 8.79 (d, J=6.5 Hz, 1H), 7.65-7.53 (m, 1H), 7.48-7.41 (m, 1H), 7.32-7.21 (m, 2H), 7.18-7.11 (m, 1H), 5.25 (d, J=4.5 Hz, 2H), 4.78 (d, J=7.0 Hz, 1H), 4.32 (d, J=11.0 Hz, 1H), 4.03 (d, J=13.1 Hz, 1H), 3.10-2.99 (m, 2H), 2.85 (dd, J=6.0, 16.6 Hz, 1H), 2.64 (dd, J=7.0, 16.6 Hz, 1H), 2.25-1.90 (m, 4H), 1.35 (s, 9H); LCMS m/z=624.1 [M+H]+.

Example 22: Compound 22

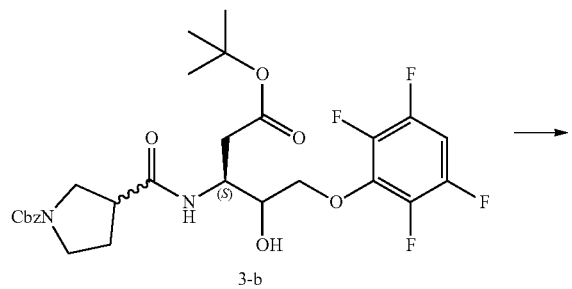

3-b

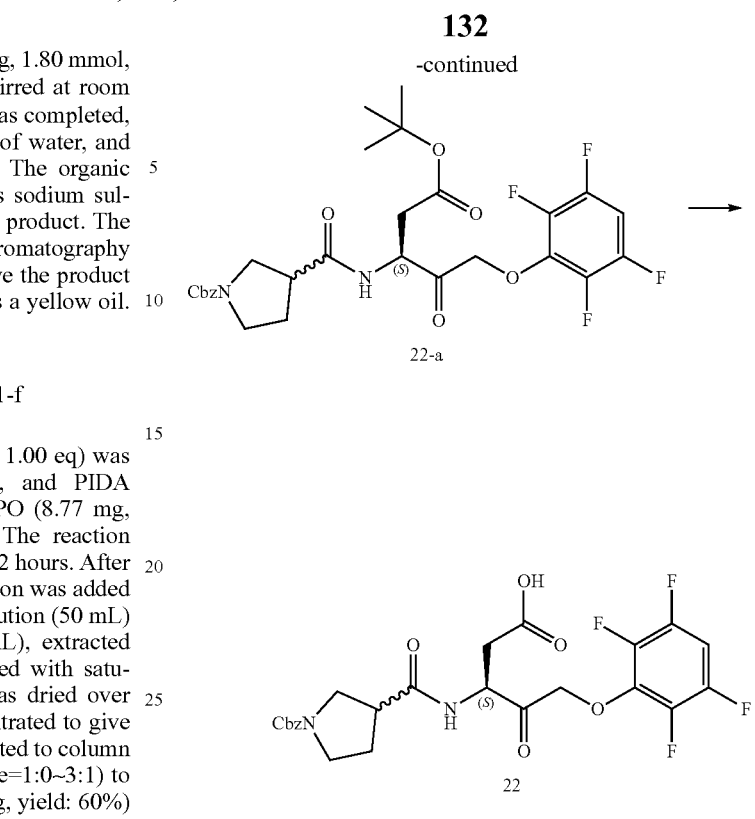

22-a

Step 1: Synthesis of Compound 22-a

Compound 3-b (100.00 mg, 171.07 μmol, 1.00 eq) was dissolved in dichloromethane (5.00 mL), and PIDA (220.41 mg, 684.28 μmol, 4.00 eq) and TEMPO (5.38 mg, 34.21 μmol, 0.20 eq) were added thereto. The reaction solution was stirred at room temperature for 12 hours. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was purified by preparative silica gel plates (petroleum ether:ethyl acetate=2:1) to give the product of compound 22-a (50.00 mg, yield: 44%) as a yellow oil.

Step 2: Synthesis of Compound 22

Compound 22-a (100.00 mg, 171.66 μmol, 1.00 eq) was dissolved in dichloromethane (20.00 mL), and trifluoroacetic acid (10 mL) was added thereto. The reaction solution was stirred at room temperature for 0.8 hour. After the reaction was completed, the reaction solution was spin-dried to give a crude product. The crude product was purified by preparative HPLC (under trifluoroacetic acid condition), and lyophilized to give the product of compound 22 (14.00 mg, yield: 15%). $^1$H NMR (400 MHz, DMSO-$d_6$) δ=8.71-8.39 (m, 1H), 7.71-7.45 (m, 1H), 7.32-7.25 (m, 1H), 7.34 (s, 5H), 5.34-5.08 (m, 1H), 5.06-5.00 (m, 2H), 4.70-4.57 (m, 1H), 3.60-3.50 (m, 2H), 3.10-2.56 (m, 4H), 2.38-2.24 (m, 1H), 2.16-1.82 (m, 2H), 1.34-1.12 (m, 1H).

Example 23: Compound 23

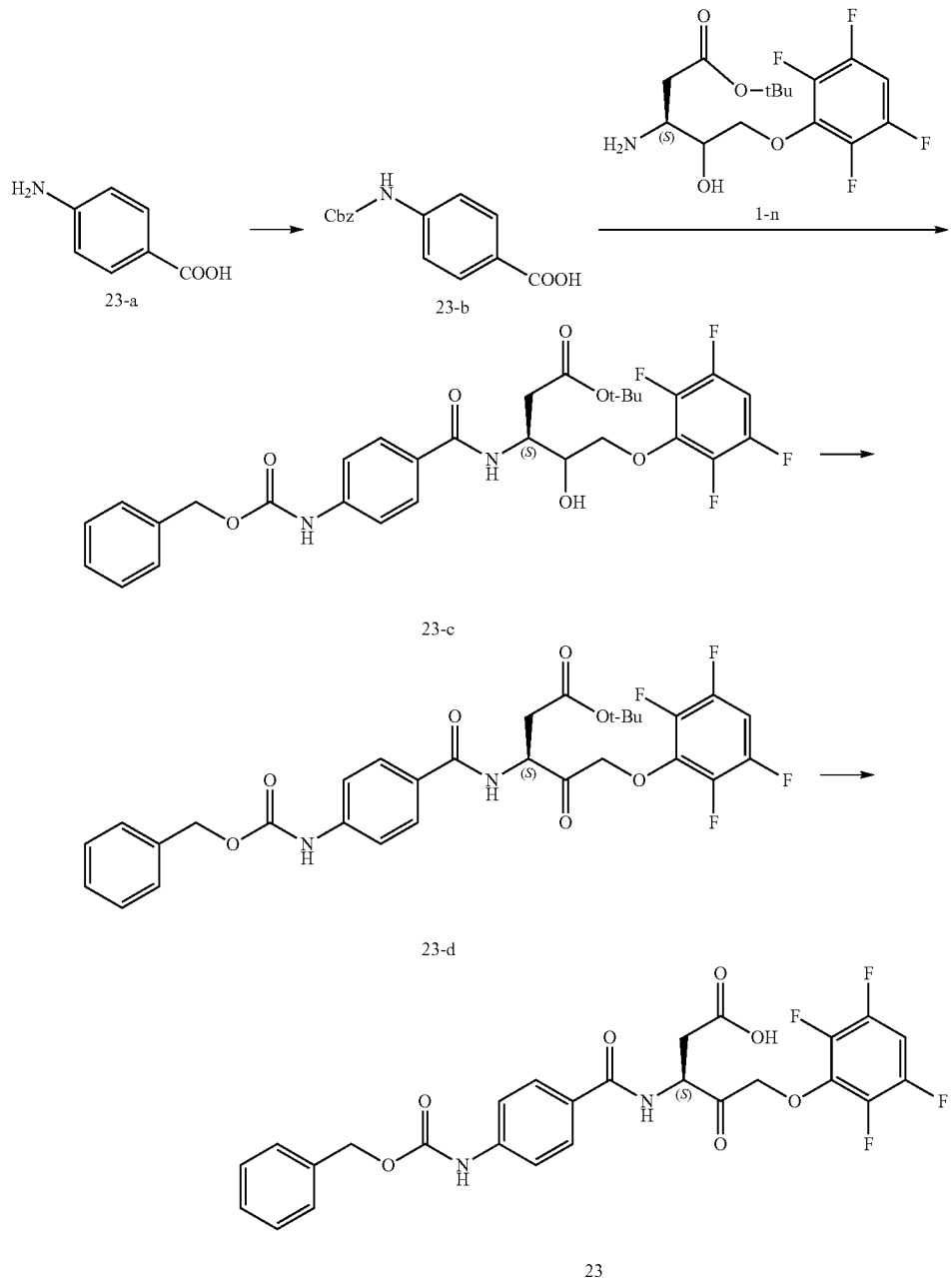

Step 1: Synthesis of Compound 23-b

Compound 23-a (1.78 g, 13.00 mmol, 1.00 eq) and sodium hydrogen carbonate solution (8.74 g, 104.00 mmol, 4.05 mL, 8.00 eq) were dissolved in water (100 mL) and dioxane (100 mL). The system was cooled down to 0° C., added with CbzCl (2.33 g, 13.65 mmol, 1.94 mL, 1.05 eq), and the reaction was stirred at room temperature for 15 hours. After the reaction was completed, 1 N dilute hydrochloric acid was added to adjust the pH of the solution to about 3, and precipitates appeared. The precipitates were filtered, washed with water, and dried to give the product of compound 23-b (1.43 g, yield: 41%).

Step 2: Synthesis of Compound 23-c

Compound 23-b (455.73 mg, 1.68 mmol, 1.40 eq) and HOBt (227.00 mg, 1.68 mmol, 1.40 eq) were dissolved in dichloromethane (10 mL), added with EDCl (322.06 mg, 1.68 mmol, 1.40 eq), and stirred at room temperature for 15 min. Compound 1-n (423.97 mg, 1.2 mmol, 1.00 eq) and NMM (364.14 mg, 3.60 mmol, 395.80 μL, 3.00 eq) were then dissolved in dichloromethane, added to the above solution, and stirred at room temperature for 16 hours. After the reaction was completed, the reaction solution was added with 80 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 23-c (400.00 mg, yield: 49%) as a yellow oil. LCMS m/z=729.2 [M+Na]+.

Step 3: Synthesis of Compound 23-d

Compound 23-c (150.00 mg, 247.30 μmol, 1.00 eq) was dissolved in dichloromethane (10.00 mL), and PIDA (318.62 mg, 989.20 μmol, 4.00 eq) and TEMPO (7.78 mg, 49.46 μmol, 0.20 eq) were added thereto. The reaction solution was stirred at room temperature for 24 hours. After the reaction was completed, the reaction solution was added with saturated sodium hydrogen carbonate solution (20 mL) and saturated sodium sulfite solution (20 mL), extracted with dichloromethane (30 mL×3), and washed with saturated brine (100 mL). The organic phase was dried over anhydrous sodium sulfate, filtered and concentrated to give a crude product. The crude product was subjected to column chromatography (petroleum ether:ethyl acetate=1:0~3:1) to give the product of compound 23-d (130.00 mg, yield: 74%) as a yellow oil. LCMS m/z=605.3 [M+H]+.

Step 4: Synthesis of Compound 23

Compound 23-d (130.00 mg, 215.04 μmol, 1.00 eq) was dissolved in dichloromethane (6.00 mL), and trifluoroacetic acid (4.62 g, 40.52 mmol, 3.00 mL) was added thereto. The reaction solution was stirred at room temperature for 2 hours. After the reaction was completed, the reaction solution was spin-dried to give a crude product. The crude product was purified by preparative HPLC (under trifluoroacetic acid condition), and lyophilized to give the product of compound 23 (75.00 mg, yield: 64%). $^1$H NMR (400 MHz, DMSO-$d_6$) δ=10.11 (s, 1H), 8.84 (d, J=7.5 Hz, 1H), 7.82 (d, J=8.5 Hz, 2H), 7.63-7.51 (m, 3H), 7.47-7.36 (m, 6H), 5.30 (d, J=4.5 Hz, 2H), 5.19 (s, 2H), 4.84 (d, J=7.0 Hz, 1H), 2.90 (dd, J=6.5, 16.6 Hz, 1H), 2.66 (dd, J=7.0, 16.6 Hz, 1H); LCMS m/z=549.1 [M+H]+.

Example 24: Compound 24

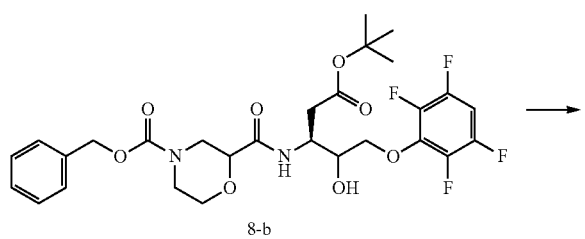

8-b

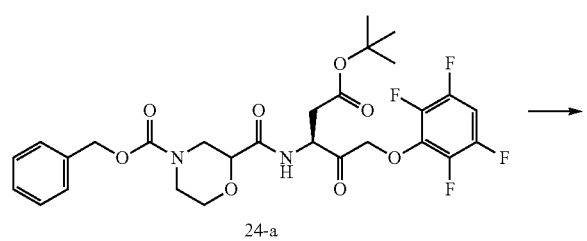

24-a

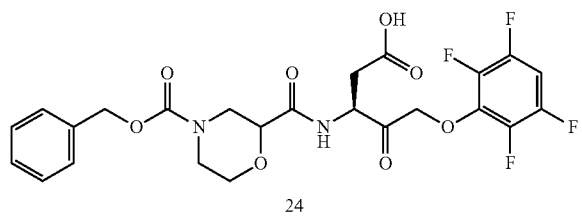

24

Step 1: Synthesis of Compound 24-a

Compound 8-b (117.00 mg, 194.82 μmol, 1.00 eq) was dissolved in dichloromethane (4.00 mL), and PIDA (242.85 mg, 753.95 μmol, 3.87 eq) and TEMPO (6.13 mg, 38.96 μmol, 0.20 eq) were added thereto. The reaction solution was stirred at 27° C. for 16 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was purified by preparative silica gel plates (petroleum ether:ethyl acetate=2:1) to give the product of compound 24-a (90.00 mg, yield: 63%) as a colorless oil. LCMS m/z=621.3 [M+Na]+.

Step 2: Synthesis of Compound 24

Compound 24-a (90.00 mg, 150.37 μmol, 1.00 eq) was dissolved in dichloromethane (3.20 mL), and trifluoroacetic acid (2.47 g, 21.63 mmol, 1.60 mL, 143.85 eq) was added thereto. The reaction solution was stirred at 27° C. for 1 hour under the protection of nitrogen gas. After the reaction was completed, the reaction solution was spin-dried to give a crude product. The crude product was purified by preparative HPLC (under trifluoroacetic acid condition), and lyophilized to give the product of compound 24 (25.60 mg, yield: 31%). $^1$H NMR (400 MHz, DMSO-$d_6$) δ=8.36 (dd, J=3.76, 7.78 Hz, 1H), 7.51-7.70 (m, 1H), 7.28-7.42 (m, 5H), 5.15-5.28 (m, 2H), 5.11 (s, 2H), 4.69-4.78 (m, 1H), 3.86-4.10 (m, 3H), 3.50-3.58 (m, 2H), 2.75-3.14 (m, 3H), 2.58-2.68 (m, 1H); LCMS m/z=543.0 [M+H]+.

Example 25: Compound 25

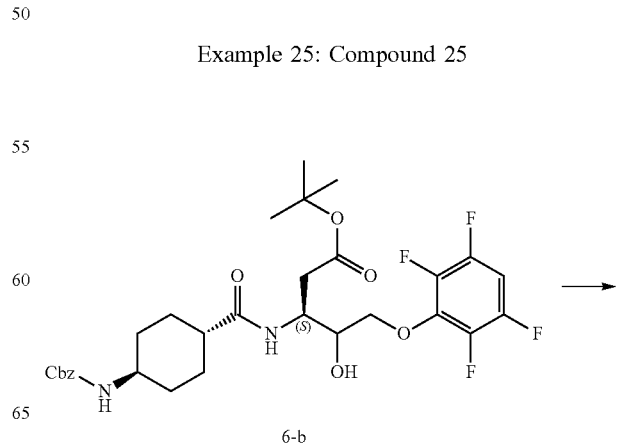

6-b

137

-continued

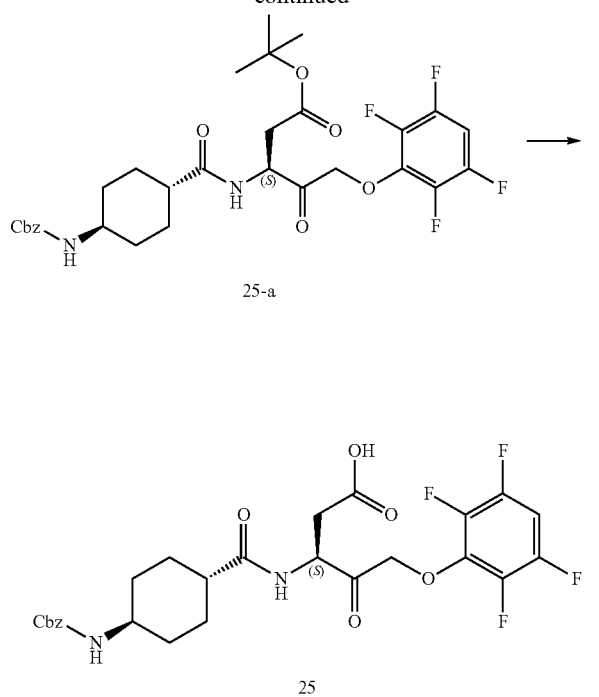

25-a

25

Step 1: Synthesis of Compound 25-a

Compound 6-b (150.00 mg, 244.85 µmol, 1.00 eq) was dissolved in dichloromethane (5.00 mL), and PIDA (315.47 mg, 979.42 µmol, 4.00 eq) and TEMPO (7.70 mg, 48.97 µmol, 0.20 eq) were added thereto. The reaction solution was stirred at 25° C. for 5 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was purified by preparative silica gel plates (petroleum ether:ethyl acetate=2:1) to give the product of compound 25-a (130.00 mg, crude) as a colorless oil.

Step 2: Synthesis of Compound 25

Compound 25-a (100.00 mg, 163.78 µmol, 1.00 eq) was dissolved in dichloromethane (20.00 mL), and trifluoroacetic acid (10 mL) was added thereto. The reaction solution was stirred at 25° C. for 0.8 hour under the protection of nitrogen gas. After the reaction was completed, the reaction solution was spin-dried to give a crude product. The crude product was purified by preparative HPLC (under trifluoroacetic acid condition), and lyophilized to give the product of compound 25 (15.00 mg, yield: 15%). $^1$H NMR (400 MHz, DMSO-d$_6$) δ=8.39-8.28 (m, 1H), 7.63-7.49 (m, 1H), 7.33 (s, 5H), 7.22-7.11 (m, 1H), 5.18 (d, J=9.5 Hz, 2H), 4.98 (s, 2H), 4.62-4.49 (m, 1H), 3.28-3.15 (m, 1H), 2.76-2.64 (m, 1H), 2.60-2.52 (m, 1H), 2.15-1.93 (m, 1H), 1.89-1.64 (m, 4H), 1.22 (br. s., 5H).

138

Example 26: Compound 26

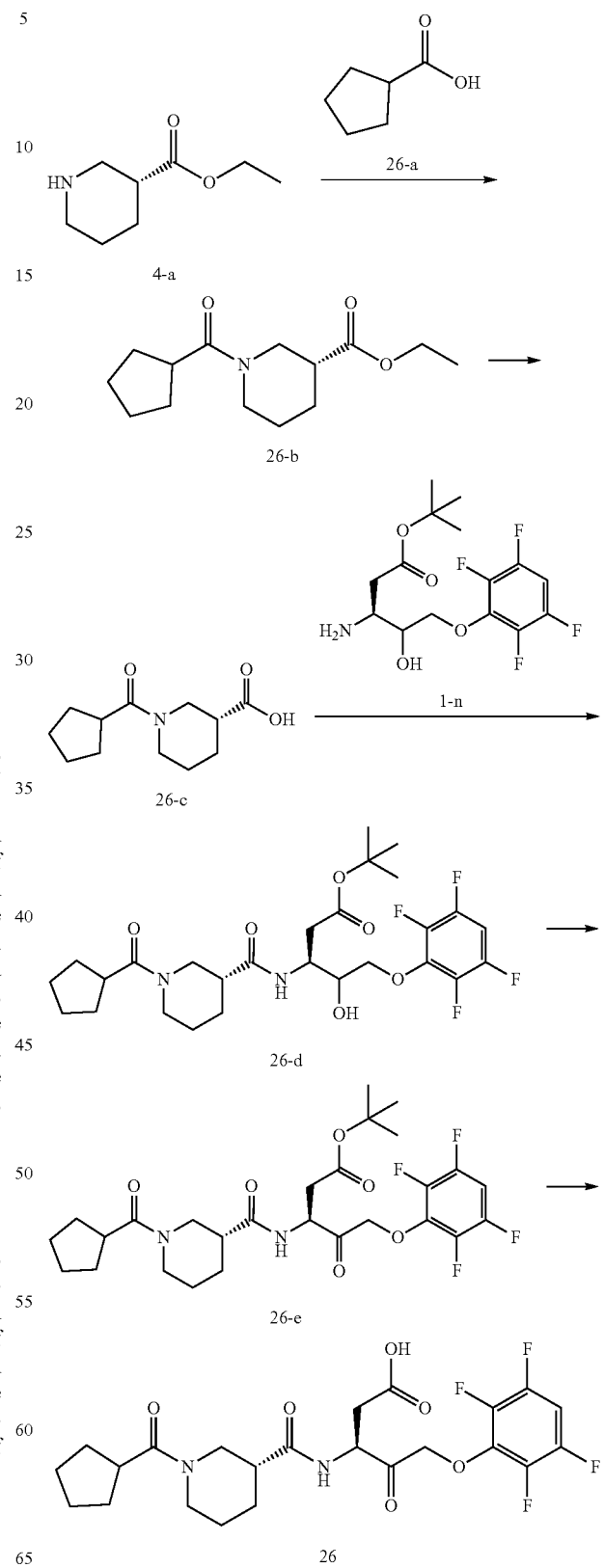

Step 1: Synthesis of Compound 26-b

Compound 26-a (907.54 mg, 7.95 mmol, 864.33 μL, 1.00 eq) was dissolved in dichloromethane (30.00 mL), and compound 4-a (1.25 g, 7.95 mmol, 1.00 eq), EDCl (2.09 g, 10.89 mmol, 1.37 eq), HOBt (1.47 g, 10.89 mmol, 1.37 eq) and NMM (2.41 g, 23.85 mmol, 2.62 mL, 3.00 eq) were added thereto. The reaction solution was stirred at 18° C. for 15 hours under the protection of nitrogen gas. After the reaction was completed, the reaction solution was added with 200 mL of water, and extracted with dichloromethane (200 mL×3). The organic phase was dried over anhydrous sodium sulfate, filtered and concentrated to give a crude product. The crude product was subjected to column chromatography (petroleum ether:ethyl acetate=1:0~5:1) to give the product of compound 26-b (1.60 g, yield: 79%) as a colorless oil. LCMS m/z=254.4 [M+H]$^+$.

Step 2: Synthesis of Compound 26-c

Compound 26-b (1.60 g, 6.32 mmol, 1.00 eq) was dissolved in tetrahydrofuran (20.00 mL), and a solution of LiOH.H$_2$O (397.51 mg, 9.48 mmol, 1.50 eq) dissolved in water (20.00 mL) was added to the above solution. The reaction solution was stirred at 18° C. for 1 hour, then supplementarily added with LiOH.H$_2$O (397.51 mg, 9.48 mmol, 1.50 eq), and stirred for another 1 hour. After the reaction was completed, the reaction solution was adjusted to pH of 5 with 2 N dilute hydrochloric acid, added with 150 mL of water, and extracted with dichloromethane (150 mL×3). The organic phase was dried over anhydrous sodium sulfate, filtered and concentrated to give the product of compound 26-c (1.30 g, yield: 91%), which was used directly in the next step without purification. $^1$H NMR (400 MHz, CHLOROFORM-d) δ=4.17-4.64 (m, 1H), 3.79-4.05 (m, 1H), 3.06-3.42 (m, 1H), 2.84-3.05 (m, 2H), 2.50 (d, J=3.26 Hz, 1H), 2.05-2.17 (m, 1H), 1.66-1.94 (m, 9H), 1.57 (d, J=4.52 Hz, 2H).

Step 3: Synthesis of Compound 26-d

Compound 1-n (500.00 mg, 1.42 mmol, 1.00 eq) was dissolved in dichloromethane (20.00 mL), and compound 26-c (319.90 mg, 1.42 mmol, 1.00 eq), EDCl (372.93 mg, 1.95 mmol, 1.37 eq), HOBt (262.86 mg, 1.95 mmol, 1.37 eq) and NMM (430.90 mg, 4.26 mmol, 468.37 μL, 3.00 eq) were added thereto. The reaction solution was stirred at 18° C. for 13 hours under the protection of nitrogen gas. After the reaction was completed, the reaction solution was added with 150 mL of water, and extracted with dichloromethane (150 mL×3). The organic phases were combined, dried over anhydrous sodium sulfate, filtered and concentrated to give a crude product. The crude product was subjected to column chromatography (petroleum ether:ethyl acetate=1:0~5:4) to give the product of compound 26-d (550.00 mg, yield: 65%) as a colorless oil. LCMS m/z=561.6 [M+H]$^+$.

Step 4: Synthesis of Compound 26-e

Compound 26-d (550.00 mg, 981.13 μmol, 1.00 eq) was dissolved in dichloromethane (20.00 mL), and PIDA (1.22 g, 3.80 mmol, 3.87 eq) and TEMPO (46.28 mg, 294.34 μmol, 0.30 eq) were added thereto. The reaction solution was stirred at 18° C. for 15 hours under the protection of nitrogen gas. After the reaction was completed, the reaction solution was added with 200 mL of ethyl acetate. The solution was washed successively with saturated sodium hydrogen carbonate (100 mL), saturated brine (100 mL) and water (100 mL). The organic phase was dried over anhydrous sodium sulfate, filtered and concentrated to give a crude product. The crude product was subjected to column chromatography (petroleum ether:ethyl acetate=10:1~5:4) to give the product of compound 26-e (230.00 mg, yield: 36%) as a pale yellow oil. LCMS m/z=559.2 [M+H]$^+$.

Step 5: Synthesis of Compound 26

Compound 26-e (230.00 mg, 411.77 μmol, 1.00 eq) was dissolved in dichloromethane (9.00 mL), and trifluoroacetic acid (6.75 g, 59.23 mmol, 4.38 mL, 143.85 eq) was added thereto. The reaction solution was stirred at 15° C. for 1 hour under the protection of nitrogen gas. After the reaction was completed, the reaction solution was spin-dried to give a crude product. The crude product was purified by preparative HPLC (under trifluoroacetic acid condition), and lyophilized to give the product of compound 26 (121.20 mg, yield: 59%). $^1$H NMR (400 MHz, DMSO-d$_6$) δ=8.45-8.57 (m, 1H), 7.50-7.66 (m, 1H), 5.14-5.30 (m, 2H), 4.60 (q, J=6.53 Hz, 1H), 4.20-4.39 (m, 1H), 3.89 (d, J=13.05 Hz, 1H), 2.91-3.13 (m, 2H), 2.54-2.81 (m, 3H), 2.18-2.38 (m, 1H), 1.16-1.93 (m, 12H); LCMS m/z=503.0 [M+H]$^+$.

Example 27: Compound 27

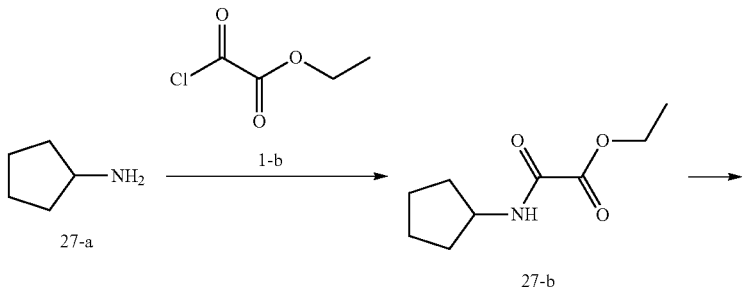

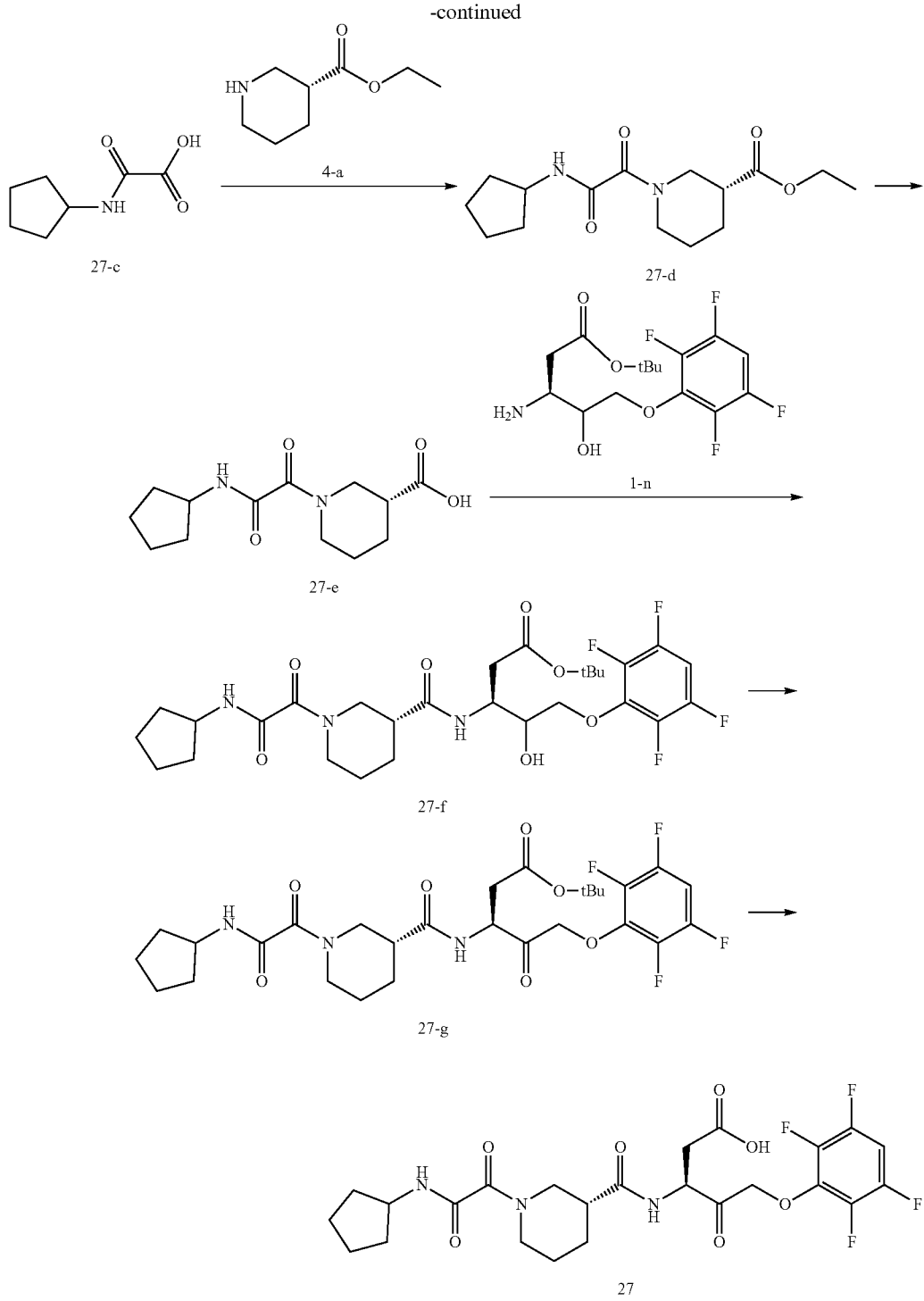

Step 1: Synthesis of Compound 27-b

Compound 27-a (2.00 g, 23.49 mmol, 2.33 mL, 1.00 eq) was dissolved in dichloromethane (40.00 mL), and triethylamine (4.75 g, 46.98 mmol, 6.51 mL, 2.00 eq) and compound 1-b (3.85 g, 28.19 mmol, 3.16 mL, 1.20 eq) were successively added thereto. The reaction solution was stirred at 20° C. for 16 hours. After the reaction was completed, the reaction solution was added with water (150 mL) and ethyl acetate (250 mL) for extraction. The organic phase was washed with water (150 mL) and brine (150 mL), dried over anhydrous sodium sulfate, filtered, and concentrated to give a crude product. The crude product was subjected to column chromatography (petroleum ether:ethyl acetate=1:0~2:1) to give the product of compound 27-b (4.20 g, yield: 95%) as a yellow oil. $^1$H NMR (400 MHz, CHLOROFORM-d) δ=7.05 (br. s., 1H), 4.34 (q, J=7.28 Hz, 2H), 4.23 (sxt, J=7.08 Hz, 1H), 1.97-2.09 (m, 2H), 1.57-1.77 (m, 4H), 1.47 (qd, J=6.38, 12.49 Hz, 2H), 1.38 (t, J=7.15 Hz, 3H).

Step 2: Synthesis of Compound 27-c

Compound 27-b (500.00 mg, 2.70 mmol, 1.00 eq) was dissolved in tetrahydrofuran (8.00 mL), and a solution of LiOH.H₂O (339.88 mg, 8.10 mmol, 3.00 eq) dissolved in water (8.00 mL) was added to the above solution. The reaction solution was stirred at 20° C. for 1 hour. After the reaction was completed, the reaction solution was adjusted to pH of 6 with 2 N dilute hydrochloric acid, added with water (50 mL), and extracted with dichloromethane (50 mL×3). The organic phase was dried over anhydrous sodium sulfate, filtered and concentrated to give the product of compound 27-c (290.00 mg, crude) as a pale yellow solid, which was used directly in the next step without purification. $^1$H NMR (400 MHz, CHLOROFORM-d) δ=7.29 (br. s., 1H), 4.21 (sxt, J=6.98 Hz, 1H), 1.98-2.11 (m, 2H), 1.60-1.81 (m, 4H), 1.47-1.60 (m, 2H).

Step 3: Synthesis of Compound 27-d

Compound 27-c (612.96 mg, 3.90 mmol, 1.20 eq) and HATU (2.47 g, 6.50 mmol, 2.00 eq) were dissolved in dichloromethane (60 mL), and stirred at room temperature for min. Compound 4-a (510.93 mg, 3.25 mmol, 1.00 eq) and N,N-diisopropylethylamine (1.26 g, 9.75 mmol, 1.70 mL, 3.00 eq) were then added, and stirred at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 27-d (608.00 mg, yield: 59%) as a yellow oil. $^1$H NMR (400 MHz, CHLOROFORM-d) δ=7.17 (br. s., 1H), 4.75-4.61 (m, 1H), 4.49 (d, J=13.1 Hz, 0.5H), 4.20-4.07 (m, 3H), 4.06-4.00 (m, 0.5H), 3.62-3.53 (m, 0.5H), 3.17 (t, J=12.2 Hz, 0.5H), 3.04 (t, J=11.5 Hz, 0.5H), 3.00-2.91 (m, 0.5H), 2.64-2.54 (m, 0.5H), 2.48 (t, J=10.4 Hz, 0.5H), 2.13-1.91 (m, 4H), 1.83-1.59 (m, 6H), 1.49-1.39 (m, 2H), 1.27-1.19 (m, 3H); LCMS m/z=297.1 [M+H]⁺.

Step 4: Synthesis of Compound 27-e

Compound 27-d (444.54 mg, 1.50 mmol, 1.00 eq) was dissolved in tetrahydrofuran (5.00 mL), and a solution of LiOH.H₂O (96.88 mg, 2.31 mmol, 2.00 eq) dissolved in water (5.00 mL) was added to the above solution. The reaction solution was maintained at 25° C. and stirred for 2 hours. After the reaction was completed, the reaction solution was adjusted to pH of 6 with 2 N dilute hydrochloric acid, added with 20 mL of water, and extracted with dichloromethane (20 mL×3). The organic phase was dried over anhydrous sodium sulfate, filtered and concentrated to give the product of compound 27-e (254.00 mg, crude) as a pale yellow oil, which was used directly in the next step without purification. LCMS m/z=269.0 [M+H]⁺; 290.9 [M+Na]⁺.

Step 5: Synthesis of Compound 27-f

Compound 27-e (254.89 mg, 950.00 μmol, 1.19 eq) and HATU (608.37 mg, 1.60 mmol, 2.00 eq) were dissolved in dichloromethane (15 mL), and stirred at room temperature for 15 min. Compound 1-n (282.65 mg, 800.00 μmol, 1.00 eq) and N,N-diisopropylethylamine (310.18 mg, 2.40 mmol, 419.16 μL, 3.00 eq) were then added, and stirred at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 27-f (138.00 mg, yield: 22%) as a yellow oil. LCMS m/z=626.1 [M+Na]⁺.

Step 6: Synthesis of Compound 27-g

Compound 27-f (138.00 mg, 228.63 μmol, 1.00 eq) was dissolved in dichloromethane (10.00 mL), and PIDA (294.56 mg, 914.51 μmol, 4.00 eq) and TEMPO (7.19 mg, 45.73 μmol, 0.20 eq) were added thereto. The reaction solution was stirred at room temperature for 54 hours. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was subjected to column chromatography (petroleum ether:ethyl acetate=1:0~2:1) to give the product of compound 27-g (75.00 mg, yield: 47%) as a yellow oil. LCMS m/z=624.3 [M+Na]⁺.

Step 7: Synthesis of Compound 27

Compound 27-g (70.00 mg, 116.36 μmol, 1.00 eq) was dissolved in dichloromethane (3.00 mL), and trifluoroacetic acid (4.62 g, 40.52 mmol, 1.5 mL) was added thereto. The reaction solution was stirred at room temperature for 2 hours. After the reaction was completed, the reaction solution was spin-dried to give a crude product. The crude product was purified by preparative HPLC (under trifluoroacetic acid condition), and lyophilized to give the product of compound 27 (62.00 mg, yield: 97%). $^1$H NMR (400 MHz, DMSO-d₆) δ=8.67-8.56 (m, 2H), 7.63-7.52 (m, 1H), 5.32-5.14 (m, 2H), 4.68-4.55 (m, 1H), 4.32-4.17 (m, 1H), 4.06-4.01 (m, 1H), 3.62 (t, J=13.8 Hz, 1H), 3.19-2.95 (m, 1H), 2.78-2.68 (m, 2H), 2.65-2.57 (m, 1H), 2.46-2.29 (m, 1H), 2.01-1.87 (m, 1H), 1.86-1.76 (m, 2H), 1.65-1.38 (m, 9H); LCMS m/z=546.1 [M+H]⁺.

Example 28: Compound 28

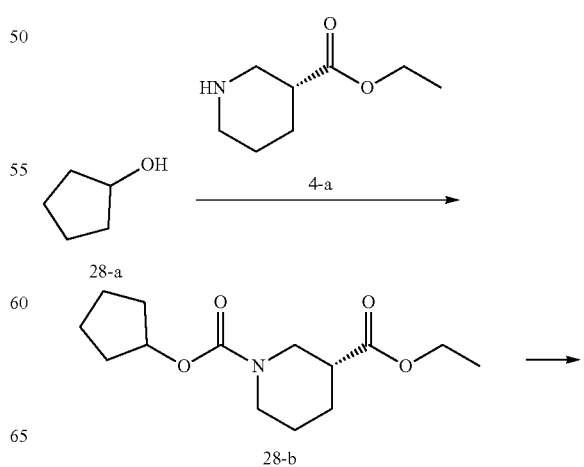

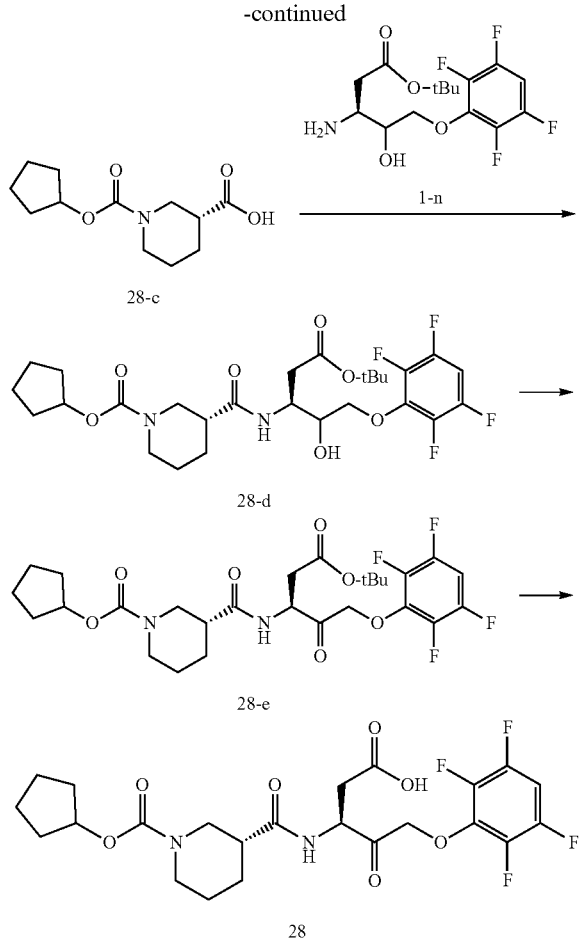

Step 1: Synthesis of Compound 28-b

Compound 28-a (775.17 mg, 9.00 mmol, 815.97 μL, 3.00 eq) and CDI (1.46 g, 9.00 mmol, 3.00 eq) were dissolved in tetrahydrofuran (40 mL), and stirred at room temperature for 1.5 hours. Compound 4-a (921.90 mg, 3.00 mmol, 1.00 eq) and triethylamine (1.52 g, 15.00 mmol, 2.08 mL, 5.00 eq) were then added, and stirred at 80° C. for 15 hours. After the reaction was completed, the reaction solution was added with 150 mL of dichloromethane for dilution, and washed with saturated sodium hydrogen carbonate solution (150 mL) and saturated NH$_4$Cl (100 mL). The organic phase was dried over anhydrous sodium sulfate, filtered, concentrated, and separated by column chromatography (petroleum ether:ethyl acetate=1:0~10:1) to give the product of compound 28-b (245.00 mg, yield: 10%). $^1$H NMR (400 MHz, CHLOROFORM-d) δ=5.09 (t, J=5.8 Hz, 1H), 4.13 (q, J=7.0 Hz, 2H), 3.93 (br. s., 1H), 2.99 (br. s., 1H), 2.88-2.75 (m, 1H), 2.42 (br. s., 1H), 2.09-2.00 (m, 1H), 1.82 (dd, J=5.5, 11.0 Hz, 2H), 1.76-1.66 (m, 6H), 1.64-1.52 (m, 3H), 1.49-1.39 (m, 1H), 1.25 (t, J=7.0 Hz, 3H); LCMS m/z=270.0 [M+H]$^+$.

Step 2: Synthesis of Compound 28-c

Compound 28-b (240.00 mg, 891.07 μmol, 1.00 eq) was dissolved in tetrahydrofuran (5.00 mL), and a solution of LiOH·H$_2$O (74.78 mg, 1.78 mmol, 2.00 eq) dissolved in water (5.00 mL) was added to the above solution. The reaction solution was maintained at 25° C. and stirred for 2 hours. After the reaction was completed, the reaction solution was adjusted to pH of 6 with 2 N dilute hydrochloric acid, added with 30 mL of water, and extracted with dichloromethane (20 mL×3). The organic phase was dried over anhydrous sodium sulfate, filtered and concentrated to give the product of compound 28-c (178.00 mg, crude) as a pale yellow oil, which was used directly in the next step without purification. LCMS m/z=264.1 [M+Na]$^+$.

Step 3: Synthesis of Compound 28-d

Compound 28-c (175.17 mg, 726.00 μmol, 1.21 eq) and HATU (456.28 mg, 1.20 mmol, 2.00 eq) were dissolved in dichloromethane (15 mL), and stirred at room temperature for 15 min. Compound 1-n (211.99 mg, 600.00 μmol, 1.00 eq) and N,N-diisopropylethylamine (232.63 mg, 1.80 mmol, 314.37 μL, 3.00 eq) were then added, and stirred at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 28-d (310.00 mg, yield: 78%) as a yellow oil. LCMS m/z=577.1 [M+H]$^+$; 599.1 [M+Na]$^+$.

Step 4: Synthesis of Compound 28-e

Compound 28-d (310.00 mg, 537.65 μmol, 1.00 eq) was dissolved in dichloromethane (20.00 mL), and PIDA (692.71 mg, 2.15 mmol, 4.00 eq) and TEMPO (16.91 mg, 107.53 μmol, 0.20 eq) were added thereto. The reaction solution was stirred at room temperature for 48 hours. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was subjected to column chromatography (petroleum ether:ethyl acetate=1:0~3:1) to give the product of compound 28-e (247.00 mg, yield: 69%) as a yellow oil. LCMS m/z=575.1 [M+H]$^+$; 597.1 [M+Na]$^+$.

Step 5: Synthesis of Compound 28

Compound 28-e (247.00 mg, 429.89 μmol, 1.00 eq) was dissolved in dichloromethane (5.00 mL), and trifluoroacetic acid (4.62 g, 40.52 mmol, 3.00 mL) was added thereto. The reaction solution was stirred at room temperature for 1.5 hours. After the reaction was completed, the reaction solution was spin-dried to give a crude product. The crude product was purified by preparative HPLC (under trifluoroacetic acid condition), and lyophilized to give the product of compound 28 (202.00 mg, yield: 88%). $^1$H NMR (400 MHz, DMSO-d$_6$) δ=8.54 (d, J=7.0 Hz, 1H), 7.63-7.51 (m, 1H), 5.29-5.15 (m, 2H), 4.96 (br. s., 1H), 4.61 (q, J=6.5 Hz, 1H), 3.94-3.80 (m, 2H), 2.88-2.70 (m, 3H), 2.60 (dd, J=6.8, 16.8 Hz, 1H), 2.31 (t, J=10.5 Hz, 1H), 1.88-1.72 (m, 4H), 1.62-1.52 (m, 6H), 1.39-1.27 (m, 2H); LCMS m/z=519.1 [M+H]$^+$; 541.0 [M+Na]$^+$.

Example 29: Compound 29

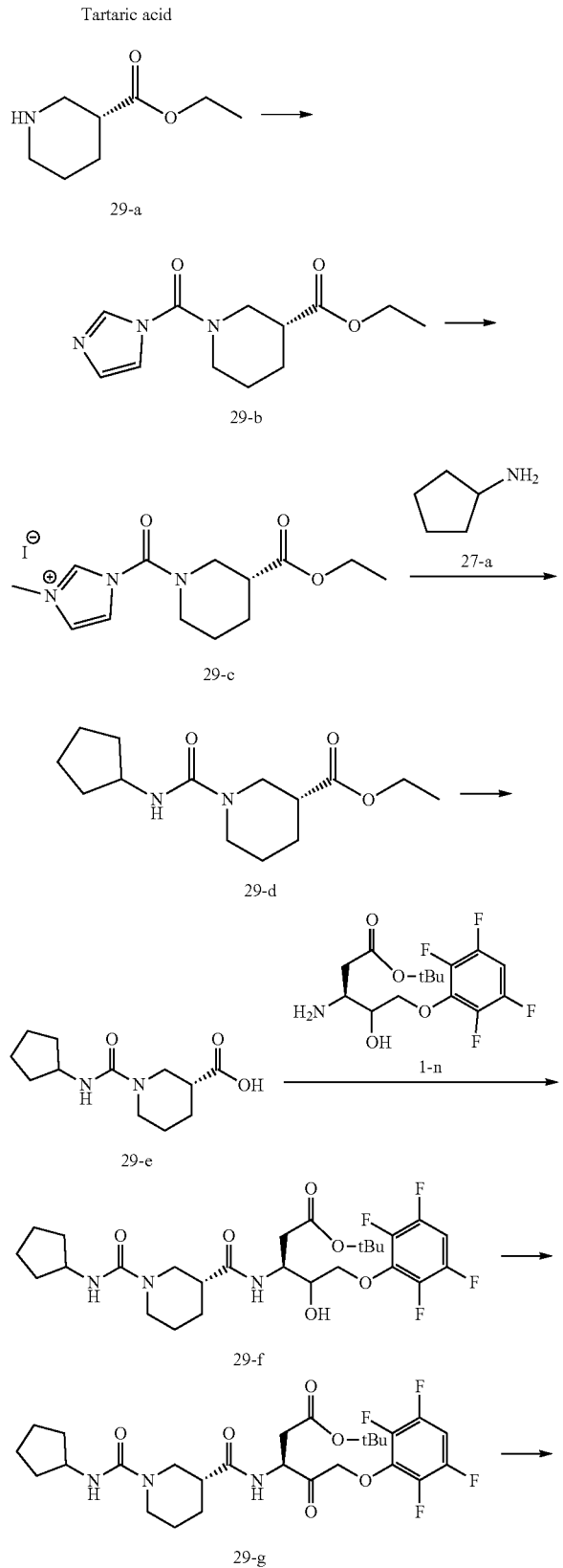

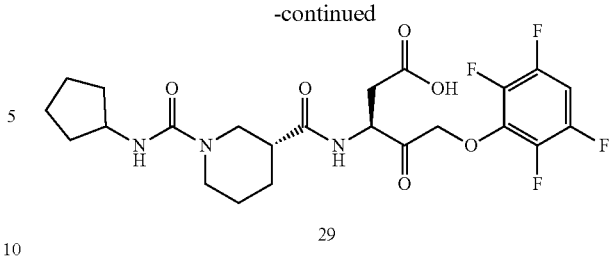

Step 1: Synthesis of Compound 29-b

Triethylamine (4.05 g, 40.00 mmol, 5.55 mL, 2.00 eq) and CDI (3.41 g, 21.00 mmol, 1.05 eq) were dissolved in dichloromethane (100 mL), and added with compound 29-a (6.15 g, 20.00 mmol, 1.00 eq) in an ice bath. The reaction solution was stirred at room temperature for 19 hours. After the reaction was completed, the reaction solution was added with 150 mL of dichloromethane for dilution, and washed with water (150 mL) and saturated brine (100 mL). The organic phase was dried over anhydrous sodium sulfate, filtered, concentrated, to give the product of compound 29-b (4.85 g, crude). LCMS m/z=251.9 [M+H]$^+$.

Step 2: Synthesis of Compound 29-c

Compound 29-b (4.85 g, 19.30 mmol, 1.00 eq) was dissolved in acetonitrile (20.00 mL), and MeI (9.37 g, 66.01 mmol, 4.11 mL, 3.42 eq) was added to the above solution. The reaction solution was maintained at 25° C. and stirred for 24 hours. After the reaction was completed, the organic solvent was concentrated to give the product of compound 29-c (7.83 g, crude) as a pale yellow oil, which was used directly in the next step without purification.

Step 3: Synthesis of Compound 29-d

Compound 29-c (1.18 g, 3.00 mmol, 1.00 eq) was dissolved in dichloromethane (15 mL), and added with compound 27-a (255.45 mg, 3.00 mmol, 297.03 μL, 1.00 eq) and triethylamine (303.57 mg, 3.00 mmol, 415.85 μL, 3 eq). The reaction was warmed up to room temperature, and stirred for 24 hours. After the reaction was completed, the reaction solution was added with dichloromethane (150 mL) for dilution, and washed with 2 N dilute hydrochloric acid (100 mL). The organic phases were combined, dried over anhydrous sodium sulfate, filtered and concentrated to give a crude product. The crude product was subjected to column chromatography (petroleum ether:ethyl acetate=1:0~5:2) to give the product of compound 29-d (700.00 mg, yield: 76%) as a yellow oil. $^1$H NMR (400 MHz, CHLOROFORM-d) δ=4.58 (d, J=6.0 Hz, 1H), 4.19-4.04 (m, 3H), 3.79 (dd, J=3.5, 13.1 Hz, 1H), 3.50 (td, J=4.6, 13.3 Hz, 1H), 3.23-3.08 (m, 2H), 2.49 (td, J=4.6, 8.8 Hz, 1H), 2.03-1.91 (m, 3H), 1.81-1.71 (m, 2H), 1.69-1.54 (m, 5H), 1.40-1.30 (m, 2H), 1.26 (t, J=7.3 Hz, 3H); LCMS m/z=269.0 [M+H]$^+$.

Step 4: Synthesis of Compound 29-e

Compound 29-d (335.44 mg, 1.25 mmol, 1.00 eq) was dissolved in tetrahydrofuran (10.00 mL), and a solution of LiOH.H$_2$O (104.90 mg, 2.50 mmol, 2.00 eq) dissolved in water (10.00 mL) was added to the above solution. The reaction solution was maintained at 25° C. and stirred for 2 hours. After the reaction was completed, the reaction solution was adjusted to pH of 6 with 2 N dilute hydrochloric acid, added with 30 mL of water, and extracted with dichloromethane (20 mL×3). The organic phase was dried over anhydrous sodium sulfate, filtered and concentrated to give the product of compound 29-e (320.00 mg, crude) as a pale yellow oil, which was used directly in the next step without purification. LCMS m/z=263.0 [M+Na]+.

Step 5: Synthesis of Compound 29-f

Compound 29-e (300.38 mg, 1.25 mmol, 1.25 eq) and HATU (760.46 mg, 2.00 mmol, 2.00 eq) were dissolved in dichloromethane (15 mL), and stirred at room temperature for 15 min. Compound 1-n (353.31 mg, 1.00 mmol, 1.00 eq) and N,N-diisopropylethylamine (387.72 mg, 3.00 mmol, 523.95 µL, 3.00 eq) were then added, and stirred at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~0:1) to give the product of compound 29-f (330.00 mg, yield: 28%) as a yellow oil. LCMS m/z=576.2 [M+H]+; 598.2 [M+Na]+.

Step 6: Synthesis of Compound 29-g

Compound 29-f (330.00 mg, 573.32 µmol, 1.00 eq) was dissolved in dichloromethane (20.00 mL), and PIDA (738.67 mg, 2.29 mmol, 4.00 eq) and TEMPO (18.03 mg, 114.66 µmol, 0.20 eq) were added thereto. The reaction solution was stirred at room temperature for 72 hours. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was subjected to column chromatography (petroleum ether:ethyl acetate=1:0~5:4) to give the product of compound 29-g (29.00 mg, yield: 9%) as a yellow oil.

Step 7: Synthesis of Compound 29

Compound 29-g (29.00 mg, 50.56 µmol, 1.00 eq) was dissolved in dichloromethane (3.00 mL), and trifluoroacetic acid (4.62 g, 40.52 mmol, 3.00 mL) was added thereto. The reaction solution was stirred at room temperature for 1.5 hours. After the reaction was completed, the reaction solution was spin-dried to give a crude product. The crude product was purified by preparative HPLC (under trifluoroacetic acid condition), and lyophilized to give the product of compound 29 (7.80 mg, yield: 30%). LCMS m/z=518.1 [M+H]+; 540.1 [M+Na]+.

Example 30: Compound 30

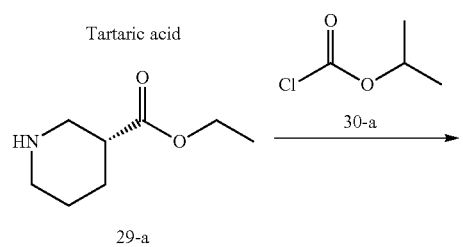

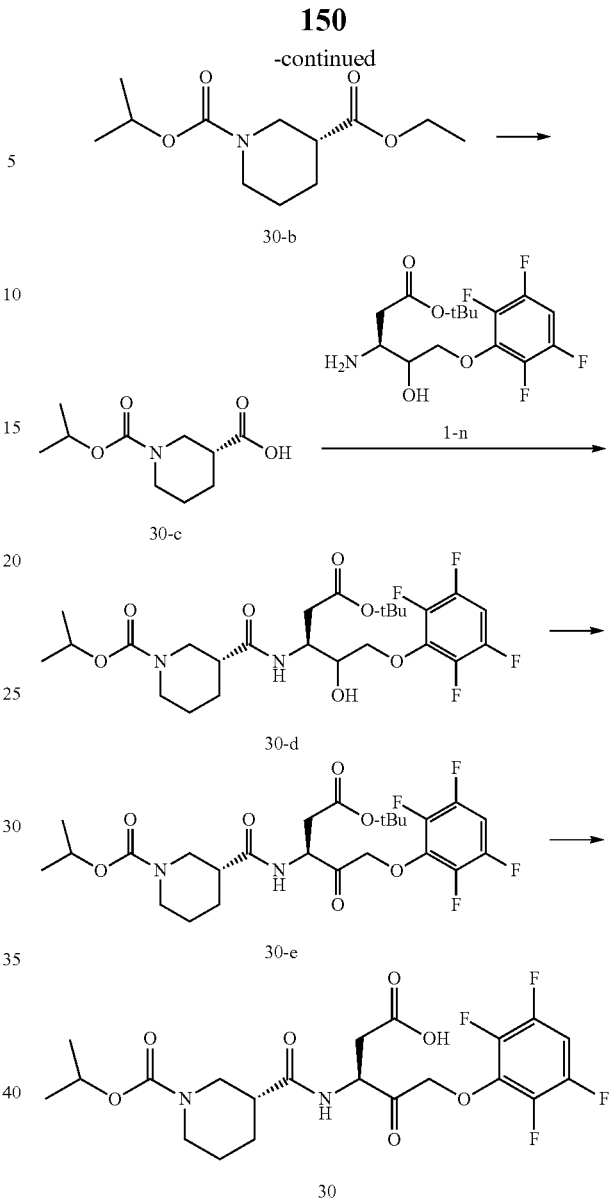

Step 1: Synthesis of Compound 30-b

Triethylamine (2.02 g, 20.00 mmol, 2.77 mL, 4.00 eq) and compound 29-a (1.54 g, 5.00 mmol, 1.00 eq) were dissolved in dichloromethane (100 mL), and added with compound 30-a (919.13 mg, 7.50 mmol, 1.04 mL, 1.50 eq) in an ice bath. The reaction was warmed up to room temperature, and stirred for 18 hours. After the reaction was completed, the reaction solution was added with 150 mL of dichloromethane for dilution, and washed with saturated sodium hydrogen carbonate solution (150 mL) and saturated NH4Cl (100 mL). The organic phases were combined, dried over anhydrous sodium sulfate, filtered and concentrated to give a crude product. The crude product was subjected to column chromatography (petroleum ether:ethyl acetate=1:0~10:1) to give the product of compound 30-b (1.09 g, yield: 90%) as a yellow oil. LCMS m/z=244.0 [M+H]+.

Step 2: Synthesis of Compound 30-c

Compound 30-b (364.95 mg, 1.50 mmol, 1.00 eq) was dissolved in tetrahydrofuran (10.00 mL), and a solution of LiOH.H$_2$O (125.88 mg, 3.00 mmol, 2.00 eq) dissolved in water (10.00 mL) was added to the above solution. The reaction solution was maintained at 25° C. and stirred for 2 hours. After the reaction was completed, the reaction solution was adjusted to pH of 6 with 2 N dilute hydrochloric acid, added with 50 mL of water, and extracted with dichloromethane (30 mL×3). The organic phase was dried over anhydrous sodium sulfate, filtered and concentrated to give the product of compound 30-c (430.00 mg, crude) as a pale yellow oil, which was used directly in the next step without purification. LCMS m/z=238.0 [M+Na]$^+$.

Step 3: Synthesis of Compound 30-d

Compound 30-c (322.87 mg, 1.50 mmol, 1.25 eq) and HATU (912.55 mg, 2.40 mmol, 2.00 eq) were dissolved in dichloromethane (20 mL), and stirred at room temperature for 15 min. Compound 1-n (423.97 mg, 1.20 mmol, 1.00 eq) and N,N-diisopropylethylamine (465.26 mg, 3.60 mmol, 628.73 µL, 3.00 eq) were then added, and stirred at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 30-d (709.00 mg, yield: 58%, purity: 53.8%) as a yellow oil. LCMS m/z=573.1 [M+Na]$^+$.

Step 4: Synthesis of Compound 30-e

Compound 30-d (660.65 mg, 1.20 mmol, 1.00 eq) was dissolved in dichloromethane (20.00 mL), and PIDA (1.55 g, 4.80 mmol, 4.00 eq) and TEMPO (37.74 mg, 240.00 µmol, 0.20 eq) were added thereto. The reaction solution was stirred at room temperature for 48 hours. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was subjected to column chromatography (petroleum ether:ethyl acetate=1:0~3:1) to give the product of compound 30-e (427.00 mg, yield: 56%) as a yellow oil. LCMS m/z=571.1 [M+Na]$^+$.

Step 5: Synthesis of Compound 30

Compound 30-e (420.00 mg, 765.70 µmol, 1.00 eq) was dissolved in dichloromethane (3.00 mL), and trifluoroacetic acid (4.62 g, 40.52 mmol, 3.00 mL) was added thereto. The reaction solution was stirred at room temperature for 1.5 hours. After the reaction was completed, the reaction solution was spin-dried to give a crude product. The crude product was purified by preparative HPLC (under trifluoroacetic acid condition), and lyophilized to give the product of compound 30 (292.00 mg, yield: 77%). $^1$H NMR (400 MHz, DMSO-d$_6$) δ=8.54 (d, J=7.0 Hz, 1H), 7.63-7.51 (m, 1H), 5.29-5.15 (m, 2H), 4.96 (m, 1H), 4.61 (q, J=6.5 Hz, 1H), 3.94-3.80 (m, 2H), 2.88-2.70 (m, 3H), 2.60 (dd, J=6.8, 16.8 Hz, 1H), 2.31 (t, J=10.5 Hz, 1H), 1.88-1.79 (m, 1H), 1.72-1.62 (m, 1H), 1.57-1.46 (m, 1H), 1.38-1.27 (m, 1H), 1.19 (s, 3H), 1.17 (s, 3H); LCMS m/z=493.0 [M+H]$^+$; 515.1 [M+Na]$^+$.

Example 31: Compound 31

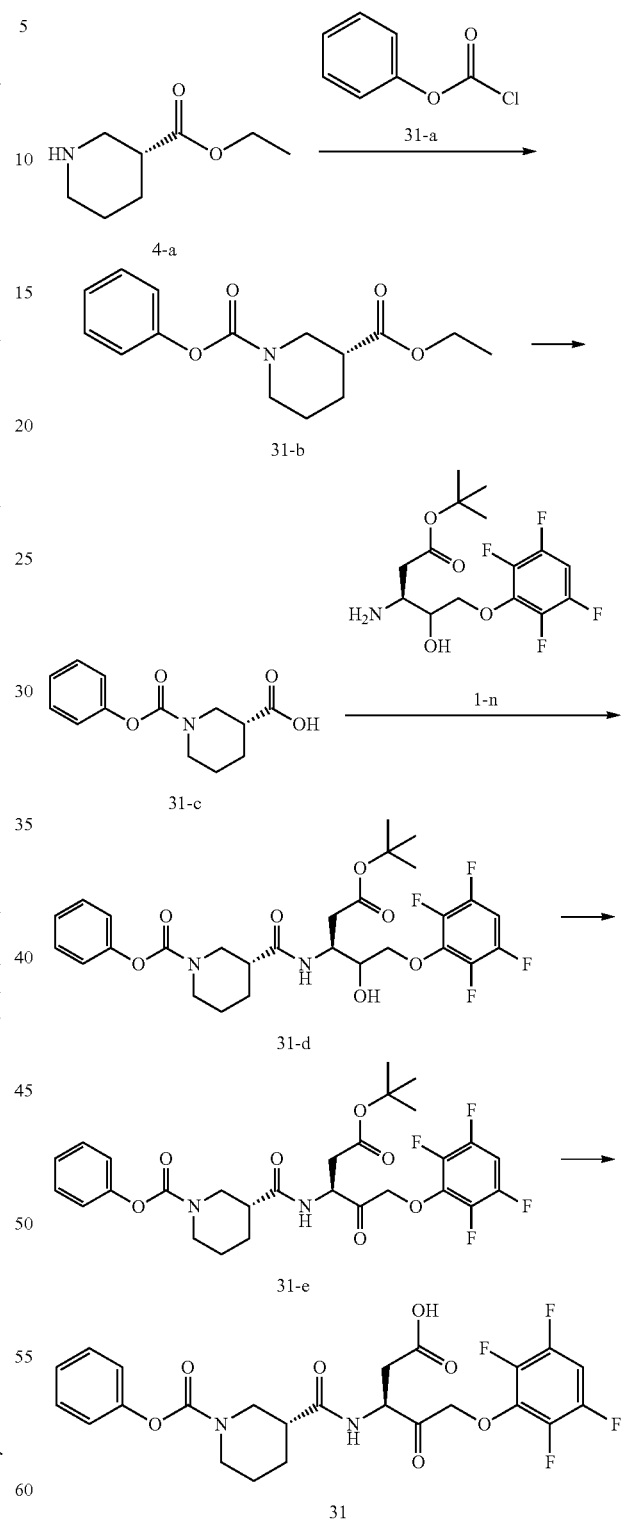

Step 1: Synthesis of Compound 31-b

Compound 4-a (500.00 mg, 3.18 mmol, 1.00 eq) and triethylamine (643.66 mg, 6.36 mmol, 881.73 µL, 2.00 eq)

were dissolved in dichloromethane (15.00 mL), and compound 31-a (746.84 mg, 4.77 mmol, 597.47 μL, 1.50 eq) was added thereto. The reaction solution was stirred at 18° C. for 15 hours. After the reaction was completed, the reaction solution was added with 150 mL of water, and extracted with dichloromethane (150 mL×3). The organic phase was dried over anhydrous sodium sulfate, filtered and concentrated to give a crude product. The crude product was subjected to column chromatography (petroleum ether:ethyl acetate=1:0~4:1) to give the product of compound 31-b (700.00 mg, yield: 79%) as a colorless oil. LCMS m/z=277.9 [M+H]$^+$.

Step 2: Synthesis of Compound 31-c

Compound 31-b (300.00 mg, 1.08 mmol, 1.00 eq) was dissolved in tetrahydrofuran (8.00 mL), and a solution of LiOH.H$_2$O (67.98 mg, 1.62 mmol, 1.50 eq) dissolved in water (8.00 mL) was added to the above solution. The reaction solution was stirred at 6° C. for 1.5 hours. After the reaction was completed, the reaction solution was adjusted to pH of 5 with 2 N dilute hydrochloric acid, added with 100 mL of water, and extracted with dichloromethane (100 mL×3). The organic phase was dried over anhydrous sodium sulfate, filtered and concentrated to give the product of compound 31-c (250.00 mg, crude) as a colorless oil, which was used directly in the next step without purification. $^1$H NMR (400 MHz, CHLOROFORM-d) δ=7.32-7.41 (m, 2H), 7.17-7.24 (m, 1H), 7.11 (d, J=7.78 Hz, 2H), 4.28 (d, J=14.31 Hz, 1H), 3.90-4.21 (m, 1H), 3.36-3.82 (m, 1H), 3.05-3.18 (m, 1H), 2.64 (br. s., 1H), 2.16 (br. s., 1H), 1.55-1.91 (m, 3H).

Step 3: Synthesis of Compound 31-d

Compound 1-n (353.31 mg, 1.00 mmol, 1.00 eq) was dissolved in dichloromethane (15.00 mL), and compound 31-c (250.00 mg, 1.00 mmol, 1.00 eq), EDCl (262.63 mg, 1.37 mmol, 1.37 eq), HOBt (185.11 mg, 1.37 mmol, 1.37 eq) and NMM (303.45 mg, 3.00 mmol, 329.84 μL, 3.00 eq) were added thereto. The reaction solution was stirred at 6° C. for 15 hours under the protection of nitrogen gas. After the reaction was completed, the reaction solution was added with 150 mL of water, and extracted with dichloromethane (150 mL×3). The organic phases were combined, dried over anhydrous sodium sulfate, filtered and concentrated to give a crude product. The crude product was subjected to column chromatography (petroleum ether:ethyl acetate=1:0~3:2) to give the product of compound 31-d (350.00 mg, yield: 58%) as a colorless solid. LCMS m/z=607.3 [M+Na]$^+$.

Step 4: Synthesis of Compound 31-e

Compound 31-d (300.00 mg, 513.21 μmol, 1.00 eq) was dissolved in dichloromethane (10.00 mL), and PIDA (639.73 mg, 1.99 mmol, 3.87 eq) and TEMPO (24.21 mg, 153.96 μmol, 0.30 eq) were added thereto. The reaction solution was stirred at 15° C. for 17 hours under the protection of nitrogen gas. After the reaction was completed, the reaction solution was added with 150 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=1:0~2:1) to give the product of compound 31-e (190.00 mg, yield: 46%) as a colorless oil. LCMS m/z=605.1 [M+Na]$^+$.

Step 5: Synthesis of Compound 31

Compound 31-e (190.00 mg, 326.16 μmol, 1.00 eq) was dissolved in dichloromethane (6.00 mL), and trifluoroacetic acid (4.62 g, 40.52 mmol, 3.00 mL, 124.23 eq) was added thereto. The reaction solution was stirred at 15° C. for 1 hour under the protection of nitrogen gas. After the reaction was completed, the reaction solution was spin-dried to give a crude product. The crude product was purified by preparative HPLC (under trifluoroacetic acid condition), and lyophilized to give the product of compound 31 (89.50 mg, yield: 52%). $^1$H NMR (400 MHz, DMSO-d$_6$) δ=12.41 (br. s., 1H), 8.58 (d, J=7.53 Hz, 1H), 7.50-7.68 (m, 1H), 7.34-7.41 (m, 2H), 7.17-7.25 (m, 1H), 7.11 (d, J=8.03 Hz, 2H), 5.14-5.32 (m, 2H), 4.63 (q, J=6.53 Hz, 1H), 3.79-4.15 (m, 2H), 3.10-3.47 (m, 1H), 2.83-3.08 (m, 2H), 2.70-2.80 (m, 1H), 2.55-2.65 (m, 1H), 1.91 (d, J=11.04 Hz, 1H), 1.74 (d, J=8.03 Hz, 1H), 1.54-1.67 (m, 1H), 1.46 (br. s., 1H); LCMS m/z=527.0 [M+H]$^+$.

Example 32: Compound 32

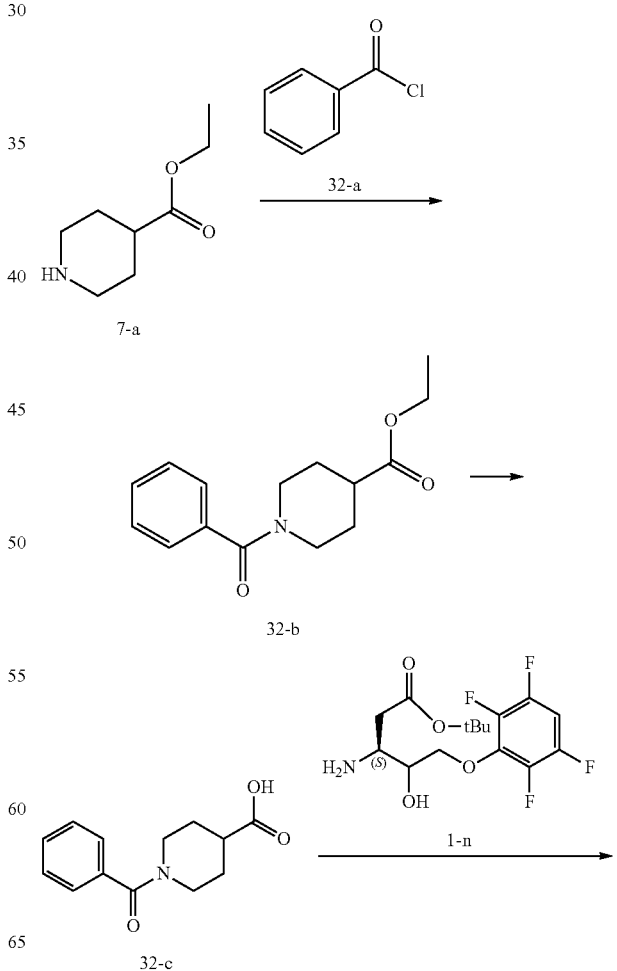

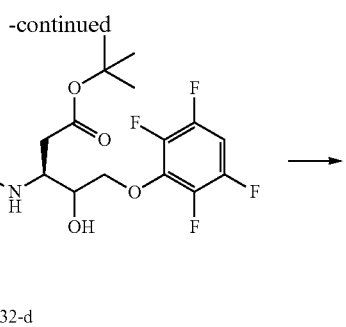

32-d 32-e

32

Step 1: Synthesis of Compound 32-b

Compound 7-a (559.19 mg, 3.56 mmol, 548.23 μL, 1.00 eq) and triethylamine (1.08 g, 10.68 mmol, 1.48 mL, 3.00 eq) were dissolved in dichloromethane (10.00 mL), and compound 32-a (500.00 mg, 3.56 mmol, 413.22 μL, 1.00 eq) was slowly added thereto with the temperature maintained at 0° C. After the addition was completed, the reaction was maintained at a temperature of 25° C. and stirred for 1 hour. After the reaction was completed, the reaction solution was added with water (50 mL) for quenching, and then extracted with dichloromethane (20 mL×3). The organic phases were combined, washed with water (30 mL) and saturated brine (30 mL), dried over anhydrous sodium sulfate, and then concentrated to give a crude product. The crude product was purified by column chromatography (petroleum ether:ethyl acetate=1:0~1:1) to give compound 32-b (500.00 mg, yield: 54%). $^1$H NMR (400 MHz, CHLOROFORM-d) δ=7.39 (brs, 5H), 5.29 (s, 1H), 4.64-4.48 (m, 1H), 4.20-4.10 (m, 2H), 3.91-3.57 (m, 1H), 3.12-2.97 (m, 2H), 2.71-2.45 (m, 1H), 1.80-1.67 (m, 2H), 1.26 (t, J=7.0 Hz, 3H).

Step 2: Synthesis of Compound 32-c

Compound 32-b (500.00 mg, 1.91 mmol, 1.00 eq) was dissolved in a mixed solvent of tetrahydrofuran (10.00 mL) and water (10.00 mL), and LiOH.H$_2$O (321.14 mg, 7.65 mmol, 4.00 eq) was added thereto. The mixture was stirred at a temperature of 25° C. for 2 hours. After the reaction was completed, the reaction solution was adjusted to pH of about 6 with dilute hydrochloric acid (1 N). The aqueous phase was then extracted with ethyl acetate (50 mL×3). The combined organic phases were washed with brine (50 mL) and water (50 mL), dried over anhydrous sodium sulfate, filtered and concentrated to give compound 32-c (400.00 mg, yield: 90%) as a yellow oil. $^1$H NMR (400 MHz, CHLOROFORM-d) δ=7.45-7.33 (m, 5H), 4.66-4.36 (m, 1H), 3.88-3.67 (m, 2H), 3.08 (br. s., 2H), 2.62 (s, 1H), 2.14-1.59 (m, 4H).

Step 3: Synthesis of Compound 32-d

Compounds 32-c (200.00 mg, 857.41 μmol, 1.00 eq) and 1-n (302.93 mg, 857.41 μmol, 1.00 eq) were dissolved in dichloromethane (20 mL), and EDCl (225.18 mg, 1.17 mmol, 1.37 eq), HOBt (158.72 mg, 1.17 mmol, 1.37 eq) and NMM (260.18 mg, 2.57 mmol, 282.80 μL, 3.00 eq) were added thereto and stirred at room temperature for 15 min. The reaction was stirred at room temperature for another 2 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was purified by preparative TLC (petroleum ether:ethyl acetate=2:1) to give the product of compound 32-d (220.00 mg, yield: 45%). $^1$H NMR (400 MHz, CHLOROFORM-d) δ=7.40 (br. s., 5H), 6.89-6.76 (m, 1H), 6.73-6.61 (m, 1H), 4.82-4.60 (m, 1H), 4.36-4.15 (m, 3H), 4.14-4.04 (m, 1H), 3.92-3.73 (m, 1H), 3.59-3.41 (m, 1H), 3.13-2.81 (m, 3H), 2.74 (s, 1H), 2.60 (d, J=4.5 Hz, 2H), 2.46-2.31 (m, 1H), 1.65-1.60 (m, 2H), 1.46 (s, 9H).

Step 4: Synthesis of Compound 32-e

Compound 32-d (150.00 mg, 263.82 μmol, 1.00 eq) was dissolved in dichloromethane (20.00 mL), and PIDA (339.91 mg, 1.06 mmol, 4.00 eq) and TEMPO (8.30 mg, 52.76 μmol, 0.20 eq) were added thereto. The reaction solution was stirred at room temperature for 5 hours. After the reaction was completed, the reaction solution was added with saturated sodium hydrogen carbonate solution (25 mL) and saturated sodium sulfite solution (25 mL), extracted with dichloromethane (40 mL×3), and washed with saturated brine (50 mL). The organic phase was dried over anhydrous sodium sulfate, filtered and concentrated to give a crude product. The crude product was purified by preparative TLC (petroleum ether:ethyl acetate=2:1) to give the product of compound 32-e (40.00 mg, crude) as a yellow oil, which was used directly in the next step without purification.

Step 5: Synthesis of Compound 32

Compound 32-e (40.00 mg, 70.60 μmol, 1.00 eq) was dissolved in dichloromethane (2.00 mL), and trifluoroacetic acid (1.00 mL) was added thereto. The reaction solution was stirred at room temperature for 2 hours. After the reaction was completed, the reaction solution was spin-dried to give a crude product. The crude product was purified by preparative HPLC (under trifluoroacetic acid condition), and lyophilized to give the product of compound 32 (8.00 mg, yield: 11%). $^1$H NMR (400 MHz, DMSO-d$_6$) δ=8.45-8.33 (m, 1H), 7.59-7.49 (m, 1H), 7.43 (br. s., 3H), 7.35 (br. s., 2H), 5.26-5.00 (m, 2H), 4.69-4.53 (m, 1H), 4.49-4.31 (m, 1H), 2.91-2.61 (m, 5H), 1.86-1.34 (m, 6H).

Example 33: Compound 33

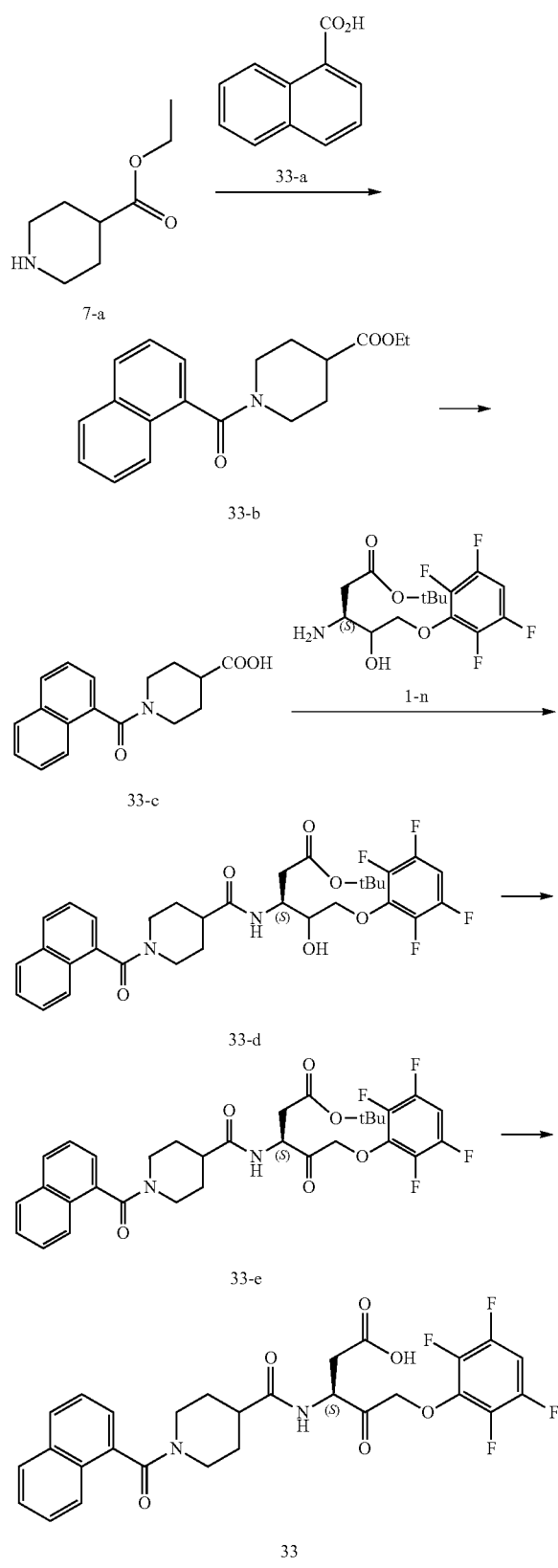

Step 1: Synthesis of Compound 33-b

Compound 33-a (1.73 g, 10.05 mmol, 1.00 eq) and HOBT (2.04 g, 15.08 mmol, 1.50 eq) were dissolved in dichloromethane (10 mL), added with EDCl (2.89 g, 15.08 mmol, 1.50 eq), and stirred at room temperature for 15 min. Compound 7-a (1.58 g, 10.05 mmol, 1.55 mL, 1.00 eq) and N,N-diisopropylethylamine (2.60 g, 20.10 mmol, 3.51 mL, 2.00 eq) were then dissolved in dichloromethane, added to the above solution, and stirred at room temperature for 15 hours. After the reaction was completed, the reaction solution was added with 80 mL of water, and extracted with dichloromethane (80 mL×3). The organic phases were combined, dried over anhydrous sodium sulfate, filtered and concentrated to give the product of compound 33-b (4.37 g, crude) as a yellow oil, which was used directly in the next step without purification. LCMS m/z=311.9 [M+H]$^+$.

Step 2: Synthesis of Compound 33-c

Compound 33-b (3.13 g, 10.05 mmol, 1.00 eq) was dissolved in tetrahydrofuran (50.00 mL), and a solution of LiOH.H$_2$O (843.40 mg, 20.10 mmol, 2.00 eq) dissolved in water (50.00 mL) was added to the above solution. The reaction solution was maintained at 25° C. and stirred for 2 hours. After the reaction was completed, the reaction solution was adjusted to pH of 6 with 2 N dilute hydrochloric acid, added with 100 mL of water, and extracted with dichloromethane (60 mL×3). The organic phase was dried over anhydrous sodium sulfate, filtered and concentrated to give the product of compound 33-c (3.48 g, crude) as a pale a yellow oil, which was used directly in the next step without purification. LCMS m/z=283.9 [M+H]$^+$.

Step 3: Synthesis of Compound 33-d

Compound 33-c (176.42 mg, 622.69 μmol, 1.10 eq) and HOBT (114.72 mg, 849.12 μmol, 1.50 eq) were dissolved in dichloromethane (15 mL), added with EDCl (162.75 mg, 849.12 μmol, 1.50 eq), and stirred at room temperature for 15 mins. Compound 1-n (200.00 mg, 566.08 μmol, 1.00 eq) and N,N-diisopropylethylamine (146.32 mg, 1.13 mmol, 197.73 μL, 2.00 eq) were then dissolved in dichloromethane, added to the above solution, and stirred at room temperature for 15 hours. After the reaction was completed, the reaction solution was added with 80 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 33-d (228.00 mg, yield: 65%) as a yellow oil. LCMS m/z=619.3 [M+H]$^+$; 641.3 [M+Na]$^+$.

Step 4: Synthesis of Compound 33-e

Compound 33-d (130.00 mg, 210.15 μmol, 1.00 eq) was dissolved in dichloromethane (20.00 mL), and sodium hydrogen carbonate solution (88.27 mg, 1.05 mmol, 40.87 μL, 5.00 eq) and DMP (178.26 mg, 420.30 μmol, 130.12 μL, 2.00 eq) were added thereto. The reaction solution was stirred at room temperature for 15 hours. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was subjected to column chromatography (petroleum ether:ethyl acetate=1:0~2:1) to give the product of compound 33-e (119.00 mg, yield: 63%) as a yellow oil. LCMS m/z=617.3 [M+H]⁺; 639.3 [M+Na]⁺.

Step 5: Synthesis of Compound 33

Compound 33-e (85.00 mg, 137.85 μmol, 1.00 eq) was dissolved in ethyl acetate (5.00 mL), and HCl/EtOAc (4 M, 6.00 mL) was added thereto. The reaction solution was stirred at room temperature for 1.5 hours. After the reaction was completed, the reaction solution was spin-dried to give a crude product. The crude product was purified by preparative HPLC (under formic acid condition), and lyophilized to give the product of compound 33 (45.00 mg, yield: 58%). $^1$H NMR (400 MHz, DMSO-d$_6$) δ=8.42 (br. s, 1H), 7.97 (d, J=7.6 Hz, 2H), 7.73 (d, J=24.8 Hz, 1H), 7.56 (d, J=6.0 Hz, 4H), 7.40 (dd, J=24.8, 6.8 Hz, 1H), 4.63 (br. s, 2H), 3.28-3.21 (m, 1H), 3.00-2.93 (m, 2H), 2.69-2.60 (m, 2H), 1.86 (br. s, 1H), 1.64-1.43 (m, 2H), 1.22 (br. s, 1H); LCMS m/z=561.2 [M+H]⁺; 583.2 [M+Na]⁺.

Example 34: Compound 34

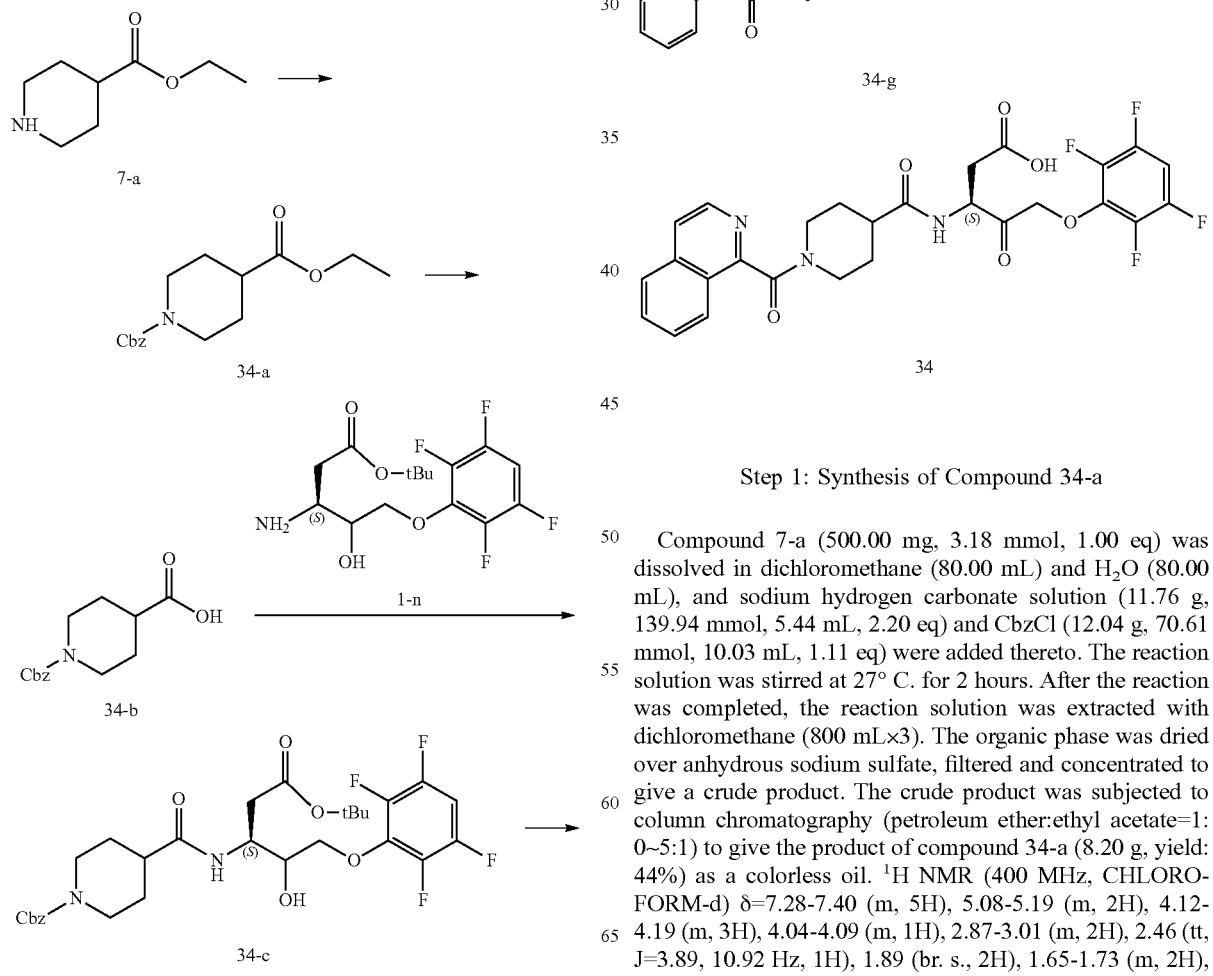

Step 1: Synthesis of Compound 34-a

Compound 7-a (500.00 mg, 3.18 mmol, 1.00 eq) was dissolved in dichloromethane (80.00 mL) and H₂O (80.00 mL), and sodium hydrogen carbonate solution (11.76 g, 139.94 mmol, 5.44 mL, 2.20 eq) and CbzCl (12.04 g, 70.61 mmol, 10.03 mL, 1.11 eq) were added thereto. The reaction solution was stirred at 27° C. for 2 hours. After the reaction was completed, the reaction solution was extracted with dichloromethane (800 mL×3). The organic phase was dried over anhydrous sodium sulfate, filtered and concentrated to give a crude product. The crude product was subjected to column chromatography (petroleum ether:ethyl acetate=1: 0~5:1) to give the product of compound 34-a (8.20 g, yield: 44%) as a colorless oil. $^1$H NMR (400 MHz, CHLOROFORM-d) δ=7.28-7.40 (m, 5H), 5.08-5.19 (m, 2H), 4.12-4.19 (m, 3H), 4.04-4.09 (m, 1H), 2.87-3.01 (m, 2H), 2.46 (tt, J=3.89, 10.92 Hz, 1H), 1.89 (br. s., 2H), 1.65-1.73 (m, 2H), 1.24-1.28 (m, 3H).

Step 2: Synthesis of Compound 34-b

Compound 34-a (8.87 g, 30.45 mmol, 1.00 eq) was dissolved in tetrahydrofuran (60.00 mL), and a solution of LiOH.H$_2$O (3.83 g, 91.34 mmol, 3.00 eq) dissolved in H$_2$O (60.00 mL) was added to the above solution. The reaction solution was stirred at 27° C. for 2 hours. After the reaction was completed, the reaction solution was adjusted to pH of 6 with 2 N dilute hydrochloric acid, added with 300 mL of water, and extracted with dichloromethane (300 mL×3). The organic phase was dried over anhydrous sodium sulfate, filtered and concentrated to give the product of compound 34-b (7.45 g, crude) as a colorless oil, which was used directly in the next step without purification. $^1$H NMR (400 MHz, CHLOROFORM-d) δ=7.28-7.41 (m, 5H), 5.14 (s, 2H), 3.72-3.81 (m, 1H), 2.96 (t, J=11.04 Hz, 2H), 2.52 (tt, J=3.83, 10.73 Hz, 1H), 1.82-2.01 (m, 3H), 1.61-1.76 (m, 2H).

Step 3: Synthesis of Compound 34-c

Compound 1-n (5.00 g, 14.15 mmol, 1.00 eq) was dissolved in dichloromethane (90.00 mL), and compound 34-b (3.73 g, 14.15 mmol, 1.00 eq), EDCl (3.72 g, 19.39 mmol, 1.37 eq), HOBt (2.62 g, 19.39 mmol, 1.37 eq) and NMM (4.29 g, 42.45 mmol, 4.66 mL, 3.00 eq) were added thereto. The reaction solution was stirred at 27° C. for 16 hours under the protection of nitrogen gas. After the reaction was completed, the reaction solution was added with 400 mL of water, and extracted with dichloromethane (400 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 34-c (4.60 g, yield: 43%) as a colorless oil. $^1$H NMR (400 MHz, CHLOROFORM-d) δ=7.29-7.40 (m, 5H), 6.75-6.87 (m, 1H), 6.63 (d, J=8.28 Hz, 1H), 5.13 (s, 2H), 4.09-4.41 (m, 7H), 3.50-3.59 (m, 1H), 2.75 (dd, J=6.40, 16.44 Hz, 1H), 2.64-2.70 (m, 1H), 2.53-2.62 (m, 1H), 2.29 (tt, J=3.67, 11.39 Hz, 1H), 1.81 (br. s., 2H), 1.57-1.67 (m, 2H), 1.45-1.47 (m, 9H).

Step 4: Synthesis of Compound 34-d

Compound 34-c (4.25 g, 7.10 mmol, 1.00 eq) was dissolved in methanol (200.00 mL), and Pd/C (420.00 mg, purity of 10%) was added to the solution. The reaction solution was stirred in a hydrogen atmosphere (hydrogen balloon) at 27° C. for 2 hours. After the reaction was completed, the reaction solution was filtered through diatomaceous earth, and the filter cake was washed with methanol (200 mL). The resulting filtrate was concentrated to give the product of compound 34-d (3.26 g, crude), which was used directly in the next step without purification. $^1$H NMR (400 MHz, CHLOROFORM-d) δ=6.75-6.87 (m, 1H), 6.29-6.64 (m, 1H), 4.05-4.37 (m, 4H), 2.98-3.18 (m, 2H), 2.44-2.93 (m, 4H), 2.18-2.30 (m, 1H), 2.01 (s, 1H), 1.52-1.86 (m, 5H), 1.37-1.49 (m, 9H).

Step 5: Synthesis of Compound 34-f

Compound 34-d (60.00 mg, 129.19 μmol, 1.00 eq) was dissolved in dichloromethane (8.00 mL), and compound 34-e (22.37 mg, 129.19 μmol, 1.00 eq), EDCl (33.93 mg, 176.98 μmol, 1.37 eq), HOBt (23.91 mg, 176.98 μmol, 1.37 eq) and NMM (39.20 mg, 387.56 μmol, 42.61 μL, 3.00 eq) were added thereto. The reaction solution was stirred at 27° C. for 16 hours under the protection of nitrogen gas. After the reaction was completed, the reaction solution was added with 80 mL of water, and extracted with dichloromethane (80 mL×3). The organic phases were combined, dried over anhydrous sodium sulfate, filtered and concentrated to give a crude product. The crude product was subjected to column chromatography (dichloromethane/methanol; 0-10%) to give the product of compound 34-f (61.00 mg, yield: 59%) as a colorless oil. LCMS m/z=620.3 [M+H]$^+$.

Step 6: Synthesis of Compound 34-g

Compound 34-f (61.00 mg, 75.81 μmol, 1.00 eq) was dissolved in dichloromethane (4.00 mL), and PIDA (94.50 mg, 293.38 μmol, 3.87 eq) and TEMPO (3.58 mg, 22.74 μmol, 0.30 eq) were added thereto. The reaction solution was stirred at 27° C. for 16 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was purified by preparative silica gel plates (dichloromethane:methanol=15:1) to give the product of compound 34-g (36.00 mg, yield: 68%) as a colorless oil. LCMS m/z=618.3 [M+H]$^+$.

Step 7: Synthesis of Compound 34

Compound 34-g (36.00 mg, 58.29 μmol, 1.00 eq) was dissolved in dichloromethane (2.00 mL), and trifluoroacetic acid (956.08 mg, 8.39 mmol, 620.83 μL, 143.85 eq) was added thereto. The reaction solution was stirred at 25° C. for 1 hour under the protection of nitrogen gas. After the reaction was completed, the reaction solution was spin-dried to give a crude product. The crude product was purified by preparative HPLC (under trifluoroacetic acid condition), and lyophilized to give the product of compound 34 (21.00 mg, yield: 64%). $^1$H NMR (400 MHz, DMSO-d$_6$) δ=8.44-8.55 (m, 2H), 8.06 (d, J=8.03 Hz, 1H), 7.88-7.95 (m, 2H), 7.85 (t, J=7.53 Hz, 1H), 7.70-7.76 (m, 1H), 7.48-7.63 (m, 1H), 5.11-5.29 (m, 2H), 4.54-4.67 (m, 2H), 3.18 (d, J=13.55 Hz, 1H), 2.94-3.07 (m, 2H), 2.65-2.78 (m, 1H), 2.52-2.62 (m, 2H), 1.89 (t, J=8.78 Hz, 1H), 1.50-1.70 (m, 2H), 1.34-1.48 (m, 1H); LCMS m/z=562.1 [M+H]$^+$.

Example 35: Compound 35

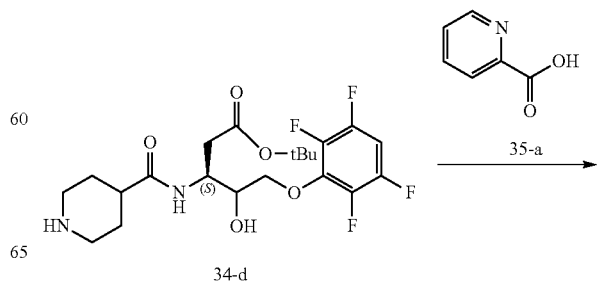

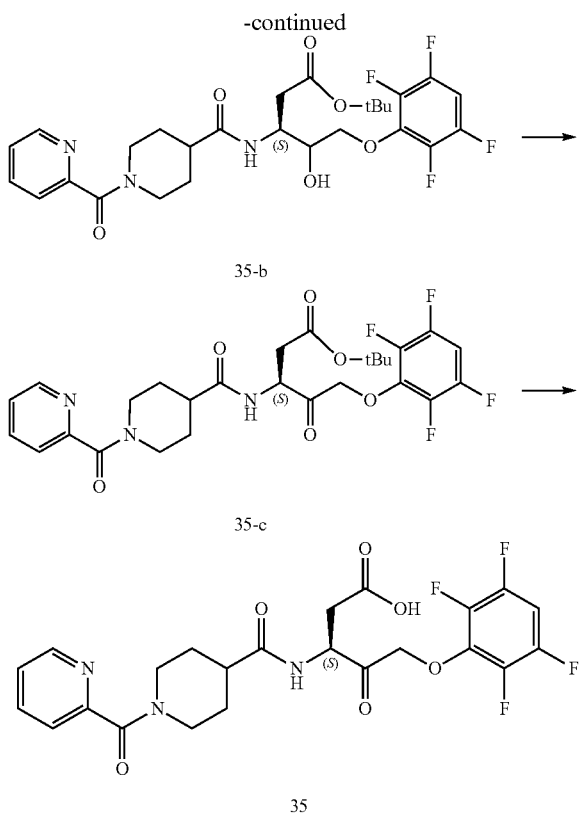

Step 1: Synthesis of Compound 35-b

Compound 35-a (43.09 mg, 350.00 μmol, 1.40 eq) and HOBT (50.67 mg, 375.00 μmol, 1.50 eq) were dissolved in dichloromethane (20 mL), added with EDCl (71.89 mg, 375.00 μmol, 1.50 eq), and stirred at room temperature for 15 min. Compound 34-d (116.11 mg, 250.00 μmol, 1.00 eq) and NMM (75.86 mg, 750.00 μmol, 82.46 μL, 3.00 eq) were then added, and stirred at room temperature for 16 hours. After the reaction was completed, the reaction solution was added with 150 mL of water, and extracted with dichloromethane (80 mL×3). The organic phases were combined, dried over anhydrous sodium sulfate, filtered and concentrated to give the product of compound 35-b (182 mg, crude) as a yellow oil, which was used directly in the next step without purification. LCMS m/z=570.3 [M+H]⁺; 592.3 [M+Na]⁺.

Step 2: Synthesis of Compound 35-c

Compound 35-b (142.39 mg, 250.00 μmol, 1.00 eq) was dissolved in dichloromethane (20.00 mL), and PIDA (322.10 mg, 1.00 mmol, 4.00 eq) and TEMPO (7.86 mg, 50.00 μmol, 0.20 eq) were added thereto. The reaction solution was stirred at room temperature for 54 hours. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was subjected to column chromatography (dichloromethane:methanol=1:0~10:1) to give the product of compound 35-c (105.00 mg, yield: 34%) as a yellow oil. LCMS m/z=568.2 [M+H]⁺.

Step 3: Synthesis of Compound 35

Compound 35-c (113.00 mg, 199.11 μmol, 1.00 eq) was dissolved in dichloromethane (3.00 mL), and trifluoroacetic acid (4.62 g, 40.52 mmol, 3.00 mL) was added thereto. The reaction solution was stirred at room temperature for 1.5 hours. After the reaction was completed, the reaction solution was spin-dried to give a crude product. The crude product was purified by preparative HPLC (under trifluoroacetic acid condition), and lyophilized to give the product of compound 35 (24.40 mg, yield: 24%). ¹H NMR (400 MHz, DMSO-d₆) δ=8.60 (d, J=5.0 Hz, 1H), 8.47 (d, J=7.6 Hz, 1H), 7.94 (t, J=7.6 Hz, 1H), 7.62-7.52 (m, 2H), 7.49 (dd, J=4.8, 7.6 Hz, 1H), 5.22 (dd, J=3.6, 10.2 Hz, 2H), 4.62 (d, J=6.4 Hz, 1H), 4.47 (d, J=13.2 Hz, 1H), 3.09-3.01 (m, 1H), 2.93-2.81 (m, 1H), 2.75 (dd, J=6.0, 12 Hz, 1H), 2.64-2.53 (m, 2H), 1.82 (br. s., 1H), 1.72-1.60 (m, 1H), 1.60-1.47 (m, 2H); LCMS m/z=512.1 [M+H]⁺.

Example 36: Compound 36

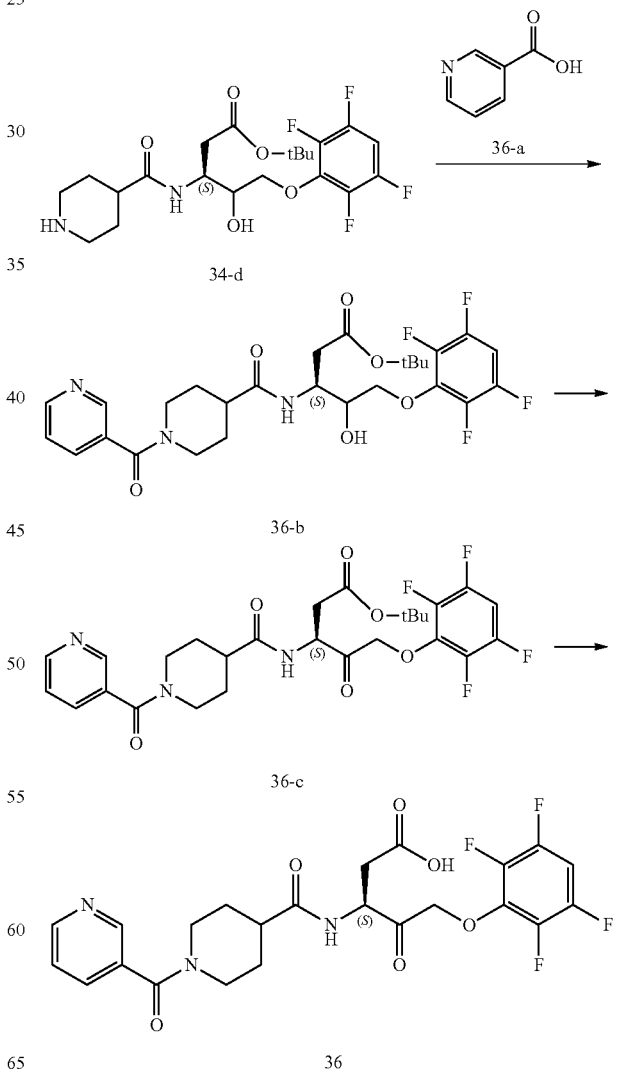

Step 1: Synthesis of Compound 36-b

Compound 34-d (200.00 mg, 430.62 µmol, 1.00 eq) was dissolved in dichloromethane (5.00 mL), and compound 36-a (53.01 mg, 430.62 µmol, 36.06 µL, 1.00 eq), EDCl (113.09 mg, 589.95 µmol, 1.37 eq), HOBt (79.71 mg, 589.95 µmol, 1.37 eq) and NMM (130.67 mg, 1.29 mmol, 142.03 µL, 3.00 eq) were added thereto. The reaction solution was stirred at 27° C. for 16 hours under the protection of nitrogen gas. After the reaction was completed, the reaction solution was added with 100 mL of water, and extracted with dichloromethane (100 mL×3). The organic phases were combined, dried over anhydrous sodium sulfate, filtered and concentrated to give a crude product. The crude product was purified by preparative silica gel plates (dichloromethane:methanol=15:1) to give the product of compound 36-b (120.00 mg, yield: 46%) as a colorless oil. LCMS m/z=570.3 [M+H]$^+$.

Step 2: Synthesis of Compound 36-c

Compound 36-b (120.00 mg, 210.70 µmol, 1.00 eq) was dissolved in dichloromethane (6.00 mL), and PIDA (262.64 mg, 815.39 µmol, 3.87 eq) and TEMPO (6.63 mg, 42.14 µmol, 0.20 eq) were added thereto. The reaction solution was stirred at 27° C. for 16 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was purified by preparative silica gel plates (dichloromethane:methanol=15:1) to give the product of compound 36-c (110.00 mg, yield: 86%) as a colorless oil. LCMS m/z=568.2 [M+H]$^+$.

Step 3: Synthesis of Compound 36

Compound 36-c (110.00 mg, 193.82 µmol, 1.00 eq) was dissolved in dichloromethane (4.00 mL), and trifluoroacetic acid (3.18 g, 27.88 mmol, 2.06 mL, 143.85 eq) was added thereto. The reaction solution was stirred at 27° C. for 1 hour under the protection of nitrogen gas. After the reaction was completed, the reaction solution was spin-dried to give a crude product. The crude product was purified by preparative HPLC (under trifluoroacetic acid condition), and lyophilized to give the product of compound 36 (46.10 mg, yield: 47%). $^1$H NMR (400 MHz, DMSO-d$_6$) δ=8.65-8.78 (m, 2H), 8.46 (d, J=7.53 Hz, 1H), 8.02 (d, J=8.03 Hz, 1H), 7.50-7.69 (m, 2H), 5.13-5.30 (m, 2H), 4.61 (q, J=7.03 Hz, 1H), 4.23-4.52 (m, 2H), 3.55 (d, J=10.54 Hz, 1H), 3.12 (br. s., 1H), 2.86 (d, J=9.03 Hz, 1H), 2.64-2.78 (m, 1H), 2.58 (dd, J=6.78, 16.81 Hz, 1H), 1.44-1.88 (m, 4H); LCMS m/z=512.1 [M+H]$^+$.

Example 37: Compound 37

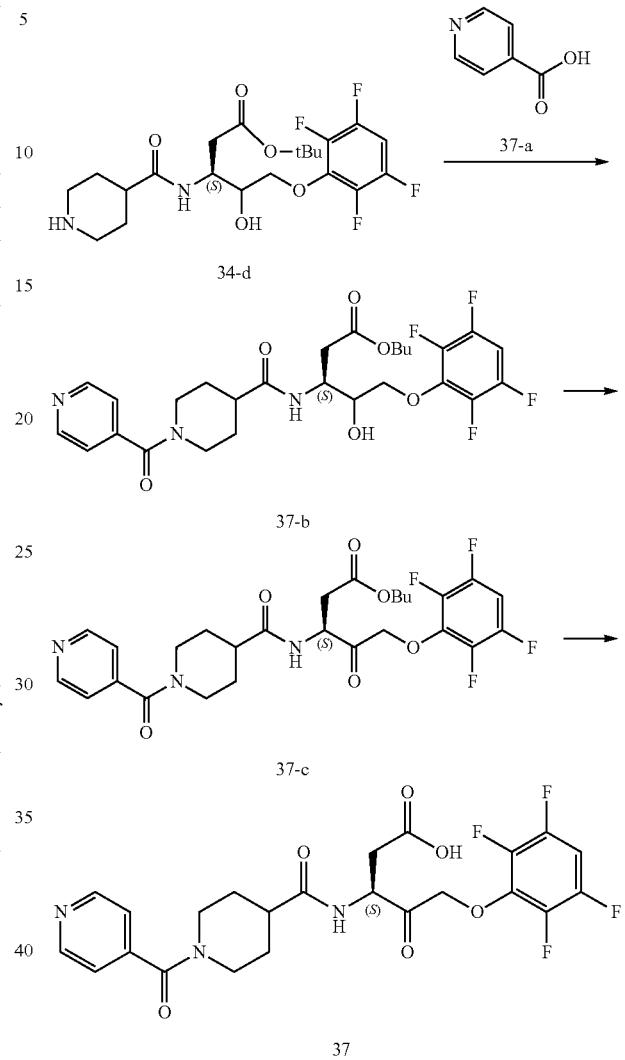

Step 1: Synthesis of Compound 37-b

Compound 34-d (200.00 mg, 430.62 µmol, 1.00 eq) was dissolved in dichloromethane (5.00 mL), and compound 37-a (63.62 mg, 516.74 µmol, 1.20 eq), EDCl (112.27 mg, 585.64 µmol, 1.36 eq), HOBt (79.13 mg, 585.64 µmol, 1.36 eq) and NMM (130.67 mg, 1.29 mmol, 142.03 µL, 3.00 eq) were added thereto. The reaction solution was stirred at 25° C. for 12 hours under the protection of nitrogen gas. After the reaction was completed, the reaction solution was added with 100 mL of water, and extracted with dichloromethane (50 mL×3). The organic phases were combined, dried over anhydrous sodium sulfate, filtered and concentrated to give a crude product. The crude product was subjected to column chromatography (dichloromethane:methanol=100:0~100:10) to give the product of compound 37-b (150.00 mg, yield: 48) as a yellow oil.

Step 2: Synthesis of Compound 37-c

Compound 37-b (100.00 mg, 175.58 µmol, 1.00 eq) was dissolved in dichloromethane (5.00 mL), and PIDA (226.22 mg, 702.32 µmol, 4.00 eq) and TEMPO (5.52 mg, 35.12 µmol, 0.20 eq) were added thereto. The reaction solution was stirred at 25° C. for 12 hours under the protection of nitrogen gas. After the reaction was completed, the reaction solution was added with 50 mL of ethyl acetate. The solution was washed successively with saturated sodium hydrogen carbonate (20 mL), saturated brine (20 mL) and water (20 mL). The organic phase was dried over anhydrous sodium sulfate, filtered and concentrated to give a crude product. The crude product was purified by preparative silica gel plates (petroleum ether:ethyl acetate=2:1) to give the product of compound 37-c (70.00 mg, yield: 23%) as a yellow oil.

Step 3: Synthesis of Compound 37

Compound 37-c (50.00 mg, 88.10 µmol, 1.00 eq) was dissolved in dichloromethane (4.00 mL), and trifluoroacetic acid (1 mL) was added thereto. The reaction solution was stirred at 25° C. for 0.8 hour under the protection of nitrogen gas. After the reaction was completed, the reaction solution was spin-dried to give a crude product. The crude product was purified by preparative HPLC (under trifluoroacetic acid condition), and lyophilized to give the product of compound 37 (10.00 mg, yield: 21%), LCMS m/z=512.2 [M+H]$^+$.

Example 38: Compound 38

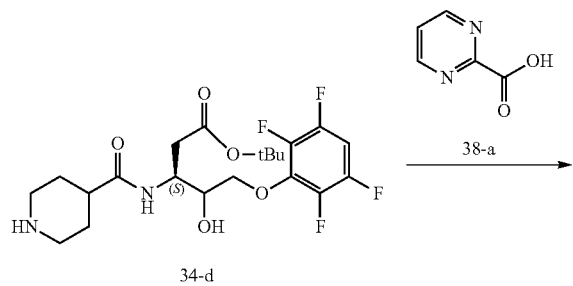

34-d

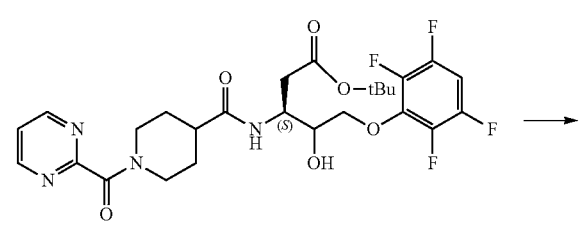

38-b

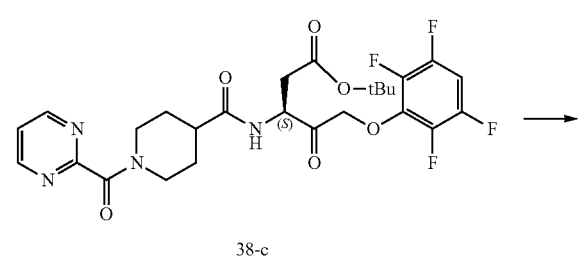

38-c

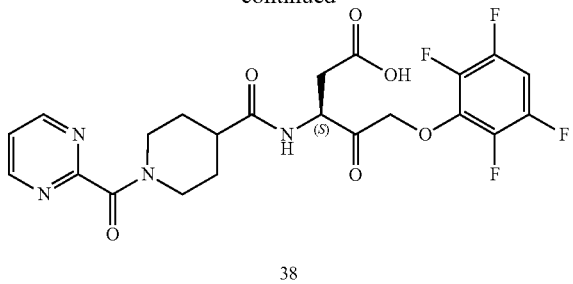

38

Step 1: Synthesis of Compound 38-b

Compound 38-a (43.43 mg, 350.00 µmol, 1.40 eq) and HOBT (50.67 mg, 375.00 µmol, 1.50 eq) were dissolved in dichloromethane (20 mL), added with EDCl (71.89 mg, 375.00 µmol, 1.50 eq), and stirred at room temperature for 15 min. Compound 34-d (116.11 mg, 250.00 µmol, 1.00 eq) and NMM (75.86 mg, 750.00 µmol, 82.46 µL, 3.00 eq) were then added, and stirred at room temperature for 16 hours. After the reaction was completed, the reaction solution was added with 150 mL of water, and extracted with dichloromethane (80 mL×3). The organic phases were combined, dried over anhydrous sodium sulfate, filtered and concentrated to give the product of compound 38-b (182 mg, crude) as a yellow oil, which was used directly in the next step without purification. LCMS m/z=571.3 [M+H]$^+$; 593.3 [M+Na]$^+$.

Step 2: Synthesis of Compound 38-c

Compound 38-b (142.63 mg, 250.00 µmol, 1.00 eq) was dissolved in dichloromethane (20.00 mL), and PIDA (322.10 mg, 1.00 mmol, 4.00 eq) and TEMPO (7.86 mg, 50.00 µmol, 0.20 eq) were added thereto. The reaction solution was stirred at room temperature for 54 hours. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was subjected to column chromatography (dichloromethane:methanol=1:0~10:1) to give the product of compound 38-c (113.00 mg, yield: 52%) as a yellow oil. LCMS m/z=569.2 [M+H]$^+$; 591.2 [M+Na]$^+$.

Step 3: Synthesis of Compound 38

Compound 38-c (113.00 mg, 198.76 µmol, 1.00 eq) was dissolved in dichloromethane (3.00 mL), and trifluoroacetic acid (4.62 g, 40.52 mmol, 3.00 mL) was added thereto. The reaction solution was stirred at room temperature for 1.5 hours. After the reaction was completed, the reaction solution was spin-dried to give a crude product. The crude product was purified by preparative HPLC (under trifluoroacetic acid condition), and lyophilized to give the product of compound 38 (8.80 mg, yield: 7%). $^1$H NMR (400 MHz, CHLOROFORM-d) δ=8.84 (d, J=5.0 Hz, 2H), 7.43 (t, J=7.6 Hz, 1H), 6.81 (br. s., 2H), 5.20-4.90 (m, 1H), 4.66 (br. s., 1H), 4.37 (br. s., 1H), 3.64 (d, J=13.2 Hz, 1H), 3.16 (d, J=10.0 Hz, 1H), 3.01 (br. s., 2H), 2.75 (br. s., 3H), 2.06 (br. s., 1H), 1.84 (d, J=10.0 Hz, 3H); LCMS m/z=513.1 [M+H]$^+$.

Example 39: Compound 39

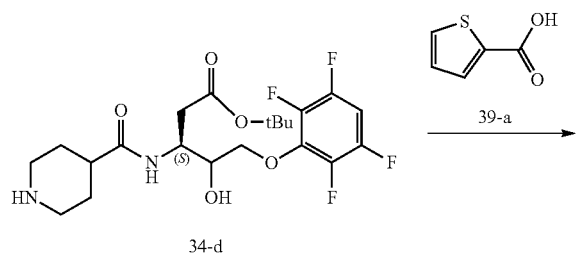

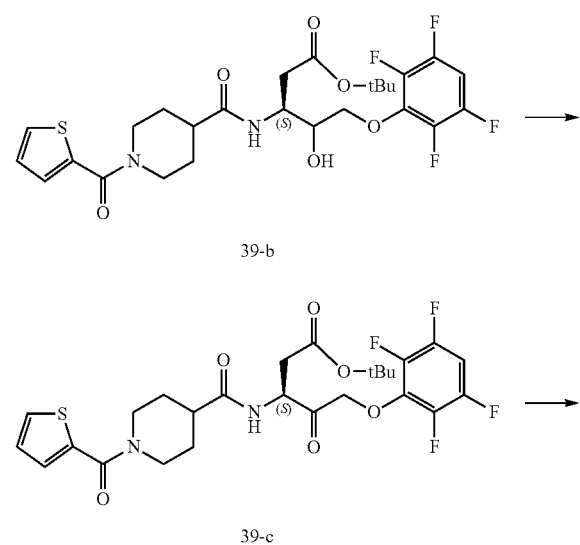

Step 1: Synthesis of Compound 39-b

Compound 34-d (110.00 mg, 236.84 μmol, 1.00 eq) was dissolved in dichloromethane (8.00 mL), and compound 39-a (30.35 mg, 236.84 μmol, 1.00 eq), EDCl (62.20 mg, 324.47 μmol, 1.37 eq), HOBt (43.84 mg, 324.47 μmol, 1.37 eq) and NMM (71.87 mg, 710.52 μmol, 78.12 μL, 3.00 eq) were added thereto. The reaction solution was stirred at 25° C. for 16 hours under the protection of nitrogen gas. After the reaction was completed, the reaction solution was added with 80 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~1:1) to give the product of compound 39-b (75.00 mg, yield: 46%) as a colorless oil. LCMS m/z=575.1 [M+H]$^+$.

Step 2: Synthesis of Compound 39-c

Compound 39-b (75.00 mg, 130.53 μmol, 1.00 eq) was dissolved in dichloromethane (4.00 mL), and PIDA (162.71 mg, 505.14 μmol, 3.87 eq) and TEMPO (6.16 mg, 39.16 μmol, 0.30 eq) were added thereto. The reaction solution was stirred at 25° C. for 16 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was purified by preparative silica gel plates (petroleum ether:ethyl acetate=1:1) to give the product of compound 39-c (51.00 mg, yield: 64%) as a colorless oil. LCMS m/z=573.1 [M+H]$^+$.

Step 3: Synthesis of Compound 39

Compound 39-c (51.00 mg, 89.07 μmol, 1.00 eq) was dissolved in dichloromethane (2.00 mL), and trifluoroacetic acid (1.46 g, 12.81 mmol, 948.05 μL, 143.85 eq) was added thereto. The reaction solution was stirred at 25° C. for 1 hour under the protection of nitrogen gas. After the reaction was completed, the reaction solution was spin-dried to give a crude product. The crude product was purified by preparative HPLC (under trifluoroacetic acid condition), and lyophilized to give the product of compound 39 (24.40 mg, yield: 53%). $^1$H NMR (400 MHz, DMSO-d$_6$) δ=8.47 (d, J=7.53 Hz, 1H), 7.74 (d, J=5.02 Hz, 1H), 7.51-7.64 (m, 1H), 7.38 (d, J=3.01 Hz, 1H), 7.09-7.14 (m, 1H), 5.14-5.30 (m, 2H), 4.61 (q, J=6.86 Hz, 1H), 4.15-4.40 (m, 2H), 3.03 (br. s., 2H), 2.70-2.79 (m, 1H), 2.58 (dd, J=6.78, 16.81 Hz, 2H), 1.76 (d, J=4.52 Hz, 2H), 1.45-1.60 (m, 2H); LCMS m/z=517.0 [M+H]$^+$.

Example 40: Compound 40

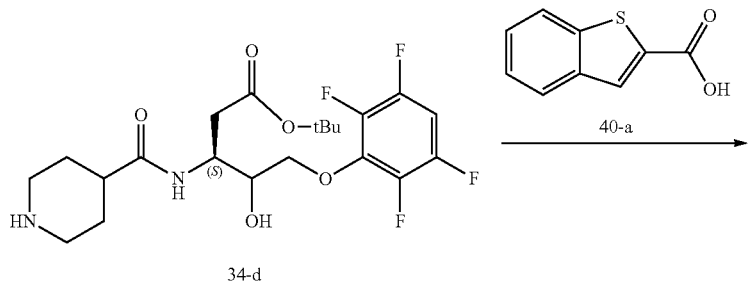

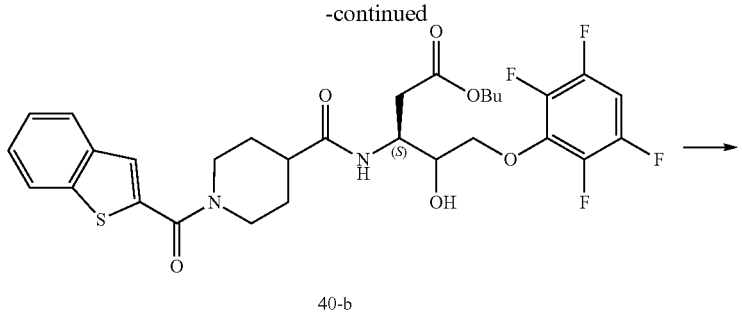

40-b

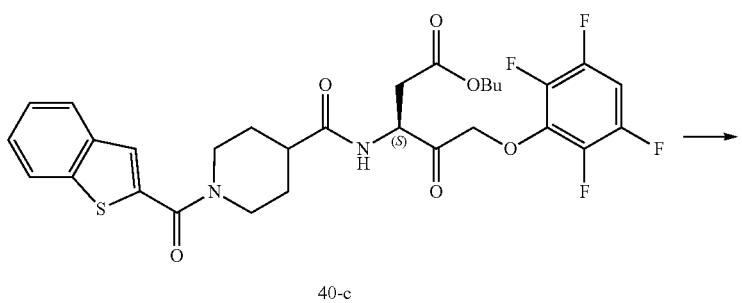

40-c

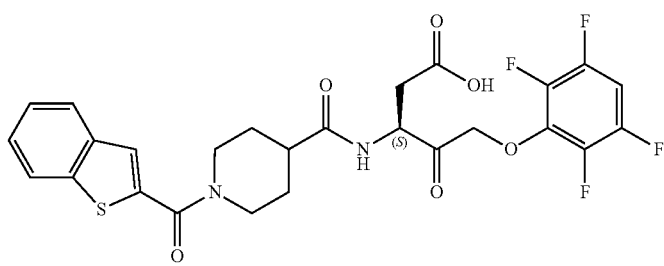

40

Step 1: Synthesis of Compound 40-b

Compound 34-d (200.00 mg, 430.62 μmol, 1.00 eq) was dissolved in dichloromethane (8.00 mL), and compound 40-a (92.09 mg, 516.74 μmol, 1.20 eq), EDCl (112.27 mg, 585.64 μmol, 1.36 eq), HOBt (79.13 mg, 585.64 μmol, 1.36 eq) and NMM (130.67 mg, 1.29 mmol, 142.03 μL, 3.00 eq) were added thereto. The reaction solution was stirred at 25° C. for 12 hours under the protection of nitrogen gas. After the reaction was completed, the reaction solution was added with 80 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=100:0~100:100) to give the product of compound 40-b (160.00 mg, yield: 54%).

Step 2: Synthesis of Compound 40-c

Compound 40-b (100.00 mg, 160.09 μmol, 1.00 eq) was dissolved in dichloromethane (4.00 mL), and PIDA (206.26 mg, 640.37 μmol, 4.00 eq) and TEMPO (5.03 mg, 32.02 μmol, 0.20 eq) were added thereto. The reaction solution was stirred at 25° C. for 5 hours under the protection of nitrogen gas. After the reaction was completed, the reaction solution was added with 50 mL of ethyl acetate. The solution was washed successively with saturated sodium hydrogen carbonate (20 mL), saturated brine (20 mL) and water (20 mL). The organic phase was dried over anhydrous sodium sulfate, filtered and concentrated to give a crude product. The crude product was purified by preparative silica gel plates (petroleum ether:ethyl acetate=2:1) to give the product of compound 40-c (60.00 mg, yield: 54%) as a yellow oil.

Step 3: Synthesis of Compound 40

Compound 40-c (60.00 mg, 96.37 μmol, 1.00 eq) was dissolved in dichloromethane (2.00 mL), and trifluoroacetic acid (1 mL) was added thereto. The reaction solution was stirred at 25° C. for 0.8 hour under the protection of nitrogen gas. After the reaction was completed, the reaction solution was spin-dried to give a crude product. The crude product was purified by preparative HPLC (under trifluoroacetic acid condition), and lyophilized to give the product of compound 40 (15.00 mg, yield: 26%). $^1$H NMR (400 MHz, DMSO-$d_6$) δ=8.51-8.45 (m, 1H), 8.05-7.97 (m, 1H), 7.95-7.86 (m, 1H), 7.69 (s, 1H), 7.47-7.40 (m, 2H), 5.29-5.14 (m, 2H), 4.65-4.57 (m, 1H), 4.40-4.17 (m, 3H), 2.79-2.52 (m, 4H), 1.87-1.72 (m, 3H), 1.65-1.50 (m, 3H).

Example 41: Compound 41

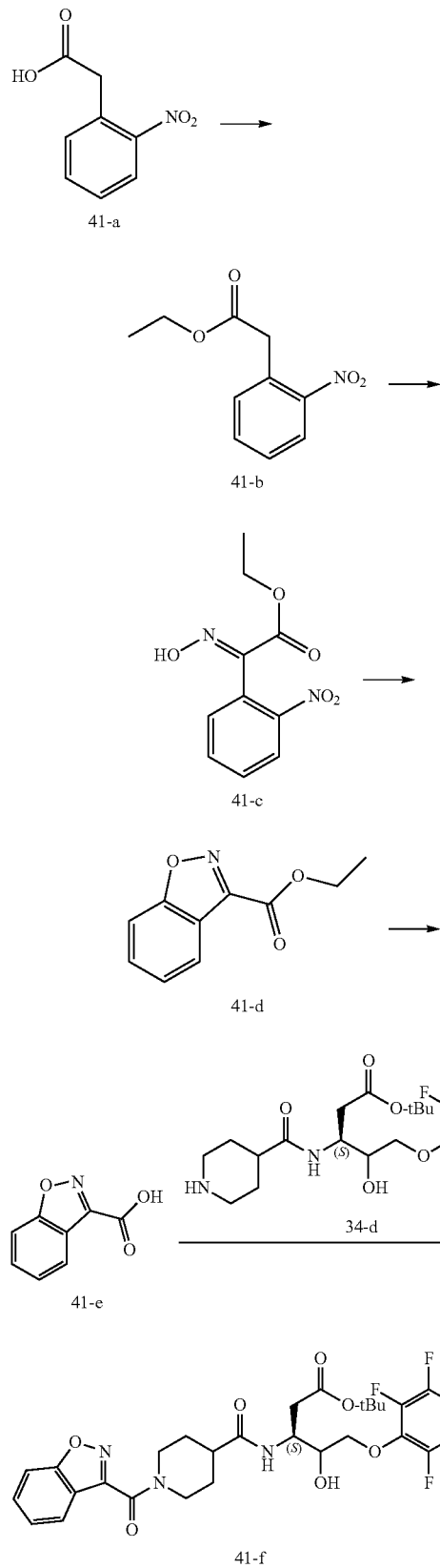

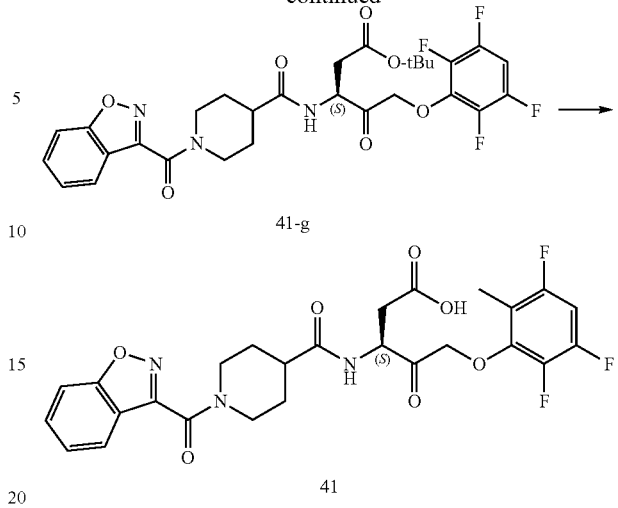

Step 1: Synthesis of Compound 41-b

Compound 41-a (10.00 g, 55.20 mmol, 1.00 eq) was dissolved in ethanol (120.00 mL), and $H_2SO_4$ (4.60 g, 46.92 mmol, 2.50 mL, 0.85 eq) was added thereto. The reaction solution was stirred under reflux for 2 hours. After the reaction was completed, the reaction solution was concentrated, then added with ethyl acetate (250 mL) and saturated sodium carbonate (100 mL), and separated. The organic phase was further washed with saturated sodium carbonate (100 mL) and brine (100 mL), and then dried over anhydrous sodium sulfate, filtered, and concentrated to give the product of compound 41-b (11.00 g, crude) as a pale yellow solid, which was used directly in the next step without purification. $^1$H NMR (400 MHz, CHLOROFORM-d) δ=8.12 (d, J=8.03 Hz, 1H), 7.56-7.65 (m, 1H), 7.44-7.53 (m, 1H), 7.37 (d, J=7.53 Hz, 1H), 4.18 (q, J=7.28 Hz, 2H), 4.03 (s, 2H), 1.26 (t, J=7.15 Hz, 3H).

Step 2: Synthesis of Compound 41-c

Compound 41-b (12.60 g, 60.23 mmol, 1.00 eq) was dissolved in ethanol (130.00 mL), isoamyl nitrite (8.04 g, 68.66 mmol, 9.24 mL, 1.14 eq) was added thereto, and the reaction solution was heated up to 60° C. And then, a solution of sodium ethoxide prepared from sodium (1.52 g, 66.25 mmol, 1.57 mL, 1.10 eq) and ethanol (63.00 mL) was added dropwise to the above solution. After the addition was completed, the reaction solution was maintained at 60° C., and heated with stirring for 2 hours. After the reaction was completed, the reaction solution was cooled down to 20° C., adjusted to pH of 7 with 2 N dilute hydrochloric acid, and then extracted with ethyl acetate (250 mL×3). The organic phases were combined, washed with water (100 mL) and brine (100 mL), dried over anhydrous sodium sulfate, filtered, and then concentrated to about 30 mL of solvent. After filtration, the filter cake was washed twice with petroleum ether (100 mL), and concentrated to give the product of compound 41-c (8.00 g, crude) as a pale yellow solid, which was used directly in the next step without purification. $^1$H NMR (400 MHz, DMSO-$d_6$) δ=12.75 (s, 1H), 8.15-8.23 (m, 1H), 7.81-7.88 (m, 1H), 7.66-7.75 (m, 1H), 7.53 (dd, J=1.00, 7.53 Hz, 1H), 4.21 (q, J=7.19 Hz, 2H), 1.16-1.27 (m, 3H).

Step 3: Synthesis of Compound 41-d

Compound 41-c (8.00 g, 33.59 mmol, 1.00 eq) was dissolved in diglyme (80.00 mL), and the above solution was added dropwise to a mixed solution of sodium hydride (2.02 g, 50.39 mmol, purity of 60%, 1.50 eq) and diglyme (110.00 mL) with vigorously stirring under the protection of nitrogen gas. The reaction solution was slowly warmed up to 150° C., and stirred for 5 hours. After the reaction was completed, the reaction solution was added with 200 mL of water, and extracted with ethyl acetate (400 mL). The organic phase was washed with water (150 mL×2), dried over anhydrous sodium sulfate, filtered, concentrated, and then dissolved in heated petroleum ether. The above solution was cooled down to 0° C., the precipitated solid was filtered, and the product of compound 41-d (3.32 g, yield: 44%) as a pale yellow solid was obtained by concentration. $^1$H NMR (400 MHz, DMSO-$d_6$) δ=8.04-8.11 (m, 1H), 7.91 (d, J=8.53 Hz, 1H), 7.76 (t, J=7.78 Hz, 1H), 7.55 (t, J=7.53 Hz, 1H), 4.48 (q, J=7.36 Hz, 2H), 1.40 (t, J=7.03 Hz, 3H).

Step 4: Synthesis of Compound 41-e

Compound 41-d (3.32 g, 17.37 mmol, 1.00 eq) was dissolved in 70% sulfuric acid solution (80.00 mL), and the resulting reaction solution was stirred at 80° C. for 3.5 hours. After the reaction was completed, the reaction solution was added with 150 mL of ice water, and extracted with ethyl acetate (300 mL). The organic phase was washed with water (100 mL×2), dried over anhydrous sodium sulfate, filtered and concentrated to give the product of compound 41-e (1.50 g, crude) as a gray solid, which was used directly in the next step without purification. $^1$H NMR (400 MHz, DMSO-$d_6$) δ=8.09 (d, J=8.03 Hz, 1H), 7.89 (d, J=8.53 Hz, 1H), 7.74 (t, J=7.53 Hz, 1H), 7.52 (t, J=7.53 Hz, 1H).

Step 5: Synthesis of Compound 41-f

Compound 34-d (250.00 mg, 538.27 μmol, 1.00 eq) was dissolved in dichloromethane (5.00 mL), and compound 41-e (87.81 mg, 538.27 μmol, 1.00 eq), EDCl (141.37 mg, 737.43 μmol, 1.37 eq), HOBt (99.64 mg, 737.43 μmol, 1.37 eq) and NMM (163.34 mg, 1.61 mmol, 177.54 μL, 3.00 eq) were added thereto. The reaction solution was stirred at 27° C. for 18 hours under the protection of nitrogen gas. After the reaction was completed, the reaction solution was added with 100 mL of water, and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~1:1) to give the product of compound 41-f (185.00 mg, yield: 50%) as a pale yellow oil. LCMS m/z=632.2 [M+Na]$^+$.

Step 6: Synthesis of Compound 41-g

Compound 41-f (185.00 mg, 303.50 μmol, 1.00 eq) was dissolved in dichloromethane (6.00 mL), and PIDA (378.32 mg, 1.17 mmol, 3.87 eq) and TEMPO (9.55 mg, 60.70 μmol, 0.20 eq) were added thereto. The reaction solution was stirred at 27° C. for 16 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was subjected to column chromatography (petroleum ether:ethyl acetate=1:0~1:1) to give the product of compound 41-g (36.00 mg, yield: 20%) as a colorless oil. LCMS m/z=630.2 [M+Na]$^+$.

Step 7: Synthesis of Compound 41

Compound 41-g (170.00 mg, 279.81 μmol, 1.00 eq) was dissolved in dichloromethane (6.00 mL), and trifluoroacetic acid (4.59 g, 40.25 mmol, 2.98 mL, 143.85 eq) was added thereto. The reaction solution was stirred at 27° C. for 1 hour under the protection of nitrogen gas. After the reaction was completed, the reaction solution was spin-dried to give a crude product. The crude product was purified by preparative HPLC (under trifluoroacetic acid condition), and lyophilized to give the product of compound 41 (82.70 mg, yield: 54%). $^1$H NMR (400 MHz, DMSO-$d_6$) δ=8.49 (d, J=7.03 Hz, 1H), 7.83-7.92 (m, 2H), 7.74 (t, J=7.78 Hz, 1H), 7.52-7.64 (m, 1H), 7.48 (t, J=7.53 Hz, 1H), 5.14-5.30 (m, 2H), 4.62 (q, J=6.53 Hz, 1H), 4.52 (d, J=13.05 Hz, 1H), 3.98 (d, J=13.55 Hz, 1H), 3.24 (t, J=11.54 Hz, 1H), 3.02 (t, J=11.80 Hz, 1H), 2.65-2.80 (m, 1H), 2.59 (dd, J=6.78, 16.31 Hz, 2H), 1.88 (br. s., 1H), 1.75 (br. s., 1H), 1.48-1.66 (m, 2H); LCMS m/z=552.1 [M+H]$^+$.

Example 42: Compound 42

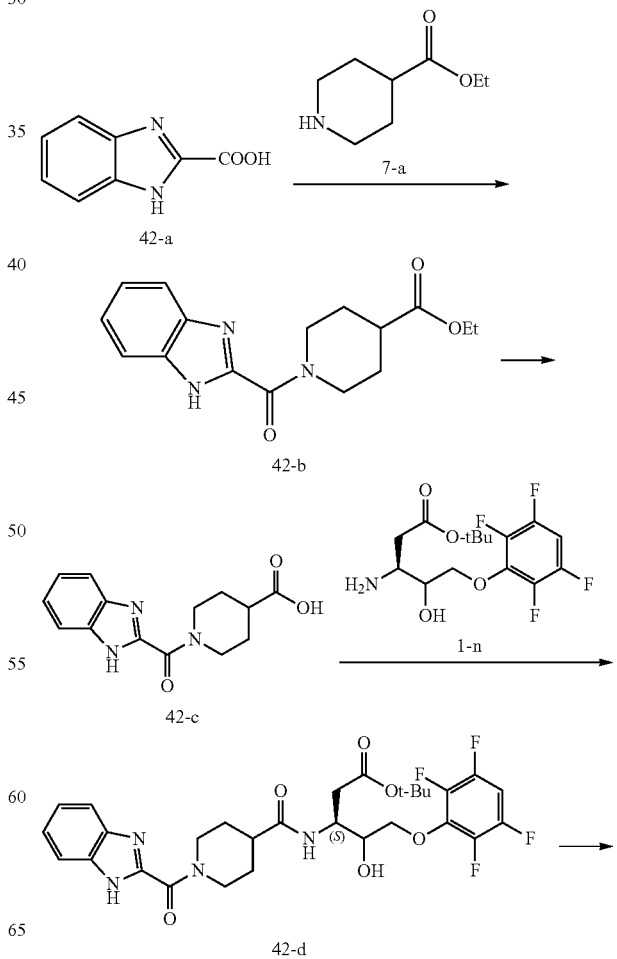

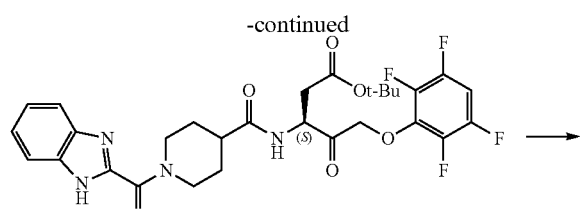

42-e

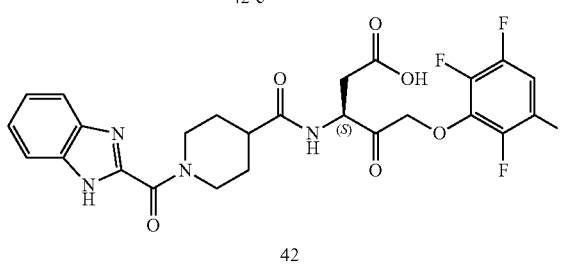

42

Step 1: Synthesis of Compound 42-b

Compound 42-a (250.52 mg, 1.55 mmol, 1.03 eq) and HATU (1.14 g, 3.00 mmol, 2.00 eq) were dissolved in dichloromethane (20 mL), and stirred at room temperature for 15 min. Compound 7-a (235.82 mg, 1.50 mmol, 231.19 μL, 1.00 eq) and N,N-diisopropylethylamine (581.58 mg, 4.50 mmol, 785.92 μL, 3.00 eq) were then added, and stirred at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~5:2) to give the product of compound 42-b (288.00 mg, yield: 50%) as a yellow oil. LCMS m/z=302.0 [M+H]$^+$.

Step 2: Synthesis of Compound 42-c

Compound 42-b (118.00 mg, 391.58 μmol, 1.00 eq) was dissolved in tetrahydrofuran (5.00 mL), and a solution of LiOH.H$_2$O (32.86 mg, 783.17 μmol, 2.00 eq) dissolved in H$_2$O (5.00 mL) was added to the above solution. The reaction solution was maintained 25° C. and stirred for 2 hours. After the reaction was completed, the reaction solution was adjusted to pH of 6 with 2 N dilute hydrochloric acid, added with 50 mL of water, and extracted with dichloromethane (30 mL×3). The organic phase was dried over anhydrous sodium sulfate, filtered and concentrated to give the product of compound 42-c (98.00 mg, crude) as a pale yellow oil, which was used directly in the next step without purification. LCMS m/z=273.9 [M+H]$^+$.

Step 3: Synthesis of Compound 42-d

Compound 42-c (98.00 mg, 358.59 μmol, 1.02 eq) and HATU (266.16 mg, 700.00 μmol, 2.00 eq) were dissolved in dichloromethane (20 mL), and stirred at room temperature for 15 min. Compound 1-n (123.66 mg, 350.00 μmol, 1.00 eq) and N,N-diisopropylethylamine (135.70 mg, 1.05 mmol, 183.38 μL, 3.00 eq) were then added, and stirred at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 42-d (100.00 mg, yield: 46%) as a yellow oil, LCMS m/z=609.2 [M+H]$^+$.

Step 4: Synthesis of Compound 42-e

Compound 42-d (100.00 mg, 164.32 μmol, 1.00 eq) was dissolved in dichloromethane (20.00 mL), and PIDA (211.71 mg, 657.27 μmol, 4.00 eq) and TEMPO (5.17 mg, 32.86 μmol, 0.20 eq) were added thereto. The reaction solution was stirred at room temperature for 62 hours. After the reaction was completed, the reaction solution was added with saturated sodium hydrogen carbonate solution (50 mL) and saturated sodium sulfite solution (50 mL), extracted with dichloromethane (30 mL×3), and washed with saturated brine (50 mL). The organic phase was dried over anhydrous sodium sulfate, filtered and concentrated to give a crude product. The crude product was subjected to column chromatography (petroleum ether:ethyl acetate=1:0~2:1) to give the product of compound 42-e (45.00 mg, yield: 45%) as a yellow oil. LCMS m/z=607.3 [M+H]$^+$.

Step 5: Synthesis of Compound 42

Compound 42-e (45.00 mg, 74.19 μmol, 1.00 eq) was dissolved in dichloromethane (3.00 mL), and trifluoroacetic acid (4.62 g, 40.52 mmol, 3.00 mL) was added thereto. The reaction solution was stirred at room temperature for 1.5 hours. After the reaction was completed, the reaction solution was spin-dried to give a crude product. The crude product was purified by preparative HPLC (under trifluoroacetic acid condition), and lyophilized to give the product of compound 42 (38.00 mg, yield: 88%). $^1$H NMR (400 MHz, DMSO-d$_6$) δ=8.53 (d, J=7.5 Hz, 1H), 7.65 (dd, J=3.1, 5.9 Hz, 2H), 7.61-7.49 (m, 1H), 7.29 (dd, J=3.3, 6.0 Hz, 2H), 5.40 (d, J=13.1 Hz, 1H), 5.32-5.15 (m, 2H), 4.63 (q, J=6.7 Hz, 1H), 4.53 (d, J=12.8 Hz, 1H), 3.36 (t, J=11.8 Hz, 1H), 2.95 (t, J=11.9 Hz, 1H), 2.82-2.71 (m, 1H), 2.66-2.55 (m, 2H), 1.84 (br. s., 2H), 1.71-1.50 (m, 2H); LCMS m/z=550.9 [M+H]$^+$.

Example 43: Compound 43

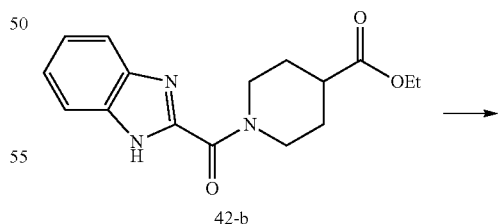

42-b

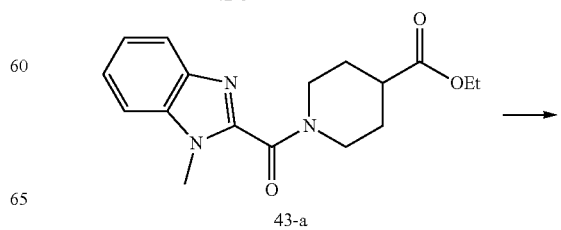

43-a

-continued

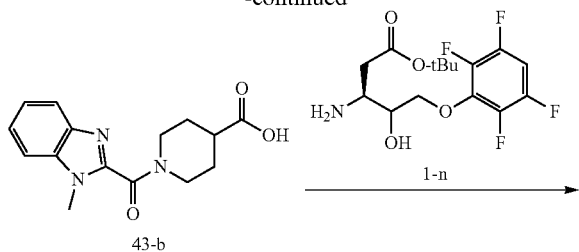

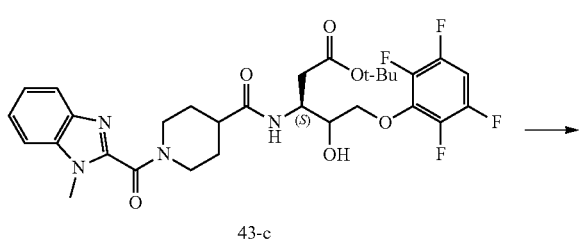

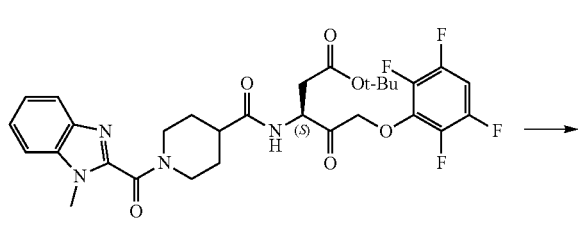

Step 1: Synthesis of Compound 43-a

Compound 42-b (132.00 mg, 438.04 µmol, 1.00 eq) was dissolved in DMF (20 mL), added with K$_2$CO$_3$ (181.63 mg, 1.31 mmol, 3.00 eq) and MeI (506.00 mg, 3.56 mmol, 221.93 µL, 8.14 eq), and stirred at room temperature for 2.5 hours. After the reaction was completed, the reaction solution was added with 150 mL of water, and extracted with ethyl acetate (80 mL×3). The organic phases were combined, dried over anhydrous sodium sulfate, filtered and concentrated to give the product of compound 43-a (150 mg, crude) as a yellow oil, which was used directly in the next step without purification. LCMS m/z=316.0 [M+H]$^+$.

Step 2: Synthesis of Compound 43-b

Compound 43-a (126.15 mg, 400.00 µmol, 1.00 eq) was dissolved in tetrahydrofuran (5.00 mL), and a solution of LiOH.H$_2$O (33.57 mg, 800.00 µmol, 2.00 eq) dissolved in H$_2$O (5.00 mL) was added to the above solution. The reaction solution was maintained at 25° C. and stirred for 2 hours. After the reaction was completed, the reaction solution was adjusted to pH of 6 with 2 N dilute hydrochloric acid, added with 50 mL of water, and extracted with dichloromethane (30 mL×3). The organic phase was dried over anhydrous sodium sulfate, filtered and concentrated to give the product of compound 43-b (150.00 mg, crude) as a pale yellow oil, which was used directly in the next step without purification. LCMS m/z=287.9 [M+H]$^+$.

Step 3: Synthesis of Compound 43-c

Compound 43-b (114.92 mg, 400.00 µmol, 1.05 eq) and HATU (288.97 mg, 760.00 µmol, 2.00 eq) were dissolved in dichloromethane (20 mL), and stirred at room temperature for 15 min. Compound 1-n (134.26 mg, 380.00 µmol, 1.00 eq) and N,N-diisopropylethylamine (147.33 mg, 1.14 mmol, 199.10 µL, 3.00 eq) were then added, and stirred at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 43-c (200.00 mg, yield: 50%) as a yellow oil. LCMS m/z=623.3 [M+H]$^+$.

Step 4: Synthesis of Compound 43-d

Compound 43-c (200.00 mg, 321.23 µmol, 1.00 eq) was dissolved in dichloromethane (20.00 mL), and PIDA (413.87 mg, 1.28 mmol, 4.00 eq) and TEMPO (10.10 mg, 64.25 µmol, 0.20 eq) were added thereto. The reaction solution was stirred at room temperature for 72 hours. After the reaction was completed, the reaction solution was added with saturated sodium hydrogen carbonate solution (50 mL) and saturated sodium sulfite solution (50 mL), extracted with dichloromethane (30 mL×3), and washed with saturated brine (50 mL). The organic phase was dried over anhydrous sodium sulfate, filtered and concentrated to give a crude product. The crude product was subjected to column chromatography (petroleum ether:ethyl acetate=1:0~3:2) to give the product of compound 43-d (16.00 mg, yield: 7%) as a yellow oil. LCMS m/z=621.1 [M+H]$^+$; 643.1 [M+Na]$^+$.

Step 5: Synthesis of Compound 43

Compound 43-d (16.00 mg, 25.78 µmol, 1.00 eq) was dissolved in dichloromethane (3.00 mL), and trifluoroacetic acid (4.62 g, 40.52 mmol, 3.00 mL) was added thereto. The reaction solution was stirred at room temperature for 1.5 hours. After the reaction was completed, the reaction solution was spin-dried to give a crude product. The crude product was purified by preparative HPLC (under trifluoroacetic acid condition), and lyophilized to give the product of compound 43 (12.00 mg, yield: 76%). $^1$H NMR (400 MHz, DMSO-d$_6$) δ=8.60 (d, J=7.0 Hz, 1H), 7.79-7.68 (m, 2H), 7.63 (d, J=6.0 Hz, 1H), 7.47-7.32 (m, 2H), 5.29 (dd, J=3.5, 12.5 Hz, 2H), 4.68 (q, J=6.9 Hz, 1H), 4.57 (d, J=13.1 Hz, 1H), 4.36-4.32 (m, 1H), 4.13-4.10 (m, 1H), 3.90 (s, 3H), 3.25 (t, J=11.5 Hz, 1H), 3.07-2.97 (m, 1H), 2.82 (dd, J=5.5, 16.6 Hz, 1H), 2.69-2.62 (m, 2H), 1.92 (br. s., 1H), 1.85-1.75 (m, 1H), 1.74-1.59 (m, 2H); LCMS m/z=565.0 [M+H]$^+$.

Example 44: Compound 44

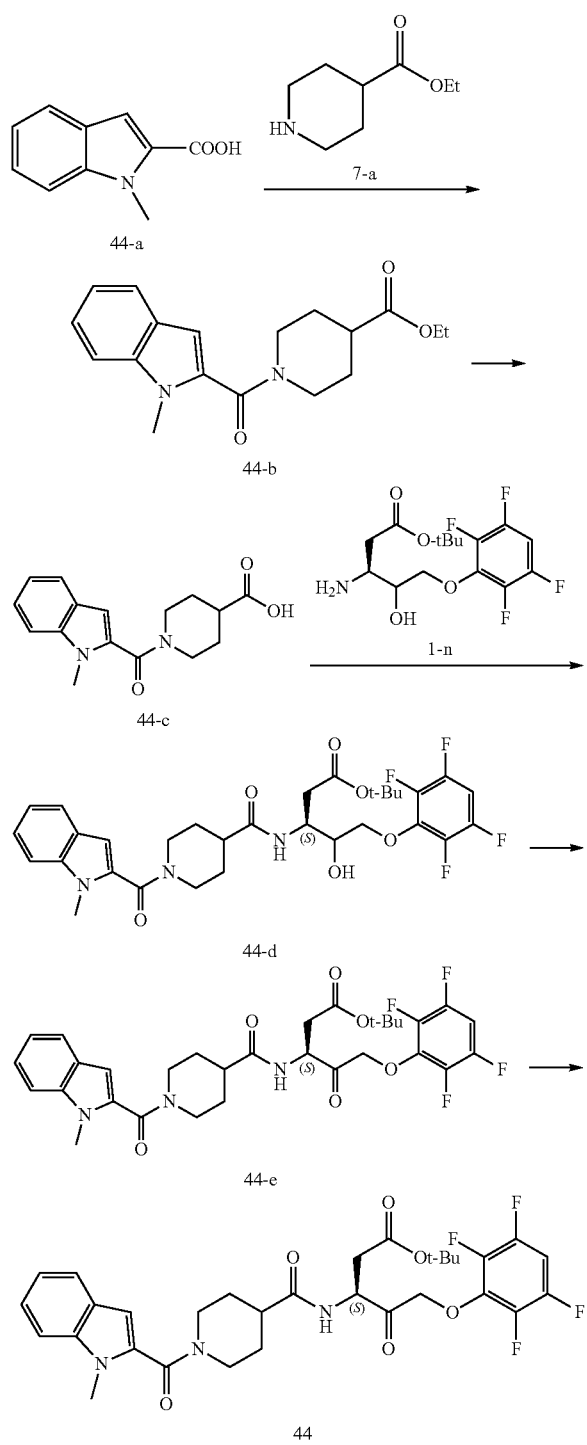

Step 1: Synthesis of Compound 44-b

Compound 44-a (840.86 mg, 4.80 mmol, 1.20 eq) and HATU (3.04 g, 8.00 mmol, 2.00 eq) were dissolved in dichloromethane (20 mL), and stirred at room temperature for 15 min. Compound 7-a (628.84 mg, 4.00 mmol, 616.51 µL, 1.00 eq) and N,N-diisopropylethylamine (1.55 g, 12.00 mmol, 2.10 mL, 3.00 eq) were then added, and stirred at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 44-b (1.09 g, yield: 87%) as a yellow oil. LCMS m/z=315.0 [M+H]$^+$.

Step 2: Synthesis of Compound 44-c

Compound 44-b (475.00 mg, 1.51 mmol, 1.00 eq) was dissolved in tetrahydrofuran (5.00 mL), and a solution of LiOH.H$_2$O (126.80 mg, 3.02 mmol, 2.00 eq) dissolved in H$_2$O (5.00 mL) was added to the above solution. The reaction solution was maintained at 25° C. and stirred for 2 hours. After the reaction was completed, the reaction solution was adjusted to pH of 6 with 2 N dilute hydrochloric acid, added with 50 mL of water, and extracted with dichloromethane (30 mL×3). The organic phase was dried over anhydrous sodium sulfate, filtered and concentrated to give the product of compound 44-c (483.00 mg, crude) as a pale yellow oil, which was used directly in the next step without purification. LCMS m/z=286.9 [M+H]$^+$.

Step 3: Synthesis of Compound 44-d

Compound 44-c (372.23 mg, 1.30 mmol, 1.30 eq) and HATU (760.46 mg, 2.00 mmol, 2.00 eq) were dissolved in dichloromethane (20 mL), and stirred at room temperature for 15 min. Compound 1-n (353.31 mg, 1.00 mmol, 1.00 eq) and N,N-diisopropylethylamine (387.72 mg, 3.00 mmol, 523.95 µL, 3.00 eq) were then added, and stirred at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 44-d (424.00 mg, yield: 65%) as a yellow oil. LCMS m/z=622.2 [M+H]$^+$.

Step 4: Synthesis of Compound 44-e

Compound 44-d (250.00 mg, 402.17 µmol, 1.00 eq) was dissolved in dichloromethane (20.00 mL), and PIDA (518.16 mg, 1.61 mmol, 4.00 eq) and TEMPO (12.65 mg, 80.43 µmol, 0.20 eq) were added thereto. The reaction solution was stirred at room temperature for 20 hours. After the reaction was completed, the reaction solution was added with saturated sodium hydrogen carbonate solution (50 mL) and saturated sodium sulfite solution (50 mL), extracted with dichloromethane (30 mL×3), and washed with saturated brine (50 mL). The organic phase was dried over anhydrous sodium sulfate, filtered and concentrated to give a crude product. The crude product was subjected to column chromatography (petroleum ether:ethyl acetate=1:0~5:3) to give the product of compound 44-e (105.00 mg, yield: 26%) as a yellow oil. LCMS m/z=620.2 [M+H]$^+$; 642.2 [M+Na]$^+$.

Step 5: Synthesis of Compound 44

Compound 44-e (100.00 mg, 161.39 µmol, 1.00 eq) was dissolved in dichloromethane (3.00 mL), and trifluoroacetic acid (4.62 g, 40.52 mmol, 3.00 mL) was added thereto. The reaction solution was stirred at room temperature for 2 hours. After the reaction was completed, the reaction solution was spin-dried to give a crude product. The crude product was purified by preparative HPLC (under trifluoroacetic acid condition), and lyophilized to give the product of compound 44 (39.00 mg, yield: 39%). $^1$H NMR (400 MHz, DMSO-d$_6$) δ=8.51 (d, J=7.5 Hz, 1H), 7.63-7.54 (m, 2H), 7.51 (d, J=8.5 Hz, 1H), 7.25 (t, J=7.5 Hz, 1H), 7.13-7.07 (m, 1H), 6.63 (s, 1H), 5.31-5.16 (m, 2H), 4.63 (q, J=7.0 Hz, 1H), 4.11-4.03 (m, 2H), 3.75 (s, 3H), 3.15-3.04 (m, 1H), 2.99-2.90 (m, 1H), 2.81-2.72 (m, 1H), 2.64-2.54 (m, 2H), 1.83-1.75 (m, 2H), 1.61-1.54 (m, 2H); LCMS m/z=564.1 [M+H]$^+$.

Example 45: Compound 45

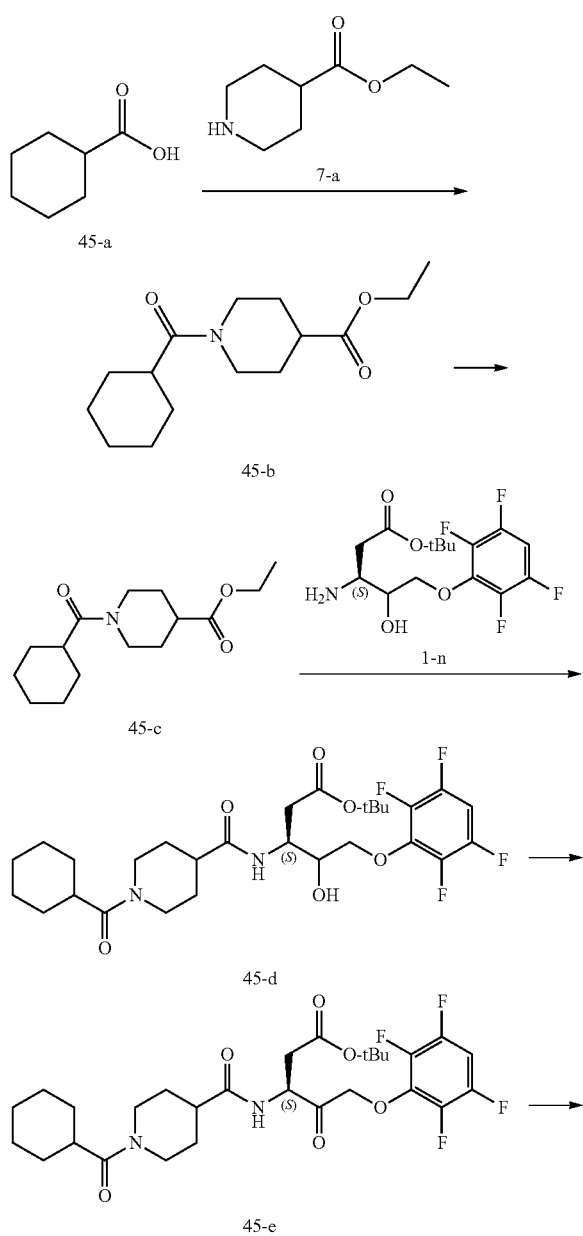

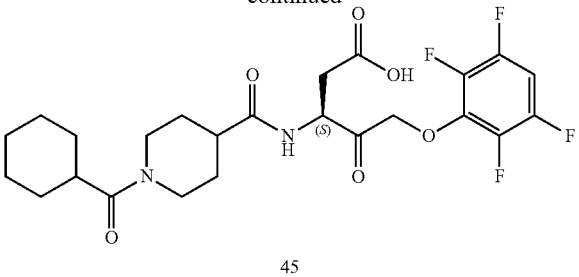

Step 1: Synthesis of Compound 45-b

Compound 45-a (2.69 g, 20.99 mmol, 2.61 mL, 1.10 eq) and HOBT (3.87 g, 28.62 mmol, 1.50 eq) were dissolved in dichloromethane (90 mL), added with EDCl (5.49 g, 28.62 mmol, 1.50 eq), and stirred at room temperature for 15 min. Compound 7-a (3.00 g, 19.08 mmol, 2.94 mL, 1.00 eq) and N,N-diisopropylethylamine (4.93 g, 38.16 mmol, 6.66 mL, 2.00 eq) were then dissolved in dichloromethane, added to the above solution, and stirred at room temperature for 15 hours. After the reaction was completed, the reaction solution was added with 80 mL of water, and extracted with dichloromethane (80 mL×3). The organic phases were combined, dried over anhydrous sodium sulfate, filtered and concentrated to give the product of compound 45-b (7.57 g, crude) as a yellow oil, which was used directly in the next step without purification. LCMS m/z=268.0 [M+H]$^+$.

Step 2: Synthesis of Compound 45-c

Compound 45-b (5.10 g, 19.08 mmol, 1.00 eq) was dissolved in tetrahydrofuran (50.00 mL), and a solution of LiOH.H$_2$O (1.60 g, 38.16 mmol, 2.00 eq) dissolved in H$_2$O (50.00 mL) was added to the above solution. The reaction solution was maintained at 25° C. and stirred for 2 hours. After the reaction was completed, the reaction solution was adjusted to pH of 6 with 2 N dilute hydrochloric acid, added with 200 mL of water, and extracted with dichloromethane (100 mL×3). The organic phase was dried over anhydrous sodium sulfate, filtered and concentrated to give the product of compound 45-c (5.91 g, crude) as a pale yellow oil, which was used directly in the next step without purification. LCMS m/z=239.9 [M+H]$^+$.

Step 3: Synthesis of Compound 45-d

Compound 45-c (135.47 mg, 566.08 μmol, 1.00 eq) and HOBT (114.72 mg, 849.12 μmol, 1.50 eq) were dissolved in dichloromethane (20 mL), added with EDCl (162.75 mg, 849.12 μmol, 1.50 eq), and stirred at room temperature for 15 min. Compound 1-n (200.00 mg, 566.08 μmol, 1.00 eq) and N,N-diisopropylethylamine (146.32 mg, 1.13 mmol, 197.73 μL, 2.00 eq) were then dissolved in dichloromethane, added to the above solution, and stirred at room temperature for 15 hours. After the reaction was completed, the reaction solution was added with 80 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 45-d (254.00 mg, yield: 78%) as a yellow oil. LCMS m/z=575.3 [M+H]$^+$; 597.3 [M+Na]$^+$.

Step 4: Synthesis of Compound 45-e

Compound 45-d (226.00 mg, 393.32 μmol, 1.00 eq) was dissolved in dichloromethane (20.00 mL), and sodium hydrogen carbonate solution (165.21 mg, 1.97 mmol, 76.49 μL, 5.00 eq) and DMP (333.64 mg, 786.63 μmol, 243.54 μL, 2.00 eq) were added thereto. The reaction solution was stirred at room temperature for 0.5 hour. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was subjected to column chromatography (petroleum ether:ethyl acetate=1:0~2:1) to give the product of compound 45-e (171.00 mg, yield: 76%) as a yellow oil. LCMS m/z=573.2 [M+H]$^+$; 595.3 [M+Na]$^+$.

Step 5: Synthesis of Compound 45

Compound 45-e (120.00 mg, 209.57 μmol, 1.00 eq) was dissolved in ethyl acetate (5.00 mL), and HCl/EtOAc (7.00 mL) was added thereto. The reaction solution was stirred at room temperature for 2 hours. After the reaction was completed, the reaction solution was spin-dried to give a crude product. The crude product was purified by preparative HPLC (under formic acid condition), and lyophilized to give the product of compound 45 (61.00 mg, yield: 56%). $^1$H NMR (400 MHz, DMSO-d$_6$) δ=8.40 (d, J=7.5 Hz, 1H), 7.61-7.52 (m, 1H), 4.61 (d, J=6.0 Hz, 1H), 4.35 (d, J=12.0 Hz, 1H), 3.92 (d, J=12.0 Hz, 1H), 3.01 (d, J=12.0 Hz, 1H), 2.67 (td, J=12.0 Hz, 6.0 Hz 1H), 2.53-2.55 (m, 2H), 2.45-2.43 (m, 1H), 1.72-1.52 (m, 7H), 1.48-1.08 (m, 7H); LCMS m/z=517.2 [M+H]$^+$; 539.2 [M+Na]$^+$.

Example 46: Compound 46

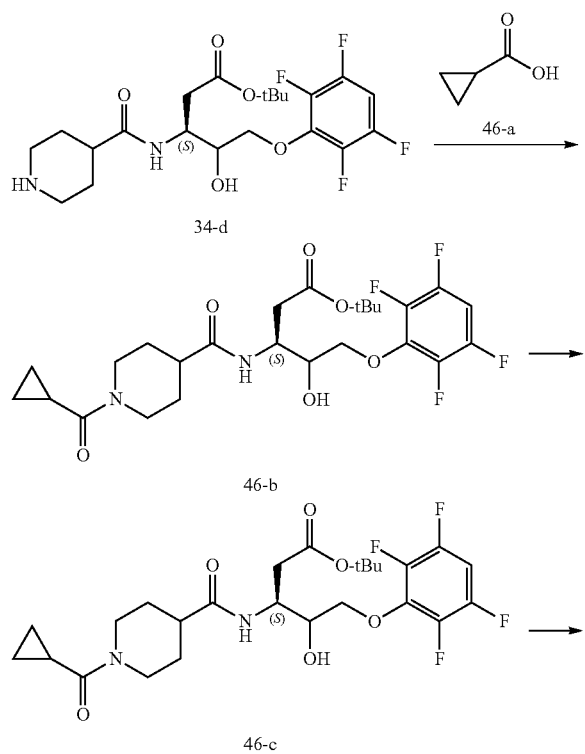

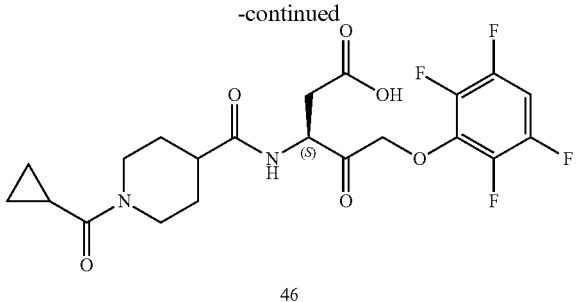

Step 1: Synthesis of Compound 46-b

Compound 34-d (250.00 mg, 538.27 μmol, 1.00 eq) was dissolved in dichloromethane (8.00 mL), and compound 46-a (46.34 mg, 538.27 μmol, 42.51 μL, 1.00 eq), EDCl (141.37 mg, 737.43 μmol, 1.37 eq), HOBt (99.64 mg, 737.43 μmol, 1.37 eq) and NMM (163.34 mg, 1.61 mmol, 177.54 μL, 3.00 eq) were added thereto. The reaction solution was stirred at 27° C. for 16 hours under the protection of nitrogen gas. After the reaction was completed, the reaction solution was added with 100 mL of water, and extracted with dichloromethane (100 mL×3). The organic phases were combined, dried over anhydrous sodium sulfate, filtered and concentrated to give a crude product. The crude product was purified by preparative silica gel plates (petroleum ether: ethyl acetate=1:1) to give the product of compound 46-b (150.00 mg, yield: 49%) as a colorless oil. $^1$H NMR (400 MHz, CHLOROFORM-d) δ=6.76-6.88 (m, 1H), 6.68 (d, J=8.28 Hz, 1H), 4.49-4.68 (m, 1H), 4.07-4.41 (m, 5H), 3.08-3.25 (m, 1H), 2.54-2.80 (m, 3H), 2.33-2.44 (m, 1H), 1.71-1.78 (m, 3H), 1.61 (dd, J=6.27, 11.29 Hz, 1H), 1.41-1.52 (m, 9H), 1.22-1.33 (m, 1H), 0.93-1.02 (m, 2H), 0.71-0.80 (m, 2H). LCMS m/z=533.3 [M+H]$^+$.

Step 2: Synthesis of Compound 46-c

Compound 46-b (150.00 mg, 281.67 μmol, 1.00 eq) was dissolved in dichloromethane (6.00 mL), and PIDA (351.11 mg, 1.09 mmol, 3.87 eq) and TEMPO (8.86 mg, 56.33 μmol, 0.20 eq) were added thereto. The reaction solution was stirred at 27° C. for 16 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was purified by preparative silica gel plates (petroleum ether:ethyl acetate=1:1) to give the product of compound 46-c (116.00 mg, yield: 71%) as a colorless oil. LCMS m/z=531.3 [M+H]$^+$.

Step 3: Synthesis of Compound 46

Compound 46-c (116.00 mg, 218.66 μmol, 1.00 eq) was dissolved in dichloromethane (5.00 mL), and trifluoroacetic acid (3.59 g, 31.45 mmol, 2.33 mL, 143.85 eq) was added thereto. The reaction solution was stirred at 27° C. for 1 hour under the protection of nitrogen gas. After the reaction was completed, the reaction solution was spin-dried to give a crude product. The crude product was purified by preparative HPLC (under trifluoroacetic acid condition), and lyophilized to give the product of compound 46 (58.70 mg, yield: 57%). $^1$H NMR (400 MHz, DMSO-d$_6$) δ=8.45 (d, J=7.53 Hz, 1H), 7.51-7.66 (m, 1H), 5.14-5.29 (m, 2H), 4.60 (q, J=7.03 Hz, 1H), 4.17-4.40 (m, 2H), 3.10 (br. s., 1H), 2.70-2.79 (m, 1H), 2.53-2.68 (m, 2H), 2.44 (br. s., 1H), 1.91-2.02 (m, 1H), 1.60-1.83 (m, 2H), 1.20-1.57 (m, 2H), 0.62-0.75 (m, 4H); LCMS m/z=475.1 [M+H]$^+$.

Example 47: Compound 47

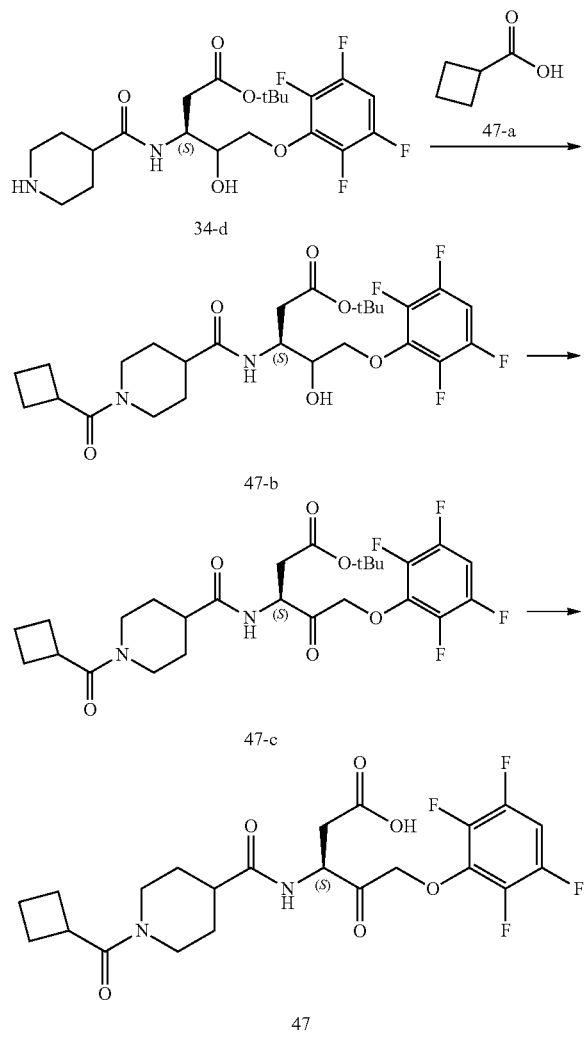

Step 1: Synthesis of Compound 47-b

Compound 34-d (250.00 mg, 538.27 μmol, 1.00 eq) was dissolved in dichloromethane (8.00 mL), and compound 47-a (53.89 mg, 538.27 μmol, 51.32 μL, 1.00 eq), EDCl (141.37 mg, 737.43 μmol, 1.37 eq), HOBt (99.64 mg, 737.43 μmol, 1.37 eq) and NMM (163.34 mg, 1.61 mmol, 177.54 μL, 3.00 eq) were added thereto. The reaction solution was stirred at 27° C. for 16 hours under the protection of nitrogen gas. After the reaction was completed, the reaction solution was added with 100 mL of water, and extracted with dichloromethane (100 mL×3). The organic phases were combined, dried over anhydrous sodium sulfate, filtered and concentrated to give a crude product. The crude product was purified by preparative silica gel plates (petroleum ether: ethyl acetate=1:1) to give the product of compound 47-b (150.00 mg, yield: 45%) as a colorless oil. $^1$H NMR (400 MHz, CHLOROFORM-d) δ=6.76-6.87 (m, 1H), 6.66 (d, J=8.03 Hz, 1H), 4.58 (d, J=12.80 Hz, 1H), 4.03-4.40 (m, 4H), 3.75 (d, J=13.80 Hz, 1H), 3.24 (quin, J=8.53 Hz, 1H), 2.97 (t, J=12.67 Hz, 1H), 2.71-2.79 (m, 1H), 2.51-2.69 (m, 2H), 2.28-2.40 (m, 3H), 2.14 (dd, J=3.76, 8.03 Hz, 2H), 1.80-2.06 (m, 5H), 1.54-1.65 (m, 2H), 1.41-1.50 (m, 9H). LCMS m/z=569.3 [M+Na]$^+$.

Step 2: Synthesis of Compound 47-c

Compound 47-b (150.00 mg, 274.45 μmol, 1.00 eq) was dissolved in dichloromethane (6.00 mL), and PIDA (342.11 mg, 1.06 mmol, 3.87 eq) and TEMPO (8.63 mg, 54.89 μmol, 0.20 eq) were added thereto. The reaction solution was stirred at 27° C. for 16 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was purified by preparative silica gel plates (petroleum ether:ethyl acetate=1:1) to give the product of compound 47-c (114.00 mg, yield: 70%) as a colorless oil. LCMS m/z=567.2 [M+Na]$^+$.

Step 3: Synthesis of Compound 47

Compound 47-c (114.00 mg, 209.35 μmol, 1.00 eq) was dissolved in dichloromethane (5.00 mL), and trifluoroacetic acid (3.43 g, 30.11 mmol, 2.23 mL, 143.85 eq) was added thereto. The reaction solution was stirred at 27° C. for 1 hour under the protection of nitrogen gas. After the reaction was completed, the reaction solution was spin-dried to give a crude product. The crude product was purified by preparative HPLC (under trifluoroacetic acid condition), and lyophilized to give the product of compound 47 (53.40 mg, yield: 52%). $^1$H NMR (400 MHz, DMSO-d$_6$) δ=8.42 (d, J=7.03 Hz, 1H), 7.57 (tt, J=7.28, 10.79 Hz, 1H), 5.13-5.28 (m, 2H), 4.59 (q, J=6.53 Hz, 1H), 4.24-4.38 (m, 1H), 3.69 (br. s., 2H), 3.32 (quin, J=8.53 Hz, 1H), 2.83-2.98 (m, 1H), 2.66-2.77 (m, 1H), 2.54-2.61 (m, 2H), 2.30-2.44 (m, 1H), 2.00-2.20 (m, 4H), 1.80-1.94 (m, 1H), 1.60-1.78 (m, 3H), 1.22-1.46 (m, 2H); LCMS m/z=489.1 [M+H]$^+$.

Example 48: Compound 48

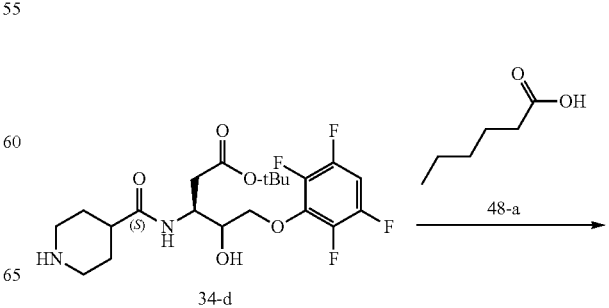

189

-continued

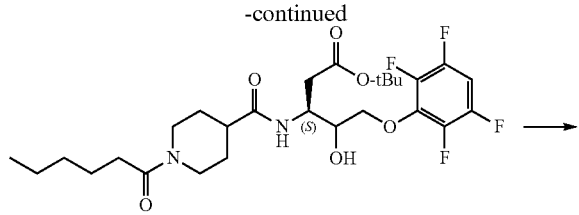

48-b

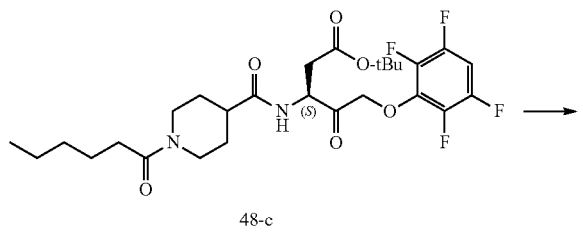

48-c

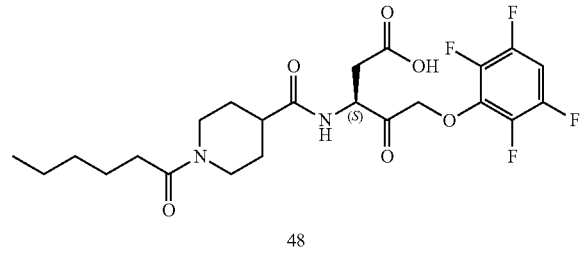

48

Step 1: Synthesis of Compound 48-b

Compound 34-d (200.00 mg, 430.62 μmol, 1.00 eq) was dissolved in dichloromethane (1.00 mL), and compound 48-a (50.02 mg, 430.62 μmol, 53.79 μL, 1.00 eq), EDCl (113.09 mg, 589.95 μmol, 1.37 eq), HOBt (79.71 mg, 589.95 μmol, 1.37 eq) and NMM (130.67 mg, 1.29 mmol, 142.03 μL, 3.00 eq) were added thereto. The reaction solution was stirred at 27° C. for 16 hours under the protection of nitrogen gas. After the reaction was completed, the reaction solution was added with 100 mL of water, and extracted with dichloromethane (100 mL×3). The organic phases were combined, dried over anhydrous sodium sulfate, filtered and concentrated to give a crude product. The crude product was purified by preparative silica gel plates (petroleum ether: ethyl acetate=1:1) to give the product of compound 48-b (94.00 mg, yield: 33%) as a colorless oil. LCMS m/z=563.3 [M+H]$^+$.

Step 2: Synthesis of Compound 48-c

Compound 48-b (94.00 mg, 167.08 μmol, 1.00 eq) was dissolved in dichloromethane (5.00 mL), and PIDA (208.28 mg, 646.60 μmol, 3.87 eq) and TEMPO (5.25 mg, 33.42 μmol, 0.20 eq) were added thereto. The reaction solution was stirred at 27° C. for 16 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was purified by preparative silica gel plates (petroleum ether:ethyl acetate=1:1) to give the product of compound 48-c (80.00 mg, yield: 62%) as a colorless oil. LCMS m/z=583.3 [M+Na]$^+$.

190

Step 3: Synthesis of Compound 48

Compound 48-c (70.00 mg, 124.87 μmol, 1.00 eq) was dissolved in dichloromethane (4.00 mL), and trifluoroacetic acid (2.05 g, 17.96 mmol, 1.33 mL, 143.85 eq) was added thereto. The reaction solution was stirred at 27° C. for 1 hour under the protection of nitrogen gas. After the reaction was completed, the reaction solution was spin-dried to give a crude product. The crude product was purified by preparative HPLC (under trifluoroacetic acid condition), and lyophilized to give the product of compound 48 (22.70 mg, yield: 36%). $^1$H NMR (400 MHz, DMSO-d$_6$) δ=8.42 (br. s., 1H), 7.51-7.65 (m, 1H), 5.20 (br. s., 1H), 4.60 (br. s., 1H), 4.34 (d, J=13.05 Hz, 1H), 3.86 (d, J=13.55 Hz, 1H), 2.99 (t, J=12.05 Hz, 1H), 2.70 (dd, J=10.79, 16.81 Hz, 1H), 2.57 (d, J=12.55 Hz, 1H), 2.36-2.47 (m, 2H), 2.20-2.35 (m, 2H), 1.61-1.77 (m, 2H), 1.18-1.53 (m, 8H), 0.86 (t, J=6.78 Hz, 3H); LCMS m/z=505.1 [M+H]$^+$.

Example 49: Compound 49

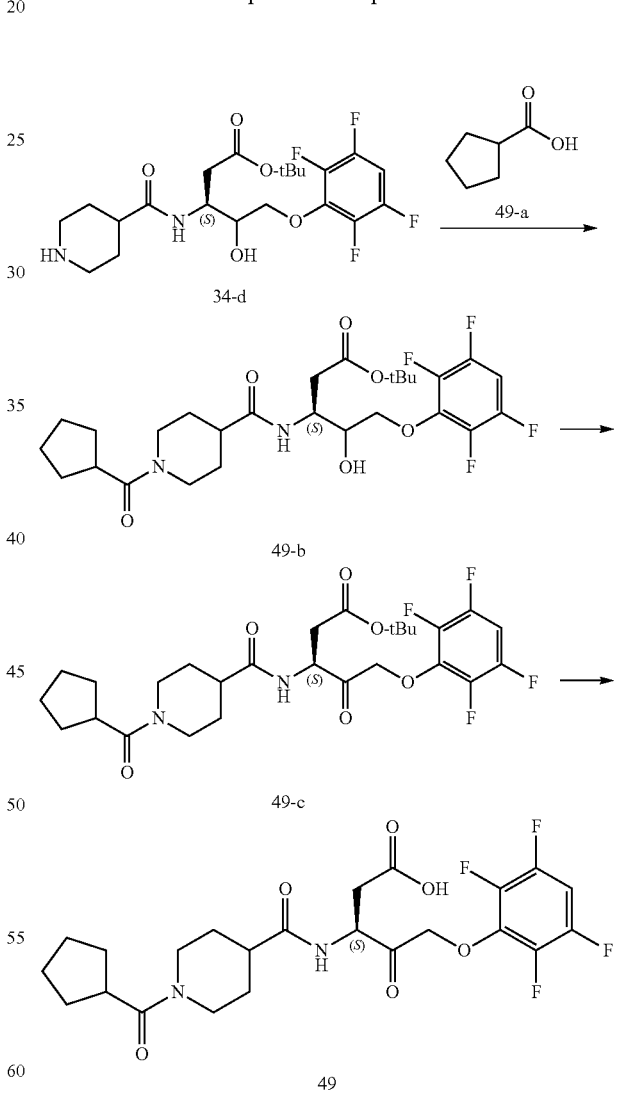

Step 1: Synthesis of Compound 49-b

Compound 34-d (250.00 mg, 538.27 μmol, 1.00 eq) was dissolved in dichloromethane (6.00 mL), and compound 49-a (61.44 mg, 538.27 μmol, 58.51 μL, 1.00 eq), EDCl (141.37 mg, 737.43 μmol, 1.37 eq), HOBt (99.64 mg, 737.43 μmol, 1.37 eq) and NMM (163.34 mg, 1.61 mmol, 177.54 μL, 3.00 eq) were added thereto. The reaction solution was stirred at 27° C. for 16 hours under the protection of nitrogen gas. After the reaction was completed, the reaction solution was added with 100 mL of water, and extracted with dichloromethane (100 mL×3). The organic phases were combined, dried over anhydrous sodium sulfate, filtered and concentrated to give a crude product. The crude product was purified by preparative silica gel plates (petroleum ether: ethyl acetate=1:1) to give the product of compound 49-b (130.00 mg, yield: 40%) as a colorless oil. LCMS m/z=583.3 [M+Na]$^+$.

Step 2: Synthesis of Compound 49-c

Compound 49-b (130.00 mg, 231.90 μmol, 1.00 eq) was dissolved in dichloromethane (6.00 mL), and PIDA (289.07 mg, 897.46 μmol, 3.87 eq) and TEMPO (10.94 mg, 69.57 μmol, 0.30 eq) were added thereto. The reaction solution was stirred at 27° C. for 16 hours under the protection of nitrogen gas. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was purified by preparative silica gel plates (petroleum ether:ethyl acetate=1:1) to give the product of compound 49-c (100.00 mg, yield: 71%) as a colorless oil. LCMS m/z=581.2 [M+Na]$^+$.

Step 3: Synthesis of Compound 49

Compound 49-c (100.00 mg, 179.03 μmol, 1.00 eq) was dissolved in dichloromethane (4.00 mL), and trifluoroacetic acid (2.94 g, 25.75 mmol, 1.91 mL, 143.85 eq) was added thereto. The reaction solution was stirred at 27° C. for 1 hour under the protection of nitrogen gas. After the reaction was completed, the reaction solution was spin-dried to give a crude product. The crude product was purified by preparative HPLC (under trifluoroacetic acid condition), and lyophilized to give the product of compound 49 (18.20 mg, yield: 20%). $^1$H NMR (400 MHz, DMSO-$d_6$) δ=8.44 (d, J=7.03 Hz, 1H), 7.48-7.68 (m, 1H), 5.12-5.30 (m, 2H), 4.59 (q, J=6.53 Hz, 1H), 4.25-4.40 (m, 1H), 3.97 (d, J=13.05 Hz, 1H), 2.82-3.07 (m, 2H), 2.68-2.79 (m, 1H), 2.53-2.64 (m, 2H), 2.31-2.45 (m, 1H), 1.21-1.81 (m, 13H); LCMS m/z=503.3 [M+H]$^+$.

Example 50: Compound 50

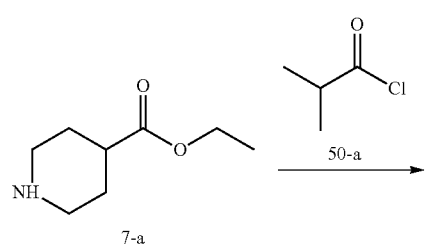

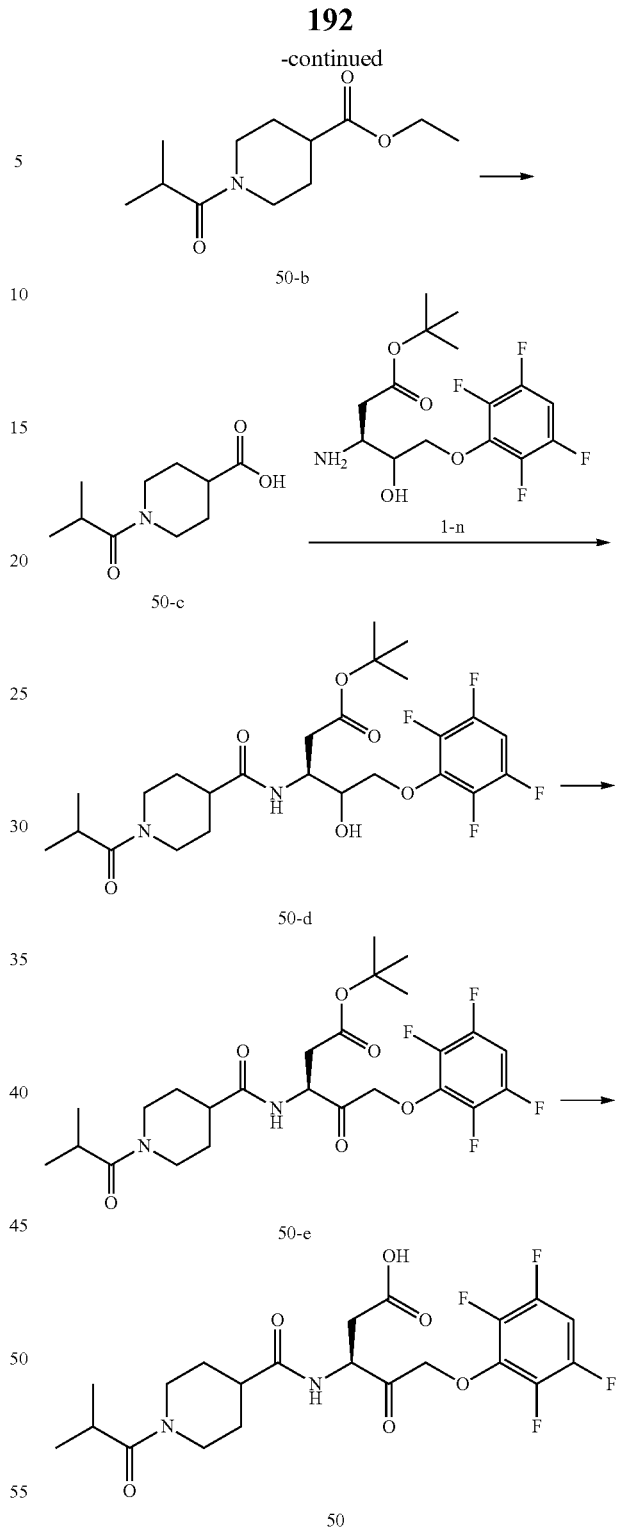

Step 1: Synthesis of Compound 50-b

Compound 7-a (2.00 g, 12.72 mmol, 1.96 mL, 1.0 eq) was dissolved in dichloromethane (20.00 mL), and triethylamine (3.86 g, 38.16 mmol, 5.29 mL, 3.00 eq) was added to the solution in one portion at 0° C. Compound 50-a (1.36 g, 12.72 mmol, 1.33 mL, 1 eq) was then added dropwise to the reaction solution at 0° C. The reaction solution was stirred at 0° C. for 2 hours, followed by stirring at 20° C. for another 2 hours. After the reaction was completed, the reaction solution was diluted with 40 mL of water, and extracted with dichloromethane (50 mL×3). The organic phases were combined, washed with saturated brine (100 mL), dried over anhydrous sodium sulfate, filtered, and concentrated to give a crude product. The crude product was subjected to column chromatography (petroleum ether:ethyl acetate=10:1~4:1) to give the product of compound 50-b (2.20 g, yield: 76%) as a yellow oil. $^1$H NMR (400 MHz, CHLOROFORM-d) δ=4.46 (d, J=12.8 Hz, 1H), 4.15 (dq, J=1.9, 7.1 Hz, 2H), 3.90 (d, J=13.3 Hz, 1H), 3.12 (t, J=12.4 Hz, 1H), 2.85-2.72 (m, 2H), 2.59-2.48 (m, 1H), 1.95 (d, J=12.4 Hz, 2H), 1.75-1.55 (m, 2H), 1.26 (dt, J=1.9, 7.1 Hz, 3H), 1.12 (br. s., 6H).

Step 2: Synthesis of Compound 50-c

Compound 50-b (500.00 mg, 2.20 mmol, 1.00 eq) was dissolved in THF (10.00 mL) and H$_2$O (10.00 mL), and LiOH.H$_2$O (276.90 mg, 6.60 mmol, 3.00 eq) was added to the solution, followed by stirring at room temperature (T=10° C.) for 12 hours. After the reaction was completed, the reaction solution was washed with dichloromethane (30 mL×3), and then the aqueous phase was adjusted to pH=3 with 2N dilute hydrochloric acid (10 mL). The aqueous phase was extracted with dichloromethane (30 mL×3). The organic phases were combined, washed with saturated brine (30 mL×2), dried over anhydrous sodium sulfate, filtered and concentrated, to give compound 50-c (340.00 mg, yield: 78%), which was used directly in the next step without purification. LCMS m/z=200.1[M+1]$^+$.

Step 3: Synthesis of Compound 50-d

Compound 1-n (203.92 mg, 577.16 μmol, 1.00 eq) was dissolved in dichloromethane (10.00 mL). Compound 50-c (115.00 mg, 577.16 μmol, 1.00 eq), NMM (175.14 mg, 1.73 mmol, 190.37 μL, 3.00 eq), HOBt (106.84 mg, 790.72 μmol, 1.37 eq) and EDCl (151.58 mg, 790.72 μmol, 1.37 eq) were added to the solution under the protection of nitrogen gas. The reaction solution was stirred at 18° C. for 24 hours. After the reaction was completed, the reaction solution was added with 20 mL of water, and extracted with dichloromethane (30 mL×3). The organic phases were combined, dried over anhydrous sodium sulfate, filtered and concentrated to give a crude product.

The crude product was subjected to column chromatography (petroleum ether:ethyl acetate=10:0~1:1) to give the product of compound 50-d (520.00 mg, yield: 92%) as a colorless oil. LCMS m/z=535.1 [M+H]$^+$.

Step 4: Synthesis of Compound 50-e

Compound 50-d (230.00 mg, 430.28 μmol, 1.00 eq) was dissolved in dichloromethane (10.00 mL), and PIDA (536.35 mg, 1.67 mmol, 3.87 eq) and TEMPO (20.30 mg, 129.08 μmol, 0.30 eq) were added thereto. The reaction solution was stirred at room temperature of 10° C. for 12 hours. After the reaction was completed, the reaction solution was added with saturated NaHSO$_3$ (20 mL), and extracted with dichloromethane (30 mL×3). The organic phase was washed with saturated brine (20 mL×3), dried over anhydrous sodium sulfate, filtered and concentrated to give a crude product. The crude product was subjected to column chromatography (petroleum ether:ethyl acetate=10:1~2:1) to give the product of compound 50-e (200.00 mg, yield: 87%) as a colorless oil. LCMS m/z=533.1 [M+H]$^+$, 1H NMR (400 MHz, DMSO-d6) δ=8.43 (d, J=7.70 Hz, 1H), 7.50-7.69 (m, 1H), 5.15-5.25 (m, 2H), 4.58-4.71 (m, 1H), 4.36 (d, J=12.59 Hz, 1H), 3.95 (d, J=12.72 Hz, 1H), 3.04 (t, J=12.29 Hz, 1H), 2.80-2.92 (m, 1H), 2.67-2.78 (m, 1H), 2.52-2.64 (m, 2H), 2.37-2.49 (m, 2H), 1.37 (s, 9H), 0.98 (t, J=5.56 Hz, 6H).

Step 5: Synthesis of Compound 50

Compound 50-e (210.00 mg, 392.86 μmol, 1.00 eq) was dissolved in dichloromethane (10.00 mL), and trifluoroacetic acid (7.70 g, 67.53 mmol, 5.00 mL, 171.90 eq) was added thereto at 0° C. The reaction solution was stirred at 0° C.-10° C. for 12 hours. After the reaction was completed, the reaction solution was spin-dried to give a crude product. The crude product was purified by preparative HPLC (under trifluoroacetic acid condition), and lyophilized to give the product of compound 50 (44.50 mg, yield: 24%). 1H NMR (400 MHz, DMSO-d6) δ=8.46 (d, J=7.53 Hz, 1H), 7.52-7.61 (m, 1H), 5.15-5.27 (m, 2H), 4.58-4.69 (m, 1H), 4.24-4.43 (m, 2H), 3.00-3.10 (m, 1H), 2.85-2.91 (m, 1H), 2.72-2.79 (m, 1H), 2.58 (dd, J=16.88, 6.84 Hz, 4H), 2.40-2.50 (m, 2H), 0.98-1.01 (m, 6H).

Example 51: Compound 51

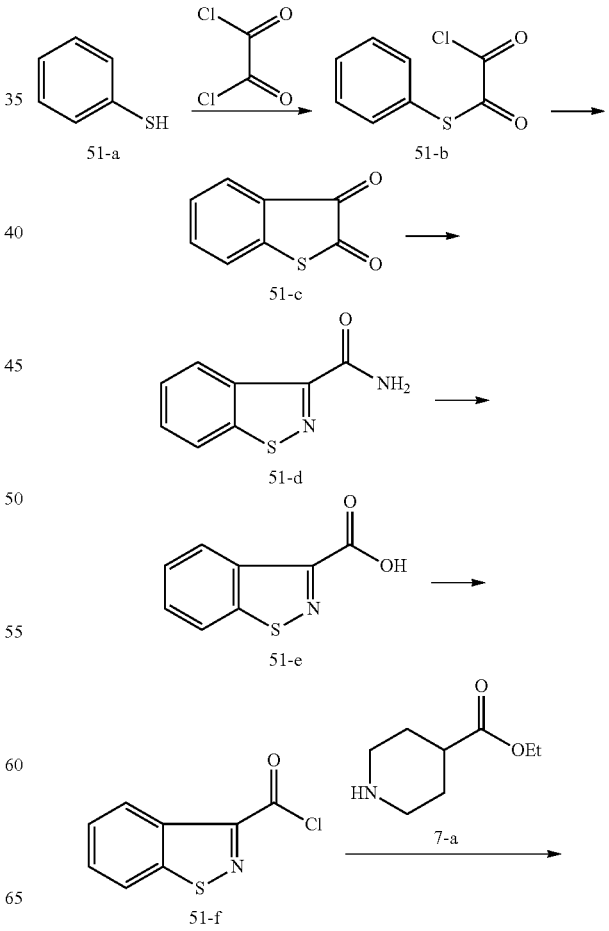

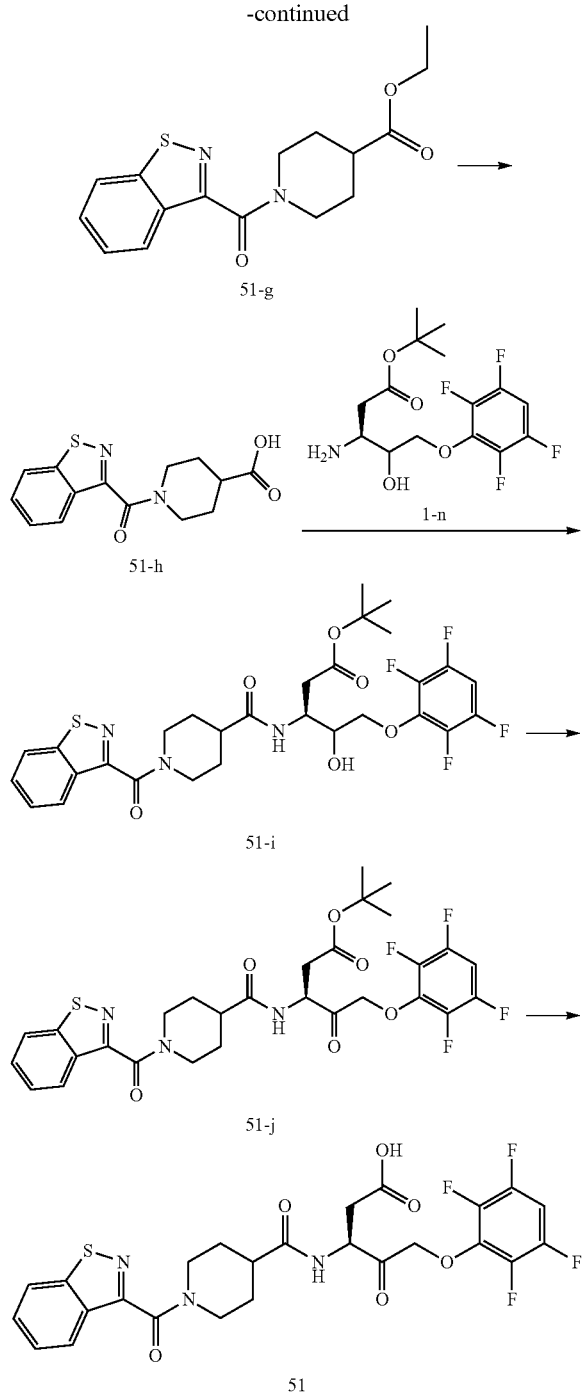

Step 2: Synthesis of Compound 51-c

Compound 51-b (131.41 g, crude) was dissolved in dichloromethane (300.00 mL), and AlCl$_3$ (95.19 g, 713.90 mmol, 1.09 eq) was added slowly in portions to the reaction solution at 0° C. After the addition was completed, the reaction solution was stirred at 40° C. for 1.5 hours. After the reaction was completed, the above reaction solution was cooled down to 25° C., carefully poured into ice water with stirring (500.00 mL), and then separated. The organic phase was washed respectively with saturated sodium hydrogen carbonate solution (300 mL) and saturated brine (500.00 mL), dried over anhydrous sodium sulfate, filtered, and concentrated to give a crude product. The crude product was recrystallized in dichloromethane and cyclohexane (V:V=1:1) to give compound 51-c (36.80 g, crude). $^1$H NMR (400 MHz, CHLOROFORM-d) δ=7.86 (d, J=7.7 Hz, 1H), 7.71 (dt, J=1.4, 7.7 Hz, 1H), 7.47-7.37 (m, 2H).

Step 3: Synthesis of Compound 51-d

Compound 51-c (2.00 g, 12.18 mmol, 1.0 eq) was dissolved in ammonium hydroxide (10.00 mL), and the reaction solution was added with hydrogen peroxide (1.38 g, 12.18 mmol, 1.17 mL, content of 30%, 1.00 eq) at 5° C.-10° C. The above reaction solution was stirred at 5° C.-10° C. for another 2 hours. After the reaction was completed, the reaction solution was filtered. The filter cake was washed with water (20.00 mL), and then dried to give compound 51-d (1.65 g, crude). $^1$H NMR (400 MHz, CHLOROFORM-d) δ=8.97 (dd, J=1.1, 7.2 Hz, 1H), 7.99-7.95 (m, 1H), 7.61-7.51 (m, 2H), 7.31 (br. s., 1H), 5.80 (br. s., 1H). LCMS m/z 179.0[M+H]$^+$.

Step 4: Synthesis of Compound 51-e

Compound 51-d (1.65 g, 9.26 mmol, 1.0 eq) was dissolved in 1M sodium hydroxide solution (10.00 mL), and the above reaction solution was stirred at 100° C. for 1 hour. After the reaction was completed, the above reaction solution cooled down to room temperature, added with water (20.00 mL), and then extracted three times with dichloromethane (30.00 mL×3). The aqueous phase was adjusted to pH of 3-4 with 6M hydrochloric acid, and then white precipitate was precipitated, filtered and dried to give compound 51-e (310.00 mg, yield: 19%). $^1$H NMR (400 MHz, DMSO-d6) δ=8.65 (d, J=8.2 Hz, 1H), 8.33 (d, J=8.2 Hz, 1H), 7.72-7.58 (m, 2H). LCMS m/z 180.0[M+H]$^+$.

Step 5: Synthesis of Compound 51-f

Compound 51-e (310.00 mg, 1.73 mmol, 1.00 eq) was dissolved in dichloromethane (10.00 mL) and tetrahydrofuran (5.00 mL). Oxalyl chloride (241.54 mg, 1.90 mmol, 166.58 μL, 1.10 eq) and DMF (1.26 mg, 17.30 μmol, 1.33 μL, 0.01 eq) were then slowly added dropwise to the reaction solution. The above reaction solution was stirred at 20° C. for 2 hours. After the reaction was completed, the reaction solution was directly concentrated under vacuum to give compound 51-f (340.00 mg, crude).

Step 6: Synthesis of Compound 51-g

Compounds 51-f (340 mg, 1.72 mmol, 1.0 eq) and 7-a (405.60 mg, 2.58 mmol, 397.65 μL, 1.50 eq) were dissolved in dichloromethane (10.00 mL), and then triethylamine (522.23 mg, 5.16 mmol, 715.38 μL, 3.00 eq) was added to

Step 1: Synthesis of Compound 51-b

Oxalyl chloride (89.97 g, 708.79 mmol, 62.05 mL, 1.38 eq) was dissolved in tetrahydrofuran (250 mL), and compound 51-a (56.59 g, 513.61 mmol, 52.40 mL, 1.00 eq) was dissolved in tetrahydrofuran (250 mL). A solution of oxalyl chloride in tetrahydrofuran was slowly added dropwise to the solution of compound 51-a in tetrahydrofuran. After the dropwise addition was completed, the reaction solution was stirred at 50° C. for 48 hours. After the reaction was completed, the reaction solution was directly concentrated and spin-dried to give compound 51-b (131.41 g, crude).

the above solution at 0° C. The reaction solution was then stirred at 20° C. for 2 hours. After the reaction was completed, the above reaction solution was added with water (50.00 mL), and extracted three times with dichloromethane (30 mL×3). The organic phases were combined, washed with saturated brine (50.00 mL), dried, concentrated, and purified by column chromatography (petroleum ether:ethyl acetate=10:1~5:1) to give compound 51-g (460.00 mg, yield: 84%). $^1$H NMR (400 MHz, CHLOROFORM-d) δ=8.23 (d, J=8.2 Hz, 1H), 7.97 (d, J=8.2 Hz, 1H), 7.57 (dt, J=1.1, 7.6 Hz, 1H), 7.52-7.46 (m, 1H), 4.69-4.58 (m, 1H), 4.17 (q, J=7.2 Hz, 2H), 4.04 (td, J=3.5, 13.8 Hz, 1H), 3.30-3.12 (m, 2H), 2.64 (tt, J=4.1, 10.6 Hz, 1H), 2.16-2.07 (m, 1H), 1.99-1.75 (m, 3H), 1.30-1.25 (m, 3H). LCMS m/z 319.0[M+H]$^+$.

Step 7: Synthesis of Compound 51-h

Compound 51-g (460.00 mg, 1.44 mmol, 1.00 eq) was dissolved in a mixed solution of tetrahydrofuran (10.00 mL) and water (10.00 mL), and then LiOH.H$_2$O (90.63 mg, 2.16 mmol, 1.50 eq) was added to the above solution. The above reaction solution was stirred at 25° C. for 16 hours. After the reaction was completed, the reaction solution was added with water (50.00 mL), and extracted with dichloromethane (20 mL×3) three times. The pH aqueous phase was adjusted to pH of 3-4 with 6M hydrochloric acid. The aqueous phase was then extracted reversely with ethyl acetate (30 mL×3). The organic phases were combined, washed with saturated brine (60.00 mL), dried, filtered, and concentrated to give compound 51-h (430.00 mg, crude). $^1$H NMR (400 MHz, DMSO-d$_6$) δ=12.35 (s, 1H), 8.31 (d, J=8.2 Hz, 1H), 8.09 (d, J=8.2 Hz, 1H), 7.71-7.65 (m, 1H), 7.60-7.53 (m, 1H), 4.45 (d, J=13.2 Hz, 1H), 3.65-3.58 (m, 2H), 3.23-3.06 (m, 2H), 2.69-2.56 (m, 1H), 1.84-1.74 (m, 2H), 1.67-1.43 (m, 1H).

Step 7: Synthesis of Compound 51-i

Compounds 51-h (215.00 mg, 740.51 μmol, 1.00 eq) and 1-n (261.63 mg, 740.51 μmol, 1.00 eq) were dissolved in dichloromethane (10.00 mL), and EDCl (194.48 mg, 1.01 mmol, 1.37 eq), HOBt (137.08 mg, 1.01 mmol, 1.37 eq) and NMM (224.71 mg, 2.22 mmol, 244.25 μL, 3.00 eq) were added to the above reaction solution. The reaction solution was then stirred at 18° C. for 5 hours under a nitrogen gas atmosphere. After the reaction was completed, the above reaction solution was added with water (50.00 mL), and extracted with dichloromethane (30 mL×3) three times. The organic phases were combined, washed with saturated brine (50.00 mL), dried, concentrated, and purified by column chromatography (petroleum ether:ethyl acetate=5:1~1:1) to give compound 51-i (210.00 mg, yield: 45%). LCMS m/z 570.0[M−56+H]$^+$.

Step 8: Synthesis of Compound 51-j

Compound 51-i (210.00 mg, 335.66 μmol, 1.0 eq) was dissolved in dichloromethane (10.00 mL), and TEMPO (15.83 mg, 100.70 μmol, 0.30 eq) and PIDA (418.41 mg, 1.30 mmol, 3.87 eq) were added to the above reaction solution. The above reaction solution was the stirred at 25° C. for 64 hours under a nitrogen gas atmosphere. After the reaction was completed, the above reaction solution was added with water (50.00 mL), and extracted with dichloromethane (30 mL×3) three times. The organic phases were combined, washed with saturated brine (60.00 mL), dried, concentrated, and purified by column chromatography (pe-troleum ether:ethyl acetate=5:1~1:1) to give compound 51-j (170.00 mg, yield: 81%). LCMS m/z 568.1[M−56+H]$^+$.

Step 9: The Synthesis of Compound 51

Compound 51-j (170.00 mg, 272.61 μmol, 1.00 eq) was dissolved in dichloromethane (6.0 mL), and trifluoroacetic acid (4.63 g, 40.65 mmol, 3.01 mL, 149.12 eq) was added thereto. The reaction solution was stirred at 25° C. for 2 hours. After the reaction was completed, the reaction solution was spin-dried to give a crude product. The crude product was purified by preparative HPLC (under trifluoroacetic acid condition), and lyophilized to give the product of compound 51 (30.00 mg, yield: 19%). $^1$H NMR (400 MHz, DMSO-d$_6$) δ=8.50 (d, J=7.5 Hz, 1H), 8.30 (d, J=8.2 Hz, 1H), 8.08 (d, J=8.2 Hz, 1H), 7.68 (t, J=7.5 Hz, 1H), 7.61-7.51 (m, 2H), 5.31-5.13 (m, 2H), 4.67-4.51 (m, 2H), 3.71 (d, J=13.4 Hz, 1H), 3.19-3.08 (m, 1H), 3.00 (t, J=11.9 Hz, 1H), 2.81-2.69 (m, 1H), 2.64-2.54 (m, 2H), 1.89 (br. s., 1H), 1.73-1.45 (m, 3H). LCMS: 568.1[M+H]$^+$.

Example 52: Compound 52

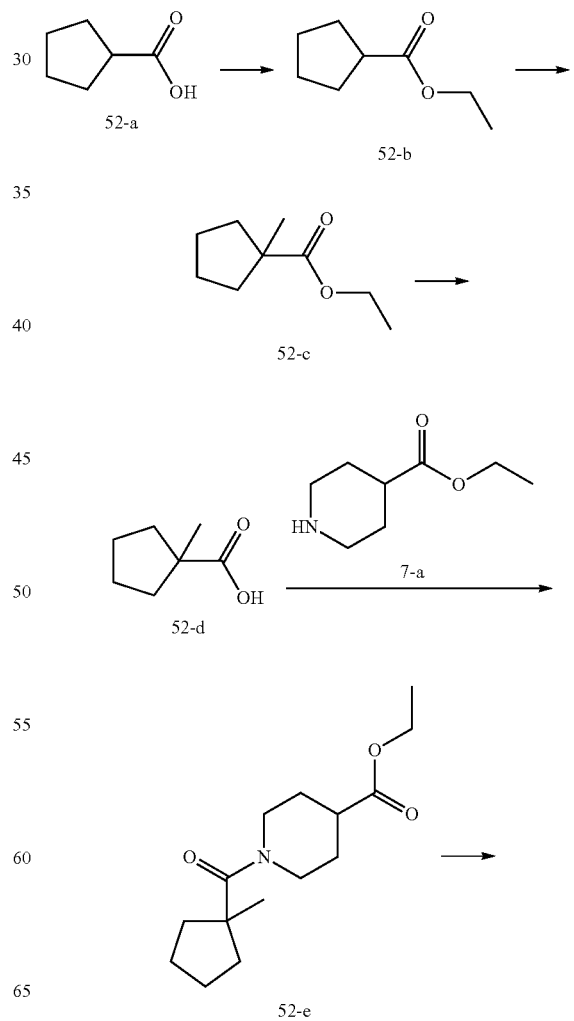

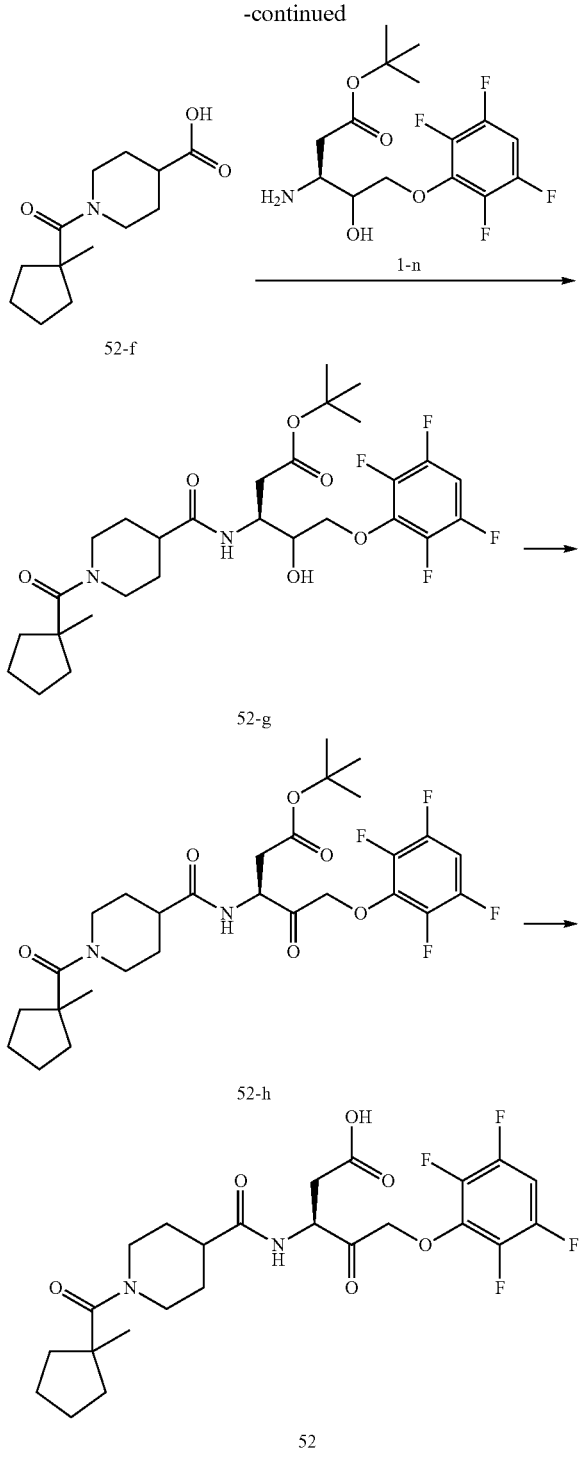

Step 1: Synthesis of Compound 52-b

A mixture solution of compound 52-a (15.00 g, 131.42 mmol, 14.29 mL, 1.00 eq), ethanol (70.00 mL) and concentrated sulfuric acid (1.84 g, 18.40 mmol, 1.00 mL, 98%, 0.14 eq) was stirred under reflux for 5 hours. After the reaction was completed, the reaction solution was concentrated, cooled down to room temperature, slowly added with crushed ice (150 mL) with stirring, and extracted with dichloromethane (200 mL). The organic phase was washed with saturated sodium hydrogen carbonate (150 mL) and water (100 mL), and then dried over anhydrous sodium sulfate, filtered, and concentrated to give a crude product. The crude product was subjected to column chromatography (petroleum ether:ethyl acetate=1:0~9:1) to give the product of compound 52-b (10.00 g, yield: 54%) as a colourless liquid. $^1$H NMR (400 MHz, CHLOROFORM-d) δ=4.05-4.16 (m, 2H), 2.70 (q, J=7.97 Hz, 1H), 1.50-1.94 (m, 8H), 1.24 (t, J=7.03 Hz, 3H).

Step 2: Synthesis of Compound 52-c

Compound 52-b (2.00 g, 14.06 mmol, 1.00 eq) was dissolved in tetrahydrofuran (130.00 mL), and LDA (2 M, 7.03 mL, 1.00 eq) was added dropwise under the protection of nitrogen gas at −78° C. After stirring at −78° C. for 2 hours, the above solution was added with MeI (3.50 g, 24.66 mmol, 1.54 mL, 1.75 eq), and the reaction solution was stirred at 20° C. for 16 hours. After the reaction was completed, the reaction solution was added with water at 0° C. for quenching, and then extracted with ethyl acetate (100 mL×3). The organic phases were combined, washed with brine (150 mL), dried over anhydrous sodium sulfate, filtered, and concentrated to give a crude product. The crude product was subjected to column chromatography (petroleum ether:ethyl acetate=1:0~9:1) to give the product of compound 52-c (1.70 g, yield: 77%) as a yellow liquid. $^1$H NMR (400 MHz, CHLOROFORM-d) δ=4.12 (q, J=7.19 Hz, 2H), 2.04-2.15 (m, 2H), 1.62-1.74 (m, 4H), 1.41-1.52 (m, 2H), 1.21-1.29 (m, 6H).

Step 3: Synthesis of Compound 52-d

Compound 52-c (537.00 mg, 3.44 mmol, 1.00 eq) was dissolved in methanol (3.00 mL), and sodium hydroxide solution (2 M, 2.29 mL, 1.33 eq) was added to the above solution. The reaction solution was maintained at 60° C., with stirring for 16 hours. After the reaction was completed, the reaction solution was concentrated, and adjusted to pH of 5 with 2 N dilute hydrochloric acid. This solution was added with 100 mL of water, and extracted with ethyl acetate (100 mL×2). The organic phases were combined, washed with brine (100 mL), dried over anhydrous sodium sulfate, filtered, and concentrated to give the product of compound 52-d (390.00 mg, crude) as a yellow liquid, which was used directly in the next step without purification. $^1$H NMR (400 MHz, CHLOROFORM-d) δ=2.08-2.21 (m, 2H), 1.71 (d, J=3.26 Hz, 4H), 1.45-1.56 (m, 2H), 1.28 (s, 3H).

Step 4: Synthesis of Compound 52-e

Compound 52-d (370.00 mg, 2.89 mmol, 1.00 eq) was dissolved in dichloromethane (30.00 mL), and compound 7-a (545.20 mg, 3.47 mmol, 534.51 µL, 1.20 eq), EDCl (759.00 mg, 3.96 mmol, 1.37 eq), HOBt (534.98 mg, 3.96 mmol, 1.37 eq) and NMM (876.97 mg, 8.67 mmol, 953.23 µL, 3.00 eq) were added thereto. The reaction solution was stirred at 20° C. for 18 hours. After the reaction was completed, the reaction solution was added with 100 mL of water, and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 52-e (430.00 mg, yield: 49%) as a colorless oil. $^1$H NMR (400 MHz, CHLOROFORM-d) δ=4.17-4.34 (m, 2H), 4.14 (q, J=7.03 Hz, 2H), 2.84-3.02 (m, 2H), 2.47-2.58 (m, 1H), 2.12-2.23 (m, 2H), 1.92 (dd, J=2.64, 13.18 Hz, 2H), 1.51-1.71 (m, 8H), 1.23-1.28 (m, 6H).

Step 5: Synthesis of Compound 52-f

Compound 52-e (430.00 mg, 1.61 mmol, 1.00 eq) was dissolved in tetrahydrofuran (15.00 mL), and a solution of LiOH.H₂O (202.67 mg, 4.83 mmol, 3.00 eq) dissolved in H₂O (15.00 mL) was added to the above solution. The reaction solution was stirred at 15° C. for 2 hours. After the reaction was completed, the reaction solution was adjusted to pH of 5 with 2 N dilute hydrochloric acid. This solution was added with 100 mL of water, and extracted with dichloromethane (100 mL×3). The organic phase was dried over anhydrous sodium sulfate, filtered and concentrated to give the product of compound 52-f (390.00 mg, crude) as a pale yellow solid, which was used directly in the next step without purification. ¹H NMR (400 MHz, CHLOROFORM-d) δ=4.24 (br. s., 2H), 2.98 (br. s., 2H), 2.54-2.66 (m, 1H), 2.12-2.23 (m, 2H), 1.97 (dd, J=3.01, 13.55 Hz, 2H), 1.55-1.74 (m, 8H), 1.27 (s, 3H).

Step 6: Synthesis of Compound 52-g

Compound 1-n (140.00 mg, 396.25 μmol, 1.00 eq) was dissolved in dichloromethane (15.00 mL), and compound 52-f (170.00 mg, 710.38 μmol, 1.79 eq), EDCl (104.07 mg, 542.87 μmol, 1.37 eq), HOBt (73.35 mg, 542.87 μmol, 1.37 eq) and NMM (120.24 mg, 1.19 mmol, 130.70 μL, 3.00 eq) were added thereto. The reaction solution was stirred under the protection of nitrogen gas at 20° C. for 16 hours. After the reaction was completed, the reaction solution was added with 100 mL of water, and extracted with dichloromethane (100 mL×3). The organic phases were combined, dried over anhydrous sodium sulfate, filtered and concentrated to give a crude product. The crude product was subjected to column chromatography (petroleum ether:ethyl acetate=4:1~1:1) to give the product of compound 52-g (170.00 mg, yield: 51%) as a colorless oil. LCMS m/z=575.1 [M+H]⁺.

Step 7: Synthesis of Compound 52-h

Compound 52-g (170.00 mg, 295.85 μmol, 1.00 eq) was dissolved in dichloromethane (15.00 mL), and PIDA (368.79 mg, 1.14 mmol, 3.87 eq) and TEMPO (13.96 mg, 88.76 μmol, 0.30 eq) were added thereto. After stirring under the protection of nitrogen gas at 15° C. for 16 hours, the reaction solution was added with TEMPO (17.85 mg, 113.49 μmol, 0.30 eq), and stirred for another 48 hours. After the reaction was completed, the reaction solution was added with 100 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=4:1~1:1) to give the product of compound 52-h (140.00 mg, yield: 65%) as a yellow oil. LCMS m/z=573.2 [M+H]⁺.

Step 8: Synthesis of Compound 52

Compound 52-h (140.00 mg, 193.16 μmol, 1.00 eq) was dissolved in dichloromethane (5.00 mL), and trifluoroacetic acid (3.83 g, 33.60 mmol, 2.49 mL, 173.95 eq) was added thereto. The reaction solution was stirred under the protection of nitrogen gas at 15° C. for 1 hour. After the reaction was completed, the reaction solution was spin-dried to give a crude product. The crude product was purified by preparative HPLC (under neutral condition), and lyophilized to give the product of compound 52 (50.30 mg, yield: 49%). ¹H NMR (400 MHz, DMSO-d₆) δ=8.42 (d, J=7.03 Hz, 1H), 7.48-7.64 (m, 1H), 5.04-5.31 (m, 2H), 4.52 (q, J=6.53 Hz, 1H), 4.16 (br. s., 2H), 2.65-2.90 (m, 2H), 2.54 (br. s., 1H), 2.05 (d, J=5.52 Hz, 2H), 1.30-1.76 (m, 12H), 1.18 (s, 3H); LCMS m/z=517.2 [M+H]⁺.

Example 53: Compound 53

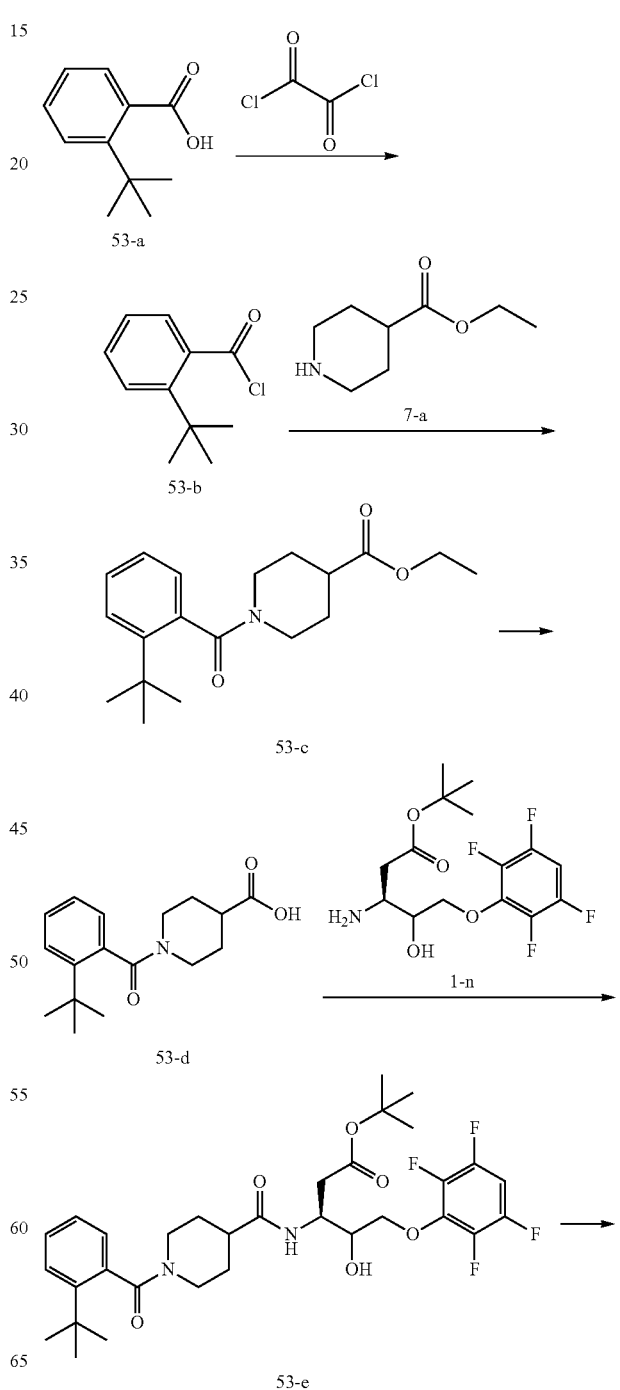

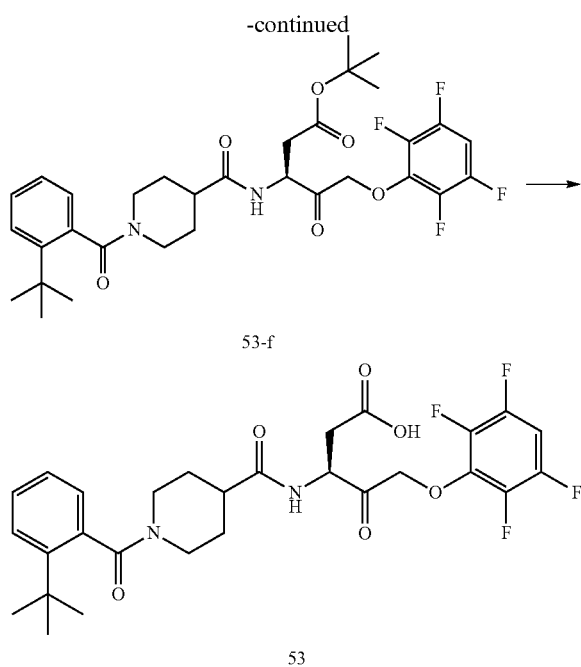

Step 1: Synthesis of Compound 53-b

Compound 53-a (600 mg, 3.37 mmol, 1.00 eq) was dissolved in dichloromethane (15 mL), added with oxalyl chloride (855.51 mg, 6.74 mmol, 590.01 μL, 2.00 eq) and DMF (123.16 mg, 1.69 mmol, 129.64 μL, 0.5 eq) at an ice bath. After stirring at the ice bath for 10 min, the reaction solution was warmed up to room temperature with stirring for 1 hour. After the reaction was completed, the reaction solution was concentrated to give a crude product of compound 53-b (670 mg, crude), which was used directly in the next step without purification.

Step 2: Synthesis of Compound 53-c

Compound 7-a (481.06 mg, 3.06 mmol, 471.63 μL, 2.00 eq) was dissolved in dichloromethane (5.00 mL), added with triethylamine (464.46 mg, 4.59 mmol, 636.25 μL, 3.00 eq) at an ice bath. After stirring for 10 min, compound 53-b (300.00 mg, 1.53 mmol, 1.00 eq) was dissolved in dichloromethane (3 mL), and added to the above reaction solution. The reaction solution was warmed up to room temperature, and stirred for 15 hours. After the reaction was completed, the reaction solution was concentrated to give a crude product. The crude product was purified by column chromatography (petroleum ether:ethyl acetate=4:1), to give the product of compound 53-c (300 mg, yield: 59%) as a colorless oil. LCMS m/z=340.0 [M+Na]$^+$.

Step 3: Synthesis of Compound 53-d

LiOH.H$_2$O (79.31 mg, 1.89 mmol, 2.00 eq) was dissolved in water (5.00 mL), and added to a solution of compound 53-c (300.00 mg, 945.12 μmol, 1.00 eq) dissolved in THF (5.00 mL). The reaction was stirred at room temperature for 1.5 hours. After the reaction was completed, the reaction solution was added with water (10 mL), adjusted to pH of 3-4 with 1 N dilute hydrochloric acid, and extracted with dichloromethane/methanol (30 mL, v/v=10:1). The organic phase was dried over anhydrous sodium sulfate, filtered, and concentrated to give the product of compound 53-d (300.00 mg, crude) as a colorless oil, which was used directly in the next step without purification. LCMS m/z=289.9 [M+H]$^+$.

Step 4: Synthesis of Compound 53-e

Compound 1-n (224.14 mg, 764.21 μmol, 1.50 eq) was dissolved in dichloromethane (8 mL), and N-methylmorpholine (154.60 mg, 1.53 mmol, 168.04 μL, 3.00 eq), EDCl (195.33 mg, 1.02 mmol, 2.00 eq), HOBt (137.68 mg, 1.02 mmol, 2.00 eq) and compound 53-d (180.00 mg, 509.47 μmol, 1.00 eq) were added thereto. The reaction was stirred at room temperature for 15 hours. After the reaction was completed, the reaction solution was concentrated to give a crude product. The crude product was purified by column chromatography (petroleum ether:ethyl acetate=3:2), to give the product of compound 53-e (270.00 mg, yield: 76%) as a colorless oil. LCMS m/z=625.3 [M+H]$^+$.

Step 5: Synthesis of Compound 53-f

Compound 53-e (270.00 mg, 432.24 μmol, 1.00 eq) was dissolved in dichloromethane (10.00 mL), and PIDA (974.57 mg, 3.03 mmol, 7.00 eq) and TEMPO (67.97 mg, 432.24 μmol, 1.00 eq) were added thereto. The reaction was stirred at room temperature for 40 hours. After the reaction was completed, the reaction solution was diluted with dichloromethane (50 mL), and washed with saturated sodium hydrogen carbonate solution (40 mL) and saturated brine (40 mL×2). The organic phase was dried over anhydrous sodium sulfate, filtered, and concentrated to give a crude product. The crude product was purified by column chromatography (petroleum ether:ethyl acetate=1:1), to give the product of compound 53-f (210.00 mg, yield: 64%) as a yellow oil. LCMS m/z=623.1 [M+H]$^+$.

Step 7: Synthesis of Compound 53

Compound 53-f (210.00 mg, 337.27 μmol, 1.00 eq) was dissolved in dichloromethane (8.00 mL), and TFA (4.00 mL, 54.03 mmol, 160.19 eq) was added thereto. The reaction was stirred at room temperature for 1 hour. After the reaction was completed, the reaction solution was spin-dried to give a crude product. The crude product was purified by preparative HPLC (in TFA condition), and lyophilized to give compound 53 (100.00 mg, yield: 52%). $^1$H NMR (400 MHz, DMSO-d$_6$) δ=8.51 (br. s., 1H), 7.45-7.72 (m, 2H), 7.17-7.41 (m, 2H), 7.03 (br. s., 1H), 5.22 (br. s., 2H), 4.86 (br. s., 1H), 4.37-4.65 (m, 2H), 2.65-3.08 (m, 4H), 1.82 (br. s., 1H), 0.95-1.67 (m, 13H); LCMS m/z=567.2 [M+H]$^+$.

Example 54: Compound 54

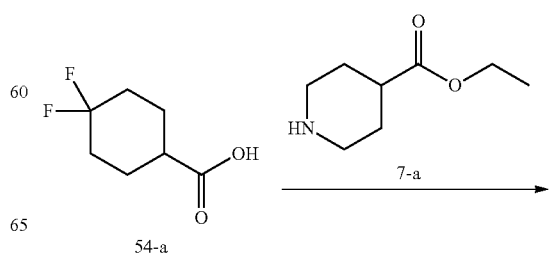

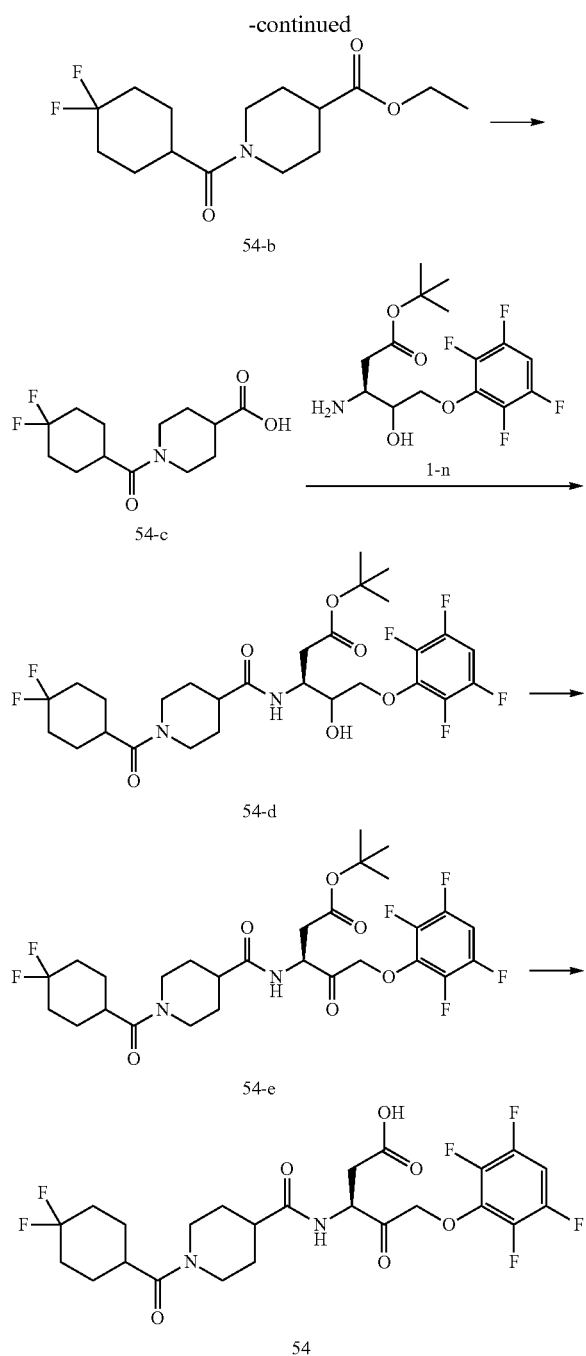

Step 1: Synthesis of Compound 54-b

Compound 54-a (361.13 mg, 2.20 mmol, 1.10 eq) and HATU (1.14 g, 3.00 mmol, 1.50 eq) were dissolved in dichloromethane (20 mL), and stirred at room temperature for 15 min. Compound 7-a (314.42 mg, 2.00 mmol, 308.25 μL, 1.00 eq) and N,N-diisopropylethylamine (775.44 mg, 6.00 mmol, 1.05 mL, 3.00 eq) were then added, followed by stirring at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 54-b (892.00 mg, yield: 94%) as a yellow oil. $^1$H NMR (400 MHz, CHLOROFORM-d) δ=4.40 (d, J=13.3 Hz, 1H), 4.18-4.07 (m, 2H), 3.83 (d, J=13.3 Hz, 1H), 3.13 (t, J=11.7 Hz, 1H), 2.60-2.48 (m, 2H), 2.22-2.07 (m, 2H), 1.98-1.52 (m, 11H), 1.24 (t, J=7.2 Hz, 3H); LCMS m/z=304.0 [M+H]$^+$.

Step 2: Synthesis of Compound 54-c

Compound 54-b (473.98 mg, 1.00 mmol, 1.00 eq) was dissolved in tetrahydrofuran (10.00 mL), and a solution of LiOH.H$_2$O (62.94 mg, 1.50 mmol, 1.50 eq) dissolved in H$_2$O (10.00 mL) was added to the above solution. The reaction solution was maintained at 25° C. and stirred for 2 hours. After the reaction was completed, the reaction solution was adjusted to pH of 6 with 2 N dilute hydrochloric acid. This solution was added with 50 mL of water, and extracted with dichloromethane (30 mL×3). The organic phase was dried over anhydrous sodium sulfate, filtered and concentrated to give the product of compound 54-c (308.00 mg, crude) as a pale yellow oil, which was used directly in the next step without purification. LCMS m/z=275.9 [M+H]$^+$.

Step 3: Synthesis of Compound 54-d

Compound 54-c (178.94 mg, 650.00 μmol, 1.30 eq) and HATU (380.23 mg, 1.00 mmol, 2.00 eq) were dissolved in dichloromethane (20 mL), and stirred at room temperature for 15 min. Compound 1-n (176.66 mg, 500.00 μmol, 1.00 eq) and N,N-diisopropylethylamine (193.86 mg, 1.50 mmol, 261.97 μL, 3.00 eq) were then added, followed by stirring at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~5:3) to give the product of compound 54-d (233.00 mg, yield: 74%) as a yellow oil. LCMS m/z=633.1 [M+Na]$^+$.

Step 4: Synthesis of Compound 54-e

Compound 54-d (230.00 mg, 376.68 μmol, 1.00 eq) was dissolved in dichloromethane (20.00 mL), and PIDA (485.32 mg, 1.51 mmol, 4.00 eq) and TEMPO (11.85 mg, 75.34 μmol, 0.20 eq) were added thereto. The reaction solution was stirred at room temperature for 62 hours. After the reaction was completed, the reaction solution was added with saturated sodium hydrogen carbonate solution (50 mL) and saturated sodium sulfite solution (50 mL), extracted with dichloromethane (30 mL×3), and washed with saturated brine (50 mL). The organic phase was dried over anhydrous sodium sulfate, filtered and concentrated to give a crude product. The crude product was subjected to column chromatography (petroleum ether:ethyl acetate=1:0~5:3) to give the product of compound 54-e (106.00 mg, yield: 43%) as a yellow oil. LCMS m/z=609.1 [M+H]$^+$; 631.1 [M+Na]$^+$.

Step 5: Synthesis of Compound 54

Compound 54-e (106.00 mg, 174.18 μmol, 1.00 eq) was dissolved in dichloromethane (4.00 mL), and trifluoroacetic acid (4.62 g, 40.52 mmol, 3.00 mL) was added thereto. The reaction solution was stirred at room temperature for 2 hours. After the reaction was completed, the reaction solution was spin-dried to give a crude product. The crude product was purified by preparative HPLC (in trifluoroacetic acid condition), and lyophilized to give the product of compound 54 (80.00 mg, yield: 77%). $^1$H NMR (400 MHz, DMSO-$d_6$) δ=8.52-8.45 (m, 1H), 7.64-7.52 (m, 1H), 5.22 (d, J=11.0 Hz, 2H), 4.60 (d, J=7.0 Hz, 1H), 4.41-4.25 (m, 2H), 3.99 (d, J=13.1 Hz, 1H), 3.12-2.98 (m, 1H), 2.87-2.68 (m, 2H), 2.63-2.55 (m, 2H), 2.47-2.49 (m, 1H), 2.07-1.87 (m, 4H), 1.79-1.65 (m, 5H), 1.61-1.49 (m, 2H), 1.39-1.27 (m, 1H); LCMS m/z=575.1 [M+Na]$^+$.

Example 55: Compound 55

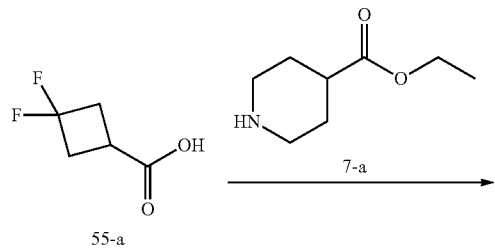

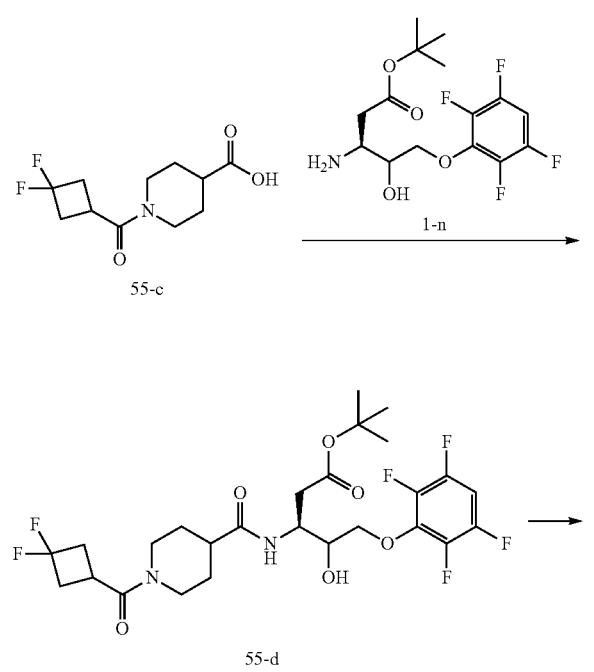

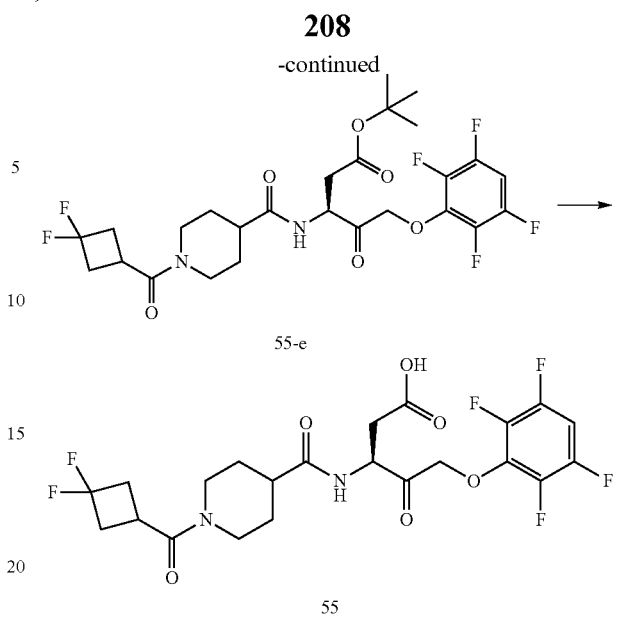

Step 1: Synthesis of Compound 55-b

Compound 55-a (299.42 mg, 2.20 mmol, 1.10 eq) and HATU (1.14 g, 3.00 mmol, 1.50 eq) were dissolved in dichloromethane (20 mL), and stirred at room temperature for 15 min. Compound 7-a (314.42 mg, 2.00 mmol, 308.25 μL, 1.00 eq) and N,N-diisopropylethylamine (775.44 mg, 6.00 mmol, 1.05 mL, 3.00 eq) were then added, followed by stirring at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 55-b (374.00 mg, yield: 68%) as a yellow oil. $^1$H NMR (400 MHz, CHLOROFORM-d) δ=4.39 (td, J=3.5, 13.1 Hz, 1H), 4.16 (q, J=7.0 Hz, 2H), 3.76-3.65 (m, 1H), 3.16-3.02 (m, 2H), 2.99-2.83 (m, 3H), 2.79-2.67 (m, 2H), 2.61-2.50 (m, 1H), 2.01-1.88 (m, 2H), 1.72-1.57 (m, 2H), 1.27 (t, J=7.2 Hz, 3H); LCMS m/z=275.9 [M+H]$^+$.

Step 2: Synthesis of Compound 55-c

Compound 55-b (192.70 mg, 700.00 μmol, 1.00 eq) was dissolved in tetrahydrofuran (10.00 mL), and a solution of LiOH.H$_2$O (58.74 mg, 1.40 mmol, 2.00 eq) dissolved in H$_2$O (10.00 mL) was added to the above solution. The reaction solution was maintained at 25° C. and stirred for 2 hours. After the reaction was completed, the reaction solution was adjusted to pH of 6 with 2 N dilute hydrochloric acid. This solution was added with 50 mL of water, and extracted with dichloromethane (30 mL×3). The organic phase was dried over anhydrous sodium sulfate, filtered and concentrated to give the product of compound 55-c (193.00 mg, crude) as a pale yellow oil, which was used directly in the next step without purification. LCMS m/z=247.8 [M+H]$^+$.

Step 3: Synthesis of Compound 55-d

Compound 55-c (81.66 mg, 600.00 μmol, 1.20 eq) and HATU (380.23 mg, 1.00 mmol, 2.00 eq) were dissolved in dichloromethane (20 mL), and stirred at room temperature for 15 min. Compound 1-n (176.66 mg, 500.00 µmol, 1.00 eq) and N,N-diisopropylethylamine (193.86 mg, 1.50 mmol, 261.97 µL, 3.00 eq) were then added, followed by stirring at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~5:3) to give the product of compound 55-d (169.00 mg, yield: 53%) as a yellow oil. LCMS m/z=605.1 [M+Na]$^+$.

Step 4: Synthesis of Compound 55-e

Compound 55-d (168.00 mg, 288.40 µmol, 1.00 eq) was dissolved in dichloromethane (20.00 mL), and PIDA (371.57 mg, 1.15 mmol, 4.00 eq) and TEMPO (9.07 mg, 57.68 µmol, 0.20 eq) were added thereto. The reaction solution was stirred at room temperature for 40 hours. After the reaction was completed, the reaction solution was added with saturated sodium hydrogen carbonate solution (50 mL) and saturated sodium sulfite solution (50 mL), extracted with dichloromethane (30 mL×3), and washed with saturated brine (50 mL). The organic phase was dried over anhydrous sodium sulfate, filtered and concentrated to give a crude product. The crude product was subjected to column chromatography (petroleum ether:ethyl acetate=1:0~5:3) to give the product of compound 55-e (126.00 mg, yield: 67%) as a yellow oil. LCMS m/z=603.1 [M+Na]$^+$.

Step 5: Synthesis of Compound 55

Compound 55-e (126.00 mg, 217.05 µmol, 1.00 eq) was dissolved in dichloromethane (4.00 mL), and trifluoroacetic acid (4.62 g, 40.52 mmol, 3.00 mL) was added thereto. The reaction solution was stirred at room temperature for 2 hours. After the reaction was completed, the reaction solution was spin-dried to give a crude product. The crude product was purified by preparative HPLC (in trifluoroacetic acid condition), and lyophilized to give the product of compound 55 (84.00 mg, yield: 72%). $^1$H NMR (400 MHz, DMSO-d$_6$) δ=8.45 (d, J=7.5 Hz, 1H), 7.64-7.52 (m, 1H), 5.22 (d, J=10.0 Hz, 1H), 4.60 (d, J=7.0 Hz, 1H), 4.32-4.25 (m, 1H), 3.76 (d, J=13.6 Hz, 1H), 3.31-3.17 (m, 1H), 3.05-2.92 (m, 1H), 2.81-2.71 (m, 5H), 2.67-2.55 (m, 2H), 2.48-2.38 (m, 1H), 1.71 (br. s., 2H), 1.51-1.30 (m, 2H); LCMS m/z=525.1 [M+H]$^+$; 547.1 [M+Na]$^+$.

Example 56: Compound 56

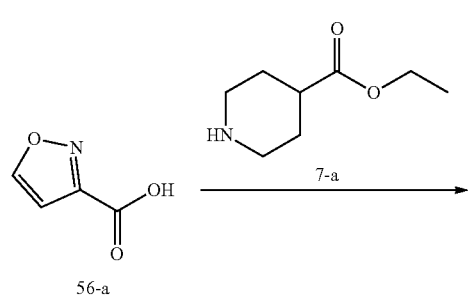

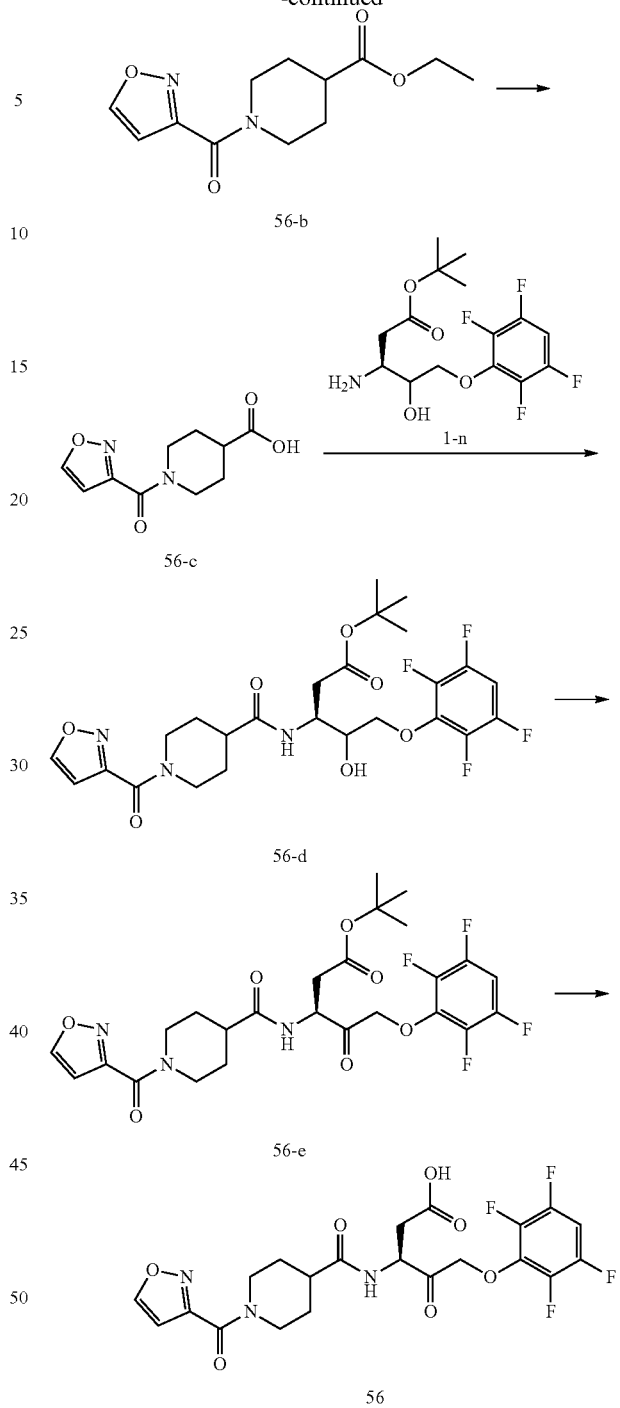

Step 1: Synthesis of Compound 56-b

Under the protection of nitrogen gas, compound 56-a (230.00 mg, 2.03 mmol, 1.00 eq) was dissolved in dichloromethane (5 mL), and then HOBt (376.55 mg, 2.79 mmol, 1.37 eq), EDCl (534.22 mg, 2.79 mmol, 1.37 eq), NMM (617.26 mg, 6.10 mmol, 670.93 µL, 3.00 eq) were added thereto, and finally compound 7-a (415.72 mg, 2.64 mmol, 407.57 µL, 1.30 eq) as a substrate was added thereto. The reaction was stirred at 15° C. for 18 hours. The reaction system was added with 40 mL of ethyl acetate and 40 mL of water, and separated. The aqueous phase was further extracted once with ethyl acetate (30 mL). The combined organic phases were washed once with 50 mL of water and 50 mL of saturated brine. The organic phase was dried over anhydrous sodium sulfate, filtered and concentrated to give a crude product. The crude product was subjected to column chromatography (petroleum ether:ethyl acetate=1:0~3:2) to give compound 56-b (243.00 mg, yield: 47%) as a brown liquid. LCMS m/z=252.9 [M+H]+.

Step 2: Synthesis of Compound 56-c

Compound 56-b (240.00 mg, 951.36 μmol, 1.00 eq) was dissolved in tetrahydrofuran (6 mL), and then a solution of LiOH.H₂O (36.46 mg, 1.52 mmol, 1.60 eq) dissolved in H₂O (6 mL) was added thereto. The reaction system was stirred at 15° C. for 2 hours. The reaction system was acidified to pH of about 4 with 1N hydrochloric acid, and then extracted four times with ethyl acetate (30 mL). The combined organic phases were washed with 40 mL of saturated brine, dried over anhydrous sodium sulfate, and then spin-dried to give the crude liquid product of compound 56-c (186 mg, crude) as a yellow oil. LCMS m/z=224.9 [M+H]+; 247[M+Na]+.

Step 3: Synthesis of Compound 56-d

Under the protection of nitrogen gas, compound 56-c (152.62 mg, 680.71 μmol, 1.30 eq) was dissolved in dichloromethane (5 mL), and then HATU (398.19 mg, 1.05 mmol, 2.00 eq), N,N-diisopropylethylamine (203.02 mg, 1.57 mmol, 274.35 μL, 3.00 eq) were added thereto, and finally compound 1-n (185.00 mg, 523.62 μmol, 1.00 eq) as a substrate was added thereto. The reaction was stirred at 15° C. for 16 hours. The reaction system was added with 20 mL of ethyl acetate and 20 mL of water, and separated. The aqueous phase was further extracted once with ethyl acetate (20 mL). The combined organic phases were separately washed once with 30 mL of water and 30 mL of saturated brine, and then dried and spin-dried to give a crude product. The crude product was subjected to column chromatography (petroleum ether:ethyl acetate=1:0~1:2) to give compound 56-d (234.00 mg, yield: 80%) as a brown liquid. LCMS m/z=582.0 [M+Na]+.

Step 4: Synthesis of Compound 56-e

Compound 56-d (234.00 mg, 418.22 μmol, 1.00 eq) was dissolved in dichloromethane (6 mL), and PIDA (269.42 mg, 836.44 μmol, 2.00 eq) and TEMPO (39.46 mg, 250.93 μmol, 0.60 eq) were added under the protection of nitrogen gas. The reaction system was stirred at 15° C. for 60 hours. The system was added with ethyl acetate (20 mL), and washed respectively with saturated sodium hydrogen carbonate solution (20 mL), water (20 mL) and saturated brine (20 mL). The organic phase was dried over anhydrous sodium sulfate, filtered, and spin-dried to give a crude product. The crude product was subjected to column chromatography (petroleum ether:ethyl acetate=1:0~1:2) to give compound 56-e (135.00 mg, yield: 58%) as a brown liquid. LCMS m/z=580 [M+Na]+.

Step 5: Synthesis of Compound 56

Compound 56-e (135.00 mg, 242.16 μmol, 1.00 eq) was dissolved in dichloromethane (5 mL), and trifluoroacetic acid (5.52 g, 48.43 mmol, 3.58 mL, 200.00 eq) was added thereto under the protection of nitrogen gas. The system was stirred at 15° C. for 1 hour. After the reaction was completed, the reaction solution was spin-dried to give a crude product. The crude product was purified by preparative HPLC (in trifluoroacetic acid condition), spin-dried, and dissolved in acetonitrile (20 mL), and the solution was added with water (20 mL), evenly mixed, and lyophilized to give compound 56 (58.00 mg, yield: 48%). ¹H NMR (400 MHz, DMSO-d6) δ=9.07 (s, 1H), 8.48 (d, J=7.53 Hz, 1H), 7.50-7.66 (m, 1H), 6.81 (s, 1H), 5.08-5.32 (m, 2H), 4.55-4.67 (m, 1H), 4.42 (d, J=13.05 Hz, 1H), 4.12-4.21 (m, 2H), 3.85 (d, J=13.55 Hz, 2H), 3.15 (t, J=11.80 Hz, 1H), 2.90 (t, J=11.80 Hz, 1H), 2.67-2.79 (m, 1H), 1.64-1.88 (m, 2H), 1.42-1.59 (m, 2H).

Example 57: Compound 57

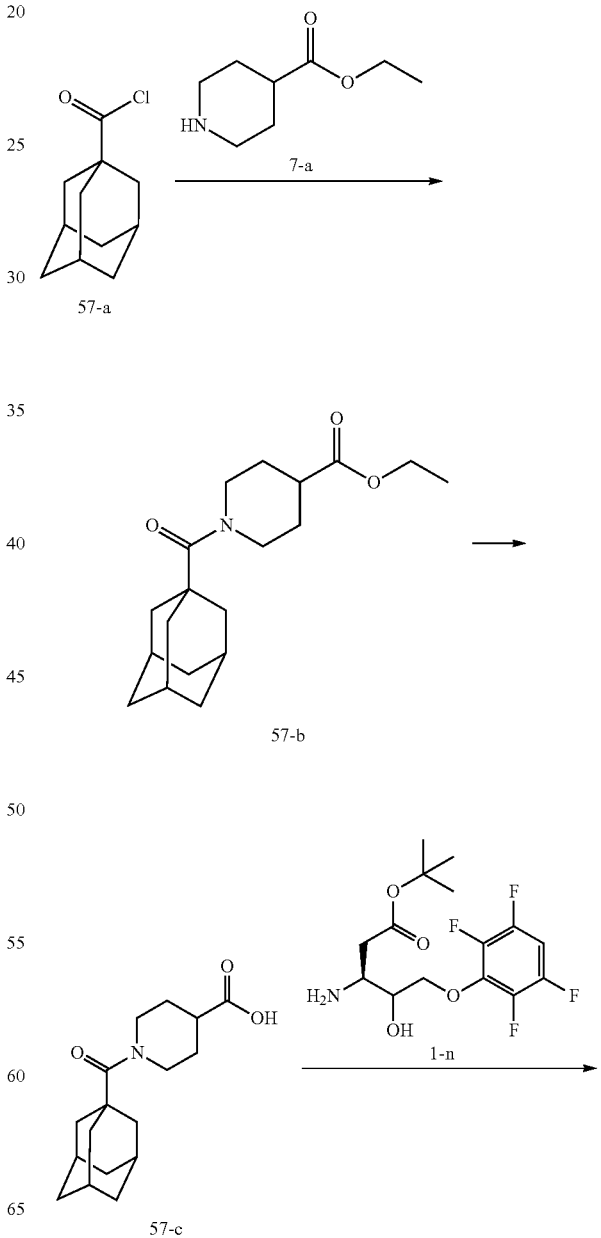

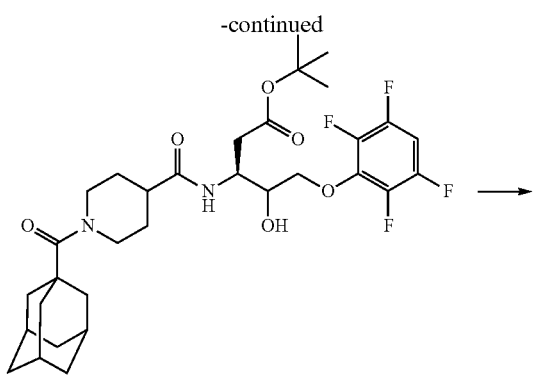

57-d

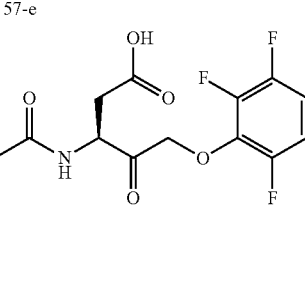

57-e

57

Step 1: Synthesis of Compound 57-b

Compound 7-a (314.42 mg, 2.00 mmol, 308.25 μL, 1.00 eq) and N,N-diisopropylethylamine (387.72 mg, 3.00 mmol, 523.95 μL, 1.50 eq) were dissolved in dichloromethane (10 mL), and compound 57-a (417.25 mg, 2.10 mmol, 1.05 eq) was added thereto, followed by stirring at room temperature for 1.5 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 57-b (612.00 mg, yield: 96%) as a yellow oil. $^1$H NMR (400 MHz, CHLOROFORM-d) δ=4.37 (d, J=13.1 Hz, 2H), 4.13 (q, J=7.0 Hz, 2H), 2.95 (t, J=11.5 Hz, 2H), 2.59-2.47 (m, 1H), 2.07-1.95 (m, 9H), 1.91 (dd, J=3.0, 13.6 Hz, 2H), 1.77-1.59 (m, 8H), 1.25 (t, J=7.3 Hz, 3H); LCMS m/z=342.1 [M+Na]$^+$.

Step 2: Synthesis of Compound 57-c

Compound 57-b (223.61 mg, 700.00 μmol, 1.00 eq) was dissolved in tetrahydrofuran (10.00 mL), and a solution of LiOH.H$_2$O (58.74 mg, 1.40 mmol, 2.00 eq) dissolved in H$_2$O (10.00 mL) was added to the above solution. The reaction solution was maintained at 25° C. and stirred for 2 hours. After the reaction was completed, the reaction solution was adjusted to pH of 6 with 2 N dilute hydrochloric acid. This solution was added with 50 mL of water, and extracted with dichloromethane (30 mL×3). The organic phase was dried over anhydrous sodium sulfate, filtered and concentrated to give the product of compound 57-c (221.00 mg, crude) as a pale yellow oil, which was used directly in the next step without purification. LCMS m/z=292.1 [M+H]$^+$.

Step 3: Synthesis of Compound 57-d

Compound 57-c (145.69 mg, 500.00 μmol, 1.00 eq) and HATU (380.23 mg, 1.00 mmol, 2.00 eq) were dissolved in dichloromethane (20 mL), followed by stirring at room temperature for 15 min. Compound 1-n (176.66 mg, 500.00 μmol, 1.00 eq) and N,N-diisopropylethylamine (193.86 mg, 1.50 mmol, 261.97 μL, 3.00 eq) were then added, and stirred at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~5:3) to give the product of compound 57-d (303.00 mg, yield: 88%) as a yellow oil. LCMS m/z=627.2 [M+H]$^+$; 649.2 [M+Na]$^+$.

Step 4: Synthesis of Compound 57-e

Compound 57-d (303.00 mg, 483.50 μmol, 1.00 eq) was dissolved in dichloromethane (20.00 mL), and PIDA (622.94 mg, 1.93 mmol, 4.00 eq) and TEMPO (15.21 mg, 96.70 μmol, 0.20 eq) were added thereto. The reaction solution was stirred at room temperature for 40 hours. After the reaction was completed, the reaction solution was added with saturated sodium hydrogen carbonate solution (50 mL) and saturated sodium sulfite solution (50 mL), extracted with dichloromethane (30 mL×3), and washed with saturated brine (50 mL). The organic phase was dried over anhydrous sodium sulfate, filtered and concentrated to give a crude product. The crude product was subjected to column chromatography (petroleum ether:ethyl acetate=1:0~5:3) to give the product of compound 57-e (252.00 mg, yield: 77%) as a yellow oil. LCMS m/z=625.2 [M+H]$^+$; 647.2 [M+Na]$^+$.

Step 5: Synthesis of Compound 57

Compound 57-e (252.00 mg, 403.42 μmol, 1.00 eq) was dissolved in dichloromethane (4.00 mL), and trifluoroacetic acid (4.62 g, 40.52 mmol, 3.00 mL) was added thereto. The reaction solution was stirred at room temperature for 2 hours. After the reaction was completed, the reaction solution was spin-dried to give a crude product. The crude product was purified by preparative HPLC (in trifluoroacetic acid condition), and lyophilized to give the product of compound 57 (174.00 mg, yield: 73%). $^1$H NMR (400 MHz, DMSO-d$_6$) δ=8.46 (d, J=7.5 Hz, 1H), 7.61-7.51 (m, 1H), 5.29-5.15 (m, 2H), 4.61 (q, J=6.5 Hz, 1H), 4.35 (d, J=12.5 Hz, 2H), 2.86-2.71 (m, 4H), 2.58 (dd, J=7.0, 16.6 Hz, 1H), 2.49-2.42 (m, 1H), 1.97 (br. s., 3H), 1.89 (br. s., 6H), 1.73-1.65 (m, 8H), 1.45-1.34 (m, 2H); LCMS m/z=569.1 [M+H]+; 591.1 [M+Na]+.

Example 58: Compound 58

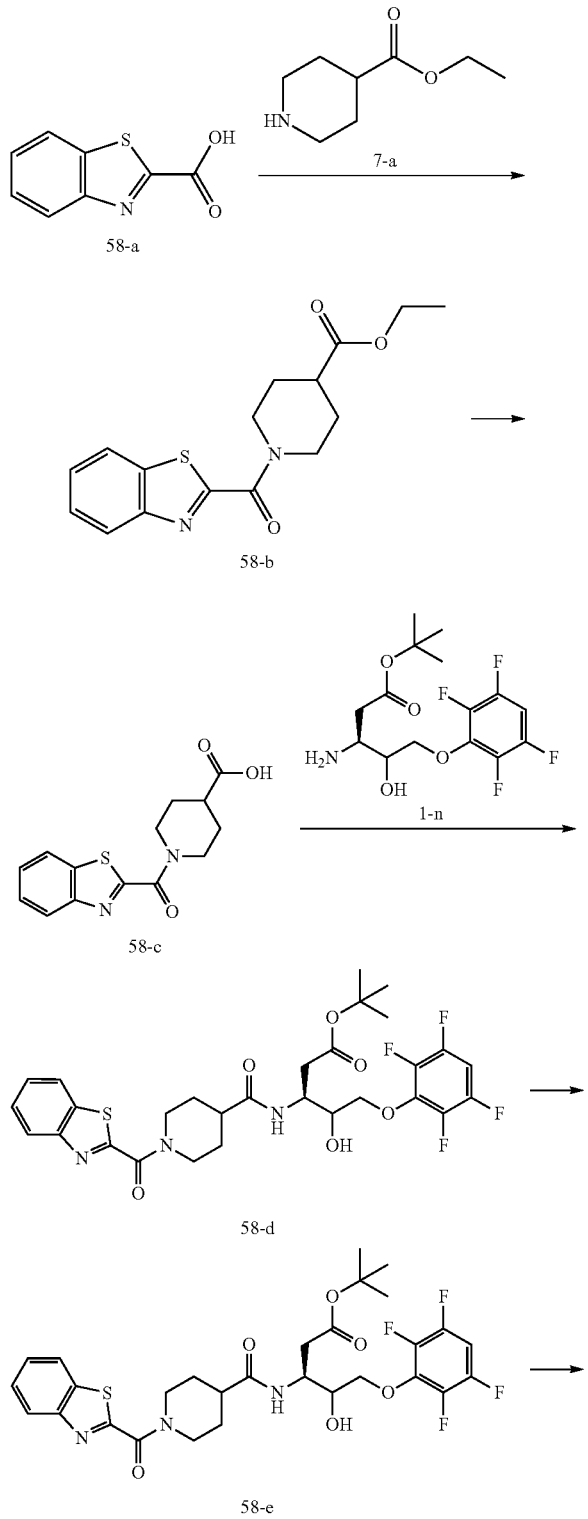

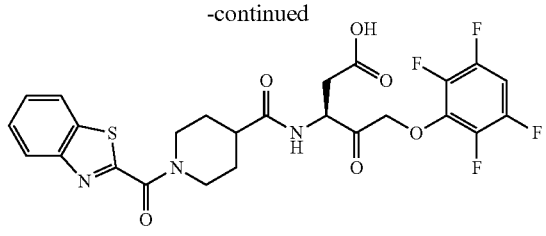

Step 1: Synthesis of Compound 58-b

Under the protection of nitrogen gas, compound 58-a (300.00 mg, 1.67 mmol, 1.00 eq) was dissolved in DMF (5 mL), and then HATU (1.27 g, 3.34 mmol, 2.00 eq), N,N-diisopropylethylamine (647.49 mg, 5.01 mmol, 874.99 μL, 3.00 eq) were added thereto, and finally compound 7-a (341.30 mg, 2.17 mmol, 334.61 μL, 1.30 eq) as a substrate was added thereto. The reaction was stirred at 20° C. for 18 hours. The reaction system was added with 20 mL of ethyl acetate and 20 mL of water, and separated. The aqueous phase was further extracted three times with ethyl acetate (30 mL). The combined organic phases were washed separately with 50 mL of water and 50 mL of saturated brine, and then dried and spin-dried to give a crude product. The crude product was subjected to column chromatography (petroleum ether:ethyl acetate=1:0~7:3) to give compound 58-b (187.00 mg, yield: 33%) as a brown liquid. LCMS m/z=318.9 [M+H]+.

Step 2: Synthesis of Compound 58-c

Compound 58-b (186.00 mg, 584.19 μmol, 1.00 eq) was dissolved in tetrahydrofuran (5 mL), and then LiOH.H₂O (27.98 mg, 1.17 mmol, 2.00 eq) was dissolved in water (5 mL). The formulated solution was slowly added to compound 58-b. The reaction system was stirred at 15° C. for 2 hours. The reaction system was acidified to pH of about 4 with 1N hydrochloric acid, and then extracted four times with ethyl acetate (10 mL). The combined organic phases were washed once with 20 mL of saturated brine, dried over anhydrous sodium sulfate, and then spin-dried to give the crude liquid product of compound 58-c (135.00 mg, crude) as a yellow oil, LCMS m/z=290.9 [M+H]+.

Step 3: Synthesis of Compound 58-d

Under the protection of nitrogen gas, compound 58-c (135.00 mg, 464.97 μmol, 1.20 eq) was dissolved in dichloromethane (5 mL), and then HATU (294.66 mg, 774.95 μmol, 2.00 eq), N,N-diisopropylethylamine (150.23 mg, 1.16 mmol, 203.02 μL, 3.00 eq) were added thereto, and finally compound 1-n (136.90 mg, 387.48 μmol, 1.00 eq) as a substrate was added thereto. The reaction was stirred at 15° C. for 58 hours. The reaction system was added with 20 mL of ethyl acetate and 20 mL of water, and separated. The aqueous phase was further extracted once with ethyl acetate (20 mL). The combined organic phases were washed separately with 30 mL of water and 30 mL of saturated brine, and then dried and spin-dried to give a crude product. The crude product was subjected to column chromatography (petroleum ether:ethyl acetate=1:0~1:2) to give compound 58-d (135.00 mg, yield: 55%) as a colorless liquid. LCMS m/z=626.1 [M+H]+.

Step 4: Synthesis of Compound 58-e

Compound 58-d (135.00 mg, 215.78 μmol, 1.00 eq) was dissolved in dichloromethane (5 mL), and PIDA (208.51 mg, 647.34 μmol, 3.00 eq) and TEMPO (23.75 mg, 151.05 μmol, 0.70 eq) was added thereto under the protection of nitrogen gas. The reaction system was stirred at 20° C. for 60 hours. The reaction system was added with ethyl acetate (20 mL), and washed respectively with saturated sodium hydrogen carbonate solution (20 mL), water (20 mL) and saturated brine (20 mL). The organic phase was dried over anhydrous sodium sulfate, filtered, and spin-dried to give a crude product. The crude product was subjected to column chromatography (petroleum ether:ethyl acetate=1:0~1:2) to give compound 58-e (101.00 mg, yield: 75%) as a brown liquid. LCMS m/z=624.1[M+H]⁺; 646.1[M+H]⁺.

Step 5: Synthesis of Compound 58

Compound 58-e (101.00 mg, 161.96 μmol, 1.00 eq) was dissolved in dichloromethane (5 mL), and trifluoroacetic acid (3.32 g, 29.15 mmol, 2.16 mL, 180.00 eq) was added thereto under the protection of nitrogen gas. The system was stirred at 15° C. for 1 hour. After the reaction was completed, the reaction solution was spin-dried to give a crude product. The crude product was purified by preparative HPLC (in trifluoroacetic acid condition), spin-dried and then dissolved with acetonitrile (20 mL), and the obtained solution was added with water (20 mL), evenly mixed and lyophilized to give compound 58 (20.00 mg, yield: 22%). ¹H NMR (400 MHz, DMSO-d6) δ=8.49 (d, J=7.53 Hz, 1H), 8.09-8.23 (m, 2H), 7.51-7.65 (m, 3H), 5.14-5.31 (m, 2H), 5.06 (d, J=13.55 Hz, 1H), 4.62 (q, J=6.86 Hz, 1H), 4.45 (d, J=13.05 Hz, 1H), 2.90-3.07 (m, 1H), 2.64-2.81 (m, 2H), 2.59 (dd, J=7.03, 16.56 Hz, 2H), 1.84 (br. s., 2H), 1.48-1.71 (m, 2H).

Example 59: Compound 59

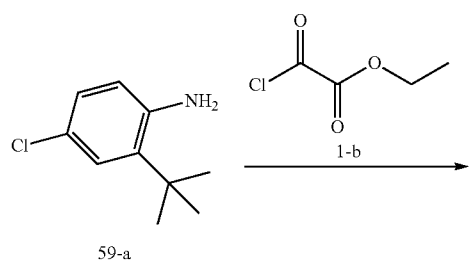

59-a

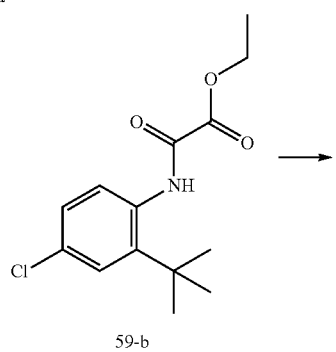

59-b

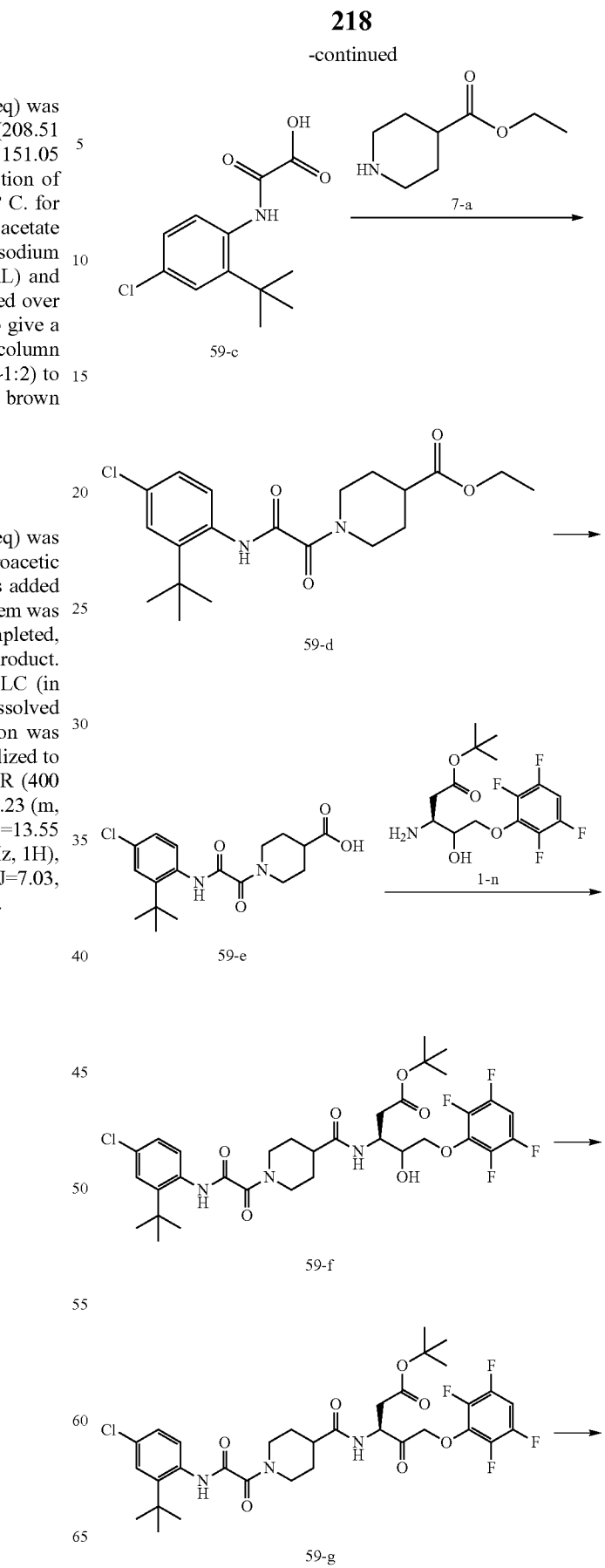

-continued

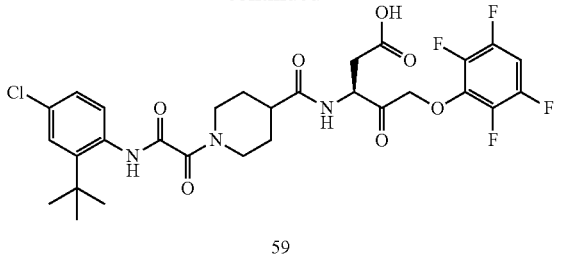

59

Step 1: Synthesis of Compound 59-b

Compound 59-a (200.00 mg, 1.09 mmol, 1.00 eq) was dissolved in dichloromethane (5.00 mL), and triethylamine (220.59 mg, 2.18 mmol, 302.18 µL, 2.00 eq) and compound 1-b (141.38 mg, 1.04 mmol, 115.88 µL, 0.95 eq) were successively added thereto at 0° C. After the reaction solution was stirred at 10° C. for 6 hours, compound 1-b (44.65 mg, 327.00 µmol, 36.59 µL, 0.30 eq) was supplemented. After the above reaction solution was stirred for 15 hours, compound 1-b (100.00 mg, 732.44 µmol, 81.97 µL, 0.67 eq) was further supplemented, and the reaction solution was maintained at 10° C. and reacted for another 0.5 hour. After the reaction was completed, added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~9:1) to give the product of compound 59-b (260.00 mg, yield: 72%). $^1$H NMR (400 MHz, CHLOROFORM-d) δ=9.21 (br. s., 1H), 8.00 (d, J=8.78 Hz, 1H), 7.39 (d, J=2.01 Hz, 1H), 7.25 (d, J=2.01 Hz, 1H), 4.46 (q, J=7.28 Hz, 2H), 1.42-1.51 (m, 12H).

Step 2: Synthesis of Compound 59-c

Compound 59-b (260.00 mg, 916.30 µmol, 1.00 eq) was dissolved in tetrahydrofuran (10.00 mL), and a solution of LiOH.H$_2$O (57.67 mg, 1.37 mmol, 1.50 eq) dissolved in H$_2$O (10.00 mL) was added to the above solution. The reaction solution was stirred at 10° C. for 1 hour. After the reaction was completed, the reaction solution was adjusted to pH of 5 with 2 N dilute hydrochloric acid. This solution was added with water (80 mL), and extracted with dichloromethane (80 mL×3). The organic phase was dried over anhydrous sodium sulfate, filtered and concentrated to give the product of compound 59-c (210.00 mg, crude), which was used directly in the next step without purification. $^1$H NMR (400 MHz, CHLOROFORM-d) δ=9.31 (br. s., 1H), 7.92 (d, J=8.53 Hz, 1H), 7.42 (d, J=2.01 Hz, 1H), 7.29 (d, J=2.51 Hz, 1H), 1.47 (s, 9H).

Step 3: Synthesis of Compound 59-d

Compound 59-c (210.00 mg, 821.27 µmol, 1.00 eq) was dissolved in dichloromethane (10.00 mL), and compound 7-a (142.02 mg, 903.40 µmol, 139.24 µL, 1.10 eq), EDCl (215.69 mg, 1.13 mmol, 1.37 eq), HOBt (152.03 mg, 1.13 mmol, 1.37 eq) and NMM (249.22 mg, 2.46 mmol, 270.89 µL, 3.00 eq) were added thereto. The reaction solution was stirred under the protection of nitrogen gas at 10° C. for 14 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=0~20%) to give the product of compound 59-d (190.00 mg, yield: 56%) as a colorless oil. LCMS m/z=395.1 [M+H]$^+$.

Step 4: Synthesis of Compound 59-e

Compound 59-d (190.00 mg, 481.15 µmol, 1.00 eq) was dissolved in tetrahydrofuran (8.00 mL), and a solution of LiOH.H$_2$O (40.38 mg, 962.30 µmol, 2.00 eq) dissolved in H$_2$O (8.00 mL) was added to the above solution. The reaction solution was stirred at 10° C. for 1 hour. After the reaction was completed, the reaction solution was adjusted to pH of 5 with 2 N dilute hydrochloric acid. This solution was added with water (80 mL), and extracted with dichloromethane (80 mL×5). The organic phase was dried over anhydrous sodium sulfate, filtered and concentrated to give the product of compound 59-e (190.00 mg, crude), which was used directly in the next step without purification. LCMS m/z=389.0 [M+Na]$^+$.

Step 5: Synthesis of Compound 59-f

Compound 59-e (190.00 mg, 517.94 µmol, 1.00 eq) was dissolved in dichloromethane (10.00 mL), and compound 1-n (201.29 mg, 569.73 µmol, 1.10 eq), EDCl (136.03 mg, 709.57 µmol, 1.37 eq), HOBt (95.88 mg, 709.57 µmol, 1.37 eq) and NMM (157.17 mg, 1.55 mmol, 170.83 µL, 3.00 eq) were added thereto. The reaction solution was stirred under the protection of nitrogen gas at 10° C. for 14 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~4:1) to give the product of compound 59-f (220.00 mg, yield: 60%) as a colorless oil. LCMS m/z=702.2 [M+H]$^+$.

Step 6: Synthesis of Compound 59-g

Compound 59-f (220.00 mg, 313.33 µmol, 1.00 eq) was dissolved in dichloromethane (15.00 mL), and PIDA (390.58 mg, 1.21 mmol, 3.87 eq) and TEMPO (14.78 mg, 94.00 µmol, 0.30 eq) were added thereto. After the reaction solution was stirred under the protection of nitrogen gas at 10° C. for 15 hours, TEMPO (49.27 mg, 313.33 µmol, 1.00 eq) was supplemented, and the reaction was stirred for another 5 hours. After the reaction was completed, the reaction solution was added with 150 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=1:0~3:2) to give the product of compound 59-g (140.00 mg, yield: 56%) as a colorless oil. LCMS m/z=700.3 [M+H]$^+$.

Step 7: Synthesis of Compound 59

Compound 59-g (140.00 mg, 199.97 µmol, 1.00 eq) was dissolved in dichloromethane (6.00 mL), and trifluoroacetic acid (4.49 g, 39.34 mmol, 2.91 mL, 196.71 eq) was added thereto. The reaction solution was stirred under the protection of nitrogen gas at 10° C. for 1 hour. After the reaction was completed, the reaction solution was concentrated to give a crude product. The crude product was purified by preparative HPLC (in trifluoroacetic acid condition), and lyophilized to give the product of compound 59 (50.40 mg, yield: 39%). $^1$H NMR (400 MHz, DMSO-$d_6$) δ=10.11 (s, 1H), 8.49 (d, J=7.53 Hz, 1H), 7.50-7.64 (m, 1H), 7.39 (d, J=2.01 Hz, 1H), 7.32 (dd, J=2.26, 8.28 Hz, 1H), 7.16 (d, J=8.53 Hz, 1H), 5.15-5.30 (m, 2H), 4.62 (q, J=7.03 Hz, 1H), 4.30 (d, J=13.05 Hz, 1H), 3.98 (d, J=13.05 Hz, 1H), 3.20 (t, J=12.30 Hz, 1H), 2.71-2.93 (m, 2H), 2.53-2.65 (m, 2H), 1.73-1.85 (m, 2H), 1.45-1.69 (m, 2H), 1.33 (s, 9H); LCMS m/z=644.0 [M+H]$^+$.

Example 60: Compound 60

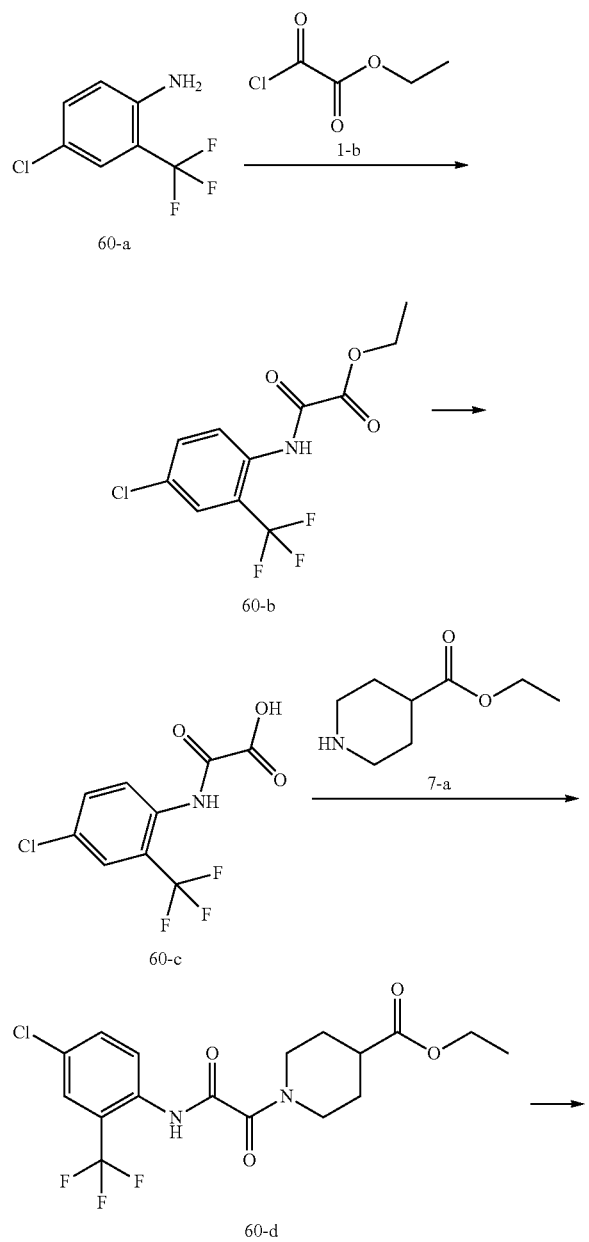

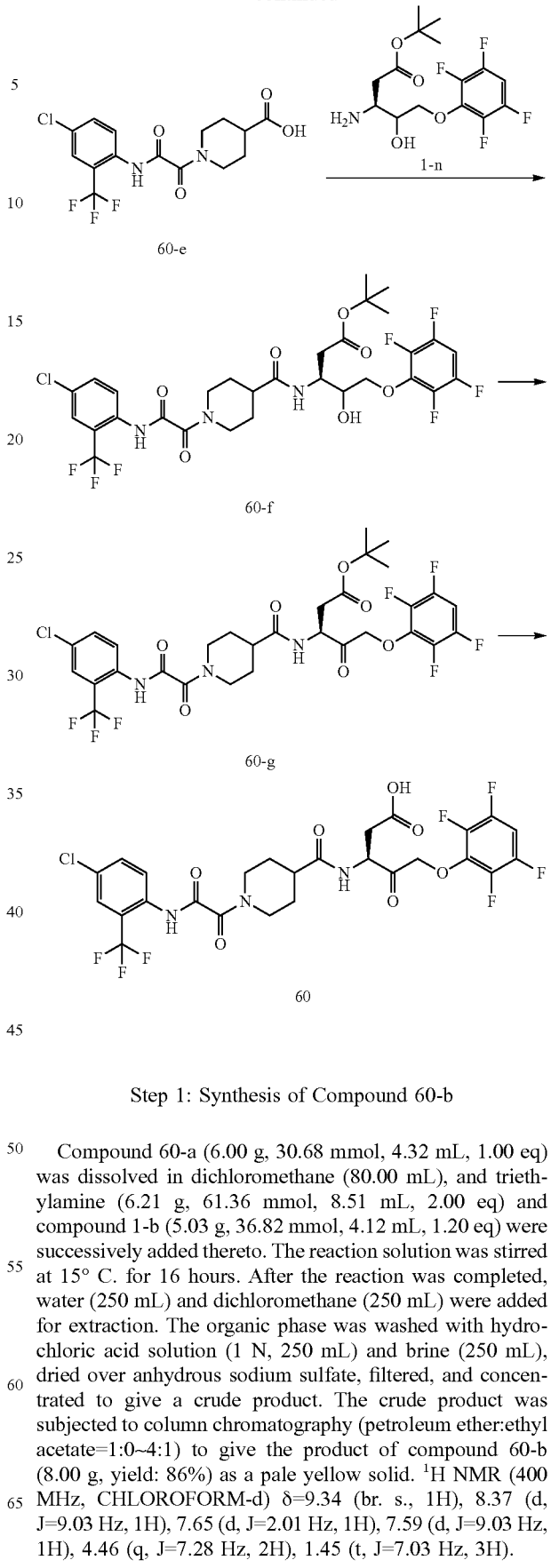

Step 1: Synthesis of Compound 60-b

Compound 60-a (6.00 g, 30.68 mmol, 4.32 mL, 1.00 eq) was dissolved in dichloromethane (80.00 mL), and triethylamine (6.21 g, 61.36 mmol, 8.51 mL, 2.00 eq) and compound 1-b (5.03 g, 36.82 mmol, 4.12 mL, 1.20 eq) were successively added thereto. The reaction solution was stirred at 15° C. for 16 hours. After the reaction was completed, water (250 mL) and dichloromethane (250 mL) were added for extraction. The organic phase was washed with hydrochloric acid solution (1 N, 250 mL) and brine (250 mL), dried over anhydrous sodium sulfate, filtered, and concentrated to give a crude product. The crude product was subjected to column chromatography (petroleum ether:ethyl acetate=1:0~4:1) to give the product of compound 60-b (8.00 g, yield: 86%) as a pale yellow solid. $^1$H NMR (400 MHz, CHLOROFORM-d) δ=9.34 (br. s., 1H), 8.37 (d, J=9.03 Hz, 1H), 7.65 (d, J=2.01 Hz, 1H), 7.59 (d, J=9.03 Hz, 1H), 4.46 (q, J=7.28 Hz, 2H), 1.45 (t, J=7.03 Hz, 3H).

Step 2: Synthesis of Compound 60-c

Compound 60-b (600.00 mg, 2.03 mmol, 1.00 eq) was dissolved in tetrahydrofuran (10.00 mL), and a solution of LiOH.H$_2$O (127.77 mg, 3.04 mmol, 1.50 eq) dissolved in H$_2$O (10.00 mL) was added to the above solution. The reaction solution was stirred at 15° C. for 1 hour. After the reaction was completed, the reaction solution was adjusted to pH of 5 with 2 N dilute hydrochloric acid. This solution was added with water (100 mL), and extracted with dichloromethane (100 mL×3). The organic phase was dried over anhydrous sodium sulfate, filtered and concentrated to give the product of compound 60-c (290.00 mg, crude), which was used directly in the next step without purification. $^1$H NMR (400 MHz, CHLOROFORM-d) δ=9.39 (br. s., 1H), 8.28 (d, J=8.78 Hz, 1H), 7.68 (s, 1H), 7.61 (d, J=8.78 Hz, 1H).

Step 3: Synthesis of Compound 60-d

Compound 60-c (430.00 mg, 1.61 mmol, 1.00 eq) was dissolved in dichloromethane (8.00 mL), and compound 7-a (253.11 mg, 1.61 mmol, 248.15 μL, 1.00 eq), EDCl (422.83 mg, 2.21 mmol, 1.37 eq), HOBt (298.03 mg, 2.21 mmol, 1.37 eq) and NMM (488.55 mg, 4.83 mmol, 531.04 μL, 3.00 eq) were added thereto. The reaction solution was stirred under the protection of nitrogen gas at 15° C. for 14 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 60-d (260.00 mg, yield: 38%) as a colorless oil. LCMS m/z=407.0 [M+H]$^+$.

Step 4: Synthesis of Compound 60-e

Compound 60-d (260.00 mg, 639.17 μmol, 1.00 eq) was dissolved in tetrahydrofuran (8.00 mL), and a solution of LiOH.H$_2$O (40.23 mg, 958.75 μmol, 1.50 eq) dissolved in H$_2$O (8.00 mL) was added to the above solution. The reaction solution was stirred at 15° C. for 1 hour. After the reaction was completed, the reaction solution was adjusted to pH of 5 with 2 N dilute hydrochloric acid. This solution was added with water (100 mL), and extracted with dichloromethane (100 mL×3). The organic phase was dried over anhydrous sodium sulfate, filtered and concentrated to give the product of compound 60-e (230.00 mg, crude) as a colorless oil, which was used directly in the next step without purification. LCMS m/z=379.0 [M+H]$^+$.

Step 5: Synthesis of Compound 60-f

Compound 1-n (236.02 mg, 668.02 μmol, 1.10 eq) was dissolved in dichloromethane (15.00 mL), and compound 60-e (230.00 mg, 607.29 μmol, 1.00 eq), EDCl (159.49 mg, 831.99 μmol, 1.37 eq), HOBt (112.42 mg, 831.99 μmol, 1.37 eq) and NMM (184.28 mg, 1.82 mmol, 200.31 μL, 3.00 eq) were added thereto. The reaction solution was stirred under the protection of nitrogen gas at 15° C. for 14 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~3:2) to give the product of compound 60-f (260.00 mg, yield: 60%). LCMS m/z=714.1 [M+H]$^+$.

Step 6: Synthesis of Compound 60-g

Compound 60-f (210.00 mg, 294.11 μmol, 1.00 eq) was dissolved in dichloromethane (10.00 mL), and PIDA (366.62 mg, 1.14 mmol, 3.87 eq) and TEMPO (13.87 mg, 88.23 μmol, 0.30 eq) were added thereto. The reaction solution was stirred under the protection of nitrogen gas at 15° C. for 15 hours. The reaction solution was added with 150 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=1:0~3:2) to give the product of compound 60-g (160.00 mg, yield: 70%). LCMS m/z=712.2 [M+H]$^+$.

Step 7: Synthesis of Compound 60

Compound 60-g (160.00 mg, 224.72 μmol, 1.00 eq) was dissolved in dichloromethane (6.50 mL), and trifluoroacetic acid (5.04 g, 44.20 mmol, 3.27 mL, 196.71 eq) was added thereto. The reaction solution was stirred under the protection of nitrogen gas at 15° C. for 1 hour. After the reaction was completed, the reaction solution was concentrated to give a crude product. The crude product was purified by preparative HPLC (in trifluoroacetic acid condition), and lyophilized to give the product of compound 60 (45.00 mg, yield: 31%). $^1$H NMR (400 MHz, DMSO-d$_6$) δ=10.65 (s, 1H), 8.49 (d, J=7.53 Hz, 1H), 7.87 (d, J=2.01 Hz, 1H), 7.78-7.85 (m, 1H), 7.51-7.67 (m, 2H), 5.14-5.30 (m, 2H), 4.61 (q, J=6.02 Hz, 1H), 4.28 (d, J=13.05 Hz, 1H), 3.84 (d, J=13.55 Hz, 1H), 3.17 (t, J=11.80 Hz, 1H), 2.65-2.88 (m, 2H), 2.53-2.64 (m, 2H), 1.78 (d, J=9.54 Hz, 2H), 1.44-1.67 (m, 2H); LCMS m/z=656.1 [M+H]$^+$.

Example 61: Compound 61

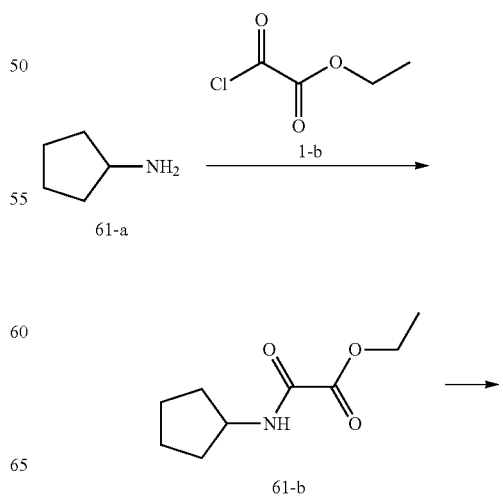

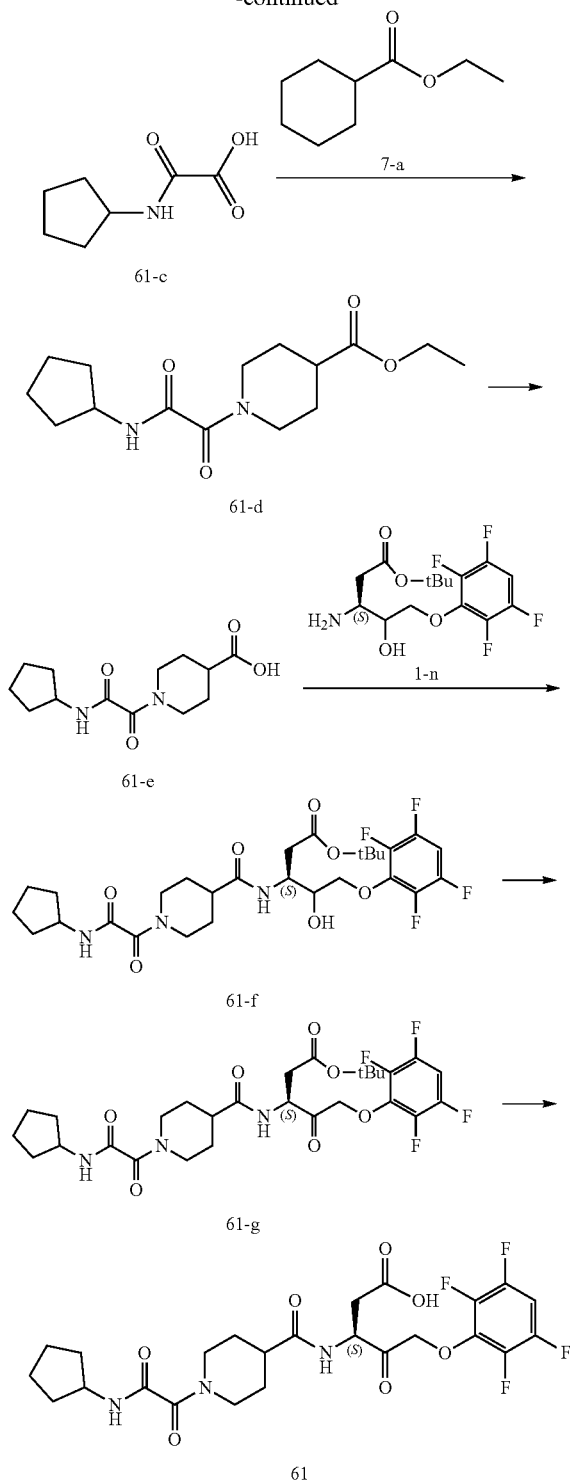

Step 1: Synthesis of Compound 61-b

Compound 61-a (2.00 g, 23.49 mmol, 2.33 mL, 1.00 eq) was dissolved in dichloromethane (40.00 mL), and triethylamine (4.75 g, 46.98 mmol, 6.51 mL, 2.00 eq) and compound 1-b (3.85 g, 28.19 mmol, 3.16 mL, 1.20 eq) were successively added thereto. The reaction solution was stirred at 20° C. for 16 hours. After the reaction was completed, water (150 mL) and ethyl acetate (250 mL) was added for extraction. The organic phase was washed with water (150 mL) and brine (150 mL), dried over anhydrous sodium sulfate, filtered, and concentrated to give a crude product. The crude product was subjected to column chromatography (petroleum ether:ethyl acetate=1:0~2:1) to give the product of compound 61-b (4.20 g, yield: 95%) as a yellow oil. $^1$H NMR (400 MHz, CHLOROFORM-d) δ=7.05 (br. s., 1H), 4.34 (q, J=7.28 Hz, 2H), 4.23 (sxt, J=7.08 Hz, 1H), 1.97-2.09 (m, 2H), 1.57-1.77 (m, 4H), 1.47 (qd, J=6.38, 12.49 Hz, 2H), 1.38 (t, J=7.15 Hz, 3H).

Step 2: Synthesis of Compound 61-c

Compound 61-b (500.00 mg, 2.70 mmol, 1.00 eq) was dissolved in tetrahydrofuran (8.00 mL), and a solution of LiOH.H$_2$O (339.88 mg, 8.10 mmol, 3.00 eq) dissolved in H$_2$O (8.00 mL) was added to the above solution. The reaction solution was stirred at 20° C. for 1 hour. After the reaction was completed, the reaction solution was adjusted to pH of 6 with 2 N dilute hydrochloric acid. This solution was added with water (50 mL), and extracted with dichloromethane (50 mL×3). The organic phase was dried over anhydrous sodium sulfate, filtered and concentrated to give the product of compound 61-c (290.00 mg, crude) as a pale yellow solid, which was used directly in the next step without purification. $^1$H NMR (400 MHz, CHLOROFORM-d) δ=7.29 (br. s., 1H), 4.21 (sxt, J=6.98 Hz, 1H), 1.98-2.11 (m, 2H), 1.60-1.81 (m, 4H), 1.47-1.60 (m, 2H).

Step 3: Synthesis of Compound 61-d

Compound 61-c (145.00 mg, 922.57 μmol, 1.00 eq) was dissolved in dichloromethane (8.00 mL), and compound 7-a (145.04 mg, 922.57 μmol, 142.20 μL, 1.00 eq), EDCl (242.29 mg, 1.26 mmol, 1.37 eq), HOBt (170.78 mg, 1.26 mmol, 1.37 eq) and NMM (279.95 mg, 2.77 mmol, 304.29 μL, 3.00 eq) were added thereto. The reaction solution was stirred under the protection of nitrogen gas at 20° C. for 15 hours. After the reaction was completed, the reaction solution was added with water (80 mL), and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 61-d (166.00 mg, yield: 58%) as a colorless oil. $^1$H NMR (400 MHz, CHLOROFORM-d) δ=7.16 (d, J=5.52 Hz, 1H), 4.81 (td, J=3.42, 13.74 Hz, 1H), 4.33 (td, J=3.39, 13.55 Hz, 1H), 4.10-4.22 (m, 3H), 3.35 (ddd, J=2.76, 11.04, 13.55 Hz, 1H), 2.89-3.00 (m, 1H), 2.51-2.63 (m, 1H), 1.99 (dd, J=3.26, 13.30 Hz, 4H), 1.54-1.86 (m, 6H), 1.39-1.52 (m, 2H), 1.26 (t, J=7.15 Hz, 3H).

Step 4: Synthesis of Compound 61-e

Compound 61-d (166.00 mg, 560.13 μmol, 1.00 eq) was dissolved in tetrahydrofuran (8.00 mL), and a solution of LiOH.H$_2$O (35.25 mg, 840.20 μmol, 1.50 eq) dissolved in H$_2$O (8.00 mL) was added to the above solution. The reaction solution was stirred at 20° C. for 1 hour. After the reaction was completed, the reaction solution was adjusted to pH of 6 with 2 N dilute hydrochloric acid. This solution was added with water (80 mL), and extracted with dichloromethane (80 mL×3). The organic phase was dried over anhydrous sodium sulfate, filtered and concentrated to give the product of compound 61-e (160.00 mg, crude) as a colorless oil, which was used directly in the next step without purification. LCMS m/z=268.9 [M+H]⁺.

Step 5: Synthesis of Compound 61-f

Compound 61-e (160.00 mg, 596.33 µmol, 1.00 eq) was dissolved in dichloromethane (8.00 mL), and compound 1-n (210.69 mg, 596.33 µmol, 1.00 eq), EDCl (156.61 mg, 816.97 µmol, 1.37 eq), HOBt (110.39 mg, 816.97 µmol, 1.37 eq) and NMM (180.95 mg, 1.79 mmol, 196.69 µL, 3.00 eq) were added thereto. The reaction solution was stirred under the protection of nitrogen gas at 20° C. for 15 hours. After the reaction was completed, the reaction solution was added with water (80 mL), and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~1:2) to give the product of compound 61-f (200.00 mg, yield: 45%) as a pale yellow oil. LCMS m/z=626.3 [M+Na]⁺.

Step 6: Synthesis of Compound 61-g

Compound 61-f (200.00 mg, 331.35 µmol, 1.00 eq) was dissolved in dichloromethane (5.00 mL), and PIDA (413.03 mg, 1.28 mmol, 3.87 eq) and TEMPO (15.63 mg, 99.41 µmol, 0.30 eq) were added thereto. The reaction solution was stirred under the protection of nitrogen gas at 20° C. for 15 hours. After the reaction was completed, the reaction solution was added with 100 mL of ethyl acetate. The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was subjected to column chromatography (petroleum ether:ethyl acetate=1:0~1:1) to give the product of compound 61-g (130.00 mg, yield: 55%) as a pale yellow oil. LCMS m/z=624.2 [M+Na]⁺.

Step 7: Synthesis of Compound 61

Compound 61-g (130.00 mg, 216.09 µmol, 1.00 eq) was dissolved in dichloromethane (4.60 mL), and trifluoroacetic acid (3.54 g, 31.08 mmol, 2.30 mL, 143.85 eq) was added thereto. The reaction solution was stirred under the protection of nitrogen gas at 18° C. for 1 hour. After the reaction was completed, the reaction solution was concentrated and lyophilized to give the product of compound 61 (95.30 mg, yield: 81%). ¹H NMR (400 MHz, DMSO-d₆) δ=8.64 (d, J=7.03 Hz, 1H), 8.47 (d, J=7.53 Hz, 1H), 7.50-7.69 (m, 1H), 5.13-5.30 (m, 2H), 4.60 (q, J=6.53 Hz, 1H), 4.21 (d, J=13.05 Hz, 1H), 3.96-4.09 (m, 1H), 3.64 (d, J=13.55 Hz, 2H), 3.05 (t, J=12.05 Hz, 1H), 2.65-2.79 (m, 2H), 2.58 (dd, J=7.03, 17.07 Hz, 1H), 1.35-1.87 (m, 12H); LCMS m/z=546.1 [M+H]⁺.

Example 62: Compound 62

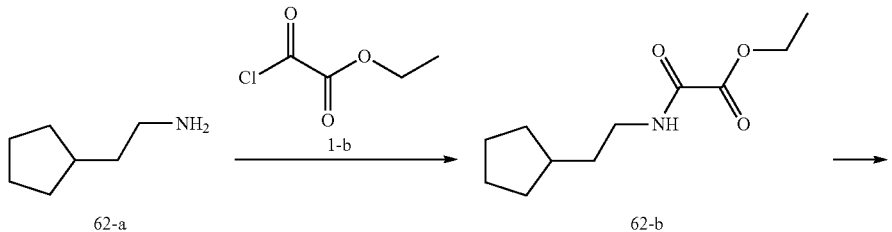

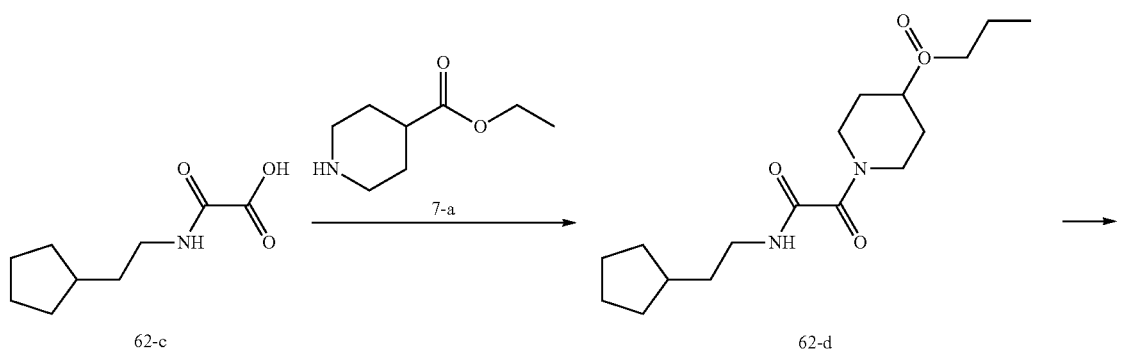

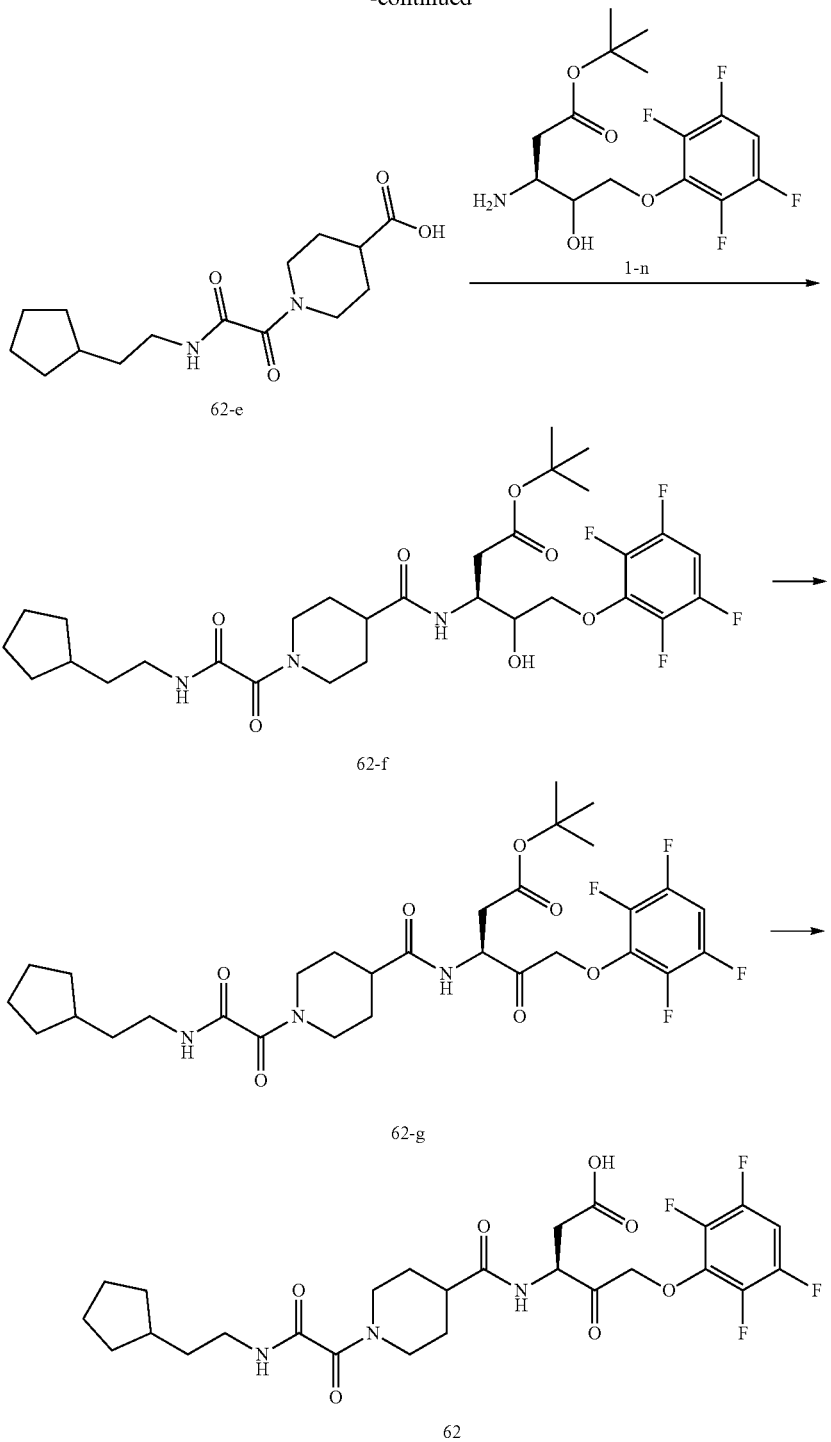

Step 1: Synthesis of Compound 62-b

Compound 62-a (100.00 mg, 883.39 μmol, 1.00 eq) was dissolved in dichloromethane (8.00 mL), and triethylamine (178.78 mg, 1.77 mmol, 244.90 μL, 2.00 eq) and compound 1-b (144.73 mg, 1.06 mmol, 118.63 μL, 1.20 eq) were successively added thereto. The reaction solution was stirred at 10° C. for 14 hours. After the reaction was completed, the reaction solution was added with water (80 mL), and extracted with dichloromethane (80 mL×3). The organic phase was dried over anhydrous sodium sulfate, filtered and concentrated to give a crude product. The crude product was subjected to column chromatography (petroleum ether:ethyl acetate=1:0~4:1) to give the product of compound 62-b (170.00 mg, yield: 89%) as a colorless oil. $^1$H NMR (400 MHz, CHLOROFORM-d) δ=7.11 (br. s., 1H), 4.34 (q, J=7.03 Hz, 2H), 3.29-3.41 (m, 2H), 1.72-1.86 (m, 3H), 1.46-1.67 (m, 6H), 1.39 (t, J=7.28 Hz, 3H), 1.12 (br. s., 2H).

Step 2: Synthesis of Compound 62-c

Compound 62-b (170.00 mg, 797.11 μmol, 1.00 eq) was dissolved in tetrahydrofuran (8.00 mL), and a solution of LiOH.H$_2$O (50.17 mg, 1.20 mmol, 1.50 eq) dissolved in H$_2$O (8.00 mL) was added to the above solution. The reaction solution was stirred at 10° C. for 1 hour. After the reaction was completed, the reaction solution was adjusted to pH of 5 with 2 N dilute hydrochloric acid. This solution was added with water (80 mL), and extracted with dichloromethane (80 mL×3). The organic phase was dried over anhydrous sodium sulfate, filtered and concentrated to give the product of compound 62-c (150.00 mg, crude), which was used directly in the next step without purification.

Step 3: Synthesis of Compound 62-d

Compound 62-c (150.00 mg, 809.85 μmol, 1.00 eq) was dissolved in dichloromethane (8.00 mL), and compound 7-a (140.05 mg, 890.84 μmol, 137.30 μL, 1.10 eq), EDCl (212.69 mg, 1.11 mmol, 1.37 eq), HOBt (149.91 mg, 1.11 mmol, 1.37 eq) and NMM (245.75 mg, 2.43 mmol, 267.12 μL, 3.00 eq) were added thereto. The reaction solution was stirred under the protection of nitrogen gas at 10° C. for 15 hours. After the reaction was completed, the reaction solution was added with water (80 mL), and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 62-d (190.00 mg, yield: 70%) as a colorless oil. $^1$H NMR (400 MHz, CHLOROFORM-d) δ=7.19 (br. s., 1H), 4.82 (d, J=13.80 Hz, 1H), 4.28-4.39 (m, 1H), 4.15 (q, J=7.11 Hz, 2H), 3.33-3.41 (m, 1H), 3.25-3.33 (m, 2H), 2.91-3.02 (m, 1H), 2.51-2.64 (m, 1H), 1.99 (dd, J=3.64, 13.68 Hz, 2H), 1.65-1.88 (m, 5H), 1.46-1.65 (m, 6H), 1.26 (t, J=7.15 Hz, 3H), 1.12 (d, J=3.51 Hz, 2H).

Step 4: Synthesis of Compound 62-e

Compound 62-d (190.00 mg, 585.66 μmol, 1.00 eq) was dissolved in tetrahydrofuran (8.00 mL), and a solution of LiOH.H$_2$O (36.86 mg, 878.49 μmol, 1.50 eq) dissolved in H$_2$O (8.00 mL) was added to the above solution. The reaction solution was stirred at 10° C. for 1 hour. After the reaction was completed, the reaction solution was adjusted to pH of 5 with 2 N dilute hydrochloric acid. This solution was added with water (80 mL), and extracted with dichloromethane (80 mL×5). The organic phase was dried over anhydrous sodium sulfate, filtered and concentrated to give the product of compound 62-e (180.00 mg, crude) as a colorless oil, which was used directly in the next step without purification.

Step 5: Synthesis of Compound 62-f

Compound 62-e (180.00 mg, 607.37 μmol, 1.00 eq) was dissolved in dichloromethane (10.00 mL), and compound 1-n (214.59 mg, 607.37 μmol, 1.00 eq), EDCl (159.51 mg, 832.10 μmol, 1.37 eq), HOBt (112.43 mg, 832.10 μmol, 1.37 eq) and NMM (184.31 mg, 1.82 mmol, 200.34 μL, 3.00 eq) were added thereto. The reaction solution was stirred under the protection of nitrogen gas at 10° C. for 15 hours. After the reaction was completed, the reaction solution was added with water (80 mL), and extracted with dichloromethane (80 mL×3). The organic phases were combined, dried over anhydrous sodium sulfate, filtered and concentrated to give a crude product. The crude product was subjected to column chromatography (petroleum ether:ethyl acetate=4:1~1:1) to give the product of compound 62-f (230.00 mg, yield: 60%) as a colorless oil. LCMS m/z=654.3 [M+Na]$^+$.

Step 6: Synthesis of Compound 62-g

Compound 62-f (230.00 mg, 364.13 μmol, 1.00 eq) was dissolved in dichloromethane (15.00 mL), and PIDA (453.89 mg, 1.41 mmol, 3.87 eq) and TEMPO (17.18 mg, 109.24 μmol, 0.30 eq) were added thereto. After the reaction solution was stirred under the protection of nitrogen gas at 10° C. for 14 hours, TEMPO (34.36 mg, 218.48 μmol, 0.60 eq) was supplemented, and the solution was further reacted for another 3 hours. After the reaction was completed, the reaction solution was added with 100 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=9:1~1:1) to give the product of compound 62-g (140.00 mg, yield: 55%) as a pale yellow oil. LCMS m/z=652.3 [M+Na]$^+$.

Step 7: Synthesis of Compound 62

Compound 62-g (140.00 mg, 222.35 μmol, 1.00 eq) was dissolved in dichloromethane (4.70 mL), and trifluoroacetic acid (3.65 g, 31.99 mmol, 2.37 mL, 143.85 eq) was added thereto. The reaction solution was stirred under the protection of nitrogen gas at 10° C. for 1 hour. After the reaction was completed, the reaction solution was concentrated to give a crude product. The crude product was purified by preparative HPLC (in trifluoroacetic acid condition), and lyophilized to give the product of compound 62 (97.00 mg, yield: 76%). $^1$H NMR (400 MHz, DMSO-d$_6$) δ=8.63 (t, J=5.27 Hz, 1H), 8.46 (d, J=7.03 Hz, 1H), 7.50-7.68 (m, 1H), 5.13-5.29 (m, 2H), 4.60 (q, J=6.86 Hz, 1H), 4.22 (d, J=13.05 Hz, 1H), 3.70 (br. s., 2H), 3.01-3.20 (m, 3H), 2.64-2.79 (m, 2H), 2.58 (dd, J=7.03, 17.07 Hz, 1H), 1.73 (br. s., 5H), 1.35-1.62 (m, 8H), 1.06 (br. s., 2H); LCMS m/z=574.1 [M+H]$^+$.

Example 63: Compound 63

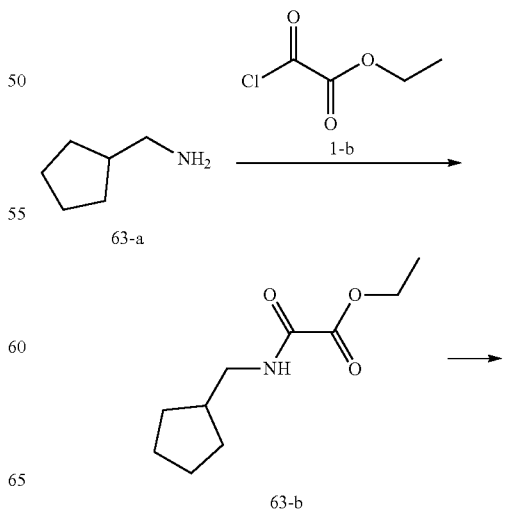

233

-continued

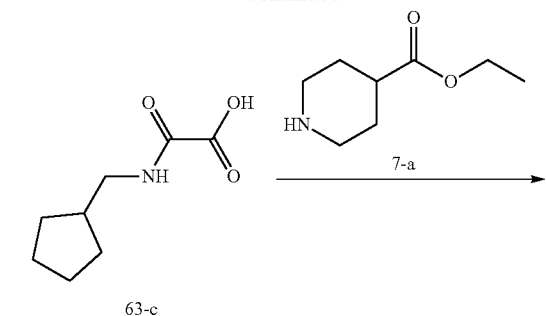

63-c

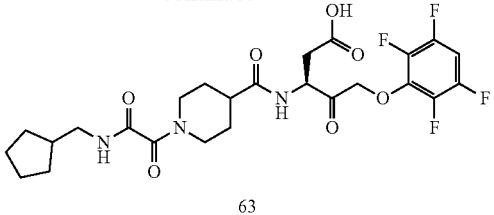

7-a →

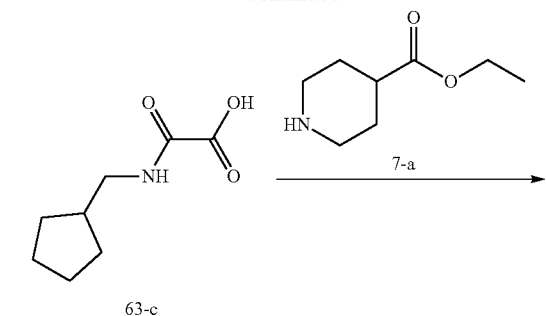

63-d

→

63-e

→

1-n 63-f

→

63-g

234

-continued

63

Step 1: Synthesis of Compound 63-b

Compound 63-a (200.00 mg, 2.02 mmol, 1.00 eq) and triethylamine (715.41 mg, 7.07 mmol, 980.02 μL, 3.50 eq) were dissolved in dichloromethane (8.00 mL), and stirred 10° C. for 0.5 hour. Compound 1-b (330.41 mg, 2.42 mmol, 270.83 μL, 1.20 eq) was added to the above solution, and the reaction solution was maintained at 10° C. and stirred for 15 hours. After the reaction was completed, the reaction solution was added with water (80 mL), and extracted with dichloromethane (80 mL×3). The organic phase was dried over anhydrous sodium sulfate, filtered and concentrated to give a crude product. The crude product was subjected to column chromatography (petroleum ether:ethyl acetate=1: 0~4:1) to give the product of compound 63-b (270.00 mg, yield: 65%) as a colorless oil. $^1$H NMR (400 MHz, CHLOROFORM-d) δ=7.14 (br. s., 1H), 4.35 (q, J=7.03 Hz, 2H), 3.29 (t, J=6.65 Hz, 2H), 2.03-2.15 (m, 1H), 1.72-1.84 (m, 2H), 1.61-1.70 (m, 2H), 1.50-1.59 (m, 2H), 1.39 (t, J=7.15 Hz, 3H), 1.14-1.30 (m, 2H).

Step 2: Synthesis of Compound 63-c

Compound 63-b (270.00 mg, 1.36 mmol, 1.00 eq) was dissolved in tetrahydrofuran (8.00 mL), and a solution of LiOH.H$_2$O (85.29 mg, 2.03 mmol, 1.50 eq) dissolved in H$_2$O (8.00 mL) was added to the above solution. The reaction solution was stirred at 10° C. for 1 hour. After the reaction was completed, the reaction solution was adjusted to pH of 5 with 2 N dilute hydrochloric acid. This solution was added with water (80 mL), and extracted with dichloromethane (80 mL×3). The organic phase was dried over anhydrous sodium sulfate, filtered and concentrated to give the product of compound 63-c (230.00 mg, crude), which was used directly in the next step without purification.

Step 3: Synthesis of Compound 63-d

Compound 63-c (230.00 mg, 1.34 mmol, 1.00 eq) was dissolved in dichloromethane (8.00 mL), and compound 7-a (232.34 mg, 1.48 mmol, 227.78 μL, 1.10 eq), EDCl (352.85 mg, 1.84 mmol, 1.37 eq), HOBt (248.71 mg, 1.84 mmol, 1.37 eq) and NMM (407.70 mg, 4.03 mmol, 443.15 μL, 3.00 eq) were added thereto. The reaction solution was stirred under the protection of nitrogen gas at 10° C. for 15 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 63-d (250.00 mg, yield: 57%) as a colorless oil. $^1$H NMR (400 MHz, CHLOROFORM-d) δ=7.21 (br. s., 1H), 4.75-4.86 (m, 1H), 4.28-4.38 (m, 1H), 4.15 (q, J=7.19 Hz, 2H), 3.35 (ddd, J=2.76, 11.04, 13.55 Hz, 1H), 3.23 (t, J=6.78 Hz, 2H), 2.90-3.03 (m, 1H), 2.52-2.63 (m, 1H), 2.03-2.13 (m, 1H), 1.99 (dd, J=3.51, 13.55 Hz, 2H), 1.69-1.86 (m, 4H), 1.49-1.67 (m, 4H), 1.15-1.31 (m, 5H).

Step 4: Synthesis of Compound 63-e

Compound 63-d (250.00 mg, 805.44 μmol, 1.00 eq) was dissolved in tetrahydrofuran (10.00 mL), and a solution of LiOH.H$_2$O (50.69 mg, 1.21 mmol, 1.50 eq) dissolved in H$_2$O (10.00 mL) was added to the above solution. The reaction solution was stirred at 10° C. for 1 hour. After the reaction was completed, the reaction solution was adjusted to pH of 5 with 2 N dilute hydrochloric acid. This solution was added with water (100 mL), and extracted with dichloromethane (100 mL×3). The organic phase was dried over anhydrous sodium sulfate, filtered and concentrated to give the product of compound 63-e (220.00 mg, crude) as a colorless oil, which was used directly in the next step without purification.

Step 5: Synthesis of Compound 63-f

Compound 63-e (160.00 mg, 566.71 μmol, 1.11 eq) was dissolved in dichloromethane (10.00 mL), and compound 1-n (180.00 mg, 509.47 μmol, 1.00 eq), EDCl (133.80 mg, 697.97 μmol, 1.37 eq), HOBt (94.31 mg, 697.97 μmol, 1.37 eq) and NMM (154.60 mg, 1.53 mmol, 168.04 μL, 3.00 eq) were added thereto. The reaction solution was stirred under the protection of nitrogen gas at 10° C. for 15 hours. After the reaction was completed, the reaction solution was added with water (80 mL), and extracted with dichloromethane (80 mL×3). The organic phases were combined, dried over anhydrous sodium sulfate, filtered and concentrated to give a crude product. The crude product was subjected to column chromatography (petroleum ether:ethyl acetate=4:1~1:1) to give the product of compound 63-f (210.00 mg, yield: 65%) as a colorless oil. LCMS m/z=618.3 [M+H]$^+$.

Step 6: Synthesis of Compound 63-g

Compound 63-f (210.00 mg, 340.01 μmol, 1.00 eq) was dissolved in dichloromethane (15.00 mL), and PIDA (423.83 mg, 1.32 mmol, 3.87 eq) and TEMPO (16.04 mg, 102.00 μmol, 0.30 eq) were added thereto. The reaction solution was stirred under the protection of nitrogen gas at 10° C. for 15 hours. The reaction solution was added with 100 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=4:1~1:1) to give the product of compound 63-g (150.00 mg, yield: 66%) as a pale yellow oil. LCMS m/z=616.3 [M+H]$^+$.

Step 7: Synthesis of Compound 63

Compound 63-g (150.00 mg, 243.66 μmol, 1.00 eq) was dissolved in dichloromethane (5.20 mL), and trifluoroacetic acid (4.00 g, 35.05 mmol, 2.60 mL, 143.85 eq) was added thereto. The reaction solution was stirred under the protection of nitrogen gas at 10° C. for 1 hour. After the reaction was completed, the reaction solution was concentrated to give a crude product. The crude product was purified by preparative HPLC (in trifluoroacetic acid condition), and lyophilized to give the product of compound 63 (91.00 mg, yield: 67%). $^1$H NMR (400 MHz, DMSO-d$_6$) δ=8.68 (t, J=5.52 Hz, 1H), 8.47 (d, J=7.03 Hz, 1H), 7.46-7.68 (m, 1H), 5.12-5.30 (m, 2H), 4.60 (q, J=6.69 Hz, 1H), 4.22 (d, J=13.05 Hz, 1H), 3.69 (d, J=13.05 Hz, 1H), 2.96-3.14 (m, 3H), 2.65-2.79 (m, 2H), 2.58 (dd, J=7.03, 17.07 Hz, 1H), 2.47 (br. s., 1H), 1.95-2.09 (m, 1H), 1.60-1.80 (m, 4H), 1.38-1.58 (m, 6H), 1.10-1.25 (m, 2H); LCMS m/z=560.1 [M+H]$^+$.

Example 64: Compound 64

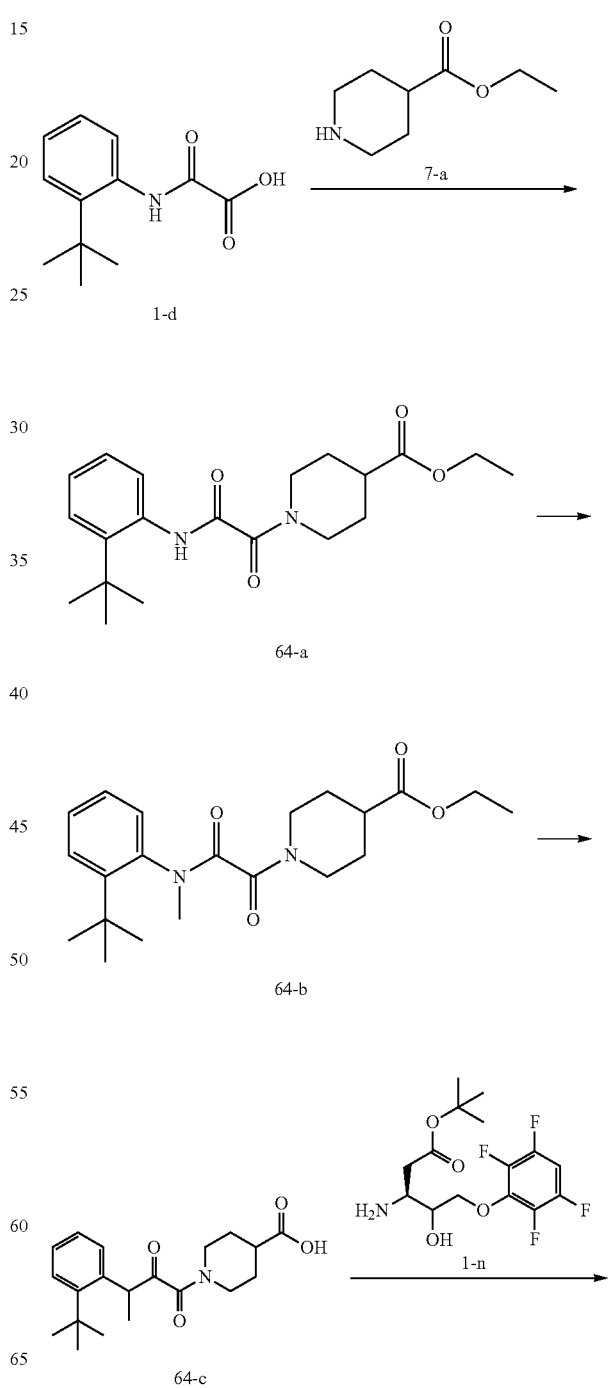

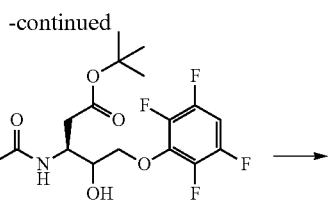

64-d

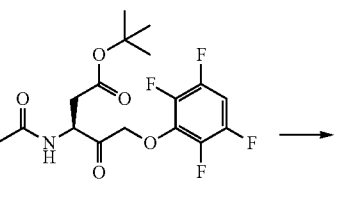

64-e

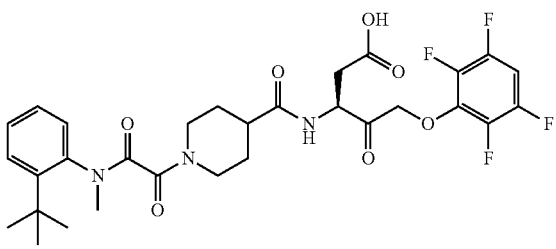

64

Step 1: Synthesis of Compound 64-a

Compound 1-d (1.00 g, 4.52 mmol, 1.00 eq) was dissolved in dichloromethane (15 mL), and N-methylmorpholine (1.37 g, 13.56 mmol, 1.49 mL, 3.00 eq), HOBt (836.72 mg, 6.19 mmol, 1.37 eq), EDCl (1.19 g, 6.19 mmol, 1.37 eq) and compound 7-a (852.66 mg, 5.42 mmol, 835.94 µL, 1.20 eq) were added thereto. The reaction was stirred at room temperature for 16 hours. After the reaction was completed, the reaction solution was added with dichloromethane (50 mL) for dilution, and then washed with saturated brine (30 mL×2). The organic phase was dried over anhydrous sodium sulfate, filtered, and concentrated to give a crude product. The crude product was purified by column chromatography (petroleum ether:ethyl acetate=1:0~3:1), to give the product of compound 64-a (1.11 g, yield: 68%) as a colorless oil. LCMS m/z=361.2 [M+H]$^+$.

Step 2: Synthesis of Compound 64-b

Compound 64-a (900 mg, 2.50 mmol, 1.00 eq) was dissolved in DMF (20.00 mL), and $Cs_2CO_3$ (2.44 g, 7.5 mmol, 3.00 eq) was added thereto. After stirring for 10 min at room temperature, the reaction solution was added with methyl iodide (532.28 mg, 3.75 mmol, 233.46 µL, 1.50 eq), and stirred at room temperature for 16 hours. After the reaction was completed, the reaction solution was added with ethyl acetate (60 mL) for dilution, and then washed with water (40 mL) and saturated brine (40 mL). The organic phase was dried over anhydrous sodium sulfate, filtered, and concentrated to give a crude product. The crude product was purified by column chromatography (petroleum ether:ethyl acetate=2:1), to give the product of compound 64-b (760 mg, yield: 77%) as a colorless oil. LCMS m/z=375.3 [M+H]$^+$.

Step 3: Synthesis of Compound 64-c $LiOH \cdot H_2O$ (166.69 mg, 6.96 mmol, 3.00 eq) was dissolved in water (8.00 mL), and then added to a solution of compound 64-b (870.00 mg, 2.32 mmol, 1.00 eq) dissolved in THF (8.00 mL). The reaction was stirred at room temperature for 3 hours. After the reaction was completed, the reaction solution was added with water (30 mL), adjusted to pH of 3-4 with 1 N dilute hydrochloric acid, and extracted with dichloromethane/methanol (50 mL×3, v/v=10:1). The organic phases were combined, dried over anhydrous sodium sulfate, filtered, and concentrated to give compound 64-c (822.00 mg, crude), which was used directly in the next step without purification. LCMS m/z=347.2 [M+H]$^+$.

Step 4: Synthesis of Compound 64-d

Compound 64-c (247.09 mg, 713.26 µmol, 1.40 eq) was dissolved in dichloromethane (10 mL), and N-methylmorpholine (154.60 mg, 1.53 mmol, 168.04 µL, 3.00 eq), EDCl (195.33 mg, 1.02 mmol, 2.00 eq), HOBt (137.68 mg, 1.02 mmol, 2.00 eq) and compound 1-n (180.00 mg, 509.47 µmol, 1.00 eq) were added thereto. The reaction was stirred at room temperature for 16 hours. After the reaction was completed, the reaction solution was added with dichloromethane (50 mL) for dilution, and then washed with water (30 mL) and saturated brine (30 mL×2). The organic phase was dried over anhydrous sodium sulfate, filtered, and concentrated to give a crude product. The crude product was purified by column chromatography (petroleum ether:ethyl acetate=1:4), to give the product of compound 64-d (276.00 mg, yield: 71%) as a colorless oil. LCMS m/z=682.3 [M+H]$^+$.

Step 5: Synthesis of Compound 64-e

Compound 64-d (276.00 mg, 404.86 µmol, 1.00 eq) was dissolved in dichloromethane (10.00 mL), and PIDA (504.67 mg, 1.57 mmol, 3.87 eq) and TEMPO (63.66 mg, 404.86 µmol, 1.00 eq) were added thereto. The reaction was stirred at room temperature for 64 hours. After the reaction was completed, the reaction solution was added with dichloromethane (50 mL) for dilution, and washed with saturated sodium hydrogen carbonate solution (30 mL) and saturated brine (30 mL×2). The organic phase was dried over anhydrous sodium sulfate, filtered, and concentrated to give a crude product. The crude product was purified by column chromatography (petroleum ether:ethyl acetate=1:1.5), to give the product of compound 64-e (215.00 mg, yield: 64%) as a yellow oil. LCMS m/z=680.1 [M+H]$^+$.

Step 6: Synthesis of Compound 64

Compound 64-e (215.00 mg, 316.32 µmol, 1.00 eq) was dissolved in dichloromethane (10.00 mL), and TFA (4.61 mL, 62.22 mmol, 196.71 eq) was added thereto. The reaction was stirred at room temperature for 2 hours. After the reaction was completed, the reaction was spin-dried to give a crude product. The crude product was purified by preparative HPLC (in TFA condition), and lyophilized to give compound 64 (105.00 mg, yield: 53%). $^1$H NMR (400 MHz, DMSO-$d_6$) δ=8.40-8.58 (m, 1H), 7.50-7.60 (m, 2H), 7.24-7.39 (m, 2H), 7.08-7.15 (m, 1H), 5.12-5.32 (m, 2H), 4.52-4.67 (m, 1H), 4.30 (br d, J=9.54 Hz, 1H), 3.79-3.96 (m, 1H), 3.71 (br d, J=13.80 Hz, 1H), 3.12-3.20 (m, 3H), 2.87 (br t, J=12.42 Hz, 1H), 2.70-2.79 (m, 1H), 2.57 (br dd, J=6.53, 16.31 Hz, 2H), 1.77 (br d, J=16.06 Hz, 2H), 1.47-1.64 (m, 2H), 1.32-1.38 (m, 9H); LCMS m/z=624.1 [M+H]$^+$.

Example 65: Compound 65
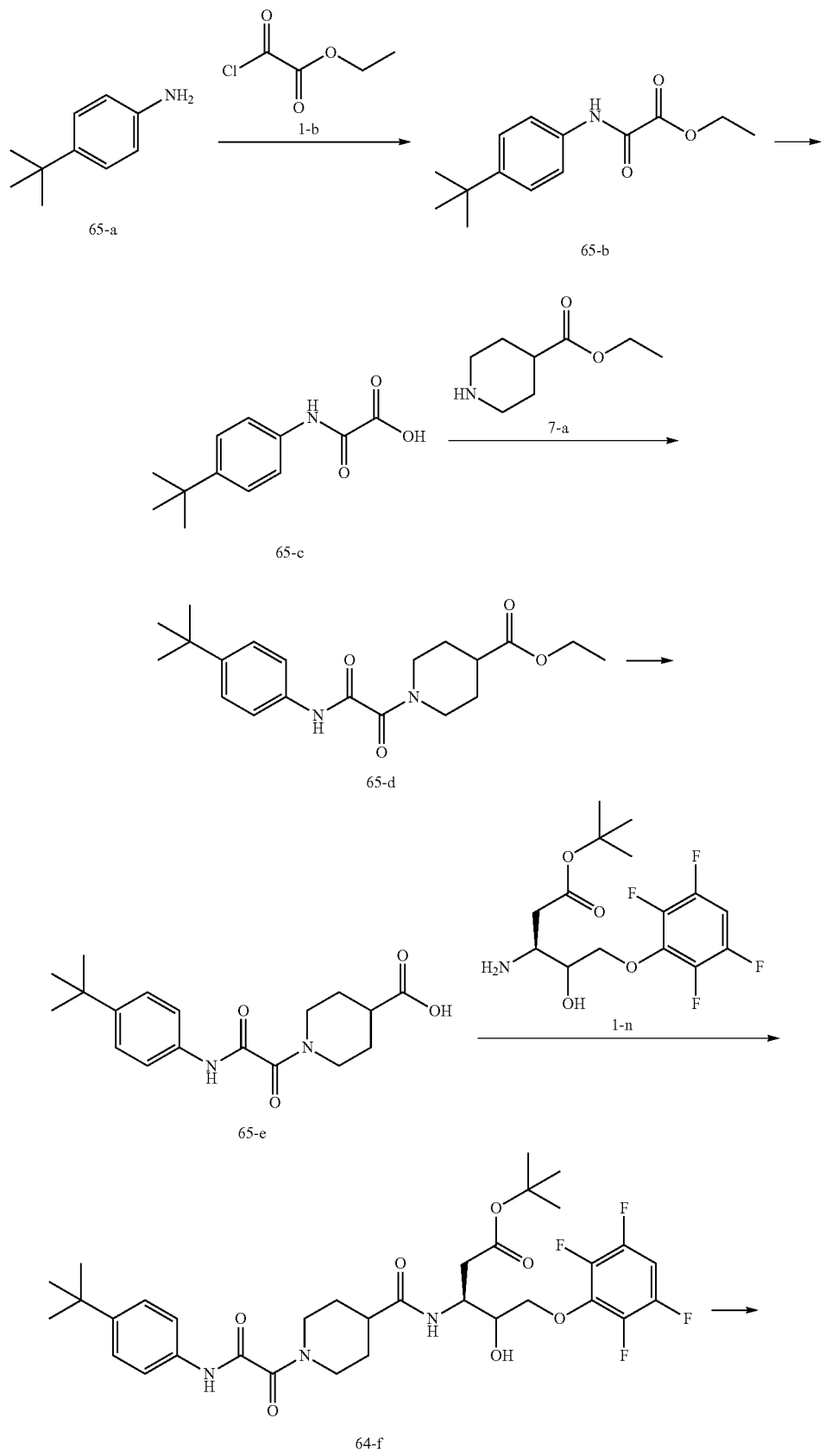

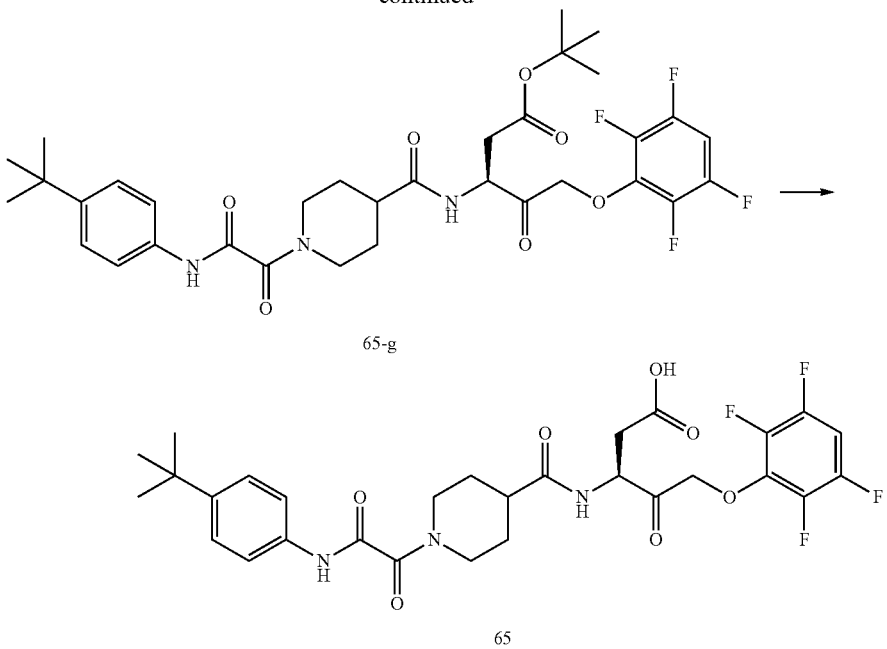

Step 1: Synthesis of Compound 65-b

Compound 65-a (2.00 g, 13.40 mmol, 2.11 mL, 1.00 eq) was dissolved in dichloromethane (30.00 mL), and triethylamine (2.71 g, 26.80 mmol, 3.71 mL, 2.00 eq) and compound 1-b (2.20 g, 16.08 mmol, 1.80 mL, 1.20 eq) were successively added thereto at 0° C. The reaction solution was stirred at 15° C. for 16 hours. After the reaction was completed, the reaction solution was added with water (150 mL), and extracted with dichloromethane (150 mL×3). The organic phase was dried over anhydrous sodium sulfate, filtered and concentrated to give a crude product. The crude product was subjected to column chromatography (petroleum ether:ethyl acetate=1:0~4:1) to give the product of compound 65-b (3.00 g, yield: 90%) as a pale yellow solid. $^1$H NMR (400 MHz, CHLOROFORM-d) δ=8.88 (br. s., 1H), 7.57 (d, J=8.78 Hz, 2H), 7.40 (d, J=8.78 Hz, 2H), 4.36-4.47 (m, 2H), 1.43 (t, J=7.15 Hz, 3H), 1.32 (s, 9H).

Step 2: Synthesis of Compound 65-c

Compound 65-b (1.00 g, 4.01 mmol, 1.00 eq) was dissolved in tetrahydrofuran (15.00 mL), and a solution of LiOH.H$_2$O (504.91 mg, 12.03 mmol, 3.00 eq) dissolved in H$_2$O (15.00 mL) was added to the above solution. The reaction solution was stirred at 15° C. for 1 hour. After the reaction was completed, the reaction solution was adjusted to pH of 5 with 2 N dilute hydrochloric acid. This solution was added with water (150 mL), and extracted with dichloromethane (150 mL×3). The organic phase was dried over anhydrous sodium sulfate, filtered and concentrated to give the product of compound 65-c (890.00 mg, crude) as a pale yellow solid, which was used directly in the next step without purification.

Step 3: Synthesis of Compound 65-d

Compound 65-c (890.00 mg, 4.02 mmol, 1.00 eq) was dissolved in dichloromethane (8.00 mL), and compound 7-a (758.38 mg, 4.82 mmol, 743.51 μL, 1.20 eq), EDCl (1.06 g, 5.51 mmol, 1.37 eq), HOBt (744.64 mg, 5.51 mmol, 1.37 eq) and NMM (1.22 g, 12.06 mmol, 1.33 mL, 3.00 eq) were added thereto. The reaction solution was stirred under the protection of nitrogen gas at 15° C. for 14 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 65-d (780.00 mg, yield: 53%). $^1$H NMR (400 MHz, CHLOROFORM-d) δ=9.12 (br. s., 1H), 7.52 (d, J=8.53 Hz, 2H), 7.38 (d, J=8.78 Hz, 2H), 4.89-4.99 (m, 1H), 4.39 (td, J=3.45, 13.43 Hz, 1H), 4.17 (q, J=7.03 Hz, 2H), 3.45 (ddd, J=2.76, 10.98, 13.61 Hz, 1H), 2.99-3.09 (m, 1H), 2.56-2.67 (m, 1H), 2.03 (dd, J=3.26, 13.55 Hz, 2H), 1.73-1.92 (m, 2H), 1.32 (s, 9H), 1.27 (t, J=7.15 Hz, 3H).

Step 4: Synthesis of Compound 65-e

Compound 65-d (770.00 mg, 2.14 mmol, 1.00 eq) was dissolved in tetrahydrofuran (15.00 mL), and a solution of LiOH.H$_2$O (269.38 mg, 6.42 mmol, 3.00 eq) dissolved in H$_2$O (15.00 mL) was added to the above solution. The reaction solution was stirred at 15° C. for 1 hour. After the reaction was completed, the reaction solution was adjusted to pH of 5 with 2 N dilute hydrochloric acid. This solution was added with water (100 mL), and extracted with dichloromethane (100 mL×3). The organic phase was dried over anhydrous sodium sulfate, filtered and concentrated to give the product of compound 65-e (700.00 mg, crude), which was used directly in the next step without purification. $^1$H NMR (400 MHz, CHLOROFORM-d) δ=9.23 (s, 1H), 7.53 (d, J=8.78 Hz, 2H), 7.38 (d, J=8.53 Hz, 2H), 4.89 (d, J=13.80 Hz, 1H), 4.34-4.43 (m, 1H), 3.43-3.53 (m, 1H), 3.03-3.13 (m, 1H), 2.63-2.73 (m, 1H), 2.02-2.12 (m, 2H), 1.78-1.86 (m, 2H), 1.32 (s, 9H)

Step 5: Synthesis of Compound 65-f

Compound 65-e (300.00 mg, 902.55 μmol, 1.77 eq) was dissolved in dichloromethane (10.00 mL), and compound 1-n (180.00 mg, 509.47 μmol, 1.00 eq), EDCl (133.80 mg, 697.97 μmol, 1.37 eq), HOBt (94.31 mg, 697.97 μmol, 1.37 eq) and NMM (154.60 mg, 1.53 mmol, 168.04 μL, 3.00 eq) were added thereto. The reaction solution was stirred under the protection of nitrogen gas at 15° C. for 16 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=4:1~1:1) to give the product of compound 65-f (280.00 mg, yield: 75%) as a colorless oil. LCMS m/z=668.1 [M+H]$^+$.

Step 6: Synthesis of Compound 65-g

Compound 65-f (280.00 mg, 419.36 μmol, 1.00 eq) was dissolved in dichloromethane (20.00 mL), and PIDA (522.74 mg, 1.62 mmol, 3.87 eq) and TEMPO (19.78 mg, 125.81 μmol, 0.30 eq) were added thereto. The reaction solution was stirred under the protection of nitrogen gas at 15° C. for 16 hours, and supplemented with TEMPO (19.78 mg, 125.81 μmol, 0.30 eq), followed by stirring for another 24 hours. After the reaction was completed, the reaction solution was added with 100 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=4:1~1:1) to give the product of compound 65-g (200.00 mg, yield: 66%) as a pale yellow oil. LCMS m/z=666.1 [M+H]$^+$.

Step 7: Synthesis of Compound 65

Compound 65-g (200.00 mg, 300.45 μmol, 1.00 eq) was dissolved in dichloromethane (8.00 mL), and trifluoroacetic acid (5.96 g, 52.26 mmol, 3.87 mL, 173.95 eq) was added thereto. The reaction solution was stirred at 15° C. under the protection of nitrogen gas for 1 hour. After the reaction was completed, the reaction solution was concentrated to give a crude product. The crude product was purified by preparative HPLC (in trifluoroacetic acid condition), and lyophilized to give the product of compound 65 (109.20 mg, yield: 60%). $^1$H NMR (400 MHz, DMSO-d$_6$) δ=10.67 (s, 1H), 8.48 (d, J=6.53 Hz, 1H), 7.49-7.66 (m, 3H), 7.35 (d, J=8.53 Hz, 2H), 5.14-5.30 (m, 2H), 4.61 (q, J=6.02 Hz, 1H), 4.28 (d, J=12.55 Hz, 1H), 3.76 (d, J=13.05 Hz, 1H), 3.14 (t, J=11.54 Hz, 1H), 2.69-2.87 (m, 2H), 2.59 (dd, J=7.03, 17.07 Hz, 2H), 1.68-1.84 (m, 2H), 1.44-1.65 (m, 2H), 1.26 (s, 9H); LCMS m/z=610.1 [M+H]$^+$.

Example 66: Compound 66

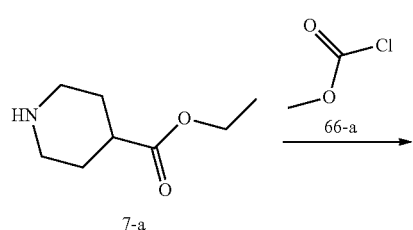

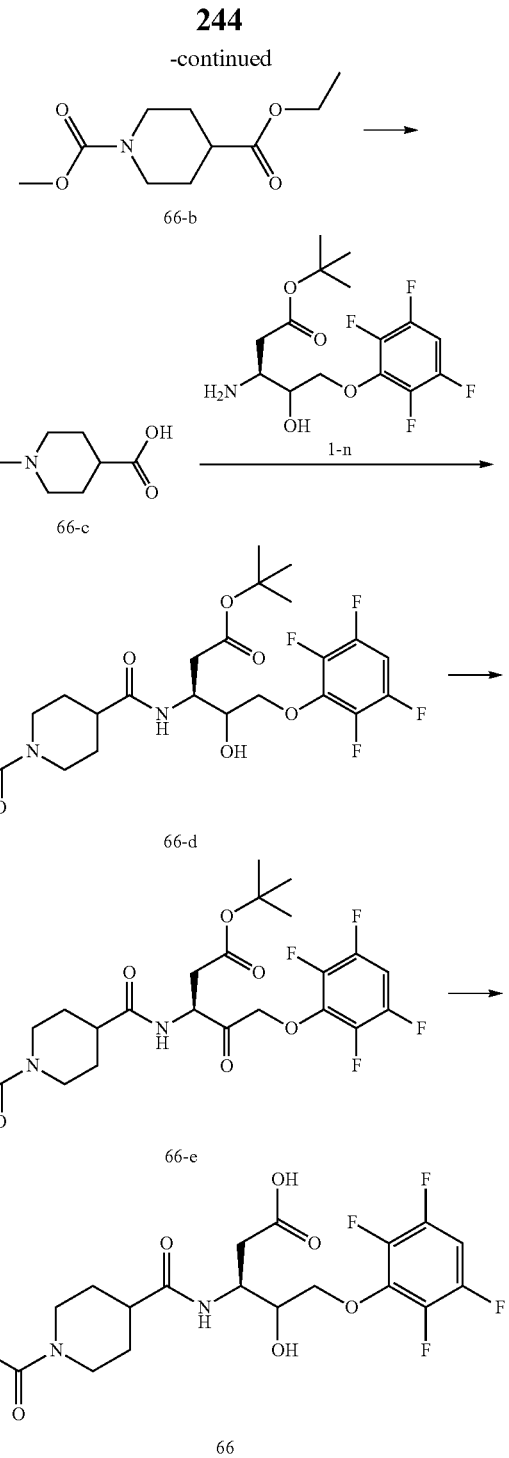

Step 1: Synthesis of Compound 66-b

Compound 7-a (2.00 g, 12.72 mmol, 1.96 mL, 1.00 eq) was dissolved in dichloromethane (20.00 mL), and triethylamine (2.57 g, 25.44 mmol, 3.53 mL, 2.00 eq) and compound 66-a (2.10 g, 22.22 mmol, 1.72 mL, 1.75 eq) were successively added thereto at 0° C. The reaction solution was stirred at 10° C. for 18 hours. After the reaction was completed, the reaction solution was added with water (150 mL), and extracted with dichloromethane (150 mL×3). The organic phase was dried over anhydrous sodium sulfate, filtered and concentrated to give a crude product. The crude product was subjected to column chromatography (petroleum ether:ethyl acetate=1:0~4:1) to give the product of compound 66-b (2.30 g, yield: 84%) as a colorless oil. $^1$H NMR (400 MHz, CHLOROFORM-d) δ=4.14 (q, J=7.11 Hz, 2H), 3.90-4.10 (m, 2H), 3.64-3.72 (m, 3H), 2.90 (t, J=11.67 Hz, 2H), 2.45 (tt, J=3.89, 10.92 Hz, 1H), 1.88 (d, J=11.80 Hz, 2H), 1.56-1.70 (m, 2H), 1.25 (t, J=7.15 Hz, 3H).

Step 2: Synthesis of Compound 66-c

Compound 66-b (300.00 mg, 1.39 mmol, 1.00 eq) was dissolved in tetrahydrofuran (10.00 mL), and a solution of LiOH.H$_2$O (87.72 mg, 2.09 mmol, 1.50 eq) dissolved in H$_2$O (10.00 mL) was added to the above solution. The reaction solution stirred at 10° C. for 1 hour. After the reaction was completed, the reaction solution was adjusted to pH of 5 with 2 N dilute hydrochloric acid. This solution was added with water (100 mL), and extracted with dichloromethane (100 mL×3). The organic phase was dried over anhydrous sodium sulfate, filtered and concentrated to give the product of compound 66-c (260.00 mg, crude) as a colorless oil, which was used directly in the next step without purification. $^1$H NMR (400 MHz, CHLOROFORM-d) δ=3.92-4.18 (m, 2H), 3.62-3.73 (m, 3H), 2.93 (t, J=11.54 Hz, 2H), 2.45-2.57 (m, 1H), 1.93 (d, J=11.80 Hz, 2H), 1.58-1.76 (m, 2H).

Step 3: Synthesis of Compound 66-d

Compound 66-c (130.00 mg, 694.48 μmol, 1.23 eq) was dissolved in dichloromethane (10.00 mL), and compound 1-n (200.00 mg, 566.08 μmol, 1.00 eq), EDCl (148.67 mg, 775.52 μmol, 1.37 eq), HOBt (104.79 mg, 775.52 μmol, 1.37 eq) and N-methylmorpholine (171.78 mg, 1.70 mmol, 186.71 μL, 3.00 eq) were added thereto. The reaction solution was stirred under the protection of nitrogen gas at 10° C. for 14 hours. After the reaction was completed, the reaction solution was added with water (80 mL), and extracted with dichloromethane (80 mL×3). The organic phases were combined, dried over anhydrous sodium sulfate, filtered and concentrated to give a crude product. The crude product was subjected to column chromatography (petroleum ether:ethyl acetate=10:1~1:1) to give the product of compound 66-d (200.00 mg, yield: 60%) as a colorless oil. LCMS m/z=545.1 [M+Na]$^+$.

Step 4: Synthesis of Compound 66-e

Compound 66-d (200.00 mg, 382.78 μmol, 1.00 eq) was dissolved in dichloromethane (15.00 mL), and PIDA (477.15 mg, 1.48 mmol, 3.87 eq) and TEMPO (18.06 mg, 114.83 μmol, 0.30 eq) were added thereto. The reaction solution was stirred under the protection of nitrogen gas at 10° C. for 15 hours. The reaction solution was added with 100 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=10:1~1:1) to give the product of compound 66-e (140.00 mg, yield: 60%) as a pale yellow oil. LCMS m/z=543.1 [M+Na]$^+$.

Step 5: Synthesis of Compound 66

Compound 66-e (118.00 mg, 226.72 μmol, 1.00 eq) was dissolved in dichloromethane (4.80 mL), and trifluoroacetic acid (369.60 mg, 3.24 mmol, 240.00 μL, 14.30 eq) was added thereto. The reaction solution was stirred under the protection of nitrogen gas at 0° C. for 1 hour. After the reaction was completed, the reaction solution was concentrated to give a crude product. The crude product was purified by preparative HPLC (in trifluoroacetic acid condition), and lyophilized to give the product of compound 66 (61.90 mg, yield: 59%). $^1$H NMR (400 MHz, DMSO-d$_6$) δ=8.44 (d, J=7.53 Hz, 1H), 7.50-7.64 (m, 1H), 5.13-5.28 (m, 2H), 4.59 (q, J=7.03 Hz, 1H), 3.94 (d, J=10.04 Hz, 2H), 3.58 (s, 3H), 2.69-2.91 (m, 3H), 2.57 (dd, J=6.78, 16.81 Hz, 1H), 2.31-2.44 (m, 1H), 1.67 (br. s., 2H), 1.40 (q, J=11.54 Hz, 2H); LCMS m/z=465.0 [M+H]$^+$.

Example 67: Compound 67

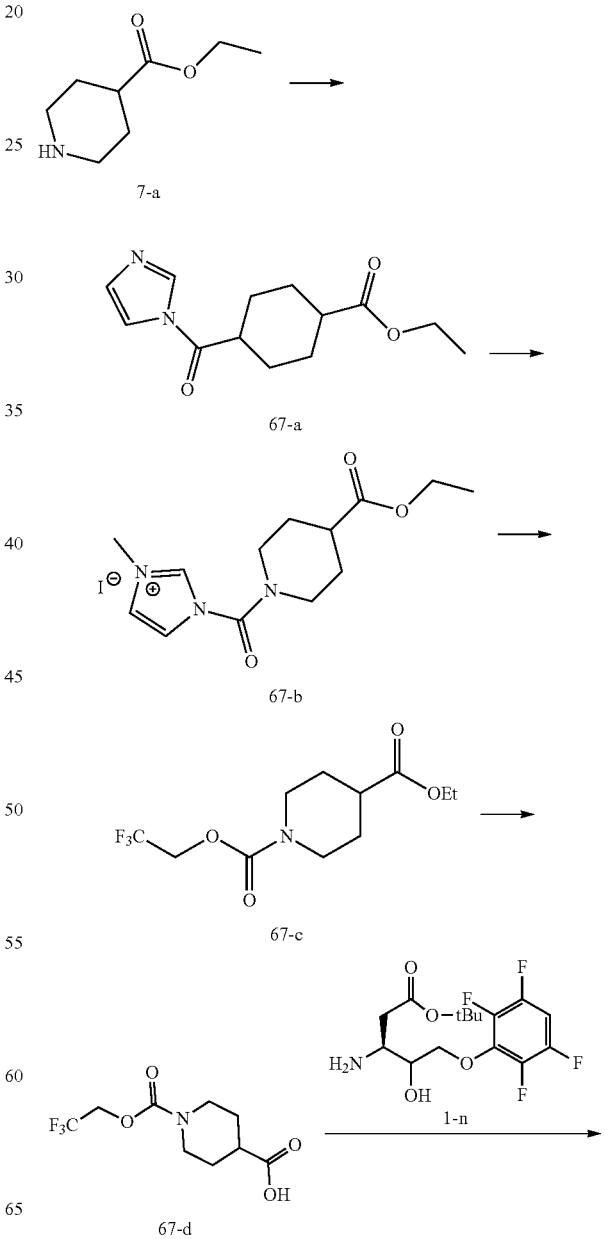

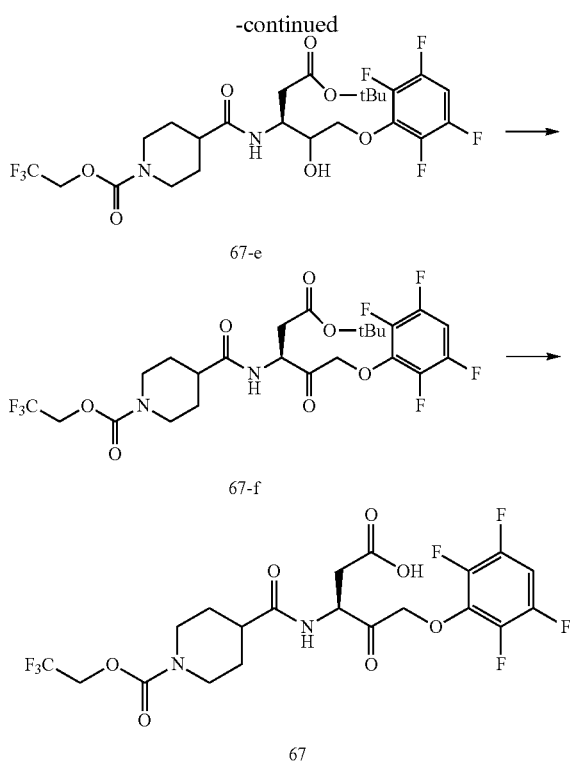

Step 1: Synthesis of Compound 67-a

Compound 7-a (4.00 g, 25.44 mmol, 3.92 mL, 1.00 eq) was dissolved in tetrahydrofuran (80 mL), and CDI (4.54 g, 27.98 mmol, 1.10 eq) was added thereto, followed by stirring for another 16 hours upon heating to reflux. After the reaction was completed, the reaction solution was directly spin-dried to give yellow oil. It was dissolved in dichloromethane (150 mL), washed with water (150 mL×2), dried over anhydrous sodium sulfate, filtered and concentrated, to give the product of compound 67-a (6.27 g, crude) as a yellow oil, which was used directly in the next step without purification. LCMS m/z=252.0 [M+H]$^+$.

Step 2: Synthesis of Compound 67-b

Compound 67-a (6.20 g, 24.67 mmol, 1.00 eq) was dissolved in acetonitrile (46.00 mL), and methyl iodide (15.26 g, 107.51 mmol, 6.69 mL, 4.36 eq) was added to the above solution. The reaction solution was stirred at 25° C. for 17 hours. After the reaction was completed, the reaction solution was directly spin-dried, to give compound 67-b (9.18 g, crude) as a yellow oil, which was used directly in the next step without purification. $^1$H NMR (400 MHz, CHLOROFORM-d) δ 10.00 (s, 1H), 7.73 (s, 1H), 7.66 (s, 1H), 4.24 (s, 3H), 4.13 (q, J=7.11 Hz, 2H), 4.06 (d, J=14.81 Hz, 2H), 3.49 (t, J=11.17 Hz, 2H), 2.60-2.72 (m, 1H), 2.09 (dd, J=3.64, 13.93 Hz, 2H), 1.77-1.91 (m, 2H), 1.25 (t, J=7.15 Hz, 3H).

Step 3: Synthesis of Compound 67-c

Compound 67-b (983.05 mg, 2.50 mmol, 1.00 eq) was dissolved in trifluoroethanol (5 mL), and triethylamine (252.98 mg, 2.50 mmol, 346.55 μL, 1.00 eq) was added thereto, followed by stirring at room temperature for 38 hours. After the reaction was completed, the reaction solution was directly spin-dried, and then subjected to column chromatography (petroleum ether:ethyl acetate=1:0~10:1) to give the product of compound 67-c (689.00 mg, yield: 97%) as a yellow oil. $^1$H NMR (400 MHz, CHLOROFORM-d) δ=4.57-4.41 (m, 2H), 4.16 (q, J=7.3 Hz, 2H), 4.06 (t, J=16.7 Hz, 2H), 3.09-2.90 (m, 2H), 2.50 (tt, J=3.9, 10.8 Hz, 1H), 1.94 (br. s., 2H), 1.76-1.62 (m, 2H), 1.27 (t, J=7.2 Hz, 3H); LCMS m/z=283.9 [M+H]$^+$.

Step 4: Synthesis of Compound 67-d

Compound 67-c (424.86 mg, 1.50 mmol, 1.00 eq) was dissolved in tetrahydrofuran (5.00 mL), and a solution of LiOH.H$_2$O (125.88 mg, 3.00 mmol, 2.00 eq) dissolved in H$_2$O (5.00 mL) was added to the above solution. The reaction solution was stirred at 25° C. for 2 hours. After the reaction was completed, the reaction solution was adjusted to pH of 6 with 2 N dilute hydrochloric acid. This solution was added with water (30 mL), and extracted with dichloromethane (20 mL×3). The organic phase was dried over anhydrous sodium sulfate, filtered and concentrated to give the product of compound 67-d (415.00 mg, crude) as a pale yellow oil, which was used directly in the next step without purification.

Step 5: Synthesis of Compound 67-e

Compound 67-d (382.79 mg, 1.50 mmol, 1.50 eq) and HATU (760.46 mg, 2.00 mmol, 2.00 eq) were dissolved in dichloromethane (15 mL), with stirring at room temperature for 15 min. Compound 1-n (353.31 mg, 1.00 mmol, 1.00 eq) and N,N-diisopropylethylamine (387.72 mg, 3.00 mmol, 523.95 μL, 3.00 eq) were then added, followed by stirring at room temperature for another 72 hours. After the reaction was completed, the reaction solution was added with water (150 mL), and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 67-e (540.00 mg, yield: 74%) as a yellow oil. LCMS m/z=613.1 [M+Na]$^+$.

Step 6: Synthesis of Compound 67-f

Compound 67-e (540.00 mg, 914.49 μmol, 1.00 eq) was dissolved in dichloromethane (20.00 mL), and PIDA (1.18 g, 3.66 mmol, 4.00 eq) and TEMPO (28.76 mg, 182.90 μmol, 0.20 eq) were added thereto. The reaction solution was stirred at room temperature for 72 hours. After the reaction was completed, the reaction solution was added with saturated sodium hydrogen carbonate solution (50 mL) and saturated sodium sulfite solution (50 mL), extracted with dichloromethane (80 mL×3), and washed with saturated brine (100 mL). The organic phase was dried over anhydrous sodium sulfate, filtered and concentrated to give a crude product. The crude product was subjected to column chromatography (petroleum ether:ethyl acetate=1:0~3:1) to give the product of compound 67-f (342.00 mg, yield: 61%) as a yellow oil. LCMS m/z=611.1 [M+Na]$^+$.

Step 7: Synthesis of Compound 67

Compound 67-f (342.00 mg, 581.17 μmol, 1.00 eq) was dissolved in dichloromethane (3.00 mL), and trifluoroacetic acid (4.62 g, 40.52 mmol, 3.00 mL) was added thereto. The reaction solution was stirred at room temperature for 1.5 hours. After the reaction was completed, the reaction solution was spin-dried to give a crude product. The crude product was purified by preparative HPLC (in trifluoroacetic acid condition), and lyophilized to give the product of compound 67 (174.00 mg, yield: 53%). $^1$H NMR (400 MHz, DMSO-$d_6$) δ=8.48 (d, J=7.5 Hz, 1H), 7.63-7.54 (m, 1H), 5.30-5.14 (m, 2H), 4.70 (q, J=9.0 Hz, 2H), 4.61 (q, J=6.5 Hz, 1H), 3.96 (br. s., 2H), 3.02-2.82 (m, 2H), 2.79-2.71 (m, 1H), 2.59 (dd, J=6.8, 16.8 Hz, 1H), 2.48-2.40 (m, 1H), 1.73 (br. s., 2H), 1.51-1.39 (m, 2H); LCMS m/z=533.0 [M+H]$^+$; 554.9 [M+Na]$^+$.

Example 68: Compound 68

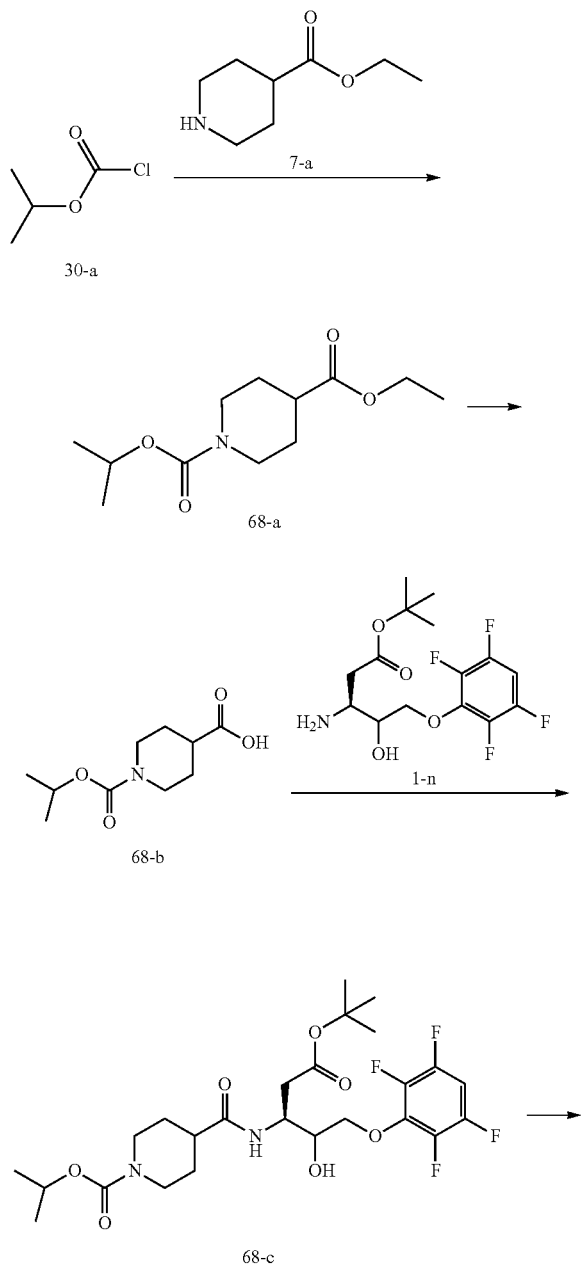

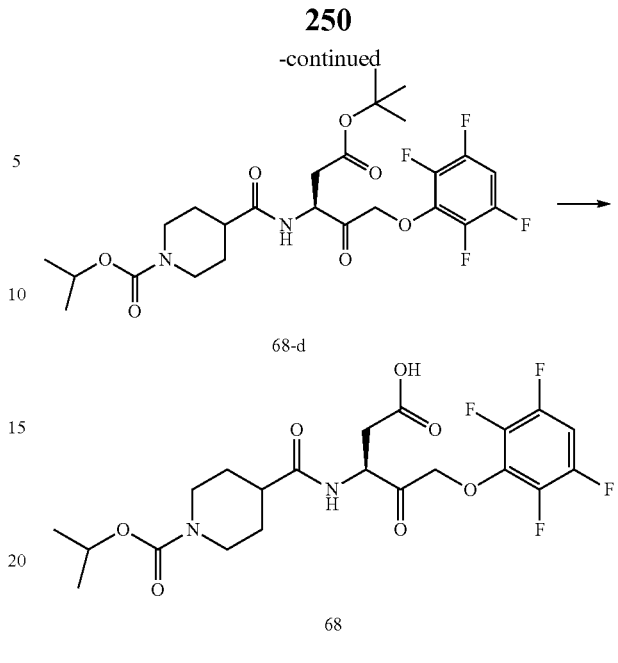

Step 1: Synthesis of Compound 68-a

Compound 7-a (1.00 g, 6.36 mmol, 980.39 μL, 1.00 eq) and triethylamine (1.29 g, 12.72 mmol, 1.76 mL, 2.00 eq) were dissolved in dichloromethane (50.00 mL), and compound 30-a (1.33 g, 10.81 mmol, 1.51 mL, 1.70 eq) was added to the above solution. The reaction solution was stirred at 18° C. for 16 hours. After the reaction was completed, the reaction solution was added with water (150 mL), and extracted with dichloromethane (150 mL×3). The organic phase was dried over anhydrous sodium sulfate, filtered and concentrated to give a crude product. The crude product was subjected to column chromatography (petroleum ether:ethyl acetate=1:0~3:1) to give the product of compound 68-a (1.50 g, yield: 73%) as a colorless oil. $^1$H NMR (400 MHz, CHLOROFORM-d) δ=4.91 (m, 1H), 4.14 (q, J=7.03 Hz, 2H), 4.07 (d, J=16.06 Hz, 2H), 2.87 (t, J=11.54 Hz, 2H), 2.44 (tt, J=3.83, 10.98 Hz, 1H), 1.88 (d, J=11.54 Hz, 2H), 1.55-1.70 (m, 2H), 1.17-1.32 (m, 9H).

Step 2: Synthesis of Compound 68-b

Compound 68-a (1.40 g, 5.75 mmol, 1.00 eq) was dissolved in tetrahydrofuran (25.00 mL), and a solution of LiOH.H$_2$O (362.17 mg, 8.63 mmol, 1.50 eq) dissolved in H$_2$O (25.00 mL) was added to the above solution. The reaction solution was stirred at 18° C. for 1 hour. After the reaction was completed, the reaction solution was adjusted to pH of 5 with 2 N dilute hydrochloric acid. This solution was added with water (150 mL), and extracted with dichloromethane (150 mL×3). The organic phase was dried over anhydrous sodium sulfate, filtered and concentrated to give the product of compound 68-b (1.05 g, crude) as a colorless solid, which was used directly in the next step without purification. $^1$H NMR (400 MHz, CHLOROFORM-d) δ=4.92 (spt, J=6.19 Hz, 1H), 3.95-4.19 (m, 2H), 2.90 (t, J=11.42 Hz, 2H), 2.51 (tt, J=3.83, 10.85 Hz, 1H), 1.83-1.98 (m, 2H), 1.57-1.74 (m, 2H), 1.24 (d, J=6.27 Hz, 6H).

Step 3: Synthesis of Compound 68-c

Compound 68-b (304.62 mg, 1.42 mmol, 1.00 eq) was dissolved in dichloromethane (20.00 mL), and compound 1-n (500.00 mg, 1.42 mmol, 1.00 eq), EDCl (371.67 mg, 1.94 mmol, 1.37 eq), HOBt (261.97 mg, 1.94 mmol, 1.37 eq) and N-methylmorpholine (429.44 mg, 4.25 mmol, 466.78 μL, 3.00 eq) were added thereto. The reaction solution was stirred under the protection of nitrogen gas at 18° C. for 15 hours. After the reaction was completed, the reaction solution was added with water (150 mL), and extracted with dichloromethane (150 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 68-c (550.00 mg, yield: 69%) as a colorless oil. LCMS m/z=573.2 [M+Na]⁺.

Step 4: Synthesis of Compound 68-d

Compound 68-c (550.00 mg, 999.02 μmol, 1.00 eq) was dissolved in dichloromethane (20.00 mL), and PIDA (1.25 g, 3.87 mmol, 3.87 eq) and TEMPO (47.13 mg, 299.71 μmol, 0.30 eq) were added thereto. The reaction solution was stirred under the protection of nitrogen gas at 18° C. for 16 hours. The reaction solution was added with ethyl acetate (200 mL). The solution was washed successively with saturated sodium hydrogen carbonate (100 mL), saturated brine (100 mL) and water (100 mL). The organic phase was dried over anhydrous sodium sulfate, filtered and concentrated to give a crude product. The crude product was subjected to column chromatography (petroleum ether:ethyl acetate=1:0~3:1) to give the product of compound 68-d (350.00 mg, yield: 54%) as a pale yellow oil. LCMS m/z=571.3 [M+Na]⁺.

Step 5: Synthesis of Compound 68

Compound 68-d (350.00 mg, 638.08 μmol, 1.00 eq) was dissolved in dichloromethane (20.00 mL), and trifluoroacetic acid (7.70 g, 67.53 mmol, 5.00 mL, 105.84 eq) was added thereto. The reaction solution was stirred under the protection of nitrogen gas at 0° C. for 1 hour. After the reaction was completed, the reaction solution was concentrated to give a crude product. The crude product was purified by preparative HPLC (in trifluoroacetic acid condition), and lyophilized to give the product of compound 68 (212.20 mg, yield: 68%). $^1$H NMR (400 MHz, DMSO-$d_6$) δ=8.44 (d, J=7.53 Hz, 1H), 7.50-7.68 (m, 1H), 5.12-5.31 (m, 2H), 4.71-4.81 (m, 1H), 4.59 (q, J=7.03 Hz, 1H), 3.94 (d, J=12.05 Hz, 2H), 2.65-2.92 (m, 3H), 2.57 (dd, J=6.78, 16.81 Hz, 1H), 2.32-2.44 (m, 1H), 1.66 (d, J=2.51 Hz, 2H), 1.39 (q, J=12.05 Hz, 2H), 1.17 (d, J=6.53 Hz, 6H); LCMS m/z=493.0 [M+H]⁺.

Example 69: Compound 69

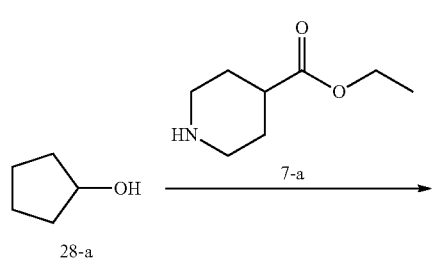

Step 1: Synthesis of Compound 69-a

Compound 28-a (1.33 g, 10.81 mmol, 1.51 mL, 1.70 eq) and CDI (2.99 g, 18.44 mmol, 2.90 eq) were dissolved in tetrahydrofuran (14.00 mL). The above solution was stirred at 18° C. for 1 hour, and then added with compound 7-a (1.00 g, 6.36 mmol, 980.39 μL, 1.00 eq) and triethylamine (2.38 g, 23.53 mmol, 3.26 mL, 3.70 eq). The reaction solution was stirred at 80° C. for 15 hours. After the reaction was completed, the reaction solution was added with water (150 mL), and extracted with dichloromethane (150 mL×3).

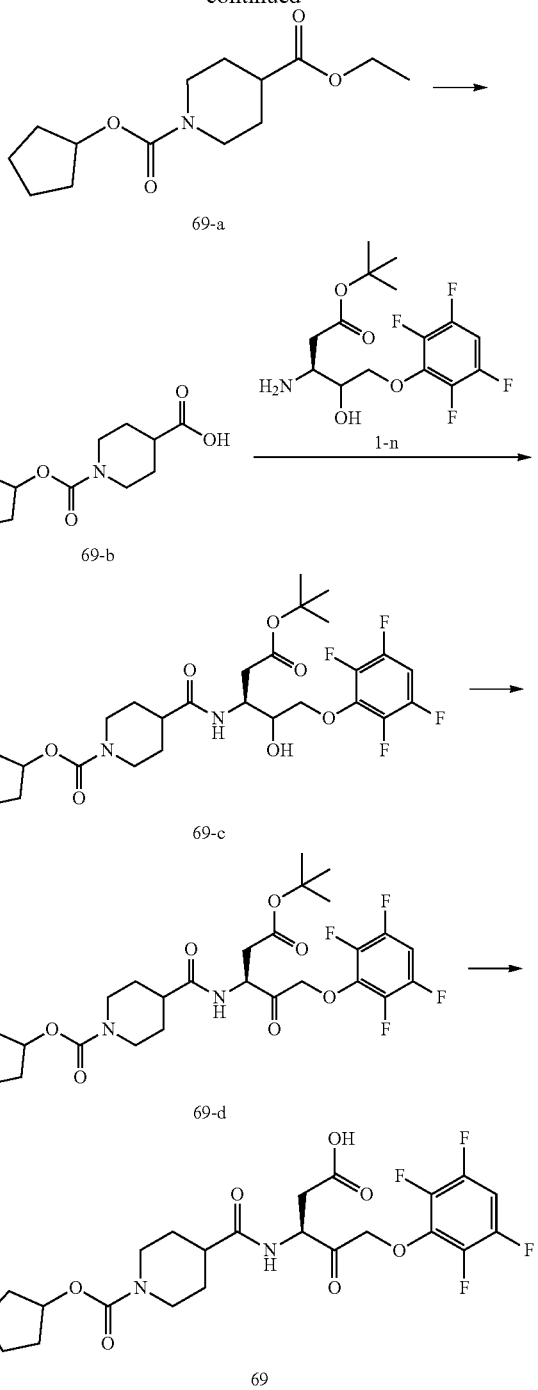

The organic phase was dried over anhydrous sodium sulfate, filtered and concentrated to give a crude product. The crude product was subjected to column chromatography (petroleum ether:ethyl acetate=1:0~3:1) to give the product of compound 69-a (1.70 g, yield: 99%) as a colorless oil. $^1$H NMR (400 MHz, CHLOROFORM-d) δ=5.08 (t, J=5.77 Hz, 1H), 4.13 (q, J=7.19 Hz, 2H), 3.85-4.08 (m, 2H), 2.85 (t, J=11.29 Hz, 2H), 2.43 (tt, J=3.83, 10.98 Hz, 1H), 1.77-1.93 (m, 5H), 1.55-1.70 (m, 7H), 1.18-1.29 (m, 3H).

Step 2: Synthesis of Compound 69-b

Compound 69-a (1.60 g, 5.94 mmol, 1.00 eq) was dissolved in tetrahydrofuran (25.00 mL), and a solution of LiOH.H$_2$O (373.89 mg, 8.91 mmol, 1.50 eq) dissolved in H$_2$O (25.00 mL) was added to the above solution. The reaction solution wad stirred at 18° C. for 1 hour. After the reaction was completed, the reaction solution was adjusted to pH of 5 with 2 N dilute hydrochloric acid. This solution was added with water (150 mL), and extracted with dichloromethane (150 mL×3). The organic phase was dried over anhydrous sodium sulfate, filtered and concentrated to give the product of compound 69-b (1.37 g, crude) as a colorless solid, which was used directly in the next step without purification. $^1$H NMR (400 MHz, CHLOROFORM-d) δ=5.10 (t, J=5.77 Hz, 1H), 3.93-4.16 (m, 2H), 2.89 (t, J=11.29 Hz, 2H), 2.50 (tt, J=3.83, 10.85 Hz, 1H), 1.60-2.01 (m, 12H).

Step 3: Synthesis of Compound 69-c

Compound 69-b (342.62 mg, 1.42 mmol, 1.00 eq) was dissolved in dichloromethane (20.00 mL), and compound 1-n (500.00 mg, 1.42 mmol, 1.00 eq), EDCl (372.93 mg, 1.95 mmol, 1.37 eq), HOBt (262.86 mg, 1.95 mmol, 1.37 eq) and N-methylmorpholine (430.90 mg, 4.26 mmol, 468.37 μL, 3.00 eq) were added thereto. The reaction solution was stirred under the protection of nitrogen gas at 18° C. for 15 hours. After the reaction was completed, the reaction solution was added with water (150 mL), and extracted with dichloromethane (150 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 69-c (550.00 mg, yield: 64%) as a colorless oil. LCMS m/z=577.3 [M+H]$^+$.

Step 4: Synthesis of Compound 69-d

Compound 69-c (550.00 mg, 953.90 μmol, 1.00 eq) was dissolved in dichloromethane (20.00 mL), and PIDA (1.19 g, 3.69 mmol, 3.87 eq) and TEMPO (45.00 mg, 286.17 μmol, 0.30 eq) were added thereto. The reaction solution was stirred under the protection of nitrogen gas at 18° C. for 16 hours. The reaction solution was added with ethyl acetate (200 mL). The solution was washed successively with saturated sodium hydrogen carbonate (100 mL), saturated brine (100 mL) and water (100 mL). The organic phase was dried over anhydrous sodium sulfate, filtered and concentrated to give a crude product. The crude product was subjected to column chromatography (petroleum ether:ethyl acetate=1:0~3:1) to give the product of compound 69-d (380.00 mg, yield: 60%) as a pale yellow oil. LCMS m/z=597.3 [M+Na]$^+$.

Step 5: Synthesis of Compound 69

Compound 69-d (380.00 mg, 661.38 μmol, 1.00 eq) was dissolved in dichloromethane (20.00 mL), and trifluoroacetic acid (15.40 g, 135.06 mmol, 10.00 mL, 204.22 eq) was added thereto. The reaction solution was stirred under the protection of nitrogen gas at 18° C. for 1 hour. After the reaction was completed, the reaction solution was concentrated to give a crude product. The crude product was purified by preparative HPLC (in trifluoroacetic acid condition), and lyophilized to give the product of compound 69 (201.50 mg, yield: 59%). $^1$H NMR (400 MHz, DMSO-d$_6$) δ=8.43 (d, J=7.53 Hz, 1H), 7.50-7.64 (m, 1H), 5.12-5.28 (m, 2H), 4.96 (t, J=5.77 Hz, 1H), 4.59 (q, J=6.53 Hz, 1H), 3.91 (br. s., 2H), 2.64-2.91 (m, 3H), 2.57 (dd, J=7.03, 16.56 Hz, 1H), 2.38 (ddd, J=3.51, 7.91, 11.17 Hz, 1H), 1.72-1.85 (m, 2H), 1.47-1.70 (m, 8H), 1.30-1.46 (m, 2H); LCMS m/z=519.0 [M+H]$^+$.

Example 70: Compound 70

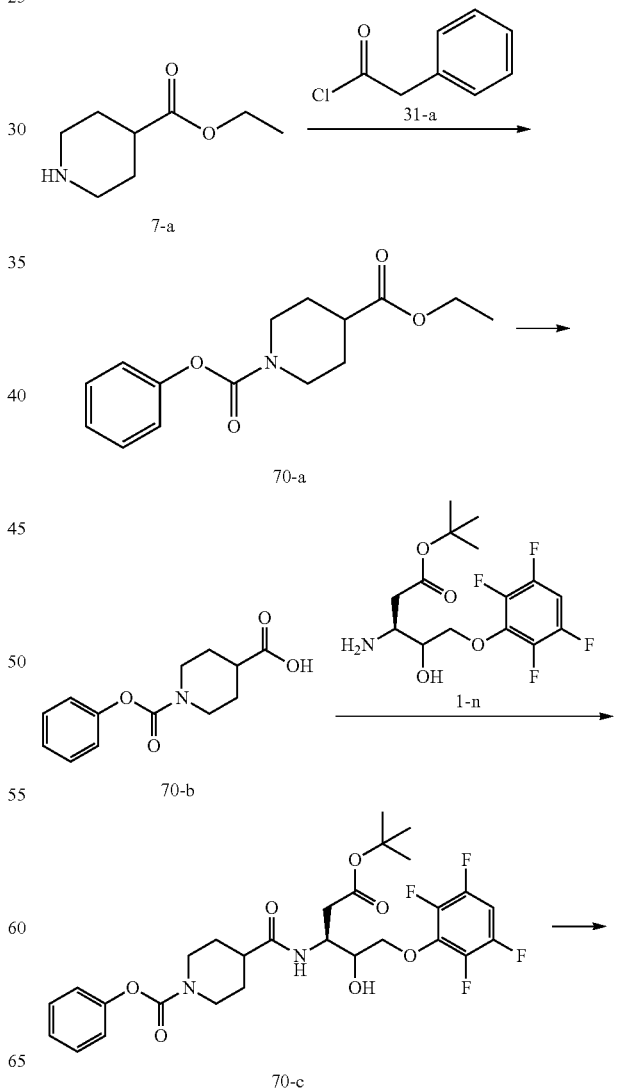

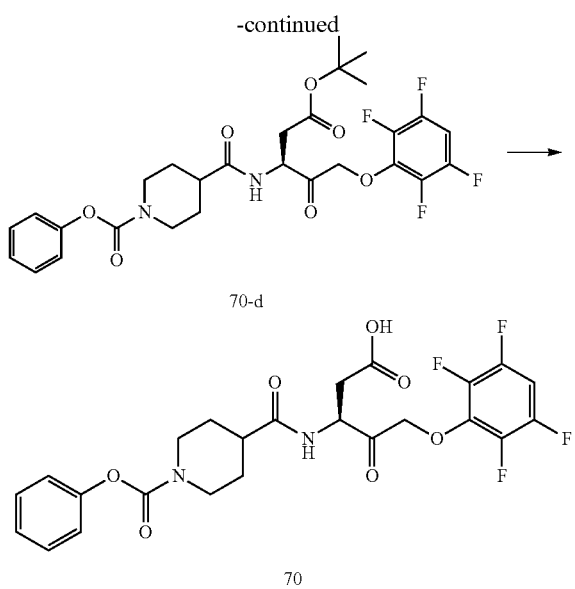

70-d

70

Step 1: Synthesis of Compound 70-a

Compound 7-a (500.00 mg, 3.18 mmol, 490.20 μL, 1.00 eq) and triethylamine (643.57 mg, 6.36 mmol, 881.60 μL, 2.00 eq) were dissolved in dichloromethane (25 mL), and compound 31-a (864.54 mg, 5.41 mmol, 677.23 μL, 1.7 eq) was slowly added to the solution, followed by stirring at room temperature (18° C.) for 3 hours. After the reaction was completed, the reaction solution was added with water (30 mL), and separated. The aqueous phase was further extracted with ethyl acetate (40 mL×3). The organic phases were combined, washed with saturated brine (40 mL×2), dried over anhydrous sodium sulfate, filtered, concentrated, and then separated with column chromatography (petroleum ether:ethyl acetate=10:1~2:1), to give the product of compound 70-a (800.00 mg, yield: 91%). LCMS m/z=278.1 [M+1]$^+$.

Step 2: Synthesis of Compound 70-b

Compound 70-a (800.00 mg, 2.88 mmol, 1.00 eq) was dissolved in tetrahydrofuran (16.00 mL), and a solution of LiOH.H$_2$O (181.27 mg, 4.32 mmol, 1.50 eq) dissolved in H$_2$O (16.00 mL) was added to the above solution. The reaction solution was stirred at 30° C. for 3 hours. After the reaction was completed, this solution was added with water (15 mL). The aqueous phase was washed with ethyl acetate (30 mL×3), adjusted to pH of 3 with 1 N dilute hydrochloric acid, and extracted with dichloromethane (30 mL×3). The combined organic phases were washed with saturated brine solution (30 mL×2), dried over anhydrous sodium sulfate, filtered, and concentrated, to give compound 70-b (600.00 mg, yield: 84%), which was used directly in the next step without purification. LCMS m/z=250.1 [M+H]$^+$.

Step 3: Synthesis of Compound 70-c

Compound 1-n (340.79 mg, 964.55 μmol, 1.00 eq) was dissolved in dichloromethane (10.00 mL). Under the protection of nitrogen gas, compound 70-b (360.64 mg, 1.45 mmol, 1.50 eq), N-methylmorpholine (292.69 mg, 2.89 mmol, 318.14 μL, 3.00 eq), HOBt (178.55 mg, 1.32 mmol, 1.37 eq) and EDCl (253.32 mg, 1.32 mmol, 1.37 eq) were added to the solution. The reaction solution was stirred at 20° C. for 16 hours. After the reaction was completed, the reaction solution was added with water (40 mL), and extracted with dichloromethane (30 mL×3). The organic phases were combined, then washed with saturated brine solution (30 mL×2), dried over anhydrous sodium sulfate, filtered, and concentrated to give a crude product. The crude product was subjected to column chromatography (petroleum ether:ethyl acetate=10:1~2:1) to give the product of compound 70-c (520.00 mg, yield: 92%) as a colorless oil. LCMS m/z=607.2 [M+Na]$^+$.

Step 4: Synthesis of Compound 70-d

Compound 70-c (520.00 mg, 889.56 μmol, 1.00 eq) was dissolved in dichloromethane (20.00 mL), and PIDA (1.11 g, 3.44 mmol, 3.87 eq) and TEMPO (41.96 mg, 266.87 μmol, 0.30 eq) were added thereto. The reaction solution was stirred at room temperature (18° C.) for 24 hours. When the compound was not completely reacted, TEMPO (13.99 mg, 88.96 μmol, 0.10 eq) and PIDA (315.18 mg, 978.52 μmol, 1.10 eq) were further added to the solution. After the reaction was completed, the reaction solution was added with saturated sodium bisulfite (50 mL), and extracted with dichloromethane (30 mL×3). The organic phase was washed with saturated brine (25 mL×2), dried over anhydrous sodium sulfate, filtered, and concentrated to give a crude product. The crude product was subjected to column chromatography (petroleum ether:ethyl acetate=10:0~2:1) to give the product of compound 70-d (450.00 mg, yield: 87%) as a colorless oil. $^1$H NMR (400 MHz, DMSO-d6) δ=1.37 (s, 9H) 4.66 (q, J=7.24 Hz, 1H) 5.22 (d, J=5.27 Hz, 2H) 5.76 (s, 1H) 7.11 (d, J=7.53 Hz, 2H) 7.16-7.27 (m, 1H) 7.36-7.44 (m, 2H) 7.58 (tt, J=10.90, 7.29 Hz, 1H) 8.45 (d, J=7.78 Hz, 1H); LCMS m/z=605.4 [M+Na]$^+$.

Step 5: Synthesis of Compound 70

Compound 70-d (170.00 mg, 291.83 μmol, 1.00 eq) was dissolved in dichloromethane (9.00 mL), and trifluoroacetic acid (5.17 g, 45.33 mmol, 3.36 mL, 176.05 eq) was added thereto at 0° C. The reaction solution was stirred at 0° C.-10° C. for 12 hours. After the reaction was completed, the reaction solution was spin-dried to give a crude product. The crude product was purified by preparative HPLC (in trifluoroacetic acid condition), and lyophilized to give the product of compound 70 (50.00 mg, yield: 36%). $^1$H NMR (400 MHz, DMSO-d$_6$) δ=8.48 (d, J=7.58 Hz, 1H), 7.57 (tt, J=10.93, 7.41 Hz, 1H), 7.37 (d, J=7.70 Hz, 2H), 7.19-7.23 (m, 1H), 7.11 (d, J=7.70 Hz, 2H), 5.32-5.18 (m, 2H), 4.62 (q, J=6.81 Hz, 1H), 4.15-4.01 (m, 2H), 3.89-3.52 (m, 2H), 2.72-2.81 (m, 1H), 2.57-2.62 (m, 1H), 2.43-2.49 (m, 2H), 1.76 (brs, 2H), 1.56 (brs, 2H); LCMS m/z=527.1 [M+H]$^+$.

Example 71: Compound 71

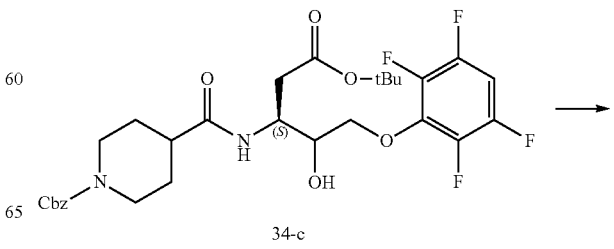

34-c

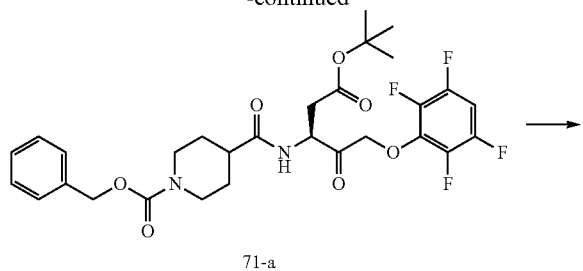

71-a

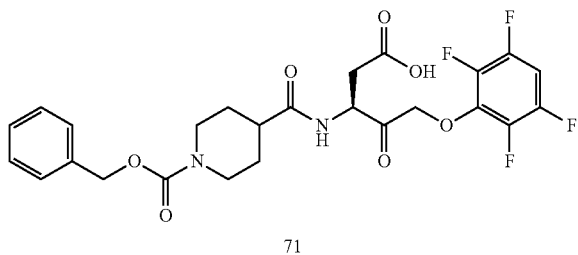

71

Step 1: Synthesis of Compound 71-a

Compound 34-c (100.00 mg, 167.06 µmol, 1.00 eq) was dissolved in dichloromethane (5.00 mL), and PIDA (215.24 mg, 668.25 µmol, 4.00 eq) and TEMPO (5.25 mg, 33.42 µmol, 0.20 eq) were added thereto. The reaction solution was stirred under the protection of nitrogen gas at 25° C. for 12 hours. After the reaction was completed, the reaction solution was added with ethyl acetate (100 mL). The solution was washed successively with saturated sodium hydrogen carbonate (50 mL), saturated brine (50 mL) and water (50 mL). The organic phase was dried over anhydrous sodium sulfate, filtered and concentrated to give a crude product. The crude product was purified by preparative silica gel plates (petroleum ether:ethyl acetate=2:1) to give the product of compound 71-a (50.0 mg, yield: 50%) as a yellow oil; LCMS m/z=619.1 [M+Na]+.

Step 3: Synthesis of Compound 71

Compound 71-a (50.00 mg, 83.81 µmol, 1.00 eq) was dissolved in dichloromethane (4.00 mL), and trifluoroacetic acid (1 mL) was added thereto. The reaction solution was stirred under the protection of nitrogen gas at 25° C. for 2 hours. After the reaction was completed, the reaction solution was spin-dried to give a crude product. The crude product was purified by preparative HPLC (in trifluoroacetic acid condition), and lyophilized to give the product of compound 71 (10.00 mg, yield: 22%). $^1$H NMR (400 MHz, CHLOROFORM-d) δ=7.40-7.29 (m, 5H), 6.89-6.77 (m, 1H), 6.54-6.37 (m, 1H), 5.12 (s, 2H), 4.95-4.83 (m, 1H), 4.72-4.58 (m, 1H), 4.30-4.16 (m, 2H), 3.12-2.97 (m, 1H), 2.96-2.68 (m, 3H), 2.36 (br. s., 2H), 1.83 (br. s., 2H), 1.66 (d, J=11.5 Hz, 2H); LCMS m/z=541.2 [M+H]+.

Example 72: Compound 72

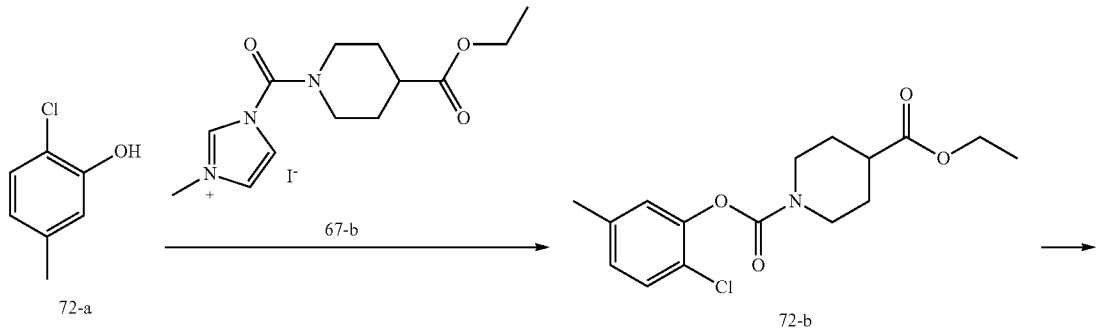

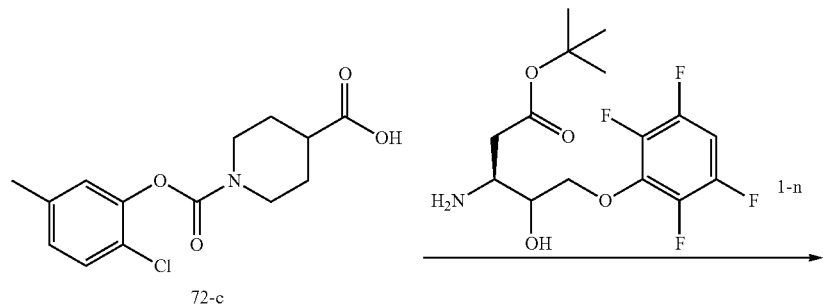

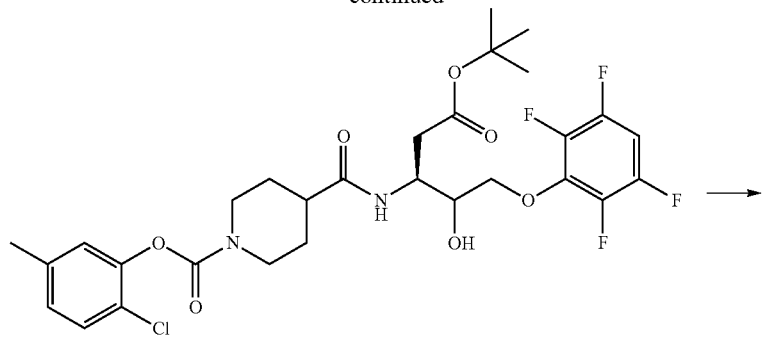

72-d

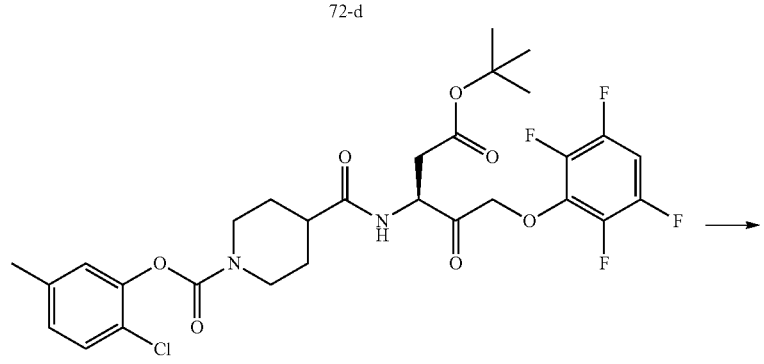

72-e

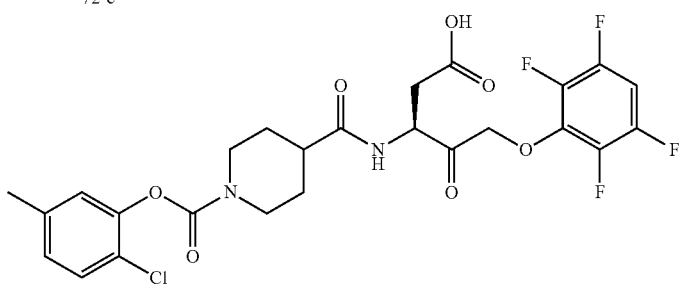

72

Step 1: Synthesis of Compound 72-b

Compound 72-a (500.00 mg, 3.51 mmol, 1.00 eq) was dissolved in acetonitrile (15.00 mL), and triethylamine (532.77 mg, 5.27 mmol, 729.82 µL, 1.50 eq) and compound 67-b (1.93 g, 4.91 mmol, 1.40 eq) were added thereto, followed by warming up to 80° C. and stirring for 20 hours. After the reaction was completed, the reaction solution was added with ethyl acetate (50 mL) for dilution, and then washed with water (30 mL) and saturated brine (40 mL×2). The organic phase was dried over anhydrous sodium sulfate, filtered, and concentrated to give a crude product. The crude product was purified by column chromatography (petroleum ether:ethyl acetate=1:0~4:1), to give the product of compound 72-b (1.06 g, yield: 89%) as a colorless oil. LCMS m/z=326.1 [M+H]$^+$.

Step 2: Synthesis of Compound 72-c

LiOH.H$_2$O (272.74 mg, 6.50 mmol, 2.00 eq) was dissolved in water (5.00 mL), and the solution was added to a solution of compound 72-b (1.06 g, 3.25 mmol, 1.00 eq) dissolved in tetrahydrofuran (5.00 mL). The reaction was stirred at room temperature for 5 hours. After the reaction was completed, the reaction solution was added with water (30 mL), adjusted to pH of 3-4 with 1 N dilute hydrochloric acid, and extracted with dichloromethane/methanol (50 mL, 10:1). The organic phase was dried over anhydrous sodium sulfate, filtered, and concentrated to give the product of compound 72-c (960.00 mg, crude) as a colorless oil, which was used directly in the next step without purification. LCMS m/z=297.9 [M+H]$^+$.

Step 3: Synthesis of Compound 72-d

Compound 72-c (227.53 mg, 764.21 µmol, 1.50 eq) was dissolved in dichloromethane (10 mL), and N-methylmorpholine (154.60 mg, 1.53 mmol, 168.04 µL, 3.00 eq), HOBt (137.68 mg, 1.02 mmol, 2.00 eq), EDCl (195.33 mg, 1.02 mmol, 2.00 eq) and compound 1-n (180.00 mg, 509.47 µmol, 1.00 eq) were added thereto. The reaction was stirred at room temperature for 5 hours. After the reaction was completed, the reaction solution was concentrated to give a crude product. The crude product was purified by column chromatography (petroleum ether:ethyl acetate=1:0~2:1), to give the product of compound 72-d (280.00 mg, yield: 72%) as a colorless oil. LCMS m/z=655.2[M+Na]$^+$.

Step 4: Synthesis of Compound 72-e

Compound 72-d (280.00 mg, 442.32 μmol, 1.00 eq) was dissolved in dichloromethane (10.00 mL), and PIDA (551.36 mg, 1.71 mmol, 3.87 eq) and TEMPO (48.69 mg, 309.62 μmol, 0.70 eq) were added thereto. The reaction was stirred at room temperature for 64 hours. After the reaction was completed, the reaction solution was added with dichloromethane (50 mL) for dilution, and washed with saturated sodium hydrogen carbonate solution (30 mL) and saturated brine (30 mL×2). The organic phase was dried over anhydrous sodium sulfate, filtered, and concentrated to give a crude product. The crude product was purified by column chromatography (petroleum ether:ethyl acetate=1:0~2:1), to give the product of compound 72-e (250.00 mg, yield: 59%) as a yellow oil, LCMS m/z=653.1 [M+Na]$^+$.

Step 5: Synthesis of Compound 72

Compound 72-e (250.00 mg, 427.89 μmol, 1.00 eq) was dissolved in dichloromethane (10.00 mL), and trifluoroacetic acid (5.00 mL, 67.53 mmol, 157.83 eq) was added thereto. The reaction was stirred at room temperature for 2 hours. After the reaction was completed, the reaction solution was spin-dried to give a crude product. The crude product was purified by preparative HPLC (in trifluoroacetic acid condition), and lyophilized to give compound 72 (153.00 mg, yield: 62%). $^1$H NMR (400 MHz, DMSO-d$_6$) δ=12.50 (br s, 1H), 8.51 (br s, 1H), 7.59 (br s, 1H), 7.41 (d, J=8.03 Hz, 1H), 7.13 (s, 1H), 7.09 (br d, J=8.03 Hz, 1H), 5.24 (br d, J=10.04 Hz, 2H), 4.62 (br s, 1H), 4.17 (br d, J=11.54 Hz, 1H), 3.99 (br d, J=12.05 Hz, 1H), 3.11 (br s, 1H), 2.94 (br s, 1H), 2.70-2.82 (m, 1H), 2.56-2.70 (m, 1H), 2.43-2.49 (m, 1H), 2.30 (s, 3H), 1.76 (br s, 2H), 1.47-1.64 (m, 2H); LCMS m/z=575.0 [M+H]$^+$.

Example 73: Compound 73

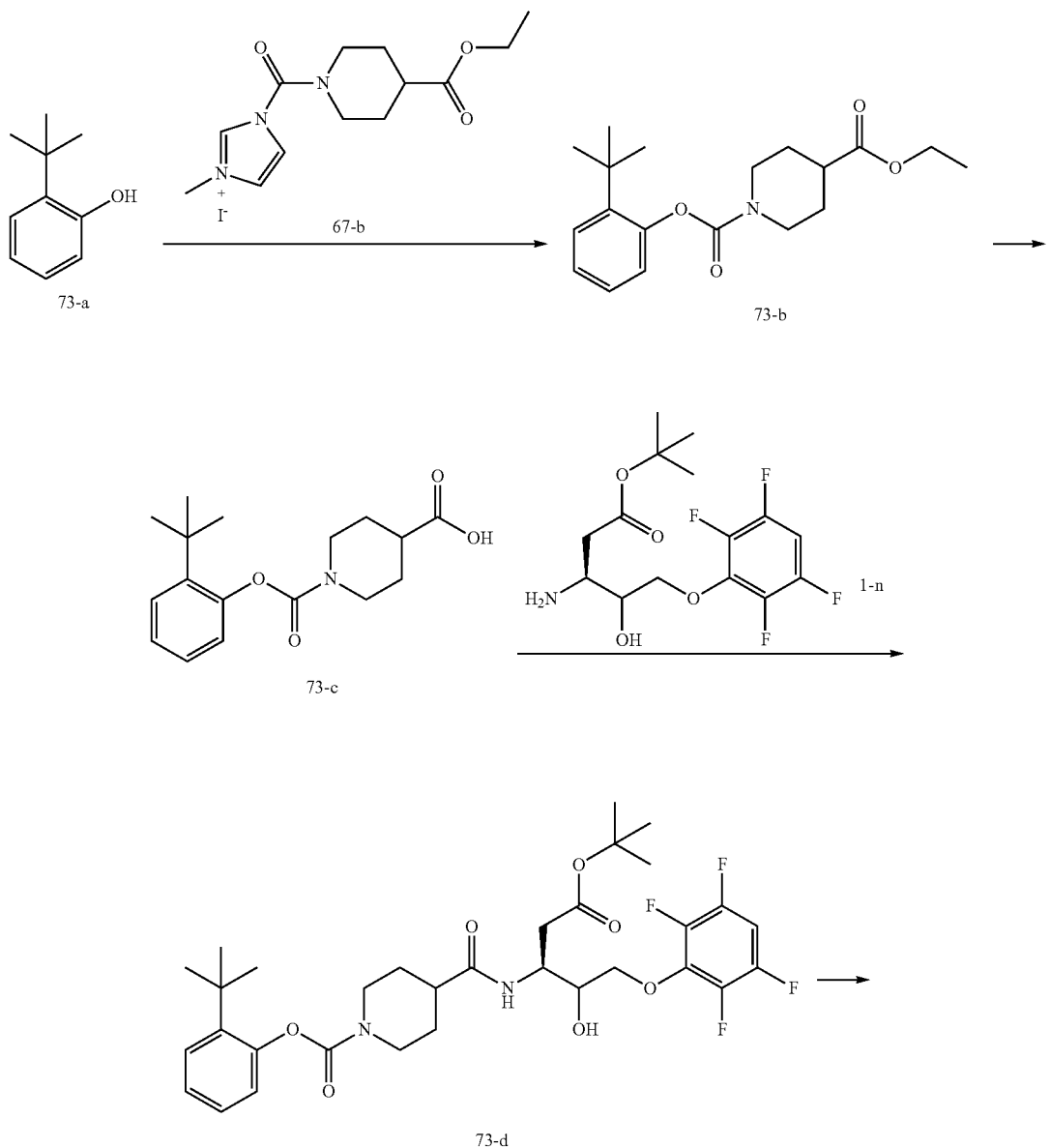

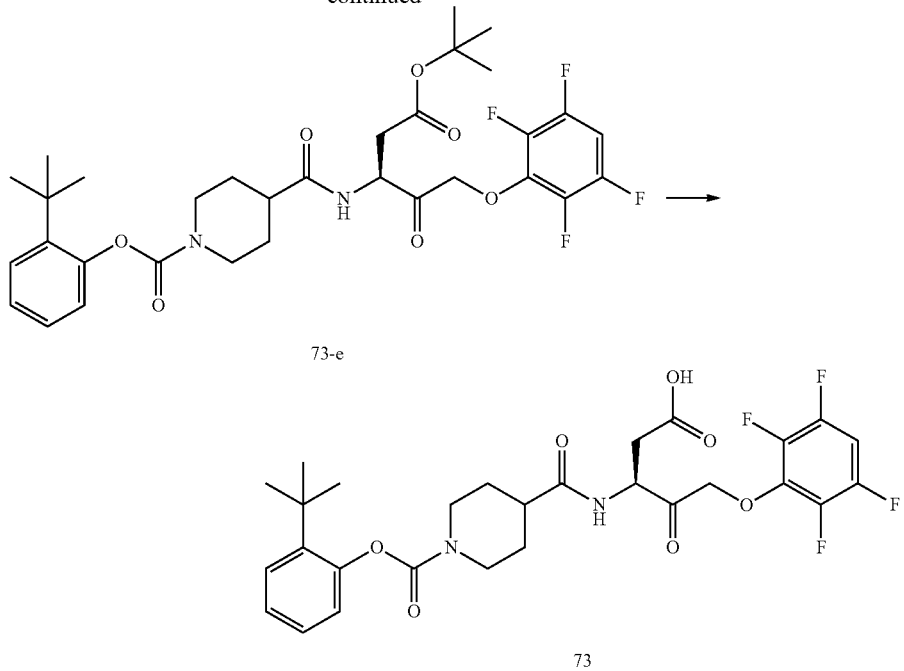

Step 1: Synthesis of Compound 73-b

Compound 73-a (500.00 mg, 3.33 mmol, 588.24 μL, 1.00 eq) was dissolved in acetonitrile (15.00 mL), and triethylamine (505.44 mg, 5.00 mmol, 692.39 μL, 1.50 eq) and compound 67-b (1.83 g, 4.66 mmol, 1.40 eq) were added thereto, followed by warming up to 80° C. and stirring for 20 hours. After the reaction was completed, the reaction solution was added with ethyl acetate (50 mL) for dilution, and then washed with water (30 mL) and saturated brine (40 mL×2). The organic phase was dried over anhydrous sodium sulfate, filtered, and concentrated to give a crude product. The crude product was purified by column chromatography (petroleum ether:ethyl acetate=1:0~4:1), to give the product of compound 73-b (1.10 g, yield: 99%) as a colorless oil. LCMS m/z=334.4 [M+H]$^+$.

Step 2: Synthesis of Compound 73-c

LiOH.H$_2$O (276.94 mg, 6.60 mmol, 2.00 eq) was dissolved in water (5.00 mL), and the solution was added to a solution of compound 73-b (1.10 g, 3.30 mmol, 1.00 eq) dissolved in tetrahydrofuran (5.00 mL). The reaction was stirred at room temperature for 5 hours. After the reaction was completed, the reaction solution was added with water (30 mL), adjusted to pH of 3-4 with 1 N dilute hydrochloric acid, and extracted with dichloromethane/methanol (50 mL, 10:1). The organic phase was dried over anhydrous sodium sulfate, filtered, and concentrated to give the product of compound 73-c (996.00 mg, crude) as a colorless oil, which was used directly in the next step without purification. LCMS m/z=328.0 [M+Na]$^+$.

Step 3: Synthesis of Compound 73-d

Compound 73-c (233.37 mg, 764.21 μmol, 1.50 eq) was dissolved in dichloromethane (10 mL), and N-methylmorpholine (154.60 mg, 1.53 mmol, 168.04 μL, 3.00 eq), HOBt (137.68 mg, 1.02 mmol, 2.00 eq), EDCl (195.33 mg, 1.02 mmol, 2.00 eq) and compound 1-n (180.00 mg, 509.47 μmol, 1.00 eq) were added thereto. The reaction was stirred at room temperature for 5 hours. After the reaction was completed, the reaction solution was concentrated to give a crude product. The crude product was purified by column chromatography (petroleum ether:ethyl acetate=1:0~2:1), to give the product of compound 73-d (260.00 mg, yield: 72%) as a colorless oil. LCMS m/z=663.0[M+Na]$^+$.

Step 4: Synthesis of Compound 73-e

Compound 73-d (260.00 mg, 405.83 μmol, 1.00 eq) was dissolved in dichloromethane (10.00 mL), and PIDA (505.88 mg, 1.57 mmol, 3.87 eq) and TEMPO (44.67 mg, 284.08 μmol, 0.70 eq) were added thereto. The reaction was stirred at room temperature for 48 hours. After the reaction was completed, the reaction solution was added with dichloromethane (50 mL) for dilution, and washed with saturated sodium hydrogen carbonate solution (30 mL) and saturated brine (30 mL×2). The organic phase was dried over anhydrous sodium sulfate, filtered, and concentrated to give a crude product. The crude product was purified by column chromatography (petroleum ether:ethyl acetate=1:0~2:1), to give the product of compound 73-e (170.00 mg, yield: 38%) as a yellow oil. LCMS m/z=661.2 [M+Na]$^+$.

Step 5: Synthesis of Compound 73

Compound 73-e (170.00 mg, 266.19 μmol, 1.00 eq) was dissolved in dichloromethane (8.00 mL), and trifluoroacetic acid (4.00 mL, 28.86 mmol, 108.41 eq) was added thereto. The reaction was stirred at room temperature for 2 hours. After the reaction was completed, the reaction solution was spin-dried to give a crude product. The crude product was purified by preparative HPLC (in trifluoroacetic acid condition), and lyophilized to give compound 73 (48.00 mg, yield: 31%). $^1$H NMR (400 MHz, DMSO-d$_6$) δ=12.48 (br s, 1H), 8.53 (br s, 1H), 7.57 (br s, 1H), 7.34 (br s, 1H), 7.06-7.28 (m, 2H), 6.95 (br s, 1H), 5.23 (br s, 2H), 4.61 (br s, 1H), 3.98-4.26 (m, 2H), 2.60-3.19 (m, 5H), 1.78 (br s, 2H), 1.49 (br s, 2H), 1.29 (br s, 9H); LCMS m/z=583.3 [M+H]⁺.

Example 74: Compound 74

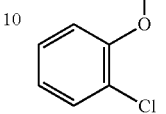

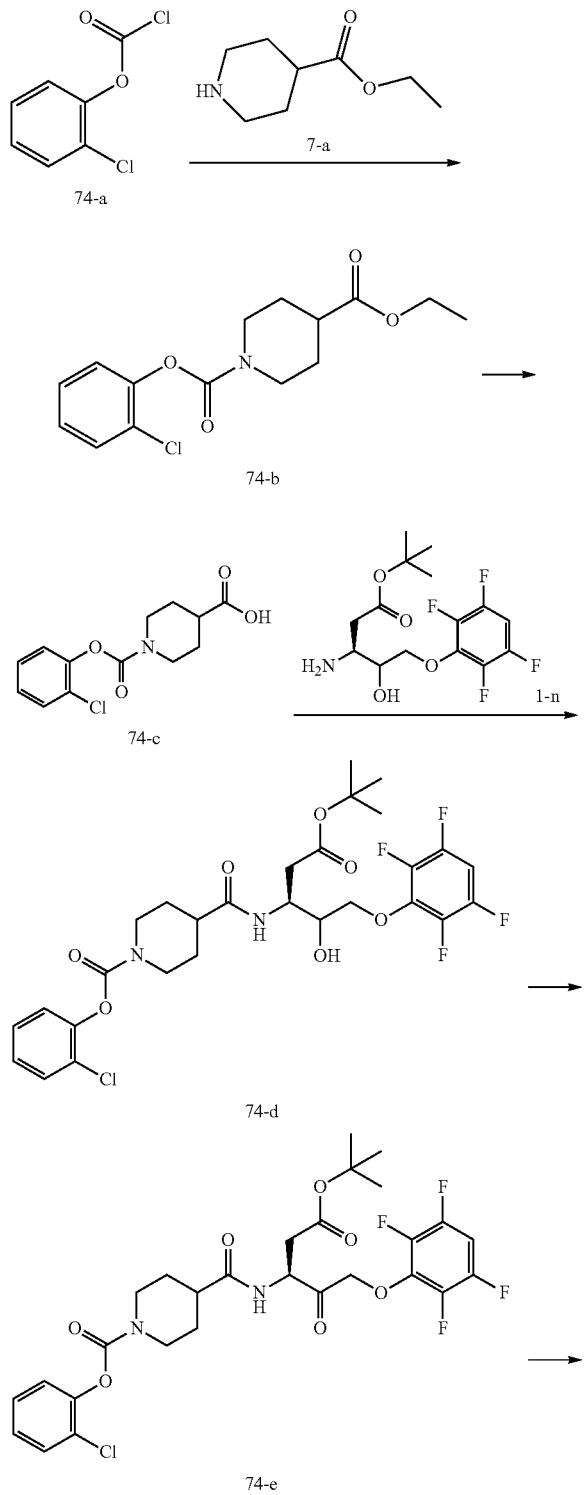

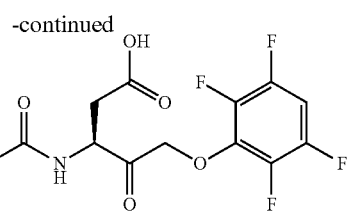

74

Step 1: Synthesis of Compound 74-b

Compound 74-a (200.00 mg, 1.05 mmol, 145.99 μL, 1.00 eq) was dissolved in dichloromethane (5 mL), and triethylamine (148.75 mg, 1.47 mmol, 203.77 μL, 1.40 eq) was added thereto, followed by stirring under the protection of nitrogen gas. Compound 7-a (214.59 mg, 1.37 mmol, 210.38 μL, 1.30 eq) was slowly added thereto with stirring, since the reaction was exothermic. After the addition was completed, the reaction system was stirred at 15° C. for 16 hours. After the reaction was completed, the reaction solution was added with 20 mL of water and 20 mL of dichloromethane, acidified to pH of about 4 with 1 N hydrochloric acid, followed by separation and extraction. The aqueous phase was further extracted once with 20 mL of ethyl acetate. The combined organic phases were washed separately with 40 mL of water and 40 mL of saturated brine, dried over anhydrous sodium sulfate, and then spin-dried to give a crude product. The crude product was subjected to column chromatography (petroleum ether:ethyl acetate=1:0~10:3) to give compound 74-b (260.00 mg, yield: 79.43%) as a colorless liquid, LCMS m/z=311.9 [M+H]⁺.

Step 2: Synthesis of Compound 74-c

Compound 74-b (260.00 mg, 833.97 μmol, 1.00 eq) was dissolved in tetrahydrofuran (6 mL), and then LiOH.H₂O (43.94 mg, 1.83 mmol, 2.20 eq) was dissolved in water (6 mL). The formulated solution was slowly added to the above solution. The reaction system was stirred at 15° C. for 2 hours. The reaction system was acidified to pH of about 4 with 1N hydrochloric acid, and then extracted four times with ethyl acetate (30 mL). The combined organic phases were washed once with saturated brine (50 mL), dried over anhydrous sodium sulfate, and then spin-dried to give the crude liquid product of compound 74-c (1.28 g, crude) as a yellow oil, LCMS m/z=283.9 [M+H]⁺.

Step 3: Synthesis of Compound 74-d

Under the protection of nitrogen gas, compound 74-c (255.00 mg, 898.81 μmol, 1.76 eq) was dissolved in dichloromethane (5 mL), HATU (387.43 mg, 1.02 mmol, 2.00 eq), N,N-diisopropylethylamine (197.53 mg, 1.53 mmol, 266.93 μL, 3.00 eq) were then added thereto, and finally compound 1-n (180.00 mg, 509.47 μmol, 1.00 eq) as a substrate were added thereto. The reaction was stirred at 15° C. for 16 hours. The reaction system was added with ethyl acetate (30 mL) and water (30 mL), and separated. The aqueous phase was further extracted once with ethyl acetate (30 mL). The combined organic phases were washed once with each of water (50 mL) and saturated brine (50 mL), dried over anhydrous sodium sulfate, and then spin-dried to give a crude product. The crude product was subjected to column chromatography (petroleum ether:ethyl acetate=1:0~3:2) to give compound 74-d (230.00 mg, yield: 59%) as a brown liquid, LCMS m/z=563.1 [M−55+H]$^+$.

Step 4: Synthesis of Compound 74-e

Compound 74-d (230.00 mg, 371.57 μmol, 1.00 eq) was dissolved in dichloromethane (10 mL), and PIDA (239.36 mg, 743.13 μmol, 2.00 eq) and TEMPO (35.06 mg, 222.94 μmol, 0.60 eq) was added thereto under the protection of nitrogen gas. The reaction system was stirred at 15° C. for 42 hours. The system was added with ethyl acetate (30 mL), and washed once with each of saturated sodium hydrogen carbonate solution (30 mL), water (30 mL) and saturated brine (30 mL). The organic phase was dried over anhydrous sodium sulfate, filtered, and spin-dried to give a crude product. The crude product was subjected to column chromatography (petroleum ether:ethyl acetate=4:1~5:3) to give compound 74-e (125.00 mg, yield: 43.62%) as a brown liquid, LCMS m/z=639.1 [M+Na]$^+$.

Step 5: Synthesis of Compound 74

Compound 74-e (125.00 mg, 202.60 μmol, 1.00 eq) was dissolved in dichloromethane (5 mL), and trifluoroacetic acid (4.16 g, 36.47 mmol, 2.70 mL, 180.00 eq) was added thereto under the protection of nitrogen gas. The system was stirred at 15° C. for 1 hour. After the reaction was completed, the reaction solution was spin-dried to give a crude product. The crude product was purified by preparative HPLC (in trifluoroacetic acid condition), spin-dried, and then dissolved with acetonitrile (20 mL). The obtained solution was added with water (20 mL), evenly mixed, and lyophilized to give compound 74 (8.00 mg, yield: 6.83%). $^1$H NMR (400 MHz, DMSO-d6) δ12.49 (br. s., 1H), 8.50 (d, J=7.53 Hz, 1H), 7.50-7.62 (m, 2H), 7.34-7.41 (m, 1H), 7.25-7.33 (m, 2H), 5.10-5.39 (m, 2H), 4.63 (q, J=6.78 Hz, 1H), 4.19 (d, J=12.05 Hz, 1H), 3.99 (d, J=11.80 Hz, 1H), 3.12 (t, J=11.92 Hz, 1H), 2.86-3.02 (m, 1H), 2.71-2.82 (m, 1H), 2.60 (dd, J=6.78, 16.81 Hz, 2H), 1.78 (br. s., 2H), 1.45-1.67 (m, 2H). LCMS m/z=561 [M+H]$^+$.

Example 75: Compound 75

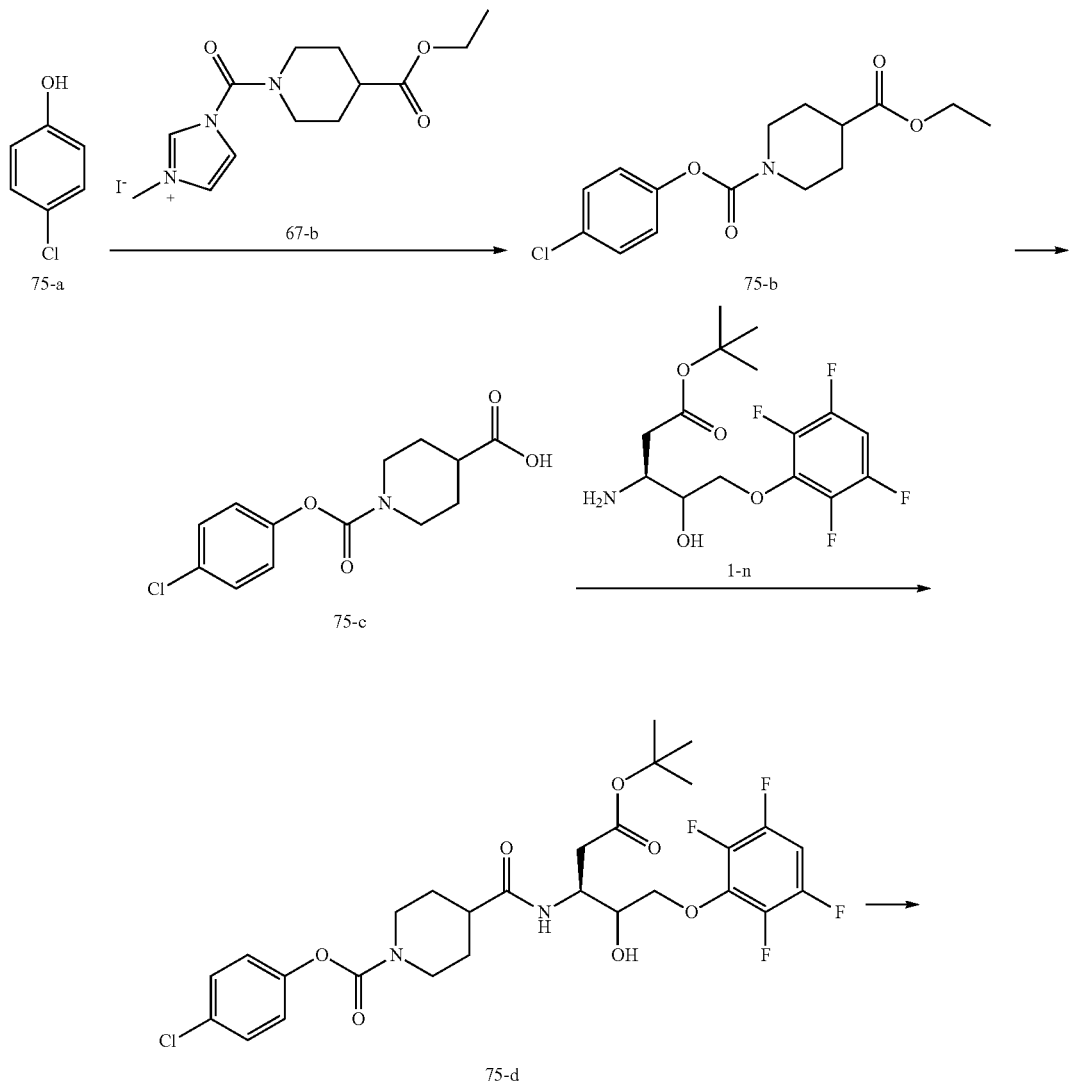

-continued

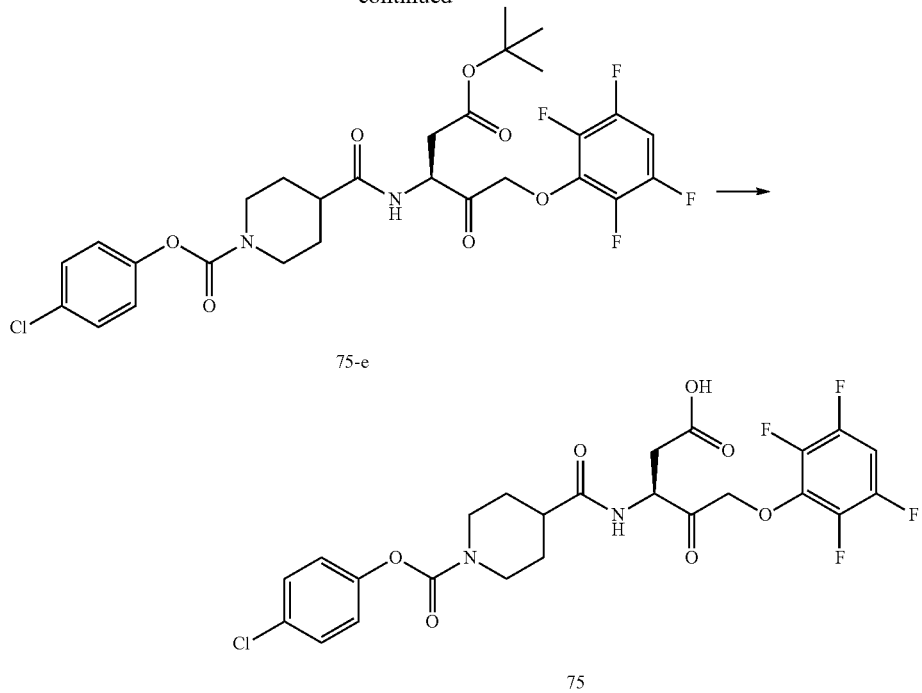

Step 1: Synthesis of Compound 75-b

Compound 75-a (500.00 mg, 3.89 mmol, 381.68 μL, 1.00 eq) was dissolved in acetonitrile (25.00 mL), and triethylamine (590.33 mg, 5.84 mmol, 808.67 μL, 1.50 eq) and compound 67-b (2.14 g, 5.45 mmol, 1.40 eq) were added thereto, followed by warming up to 80° C. and stirring for 20 hours. After the reaction was completed, the reaction solution was added with ethyl acetate (50 mL) for dilution, and then washed with water (40 mL) and saturated brine (40 mL). The organic phase was dried over anhydrous sodium sulfate, filtered and concentrated to give a crude product. The crude product was purified by column chromatography (petroleum ether:ethyl acetate=1:0~4:1) to give the product of compound 75-b (1.20 g, yield: 90%) as a colorless oil. LCMS m/z=311.9 [M+H]$^+$.

Step 2: Synthesis of Compound 75-c

LiOH.H$_2$O (269.38 mg, 6.42 mmol, 2.00 eq) was dissolved in water (8.00 mL), and the solution was added to a solution of compound 75-b (1.00 g, 3.21 mmol, 1.00 eq) dissolved in tetrahydrofuran (8.00 mL). The reaction was stirred at room temperature for 2 hours. After the reaction was completed, the reaction solution was added with water (10 mL), adjusted to pH of 3-4 with 1 N dilute hydrochloric acid, and extracted with dichloromethane/methanol (50 mL×2, 10:1). The organic phase was dried over anhydrous sodium sulfate, filtered and concentrated to give the product of compound 75-c (1.13 g, crude) as a colorless oil, which was used directly in the next step without purification. LCMS m/z=283.9 [M+H]$^+$.

Step 3: Synthesis of Compound 75-d

Compound 75-c (224.84 mg, 792.51 μmol, 1.40 eq) was dissolved in dichloromethane (10 mL), and N-methylmorpholine (171.78 mg, 1.70 mmol, 186.71 μL, 3.00 eq), HOBt (152.98 mg, 1.13 mmol, 2.00 eq), EDCl (217.04 mg, 1.13 mmol, 2.00 eq) and compound 1-n (200.00 mg, 566.08 μmol, 1.00 eq) were added thereto. The reaction was stirred at room temperature for 15 hours. After the reaction was completed, the reaction solution was concentrated to give a crude product. The crude product was purified by column chromatography (petroleum ether:ethyl acetate=1:0~2:1), to give the product of compound 75-d (350.00 mg, yield: 91%) as a colorless oil. LCMS m/z=641.1 [M+Na]$^+$.

Step 4: Synthesis of Compound 75-e

Compound 75-d (520.00 mg, 840.06 μmol, 1.00 eq) was dissolved in dichloromethane (15.00 mL), and PIDA (1.35 g, 4.20 mmol, 5.00 eq) and TEMPO (132.10 mg, 840.06 μmol, 1.00 eq) were added thereto. The reaction was stirred at room temperature for 39 hours. After the reaction was completed, the reaction solution was added with dichloromethane (40 mL) for dilution, and washed with saturated sodium hydrogen carbonate solution (30 mL) and saturated brine (30 mL×2). The organic phase was dried over anhydrous sodium sulfate, filtered and concentrated to give a crude product. The crude product was purified by column chromatography (petroleum ether:ethyl acetate=1:0~2:1), to give the product of compound 75-e (500.00 mg, yield: 68%) as a yellow oil. LCMS m/z=639.0 [M+Na]$^+$.

Step 5: Synthesis of Compound 75

Compound 75-e (500.00 mg, 810.39 μmol, 1.00 eq) was dissolved in dichloromethane (5.00 mL), and trifluoroacetic acid (5.00 mL, 67.53 mmol, 83.33 eq) was added thereto. The reaction was stirred at room temperature for 2 hours. After the reaction was completed, the reaction solution was spin-dried to give a crude product. The crude product was purified by preparative HPLC (in trifluoroacetic acid condition), and lyophilized to give compound 75 (300.00 mg, yield: 66%). $^1$H NMR (400 MHz, DMSO-$d_6$) δ=8.48 (br. s., 1H), 7.56 (br. s., 1H), 7.43 (d, J=8.53 Hz, 2H), 7.16 (d, J=8.53 Hz, 2H), 5.23 (br. s., 2H), 4.62 (br. s., 1H), 3.95-4.15 (m, 2H), 2.84-3.12 (m, 3H), 2.58-2.78 (m, 2H), 1.76 (br. s., 2H), 1.55 (br. s., 2H); LCMS m/z=583.1 [M+Na]$^+$.

Example 76: Compound 76

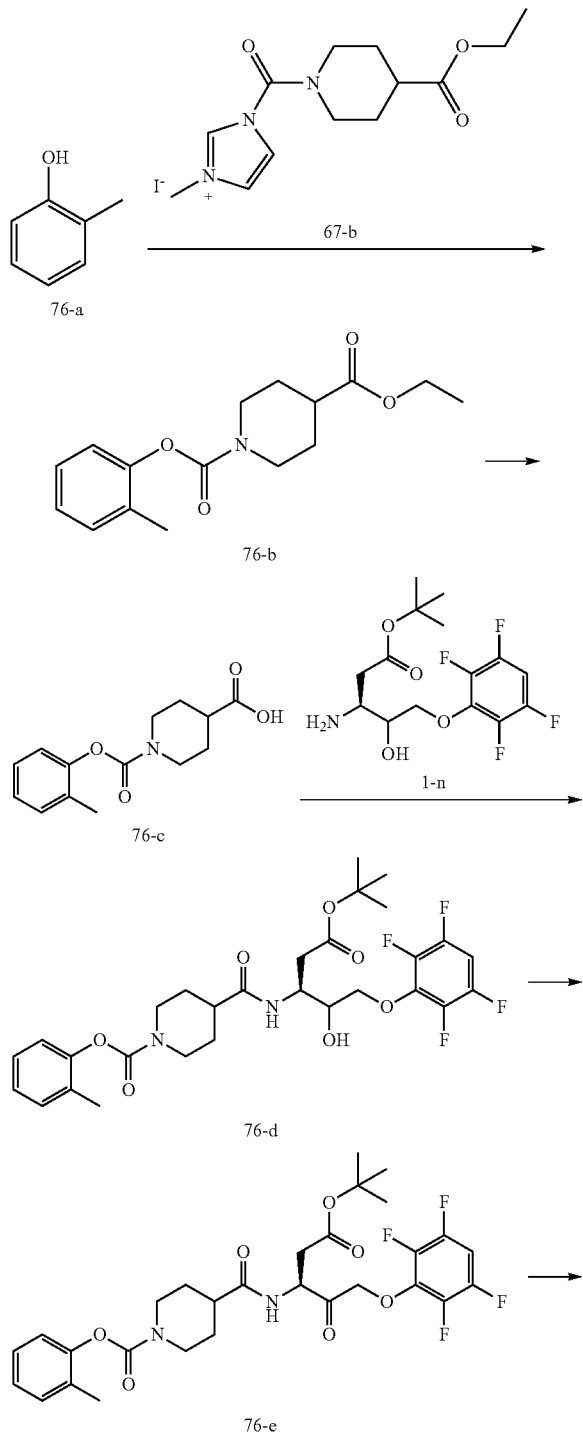

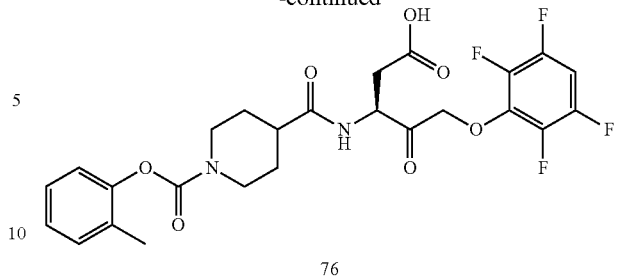

Step 1: Synthesis of Compound 76-b

Compound 76-a (500.00 mg, 4.62 mmol, 480.77 μL, 1.00 eq) was dissolved in acetonitrile (25.00 mL), and triethylamine (701.25 mg, 6.93 mmol, 960.61 μL, 1.50 eq) and compound 67-b (2.54 g, 6.47 mmol, 1.40 eq) were added thereto, followed by warmed up to 80° C. and stirring for 15 hours. After the reaction was completed, the reaction solution was concentrated, added with dichloromethane (50 mL) for dissolution, and then washed with water (40 mL) and saturated brine (40 mL). The organic phase was dried over anhydrous sodium sulfate, filtered and concentrated to give a crude product. The crude product was purified by column chromatography (petroleum ether:ethyl acetate=1:0~9:1), to give the product of compound 76-b (1.30 g, yield: 90%) as a colorless oil. LCMS m/z=292.4 [M+H]$^+$.

Step 2: Synthesis of Compound 76-c

LiOH.H$_2$O (374.28 mg, 8.92 mmol, 2.00 eq) was dissolved in water (8.00 mL), and the solution was added to a solution of compound 76-b (1.30 g, 4.46 mmol, 1.00 eq) dissolved in tetrahydrofuran (8.00 mL). The reaction was stirred at room temperature for 5 hours. After the reaction was completed, the reaction solution was added with water (10 mL), adjusted to pH of 3-4 with 1 N dilute hydrochloric acid, and extracted with dichloromethane/methanol (50 mL×2, 10:1). The organic phase was dried over anhydrous sodium sulfate, filtered, and concentrated to give the product of compound 76-c (1.15 g, crude) as a colorless oil, which was used directly in the next step without purification. LCMS m/z=263.9 [M+H]$^+$.

Step 3: Synthesis of Compound 76-d

Compound 76-c (208.66 mg, 792.51 μmol, 1.40 eq) was dissolved in dichloromethane (10 mL), and triethylamine (171.84 mg, 1.70 mmol, 235.40 μL, 3.00 eq), T$_3$P (360.23 mg, 1.13 mmol, 336.66 μL, 2.00 eq) and compound 1-n (200.00 mg, 566.08 μmol, 1.00 eq) were added thereto. The reaction was stirred at room temperature for 15 hours. After the reaction was completed, the reaction solution was added with dichloromethane (30 mL) for dilution, and washed with water (30 mL) and saturated brine (30 mL×2). The organic phase was dried over anhydrous sodium sulfate, filtered and concentrated to give a crude product. The crude product was purified by column chromatography (petroleum ether:ethyl acetate=1:0~1:1), to give the product of compound 76-d (300.00 mg, yield: 89%) as a colorless oil. LCMS m/z=621.1 [M+Na]$^+$.

Step 4: Synthesis of Compound 76-e

Compound 76-d (300.00 mg, 501.09 μmol, 1.00 eq) was dissolved in dichloromethane (10.00 mL), and PIDA (624.75 mg, 1.94 mmol, 3.87 eq) and TEMPO (78.81 mg, 501.09 μmol, 1.00 eq) were added thereto. The reaction was stirred at room temperature for 39 hours. After the reaction was completed, the reaction solution was added with dichloromethane (40 mL) for dilution, and washed with saturated sodium hydrogen carbonate solution (30 mL) and saturated brine (30 mL). The organic phase was dried over anhydrous sodium sulfate, filtered and concentrated to give a crude product. The crude product was purified by column chromatography (petroleum ether:ethyl acetate=1:0~2:1), to give the product of compound 76-e (290.00 mg, yield: 74.68%) as a yellow oil. LCMS m/z=619.1 [M+Na]$^+$.

Step 5: Synthesis of Compound 76

Compound 76-e (290.00 mg, 486.11 μmol, 1.00 eq) was dissolved in dichloromethane (5.00 mL), and trifluoroacetic acid (5.00 mL, 67.53 mmol, 138.92 eq) was added thereto. The reaction was stirred at room temperature for 2 hours. After the reaction was completed, the reaction solution was spin-dried to give a crude product. The crude product was purified by preparative HPLC (in trifluoroacetic acid condition), and lyophilized to give compound 76 (150.00 mg, yield: 57%). $^1$H NMR (400 MHz, DMSO-d$_6$) δ=12.43 (br. s., 1H), 8.48 (br. s., 1H), 7.54 (br. s., 1H), 7.17 (br. s., 4H), 4.72-5.52 (m, 2H), 3.85-4.65 (m, 3H), 2.60-3.17 (m, 5H), 2.09 (br. s., 3H), 1.32-1.86 (m, 4H); LCMS m/z=541.1 [M+H]$^+$.

Example 77: Compound 77

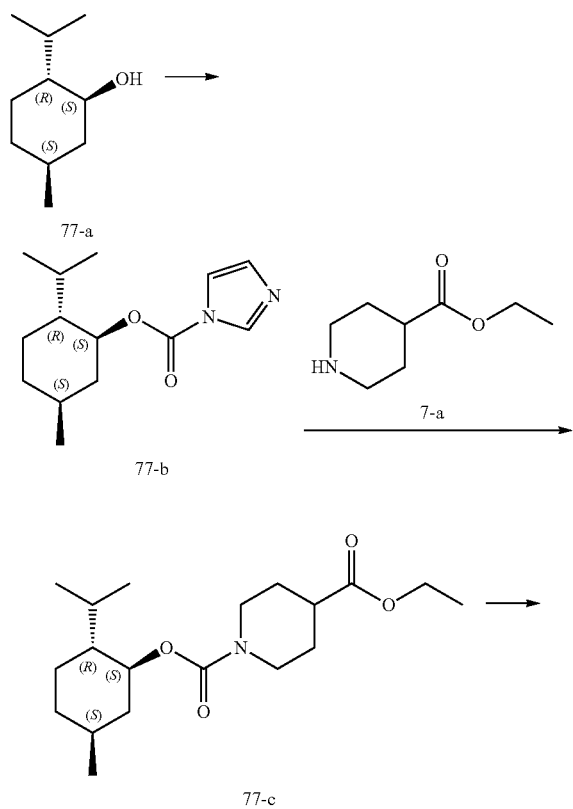

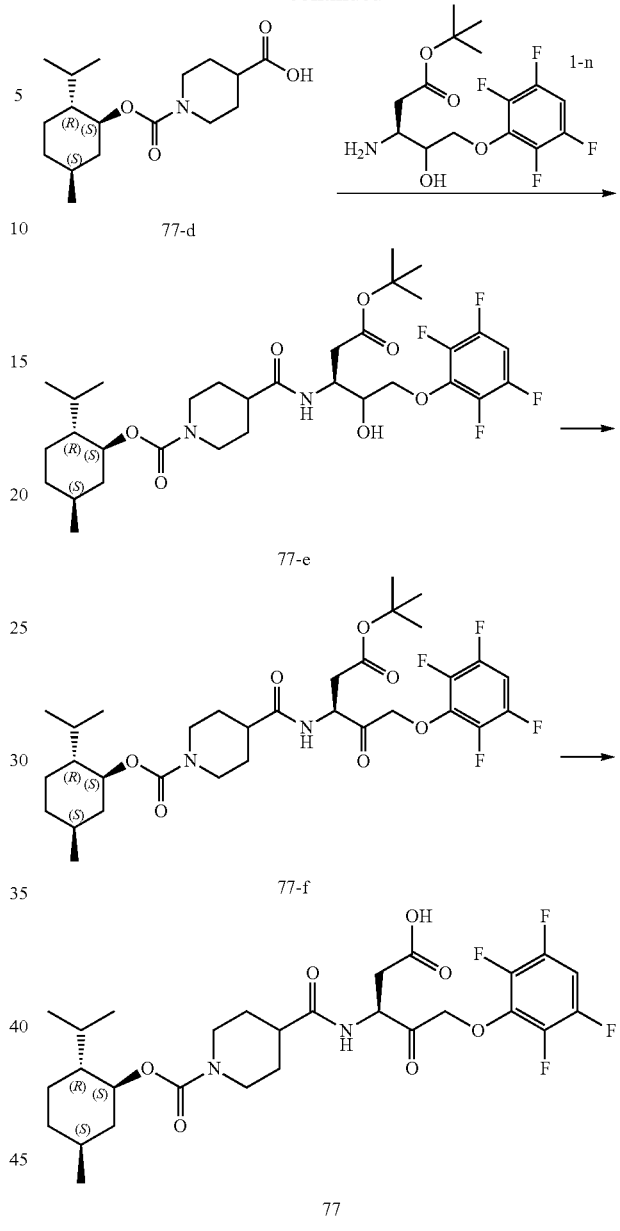

Step 1: Synthesis of Compound 77-b

Compound 77-a (15.00 g, 9.60 mmol, 1.00 eq) (pyridine, 10%) and CDI (20.24 g, 124.80 mmol, 13.00 eq) were dissolved in tetrahydrofuran (140.00 mL). The above solution was stirred at 15° C. for 3 hours. After the reaction was completed, the reaction solution was added with water (250 mL), and extracted with dichloromethane (200 mL×3). The organic phase was dried over anhydrous sodium sulfate, filtered and concentrated to give a crude product. The crude product was subjected to column chromatography (petroleum ether:ethyl acetate=1:0~5:1) to give the product of compound 77-b (2.15 g, yield: 89%) as a colorless oil. $^1$H NMR (400 MHz, CHLOROFORM-d) δ=8.13 (s, 1H), 7.42 (s, 1H), 7.07 (s, 1H), 4.89 (dt, J=4.39, 10.98 Hz, 1H), 2.13-2.21 (m, 1H), 1.92 (dtd, J=2.64, 6.92, 13.90 Hz, 1H), 1.69-1.79 (m, 2H), 1.48-1.62 (m, 2H), 1.06-1.22 (m, 2H), 0.87-1.00 (m, 7H), 0.82 (d, J=7.03 Hz, 3H).

Step 2: Synthesis of Compound 77-c

Compounds 77-b (270.00 mg, 1.08 mmol, 1.00 eq) and 7-a (203.74 mg, 1.30 mmol, 199.75 μL, 1.20 eq) were dissolved in tetrahydrofuran (10.00 mL), and triethylamine (437.14 mg, 4.32 mmol, 598.82 μL, 4.00 eq) was added to the above solution. The reaction solution was stirred at 80° C. for 14 hours, then supplemented with compound 7-a (407.49 mg, 2.59 mmol, 399.50 μL, 2.40 eq) and triethylamine (437.14 mg, 4.32 mmol, 598.82 μL, 4.00 eq). The reaction solution was stirred at 80° C. for 72 hours. After the reaction was completed, the reaction solution was added with water (100 mL), and extracted with dichloromethane (100 mL×3). The organic phase was dried over anhydrous sodium sulfate, filtered and concentrated to give a crude product. The crude product was subjected to column chromatography (petroleum ether:ethyl acetate=1:0~5:1) to give the product of compound 77-c (250.00 mg, yield: 68%) as a colorless oil. $^1$H NMR (400 MHz, CHLOROFORM-d) δ=4.55 (dt, J=4.39, 10.85 Hz, 1H), 4.15 (q, J=7.03 Hz, 2H), 4.07 (d, J=10.29 Hz, 2H), 2.82-2.95 (m, 2H), 2.45 (tt, J=3.83, 10.98 Hz, 1H), 2.05 (d, J=11.80 Hz, 1H), 1.81-1.96 (m, 3H), 1.60-1.72 (m, 4H), 1.42-1.55 (m, 1H), 1.32-1.41 (m, 1H), 1.26 (t, J=7.15 Hz, 3H), 1.00-1.13 (m, 1H), 0.92-0.99 (m, 1H), 0.90 (d, J=6.78 Hz, 6H), 0.82-0.88 (m, 1H), 0.79 (d, J=7.03 Hz, 3H).

Step 3: Synthesis of Compound 77-d

Compound 77-c (250.00 mg, 736.44 μmol, 1.00 eq) was dissolved in tetrahydrofuran (15.00 mL), and a solution of LiOH.H$_2$O (185.41 mg, 4.42 mmol, 6.00 eq) dissolved in H$_2$O (15.00 mL) was added to the above solution. The reaction solution was stirred at 15° C. for 1 hour. After the reaction was completed, the reaction solution was adjusted to pH of 5 with 2 N dilute hydrochloric acid. This solution was added with water (100 mL), and extracted with dichloromethane (100 mL×3). The organic phase was dried over anhydrous sodium sulfate, filtered and concentrated to give the product of compound 77-d (230.00 mg, crude) as a colorless oil, which was used directly in the next step without purification.

Step 4: Synthesis of Compound 77-e

Compound 77-d (230.00 mg, 738.55 μmol, 1.30 eq) was dissolved in dichloromethane (20.00 mL), and compound 1-n (200.00 mg, 566.08 μmol, 1.00 eq), EDCl (148.67 mg, 775.53 μmol, 1.37 eq), HOBt (104.79 mg, 775.53 μmol, 1.37 eq) and N-methylmorpholine (171.78 mg, 1.70 mmol, 186.72 μL, 3.00 eq) were added thereto. The reaction solution was stirred under the protection of nitrogen gas at 15° C. for 15 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 77-e (340.00 mg, yield: 81%) as a colorless oil. LCMS m/z=669.1 [M+Na]$^+$.

Step 5: Synthesis of Compound 77-f

Compound 77-e (340.00 mg, 525.74 μmol, 1.00 eq) was dissolved in dichloromethane (25.00 mL), and PIDA (655.35 mg, 2.03 mmol, 3.87 eq) and TEMPO (24.80 mg, 157.72 μmol, 0.30 eq) were added thereto. The above solution was stirred under the protection of nitrogen gas at 15° C. for 16 hours, and then supplemented with TEMPO (24.8 mg, 157.72 μmol, 0.30 eq). The reaction solution was stirred at 15° C. for another 24 hours. After the reaction was completed, the reaction solution was added with 150 mL of ethyl acetate. The solution was washed successively with saturated sodium hydrogen carbonate (100 mL), saturated brine (100 mL) and water (100 mL). The organic phase was dried over anhydrous sodium sulfate, filtered and concentrated to give a crude product. The crude product was subjected to column chromatography (petroleum ether:ethyl acetate=1:0~3:1) to give the product of compound 77-f (257.00 mg, yield: 75%) as a pale yellow oil. LCMS m/z=667.2 [M+Na]$^+$.

Step 6: Synthesis of Compound 77

Compound 77-f (310.00 mg, 480.84 μmol, 1.00 eq) was dissolved in dichloromethane (12.00 mL), and trifluoroacetic acid (9.24 g, 81.04 mmol, 6.00 mL, 168.54 eq) was added thereto. The reaction solution was stirred under the protection of nitrogen gas at 15° C. for 1 hour. After the reaction was completed, the reaction solution was concentrated to give a crude product. The crude product was purified by preparative HPLC (in trifluoroacetic acid condition), and lyophilized to give the product of compound 77 (189.90 mg, yield: 67%). $^1$H NMR (400 MHz, DMSO-d$_6$) δ=8.45 (d, J=7.53 Hz, 1H), 7.50-7.68 (m, 1H), 5.12-5.29 (m, 2H), 4.58 (q, J=6.53 Hz, 1H), 4.43 (dt, J=4.02, 10.79 Hz, 1H), 3.95 (d, J=12.05 Hz, 2H), 2.64-2.92 (m, 3H), 2.57 (dd, J=7.03, 17.07 Hz, 1H), 2.31-2.45 (m, 1H), 1.76-1.94 (m, 2H), 1.56-1.72 (m, 4H), 1.27-1.50 (m, 4H), 0.90-1.10 (m, 2H), 0.86 (dd, J=4.77, 6.27 Hz, 6H), 0.77-0.84 (m, 1H), 0.73 (d, J=6.53 Hz, 3H); LCMS m/z=611.1 [M+Na]$^+$.

Example 78: Compound 78

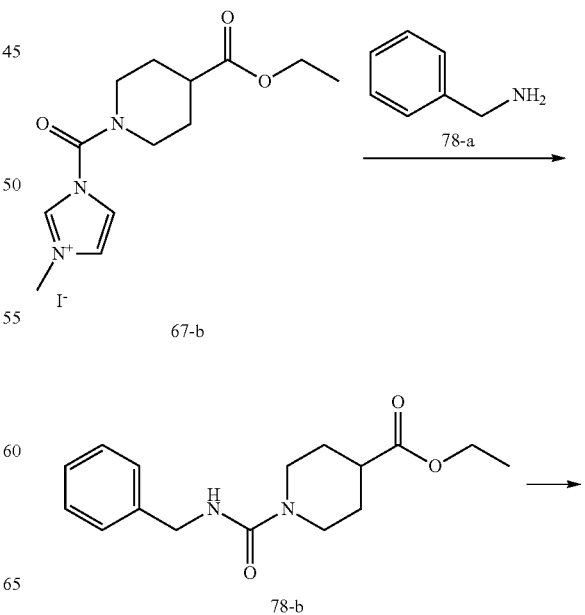

-continued

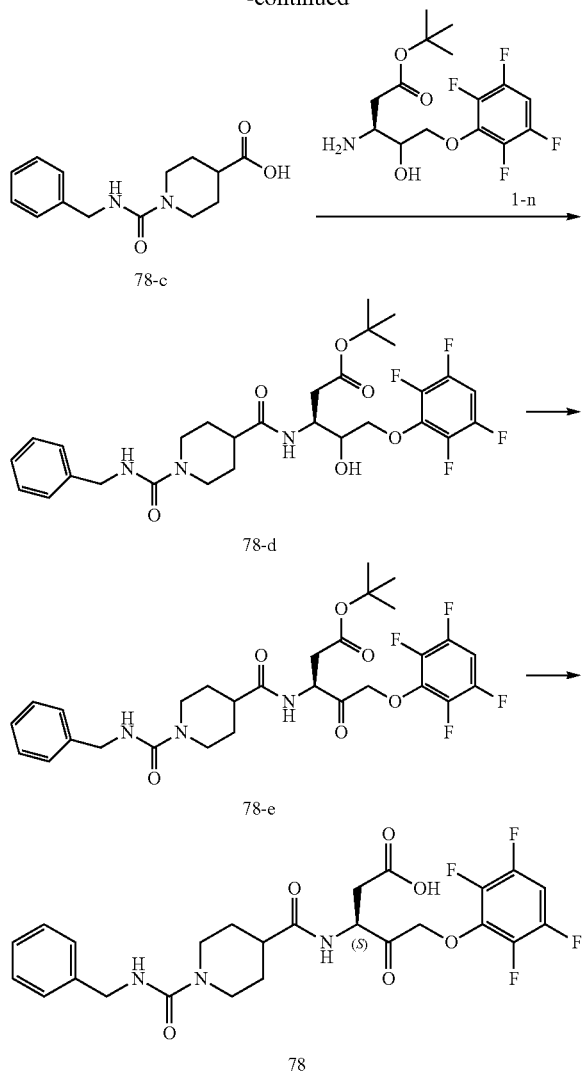

Step 1: Synthesis of Compound 78-b

Compound 67-b (1.50 g, 5.65 mmol, 1.00 eq) was dissolved in dichloromethane (15.00 mL), and compound 78-a (605.40 mg, 5.65 mmol, 617.76 μL, 1.00 eq) and triethylamine (571.72 mg, 5.65 mmol, 783.18 μL, 1.00 eq) were added to the above solution. The reaction solution was stirred at 25° C. for 48 hours. After the reaction was completed, the reaction solution was added with dichloromethane (50 mL), and the resulting solution was washed with 2 M dilute hydrochloric acid (25 mL×2). The organic phase was dried over anhydrous sodium sulfate, filtered and concentrated to give a crude product. The crude product was subjected to column chromatography (petroleum ether:ethyl acetate=1:0~1:1) to give the product of compound 78-b (1.21 g, yield: 74%) as a pale yellow solid. LCMS m/z=290.9 $[M+H]^+$.

Step 2: Synthesis of Compound 78-c

Compound 78-b (1.21 g, 4.17 mmol, 1.00 eq) was dissolved in tetrahydrofuran (10.00 mL) and water (10.00 mL), and LiOH.H$_2$O (349.95 mg, 8.34 mmol, 2.00 eq) was added to the above solution in an ice bath. The reaction solution was stirred at 0° C. for 1.5 hours. After the reaction was completed, the reaction solution was concentrated, and adjusted to pH of 2 with 2 N dilute hydrochloric acid. The precipitated pale yellow solid product was filtered out, and spin-dried to give the product of compound 78-c (1.02 g, yield: 93%), which was used directly in the next step without purification. LCMS m/z=262.9 $[M+H]^+$.

Step 3: Synthesis of Compound 78-d

Compound 78-c (163.33 mg, 622.69 μmol, 1.10 eq) and HOBt (114.72 mg, 849.12 μmol, 1.50 eq) were dissolved in dichloromethane (10.00 mL), and EDCl (162.75 mg, 849.12 μmol, 1.50 eq) was added thereto. The above solution was stirred for 15 min, and then added with a solution of compound 1-n (200.00 mg, 566.08 μmol, 1.00 eq) and N,N-diisopropylethylamine (146.32 mg, 1.13 mmol, 197.73 μL, 2.00 eq) dissolved in dichloromethane (5.00 mL). The reaction solution was stirred at 25° C. for 15 hours. After the reaction was completed, the reaction solution was added with dichloromethane, and washed respectively with saturated sodium hydrogen carbonate solution (50 mL×2) and saturated sodium chloride solution (50 mL). The organic phase was dried over anhydrous sodium sulfate, filtered and concentrated to give a crude product. The crude product was subjected to column chromatography (petroleum ether:ethyl acetate=1:0~1:2) to give the product of compound 78-d (300.00 mg, yield: 89%) as a off white oil. LCMS m/z=620.3 $[M+Na]^+$.

Step 4: Synthesis of Compound 78-e

Compound 78-d (226.00 mg, 378.18 μmol, 1.00 eq) was dissolved in dichloromethane (10.00 mL), and DMP (352.88 mg, 832.00 μmol, 257.58 μL, 2.20 eq) was added thereto under the protection of nitrogen gas at 0° C. The reaction solution was stirred at 0° C. for 5 min, and then warmed up to 30° C. and stirred for another 50 min. After the reaction was completed, the reaction solution was cooled down to 0° C., and washed with saturated sodium hydrogen carbonate solution/sodium sulfite solution (1:1, 10 mL×2). The aqueous phase was extracted with dichloromethane (20 mL). The organic phases were combined, dried over anhydrous sodium sulfate, filtered, and concentrated to give a crude product. The crude product was subjected to column chromatography (petroleum ether:ethyl acetate=5:1~1:1) to give the product of compound 78-e (186.00 mg, yield: 77%). $^1$H NMR (400 MHz, CHLOROFORM-d) δ=7.25-7.38 (m, 5H), 6.74-6.84 (m, 2H), 4.98-5.17 (m, 2H), 4.90-4.97 (m, 1H), 4.78 (t, J=5.02 Hz, 1H), 4.43 (d, J=5.52 Hz, 2H), 4.01 (dd, J=4.02, 8.03 Hz, 2H), 2.98 (dd, J=4.77, 16.81 Hz, 1H), 2.82-2.92 (m, 2H), 2.75 (dd, J=5.27, 16.81 Hz, 1H), 2.36 (tt, J=3.64, 11.42 Hz, 1H), 1.80-1.94 (m, 2H), 1.75 (d, J=4.02 Hz, 1H), 1.66 (d, J=4.02 Hz, 1H), 1.43 (s, 9H); LCMS m/z=596.3 $[M+H]^+$.

Step 5: Synthesis of Compound 78

Compound 78-e (160.00 mg, 268.65 μmol, 1.00 eq) was dissolved in ethyl acetate (5.00 mL), and hydrochloric acid ethyl acetate solution (20.00 mmol, 10.00 mL, 74.45 eq) was added thereto in an ice bath. After the addition was completed, the reaction solution was stirred at 30° C. for 50 min. After the reaction was completed, the reaction solution was spin-dried to give a crude product. The crude product was purified by preparative HPLC (in formic acid condition), and lyophilized to give the product of compound 78 (64.10 mg, yield: 44%). ¹H NMR (400 MHz, CHLOROFORM-d) δ=7.28-7.36 (m, 3H), 7.25 (br. s., 2H), 6.74-6.85 (m, 1H), 5.04 (br. s., 1H), 4.94 (d, J=6.78 Hz, 1H), 4.37 (d, J=4.52 Hz, 2H), 3.94 (d, J=12.55 Hz, 3H), 3.01 (dd, J=7.15, 17.19 Hz, 2H), 2.85 (t, J=12.55 Hz, 2H), 2.37 (br. s., 1H), 1.83 (br. s., 2H), 1.57-1.72 (m, 2H); LCMS m/z=540.3 [M+H]⁺.

Example 79: Compound 79

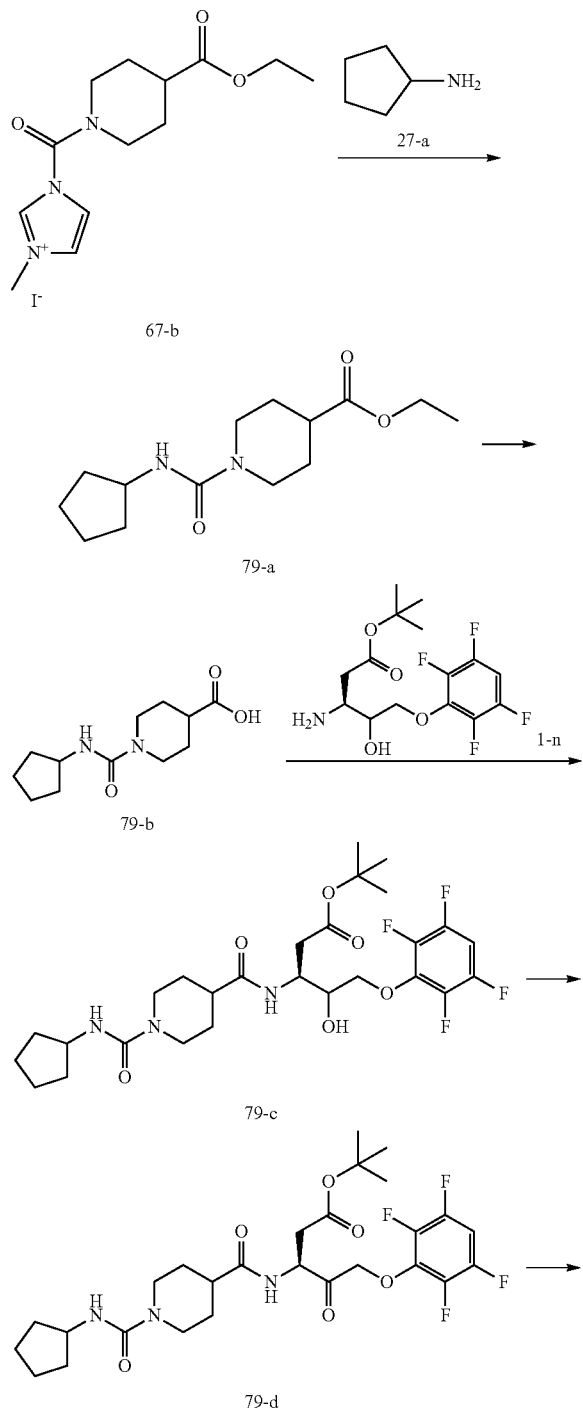

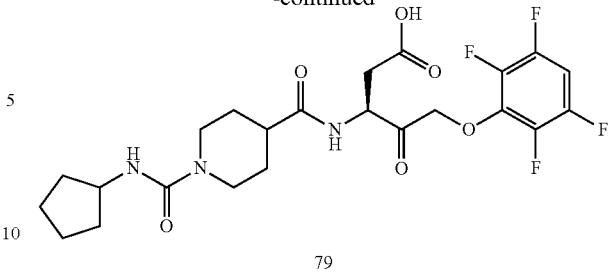

Step 1: Synthesis of Compound 79-a

Compound 67-b (1.50 g, 3.81 mmol, 1.00 eq) was dissolved in dichloromethane (37.50 mL), and compound 27-a (324.42 mg, 3.81 mmol, 377.23 μL, 1.00 eq) and triethylamine (385.53 mg, 3.81 mmol, 528.13 μL, 1.00 eq) were added to the above solution. The reaction solution was stirred at 18° C. for 17 hours. After the reaction was completed, dichloromethane (100 mL) was added, and the resulting solution was washed respectively with 1 N dilute hydrochloric acid (80 mL×2), saturated sodium chloride (80 mL) and water (80 mL). The organic phase was dried over anhydrous sodium sulfate, filtered and concentrated to give the product of compound 79-a (890.00 mg, crude) as a yellow solid, which was used directly in the next step without purification. ¹H NMR (400 MHz, CHLOROFORM-d) δ=4.37 (d, J=6.02 Hz, 1H), 4.02-4.19 (m, 3H), 3.85 (td, J=3.33, 13.43 Hz, 2H), 2.80-2.92 (m, 2H), 2.44 (tt, J=3.92, 10.89 Hz, 1H), 1.94-2.05 (m, 2H), 1.90 (dd, J=3.14, 13.43 Hz, 2H), 1.52-1.74 (m, 6H), 1.28-1.40 (m, 2H), 1.25 (t, J=7.15 Hz, 3H).

Step 2: Synthesis of Compound 79-b

Compound 79-a (890.00 mg, 3.32 mmol, 1.00 eq) was dissolved in tetrahydrofuran (25.00 mL), and a solution of LiOH.H₂O (208.96 mg, 4.98 mmol, 1.50 eq) dissolved in water (25.00 mL) was added to the above solution. The reaction solution was stirred at 18° C. for 1 hour. After the reaction was completed, the reaction solution was adjusted to pH of 5 with 2 N dilute hydrochloric acid. This solution was added with water (150 mL), and extracted with dichloromethane (150 mL×3). The organic phase was dried over anhydrous sodium sulfate, filtered and concentrated to give the product of compound 79-b (800.00 mg, crude) as a pale yellow oil, which was used directly in the next step without purification. LCMS m/z=240.9 [M+H]⁺.

Step 3: Synthesis of Compound 79-c

Compound 79-b (270.00 mg, 1.12 mmol, 1.00 eq) was dissolved in dichloromethane (20.00 mL), and compound 1-n (395.71 mg, 1.12 mmol, 1.00 eq), EDCl (294.14 mg, 1.53 mmol, 1.37 eq), HOBt (207.33 mg, 1.53 mmol, 1.37 eq) and N-methylmorpholine (339.86 mg, 3.36 mmol, 369.42 μL, 3.00 eq) were added thereto. The reaction solution was stirred under the protection of nitrogen gas at 18° C. for 15 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=5:1~1:2) to give the product of compound 79-c (300.00 mg, yield: 44%) as a pale yellow oil. LCMS m/z=576.3 [M+H]⁺.

Step 4: Synthesis of Compound 79-d

Compound 79-c (300.00 mg, 521.20 μmol, 1.00 eq) was dissolved in dichloromethane (6.00 mL), and PIDA (649.70 mg, 2.02 mmol, 3.87 eq) and TEMPO (24.59 mg, 156.36 μmol, 0.30 eq) were added thereto. The reaction solution was stirred under the protection of nitrogen gas at 18° C. for 16 hours. The reaction solution was added with 150 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=1:0~1:2) to give the product of compound 79-d (180.00 mg, yield: 57%) as a colorless oil. LCMS m/z=574.3 [M+H]⁺.

Step 5: Synthesis of Compound 79

Compound 79-d (180.00 mg, 313.82 μmol, 1.00 eq) was dissolved in dichloromethane (6.70 mL), and trifluoroacetic acid (5.15 g, 45.14 mmol, 3.34 mL, 143.85 eq) was added thereto. The reaction solution was stirred under the protection of nitrogen gas at 18° C. for 1 hour. After the reaction was completed, the reaction solution was concentrated to give a crude product. The crude product was purified by preparative HPLC (in trifluoroacetic acid condition), and lyophilized to give the product of compound 79 (81.00 mg, yield: 50%). ¹H NMR (400 MHz, DMSO-d₆) δ=12.45 (br. s., 1H), 8.40 (d, J=7.28 Hz, 1H), 7.50-7.66 (m, 1H), 6.18 (d, J=6.78 Hz, 1H), 5.13-5.28 (m, 2H), 4.58 (q, J=6.78 Hz, 1H), 3.82-4.00 (m, 3H), 2.69-2.78 (m, 1H), 2.54-2.67 (m, 3H), 2.28-2.39 (m, 1H), 1.70-1.82 (m, 2H), 1.61 (br. s., 4H), 1.29-1.52 (m, 6H); LCMS m/z=518.1 [M+H]⁺.

Example 80: Compound 80

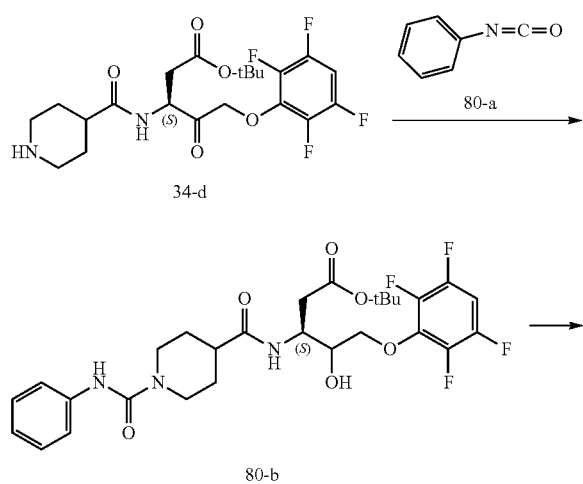

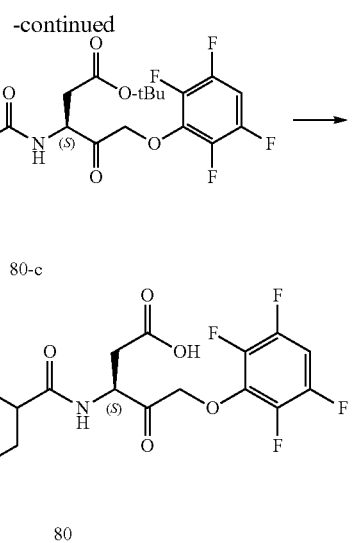

Step 1: Synthesis of Compound 80-b

Compound 34-d (200.00 mg, 430.62 μmol, 1.00 eq) was dissolved in dichloromethane (3.00 mL), and compound 80-a (2.61 g, 21.91 mmol, 2.37 mL, 50.88 eq) was added thereto. The mixture was stirred at 20° C. for 2 hours. After the reaction was completed, the reaction solution was added with water (10 mL) for quenching, and extracted with dichloromethane (10 mL×3). The organic phases were combined, dried over anhydrous sodium sulfate, filtered, and concentrated to give a crude product. The crude product was purified by column chromatography (petroleum ether:ethyl acetate=9:1~0:1) to give compound 80-b (159.00 mg, yield: 51%) as a pale yellow oil.

Step 2: Synthesis of Compound 80-c

Compound 80-b (149.00 mg, 255.32 μmol, 1.00 eq) was dissolved in dichloromethane (1.00 mL), and PIDA (149.00 mg, 255.32 μmol, 1.00 eq) and TEMPO (20.07 mg, 127.66 μmol, 0.50 eq) were added thereto. The reaction solution was stirred under the protection of nitrogen gas at 20° C. for 1 hour. The reaction solution was added with 70 mL of ethyl acetate. The solution was washed successively with saturated sodium hydrogen carbonate (40 mL), saturated brine (80 mL) and water (40 mL). The organic phase was dried over anhydrous sodium sulfate, filtered and concentrated to give a crude product. The crude product was subjected to column chromatography (petroleum ether:ethyl acetate=5: 1~1:1) to give the product of compound 80-c (27.00 mg, yield: 16%) as a pale yellow solid.

Step 3: Synthesis of Compound 80

Compound 80-c (27.00 mg, 46.43 μmol, 1.00 eq) was dissolved in dichloromethane (2.00 mL), and trifluoroacetic acid (0.2 mL) was added thereto. The reaction solution was stirred under the protection of nitrogen gas at 20° C. for 1 hour. After the reaction was completed, the reaction solution was concentrated to give a crude product. The crude product was purified by preparative HPLC (in trifluoroacetic acid condition), and lyophilized to give the product of compound 80 (13.00 mg, yield: 53%). ¹H NMR (400 MHz, DMSO-d6) δ=8.47 (s, 1H), 8.39 (d, J=7.03 Hz, 1H), 7.50-7.64 (m, 1H), 7.44 (d, J=7.53 Hz, 2H), 7.21 (t, J=7.78 Hz, 2H), 6.91 (t, J=7.28 Hz, 1H), 5.11 (br. s., 1H) 4.63 (d, J=6.53 Hz, 1H), 4.10 (d, J=13.05 Hz, 2H), 2.81 (t, J=12.80 Hz, 2H), 2.56-2.76 (m, 2H), 2.43 (t, J=11.29 Hz, 1H), 1.70 (br. s., 2H), 1.48 (q, J=11.71 Hz, 2H); LCMS m/z=526.1 [M+H]+.

Example 81: Compound 81

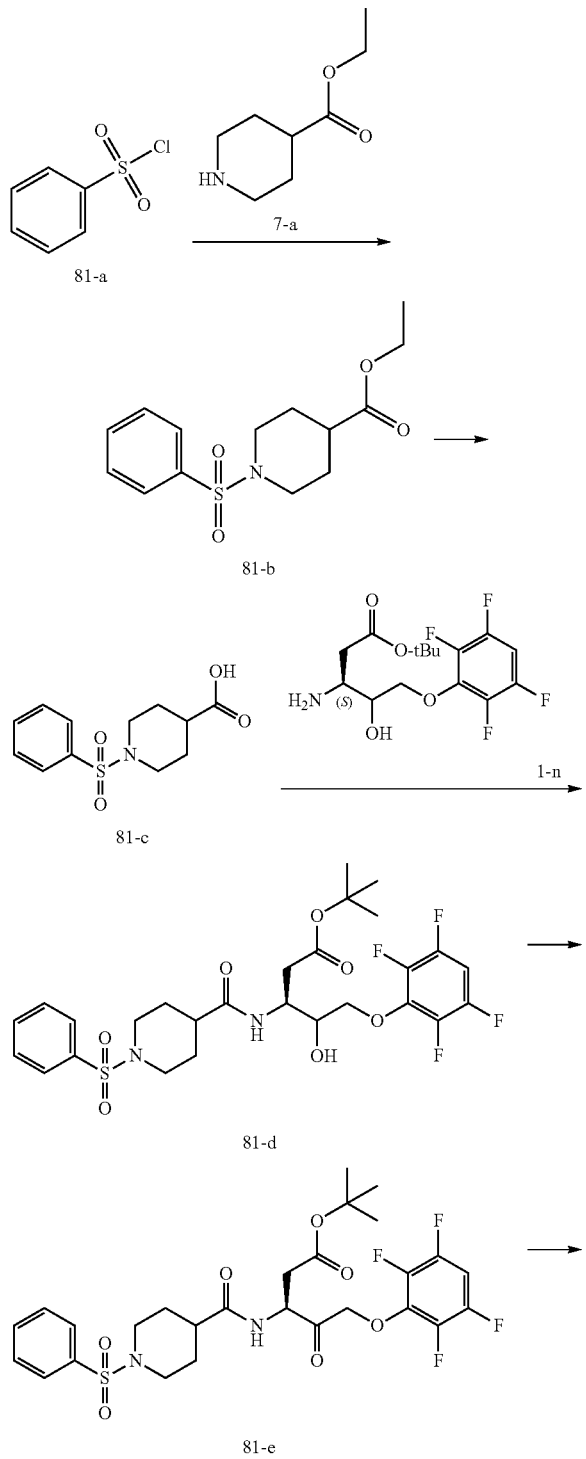

Step 1: Synthesis of Compound 81-b

Compound 7-a (1.16 g, 7.36 mmol, 1.13 mL, 1.30 eq) and triethylamine (1.72 g, 16.99 mmol, 2.35 mL, 3.00 eq) were dissolved in dichloromethane (10.00 mL), followed by slowly adding compound 81-a (1.00 g, 5.66 mmol, 724.64 µL, 1.00 eq) and stirring at room temperature for 2 hours. After the reaction was completed, the reaction was added with 100 mL of water, and extracted with dichloromethane (50 mL×3). The organic phases were combined, washed with water (50 mL) and brine (50 mL), dried over anhydrous sodium sulfate, filtered, concentrated and purified by column chromatography (petroleum ether:ethyl acetate=1:0~1:1) to give compound 81-b (1.10 g, yield: 65%).

Step 2: Synthesis of Compound 81-c

Compound 81-b (400.00 mg, 1.35 mmol, 1.00 eq) was dissolved in a mixed solvent of tetrahydrofuran (10.00 mL) and water (10.00 mL), and LiOH.H$_2$O (225.77 mg, 5.38 mmol, 4.00 eq) was added thereto. The mixture was stirred at 25° C. for 2 hours. After the reaction was completed, the reaction mixture was added with water (50 mL), adjusted to pH=7 with dilute hydrochloric acid (1 N), and extracted with ethyl acetate (50 mL×3). The organic phases were combined, washed with water (50 mL) and brine (50 mL), dried over anhydrous sodium sulfate, filtered, and concentrated to give compound 81-c (300.00 mg, yield: 83%). $^1$H NMR (400 MHz, CHLOROFORM-d) δ=7.76 (d, J=7.5 Hz, 2H), 7.60 (d, J=7.0 Hz, 1H), 7.57-7.49 (m, 2H), 3.75-3.61 (m, 2H), 2.47 (dt, J=2.3, 11.4 Hz, 2H), 2.36-2.25 (m, 1H), 1.99 (dd, J=3.5, 13.6 Hz, 2H), 1.90-1.73 (m, 2H).

Step 3: Synthesis of Compound 81-d

Compound 81-c (250.00 mg, 928.26 µmol, 1.00 eq) was dissolved in dichloromethane (10.00 mL), and compound 1-n (327.96 mg, 928.26 µmol, 1.00 eq), EDCl (243.79 mg, 1.27 mmol, 1.37 eq), HOBt (171.83 mg, 1.27 mmol, 1.37 eq) and NMM (281.68 mg, 2.78 mmol, 306.18 µL, 3.00 eq) were added thereto. The reaction solution was stirred under the protection of nitrogen gas at 25° C. for 12 hours. After the reaction was completed, the reaction solution was added with water (50 mL), and extracted with dichloromethane (50 mL×3). The organic phases were combined, dried over anhydrous sodium sulfate, filtered and concentrated to give a crude product. The crude product was subjected to column chromatography (petroleum ether:ethyl acetate=1:0~5:4) to give the product of compound 81-d (350.00 mg, yield of 62%). $^1$H NMR (400 MHz, CHLOROFORM-d) δ=7.83-7.72 (m, 2H), 7.65-7.59 (m, 1H), 7.57-7.51 (m, 2H), 6.85-

6.75 (m, 1H), 6.64-6.54 (m, 1H), 6.36-6.27 (m, 1H), 4.40-4.00 (m, 5H), 3.86-3.74 (m, 2H), 2.39 (br. s., 6H), 2.11-1.74 (m, 6H), 1.46-1.37 (m, 9H).

Step 4: Synthesis of Compound 81-e

Compound 81-d (150.00 mg, 248.09 μmol, 1.00 eq) was dissolved in dichloromethane (5.00 mL), and DMP (231.49 mg, 545.80 μmol, 168.97 μL, 2.20 eq) was added thereto. The reaction solution was stirred at 25° C. for 5 hours. The reaction solution was added with 150 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was purified by preparative silica gel plates (petroleum ether:ethyl acetate=2:1) to give the product of compound 81-e (80.00 mg, yield: 45%) as a colorless oil.

Step 5: Synthesis of Compound 81

Compound 81-e (80.00 mg, 132.76 μmol, 1.00 eq) was dissolved in dichloromethane (4 mL), and trifluoroacetic acid (1 mL) was added thereto. The reaction solution was stirred under the protection of nitrogen gas at 25° C. for 1 hour. After the reaction was completed, the reaction solution was concentrated to give a crude product. The crude product was purified by preparative HPLC (in trifluoroacetic acid condition), and lyophilized to give the product of compound 81 (12.00 mg, yield of 17%). $^1$H NMR (400 MHz, DMSO-$d_6$) δ=8.38-8.21 (m, 1H), 7.87-7.46 (m, 6H), 5.27-4.88 (m, 2H), 4.65-4.49 (m, 1H), 3.59 (d, J=11.3 Hz, 3H), 2.65 (br. s., 2H), 2.29 (t, J=11.4 Hz, 3H), 2.05-1.89 (m, 1H), 1.84-1.38 (m, 4H), 1.22 (br. s., 1H).

Example 82: Compound 82

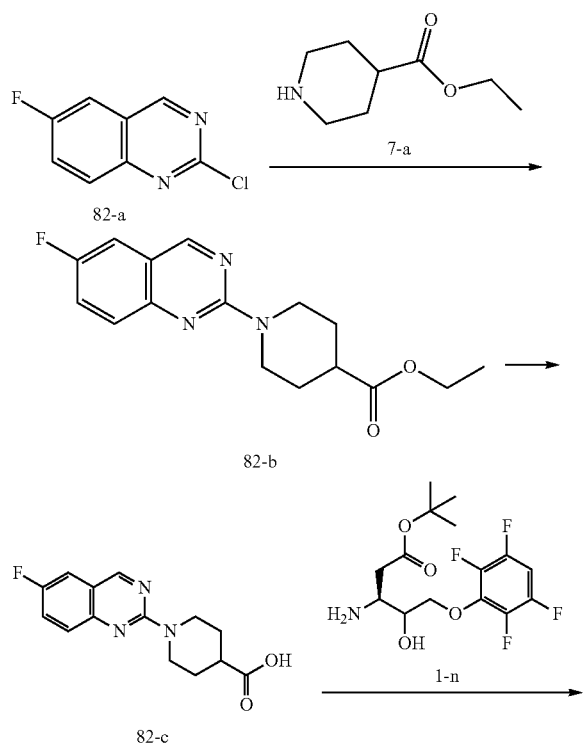

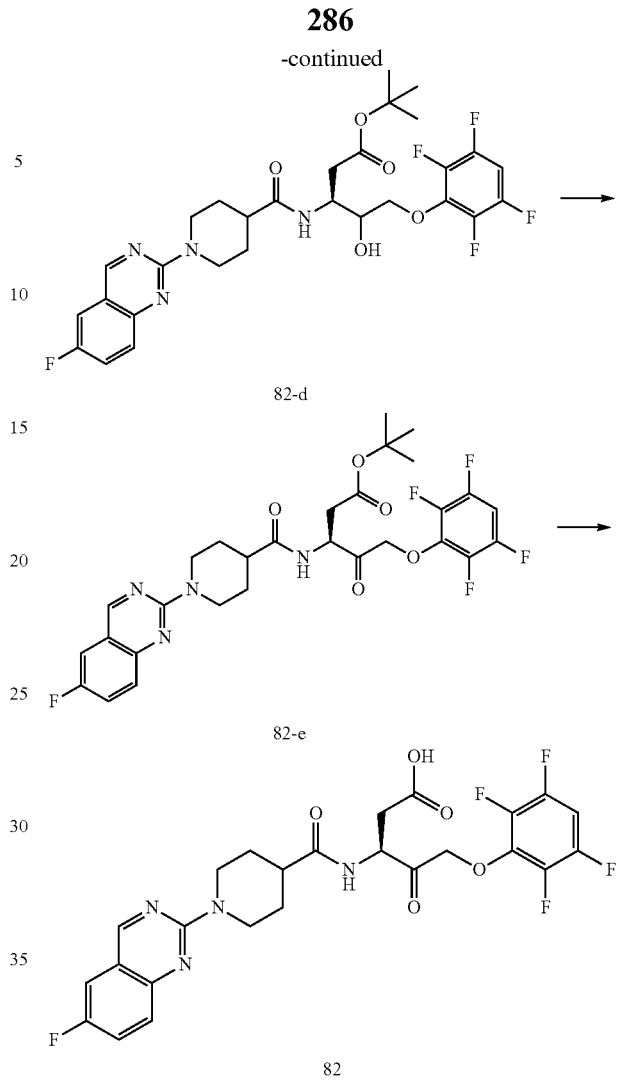

Step 1: Synthesis of Compound 82-b

Compounds 82-a (190.00 mg, 1.04 mmol, 1.00 eq), 7-a (196.32 mg, 1.25 mmol, 192.47 μL, 1.20 eq) and $K_2CO_3$ (431.48 mg, 3.12 mmol, 3.00 eq) were dissolved in DMSO (8.00 mL). The above solution was stirred at 110° C. for 18 hours. After the reaction was completed, the reaction solution was added with ethyl acetate (150 mL), and washed with water (100 mL×3). The organic phase was dried over anhydrous sodium sulfate, filtered and concentrated to give a crude product. The crude product was subjected to column chromatography (petroleum ether:ethyl acetate=1:0~5:1) to give the product of compound 82-b (138.00 mg, yield: 41%) as a yellow oil. $^1$H NMR (400 MHz, CHLOROFORM-d) δ=8.96 (s, 1H), 7.56 (dd, J=4.77, 9.29 Hz, 1H), 7.44 (dt, J=2.76, 8.91 Hz, 1H), 7.29 (d, J=2.51 Hz, 1H), 4.82 (td, J=3.39, 13.30 Hz, 2H), 4.11-4.21 (m, 2H), 3.08-3.20 (m, 2H), 2.61 (tt, J=3.64, 11.17 Hz, 1H), 2.03 (dd, J=3.01, 13.55 Hz, 2H), 1.70-1.83 (m, 2H), 1.27 (t, J=7.28 Hz, 3H).

Step 2: Synthesis of Compound 82-c

Compound 82-b (138.00 mg, 454.95 μmol, 1.00 eq) was dissolved in tetrahydrofuran (10.00 mL), and a solution of $LiOH·H_2O$ (190.90 mg, 4.55 mmol, 10.00 eq) dissolved in H₂O (10.00 mL) was added to the above solution. The reaction solution was stirred at 10° C. for 2 hours. After the reaction was completed, the reaction solution was adjusted to pH of 5 with 2 N dilute hydrochloric acid. This solution was added with water (100 mL), and extracted with dichloromethane (100 mL×3). The organic phase was dried over anhydrous sodium sulfate, filtered and concentrated to give the product of compound 82-c (129.00 mg, crude) as a yellow solid, which was used directly in the next step without purification. LCMS m/z=275.9 [M+H]⁺.

Step 3: Synthesis of Compound 82-d

Compound 82-c (129.00 mg, 468.61 µmol, 1.00 eq) was dissolved in dichloromethane (15.00 mL), and compound 1-n (180.47 mg, 510.78 µmol, 1.09 eq), EDCl (123.07 mg, 642.00 µmol, 1.37 eq), HOBt (86.75 mg, 642.00 µmol, 1.37 eq) and NMM (142.20 mg, 1.41 mmol, 154.57 µL, 3.00 eq) were added thereto. The reaction solution was stirred under the protection of nitrogen gas at 20° C. for 15 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=5:1~1:1) to give the product of compound 82-d (200.00 mg, yield: 69%) as a yellow solid. LCMS m/z=611.2 [M+H]⁺.

Step 4: Synthesis of Compound 82-e

Compound 82-d (200.00 mg, 327.56 µmol, 1.00 eq) was dissolved in dichloromethane (20.00 mL), and PIDA (408.32 mg, 1.27 mmol, 3.87 eq) and TEMPO (51.51 mg, 327.56 µmol, 1.00 eq) were added thereto. The reaction solution was stirred under the protection of nitrogen gas at 20° C. for 63 hours. The reaction solution was added with 100 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=1:0~2:1) to give the product of compound 82-e (100.00 mg, yield: 41%) as a yellow solid. LCMS m/z=609.1 [M+H]⁺.

Step 5: Synthesis of Compound 82

Compound 82-e (100.00 mg, 164.32 µmol, 1.00 eq) was dissolved in dichloromethane (5.00 mL), and trifluoroacetic acid (3.53 g, 30.93 mmol, 2.29 mL, 188.24 eq) was added thereto. The reaction solution was stirred under the protection of nitrogen gas at 10° C. for 1 hour. After the reaction was completed, the reaction solution was concentrated to give a crude product. The crude product was purified by preparative HPLC (in trifluoroacetic acid condition), and lyophilized to give the product of compound 82 (26.70 mg, yield: 29%) as a pale yellow solid. ¹H NMR (400 MHz, DMSO-d₆) δ=9.22 (s, 1H), 8.47 (d, J=7.53 Hz, 1H), 7.62-7.71 (m, 2H), 7.51-7.61 (m, 2H), 5.14-5.29 (m, 2H), 4.77 (d, J=13.05 Hz, 2H), 4.60 (q, J=7.03 Hz, 1H), 3.04 (t, J=11.80 Hz, 2H), 2.70-2.80 (m, 1H), 2.58 (dd, J=6.78, 16.81 Hz, 2H), 1.74-1.86 (m, 2H), 1.53 (q, J=11.54 Hz, 2H); LCMS m/z=553.0 [M+H]⁺.

Example 83: Compound 83

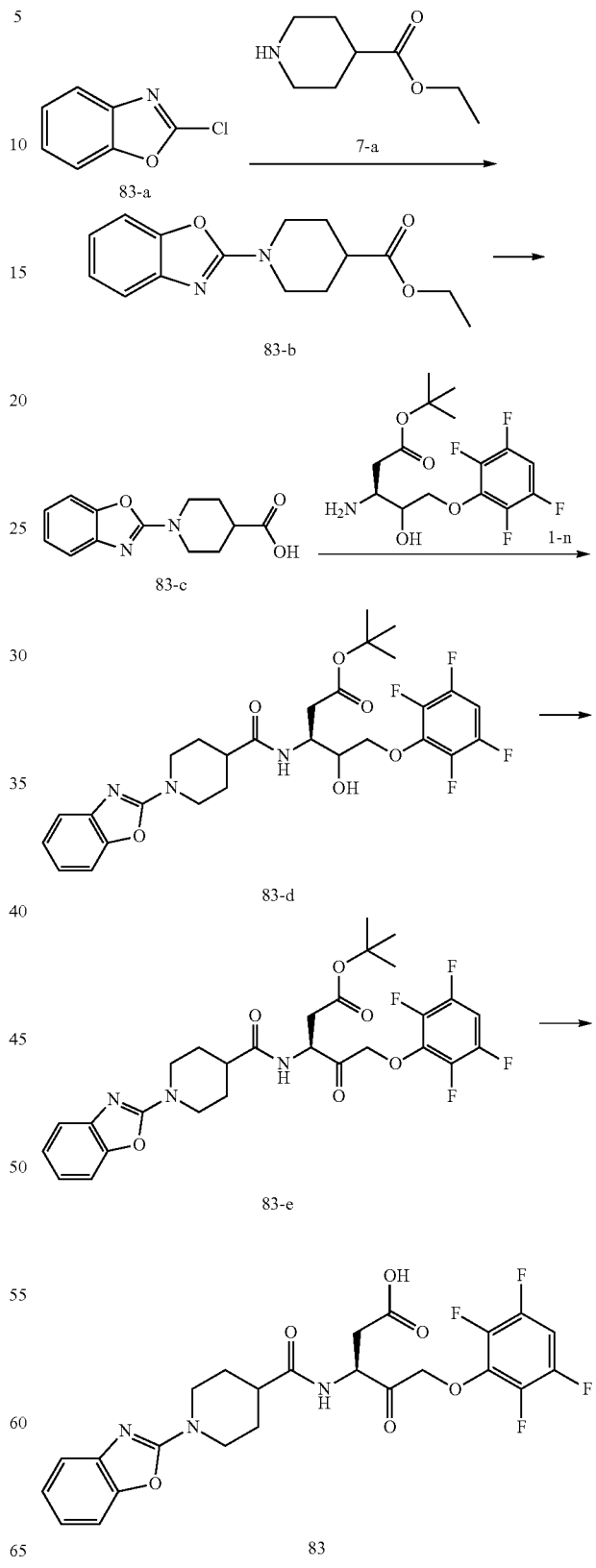

Step 1: Synthesis of Compound 83-b

Compound 83-a (500.00 mg, 3.26 mmol, 370.37 μL, 1.00 eq) was dissolved in dichloromethane (10.00 mL), and triethylamine (329.88 mg, 3.26 mmol, 451.89 μL, 1.00 eq) was added in one portion. Compound 7-a (512.50 mg, 3.26 mmol, 502.46 μL, 1.00 eq) was further added to the solution. The reaction solution was stirred at 15° C. for 16 hours. After the reaction was completed, the reaction solution was diluted with 20 mL of water, and extracted with dichloromethane (30 mL×3). The organic phases were combined, washed with saturated brine (20 mL×2), dried over anhydrous sodium sulfate, filtered, and concentrated to give the product of compound 83-b (880.00 mg, yield: 98%) as a yellow oil. The product was used directly in the next step without purification. $^1$H NMR (400 MHz, CHLORO-FORM-0 δ=7.36 (d, J=7.28 Hz, 1H), 7.25 (d, J=8.16 Hz, 1H), 7.17 (td, J=7.65, 1.00 Hz, 1H), 6.99-7.06 (m, 1H), 4.24 (dt, J=13.55, 3.89 Hz, 2H), 4.08-4.21 (m, 2H), 3.15-3.31 (m, 2H), 2.57 (tt, J=10.84, 3.84 Hz, 1H), 1.98-2.12 (m, 2H), 1.74-1.93 (m, 2H), 1.14-1.40 (m, 3H).

Step 2: Synthesis of Compound 83-c

Compound 83-b (920.00 mg, 3.35 mmol, 1.00 eq) was dissolved in THF (18.00 mL) and H$_2$O (18.00 mL), and LiOH.H$_2$O (421.70 mg, 10.05 mmol, 3.00 eq) was added to the solution. The reaction solution was stirred at 18° C. for 3 hours. After the reaction was completed, the reaction solution was adjusted to pH=3 with 2N dilute hydrochloric acid solution (20 mL), and then extracted with dichloromethane (30 mL×3). The organic phases were combined, washed with saturated brine (30 mL×2), dried over anhydrous sodium sulfate, filtered, concentrated and separated to give compound 83-c (800.00 mg, yield: 97%), which was used directly in the next step without purification. $^1$H NMR (300 MHz, METHANOL-d4) δ=7.25-7.35 (m, 2H), 7.17 (td, J=7.68, 1.04 Hz, 1H), 6.98-7.10 (m, 1H), 4.17 (dt, J=13.42, 3.56 Hz, 2H), 3.22-3.30 (m, 2H), 2.63 (tt, J=10.83, 3.96 Hz, 1H), 1.98-2.18 (m, 2H), 1.64-1.90 (m, 2H).

Step 3: Synthesis of Compound 83-d

Compound 83-c (200 mg, 566.16 μmol, 1 eq) was dissolved in dichloromethane (5.00 mL). Compound 1-n (170.00 mg, 690.62 μmol, 1.22 eq), EDCl (223.55 mg, 1.17 mmol, 2.06 eq), HOBt (157.57 mg, 1.17 mmol, 2.06 eq), NMM (257.67 mg, 2.55 mmol, 280.08 μL, 4.50 eq) was added to the above solution under the protection of nitrogen gas. Under the protection of nitrogen gas, the reaction solution was stirred at 10° C. for 16 hours. After the reaction was completed, the reaction solution was added with 10 mL of water, and extracted with dichloromethane (30 mL×3). The organic phases were combined, washed with saturated brine (30 mL×2), dried over anhydrous sodium sulfate, filtered and concentrated to give a crude product. The crude product was subjected to column chromatography (petroleum ether:ethyl acetate=10:1~2:1) to give the product of compound 83-d (220.00 mg, yield: 64.16%) as a colorless oil. LCMS m/z=582.1 [M+H]$^+$.

Step 4: Synthesis of Compound 83-e

Compound 83-d (220.00 mg, 378.29 μmol, 1.00 eq) was dissolved in dichloromethane (10.00 mL), and PIDA (605.58 mg, 1.88 mmol, 4.97 eq) and TEMPO (23.79 mg, 151.32 μmol, 0.40 eq) were added thereto. The reaction solution was stirred at room temperature (10° C.) for 12 hours. After the reaction was completed, the reaction solution was added with saturated NaHSO$_3$ (20 mL), and extracted with dichloromethane (30 mL×4). The organic phase was washed with saturated brine (30 mL×2), dried over anhydrous sodium sulfate, filtered and concentrated to give a crude product. The crude product was subjected to column chromatography (petroleum ether:ethyl acetate=10:1~2:1) to give the product of compound 83-e (170.00 mg, crude) as a colorless oil. LCMS m/z=580.1 [M+H]$^+$.

Step 5: Synthesis of Compound 83

Compound 83-e (170.00 mg, 293.34 μmol, 1.00 eq) was dissolved in dichloromethane (10.00 mL), and trifluoroacetic acid (7.70 g, 67.53 mmol, 5.00 mL, 171.90 eq) was added thereto at 0° C. Under the protection of nitrogen gas, the reaction solution was stirred at 0° C.-10° C. for 12 hours. After the reaction was completed, the reaction solution was spin-dried to give a crude product. The crude product was purified by preparative HPLC (in trifluoroacetic acid condition), and lyophilized to give the product of compound 83. $^1$H NMR (400 MHz, DMSO-d6) δ=8.49 (d, J=7.58 Hz, 1H), 7.49-7.68 (m, 1H), 7.39 (d, J=7.95 Hz, 1H), 7.28 (d, J=7.83 Hz, 1H), 7.11-7.16 (m, 1H), 6.99-7.03 (m, 1H), 5.16-5.33 (m, 2H), 4.61 (q, J=6.77 Hz, 1H), 4.13 (d, J=13.20 Hz, 2H), 3.12-3.19 (m, 2H), 2.72-2.80 (m, 1H), 2.54-2.62 (m, 2H), 1.75-1.85 (m, 2H), 1.61 (d, J=9.17 Hz, 2H).

Example 84: Compound 84

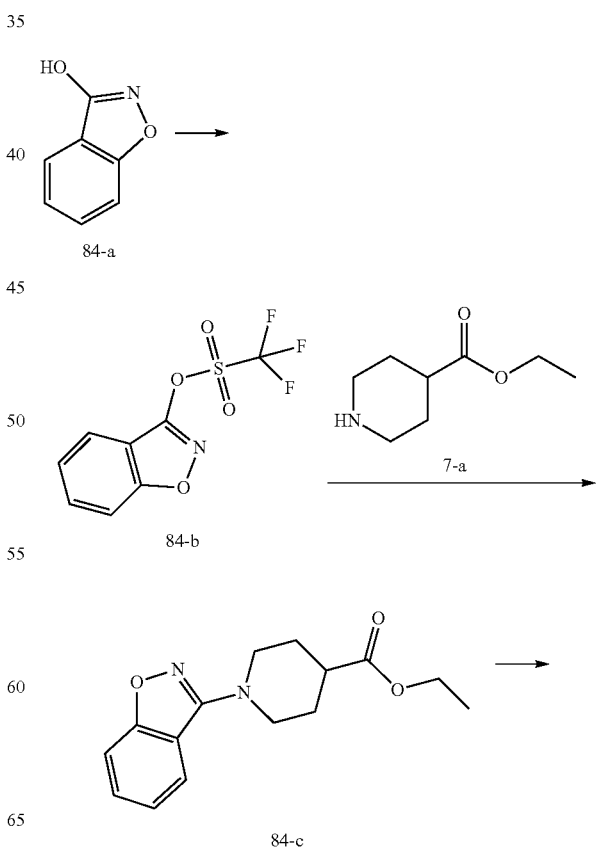

-continued

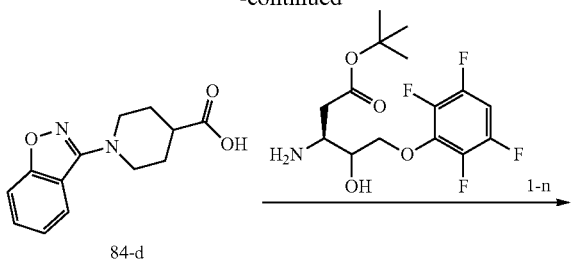

84-d

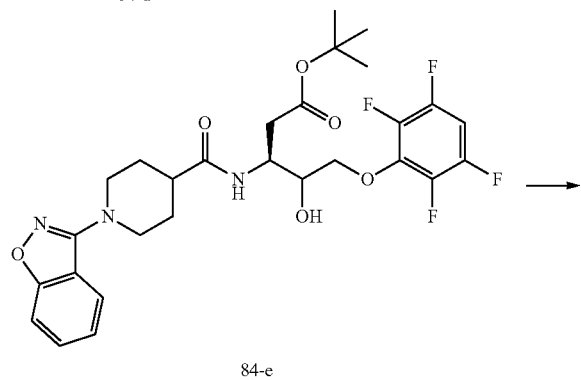

84-e

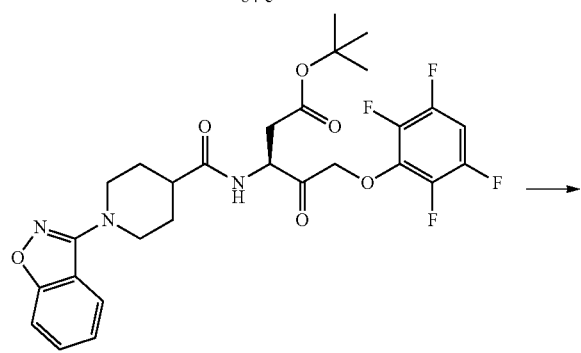

84-f

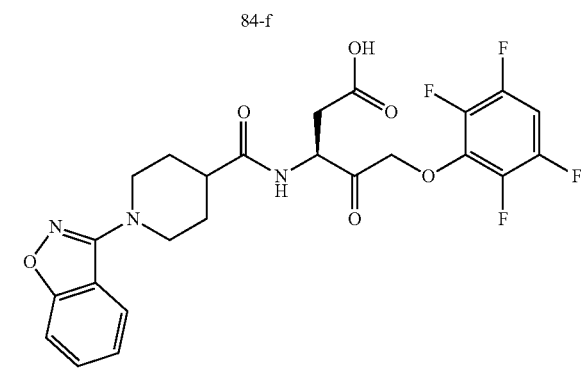

84

Step 1: Synthesis of Compound 84-b

Compound 84-a (2.00 g, 14.80 mmol, 1.00 eq) and triethylamine (4.49 g, 44.40 mmol, 6.15 mL, 3.00 eq) were dissolved in dichloromethane (20.00 mL). After the above solution was cooled in an ice bath, a solution of trifluoromethanesulfonic anhydride (5.01 g, 17.76 mmol, 2.93 mL, 1.20 eq) in dichloromethane (8 mL) was added dropwise. The reaction solution was stirred at 0° C. for 1 hour. After the reaction was completed, the reaction solution was added with ice water (200 mL), and extracted with dichloromethane (150 mL×3). The organic phase was dried over anhydrous sodium sulfate, filtered and concentrated to give a crude product. The crude product was subjected to column chromatography (petroleum ether:ethyl acetate=1:0~5:1) to give the product of compound 84-b (4.00 g, crude) as a brown oil, which was used directly in the next step without purification.

Step 2: Synthesis of Compound 84-c

Compound 84-b (4.00 g, 14.97 mmol, 1.00 eq) was dissolved in acetonitrile (48.00 mL), and compound 7-a (3.22 g, 20.51 mmol, 3.16 mL, 1.37 eq) and $Cs_2CO_3$ (7.37 g, 22.60 mmol, 1.51 eq) were added to the above solution. The reaction solution was stirred at 20° C. for 16 hours. After the reaction was completed, the reaction solution was added with water (150 mL), and extracted with dichloromethane (150 mL×3). The organic phase was dried over anhydrous sodium sulfate, filtered and concentrated to give a crude product. The crude product was subjected to column chromatography (petroleum ether:ethyl acetate=1:0~5:1) to give the product of compound 84-c (150.00 mg, yield: 4%) as a pale yellow oil. LCMS m/z=274.9 [M+H]$^+$.

Step 3: Synthesis of Compound 84-d

Compound 84-c (150.00 mg, 546.83 μmol, 1.00 eq) was dissolved in tetrahydrofuran (10.00 mL), and a solution of LiOH.$H_2O$ (137.67 mg, 3.28 mmol, 6.00 eq) dissolved in $H_2O$ (10.00 mL) was added to the above solution. The reaction solution was stirred at 10° C. for 2 hours. After the reaction was completed, the reaction solution was adjusted to pH of 5 with 2 N dilute hydrochloric acid. This solution was added with water (100 mL), and extracted with dichloromethane (100 mL×3). The organic phase was dried over anhydrous sodium sulfate, filtered and concentrated to give the product of compound 84-d (135.00 mg, crude) as a pale yellow solid, which was used directly in the next step without purification. LCMS m/z=246.8 [M+H]$^+$.

Step 4: Synthesis of Compound 84-e

Compound 84-d (135.00 mg, 548.20 μmol, 1.00 eq) was dissolved in dichloromethane (15.00 mL), and compound 1-n (193.68 mg, 548.20 μmol, 1.00 eq), EDCl (143.97 mg, 751.03 μmol, 1.37 eq), HOBt (101.48 mg, 751.03 μmol, 1.37 eq) and NMM (166.35 mg, 1.64 mmol, 180.82 μL, 3.00 eq) were added thereto. The reaction solution was stirred under the protection of nitrogen gas at 20° C. for 16 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 84-e (220.00 mg, yield: 67%) as a colorless oil. LCMS m/z=582.1 [M+H]$^+$.

Step 5: Synthesis of Compound 84-f

Compound 84-e (220.00 mg, 378.30 μmol, 1.00 eq) was dissolved in dichloromethane (20.00 mL), and PIDA (220.00 mg, 378.30 μmol, 1.00 eq) and TEMPO (17.85 mg, 113.49 μmol, 0.30 eq) were added thereto. The above solution was stirred under the protection of nitrogen gas at 15° C. for 16 hours, and then TEMPO (17.85 mg, 113.49 μmol, 0.30 eq) was supplemented. The reaction solution was stirred at 15° C. for another 24 hours. After the reaction was completed, the reaction solution was added with 100 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=1:0~2:1) to give the product of compound 84-f (180.00 mg, yield: 71%) as a pale yellow oil. LCMS m/z=580.1 [M+H]$^+$.

Step 6: Synthesis of Compound 84

Compound 84-f (180.00 mg, 310.59 μmol, 1.00 eq) was dissolved in dichloromethane (8.00 mL), and trifluoroacetic acid (6.16 g, 54.03 mmol, 4.00 mL, 173.95 eq) was added thereto. The reaction solution was stirred under the protection of nitrogen gas at 15° C. for 1 hour. After the reaction was completed, the reaction solution was concentrated to give a crude product. The crude product was purified by preparative HPLC (in trifluoroacetic acid condition), and lyophilized to give the product of compound 84 (62.00 mg, yield: 38%). $^1$H NMR (400 MHz, DMSO-d$_6$) δ=8.49 (d, J=7.53 Hz, 1H), 7.98 (d, J=8.03 Hz, 1H), 7.50-7.64 (m, 3H), 7.23-7.33 (m, 1H), 5.15-5.32 (m, 2H), 4.62 (q, J=6.86 Hz, 1H), 4.02 (d, J=12.55 Hz, 2H), 3.03 (t, J=11.54 Hz, 2H), 2.71-2.80 (m, 1H), 2.59 (dd, J=6.78, 16.81 Hz, 1H), 2.44-2.48 (m, 1H), 1.66-1.88 (m, 4H); LCMS m/z=524.1 [M+H]$^+$.

Example 85: Compound 85

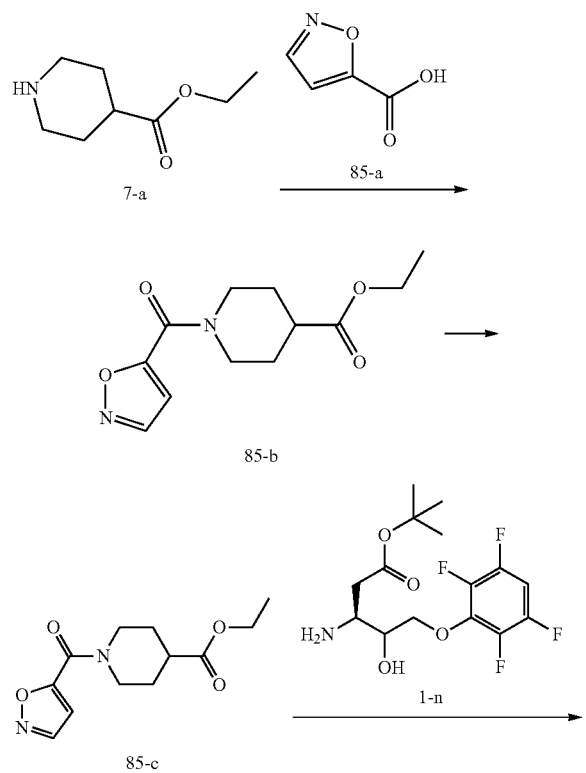

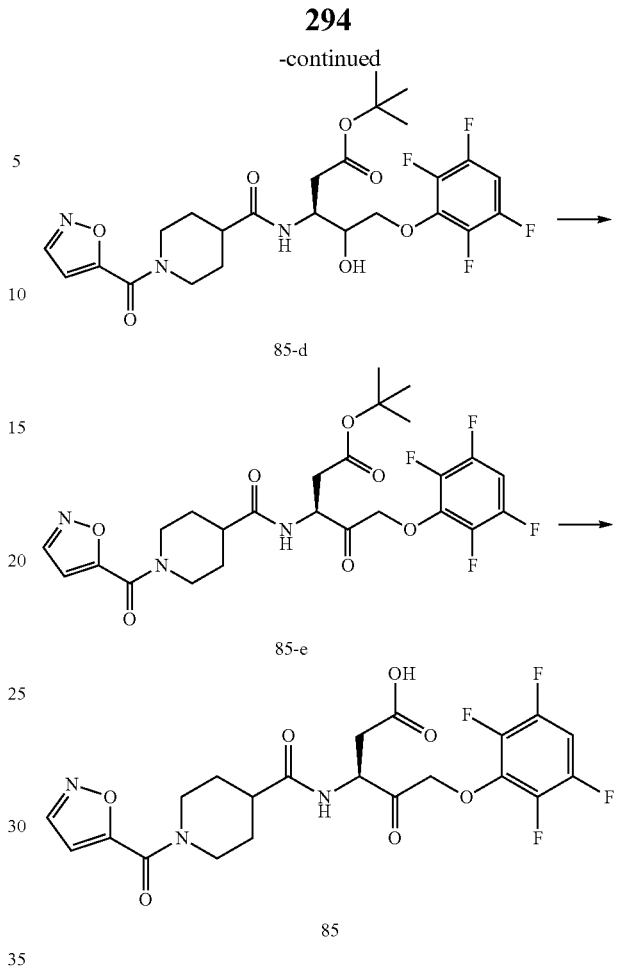

Step 1: Synthesis of Compound 85-b

Compound 85-a (200.00 mg, 1.77 mmol, 1.00 eq) was dissolved in dichloromethane (15.00 mL), and compound 7-a (305.88 mg, 1.95 mmol, 299.88 μL, 1.10 eq), EDCl (464.54 mg, 2.42 mmol, 1.37 eq), HOBt (327.43 mg, 2.42 mmol, 1.37 eq) and NMM (536.75 mg, 5.31 mmol, 583.42 μL, 3.00 eq) were added thereto. The reaction solution was stirred at 10° C. for 15 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 85-b (380.00 mg, yield: 85%) as a colorless oil. $^1$H NMR (400 MHz, CHLOROFORM-d) δ=8.31 (d, J=1.51 Hz, 1H), 6.75 (d, J=1.51 Hz, 1H), 4.44 (d, J=13.05 Hz, 1H), 4.14-4.22 (m, 2H), 4.08 (d, J=12.55 Hz, 1H), 3.30 (t, J=11.29 Hz, 1H), 3.10 (t, J=11.04 Hz, 1H), 2.57-2.68 (m, 1H), 1.99 (br. s., 2H), 1.77-1.87 (m, 2H), 1.26-1.29 (m, 3H).

Step 2: Synthesis of Compound 85-c

Compound 85-b (380.00 mg, 1.51 mmol, 1.00 eq) was dissolved in tetrahydrofuran (6.50 mL), and a solution of LiOH.H$_2$O (94.81 mg, 2.26 mmol, 1.50 eq) dissolved in H$_2$O (6.50 mL) was added to the above solution. The reaction solution was stirred at 10° C. for 1 hour. After the reaction was completed, the reaction solution was adjusted to pH of 5 with 2 N dilute hydrochloric acid. This solution was added with water (80 mL), and extracted with dichloromethane (100 mL×3). The organic phase was dried over anhydrous sodium sulfate, filtered and concentrated to give the product of compound 85-c (320.00 mg, crude) as a brown oil, which was used directly in the next step without purification.

Step 3: Synthesis of Compound 85-d

Compound 85-c (148.50 mg, 662.31 µmol, 1.30 eq) was dissolved in dichloromethane (10.00 mL), and compound 1-n (180.00 mg, 509.47 µmol, 1.00 eq), EDCl (133.80 mg, 697.97 µmol, 1.37 eq), HOBt (94.31 mg, 697.97 µmol, 1.37 eq) and NMM (154.60 mg, 1.53 mmol, 168.04 µL, 3.00 eq) were added thereto. The reaction solution was stirred under the protection of nitrogen gas at 10° C. for 14 hours. After the reaction was completed, the reaction solution was added with water (80 mL), and extracted with dichloromethane (80 mL×3). The organic phases were combined, dried over anhydrous sodium sulfate, filtered and concentrated to give a crude product. The crude product was subjected to column chromatography (petroleum ether:ethyl acetate=5:1~1:2) to give the product of compound 85-d (80.00 mg, yield: 25.82%) as a yellow oil. LCMS m/z=582.1 [M+Na]$^+$.

Step 4: Synthesis of Compound 85-e

Compound 85-d (70.00 mg, 125.11 µmol, 1.00 eq) was dissolved in dichloromethane (14.00 mL), and PIDA (155.95 mg, 484.18 µmol, 3.87 eq) and TEMPO (5.90 mg, 37.53 µmol, 0.30 eq) were added thereto. The reaction solution was stirred under the protection of nitrogen gas at 10° C. for 16 hours. After the reaction was completed, the reaction solution was added with 100 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=5:1~1:2) to give the product of compound 85-e (35.00 mg, yield: 48%) as a yellow oil. LCMS m/z=580.0 [M+Na]$^+$.

Step 5: Synthesis of Compound 85

Compound 85-e (40.00 mg, 71.75 µmol, 1.00 eq) was dissolved in dichloromethane (3.00 mL), and trifluoroacetic acid (1.54 g, 13.51 mmol, 1.00 mL, 188.24 eq) was added thereto. The reaction solution was stirred under the protection of nitrogen gas at 10° C. for 1 hour. After the reaction was completed, the reaction solution was concentrated and lyophilized to give the product of compound 85 (30.00 mg, yield: 83%). $^1$H NMR (400 MHz, DMSO-d$_6$) δ=8.74 (d, J=1.51 Hz, 1H), 8.49 (d, J=7.53 Hz, 1H), 7.48-7.69 (m, 1H), 6.92 (d, J=1.51 Hz, 1H), 5.13-5.31 (m, 2H), 4.61 (q, J=6.86 Hz, 1H), 4.36 (d, J=12.55 Hz, 1H), 3.77 (d, J=13.05 Hz, 1H), 3.20 (t, J=12.05 Hz, 1H), 2.85-2.99 (m, 1H), 2.69-2.80 (m, 1H), 2.54-2.64 (m, 2H), 1.48-1.58 (m, 2H), 1.27-1.39 (m, 2H); LCMS m/z=502.1 [M+H]$^+$.

Example 86: Compound 86

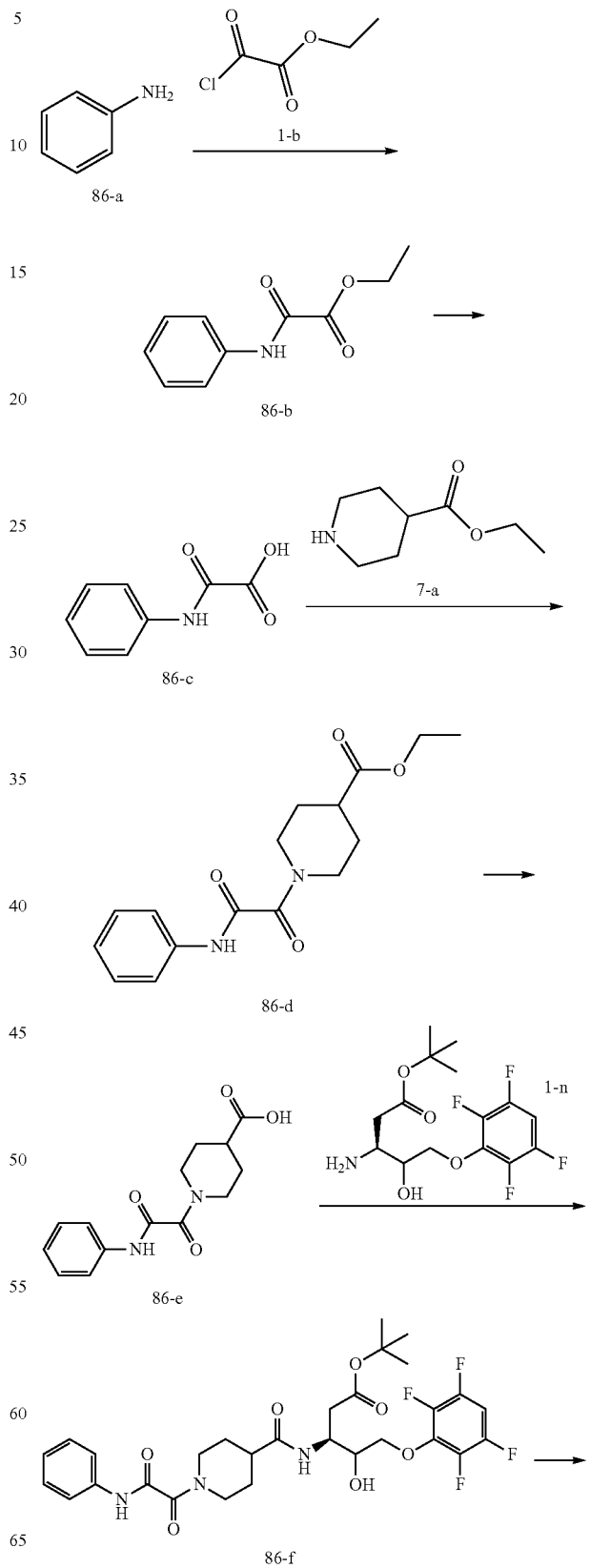

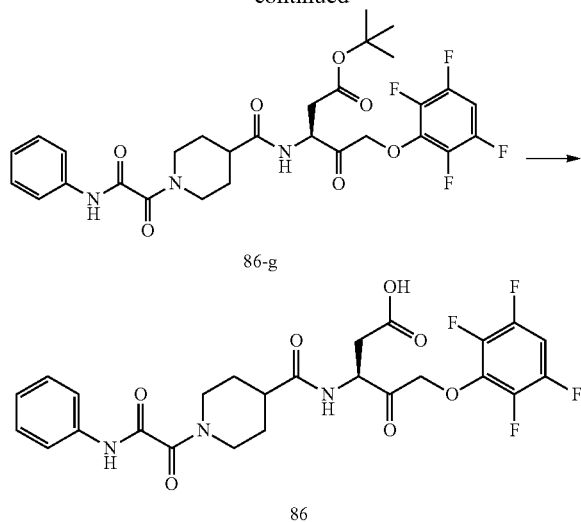

Step 1: Synthesis of Compound 86-b

Compound 86-a (2.00 g, 21.48 mmol, 1.96 mL, 1.00 eq) was dissolved in dichloromethane (20.00 mL), and triethylamine (3.04 g, 30.07 mmol, 4.16 mL, 1.40 eq) and compound 1-b (3.52 g, 25.78 mmol, 2.89 mL, 1.20 eq) were successively added to the above solution. The reaction solution was maintained at 20° C. and stirred for 2 hours. After the reaction was completed, the reaction solution was added with water (80 mL), and extracted with ethyl acetate (200 mL). The organic phase was washed with water (80 mL) and saturated sodium chloride (80 mL), dried over anhydrous sodium sulfate, filtered, and concentrated to give the product of compound 86-b (4.00 g, crude) as a pale yellow solid, which was used directly in the next step without purification. LCMS m/z=193.8 [M+H]$^+$.

Step 2: Synthesis of Compound 86-c

Compound 86-b (3.70 g, 19.15 mmol, 1.00 eq) was dissolved in tetrahydrofuran (37.00 mL), and a solution of LiOH.H$_2$O (2.41 g, 57.45 mmol, 3.00 eq) dissolved in H$_2$O (37.00 mL) was added to the above solution. The reaction solution was stirred at 25° C. for 2 hours. After the reaction was completed, the reaction solution was adjusted to pH of 6 with 2 N dilute hydrochloric acid. This solution was added with water (80 mL), and extracted with ethyl acetate (100 mL). The organic phase was washed with water (50 mL×2), dried over anhydrous sodium sulfate, filtered, and concentrated to give the product of compound 86-c (1.00 g, crude) as a pale yellow solid, which was used directly in the next step without purification. $^1$H NMR (400 MHz, DMSO-d$_6$) δ=10.69 (s, 1H), 7.76 (d, J=7.78 Hz, 2H), 7.35 (t, J=7.91 Hz, 2H), 7.09-7.18 (m, 1H).

Step 3: Synthesis of Compound 86-d

Compound 86-c (974.00 mg, 5.90 mmol, 1.00 eq) was dissolved in dichloromethane (30.00 mL), and compound 7-a (1.11 g, 7.08 mmol, 1.09 mL, 1.20 eq), EDCl (1.55 g, 8.08 mmol, 1.37 eq), HOBt (1.09 g, 8.08 mmol, 1.37 eq) and NMM (1.79 g, 17.70 mmol, 1.95 mL, 3.00 eq) were added thereto. The reaction solution was stirred at 10° C. for 15 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~5:1) to give the product of compound 86-d (1.00 g, yield: 42%) as a colorless oil. $^1$H NMR (400 MHz, CHLOROFORM-d) δ=9.18 (br. s., 1H), 7.60 (d, J=7.78 Hz, 2H), 7.36 (t, J=7.78 Hz, 2H), 7.13-7.20 (m, 1H), 4.94 (d, J=13.55 Hz, 1H), 4.39 (d, J=13.30 Hz, 1H), 4.17 (q, J=7.11 Hz, 2H), 3.39-3.52 (m, 1H), 2.98-3.12 (m, 1H), 2.55-2.67 (m, 1H), 2.04 (d, J=12.55 Hz, 2H), 1.72-1.92 (m, 2H), 1.27 (t, J=7.15 Hz, 3H).

Step 4: Synthesis of Compound 86-e

Compound 86-d (350.00 mg, 1.15 mmol, 1.00 eq) was dissolved in tetrahydrofuran (10.00 mL), and a solution of LiOH.H$_2$O (72.38 mg, 1.73 mmol, 1.50 eq) dissolved in H$_2$O (10.00 mL) was added to the above solution. After the above reaction solution was stirred at 10° C. for 1 hour, LiOH.H$_2$O (72.38 mg, 1.73 mmol, 1.50 eq) was supplemented. The reaction solution was stirred at 10° C. for another 0.5 hour. After the reaction was completed, the reaction solution was adjusted to pH of 5 with 2 N dilute hydrochloric acid. This solution was added with water (100 mL), and extracted with dichloromethane (100 mL×3). The organic phase was dried over anhydrous sodium sulfate, filtered and concentrated to give the product of compound 86-e (310.00 mg, crude) as colorless oil, which was used directly in the next step without purification.

Step 5: Synthesis of Compound 86-f

Compound 86-e (310.00 mg, 1.12 mmol, 1.98 eq) was dissolved in dichloromethane (15.00 mL), and compound 1-n (200.00 mg, 566.08 μmol, 1.00 eq), EDCl (148.67 mg, 775.53 μmol, 1.37 eq), HOBt (104.79 mg, 775.53 μmol, 1.37 eq) and NMM (171.78 mg, 1.70 mmol, 186.72 μL, 3.00 eq) were added thereto. The reaction solution was stirred under the protection of nitrogen gas at 10° C. for 15 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=4:1~1:1) to give the product of compound 86-f (200.00 mg, yield: 57.19%). LCMS m/z=612.2 [M+H]$^+$.

Step 6: Synthesis of Compound 86-g

Compound 86-f (200.00 mg, 327.02 μmol, 1.00 eq) was dissolved in dichloromethane (15.00 mL), and PIDA (407.64 mg, 1.27 mmol, 3.87 eq) and TEMPO (15.43 mg, 98.11 μmol, 0.30 eq) were added thereto. After the reaction solution was stirred under the protection of nitrogen gas at 10° C. for 16 hours, TEMPO (15.43 mg, 98.11 μmol, 0.30 eq) was supplemented. The reaction solution was stirred at 10° C. for another 24 hours.

The reaction solution was added with 100 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=1:

0~1:1) to give the product of compound 86-g (190.00 mg, yield: 88%) as a yellow oil. LCMS m/z=610.2 [M+H]$^+$.

Step 7: Synthesis of Compound 86

Compound 86-g (190.00 mg, 311.70 μmol, 1.00 eq) was dissolved in dichloromethane (8.70 mL), and trifluoroacetic acid (6.69 g, 58.67 mmol, 4.34 mL, 188.24 eq) was added thereto. The reaction solution was stirred under the protection of nitrogen gas at 10° C. for 1 hour. After the reaction was completed, the reaction solution was concentrated to give a crude product. The crude product was purified by preparative HPLC (in trifluoroacetic acid condition), and lyophilized to give the product of compound 86 (91.60 mg, yield: 53%). $^1$H NMR (400 MHz, DMSO-d$_6$) δ=10.75 (s, 1H), 8.48 (d, J=6.02 Hz, 1H), 7.64 (d, J=8.03 Hz, 2H), 7.51-7.60 (m, 1H), 7.34 (t, J=8.03 Hz, 2H), 7.08-7.15 (m, 1H), 5.14-5.30 (m, 2H), 4.56-4.65 (m, 1H), 4.28 (d, J=12.55 Hz, 1H), 3.77 (d, J=13.55 Hz, 1H), 3.15 (t, J=11.80 Hz, 1H), 2.69-2.89 (m, 2H), 2.59 (dd, J=6.78, 16.81 Hz, 2H), 1.77 (d, J=11.54 Hz, 2H), 1.44-1.64 (m, 2H); LCMS m/z=554.0 [M+H]$^+$.

Example 87: Compound 87

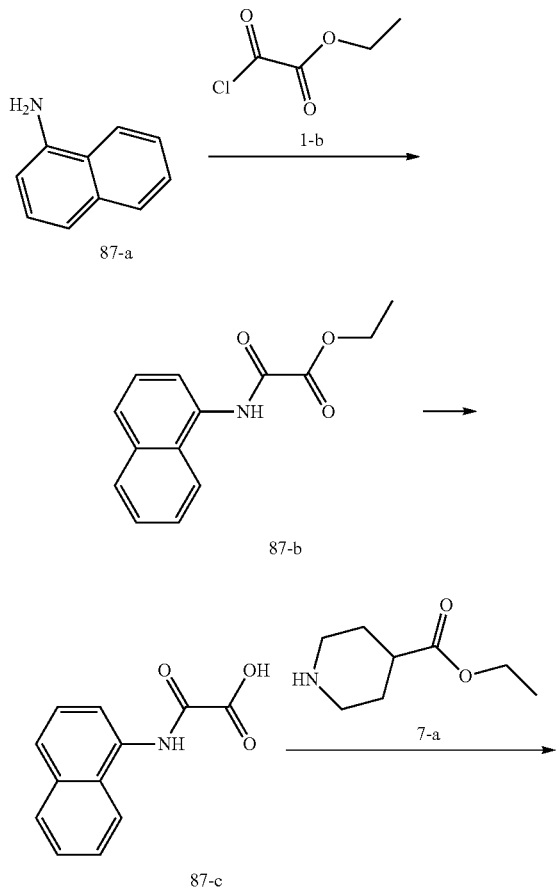

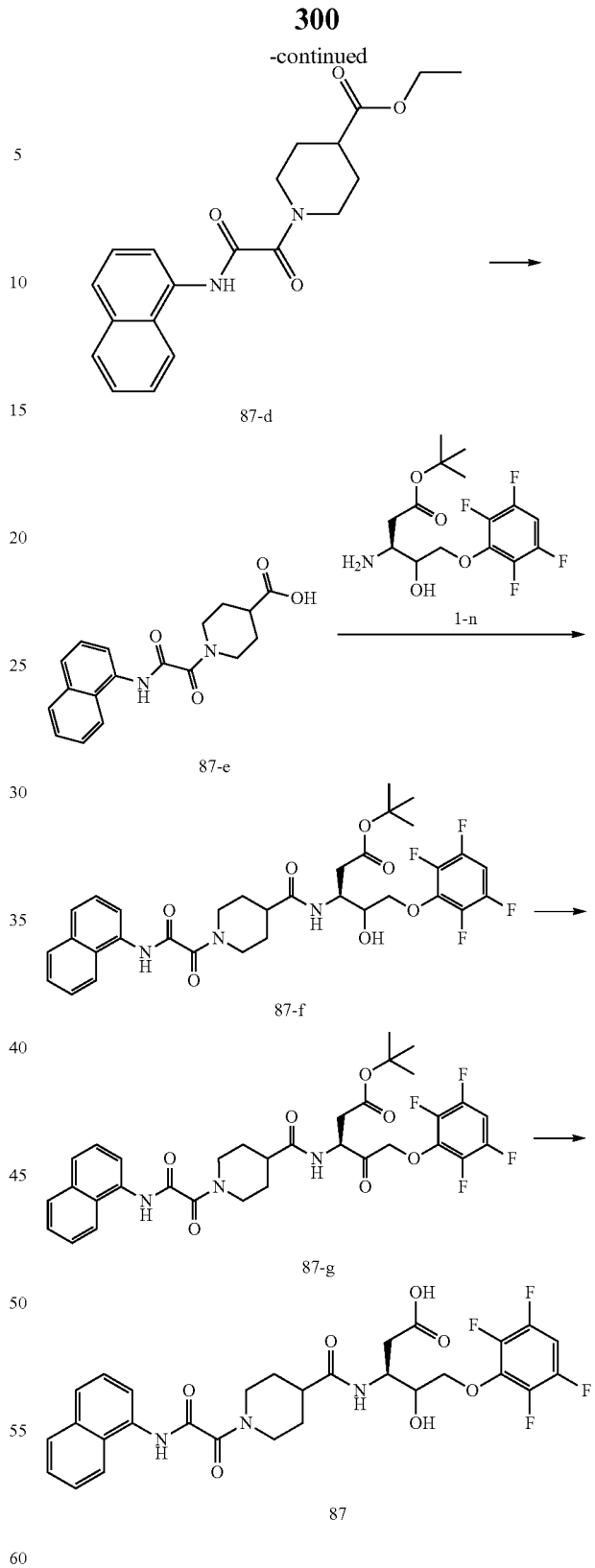

Step 1: Synthesis of Compound 87-b

Compound 87-a (2.00 g, 13.97 mmol, 1.96 mL, 1.00 eq) was dissolved in dichloromethane (30.00 mL), and triethylamine (2.83 g, 27.94 mmol, 3.88 mL, 2.00 eq) and compound 1-b (2.29 g, 16.76 mmol, 1.88 mL, 1.20 eq) were successively added to the above solution at 0° C. The reaction solution was maintained at 15° C. and stirred for 15 hours. After the reaction was completed, the reaction solution was added with water (150 mL), and extracted with dichloromethane (150 mL×3). The organic phase was dried over anhydrous sodium sulfate, filtered and concentrated to give a crude product. The crude product was subjected to column chromatography (petroleum ether:ethyl acetate=1: 0~5:1) to give the product of compound 87-b (3.00 g, yield: 88%). $^1$H NMR (400 MHz, CHLOROFORM-d) δ=9.45 (br. s., 1H), 8.18 (d, J=7.53 Hz, 1H), 7.90 (d, J=8.78 Hz, 2H), 7.75 (d, J=8.03 Hz, 1H), 7.48-7.62 (m, 3H), 4.48 (q, J=7.28 Hz, 2H), 1.48 (t, J=7.15 Hz, 3H).

Step 2: Synthesis of Compound 87-c

Compound 87-b (1.00 g, 4.11 mmol, 1.00 eq) was dissolved in tetrahydrofuran (15.00 mL), and a solution of LiOH.H$_2$O (517.47 mg, 12.33 mmol, 3.00 eq) dissolved in H$_2$O (15.00 mL) was added to the above solution. The reaction solution was stirred at 15° C. for 1 hour. After the reaction was completed, the reaction solution was adjusted to pH of 5 with 2 N dilute hydrochloric acid. This solution was added with water (150 mL), and extracted with dichloromethane (150 mL×3). The organic phase was dried over anhydrous sodium sulfate, filtered and concentrated to give the product of compound 87-c (860.00 mg, crude), which was used directly in the next step without purification.

Step 3: Synthesis of Compound 87-d

Compound 87-c (860.00 mg, 4.00 mmol, 1.00 eq) was dissolved in dichloromethane (25.00 mL), and compound 7-a (753.91 mg, 4.80 mmol, 739.12 µL, 1.20 eq), EDCl (1.05 g, 5.47 mmol, 1.37 eq), HOBt (739.77 mg, 5.47 mmol, 1.37 eq) and NMM (1.21 g, 11.99 mmol, 1.32 mL, 3.00 eq) were added thereto. The reaction solution was stirred under the protection of nitrogen gas at 15° C. for 15 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 87-d (710.00 mg, yield: 49%). $^1$H NMR (400 MHz, CHLOROFORM-d) δ=9.78 (br. s., 1H), 8.09 (d, J=7.28 Hz, 1H), 7.87-7.97 (m, 2H), 7.74 (d, J=8.28 Hz, 1H), 7.46-7.61 (m, 3H), 5.07 (td, J=3.45, 13.43 Hz, 1H), 4.46 (td, J=3.58, 13.18 Hz, 1H), 4.18 (q, J=7.11 Hz, 2H), 3.52 (ddd, J=2.76, 10.98, 13.61 Hz, 1H), 3.11 (ddd, J=3.14, 10.98, 13.49 Hz, 1H), 2.60-2.71 (m, 1H), 2.06-2.12 (m, 1H), 2.01-2.05 (m, 1H), 1.78-1.96 (m, 2H), 1.28 (t, J=7.03 Hz, 3H).

Step 4: Synthesis of Compound 87-e

Compound 87-d (710.00 mg, 2.00 mmol, 1.00 eq) was dissolved in tetrahydrofuran (15.00 mL), and a solution of LiOH.H$_2$O (251.76 mg, 6.00 mmol, 3.00 eq) dissolved in H$_2$O (15.00 mL) was added to the above solution. The reaction solution was stirred at 15° C. for 1 hour. After the reaction was completed, the reaction solution was adjusted to pH of 5 with 2 N dilute hydrochloric acid. This solution was added with water (100 mL), and extracted with dichloromethane (100 mL×3). The organic phase was dried over anhydrous sodium sulfate, filtered and concentrated to give the product of compound 87-e (650.00 mg, crude) as a colorless solid, which was used directly in the next step without purification.

Step 5: Synthesis of Compound 87-f

Compound 87-e (221.69 mg, 679.30 µmol, 1.20 eq) was dissolved in dichloromethane (10.00 mL), and compound 1-n (200.00 mg, 566.08 µmol, 1.00 eq), EDCl (148.67 mg, 775.53 µmol, 1.37 eq), HOBt (104.79 mg, 775.53 µmol, 1.37 eq) and NMM (171.78 mg, 1.70 mmol, 186.72 µL, 3.00 eq) were added thereto. The reaction solution was stirred under the protection of nitrogen gas at 15° C. for 15 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=5:1~1:2) to give the product of compound 87-f (360.00 mg, yield: 94%) as a colorless solid. LCMS m/z=684.1 [M+Na]$^+$.

Step 6: Synthesis of Compound 87-g

Compound 87-f (260.00 mg, 392.96 µmol, 1.00 eq) was dissolved in dichloromethane (8.00 mL), and Dess-Martin periodinane (200.00 mg, 471.55 µmol, 145.99 µL, 1.20 eq) was added thereto. After the reaction solution at was stirred at 15° C. for 1 hour, Dess-Martin periodinane (200.00 mg, 471.55 µmol, 145.99 µL, 1.20 eq) was supplemented. The reaction solution was stirred at 15° C. for another 0.5 hour. After the reaction was completed, the reaction solution was added with 150 mL of ethyl acetate. The solution was washed successively with 1 M sodium thiosulfate (100 mL), saturated sodium hydrogen carbonate (100 mL) and saturated sodium chloride (100 mL). The organic phase was dried over anhydrous sodium sulfate, filtered and concentrated to give a crude product. The crude product was subjected to column chromatography (petroleum ether:ethyl acetate=5:1~1:2) to give the product of compound 87-g (220.00 mg, yield: 79%) as a yellow oil, LCMS m/z=682.2 [M+Na]$^+$.

Step 7: Synthesis of Compound 87

Compound 87-g (208.00 mg, 315.33 µmol, 1.00 eq) was dissolved in dichloromethane (8.00 mL), and trifluoroacetic acid (6.06 g, 53.15 mmol, 3.94 mL, 168.54 eq) was added thereto. The reaction solution was stirred under the protection of nitrogen gas at 15° C. for 1 hour. After the reaction was completed, the reaction solution was concentrated to give a crude product. The crude product was purified by preparative HPLC (in trifluoroacetic acid condition), and lyophilized to give the product of compound 87 (113.30 mg, yield: 60%). $^1$H NMR (400 MHz, DMSO-d$_6$) δ=10.82 (s, 1H), 8.52 (d, J=7.53 Hz, 1H), 7.94-8.06 (m, 2H), 7.85 (d, J=8.03 Hz, 1H), 7.68 (d, J=7.03 Hz, 1H), 7.50-7.63 (m, 4H), 5.16-5.33 (m, 2H), 4.63 (q, J=6.53 Hz, 1H), 4.34 (d, J=13.05 Hz, 1H), 3.87 (d, J=13.55 Hz, 1H), 3.24 (t, J=12.05 Hz, 1H), 2.87 (t, J=11.54 Hz, 1H), 2.72-2.80 (m, 1H), 2.53-2.71 (m, 2H), 1.81 (br. s., 2H), 1.50-1.75 (m, 2H); LCMS m/z=604.1 [M+H]$^+$.

Example 88: Compound 88

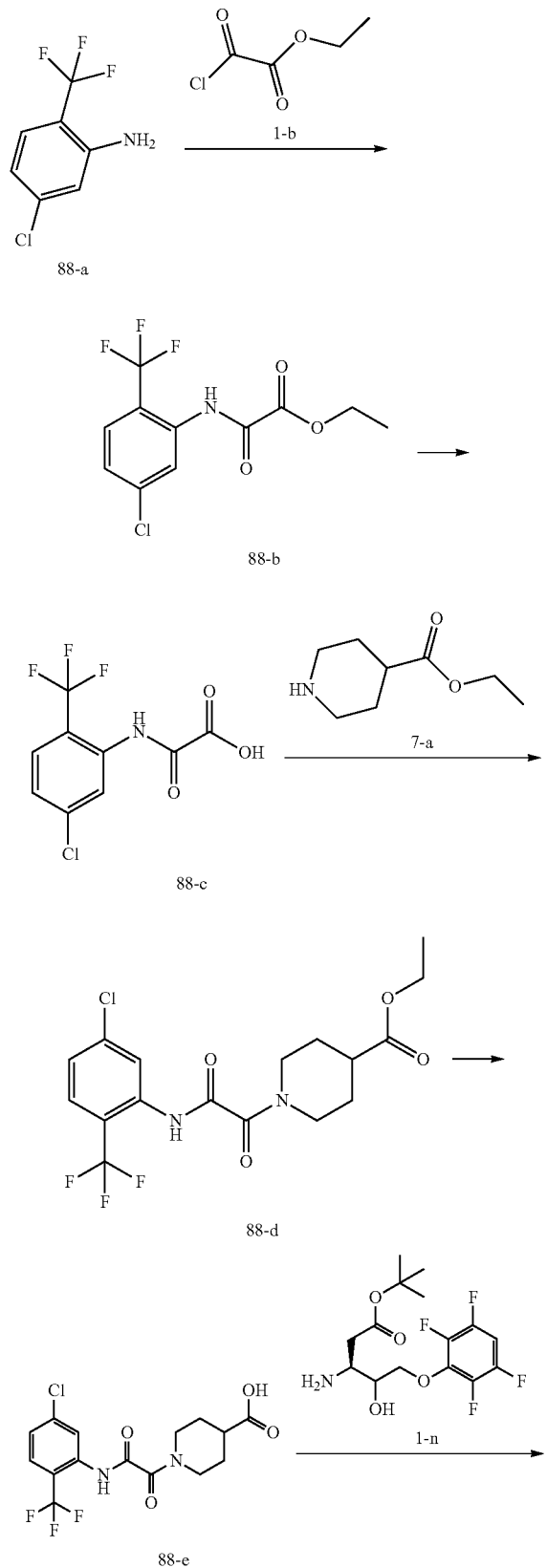

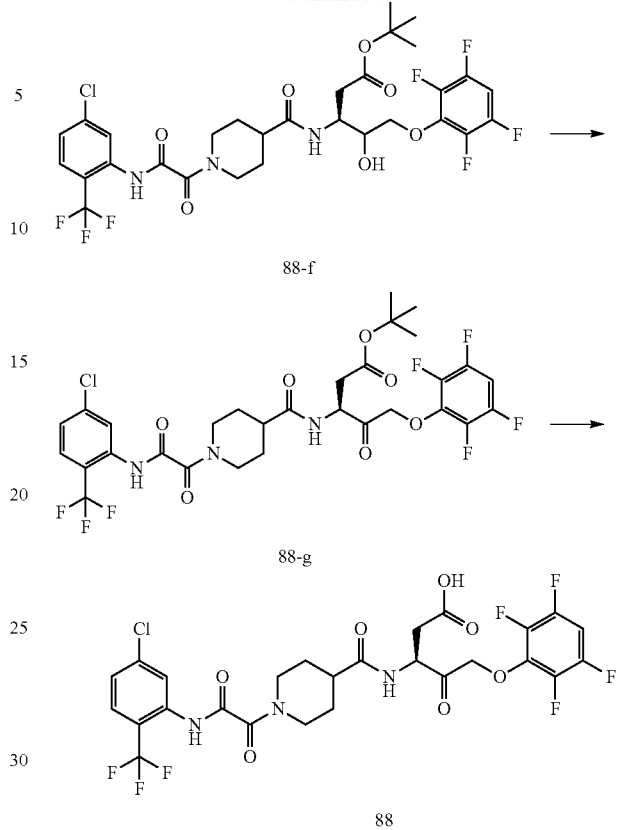

Step 1: Synthesis of Compound 88-b

Compound 88-a (1.00 g, 5.11 mmol, 1.00 eq) was dissolved in dichloromethane (25.00 mL), and triethylamine (1.03 g, 10.22 mmol, 1.42 mL, 2.00 eq) and compound 1-b (837.74 mg, 6.13 mmol, 686.67 µL, 1.20 eq) were successively added to the above solution at 0° C. The reaction solution was maintained at 15° C. and stirred for 16 hours. After the reaction was completed, the reaction solution was added with water (100 mL), and extracted with dichloromethane (100 mL×3). The organic phase was dried over anhydrous sodium sulfate, filtered and concentrated to give a crude product. The crude product was subjected to column chromatography (petroleum ether:ethyl acetate=1:0~9:1) to give the product of compound 88-b (1.07 g, yield: 60%) as a colorless oil. $^1$H NMR (400 MHz, CHLOROFORM-d) δ=9.39 (br. s., 1H), 8.48 (s, 1H), 7.59 (d, J=8.53 Hz, 1H), 7.30 (s, 1H), 4.46 (q, J=7.03 Hz, 2H), 1.45 (t, J=7.15 Hz, 3H).

Step 2: Synthesis of Compound 88-c

Compound 88-b (1.07 g, 3.62 mmol, 1.00 eq) was dissolved in tetrahydrofuran (15.00 mL), and a solution of LiOH.H$_2$O (227.84 mg, 5.43 mmol, 1.50 eq) dissolved in H$_2$O (15.00 mL) was added to the above solution. The reaction solution was stirred at 15° C. for 1 hour. After the reaction was completed, the reaction solution was adjusted to pH of 5 with 2 N dilute hydrochloric acid. This solution was added with water (150 mL), and extracted with dichloromethane (150 mL×3). The organic phase was dried over anhydrous sodium sulfate, filtered and concentrated to give the product of compound 88-c (950.00 mg, crude) as a pale yellow oil, which was used directly in the next step without purification. $^1$H NMR (400 MHz, CHLOROFORM-d) δ=9.45 (br. s., 1H), 8.42 (s, 1H), 7.63 (d, J=8.53 Hz, 1H), 7.34 (d, J=8.28 Hz, 1H).

Step 3: Synthesis of Compound 88-d

Compound 88-c (950.00 mg, 3.55 mmol, 1.00 eq) was dissolved in dichloromethane (25.00 mL), and compound 7-a (725.52 mg, 4.62 mmol, 711.29 µL, 1.30 eq), EDCl (932.39 mg, 4.86 mmol, 1.37 eq), HOBt (657.19 mg, 4.86 mmol, 1.37 eq) and NMM (1.08 g, 10.65 mmol, 1.17 mL, 3.00 eq) were added thereto. The reaction solution was stirred at 15° C. for 15 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~9:1) to give the product of compound 88-d (788.00 mg, yield: 53%) as a pale yellow oil. $^1$H NMR (400 MHz, CHLOROFORM-d) δ=9.84 (br. s., 1H), 8.44 (s, 1H), 7.58 (d, J=8.53 Hz, 1H), 7.25 (d, J=9.04 Hz, 1H), 4.93-5.03 (m, 1H), 4.32-4.44 (m, 1H), 4.17 (q, J=7.03 Hz, 2H), 3.43-3.57 (m, 1H), 3.01-3.15 (m, 1H), 2.57-2.69 (m, 1H), 1.99-2.11 (m, 2H), 1.75-1.94 (m, 2H), 1.28 (t, J=7.03 Hz, 3H).

Step 4: Synthesis of Compound 88-e

Compound 88-d (788.00 mg, 1.94 mmol, 1.00 eq) was dissolved in tetrahydrofuran (15.00 mL), and a solution of LiOH.H$_2$O (121.93 mg, 2.91 mmol, 1.50 eq) dissolved in H$_2$O (15.00 mL) was added to the above solution. After stirring at 15° C. for 1 hour, the reaction solution was supplemented with LiOH.H$_2$O (121.93 mg, 2.91 mmol, 1.50 eq). The reaction solution was stirred at 15° C. for another 1 hour. After the reaction was completed, the reaction solution was adjusted to pH of 3 with 2 N dilute hydrochloric acid. This solution was added with water (150 mL), and extracted with dichloromethane (150 mL×3). The organic phase was dried over anhydrous sodium sulfate, filtered and concentrated to give the product of compound 88-e (660.00 mg, crude), which was used directly in the next step without purification.

Step 5: Synthesis of Compound 88-f

Compound 88-e (267.00 mg, 704.99 µmol, 1.25 eq) was dissolved in dichloromethane (10.00 mL), and compound 1-n (200.00 mg, 566.08 µmol, 1.00 eq), EDCl (148.67 mg, 775.53 µmol, 1.37 eq), HOBt (104.79 mg, 775.53 µmol, 1.37 eq) and NMM (171.78 mg, 1.70 mmol, 186.72 µL, 3.00 eq) were added thereto. The reaction solution was stirred under the protection of nitrogen gas at 15° C. for 14 hours. After the reaction was completed, the reaction solution was added with water (100 mL), and extracted with dichloromethane (100 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 88-f (370.00 mg, yield: 91%). LCMS m/z=736.1 [M+Na]$^+$.

Step 6: Synthesis of Compound 88-g

Compound 88-f (370.00 mg, 518.19 µmol, 1.00 eq) was dissolved in dichloromethane (25.00 mL), and PIDA (645.94 mg, 2.01 mmol, 3.87 eq) and TEMPO (24.45 mg, 155.46 µmol, 0.30 eq) were added thereto. After stirring at 15° C. for 16 hours, the reaction solution was supplemented with TEMPO (24.45 mg, 155.46 µmol, 0.30 eq). The reaction solution was stirred at 15° C. for another 24 hours. After the reaction was completed, the reaction solution was added with 100 mL of ethyl acetate. The solution was washed successively with saturated sodium hydrogen carbonate (80 mL), saturated brine (80 mL) and water (80 mL). The organic phase was dried over anhydrous sodium sulfate, filtered and concentrated to give a crude product. The crude product was subjected to column chromatography (petroleum ether:ethyl acetate=1:0~2:1) to give the product of compound 88-g (270.00 mg, yield: 66%) as a yellow solid. LCMS m/z=734.1 [M+Na]$^+$.

Step 7: Synthesis of Compound 88

Compound 88-g (270.00 mg, 379.21 µmol, 1.00 eq) was dissolved in dichloromethane (10.00 mL), and trifluoroacetic acid (7.29 g, 63.91 mmol, 4.73 mL, 168.54 eq) was added thereto. The reaction solution was stirred under the protection of nitrogen gas at 15° C. for 1 hour. After the reaction was completed, the reaction solution was concentrated to give a crude product. The crude product was purified by preparative HPLC (in trifluoroacetic acid condition), and lyophilized to give the product of compound 88 (205.90 mg, yield: 83%). $^1$H NMR (400 MHz, DMSO-d$_6$) δ=10.70 (s, 1H), 8.50 (d, J=7.03 Hz, 1H), 7.82 (d, J=8.53 Hz, 1H), 7.73 (s, 1H), 7.48-7.65 (m, 2H), 5.13-5.31 (m, 2H), 4.62 (q, J=6.53 Hz, 1H), 4.28 (d, J=13.55 Hz, 1H), 3.90 (d, J=13.55 Hz, 1H), 3.17 (t, J=12.05 Hz, 1H), 2.66-2.93 (m, 2H), 2.53-2.65 (m, 2H), 1.77 (br. s., 2H), 1.43-1.68 (m, 2H); LCMS m/z=656.0 [M+H]$^+$.

Example 89: Compound 89

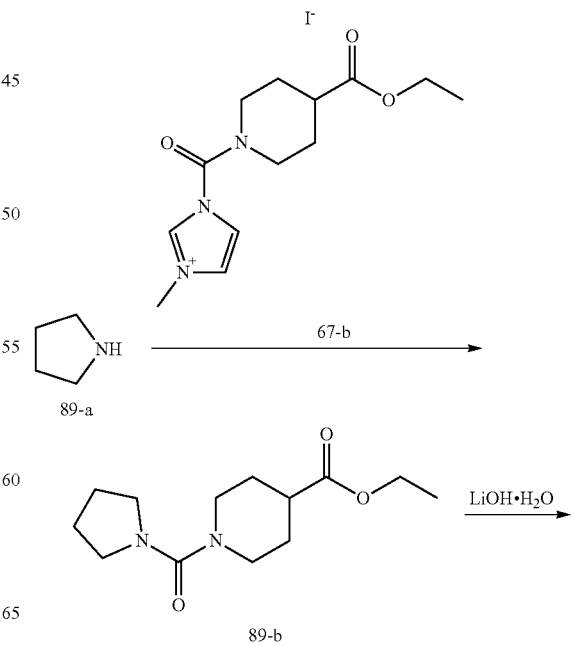

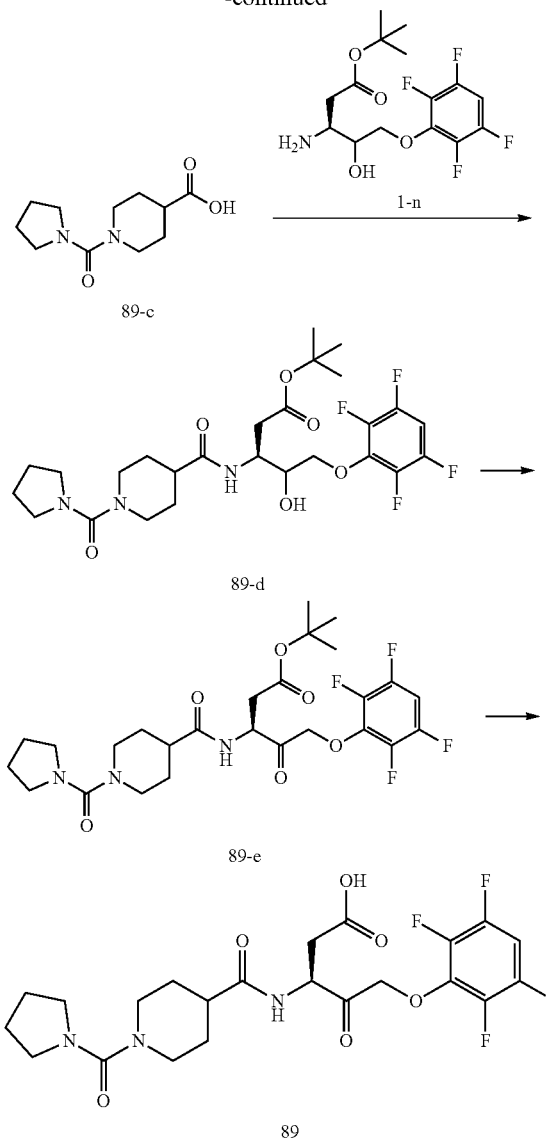

Step 1: Synthesis of Compound 89-b

Compound 89-a (500.00 mg, 7.03 mmol, 588.24 μL, 1.00 eq) was dissolved in dichloromethane (10.00 mL), and triethylamine (1.42 g, 14.06 mmol, 1.95 mL, 2.00 eq) and compound 67-b (2.76 g, 7.03 mmol, 1.00 eq) were added in an ice bath. After stirring for 30 min, the reaction solution was warmed up to room temperature and then stirred for 16 hours. After the reaction was completed, the reaction solution was added with dichloromethane (30 mL) for dilution, and then washed with water (30 mL) and saturated brine (50 mL×2). The organic phase was dried over anhydrous sodium sulfate, filtered, and concentrated to give a crude product. The crude product was purified by column chromatography (petroleum ether:ethyl acetate=1:1~1:9), to give the product of compound 89-b (1.30 g, yield: 73%) as a colorless oil. LCMS m/z=255.0 [M+H]$^+$.

Step 2: Synthesis of Compound 89-c

LiOH.H$_2$O (123.99 mg, 2.96 mmol, 1.50 eq) was dissolved in H$_2$O (5.00 mL), and the solution was added to a solution of compound 89-b (500.00 mg, 1.97 mmol, 1.00 eq) dissolved in THF (5.00 mL). The reaction was stirred at room temperature for 1 hour. After the reaction was completed, the reaction solution was added with water (20 mL), adjusted to pH of 3-4 with 1 N dilute hydrochloric acid, and extracted with dichloromethane/methanol (50 mL×3, 10:1). The organic phases were combined, dried over anhydrous sodium sulfate, filtered, and concentrated to give compound 89-c (400.00 mg, crude), which was used directly in the next step without purification. LCMS m/z=227.0 [M+H]$^+$.

Step 3: Synthesis of Compound 89-d

Compound 89-c (400.00 mg, 1.77 mmol, 1.00 eq) was dissolved in dichloromethane (10 mL), and N-methylmorpholine (537.11 mg, 5.31 mmol, 583.82 μL, 3.00 eq), HOBt (327.65 mg, 2.42 mmol, 1.37 eq), EDCl (464.85 mg, 2.42 mmol, 1.37 eq) and compound 1-n (625.36 mg, 1.77 mmol, 1.00 eq) were added thereto. The reaction was stirred at room temperature for 16 hours. After the reaction was completed, the reaction solution was added with dichloromethane (30 mL) for dilution, and then washed with water (30 mL) and saturated brine (50 mL). The organic phase was dried over anhydrous sodium sulfate, filtered, and concentrated to give a crude product. The crude product was purified by column chromatography (petroleum ether:ethyl acetate=1:1~1:8), to give the product of compound 89-d (620.00 mg, yield: 60%) as a colorless oil. LCMS m/z=584.1 [M+Na]$^+$.

Step 4: Synthesis of Compound 89-e

Compound 89-d (620.00 mg, 1.10 mmol, 1.00 eq) was dissolved in dichloromethane (20.00 mL), and PIDA (1.37 g, 4.26 mmol, 3.87 eq) and TEMPO (51.89 mg, 330.00 μmol, 0.30 eq) were added thereto. The reaction was stirred at room temperature for 40 hours. After the reaction was completed, the reaction solution was added with ethyl acetate (50 mL) for dilution, and washed with saturated sodium hydrogen carbonate solution (40 mL) and saturated brine (40 mL×2). The organic phase was dried over anhydrous sodium sulfate, filtered, and concentrated to give a crude product. The crude product was purified by column chromatography (petroleum ether:ethyl acetate=1:1~1:8), to give the product of compound 89-e (308.00 mg, yield: 50%) as a yellow oil. LCMS m/z=560.2 [M+H]$^+$.

Step 5: Synthesis of Compound 89

Compound 89-e (308.00 mg, 550.44 μmol, 1.00 eq) was dissolved in dichloromethane (16.00 mL), and TFA (8.00 mL, 108.28 mmol, 196.71 eq) was added thereto. The reaction was stirred at room temperature for 1 hour. After the reaction was completed, the reaction solution was spin-dried to give a crude product. The crude product was purified by preparative HPLC (in TFA condition), and lyophilized to give compound 89 (80.00 mg, yield: 29%). $^1$H NMR (400 MHz, DMSO-d$_6$) δ=12.47 (brs, 1H), 8.43 (d, J=7.28 Hz, 1H), 7.52-7.66 (m, 1H), 5.12-5.32 (m, 2H), 4.60 (d, J=7.03 Hz, 1H), 3.64 (d, J=13.05 Hz, 2H), 3.25 (brs., 4H), 2.54-2.79 (m, 4H), 2.31-2.42 (m, 1H), 1.74 (brs., 4H), 1.60-1.70 (m, 2H), 1.41-1.56 (m, 2H); LCMS m/z=504.1 [M+H]$^+$.

Example 90: Compound 90

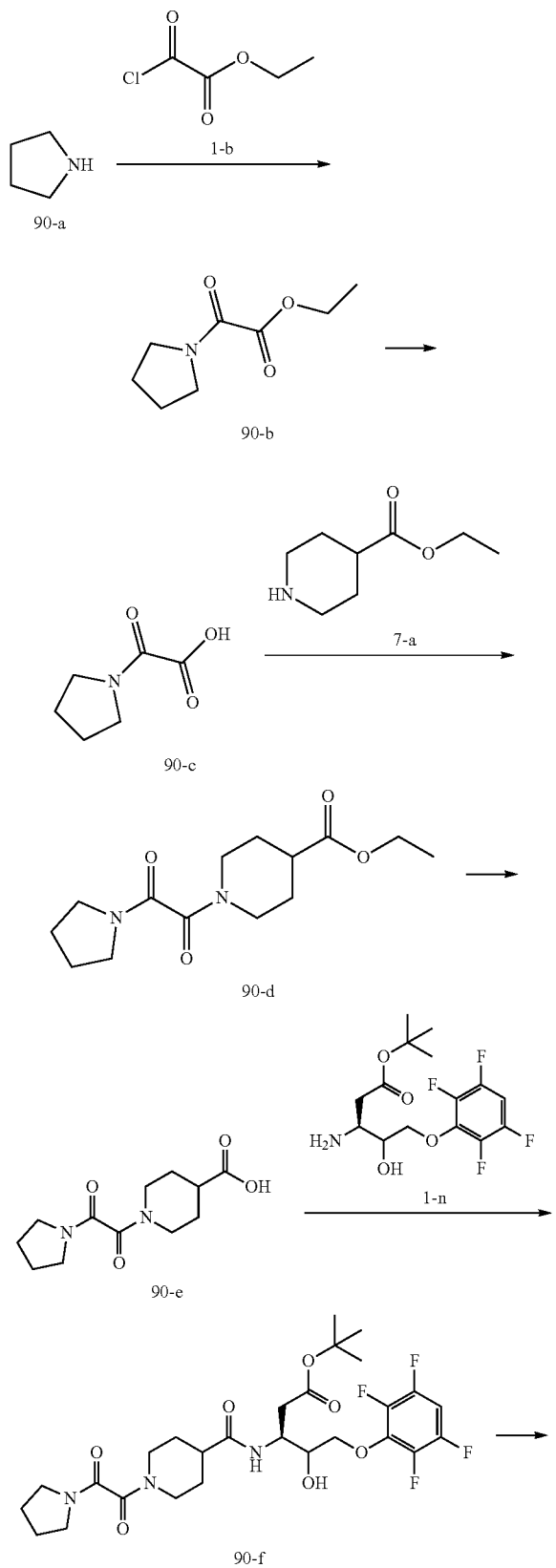

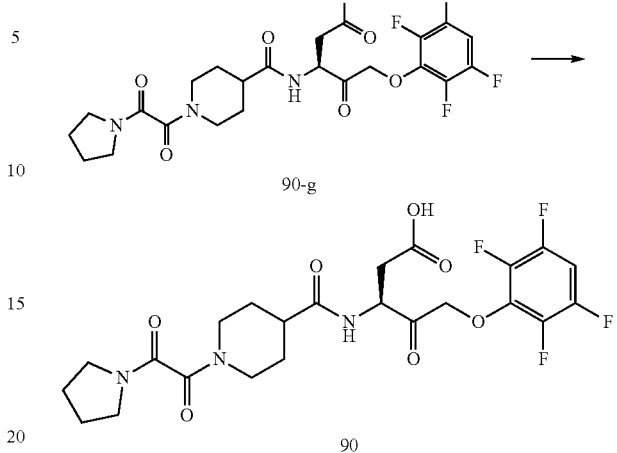

Step 1: Synthesis of Compound 90-b

Compound 90-a (1.00 g, 14.06 mmol, 1.18 mL, 1.00 eq) was dissolved in dichloromethane (20.00 mL). Triethylamine (2.85 g, 28.12 mmol, 3.90 mL, 2.00 eq) and compound 1-b (2.30 g, 16.87 mmol, 1.89 mL, 1.20 eq) were added in an ice bath. After stirring for 30 min, the reaction solution was warmed up to room temperature and stirred for 3 hours. After the reaction was completed, the reaction solution was added with dichloromethane (30 mL) for dilution, and then washed with water (30 mL×2) and saturated brine (50 mL×2). The organic phase was dried over anhydrous sodium sulfate, filtered, and concentrated to give a crude product. The crude product was purified by column chromatography (petroleum ether:ethyl acetate=3:1), to give the product of compound 90-b (1.70 g, yield: 70%) as a colorless oil. LCMS m/z=171.8 [M+H]+.

Step 2: Synthesis of Compound 90-c

LiOH.H2O (183.78 mg, 4.38 mmol, 1.50 eq) was dissolved in water (5.00 mL), and the solution was added to a solution of compound 90-b (500.00 mg, 2.92 mmol, 1.00 eq) dissolved in THF (5.00 mL). The reaction was stirred at room temperature for 1 hour. After the reaction was completed, the reaction solution was added with water (20 mL), adjusted to pH of 3-4 with 1 N dilute hydrochloric acid, and extracted with dichloromethane/methanol (50 mL×3, 10:1). The organic phases were combined, dried over anhydrous sodium sulfate, filtered, and concentrated to give compound 90-c (400.00 mg, crude), which was used directly in the next step without purification. LCMS m/z=144.1 [M+H]+.

Step 3: Synthesis of Compound 90-d

Compound 90-c (400.00 mg, 2.79 mmol, 1.00 eq) was dissolved in dichloromethane (10 mL), and N-methylmorpholine (846.63 mg, 8.37 mmol, 920.25 µL, 3.00 eq), HOBt (516.47 mg, 3.82 mmol, 1.37 eq), EDCl (732.73 mg, 3.82 mmol, 1.37 eq) and compound 7-a (526.34 mg, 3.35 mmol, 516.02 µL, 1.20 eq) were added thereto. The reaction was stirred at room temperature for 16 hours. After the reaction was completed, the reaction solution was added with dichloromethane (30 mL) for dilution, and then washed with water (30 mL) and saturated brine (50 mL). The organic phase was dried over anhydrous sodium sulfate, filtered, and concentrated to give a crude product. The crude product was purified by column chromatography (petroleum ether:ethyl acetate=1:1~1:8), to give the product of compound 90-d (450.00 mg, yield: 55%) as a colorless oil. LCMS m/z=283.0 [M+H]$^+$.

Step 4: Synthesis of Compound 90-e

LiOH.H$_2$O (100.07 mg, 2.38 mmol, 1.50 eq) was dissolved in water (5.00 mL), and the solution was added to a solution of compound 90-d (450.00 mg, 1.59 mmol, 1.00 eq) dissolved in THF (5.00 mL). The reaction was stirred at room temperature for 2 hours. After the reaction was completed, the reaction solution was added with water (20 mL), adjusted to pH of 3-4 with 1 N dilute hydrochloric acid, and extracted with dichloromethane/methanol (50 mL×3, 10:1). The organic phases were combined, dried over anhydrous sodium sulfate, filtered, and concentrated to give the product of compound 90-e (400.00 mg, crude) as a colorless oil, which was used directly in the next step without purification. LCMS m/z=254.9 [M+H]$^+$.

Step 5: Synthesis of Compound 90-f

Compound 90-e (200.00 mg, 786.53 μmol, 1.00 eq) was dissolved in dichloromethane (20 mL), and N-methylmorpholine (238.67 mg, 2.36 mmol, 259.43 μL, 3.00 eq), HOBt (145.60 mg, 1.08 mmol, 1.37 eq), EDCl (206.57 mg, 1.08 mmol, 1.37 eq) and compound 1-n (277.89 mg, 786.53 μmol, 1.00 eq) were added thereto. The reaction was stirred at room temperature for 5 hours. After the reaction was completed, the reaction solution was added with dichloromethane (30 mL) for dilution, and then washed with water (50 mL). The aqueous phase was washed with dichloromethane (50 mL×2). The organic phases were combined, dried over anhydrous sodium sulfate, filtered, and concentrated to give a crude product. The crude product was purified by column chromatography (petroleum ether:ethyl acetate=1: 1~1:10), to give the product of compound 90-f (260.00 mg, yield: 47%) as a colorless oil. LCMS m/z=590.1 [M+H]$^+$.

Step 6: Synthesis of Compound 90-g

Compound 90-f (260.00 mg, 441.00 μmol, 1.00 eq) was dissolved in dichloromethane (10.00 mL), and PIDA (549.72 mg, 1.71 mmol, 3.87 eq) and TEMPO (20.80 mg, 132.30 μmol, 0.30 eq) were added thereto. The reaction was stirred at room temperature for 40 hours. After the reaction was completed, the reaction solution was added with ethyl acetate (40 mL) for dilution, and washed with saturated sodium hydrogen carbonate solution (40 mL) and saturated brine (40 mL×2). The organic phase was dried over anhydrous sodium sulfate, filtered, and concentrated to give a crude product. The crude product was purified by column chromatography (petroleum ether:ethyl acetate=1:1~1:9), to give the product of compound 90-g (210.00 mg, yield: 64%) as a yellow oil. LCMS m/z=588.1 [M+H]$^+$.

Step 7: Synthesis of Compound 90

Compound 90-g (210.00 mg, 357.41 μmol, 1.00 eq) was dissolved in dichloromethane (10.00 mL), and TFA (5.21 mL, 70.31 mmol, 196.71 eq) was added thereto. The reaction was stirred at room temperature for 1 hour. After the reaction was completed, the reaction solution was spin-dried, to give a crude product. The crude product was purified by preparative HPLC (in TFA condition), and lyophilized to give compound 90 (60.00 mg, yield: 32%). $^1$H NMR (400 MHz, DMSO-d$_6$) δ=8.50 (d, J=7.53 Hz, 1H), 7.49-7.69 (m, 1H), 5.13-5.31 (m, 2H), 4.61 (q, J=6.53 Hz, 1H), 4.24 (d, J=12.80 Hz, 1H), 3.55 (d, J=13.30 Hz, 1H), 3.23-3.40 (m, 4H), 3.11 (t, J=11.67 Hz, 1H), 2.70-2.85 (m, 2H), 2.59 (dd, J=7.03, 16.81 Hz, 1H), 2.35-2.48 (m, 1H), 1.66-1.91 (m, 6H), 1.34-1.53 (m, 2H); LCMS m/z=532.0 [M+H]$^+$.

Example 91: Compound 91

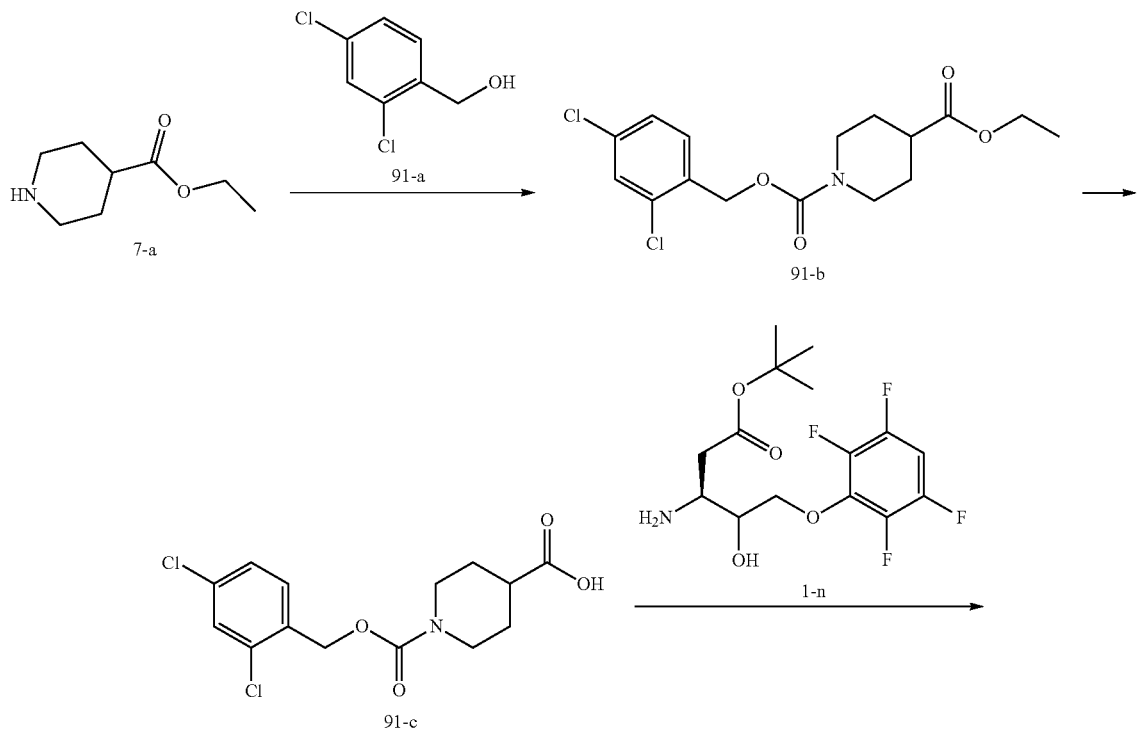

-continued

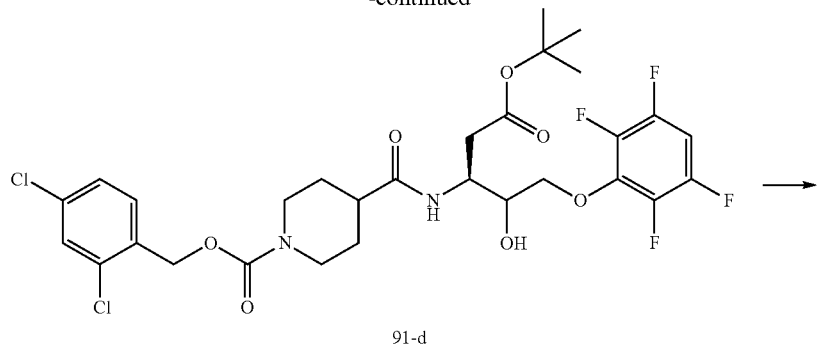

91-d

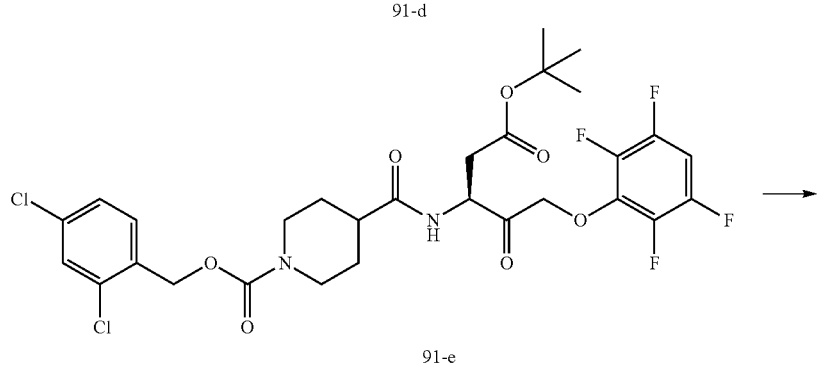

91-e

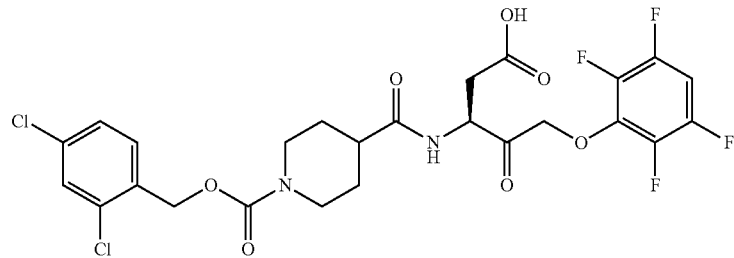

91

Step 1: Synthesis of Compound 91-b

Compound 91-a (3.38 g, 19.08 mmol, 3.00 eq) and CDI (2.99 g, 18.44 mmol, 2.90 eq) were dissolved in THF (20.00 mL). After stirring at room temperature for 1 hour, the reaction solution was added with triethylamine (2.38 g, 23.53 mmol, 3.26 mL, 3.70 eq) and compound 7-a (1.00 g, 6.36 mmol, 980.39 µL, 1.00 eq), warmed up to 80° C. under the protection of nitrogen gas, and stirred for 16 hours. After the reaction was completed, the reaction solution was added with ethyl acetate (50 mL) for dilution, and then washed with water (50 mL). The organic phase was dried over anhydrous sodium sulfate, filtered, and concentrated to give a crude product. The crude product was purified by column chromatography (petroleum ether:ethyl acetate=5:1~3:1), to give the product of compound 91-b (2.34 g, crude) as a colorless oil. LCMS m/z=360.1 [M+H]+.

Step 2: Synthesis of Compound 91-c

LiOH.H$_2$O (87.36 mg, 2.08 mmol, 1.50 eq) was dissolved in H$_2$O (5.00 mL), and the solution was added to a solution of compound 91-b (500.00 mg, 1.39 mmol, 1.00 eq) dissolved in THF (5.00 mL). The reaction was stirred at room temperature for 2 hours. After the reaction was completed, the reaction solution was added with water (30 mL), adjusted to pH of 3-4 with 1 N dilute hydrochloric acid, and extracted with dichloromethane/methanol (50 mL×2, 10:1). The organic phases were combined, dried over anhydrous sodium sulfate, filtered, and concentrated to give the product of compound 91-c (460.00 mg, crude) as a colorless oil, which was used directly in the next step without purification.

Step 3: Synthesis of Compound 91-d

Compound 91-c (200.00 mg, 602.08 mmol, 1.00 eq) was dissolved in dichloromethane (10 mL), and N-methylmorpholine (182.70 mg, 1.81 mmol, 198.59 µL, 3.00 eq), HOBt (111.45 mg, 824.85 µmol, 1.37 eq), EDCl (158.12 mg, 824.85 µmol, 1.37 eq) and compound 1-n (233.99 mg, 662.29 µmol, 1.10 eq) were added thereto. The reaction was stirred at room temperature for 16 hours. After the reaction was completed, the reaction solution was added with water (20 mL), and then extracted with dichloromethane (20 mL×2). The organic phases were combined, dried over anhydrous sodium sulfate, filtered, and concentrated to give a crude product. The crude product was purified by column chromatography (petroleum ether:ethyl acetate=1.5:1), to give the product of compound 91-d (200.00 mg, yield: 50%) as a colorless oil. LCMS m/z=689.1 [M+Na]+.

Step 4: Synthesis of Compound 91-e

Compound 91-d (200.00 mg, 299.64 µmol, 1.00 eq) was dissolved in dichloromethane (10.00 mL), and PIDA (373.51 mg, 1.16 mmol, 3.87 eq) and TEMPO (14.14 mg, 89.89 µmol, 0.30 eq) were added thereto. The reaction was stirred at room temperature for 40 hours. After the reaction was completed, the reaction solution was added with dichloromethane (50 mL) for dilution, and washed with saturated sodium hydrogen carbonate solution (30 mL) and saturated brine (30 mL×2). The organic phase was dried over anhydrous sodium sulfate, filtered, and concentrated to give a crude product. The crude product was purified by column chromatography (petroleum ether:ethyl acetate=2.3:1), to give the product of compound 91-e (160.00 mg, crude) as a yellow oil. LCMS m/z=687.1 [M+Na]$^+$.

Step 5: Synthesis of Compound 91

Compound 91-e (160.00 mg, 240.44 µmol, 1.00 eq) was dissolved in dichloromethane (7.00 mL), and TFA (3.50 mL, 47.30 mmol, 196.71 eq) was added thereto. The reaction was stirred at room temperature for 2 hours. After the reaction was completed, the reaction solution was spin-dried to give a crude product. The crude product was purified by preparative HPLC (in TFA condition), and lyophilized to give compound 91 (137.00 mg, yield: 94%). $^1$H NMR (400 MHz, DMSO-d$_6$) δ=8.44 (br s, 1H), 7.42-7.77 (m, 4H), 4.99-5.49 (m, 4H), 4.60 (br s, 1H), 3.98 (br d, J=12.55 Hz, 2H), 2.85 (br s, 2H), 2.69 (br s, 1H), 2.29-2.48 (m, 2H), 1.69 (br s, 2H), 1.43 (br d, J=11.54 Hz, 2H); LCMS m/z=608.9 [M+H]$^+$.

Example 92: Compound 92

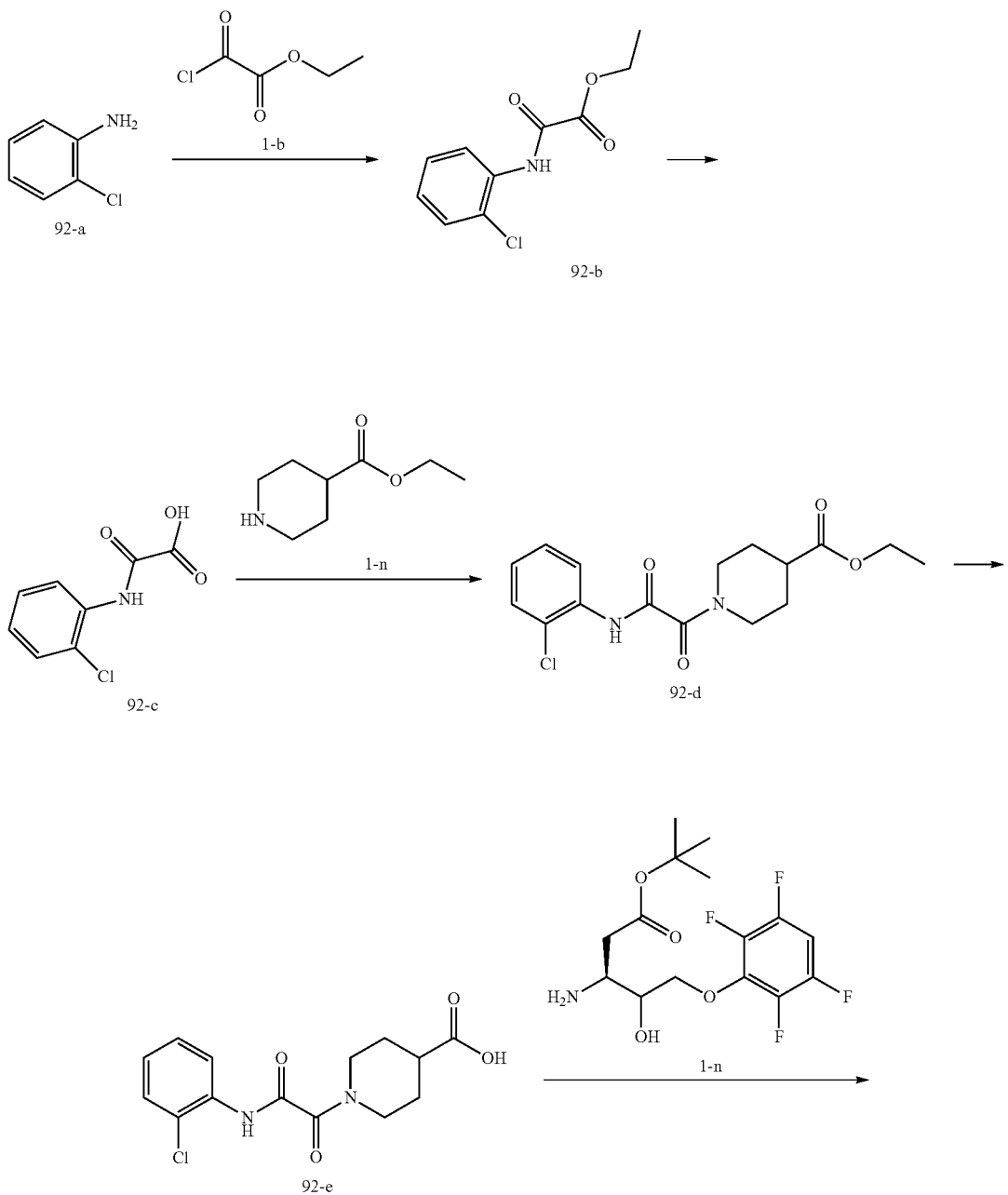

-continued

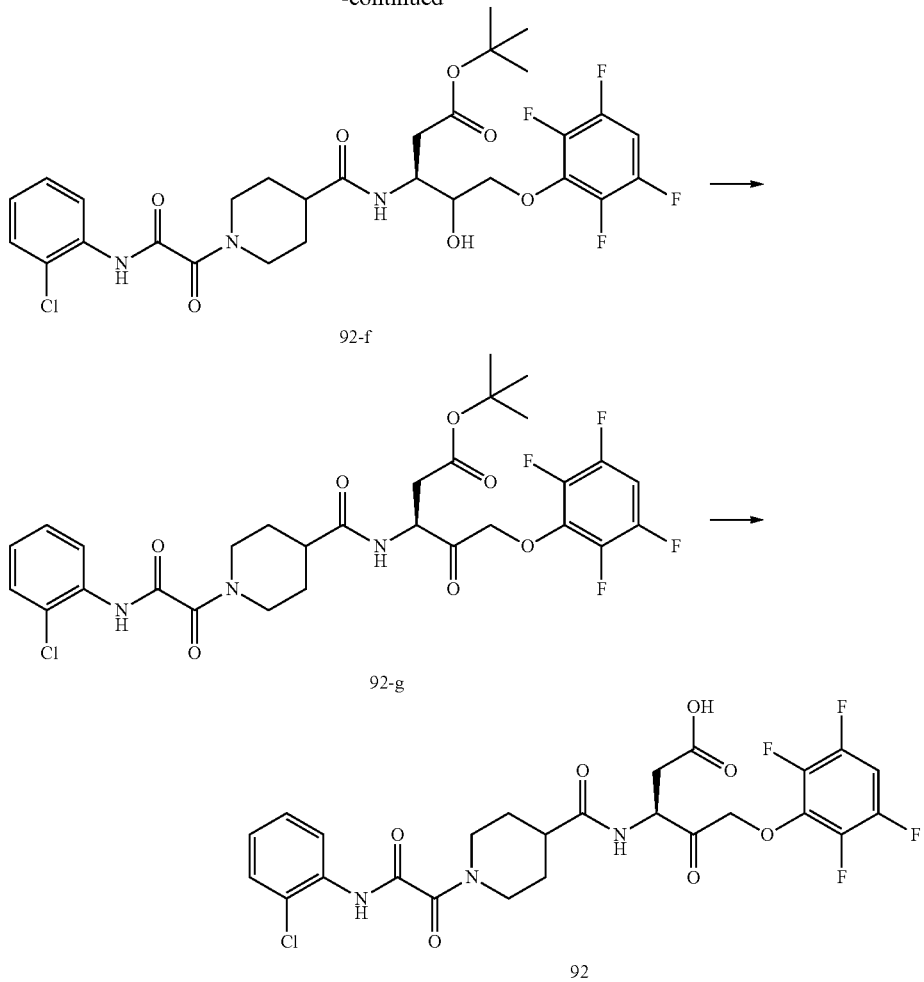

Step 1: Synthesis of Compound 92-b

Compound 92-a (300.00 mg, 2.35 mmol, 1.00 eq) was dissolved in dichloromethane (6 mL), and triethylamine (380.74 mg, 3.76 mmol, 521.56 µL, 1.60 eq) was added thereto, and stirred under the protection of nitrogen gas. Compound 1-b (417.39 mg, 3.06 mmol, 1.30 eq) was slowly added thereto with stirring, since the reaction was exothermic. After the addition was completed, the reaction system was stirred at 15° C. for 16 hours. After the reaction was completed, the reaction solution was added with 20 mL of water, and then separated and extracted. The aqueous phase was extracted once with 20 mL of ethyl acetate. The combined organic phase was washed once separately with each of hydrochloric acid and saturated brine (10 mL), dried over anhydrous sodium sulfate, and then spin-dried to give a crude product. The crude product was subjected to column chromatography (petroleum ether:ethyl acetate=1:0~5:1) to give compound 92-b (250.00 mg, yield: 47%) as a colorless liquid. LCMS m/z=227.8 [M+H]$^+$.

Step 2: Synthesis of Compound 92-c

Compound 92-b (250.00 mg, 1.10 mmol, 1.00 eq) was dissolved in tetrahydrofuran (5 mL), and then LiOH.H$_2$O (39.52 mg, 1.65 mmol, 1.50 eq) was dissolved in water (6 mL). The formulated solution was slowly added to compound 92-b. The reaction system was stirred at 15° C. for 2 hours. The reaction system was acidified to pH of about 4 with 1N hydrochloric acid, and then extracted four times with ethyl acetate (10 mL). The combined organic phases were washed once with 10 mL of saturated brine, dried over anhydrous sodium sulfate, and then spin-dried to give a crude product of compound 92-c (230.00 mg, crude).

Step 3: Synthesis of Compound 92-d

Under the protection of nitrogen gas, compound 92-c (230.00 mg, 1.20 mmol, 1.00 eq) was dissolved in dichloromethane (6 mL). EDCl (315.80 mg, 1.65 mmol, 1.37 eq), HOBt (222.59 mg, 1.65 mmol, 1.37 eq), and NMM (364.89 mg, 3.61 mmol, 396.62 µL, 3.00 eq) were added thereto, and compound 1-e (207.94 mg, 1.32 mmol, 203.87 µL, 1.10 eq) as a substrate was finally added thereto. The reaction was stirred at 15° C. for 16 hours. The reaction system was added with 40 mL of ethyl acetate and 40 mL of water, and separated. The aqueous phase was further extracted once with ethyl acetate (20 mL). The combined organic phases were washed once separately with each of water and saturated brine (40 mL), and then dried and spin-dried to give a crude product. The crude product was subjected to column chromatography (petroleum ether:ethyl acetate=1:0~1:1) to give compound 92-d (170.00 mg, yield: 42%) as a brown liquid. LCMS m/z=338.9 [M+H]$^+$.

Step 4: Synthesis of Compound 92-e

Compound 92-e (170.00 mg, 501.79 μmol, 1.00 eq) was dissolved in tetrahydrofuran (4 mL), and then LiOH.H$_2$O (18.03 mg, 752.69 μmol, 1.50 eq) was dissolved in water (4 mL). The formulated solution was slowly added to compound 92-d. The reaction system was stirred at 15° C. for 2 hours. The reaction system was acidified to pH of about 4 with 1N hydrochloric acid, and then extracted twice with ethyl acetate (20 mL). The combined organic phases were washed once separately with water (20 mL) and saturated brine (20 mL), dried over anhydrous sodium sulfate, and then spin-dried to give the crude product of compound 92-e (140.00 mg, crude) as a colorless liquid, LCMS m/z=310.9 [M+H]$^+$, 333.0 [M+Na]$^+$.

Step 5: Synthesis of Compound 92-f

Under the protection of nitrogen gas, compound 92-e (140.00 mg, 450.55 μmol, 1.10 eq) was dissolved in dichloromethane (5 mL). EDCl (107.57 mg, 561.14 μmol, 1.37 eq), HOBt (75.82 mg, 561.14 μmol, 1.37 eq), NMM (124.29 mg, 1.23 mmol, 135.10 μL, 3.00 eq) were then added thereto, and compound 1-n (144.71 mg, 409.59 μmol, 1.00 eq) as a substrate was finally added thereto. The reaction was stirred at 15° C. for 18 hours. After the reaction was completed, the reaction system was added with 20 mL of ethyl acetate and 20 mL of water once, and separated. The aqueous phase was further extracted once with ethyl acetate (20 mL). The combined organic phases were washed once separately with water (20 mL) and saturated brine (20 mL), and then dried and spin-dried to give a crude product. The crude product was subjected to column chromatography (petroleum ether:ethyl acetate=1:0~10:7) to give compound 92-f (76.00 mg, yield: 29%) as a brown liquid, LCMS m/z=668.0 [M+Na]$^+$.

Step 6: Synthesis of Compound 92-g

Compound 92-f (72.00 mg, 111.45 μmol, 1.00 eq) was dissolved in dichloromethane (5 mL), and PIDA (143.59 mg, 445.80 μmol, 4.00 eq) and TEMPO (8.76 mg, 55.72 μmol, 0.50 eq) was added under the protection of nitrogen gas. The reaction system was stirred at 15° C. for 16 hours. The system was added with ethyl acetate (20 mL), and washed once separately with saturated sodium hydrogen carbonate solution (20 mL), water (20 mL) and saturated brine (20 mL). The organic phase was dried over anhydrous sodium sulfate, filtered, and spin-dried to give a crude product. The crude product was subjected to column chromatography (petroleum ether:ethyl acetate=1:1) to give compound 92-g (34.00 mg, yield: 47%) as a brown liquid, LCMS m/z=666.1 [M+Na]$^+$.

Step 7: Synthesis of Compound 92

Compound 92-g (34.00 mg, 52.79 μmol, 1.00 eq) was dissolved in dichloromethane (5 mL), and trifluoroacetic acid (1.20 g, 10.56 mmol, 781.70 μL, 200.00 eq) was added under the protection of nitrogen gas. The system was stirred at 15° C. for 1 hour. After the reaction was completed, the reaction solution was spin-dried to give a crude product. The crude product was purified by preparative HPLC (in trifluoroacetic acid condition), spin-dried, and then dissolved with acetonitrile (20 mL). The obtained solution was added with water (20 mL), evenly mixed, and lyophilized to give compound 92 (8.30 mg, yield: 25%). $^1$H NMR NMR (400 MHz, CHLOROFORM-d) δ=9.66 (br. s., 1H), 8.33 (d, J=7.78 Hz, 1H), 7.41 (d, J=8.03 Hz, 1H), 7.27-7.35 (m, 1H), 7.07-7.16 (m, 1H), 6.84 (br. s., 1H), 6.24 (br. s., 1H), 5.13 (d, J=13.05 Hz, 2H), 4.80 (br. s., 1H), 4.58 (d, J=13.05 Hz, 1H), 4.25-4.47 (m, 1H), 3.31 (t, J=11.92 Hz, 2H), 2.85-3.01 (m, 2H), 2.53 (br. s., 1H), 2.00 (d, J=11.80 Hz, 2H), 1.67-1.91 (m, 2H).

Example 93: Compound 93

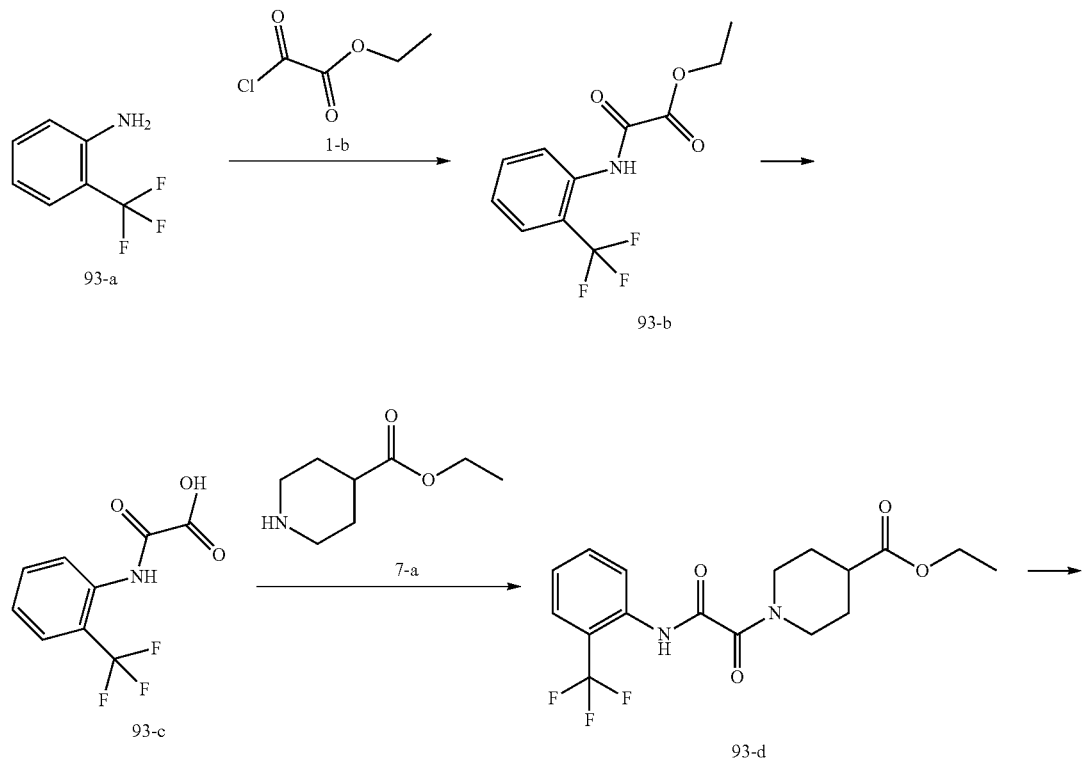

-continued
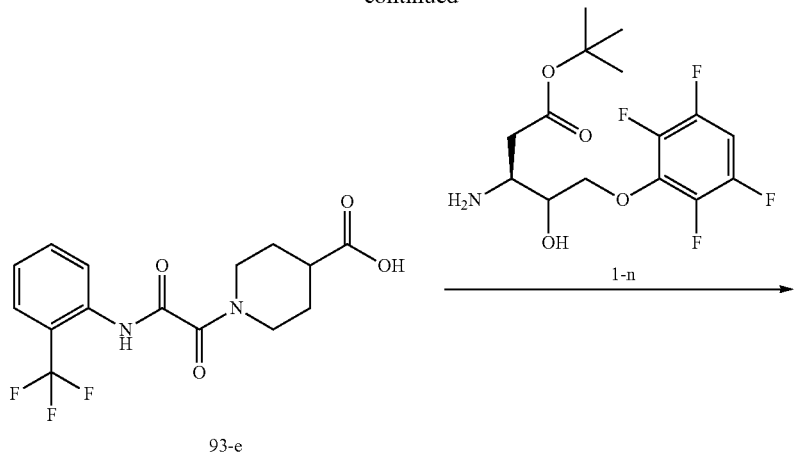
93-e
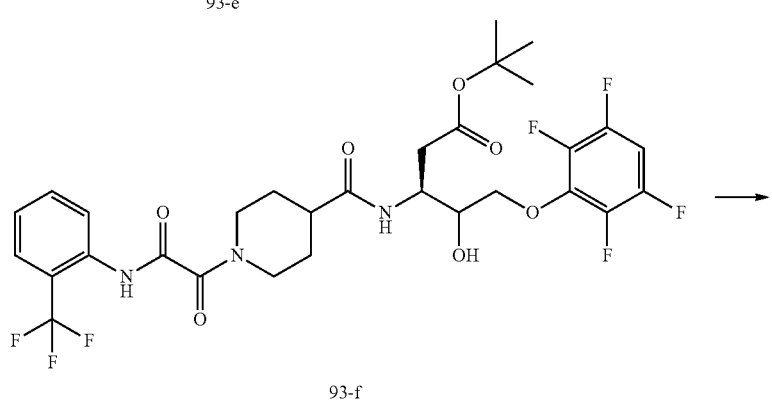
93-f
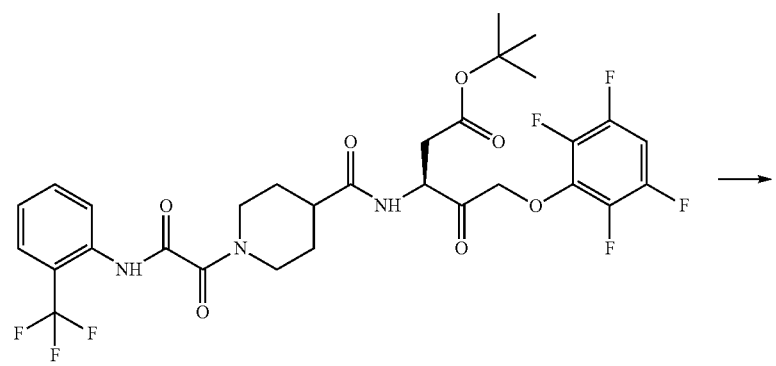
93-g
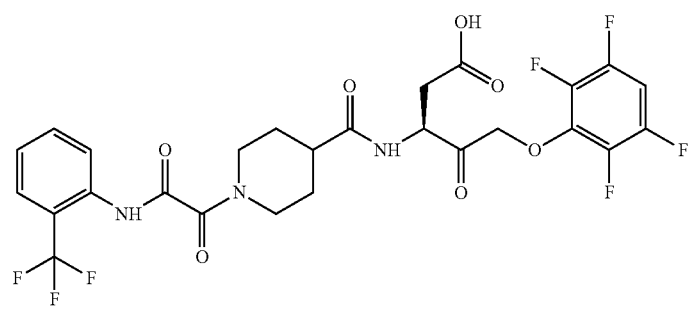
93

Step 1: Synthesis of Compound 93-b

Compound 93-a (1.00 g, 6.21 mmol, 781.25 μL, 1.00 eq) was dissolved in dichloromethane (6 mL), and triethylamine (879.75 mg, 8.69 mmol, 1.21 mL, 1.40 eq) was added thereto, and stirred under the protection of nitrogen gas. Compound 1-b (1.10 g, 8.07 mmol, 903.45 μL, 1.30 eq) was slowly added thereto with stirring, since the reaction was exothermic. After the addition was completed, the reaction system was stirred at 15° C. for 16 hours. After the reaction was completed, the reaction solution was added with 20 mL of water and 20 mL of ethyl acetate, and acidified to pH of about 4 with 1N hydrochloric acid, followed by separation and extraction. The aqueous phase was extracted once with 20 mL of ethyl acetate. The combined organic phases were washed once separately with 10 mL of water and 10 mL of saturated brine, dried over anhydrous sodium sulfate, and then spin-dried to give a crude product. The crude product was subjected to column chromatography (petroleum ether: ethyl acetate=1:0~5:1) to give compound 93-b (1.50 g, yield: 92%) as a colorless liquid. $^1$H NMR (400 MHz, DMSO-d6) δ=9.36 (br s, 1H), 8.37 (br d, J=8.28 Hz, 1H), 7.67 (br d, J=7.78 Hz, 1H), 7.58-7.63 (m, 1H), 7.31 (br t, J=7.65 Hz, 1H), 4.45 (q, J=7.03 Hz, 2H), 1.45 (t, J=7.15 Hz, 3H).

Step 2: Synthesis of Compound 93-c

Compound 93-b (1.50 g, 5.74 mmol, 1.00 eq) was dissolved in tetrahydrofuran (20 mL), and then LiOH.H$_2$O (219.96 mg, 9.18 mmol, 1.60 eq) was dissolved in water (20 mL). The formulated solutions were slowly added to compound 93-b. The reaction system was stirred at 15° C. for 2 hours. The reaction system was acidified to pH of about 4 with 1N hydrochloric acid, and then extracted four times with ethyl acetate (70 mL). The combined organic phases were washed once with 150 mL of saturated brine, dried over anhydrous sodium sulfate, and then spin-dried to give the crude liquid product of compound 93-c (1.28 g, crude) as a yellow oil. $^1$H NMR (400 MHz, CHLOROFORM-d) δ=9.91 (br. s., 1H), 9.43 (br. s., 1H), 8.27 (d, J=8.28 Hz, 1H), 7.70 (d, J=8.03 Hz, 1H), 7.65 (t, J=7.78 Hz, 1H), 7.37 (t, J=7.65 Hz, 1H).

Step 3: Synthesis of Compound 93-d

Under the protection of nitrogen gas, compound 93-c (244.69 mg, 1.05 mmol, 1.10 eq) was dissolved in dichloromethane (6 mL). HATU (725.58 mg, 1.91 mmol, 2.00 eq) and N,N-diisopropylethylamine (369.94 mg, 2.86 mmol, 499.92 μL, 3.00 eq) were then added thereto, and compound 7-a (150.00 mg, 954.14 μmol, 147.06 μL, 1.00 eq) as a substrate was finally added thereto. The reaction was stirred at 15° C. for 16 hours. The reaction system was added with 40 mL of ethyl acetate and 40 mL of water, and separated. The aqueous phase was further extracted once with ethyl acetate (20 mL). The combined organic phases were washed once separately with water and saturated brine (40 mL of each), and then dried and spin-dried to give a crude product. The crude product was subjected to column chromatography (petroleum ether:ethyl acetate=1:0~5:2) to give compound 93-d (240.00 mg, yield: 68%) as a brown liquid. $^1$H NMR (400 MHz, CHLOROFORM-d) δ=9.66 (br. s., 1H), 8.26 (d, J=8.28 Hz, 1H), 7.66 (d, J=7.78 Hz, 1H), 7.59 (t, J=7.91 Hz, 1H), 7.27-7.32 (m, 1H), 4.95 (td, J=3.54, 13.74 Hz, 1H), 4.39 (td, J=3.70, 13.18 Hz, 1H), 4.14-4.20 (m, 2H), 3.47 (ddd, J=3.01, 10.92, 13.68 Hz, 1H), 3.08 (ddd, J=3.01, 10.85, 13.49 Hz, 1H), 2.56-2.66 (m, 1H), 1.99-2.08 (m, 2H), 1.75-1.93 (m, 2H), 1.23-1.27 (m, 3H).

Step 4: Synthesis of Compound 93-e

Compound 93-d (240.00 mg, 644.57 μmol, 1.00 eq) was dissolved in tetrahydrofuran (6 mL), and then LiOH.H$_2$O (24.70 mg, 644.57 μmol, 1.60 eq) was dissolved in water (6 mL). The formulated solutions were slowly added to compound 93-d, and the reaction system was stirred at 15° C. for 3 hours. The reaction system was acidified to pH of about 4 with 1N hydrochloric acid, and then extracted four times with ethyl acetate (10 mL). The combined organic phases were washed once separately with water (20 mL) and saturated brine (20 mL), dried over anhydrous sodium sulfate, and then spin-dried to give the crude liquid product of compound 93-e (300.00 mg, crude) as a yellow oil. $^1$H NMR (400 MHz, CHLOROFORM-d) δ=9.66 (br. s., 1H), 8.26 (d, J=8.28 Hz, 1H), 7.66 (d, J=7.78 Hz, 1H), 7.59 (t, J=8.03 Hz, 1H), 7.28-7.33 (m, 1H), 4.95 (d, J=13.80 Hz, 1H), 4.39 (d, J=13.80 Hz, 1H), 4.12 (q, J=7.03 Hz, 1H), 3.52 (t, J=10.92 Hz, 1H), 3.07-3.21 (m, 1H), 2.64-2.76 (m, 1H), 2.11 (s, 1H), 1.79-1.96 (m, 2H).

Step 5: Synthesis of Compound 93-f

Under the protection of nitrogen gas, compound 93-e (240.00 mg, 697.09 μmol, 1.10 eq) was dissolved in dichloromethane (10 mL). EDCl (166.43 mg, 868.19 μmol, 1.37 eq), HOBt (117.31 mg, 868.19 μmol, 1.37 eq), NMM (192.30 mg, 1.90 mmol, 209.02 μL, 3.00 eq) were then added thereto, and compound 1-n (223.90 mg, 633.72 μmol, 1.00 eq) as a substrate was finally added thereto. The reaction was stirred at 15° C. for 40 hours. After the reaction was completed, the reaction system was added with ethyl acetate and water (20 mL of each), and separated. The aqueous phase was further extracted once with ethyl acetate (20 mL). The combined organic phases were washed once separately with water and saturated brine (20 mL of each), and then dried and spin-dried to give a crude product. The crude product was subjected to column chromatography (petroleum ether:ethyl acetate=1:0~10:7) to give compound 93-f (183.00 mg, yield: 42%) as a brown liquid, LCMS m/z=702.0 [M+Na]$^+$.

Step 6: Synthesis of Compound 93-g

Compound 93-f (183.00 mg, 269.28 μmol, 1.00 eq) was dissolved in dichloromethane (10 mL), and PIDA (425.00 mg, 1.32 mmol, 4.90 eq) and TEMPO (30.00 mg, 190.78 μmol, 0.71 eq) were added thereto under the protection of nitrogen gas. The reaction system was stirred at 15° C. for 40 hours. The system was added with ethyl acetate (40 mL), and washed once respectively with saturated sodium hydrogen carbonate solution (40 mL), water (40 mL) and saturated brine (40 mL). The organic phase was dried over anhydrous sodium sulfate, filtered, and spin-dried to give a crude product. The crude product was subjected to column chromatography (petroleum ether:ethyl acetate=1:1~1:4) to give compound 93-g (155.00 mg, yield: 85%) as a brown liquid, LCMS m/z=700.1 [M+Na]$^+$.

Step 7: Synthesis of Compound 93

Compound 93-g (34.00 mg, 52.79 μmol, 1.00 eq) was dissolved in dichloromethane (5 mL), and trifluoroacetic acid (1.20 g, 10.56 mmol, 781.70 μL, 200.00 eq) was added under the protection of nitrogen gas. The system was stirred at 15° C. for 1 hour. After the reaction was completed, the reaction solution was spin-dried to give a crude product. The crude product was purified by preparative HPLC (in trifluoroacetic acid condition), spin-dried, and then dissolved with acetonitrile (20 mL). The obtained solution was added with water (20 mL), evenly mixed, and lyophilized to give compound 93 (8.30 mg, yield: 25%). $^1$H NMR NMR (400 MHz, CHLOROFORM-d) δ=9.66 (br. s., 1H), 8.33 (d, J=7.78 Hz, 1H), 7.41 (d, J=8.03 Hz, 1H), 7.27-7.35 (m, 1H), 7.07-7.16 (m, 1H), 6.84 (br. s., 1H), 6.24 (br. s., 1H), 5.13 (d, J=13.05 Hz, 2H), 4.80 (br. s., 1H), 4.58 (d, J=13.05 Hz, 1H), 4.25-4.47 (m, 1H), 3.31 (t, J=11.92 Hz, 2H), 2.85-3.01 (m, 2H), 2.53 (br. s., 1H), 2.00 (d, J=11.80 Hz, 2H), 1.67-1.91 (m, 2H).

Example 94: Compound 94

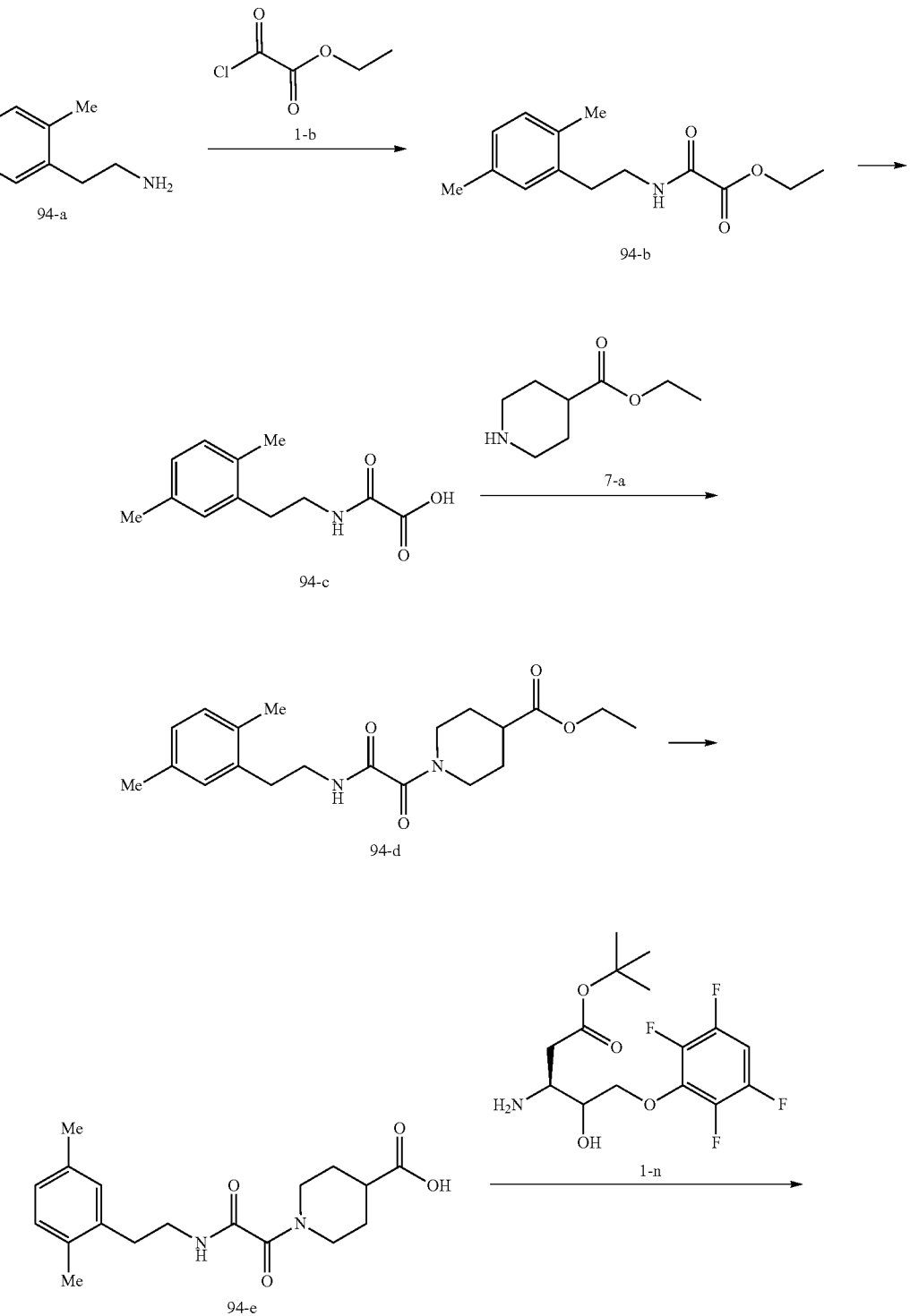

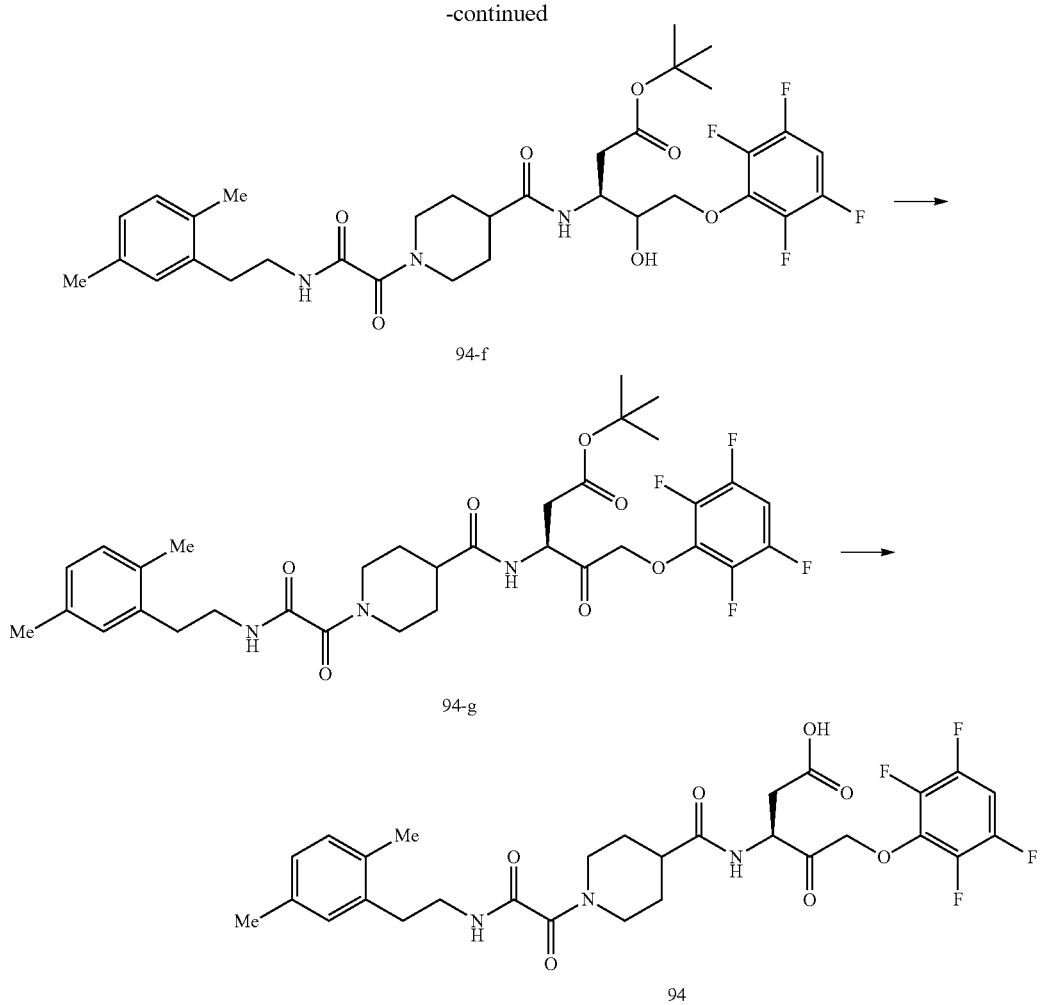

Step 1: Synthesis of Compound 94-b

Compound 94-a (1.00 g, 6.70 mmol, 1.00 eq) and triethylamine (1.36 g, 13.40 mmol, 1.86 mL, 2.00 eq) were added to dichloromethane (100 mL), maintained at 0-5° C. and stirred for 15 min. Compound 1-b (960.49 mg, 7.04 mmol, 787.29 μL, 1.05 eq) was then added to the above solution, maintained at 10° C.-20° C. and stirred for 16 hours. After the reaction was completed, the reaction solution was added with 100 mL of water, and separated. The aqueous phase was further extracted with dichloromethane (200 mL×2). The organic phases were combined, and washed with dilute hydrochloric acid (0.1 M, 150 mL) and water (100 mL). The organic phase was dried over anhydrous sodium sulfate, filtered, concentrated, and subjected to column chromatography (petroleum ether:ethyl acetate=1:0~5:2) to give the product of compound 94-b (1.62 g, yield: 96%) as a yellow oil. $^1$H NMR (400 MHz, CHLOROFORM-d) δ=7.11 (br. s., 1H), 6.99 (d, J=7.5 Hz, 1H), 6.93-6.85 (m, 2H), 4.27 (q, J=7.0 Hz, 2H), 3.52-3.43 (m, 2H), 2.77 (t, J=7.3 Hz, 2H), 2.23 (s, 6H), 1.31 (t, J=7.0 Hz, 3H); LCMS m/z=250.0 [M+H]$^+$.

Step 2: Synthesis of Compound 94-c

Compound 94-b (1.65 g, 6.62 mmol, 1.00 eq) was dissolved in tetrahydrofuran (10.00 mL), and a solution of LiOH.H$_2$O (555.43 mg, 13.24 mmol, 2.00 eq) dissolved in H$_2$O (10.00 mL) was added to the above solution. The reaction solution was maintained at 25° C. and stirred for 2 hours. After the reaction was completed, the reaction solution was adjusted to pH of 6 with 2 N dilute hydrochloric acid. This solution was added with 50 mL of water, and extracted with dichloromethane (30 mL×3). The organic phase was dried over anhydrous sodium sulfate, filtered and concentrated to give the product of compound 94-c (1.81 g, crude) as a pale yellow oil, which was used directly in the next step without purification. LCMS m/z=222.0 [M+H]$^+$.

Step 3: Synthesis of Compound 94-d

Compound 94-c (1.22 g, 5.50 mmol, 1.10 eq) and DIPEA (1.94 g, 15.00 mmol, 2.62 mL, 3.00 eq) were dissolved in dichloromethane (10 mL), and compound 7-a (786.05 mg, 5.00 mmol, 770.64 μL, 1.00 eq) was added thereto. The reaction solution was stirred at room temperature for 1.5 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~3:1) to give the product of compound 94-d (1.62 g, yield: 80%) as a yellow oil. $^1$H NMR (400 MHz, CHLOROFORM-d) δ=7.25 (br. s., 1H), 7.05 (d, J=7.5 Hz, 1H), 6.99-6.93 (m, 2H), 4.75 (d, J=14.1 Hz, 1H), 4.32 (d, J=13.6 Hz, 1H), 4.15 (q, J=7.0 Hz, 2H), 3.55-3.45 (m, 2H), 3.38-3.28 (m, 1H), 3.00-2.90 (m, 1H), 2.86-2.81 (m, 2H), 2.57 (t, J=4.0 Hz, 1H), 2.30 (d, J=2.5 Hz, 6H), 1.98 (dd, J=3.3, 13.8 Hz, 2H), 1.84-1.66 (m, 2H), 1.26 (t, J=7.3 Hz, 3H); LCMS m/z=383.1 [M+Na]$^+$.

Step 4: Synthesis of Compound 94-e

Compound 94-d (360.00 mg, 998.75 μmol, 1.00 eq) was dissolved in tetrahydrofuran (10.00 mL), and a solution of LiOH.H$_2$O (83.82 mg, 2.00 mmol, 2.00 eq) dissolved in H$_2$O (10.00 mL) was added to the above solution. The reaction solution was maintained at 25° C. and stirred for 2 hours. After the reaction was completed, the reaction solution was adjusted to pH of 6 with 2 N dilute hydrochloric acid. This solution was added with 50 mL of water, and extracted with dichloromethane (30 mL×3). The organic phase was dried over anhydrous sodium sulfate, filtered and concentrated to give the product of compound 94-e (356.00 mg, crude) as pale yellow oil, which was used directly in the next step without purification. LCMS m/z=355.1 [M+Na]$^+$.

Step 5: Synthesis of Compound 94-f

Compound 94-e (282.53 mg, 850.00 μmol, 1.70 eq) and HATU (380.23 mg, 1.00 mmol, 2.00 eq) were dissolved in dichloromethane (20 mL), and stirred at room temperature for 15 min. Compound 1-n (176.66 mg, 500.00 μmol, 1.00 eq) and DIPEA (193.86 mg, 1.50 mmol, 261.97 μL, 3.00 eq) were then added, and stirred at room temperature for another 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 94-f (156.00 mg, yield: 43%) as a yellow oil. LCMS m/z=668.4 [M+H]$^+$; 690.3 [M+Na]$^+$.

Step 6: Synthesis of Compound 94-g

Compound 94-f (150.00 mg, 224.66 μmol, 1.00 eq) was dissolved in dichloromethane (20.00 mL), and PIDA (289.45 mg, 898.62 μmol, 4.00 eq) and TEMPO (7.07 mg, 44.93 μmol, 0.20 eq) were added thereto. The reaction solution was stirred at room temperature for 40 hours. After the reaction was completed, the reaction solution was added with saturated sodium hydrogen carbonate solution (50 mL) and saturated sodium sulfite solution (50 mL), extracted with dichloromethane (30 mL×3), and washed with saturated brine (50 mL). The organic phase was dried over anhydrous sodium sulfate, filtered and concentrated to give a crude product. The crude product was subjected to column chromatography (petroleum ether:ethyl acetate=1:0~5:3) to give the product of compound 94-g (75.00 mg, yield: 43%) as a yellow oil. LCMS m/z=666.3 [M+H]$^+$; 688.3 [M+Na]$^+$.

Step 7: Synthesis of Compound 94

Compound 94-g (75.00 mg, 112.67 μmol, 1.00 eq) was dissolved in dichloromethane (4.00 mL), and trifluoroacetic acid (4.62 g, 40.52 mmol, 3.00 mL) was added thereto. The reaction solution was stirred at room temperature for 2 hours. After the reaction was completed, the reaction solution was spin-dried to give a crude product. The crude product was purified by preparative HPLC (in trifluoroacetic acid condition), and lyophilized to give the product of compound 94 (40.00 mg, yield: 56%). $^1$H NMR (400 MHz, DMSO-d$_6$) δ=8.76 (t, J=5.0 Hz, 1H), 8.45 (br. s., 1H), 7.65-7.50 (m, 1H), 7.01 (d, J=7.0 Hz, 1H), 6.95 (s, 1H), 6.91 (br. s., 1H), 5.21 (br. s., 2H), 4.63 (br. s., 1H), 4.22 (d, J=12.5 Hz, 1H), 3.57 (d, J=3.5 Hz, 1H), 3.33-3.21 (m, 3H), 2.98 (t, J=11.8 Hz, 1H), 2.78-2.58 (m, 5H), 2.24 (s., 3H), 2.22 (s., 3H), 1.79-1.60 (m, 2H), 1.53-1.36 (m, 2H); LCMS m/z=610.2 [M+H]$^+$.

Example 95: Compound 95

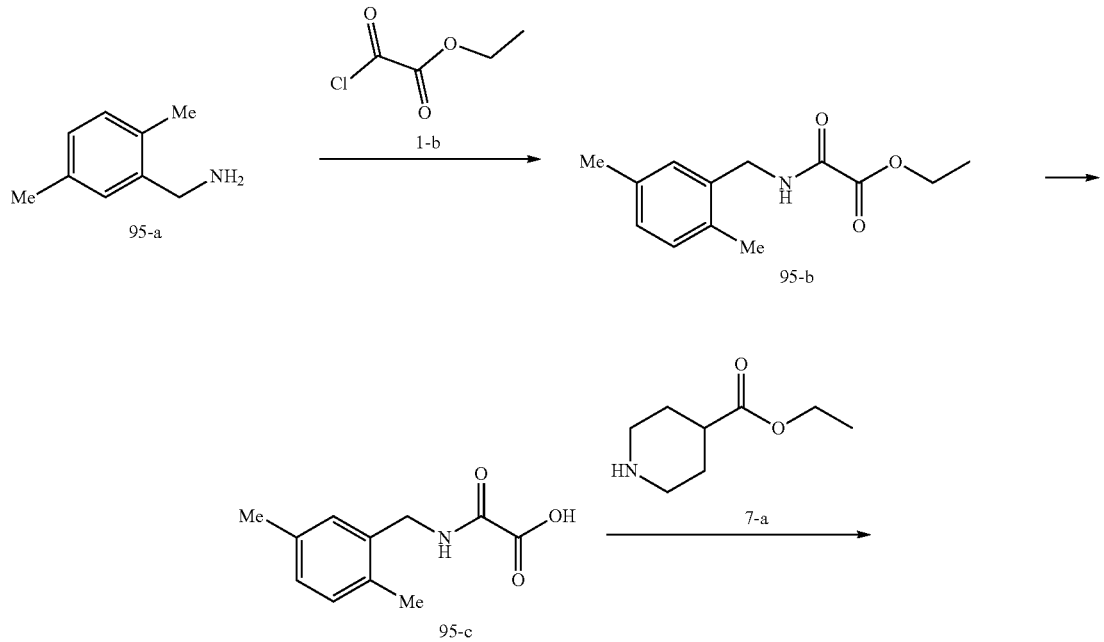

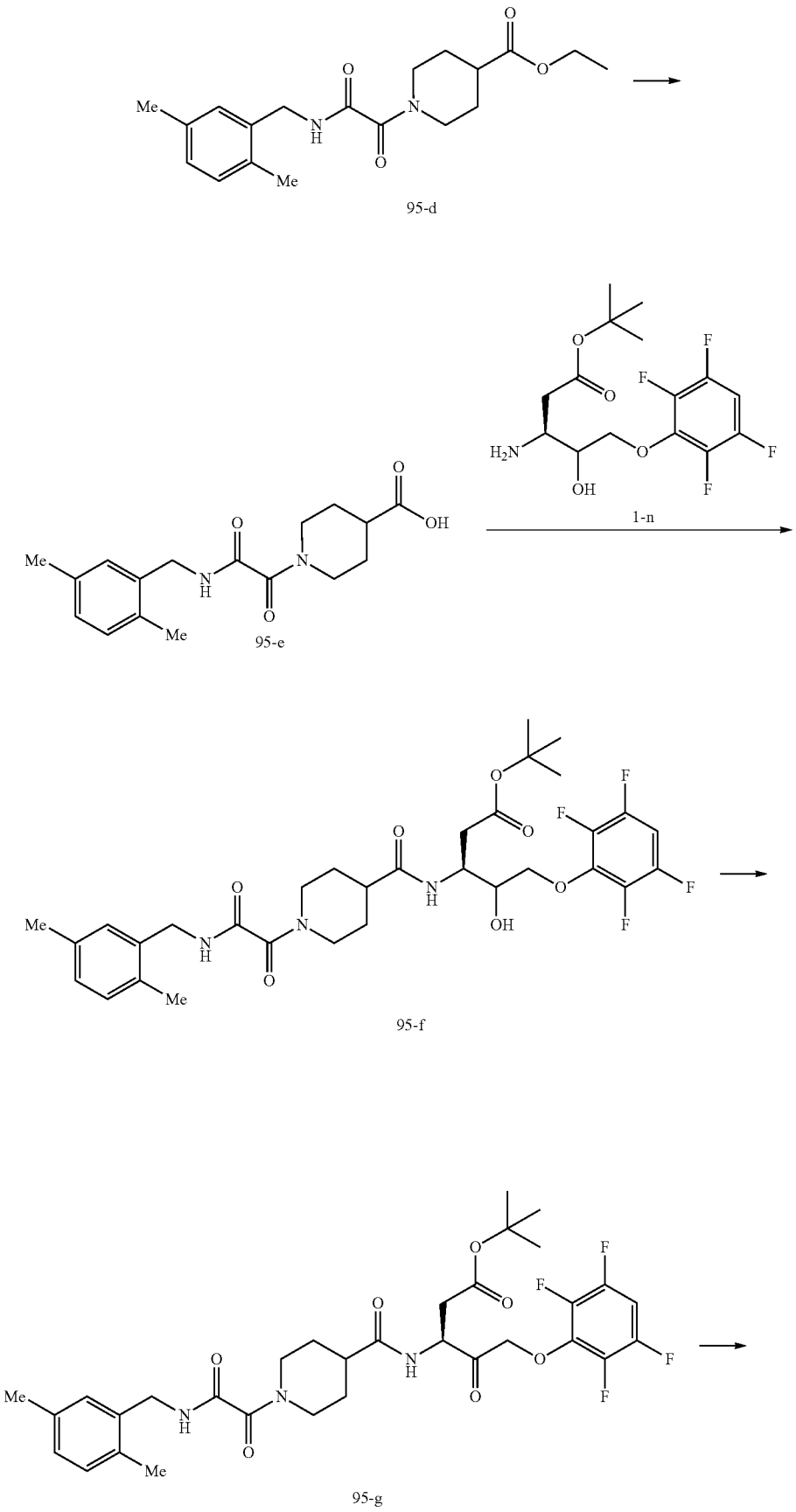

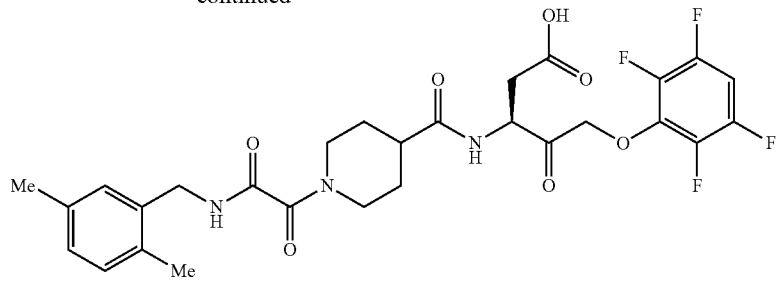

95

Step 1: Synthesis of Compound 95-b

Compound 95-a (906.52 mg, 6.70 mmol, 1.00 eq) and triethylamine (1.36 g, 13.40 mmol, 1.86 mL, 2.00 eq) were added to dichloromethane (100 mL), maintained at 0-5° C. and stirred for 15 min. Compound 1-b (960.49 mg, 7.04 mmol, 787.29 μL, 1.05 eq) was then added to the above solution, maintained at 10-20° C. and stirred for 16 hours. After the reaction was completed, the reaction solution was added with 100 mL of water, and separated. The aqueous phase was further extracted with dichloromethane (200 mL×2). The organic phases were combined, and washed with dilute hydrochloric acid (0.1 M, 150 mL) and water (100 mL). The organic phase was dried over anhydrous sodium sulfate, filtered, concentrated, and subjected to column chromatography (petroleum ether:ethyl acetate=1:0~5:2) to give the product of compound 95-b (1.23 g, yield: 78%) as a yellow oil. $^1$H NMR (400 MHz, CHLOROFORM-d) δ=7.19 (br. s., 1H), 7.12-7.02 (m, 3H), 4.49 (d, J=6.0 Hz, 2H), 4.36 (q, J=7.4 Hz, 2H), 2.30 (d, J=9.5 Hz, 6H), 1.39 (t, J=7.3 Hz, 3H); LCMS m/z=235.9 [M+H]$^+$.

Step 2: Synthesis of Compound 95-c

Compound 95-b (1.23 g, 5.23 mmol, 1.00 eq) was dissolved in tetrahydrofuran (10.00 mL), and a solution of LiOH.H$_2$O (438.72 mg, 10.46 mmol, 2.00 eq) dissolved in H$_2$O (10.00 mL) was added to the above solution. The reaction solution was maintained at 25° C. and stirred for 2 hours. After the reaction was completed, the reaction solution was adjusted to pH of 6 with 2 N dilute hydrochloric acid. This solution was added with 50 mL of water, and extracted with dichloromethane (30 mL×3). The organic phase was dried over anhydrous sodium sulfate, filtered and concentrated to give the product of compound 95-c (1.01 g, crude) as a pale yellow oil, which was used directly in the next step without purification.

Step 3: Synthesis of Compound 95-d

Compound 95-c (980.20 mg, 4.73 mmol, 1.10 eq), HATU (3.27 g, 8.60 mmol, 2.0 eq) and DIPEA (1.67 g, 12.90 mmol, 2.25 mL, 3.00 eq) were dissolved in dichloromethane (10 mL), and compound 7-a (676.00 mg, 4.30 mmol, 662.75 μL, 1.00 eq) was added thereto. The reaction solution was stirred at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~5:1) to give the product of compound 95-d (1.24 g, yield: 82%) as a yellow oil. $^1$H NMR (400 MHz, CHLOROFORM-d) δ=7.30 (br. s., 1H), 7.02-6.91 (m, 3H), 4.75 (td, J=3.7, 13.2 Hz, 1H), 4.35 (d, J=5.5 Hz, 2H), 4.24 (td, J=3.7, 13.2 Hz, 1H), 4.12-4.01 (m, 2H), 3.30 (ddd, J=3.0, 10.9, 13.7 Hz, 1H), 2.88 (ddd, J=3.3, 10.9, 13.4 Hz, 1H), 2.56-2.45 (m, 1H), 2.22 (d, J=8.0 Hz, 6H), 1.96-1.86 (m, 2H), 1.79-1.59 (m, 2H), 1.19 (t, J=7.3 Hz, 3H); LCMS m/z=347.1 [M+H]$^+$.

Step 4: Synthesis of Compound 95-e

Compound 95-d (340.00 mg, 981.47 μmol, 1.00 eq) was dissolved in tetrahydrofuran (10.00 mL), and a solution of LiOH.H$_2$O (82.36 mg, 1.96 mmol, 2.00 eq) dissolved in H$_2$O (10.00 mL) was added to the above solution. The reaction solution was maintained at 25° C. and stirred for 2 hours. After the reaction was completed, the reaction solution was adjusted to pH of 6 with 2 N dilute hydrochloric acid. This solution was added with 50 mL of water, and extracted with dichloromethane (30 mL×3). The organic phase was dried over anhydrous sodium sulfate, filtered and concentrated to give the product of compound 95-e (394.00 mg, crude) as a pale yellow oil, which was used directly in the next step without purification.

Step 5: Synthesis of Compound 95-f

Compound 95-e (270.61 mg, 850.00 μmol, 1.70 eq) and HATU (380.23 mg, 1.00 mmol, 2.00 eq) were dissolved in dichloromethane (20 mL), and stirred at room temperature for 15 min. Compound 1-n (176.66 mg, 500.00 μmol, 1.00 eq) and DIPEA (193.86 mg, 1.50 mmol, 261.97 μL, 3.00 eq) were then added, and stirred at room temperature for 18 hours. After the reaction was completed, the reaction solution was added with 150 mL of water, and extracted with dichloromethane (80 mL×3). The organic phases were combined, dried over anhydrous sodium sulfate, filtered and concentrated to give a crude product. The crude product was subjected to column chromatography (petroleum ether:ethyl acetate=1:0~2:1) to give the product of compound 95-f (240.00 mg, yield: 65%) as a yellow oil. LCMS m/z=654.4 [M+H]$^+$; 676.3 [M+Na]$^+$.

Step 6: Synthesis of Compound 95-g

Compound 95-f (260.00 mg, 397.76 μmol, 1.00 eq) was dissolved in dichloromethane (20.00 mL), and PIDA (512.47 mg, 1.59 mmol, 4.00 eq) and TEMPO (12.51 mg, 79.55 μmol, 0.20 eq) were added thereto. The reaction solution was stirred at room temperature for 40 hours. After the reaction was completed, the reaction solution was added with saturated sodium hydrogen carbonate solution (50 mL)

and saturated sodium sulfite solution (50 mL), extracted with dichloromethane (30 mL×3), and washed with saturated brine (50 mL). The organic phase was dried over anhydrous sodium sulfate, filtered and concentrated to give a crude product. The crude product was subjected to column chromatography (petroleum ether:ethyl acetate=1:0~5:3) to give the product of compound 95-g (167.00 mg, yield: 61%) as a yellow oil. LCMS m/z=674.3 [M+Na]$^+$.

Step 7: Synthesis of Compound 95

Compound 95-g (175.00 mg, 268.55 μmol, 1.00 eq) was dissolved in dichloromethane (4.00 mL), and trifluoroacetic acid (4.62 g, 40.52 mmol, 3.00 mL) was added thereto. The reaction solution was stirred at room temperature for 2 hours. After the reaction was completed, the reaction solution was spin-dried to give a crude product. The crude product was purified by preparative HPLC (in trifluoroacetic acid condition), and lyophilized to give the product of compound 95 (82.00 mg, yield: 50%). $^1$H NMR (400 MHz, DMSO-d$_6$) δ=9.06 (br t, J=5.77 Hz, 1H), 8.48 (d, J=7.03 Hz, 1H), 7.55 (ddd, J=3.51, 7.28, 10.79 Hz, 1H), 6.92-7.10 (m, 3H), 5.12-5.30 (m, 2H), 4.61 (q, J=6.53 Hz, 1H), 4.14-4.43 (m, 4H), 3.71 (br d, J=13.55 Hz, 1H), 3.09 (br t, J=11.54 Hz, 1H), 2.68-2.80 (m, 2H), 2.53-2.63 (m, 1H), 2.23 (s, 6H), 1.65-1.81 (m, 2H), 1.38-1.64 (m, 2H); LCMS m/z=596.0 [M+H]$^+$.

Example 96: Compound 96

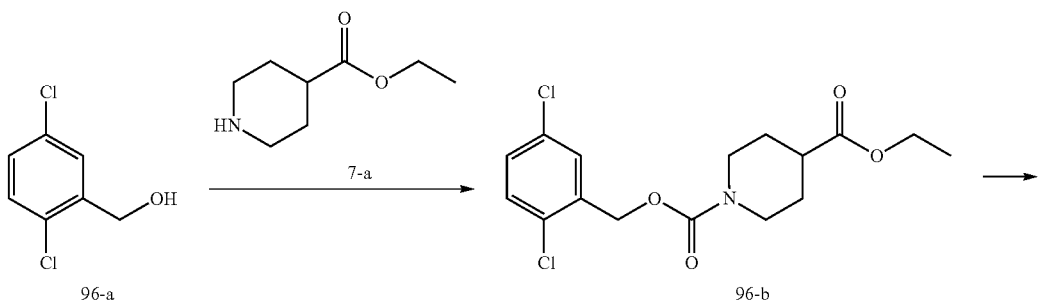

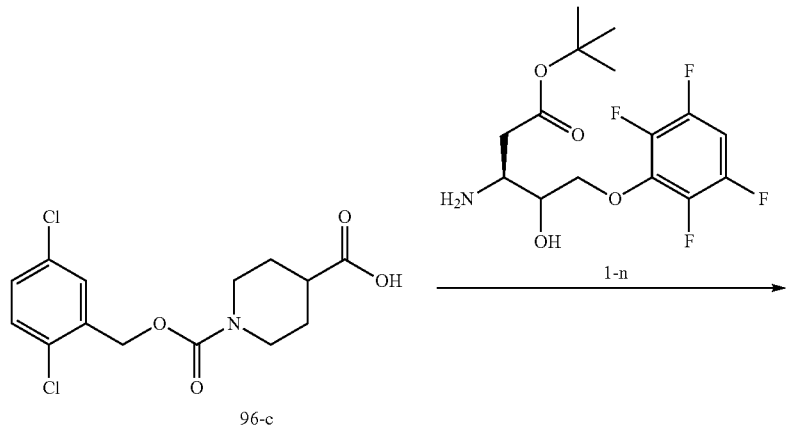

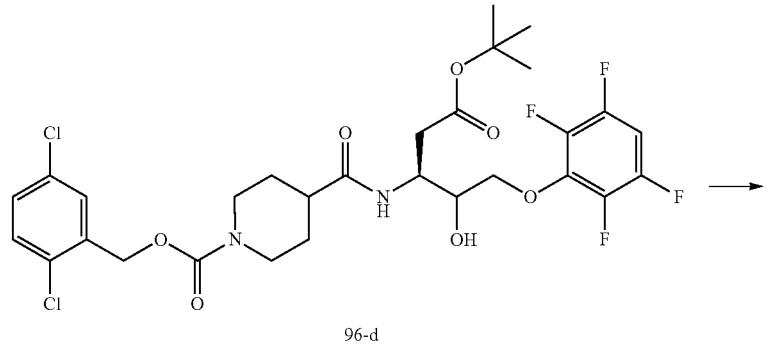

-continued

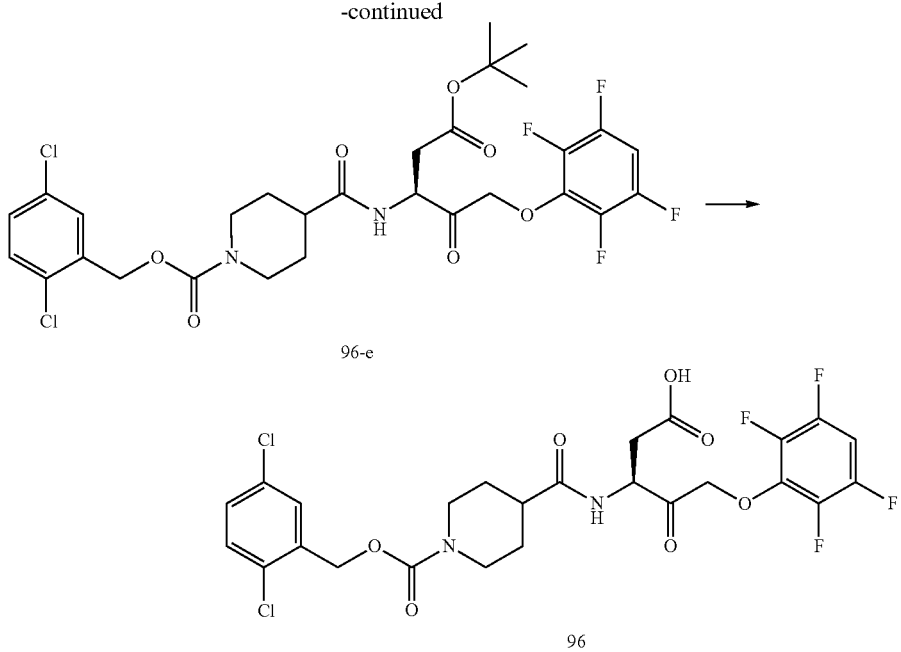

Step 1: Synthesis of Compound 96-b

Compound 96-a (1.00 g, 5.65 mmol, 1.00 eq) and CDI (2.75 g, 16.95 mmol, 3.00 eq) was dissolved in tetrahydrofuran (20 mL), and stirred at 20° C. for 1 hour. Compound 7-a (1.78 g, 11.30 mmol, 1.74 mL, 2.00 eq) and triethylamine (1.72 g, 16.95 mmol, 2.35 mL, 3.00 eq) were then added to the above solution, and stirred at 80° C. for another 15 hours. After the reaction was completed, the reaction solution was added with 100 mL of water, and separated. The aqueous phase was further extracted with dichloromethane (200 mL×2). The organic phases were combined, and washed with saturated sodium hydrogen carbonate solution (150 mL) and saturated brine (100 mL). The organic phase was dried over anhydrous sodium sulfate, filtered, concentrated, and separated by column chromatography (petroleum ether:ethyl acetate=10:1~6:1) to give the product of compound 96-b (1.9 g, yield: 93%). $^1$HNMR (400 MHz, CHLOROFORM-d) δ=7.38 (d, J=2.4 Hz, 1H), 7.34-7.28 (m, 1H), 7.26-7.22 (m, 1H), 5.21 (br. s., 2H), 4.17 (q, J=7.2 Hz, 4H), 3.09-2.89 (m, 2H), 2.50 (s, 1H), 1.99-1.89 (m, 2H), 1.76-1.64 (m, 2H), 1.28 (t, J=7.1 Hz, 3H). LCMS m/z=360.0 [M+H]$^+$.

Step 2: Synthesis of Compound 96-c

Compound 96-b (900.00 mg, 2.50 mmol, 1.00 eq) was dissolved in tetrahydrofuran (10.00 mL) and water (10.00 mL), and LiOH.H$_2$O (157.35 mg, 3.75 mmol, 1.50 eq) was then added slowly to the above solution. The reaction mixture was stirred at 18° C. for 16 hours. After the reaction was completed, the reaction solution was added with 100 mL of water, and separated. The aqueous phase was further extracted with dichloromethane (30 mL×3). The aqueous phase was adjusted to pH of 5 with 4M hydrochloric acid, and white precipitates appeared in the solution. The aqueous phase was further extracted three times with ethyl acetate (50 mL×3), and the organic phase after extraction was washed with saturated brine (100 mL). The organic phase was dried over anhydrous sodium sulfate, filtered and concentrated to give compound 96-c (700 mg, yield: 84%). $^1$H NMR (400 MHz, DMSO) δ=12.43-12.18 (m, 1H), 7.64-7.38 (m, 3H), 5.12 (s, 2H), 3.90 (d, J=13.4 Hz, 2H), 2.95 (br. s., 2H), 2.35-2.47 (m, 1H), 1.83 (dd, J=3.0, 13.3 Hz, 2H), 1.49-1.35 (m, 2H). LCMS m/z=331.9 [M+H]$^+$.

Step 3: Synthesis of Compound 96-d

Compound 96-c (320.00 mg, 2.50 mmol, 1.00 eq) and compound 1-n (340.36 mg, 960.33 μmol, 1.00 eq) as an intermediate were dissolved in dichloromethane (10 mL), and EDCl (253.00 mg, 1.32 mmol, 1.37 eq), HOBt (178.33 mg, 1.32 mmol, 1.37 eq), NMM (292.32 mg, 2.89 mmol, 317.74 μL, 3.00 eq) were then added to the reaction solution under nitrogen atmosphere. The reaction mixture was stirred at 18° C. for 4 hours. After the reaction was completed, the reaction solution was added with water (30 mL), and then extracted with dichloromethane (30 mL×3). The organic phases were combined, and washed with saturated brine (100 mL). The organic phase was dried over anhydrous sodium sulfate, filtered, and concentrated to give compound 96-d (590.00 mg, yield: 92%). LCMS m/z=689.1 [M+Na]$^+$.

Step 4: Synthesis of Compound 96-e

Compound 96-d (295.00 mg, 441.97 μmol, 1.00 eq) was dissolved in dichloromethane (10 mL), and PIDA (550.92 mg, 1.71 mmol, 3.87 eq) and TEMPO (20.85 mg, 132.59 μmol, 0.30 eq) were then added to the reaction solution under nitrogen atmosphere. The reaction solution was stirred at 20° C. for 15 hours under nitrogen atmosphere. After the reaction was completed, the reaction solution was added with water (50 mL), and then extracted with dichloromethane (30 mL×3). The organic phases were combined, and washed with saturated brine (100 mL). The organic phase was dried over anhydrous sodium sulfate, filtered, concentrated, and separated with column chromatography (petroleum ether:ethyl acetate=10:1~2:1) to give the product of compound 96-e (200.00 mg, yield: 68%). LCMS m/z=609.0 [M−55]⁺.

Step 5: Synthesis of Compound 96

Compound 96-e (200.00 mg, 300.54 μmol, 1.00 eq) was dissolved in dichloromethane (4.60 mL), and trifluoroacetic acid (4.62 g, 40.52 mmol, 3.00 mL, 134.82 eq) was added thereto. The reaction solution was stirred under the protection of nitrogen gas at 18° C. for 1 hour. After the reaction was completed, the reaction solution was spin-dried to give a crude product. The crude product was purified by preparative HPLC (in trifluoroacetic acid condition), and lyophilized to give the product of compound 96 (14 mg, yield: 8%). $^1$H NMR (400 MHz, DMSO-$d_6$) δ=8.45 (d, J=7.5 Hz, 1H), 7.63-7.49 (m, 3H), 7.49-7.44 (m, 1H), 5.28-5.15 (m, 2H), 5.12 (s, 2H), 4.60 (q, J=6.7 Hz, 1H), 3.99 (d, J=13.1 Hz, 2H), 2.79-2.65 (m, 1H), 2.58 (dd, J=7.0, 17.0 Hz, 1H), 2.46-2.39 (m, 3H), 1.70 (br. s., 2H), 1.50-1.39 (m, 2H), LCMS m/z=609.0 [M+H]⁺.

Examples 97 to 108 can be Prepared with Reference to the Above Specific Examples

| Example number | Compound | $^1$HNMR | MS | Reference Examples |
|---|---|---|---|---|
| Example 97 | (structure 97) | $^1$H NMR (400 MHz, DMSO-$d_6$) δ = 12.17-12.67 (br s, 1H), 8.47 (d, J = 7.03 Hz, 1H), 7.69-7.50 (m, 1H), 5.36-5.07 (m, 2H), 4.59 (d, J = 6.27 Hz, 1H), 4.48-4.38 (m, 1H), 3.95 (d, J = 10.54 Hz, 2H), 2.74 (dd, J = 5.40, 16.44 Hz, 3H), 2.59 (d, J = 6.53 Hz, 1H), 2.42-2.37 (m, 1H), 1.86 (d, J = 14.81 Hz, 2H), 1.68-1.60 (m, 4H), 1.47-1.28 (m, 4H), 1.03 (d, J = 11.29 Hz, 1H), 0.97-0.80 (m, 8H), 0.73 (d, J = 5.77 Hz, 3H) | LCMS m/z = 611.1 [M + Na]⁺ | Refer to the synthetic route of Example 91 |
| Example 98 | (structure 98) | $^1$H NMR (400 MHz, DMSO-$d_6$) δ = 12.42 (br s, 1H), 8.51 (d, J = 7.28 Hz, 1H), 7.69-7.77 (m, 2H), 7.50-7.62 (m, 1H), 7.39-7.46 (m, 2H), 5.14-5.32 (m, 2H), 4.57-4.67 (m, 1H), 4.13 (d, J = 12.30 Hz, 1H), 4.00 (d, J = 12.55 Hz, 1H), 3.10 (t, J = 12.17 Hz, 1H), 2.94 (t, J = 12.42 Hz, 1H), 2.71-2.82 (m, 1H), 2.60 (dd, J = 6.78, 16.81 Hz, 1H), 2.44-2.49 (m, 1H), 1.77 (s, 2H), 1.46-1.59 (m, 2H) | LCMS m/z = 617.1 [M + Na]⁺ | Refer to the synthetic route of Example 72 |
| Example 99 | (structure 99) | $^1$H NMR (400 MHz, DMSO-$d_6$) δ = 8.49 (d, J = 7.53 Hz, 1H), 7.51-7.68 (m, 1H), 7.16-7.23 (m, 1H), 7.03-7.12 (m, 2H), 6.93 (dt, J = 12.5, 7.65 Hz, 1H), 5.24 (d, J = 11.04 Hz, 2H), 4.63 (q, J = 6.53 Hz, 1H), 4.12-4.15 (m, 1H), 3.94-3.98 (m, 1H), 3.77 (s, 3H), 3.03-3.05 (m, 1H), 2.89-2.91 (m, 1H), 2.72-2.81 (m, 1H), 2.60 (dd, J = 6.78, 16.81 Hz, 1H), 2.45-2.47 (m, 1H), 1.74 (br s, 2H), 1.48-1.68 (m, 2H) | LCMS m/z = 557.1 [M + H]⁺ | Refer to the synthetic route of Example 72 |
| Example 100 | (structure 100) | $^1$H NMR (400 MHz, DMSO-$d_6$) δ = 8.44 (d, J = 7.53 Hz, 1H), 7.49-7.66 (m, 1H), 5.13-5.31 (m, 2H), 4.60 (q, J = 6.86 Hz, 1H), 4.43 (d, J = 6.53 Hz, 1H), 3.94 (d, J = 12.05 Hz, 2H), 2.66-2.84 (m, 3H), 2.58 (dd, J = 6.78, 16.81 Hz, 1H), 2.34-2.44 (m, 1H), 2.23 (s, 2H), 1.59-1.72 (m, 3H), 1.31-1.49 (m, 6H), 1.01-1.17 (m, 3H) | LCMS m/z = 545.1 [M + H]⁺ | Refer to the synthetic route of Example 91 |

-continued

| Example number | Compound | ¹HNMR | MS | Reference Examples |
|---|---|---|---|---|
| Example 101 | 101 | ¹H NMR (400 MHz, DMSO-d$_6$) δ = 10.63 (s, 1H), 8.49 (br d, J = 7.03 Hz, 1H), 7.85 (br d, J = 2.01 Hz, 1H), 7.53-7.64 (m, 2H), 7.37 (dd, J = 2.51, 8.53 Hz, 1H), 5.14-5.31 (m, 2H), 4.62 (q, J = 6.53 Hz, 1H), 4.28 (br d, J = 13.05 Hz, 1H), 3.93 (br d, J = 13.55 Hz, 1H), 3.18 (br t, J = 12.30 Hz, 2H), 2.65-2.92 (m, 2H), 2.60 (br dd, J = 6.53, 17.07 Hz, 1H), 1.46-1.86 (m, 4H), 1.24 (br s, 1H) | LCMS m/z = 622.1 [M]$^+$ | Refer to the synthetic route of Example 86 |
| Example 102 | 102 | ¹H NMR (400 MHz, DMSO-d$_6$) δ = 11.09 (s, 1H), 8.48 (d, J = 6.02 Hz, 1H), 7.88 (d, J = 7.53 Hz, 1H), 7.71-7.77 (m, 1H), 7.50-7.67 (m, 2H), 7.45 (t, J = 7.78 Hz, 1H), 5.15-5.30 (m, 2H), 4.62 (q, J = 6.53 Hz, 1H), 4.29 (d, J = 13.55 Hz, 1H), 3.99 (d, J = 13.05 Hz, 1H), 3.21 (t, J = 11.54 Hz, 1H), 2.85 (t, J = 11.29 Hz, 1H), 2.70-2.79 (m, 1H), 2.53-2.68 (m, 2H), 1.71-1.86 (m, 2H), 1.45-1.69 (m, 2H) | LCMS m/z = 579.4 [M + H]$^+$ | Refer to the synthetic route of Example 86 |
| Example 103 | 103 | ¹H NMR (400 MHz, DMSO-d6) δ = 12.47 (br, s, 1H), 8.51 (d, J = 7.5 Hz, 1H), 7.66-7.57 (m, 1H), 7.57-7.51 (m, 1H), 7.41 (t, J = 8.1 Hz, 1H), 7.37-7.31 (m, 1H), 5.32-5.15 (m, 2H), 4.63 (q, J = 6.8 Hz, 1H), 4.18 (br d, J = 12.5 Hz, 1H), 3.98 (br d, J = 12.2 Hz, 1H), 3.14 (br t, J = 11.5 Hz, 1H), 3.04-2.91 (m, 1H), 2.83-2.72 (m, 2H), 2.60 (dd, J = 6.9, 16.8 Hz, 1H), 1.78 (br s, 2H), 1.67-1.42 (m, 2H). | LCMS m/z = 594.9 [M + H]$^+$ | Refer to the synthetic route of Example 72 |
| Example 104 | 104 | ¹H NMR (400 MHz, DMSO-d6) δ = 8.48 (d, J = 7.53 Hz, 1 H), 7.51-7.64 (m, 1 H), 7.35-7.39 (m, 1 H), 7.08-7.12 (m, 1 H), 6.78-6.83 (m, 1 H), 5.12-5.32 (m, 2 H), 4.60 (q, J = 6.78 Hz, 1 H), 4.11 (d, J = 13.18 Hz, 2 H), 3.13-3.20 (m, 2 H), 2.70-2.79 (m, 1 H), 2.60 (d, J = 6.90 Hz, 2 H), 1.77-1.83 (m, 2 H), 1.59 (dd, J = 12.17, 3.01 Hz, 2 H) | LCMS m/z = 542.0 [M + H]$^+$ | Refer to the synthetic route of Example 83 |
| Example 105 | 105 | ¹H NMR (400 MHz, DMSO-d6) δ = 8.54 (dd, J = 3.0, 7.4 Hz, 1H), 7.72-7.57 (m, 1H), 5.44-5.07 (m, 2H), 4.60 (quin, J = 6.4 Hz, 1H), 4.20 (t, J = 8.3 Hz, 1H), 3.89 (t, J = 8.9 Hz, 1H), 3.79 (dd, J = 5.7, 8.2 Hz, 1H), 3.53-3.44 (m, 2H), 2.93-2.80 (m, 1H), 2.74 (dd, J = 6.0, 17.0 Hz, 1H), 2.62-2.56 (m, 2H), 1.75-1.67 (m, 2H), 1.60-1.46 (m, 6H). | LCMS m/z = 489.1 M + H$^+$. | Refer to the synthetic route of Example 26 |
| Example 106 | 106 | ¹H NMR (400 MHz, DMSO-d6) δ = 8.42-8.23 (m, 1H), 7.71-7.49 (m, 1H), 5.35-5.10 (m, 2H), 4.60 (q, J = 6.7 Hz, 1H), 3.32 (br s, 2H), 3.09-2.89 (m, 2H), 2.79-2.70 (m, 1H), 2.62-2.53 (m, 2H), 2.00-1.81 (m, 4H), 1.73-1.36 (m, 13H). | LCMS m/z = 543.2 [M + H]$^+$ | Refer to the synthetic route of Example 26 |

| Example number | Compound | ¹HNMR | MS | Reference Examples |
|---|---|---|---|---|
| Example 107 | 107 | ¹H NMR (400 MHz, DMSO-d₆) δ = 10.65 (s, 1H), 8.47 (br d, J = 7.28 Hz, 1H), 7.65 (s, 1H), 7.48-7.62 (m, 2H), 7.26 (t, J = 7.91 Hz, 1H), 7.15 (br d, J = 7.78 Hz, 1H), 5.13-5.31 (m, 2H), 4.56-4.67 (m, 1H), 4.28 (br d, J = 12.05 Hz, 1H), 3.78 (br d, J = 13.30 Hz, 1H), 3.15 (br t, J = 11.54 Hz, 1H), 2.65-2.92 (m, 2H), 2.53-2.64 (m, 2H), 1.77 (br d, J = 9.79 Hz, 2H), 1.43-1.67 (m, 2H), 1.26 (s, 9H) | LCMS m/z = 610.2 [M + H]⁺ | Refer to the synthetic route of Example 86 |
| Example 108 | 108 | ¹H NMR (400 MHz, DMSO-d₆) δ = 10.63 (s, 1H), 8.44-8.53 (m, 1H), 7.70-7.79 (m, 1H), 7.50-7.65 (m, 1H), 7.16-7.34 (m, 3H), 5.15-5.30 (m, 2H), 4.62 (q, J = 6.11 Hz, 1H), 4.28 (br d, J = 13.30 Hz, 1H), 3.79 (br d, J = 13.30 Hz, 1H), 3.17 (br t, J = 11.67 Hz, 1H), 2.66-2.88 (m, 2H), 2.52-2.63 (m, 2H), 1.77 (br d, J = 11.54 Hz, 2H), 1.45-1.69 (m, 2H) | LCMS m/z = 572.1 [M + H]⁺ | Refer to the synthetic route of Example 86 |

Example 109: Compound 109

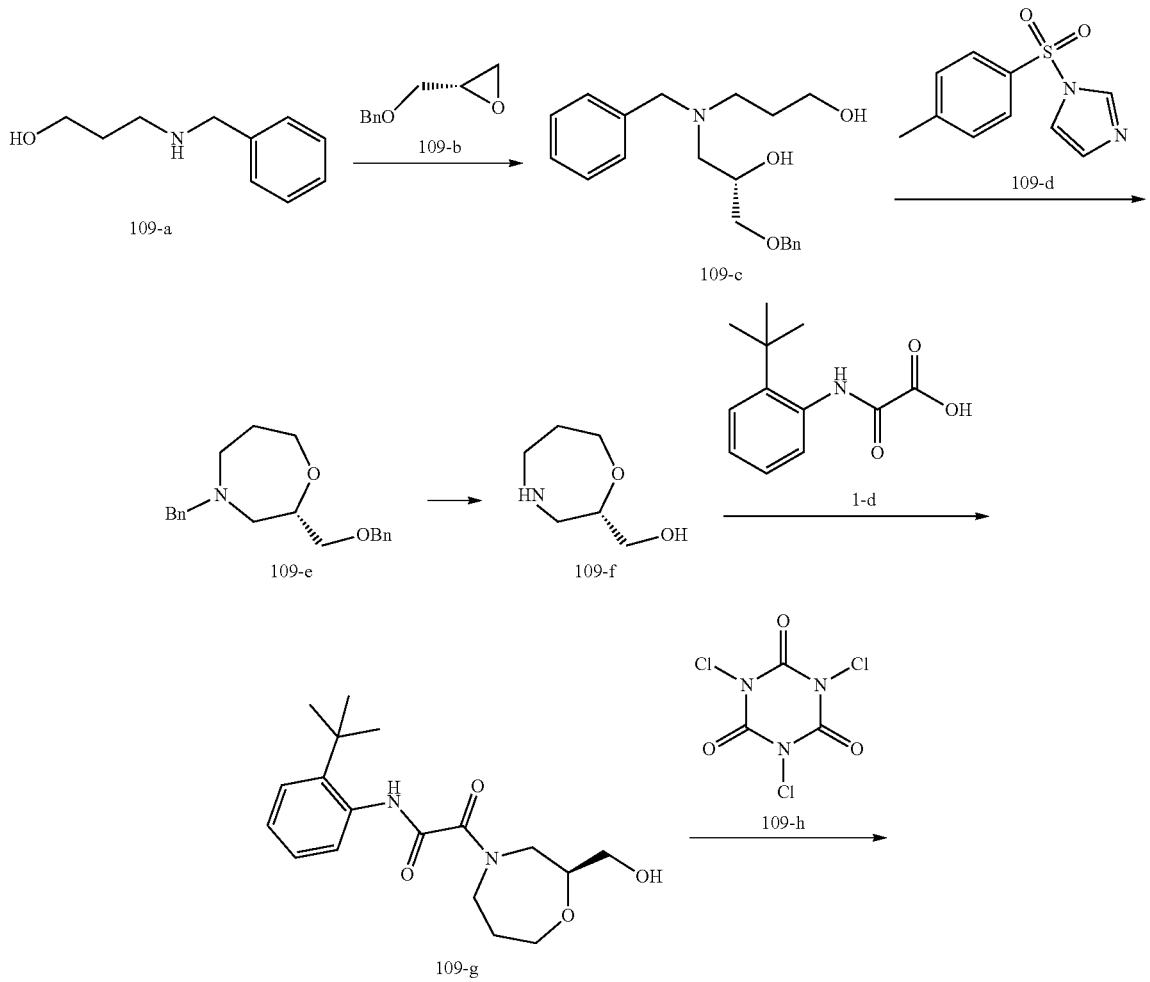

-continued
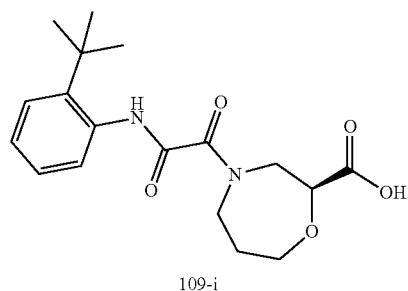
109-i
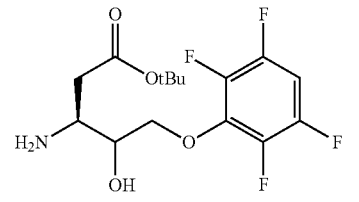
1-n
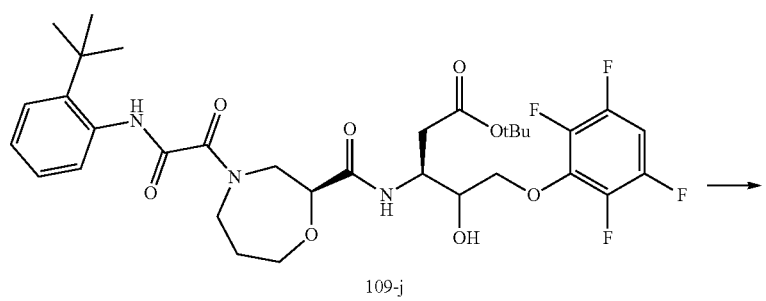
109-j
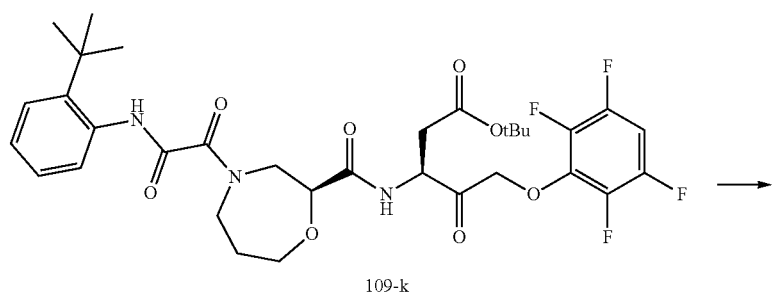
109-k
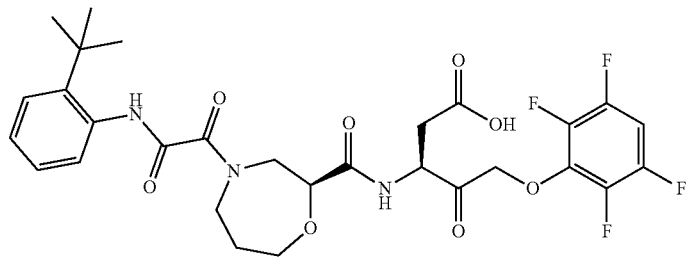
109

Step 1: Synthesis of Compound 109-c

Compounds 109-a (2.00 g, 12.10 mmol, 1.96 mL, 1.00 eq) and 109-b (1.99 g, 12.10 mmol, 1.86 mL, 1.00 eq) were dissolved in EtOH (20.00 mL). The reaction solution was stirred at 40° C. for 15 hours. After the reaction was completed, the reaction solution was concentrated to give compound 109-c (4.00 g, crude) as a colorless oil, which was used directly in the next step without purification. LCMS m/z=330.1 [M+H]$^+$.

Step 2: Synthesis of Compound 109-e

NaH (1.21 g, 30.35 mmol, 60%, 2.50 eq) was added to a mixed solution of compound 109-c (4.00 g, 12.14 mmol, 1.00 eq) in tetrahydrofuran (40.00 mL) in an ice bath, and after stirring at 0° C. for half an hour, compound 109-d (3.24 g, 14.57 mmol, 1.20 eq) was added. The reaction solution was stirred at 25° C. for 4 hours. After the reaction was completed, the reaction solution was added with saturated sodium hydrogen carbonate (50 mL), concentrated and spin-dried, extracted with ethyl acetate (100 mL×2), and separated. The organic phase was further washed with saturated brine (80 mL×2), dried over anhydrous sodium sulfate and concentrated to give a crude product. The crude product was subjected to flash column chromatography on silica gel (petroleum ether:ethyl acetate=85:15) to give compound 109-e (1.08 g, yield: 23.51%) as a colorless oil. LCMS m/z=312.1 [M+H]$^+$.

Step 3: Synthesis of Compound 109-f

Compound 109-e (800.00 mg, 2.57 mmol, 1.00 eq) was dissolved in methanol (20.00 mL), and after purging with argon gas three times, Pd(OH)$_2$—C (10%, 992.56 mg) was added thereto. The mixture was purged with hydrogen three times, and stirred for 16 hours at a pressure of 50 psi and a temperature of 45° C. After the reaction was completed, the reaction solution was filtered, and concentrated to give compound 109-f (360 mg, crude) as a colorless oil, which was used directly in the next step without purification. LCMS m/z=132.0 [M+H]$^+$.

Step 4: Synthesis of Compound 109-g

Compound 1-d (674.70 mg, 3.05 mmol, 1.00 eq), NMM (925.36 mg, 9.15 mmol, 1.01 mL, 3.00 eq), HOBt (564.50 mg, 4.18 mmol, 1.37 eq) and EDCl (800.88 mg, 4.18 mmol, 1.37 eq) were dissolved in dichloromethane (10.00 mL), and after stirring at 25° C. for 15 min, a solution of compound 109-f (400.00 mg, 3.05 mmol, 1.00 eq) dissolved in dichloromethane (25.00 mL) was added dropwise thereto. The reaction solution was stirred at 25° C. for 15 hours. After the reaction was completed, the reaction solution was directly concentrated to give a crude product. The crude product was subjected to flash column chromatography on silica gel (petroleum ether:ethyl acetate=7:3) to give compound 109-g (640 mg, yield: 62.8%) as a pale yellow oil. $^1$H NMR (400 MHz, CHLOROFORM-d) δ 9.50-9.68 (m, 1H), 7.86 (ddd, J=1.51, 7.91, 13.68 Hz, 1H), 7.45 (dd, J=1.00, 8.03 Hz, 1H), 7.30-7.31 (m, 1H), 7.25-7.30 (m, 1H), 7.17-7.22 (m, 1H), 4.32-4.90 (m, 1H), 4.01-4.25 (m, 3H), 3.35-3.90 (m, 6H), 2.07-2.15 (m, 1H), 1.48 (s, 9H).

Step 5: Synthesis of Compound 109-i

Compound 109-g (640.00 mg, 1.91 mmol, 1.00 eq) and saturated NaHCO$_3$ (26.00 mL) were dissolved in acetone (88.00 mL). The obtained solution was maintained at a temperature of 0° C., added with solid NaBr (58.96 mg, 573.00 μmol, 18.43 μL, 0.30 eq) and TEMPO (9.01 mg, 57.30 μmol, 0.03 eq), and finally added with trifluoroisocyanuric acid (976.59 mg, 4.20 mmol, 2.20 eq) slowly. After the addition was completed, the reaction solution was warmed up to 25° C., and stirred for 15 hours. After the reaction was completed, the reaction mixture was added with isopropanol (10 mL), stirred at 25° C. for 30 min, and then filtered. The filtrate was concentrated, then added with saturated Na$_2$CO$_3$ (30 mL), and washed with ethyl acetate (50 mL). The aqueous phase was acidified to pH=3-4 with hydrochloric acid solution (2N), and further extracted with ethyl acetate (50 mL×2). The organic phases after extraction were combined, dried over anhydrous sodium sulfate, filtered and concentrated to give compound 109-i (510.00 mg, yield: 76.7%) as a white solid, which was used directly in the next step. $^1$H NMR (400 MHz, CHLOROFORM-d) δ 9.55 (br d, J=17.32 Hz, 1H), 7.83-7.94 (m, 1H), 7.38-7.49 (m, 1H), 7.26-7.31 (m, 2H), 7.17-7.24 (m, 1H), 4.61-5.32 (m, 2H), 4.32-4.47 (m, 1H), 4.20-4.29 (m, 1H), 3.66-3.89 (m, 3H), 3.46-3.58 (m, 1H), 3.25-3.36 (m, 1H), 1.48 (d, J=3.26 Hz, 9H); LCMS m/z=349.1 [M+H]$^+$.

Step 6: Synthesis of Compound 109-j

Compound 109-i (400.00 mg, 1.15 mmol, 1.00 eq) was dissolved in dichloromethane (20.00 mL), and compound NMM (581.61 mg, 5.75 mmol, 632.19 μL, 5.00 eq), HOBt (212.88 mg, 1.58 mmol, 1.37 eq), EDCl (302.02 mg, 1.58 mmol, 1.37 eq) and compound 1-n (406.31 mg, 1.15 mmol, 1.00 eq) were added thereto. The reaction solution was stirred at 15° C. for 15 hours. After the reaction was completed, the reaction solution was directly concentrated to give a crude product. The crude product was subjected to flash column chromatography on silica gel (petroleum ether:ethyl acetate=1:1) to give compound 109-j (400 mg, yield: 50.89%) as a pale yellow oil. LCMS m/z=684.4 [M+H]$^+$.

Step 7: Synthesis of Compound 109-k

Compound 109-j (400.00 mg, 585.06 μmol, 1.00 eq) was dissolved in dichloromethane (20.00 mL), and diacetoxyiodobenzene (729.29 mg, 2.26 mmol, 3.87 eq) and TEMPO (176.64 mg, 1.12 mmol, 0.60 eq) were added thereto. The reaction solution was stirred at 25° C. for 39 hours. After the reaction was completed, the reaction solution was added with dichloromethane (50 mL). The solution was washed successively with water (40 mL), saturated sodium hydrogen carbonate (40 mL) and brine (40 mL). The organic phase was dried over anhydrous Na$_2$SO$_4$, filtered, and concentrated to give a crude product. The crude product was subjected to flash column chromatography on silica gel (petroleum ether:ethyl acetate=7:3) to give compound 109-k (300.00 mg, yield: 75.3%) as a pale yellow oil. LCMS m/z=682.1 [M+H]$^+$.

Step 8: Synthesis of Compound 109

Compound 109-k (140.00 mg, 205.38 μmol, 1.00 eq) was dissolved in dichloromethane (6.00 mL), and trifluoroacetic acid (770.00 mg, 6.75 mmol, 500.00 μL, 32.88 eq) was added thereto. The reaction solution was stirred at 25° C. for 4 hours. After the reaction was completed, the reaction solution was concentrated to give a crude product. The crude product was purified by prep-HPLC (in trifluoroacetic acid condition), and lyophilized to give the title compound 109 (40.00 mg, yield: 30.95%). $^1$H NMR (400 MHz, DMSO-d6) δ 12.46 (br s, 1H), 10.07 (s, 1H), 7.98-8.45 (m, 1H), 7.52-7.67 (m, 1H), 7.44 (dd, J=3.51, 5.52 Hz, 1H), 7.08-7.32 (m, 3H), 5.09-5.41 (m, 2H), 4.69-4.98 (m, 1H), 4.22-4.38 (m, 2H), 3.79-4.15 (m, 2H), 3.42-3.76 (m, 3H), 2.77-2.98 (m, 1H), 2.59-2.70 (m, 1H), 1.95 (br s, 2H), 1.35 (s, 9H); LCMS m/z=626.0 [M+H]$^+$.

Examples 110 to 114 can be Prepared with Reference to the Above Specific Examples

| Example number | compound | ¹HNMR | MS | Reference Examples |
|---|---|---|---|---|
| Example 110 | 110 | ¹H NMR (400 MHz, DMSO-d₆) δ = 12.48 (br s, 1H), 10.07 (br s, 1H), 8.43 (br s, 1H), 6.96-7.77 (m, 5H), 5.26 (s, 2H), 4.67-5.02 (m, 1H), 3.93-4.51 (m, 3H), 3.46-3.92 (m, 4H), 2.80-2.93 (m, 2H), 1.92-2.11 (m, 2H), 1.34 (s, 9H) | LCMS m/z = 626.3 [M + H]⁺ | Refer to the synthetic route of Example 109 |
| Example 111 | 111 | ¹H NMR (400 MHz, DMSO-d₆) δ = 9.95-9.98 (m, 1H), 9.88 (s, 1H), 9.83 (s, 1H), 8.21-8.30 (m, 1H), 7.49-7.80 (m, 1H), 7.38-7.46 (m, 1H), 7.17-7.29 (m, 2H), 7.08-7.13 (m, 1H), 5.16-5.28 (m, 2H), 4.65 (br d, J = 7.03 Hz, 1H), 3.62-3.85 (m, 2H), 2.75-2.93 (m 1H), 2.53-2.59 (m, 1H), 1.90-2.04 (m, 1H), 1.43-1.80 (m, 5H), 1.30-1.36 (m, 1H), 1.33 (s, 8H), 1.19 (s, 3H) | LCMS m/z = 638.3 [M + H]⁺ | Refer to Examples 20 and 9 |
| Example 112 | 112 | ¹H NMR (400 MHz, DMSO-d₆) δ = 9.87-9.97 (m, 1H), 8.15-8.28 (m, 1H), 7.50-7.67 (m, 1H), 7.37-7.46 (m, 1H), 7.04-7.29 (m, 3H), 5.17-5.28 (m, 2H), 4.62-4.75 (m, 1H), 3.61-3.89 (m, 2H), 2.76-2.85 (m, 1H), 2.75-2.95 (m, 1H), 2.53-2.57 (m, 1H), 1.90-2.05 (m, 1H), 1.70 (br dd, J = 6.78, 12.80 Hz, 2H), 1.44-1.63 (m, 4H), 1.32-1.35 (m, 10H), 1.19 (s, 3H) | LCMS m/z = 638.3 [M + H]⁺ | Refer to Examples 20 and 9 |
| Example 113 | 113 | ¹H NMR (400 MHz, DMSO-d₆) δ = 10.00 (s, 1H), 8.51-8.62 (m, 1H), 7.51-7.66 (m, 1H), 7.38-7.46 (m, 1H), 7.17-7.30 (m, 2H), 7.06-7.14 (m, 1H), 5.15-5.34 (m, 2H), 4.56-4.69 (m, 1H), 3.24-3.93 (m, 4H), 2.86-3.05 (m, 1H), 2.70-2.81 (m, 1H), 2.55-2.68 (m, 1H), 1.42-1.85 (m, 8H), 1.31-1.36 (m, 9H) | LCMS m/z = 638.3 [M + H]⁺ | Refer to the synthetic route of Example 9 |
| Example 114 | 114 | ¹H NMR (400 MHz, DMSO-d₆) δ = 9.97-10.03 (m, 1H), 8.48-8.62 (m, 1H), 7.50-7.64 (m, 1H), 7.37-7.47 (m, 1H), 7.15-7.30 (m, 2H), 7.06-7.14 (m, 1H), 5.16-5.34 (m, 2H), 4.64 (quin, J = 7.03 Hz, 1H), 3.22-3.94 (m, 4H), 2.85-3.03 (m, 1H), 2.70-2.81 (m, 1H), 2.55-2.68 (m, 1H), 1.39-1.88 (m, 8H), 1.29-1.36 (m, 9H) | LCMS m/z = 638.3 [M + H]⁺ | Refer to the synthetic route of Example 9 |

Example 115: Compound 115

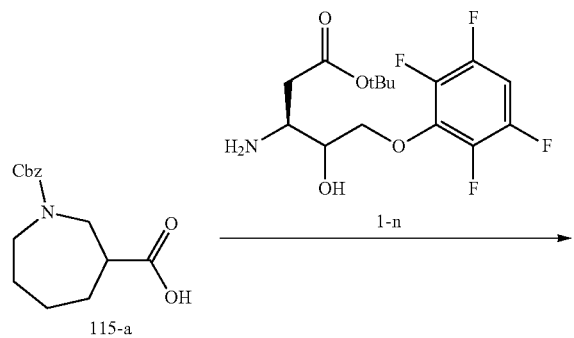

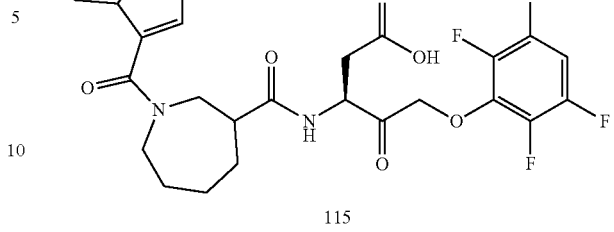

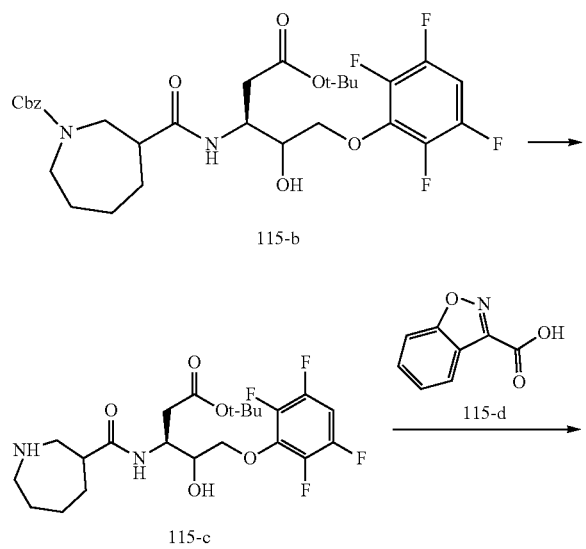

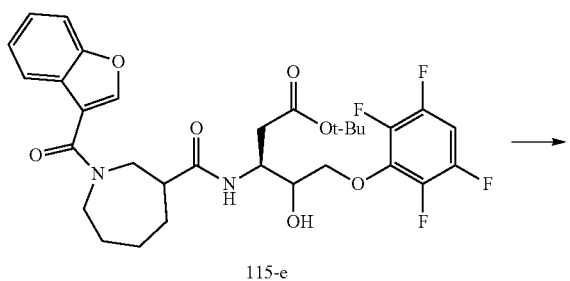

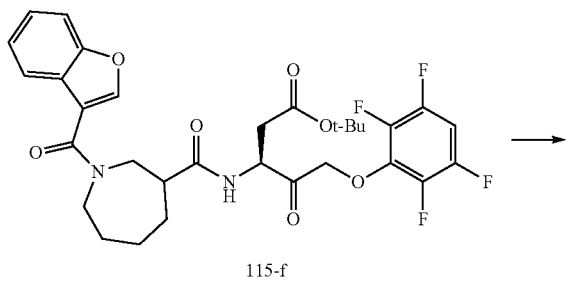

Step 1: Synthesis of Compound 115-b

Compound 115-a (3.70 g, 13.34 mmol, 1.00 eq) was dissolved in dichloromethane (40.00 mL), and NMM (4.05 g, 40.02 mmol, 4.40 mL, 3.00 eq), HOBt (2.47 g, 18.28 mmol, 1.37 eq), EDCl (3.50 g, 18.28 mmol, 1.37 eq) and compound 1-n (4.95 g, 14.01 mmol, 1.05 eq) were added thereto. The reaction solution was stirred at 25° C. for 5 hours. After the reaction was completed, the reaction solution was directly concentrated to give a crude product. The crude product was subjected to flash column chromatography on silica gel (petroleum ether:ethyl acetate=72:28) to give compound 115-b (4.3 g, yield: 47.51%) as a colorless oil. LCMS m/z=613.3 [M+H]$^+$.

Step 2: Synthesis of Compound 115-c

Compound 115-b (4.30 g, 7.02 mmol, 1.00 eq) was dissolved in methanol (45.00 mL) and tetrahydrofuran (45.00 mL), and Pd—C (10%, 430.00 mg) was added after purging with argon gas three times. The mixture was purged with hydrogen three times, and stirred for 2 hours at a pressure of 15 psi and at a temperature of 25° C. After the reaction was completed, the reaction solution was filtered and concentrated to give compound 115-c (3.5 g, crude) as a pale yellow oil, which was used directly in the next step without purification. LCMS m/z=479.2 [M+H]$^+$.

Step 3: Synthesis of Compound 115-e

Compound 115-d (143.19 mg, 877.78 μmol, 1.05 eq) was dissolved in dichloromethane (40.00 mL), and HATU (476.80 mg, 1.25 mmol, 1.50 eq), DIEA (540.21 mg, 4.18 mmol, 730.01 μL, 5.00 eq) and compound 115-c (399.77 mg, 835.98 μmol, 1.00 eq) were added thereto. The reaction solution was stirred at 25° C. for 15 hours. After the reaction was completed, the reaction solution was directly concentrated to give a crude product. The crude product was subjected to flash column chromatography on silica gel (petroleum ether:ethyl acetate=65:35) to give compound 115-e (280 mg, yield: 39.75%) as a colorless oil. LCMS m/z=624.3 [M+H]$^+$.

Step 4: Synthesis of Compound 115-f

Compound 115-e (420.00 mg, 673.52 μmol, 1.00 eq) was dissolved in dichloromethane (20.00 mL), and diacetoxyiodobenzene (839.56 mg, 2.61 mmol, 3.87 eq) and TEMPO (105.91 mg, 673.52 μmol, 1.00 eq) were added thereto. The reaction solution was stirred at 25° C. for 15 hours. After the reaction was completed, the reaction solution was added with dichloromethane (50 mL). The solution was washed successively with water (30 mL), saturated sodium hydrogen carbonate (30 mL) and brine (30 mL). The organic phase was dried over anhydrous $Na_2SO_4$, filtered, and concentrated to give a crude product. The crude product was subjected to flash column chromatography on silica gel (petroleum ether:ethyl acetate=7:3) to give compound 115-f (310.00 mg, yield: 59.83%) as a pale yellow oil. LCMS m/z=622.1 $[M+H]^+$.

Step 5: Synthesis of Compound 115

Compound 115-f (60.00 mg, 96.53 μmol, 1.00 eq) was dissolved in dichloromethane (5.00 mL), and trifluoroacetic acid (770.00 mg, 6.75 mmol, 500.00 μL, 69.96 eq) was added thereto. The reaction solution was stirred at 25° C. for 2 hours. After the reaction was completed, the reaction solution was concentrated to give a crude product. The crude product was purified by prep-HPLC (in trifluoroacetic acid condition), and lyophilized to give the title compound 115 (25.00 mg, yield: 44.88%). $^1$H NMR (400 MHz, DMSO-d6) δ 8.64 (br d, J=7.03 Hz, 1H), 7.80-7.87 (m, 1H), 7.67-7.78 (m, 1H), 7.54-7.65 (m, 1H), 7.44-7.52 (m, 1H), 7.21-7.30 (m, 1H), 5.08-5.37 (m, 2H), 4.47-4.71 (m, 1H), 4.00-4.17 (m, 1H), 3.81-3.93 (m, 1H), 3.57-3.71 (m, 1H), 3.46-3.53 (m, 1H), 2.71-2.89 (m, 2H), 2.55-2.68 (m, 1H), 1.74-1.87 (m, 4H), 1.55-1.69 (m, 1H), 1.37-1.51 (m, 1H); LCMS m/z=566.1 $[M+H]^+$.

Examples 116 to 122 can be Prepared with Reference to the Above Specific Examples

| Example number | compound | $^1$HNMR | MS | Reference Examples |
|---|---|---|---|---|
| Example 116 | 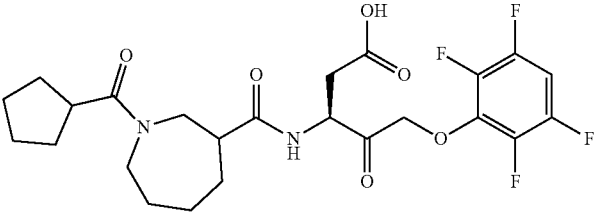<br>116 | $^1$H NMR (400 MHz, DMSO-$d_6$) δ = 8.54 (s, 1H), 7.46-7.70 (m, 1H), 5.24 (s, 2H), 4.47-4.76 (m, 1H), 3.59-3.84 (m, 2H), 3.00-3.20 (m, 2H), 2.94 (br s, 1H), 2.57-2.73 (m, 3H), 1.43-1.81 (m, 14H) | LCMS m/z = 517.3 $[M+H]^+$ | Refer to the synthetic route of Example 115 |
| Example 117 | 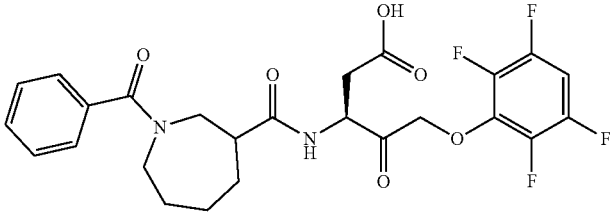<br>117 | $^1$H NMR (400 MHz, DMSO-$d_6$) δ = 8.60 (s, 1H), 7.50-7.69 (m, 1H), 7.33-7.46 (m, 5H), 5.18-5.37 (m, 1H), 4.99-5.13 (m, 1H), 4.62 (br t, J = 7.03 Hz, 1H), 4.01-4.13 (m, 1H), 3.38-3.34 (m, 2H), 2.77 (br dd, J = 5.90, 16.69 Hz, 1H), 2.55-2.71 (m, 2H), 2.29-2.37 (m, 1H), 1.36-1.84 (m, 6H) | LCMS m/z = 525.3 $[M+H]^+$ | Refer to the synthetic route of Example 115 |
| Example 118 | 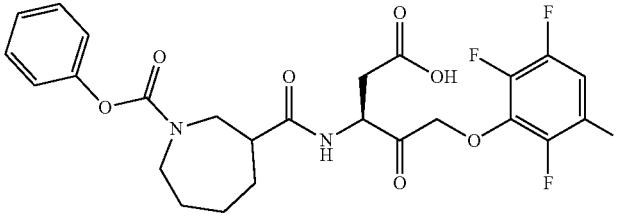<br>118 | $^1$H NMR (400 MHz, DMSO-$d_6$) δ = 8.48-8.63 (m, 1H), 7.50-7.68 (m, 1H), 7.38 (br d, J = 8.03 Hz, 1H), 7.35-7.45 (m, 1H), 7.22 (br s, 1H), 7.11 (br d, J = 7.78 Hz, 2H), 5.12-5.35 (m, 2H), 4.61 (br d, J = 6.02 Hz, 1H), 3.55-3.96 (m, 2H), 2.74-2.82 (m, 1H), 2.64-2.74 (m, 2H), 2.57-2.64 (m, 1H), 2.33 (br s, 1H), 1.37-1.90 (m, 6H) | LCMS m/z = 541.2 $[M+H]^+$ | Refer to the synthetic route of Example 115 |
| Example 119 | 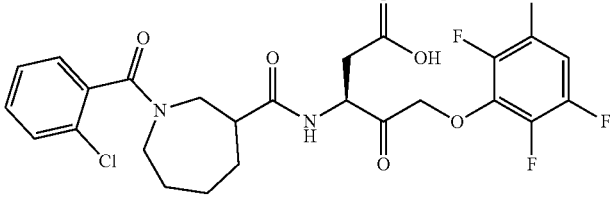<br>119 | $^1$H NMR (400 MHz, DMSO-$d_6$) δ = 8.11-8.69 (m, 1H), 7.18-7.65 (m, 5H), 4.91-5.45 (m, 2H), 4.32-4.68 (m, 1H), 4.00-4.18 (m, 1H), 3.53-3.71 (m, 1H), 3.05-3.21 (m, 2H), 2.52-2.84 (m, 3H), 1.32-1.91 (m, 6H) | LCMS m/z = 559.0 $[M+H]^+$ | Refer to the synthetic route of Example 115 |

| Example number | compound | ¹HNMR | MS | Reference Examples |
|---|---|---|---|---|
| Example 120 | 120 | ¹H NMR (400 MHz, DMSO-d₆) δ = 8.54 (t, J = 7.03 Hz, 1H), 7.46-7.60 (m, 2H), 7.32-7.40 (m, 1H), 7.20-7.30 (m, 2H), 5.09-5.29 (m, 2H), 4.59 (qd, J = 6.78, 13.05 Hz, 1H), 3.88-4.44 (m, 1H), 3.71-3.80 (m, 1H), 3.58-3.66 (m, 1H), 3.19-3.26 (m, 1H), 2.84 (d, J = 5.77 Hz, 1H), 2.69-2.77 (m, 1H), 2.57 (dd, J = 6.90, 16.94 Hz, 1H), 1.40-1.92 (m, 6H) | LCMS m/z = 575.0 [M + H]⁺ | Refer to Examples 115 and 9 |
| Example 121 | 121 | ¹H NMR (400 MHz, DMSO-d₆) δ = 8.56 (t, J = 7.28 Hz, 1H), 7.48-7.64 (m, 2H), 7.19-7.41 (m, 3H), 5.06-5.32 (m, 2H), 4.49-4.63 (m, 1H), 3.86-4.40 (m, 1H), 3.57-3.83 (m, 2H), 3.20 (dd, J = 5.77, 13.55 Hz, 1H), 2.80-2.94 (m, 1H), 2.68-2.76 (m, 1H), 2.55-2.62 (m, 1H), 1.36-1.91 (m, 6H) | LCMS m/z = 575.0 [M + H]⁺ | Refer to Examples 115 and 9 |
| Example 122 | 122 | ¹H NMR (400 MHz, DMSO-d₆) δ = 12.54 (br s, 1H), 8.64 (br s, 1H), 7.84 (dd, J = 5.52, 8.53 Hz, 1H), 7.68-7.78 (m, 1H), 7.46-7.65 (m, 2H), 7.20-7.30 (m, 1H), 5.11-5.39 (m, 2H), 4.48-4.74 (m, 1H), 4.01-4.17 (m, 1H), 3.81-3.94 (m, 1H), 3.57-3.74 (m, 1H), 3.46 (dd, J = 10.54, 13.55 Hz, 1H), 2.58-2.89 (m, 3H), 1.55-1.91 (m, 5H), 1.38-1.52 (m, 1H) | LCMS m/z = 565.9 [M + Na]⁺ | Refer to Examples 115 and 9 |

Example 123: Compound 123

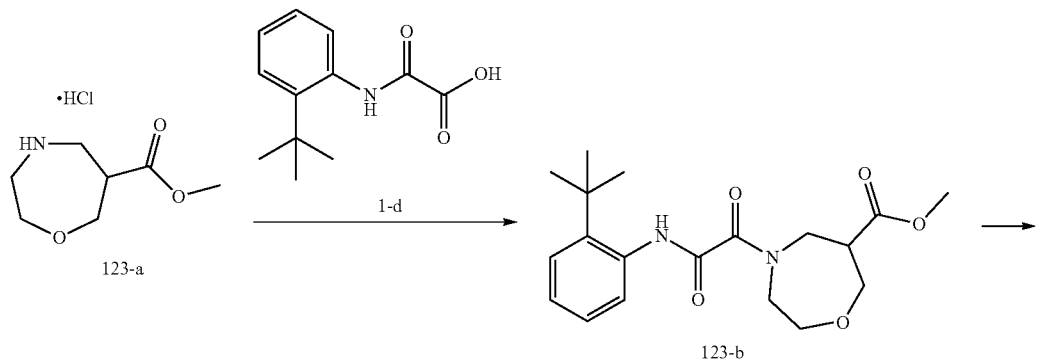

-continued
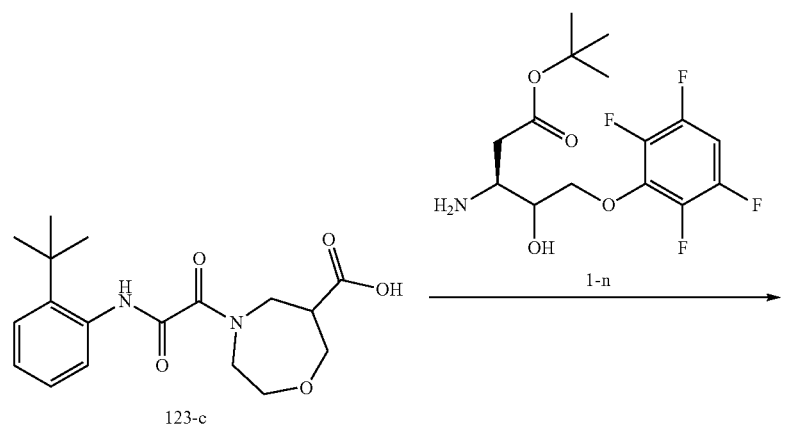
123-c
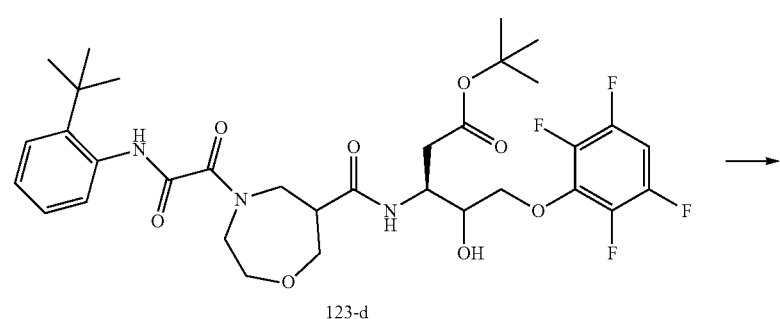
123-d
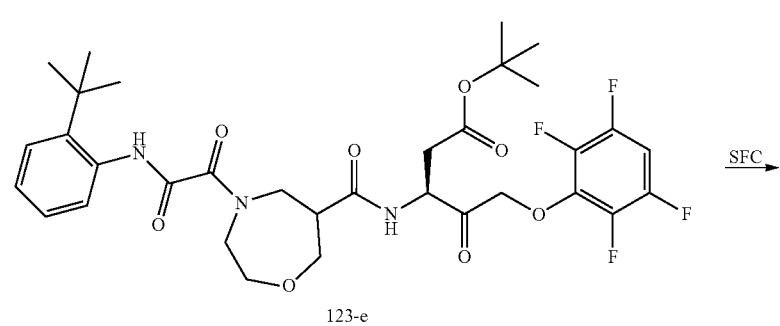
123-e
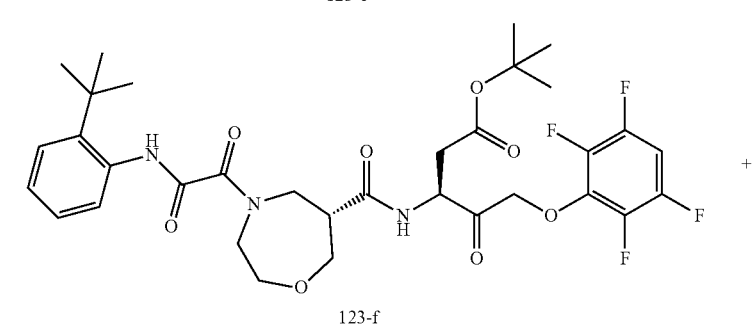
123-f
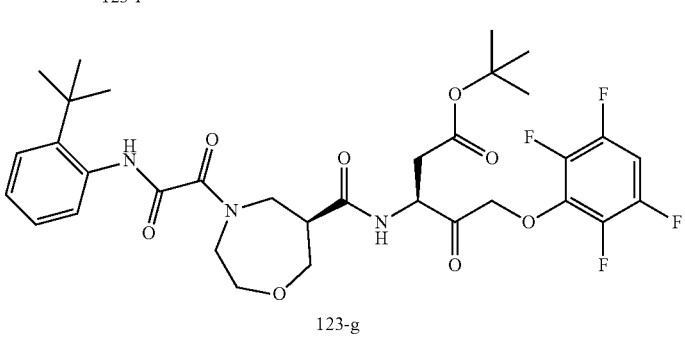
123-g -continued

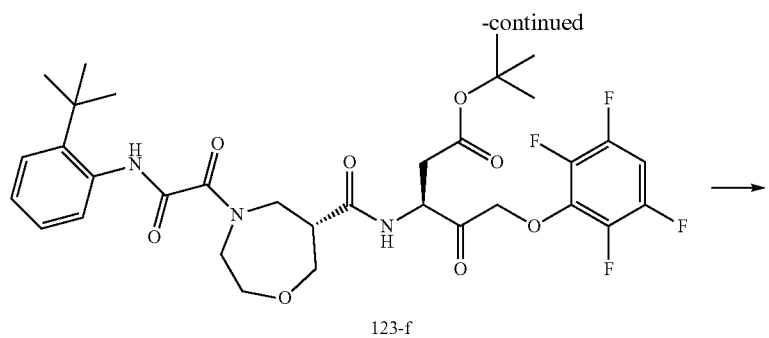

123-f

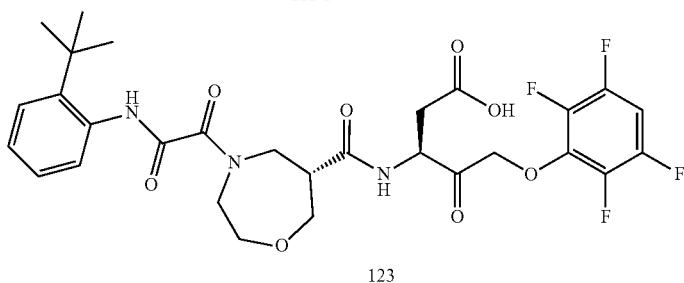

123

Step 1: Synthesis of Compound 123-b

Compound 1-d (1.87 g, 8.43 mmol, 1.10 eq) was dissolved in dichloromethane (15.00 mL), and compound 123-a (1.50 g, 7.67 mmol, 1.00 eq, HCl), HATU (4.37 g, 11.50 mmol, 1.50 eq) and DIPEA (4.95 g, 38.34 mmol, 6.70 mL, 5.00 eq) were added thereto. The reaction solution was stirred at 25° C. for 15 hours. After the reaction was completed, the reaction solution was directly concentrated to give a crude product. The crude product was subjected to column chromatography (petroleum ether:ethyl acetate=1:0~5:1) to give compound 123-b (940.00 mg, yield: 31.53%) as a yellow oil. LCMS m/z=363.1 [M+H]⁺.

Step 2: Synthesis of Compound 123-c

Compound 123-b (877.00 mg, 2.42 mmol, 1.00 eq) was dissolved in tetrahydrofuran (20.00 mL), and a solution of LiOH.H₂O (293.30 mg, 6.99 mmol, 3.00 eq) dissolved in H₂O (20.00 mL) was added to the above solution. The reaction solution was stirred at 15° C. for 1 hour, and supplemented with LiOH.H₂O (97.77 mg, 2.33 mmol, 1.00 eq). The reaction solution was stirred at 15° C. for another 1 hour. After the reaction was completed, the reaction solution was adjusted to pH of 3 with 2N HCl. This solution was added with water (80 mL), and extracted with dichloromethane (120 mL×3). The organic phase was dried over Na₂SO₄, filtered, and concentrated to give compound 123-c (820.00 mg, crude) as a pale yellow oil, which was used directly in the next step without purification. LCMS m/z=371.1 [M+Na]⁺.

Step 3: Synthesis of Compound 123-d

Compound 123-c (820.00 mg, 2.35 mmol, 1.00 eq) was dissolved in dichloromethane (30.00 mL), and compound 1-n (913.31 mg, 2.59 mmol, 1.10 eq), EDCl (617.18 mg, 3.22 mmol, 1.37 eq), HOBt (435.02 mg, 3.22 mmol, 1.37 eq) and NMM (713.11 mg, 7.05 mmol, 775.12 μL, 3.00 eq) were added thereto. The reaction solution was stirred at 15° C. for 17 hours. After the reaction was completed, the reaction solution was directly concentrated to give a crude product. The crude product was subjected to column chromatography (petroleum ether:ethyl acetate=4:1~1:1) to give compound 123-d (1.27 g, yield: 73.51%) as a pale yellow oil. LCMS m/z=706.2 [M+Na]⁺.

Step 4: Synthesis of Compound 123-e

Compound 123-d (1.28 g, 1.87 mmol, 1.00 eq) was dissolved in dichloromethane (50.00 mL), and diacetoxyiodobenzene (2.33 g, 7.25 mmol, 3.87 eq) and TEMPO (176.64 mg, 1.12 mmol, 0.60 eq) were added thereto. The reaction solution was stirred at 15° C. for 16 hours, and supplemented with TEMPO (176.64 mg, 1.12 mmol, 0.60 eq). The reaction solution was stirred at 25° C. for another 24 hours. After the reaction was completed, the reaction solution was added with 160 mL of dichloromethane. The solution was washed successively with saturated sodium hydrogen carbonate (160 mL) and water (160 mL). The organic phase was dried over Na₂SO₄, filtered and concentrated to give a crude product. The crude product was subjected to column chromatography (petroleum ether:ethyl acetate=9:1~2:1) to give compound 123-e (902.00 mg, yield: 67.86%) as a pale yellow oil. LCMS m/z=704.2 [M+Na]⁺.

Step 5: Synthesis of Compounds 123-f and 123-g

Compound 123-e (902.00 mg, 1.32 mmol, 1.00 eq) was separated via SFC to give compounds 123-f (347 mg, yield: 37.41%) and 123-g (332 mg, yield: 35.42%) as a colorless oil. 123-f: LCMS m/z=704.4 [M+Na]⁺; 123-g: LCMS m/z=682.4 [M+H]⁺.

Step 6: Synthesis of Compound 123

Compound 123-f (347.00 mg, 509.04 μmol, 1.00 eq) was dissolved in dichloromethane (31.00 mL), and trifluoroacetic acid (24.29 g, 212.99 mmol, 15.77 mL, 418.41 eq) was added thereto. The reaction solution was stirred at 15° C. for 1 hour. After the reaction was completed, the reaction solution was concentrated to give a crude product. The crude product was purified by prep-HPLC (in trifluoroacetic acid condition), and lyophilized to give the title compound 123 (252.00 mg, yield: 79.14%). ¹H NMR (400 MHz, DMSO-d₆) δ=10.06 (d, J=2.76 Hz, 1H), 8.64 (t, J=7.53 Hz, 1H), 7.48-7.68 (m, 1H), 7.37-7.45 (m, 1H), 7.09-7.29 (m, 3H), 5.14-5.34 (m, 2H), 4.62 (quin, J=6.40 Hz, 1H), 3.30-3.82 (m, 8H), 2.88-3.10 (m, 1H), 2.54-2.82 (m, 2H), 1.33 (d, J=3.01 Hz, 9H); LCMS m/z=625.9 [M+H]$^+$.

Example 124: Compound 124

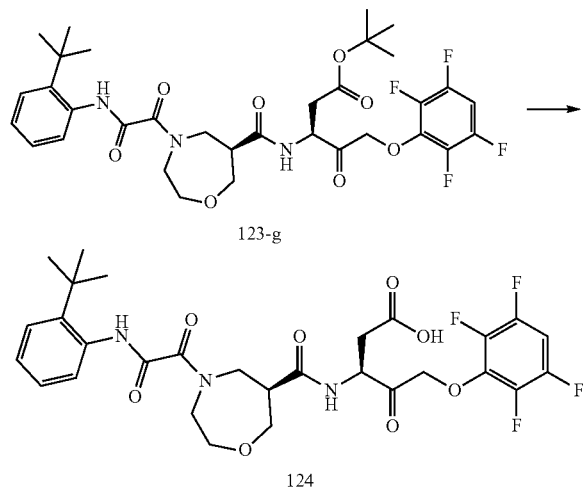

123-g

124

Step 1: Synthesis of Compound 124

Compound 123-g (332.00 mg, 487.04 μmol, 1.00 eq) was dissolved in dichloromethane (30.00 mL), and trifluoroacetic acid (23.24 g, 203.78 mmol, 15.09 mL, 418.41 eq) was added thereto. The reaction solution was stirred at 15° C. for 1 hour. After the reaction was completed, the reaction solution was concentrated to give a crude product. The crude product was purified by prep-HPLC (in trifluoroacetic acid condition), and lyophilized to give the title compound 124 (241.00 mg, yield: 79.10%). $^1$H NMR (400 MHz, DMSO-d$_6$) δ=10.06 (s, 1H), 8.58-8.68 (m, 1H), 7.50-7.69 (m, 1H), 7.38-7.47 (m, 1H), 7.19-7.30 (m, 2H), 7.11-7.18 (m, 1H), 5.13-5.35 (m, 2H), 4.65 (td, J=6.40, 13.30 Hz, 1H), 3.30-4.15 (m, 8H), 2.94-3.11 (m, 1H), 2.68-2.81 (m, 1H), 2.56-2.68 (m, 1H), 1.34 (s, 9H); LCMS m/z=625.9 [M+H]$^+$.

Examples 125 to 138 can be Prepared with Reference to the Above Specific Examples

| Example number | compound | $^1$HNMR | MS | Reference Examples |
|---|---|---|---|---|
| Example 125 | 125 | $^1$H NMR (400 MHz, DMSO-d$_6$) δ = 8.65 (t, J = 7.40 Hz, 1H), 7.95 (dt, J = 2.01, 8.03 Hz, 1H), 7.65-7.73 (m, 1H), 7.46-7.62 (m, 3H), 7.26-7.31 (m, 1H), 5.12-5.34 (m, 2H), 4.51-4.70 (m, 1H), 4.15-4.41 (m, 2H), 3.98-4.13 (m, 1H), 3.86-3.92 (m, 1H), 3.41-3.83 (m, 4H), 2.95-3.08 (m, 1H), 2.53-2.82 (m, 2H) | LCMS m/z = 628.1 [M + H]$^+$ | Refer to the synthetic route of Example 123/124 |
| Example 126 | 126 | $^1$H NMR (400 MHz, DMSO-d$_6$) δ = 8.85-8.71 (m, 1H), 7.86-7.99 (m, 1H), 7.68 (ddd, J = 1.38, 7.72, 15.25 Hz, 1H), 7.43-7.62 (m, 3H), 7.26-7.32 (m, 1H), 5.10-5.37 (m, 2H), 4.54-4.68 (m, 1H), 3.96-4.41 (m, 2H), 3.85-3.92 (m, 2H), 3.40-3.82 (m, 4H), 2.95-3.07 (m, 1H), 2.53-2.82 (m, 2H) | LCMS m/z = 628.1 [M + H]$^+$ | Refer to the synthetic route of Example 123/124 |
| Example 127 | 127 | $^1$H NMR (400 MHz, DMSO-d$_6$) δ = 8.56-8.72 (m, 1H), 7.80-7.95 (m, 2H), 7.74 (dt, J = 6.40, 7.34 Hz, 1H), 7.43-7.62 (m, 2H), 5.08-5.36 (m, 2H), 4.44-4.72 (m, 1H), 3.98-4.37 (m, 3H), 3.88-3.93 (m, 1H), 3.46-3.84 (m, 4H), 2.94-3.16 (m, 1H), 2.52-2.84 (m, 2H) | LCMS m/z = 568.0 [M + H]$^+$ | Refer to the synthetic route of Example 123/124 |

-continued

| Example number | compound | ¹HNMR | MS | Reference Examples |
|---|---|---|---|---|
| Example 128 | 128 | ¹H NMR (400 MHz, DMSO-d₆) δ = 8.55-8.76 (m, 1H), 7.67-7.96 (m, 3H), 7.43-7.62 (m, 2H), 5.05-5.39 (m, 2H), 4.45-4.69 (m, 1H), 3.99-4.31 (m, 2H), 3.83-3.91 (m, 3H), 3.46-3.79 (m, 3H), 2.93-3.15 (m, 1H), 2.51-2.85 (m, 2H) | LCMS m/z = 568.0 [M + H]⁺ | Refer to the synthetic route of Example 123/124 |
| Example 129 | 129 | ¹H NMR (400 MHz, DMSO-d₆) δ = 10.47-10.56 (m, 1H), 8.64 (t, J = 7.91 Hz, 1H), 7.65 (d, J = 8.03 Hz, 1H), 7.50-7.62 (m, 2H), 7.33-7.41 (m, 1H), 7.24-7.32 (m, 1H), 5.12-5.33 (m, 2H), 4.56-4.71 (m, 1H), 3.96-4.10 (m, 3H), 3.70-3.79 (m, 2H), 3.30-3.68 (m, 3H), 2.94-3.09 (m, 1H), 2.54-2.81 (m, 2H) | LCMS m/z = 604.1 [M + H]⁺ | Refer to the synthetic route of Example 123/124 |
| Example 130 | 130 | ¹H NMR (400 MHz, DMSO-d₆) δ = 10.46-10.56 (m, 1H), 8.64 (br dd, J = 7.53, 11.54 Hz, 1H), 7.46-7.69 (m, 3H), 7.20-7.41 (m, 2H), 5.12-5.35 (m, 2H), 4.61 (qd, J = 6.96, 14.24 Hz, 1H), 3.83-4.10 (m, 3H), 3.28-3.80 (m, 5H), 2.92-3.06 (m, 1H), 2.53-2.82 (m, 2H) | LCMS m/z = 604.1 [M + H]⁺ | Refer to the synthetic route of Example 123/124 |
| Example 131 | 131 | ¹H NMR (400 MHz, DMSO-d₆) δ = 10.59-10.70 (m, 1H), 8.63 (br t, J = 8.16 Hz, 1H), 7.67-7.76 (m, 1H), 7.48-7.65 (m, 1H), 7.14-7.34 (m, 3H), 5.12-5.35 (m, 2H), 4.54-4.69 (m, 1H), 3.29-3.89 (m, 8H), 2.93-3.08 (m, 1H), 2.53-2.81 (m, 2H) | LCMS m/z = 588.1 [M + H]⁺ | Refer to the synthetic route of Example 123/124 |
| Example 132 | 132 | ¹H NMR (400 MHz, DMSO-d₆) δ = 10.64 (d, J = 13.55 Hz, 1H), 8.64 (dd, J = 7.53, 11.54 Hz, 1H), 7.67-7.76 (m, 1H), 7.47-7.65 (m, 1H), 7.10-7.35 (m, 3H), 5.09-5.35 (m, 2H), 4.53-4.68 (m, 1H), 3.27-4.08 (m, 8H), 2.93-3.05 (m, 1H), 2.52-2.82 (m, 2H) | LCMS m/z = 588.1 [M + H]⁺ | Refer to the synthetic route of Example 123/124 |
| Example 133 | 133 | ¹H NMR (400 MHz, DMSO-d₆) δ = 10.79-10.88 (m, 1H), 8.62 (t, J = 8.28 Hz, 1H), 7.66 (tdd, J = 2.35, 4.77, 6.84 Hz, 2H), 7.48-7.62 (m, 1H), 7.10-7.23 (m, 1H), 7.11 (br s, 1H), 5.09-5.34 (m, 2H), 4.52-4.68 (m, 1H), 3.29-3.85 (m, 8H), 2.92-3.08 (m, 1H), 2.52-2.81 (m, 2H) | LCMS m/z = 588.1 [M + H]⁺ | Refer to the synthetic route of Example 123/124 |

| Example number | compound | ¹HNMR | MS | Reference Examples |
|---|---|---|---|---|
| Example 134 | 134 | ¹H NMR (400 MHz, DMSO-d₆) δ = 10.86 (br d, J = 7.53 Hz, 1H), 8.64 (dd, J = 7.53, 12.80 Hz, 1H), 7.63-7.71 (m, 2H), 7.47-7.62 (m, 1H), 7.09-7.24 (m, 2H), 5.10-5.35 (m, 2H), 4.53-4.69 (m, 1H), 3.54-4.10 (m, 8H), 2.92-3.06 (m, 1H), 2.53-2.81 (m, 2H) | LCMS m/z = 588.2 [M + H]⁺ | Refer to the synthetic route of Example 123/124 |
| Example 135 | 135 | ¹HNMR (400 MHz, CHLOROFORM-d) δ = 9.70 (br s, 1H), 9.61 (br s, 1H), 8.07-8.27 (m, 1H), 7.46-7.73 (m, 3H), 7.31 (br t, J = 7.53 Hz, 1H), 6.79 (br s, 1H), 4.74-5.26 (m, 2H), 4.63 (br dd, J = 4.39, 14.18 Hz, 1H), 4.24-4.48 (m, 2H), 3.86-4.15 (m, 6H), 3.30-3.46 (m, 1H), 3.03 (br dd, J = 7.78, 17.32 Hz, 2H) | LCMS m/z = 638.1 [M + H]⁺ | Refer to the synthetic route of Example 123/124 |
| Example 136 | 136 | ¹HNMR (400 MHz, CHLOROFORM-d) δ = 9.63 (br s, 1H), 9.55 (br s, 1H), 8.03-8.23 (m, 1H), 7.47-7.65 (m, 3H), 7.21-7.28 (m, 1H), 6.73 (br s, 1H), 4.67-5.15 (m, 2H), 4.56 (br d, J = 10.04 Hz, 1H), 4.30 (br d, J = 19.83 Hz, 2H), 3.84-4.11 (m, 6H), 3.31 (br s, 1H), 2.96 (br d, J = 19.58 Hz, 2H) | LCMS m/z = 638.1 [M + H]⁺ | Refer to the synthetic route of Example 123/124 |
| Example 137 | 137 | ¹HNMR (400 MHz, CHLOROFORM-d) δ = 9.23 (br s, 1H), 9.13 (br s, 1H), 7.87 (br s, 1H), 7.43-7.65 (m, 1H), 7.24 (br d, J = 7.53 Hz, 2H), 7.16 (br d, J = 6.53 Hz, 1H), 6.82 (br s, 1H), 4.78-5.28 (m, 2H), 4.65 (br d, J = 12.05 Hz, 1H), 3.72-4.50 (m, 8H), 3.39 (br s, 1H), 3.19 (br s, 1H), 2.94-3.12 (m, 1H), 2.25-2.37 (m, 3H) | LCMS m/z = 584.2 [M + H]⁺ | Refer to the synthetic route of Example 123/124 |
| Example 138 | 138 | ¹HNMR (400 MHz, CHLOROFORM-d) δ = 9.13 (br s, 1H), 9.04 (br s, 1H), 7.81 (br s, 1H), 7.29-7.54 (m, 1H), 7.16 (br d, J = 4.52 Hz, 2H), 7.02-7.10 (m, 1H), 6.73 (br s, 1H), 4.67-5.16 (m, 1H), 4.60 (br d, J = 13.80 Hz, 1H), 3.67-4.40 (m, 8H), 3.31 (br s, 1H), 2.84-3.15 (m, 2H), 2.24 (d, J = 7.53 Hz, 3H) | LCMS m/z = 584.2 [M + H]⁺ | Refer to the synthetic route of Example 123/124 |

Experimental Example 1: Evaluation of the Compounds on Anti-Fas-Induced Apoptosis of Jurkat Cells In Vitro Experimental Materials:
1) Cells: Human acute lymphoblastic T-cell leukemia cells, Jurkat Clone E6-1, purchased from ATCC (Cat. No. TIB-152). RPMI 1640 medium (Invitrogen) supplemented with 10% fetal bovine serum (Corning), 100 U/mL penicillin and 100 μg/mL streptomycin (Hyclone) was used and culturing the cells was performed at 37° C., 5% $CO_2$ in an incubator.
2) Reagents: Anti-Fas antibody, clone CH11, purchased from Millipore (Cat. No. 05-201); Ac-DEVD-AMC, purchased from Sigma (Cat. No. A1086).
3) Instruments: Multi-function microplate reader, Molecular Devices (SpectraMax M2e).

Experimental Method:
1) Jurkat clone E6-1 cells were inoculated with 50 μL/well in black 96-well cell culture plates (Greiner) at a density of 100,000 cells/well.
2) The compounds were serial diluted to 200× test concentration with DMSO, and then diluted to 4× test concentration with cell culture medium and added to the test plates. 6 concentration points were tested for the test compounds and control compounds; and the test concentration range was: from 1000 nM to 0.32 nM. The cell culture medium with 2% DMSO only was added in the control wells (0% inhibition); and the control compound (final concentration: 1000 nM) was further added in the control wells (100% inhibition). The final concentration of DMSO in the cell culture medium was 0.5%.

3) Anti-Fas was diluted with the cell culture medium, and then added to the test plates, with the final concentration of 50 ng/mL.
4) The cell test plates were cultured at 37° C., 5% $CO_2$ in the incubator for 24 hours. After centrifugation, the supernatant was discarded. The cells were lysed with 1% NP40 cell lysis solution, and Caspase 3 fluorescent substrate Ac-DEVD-AMC (final concentration: 10 μM) was added and incubated at 37° C. for 3-4 hours. The fluorescence intensity was measured using a multi-function microplate reader (excitation light wavelength of 360 nm, emission light wavelength of 460 nm).
5) Compound inhibition curve was fitted and $EC_{50}$ values were calculated using GraphPad Prism software.

Experimental Results:

The experimental results were shown in Table 1.

TABLE 1

Test results of the activity $EC_{50}$ for Anti-Fas-induced Jurkat cells

| Test samples | $EC_{50}$ (nM) |
| --- | --- |
| Example 1 | 137.6 |
| Example 2 | 213 |
| Example 3 | 37.37 |
| Example 4 | 20.72 |
| Example 5 | 265 |
| Example 6 | 552.1 |
| Example 7 | 66.63 |
| Example 8 | 124.5 |
| Example 9 | 65.5 |
| Example 10 | 41.59 |
| Example 11 | 27.22 |
| Example 12 | 52.54 |
| Example 13 | 75.2 |
| Example 14 | 275.3 |
| Example 15 | 244 |
| Example 16 | 417.2 |
| Example 17 | 288.7 |
| Example 18 | 557.3 |
| Example 19 | 224 |
| Example 20 | 698.1 |
| Example 21 | 97.9 |
| Example 22 | 34.16 |
| Example 23 | 214.8 |
| Example 24 | 49.7 |
| Example 25 | 70.65 |
| Example 26 | 12.61 |
| Example 27 | 21.12 |
| Example 28 | 22.05 |
| Example 29 | 57.43 |
| Example 30 | 14.54 |
| Example 31 | 21.43 |
| Example 32 | 33.08 |
| Example 33 | 43.74 |
| Example 34 | 42.99 |
| Example 35 | 25.44 |
| Example 36 | 10.35 |
| Example 37 | 23.94 |
| Example 38 | 22.04 |
| Example 39 | 9.956 |
| Example 40 | 17.72 |
| Example 41 | 18.83 |
| Example 42 | 25.2 |
| Example 43 | 38.61 |
| Example 44 | 39.74 |
| Example 45 | 29.89 |
| Example 46 | 6.405 |
| Example 47 | 6.51 |
| Example 48 | 10.39 |
| Example 49 | 5.835 |
| Example 50 | 12.25 |
| Example 51 | 27.24 |
| Example 52 | 20.99 |
| Example 53 | 67.47 |
| Example 54 | 18.32 |
| Example 55 | 10.06 |
| Example 56 | 20.37 |
| Example 57 | 19.93 |
| Example 58 | 16.58 |
| Example 59 | 156.8 |
| Example 60 | 49.56 |
| Example 61 | 50.4 |
| Example 62 | 42.37 |
| Example 63 | 38.01 |
| Example 64 | 64.67 |
| Example 65 | 130.3 |
| Example 66 | 17.71 |
| Example 67 | 14.55 |
| Example 68 | 23.2 |
| Example 69 | 29.62 |
| Example 70 | 13.83 |
| Example 71 | 29.28 |
| Example 72 | 17.93 |
| Example 73 | 30.23 |
| Example 74 | 12.28 |
| Example 75 | 25.79 |
| Example 76 | 14.11 |
| Example 77 | 96.02 |
| Example 78 | 35.93 |
| Example 79 | 26 |
| Example 80 | 17.51 |
| Example 81 | 959 |
| Example 82 | 43.98 |
| Example 83 | 23.98 |
| Example 84 | 35.02 |
| Example 85 | 16.3 |
| Example 86 | 40.06 |
| Example 87 | 42.61 |
| Example 88 | 33.83 |
| Example 89 | 8.98 |
| Example 90 | 44.24 |
| Example 91 | 61.96 |
| Example 92 | 78.55 |
| Example 93 | 25.52 |
| Example 94 | 43.88 |
| Example 95 | 33.21 |
| Example 96 | 52.84 |
| Example 97 | 111.70 |
| Example 98 | 24.39 |
| Example 99 | 20.41 |
| Example 100 | 31.46 |
| Example 101 | 61.33 |
| Example 102 | 26.79 |
| Example 103 | 19.8 |
| Example 104 | 29.8 |
| Example 105 | 27.6 |
| Example 106 | 17.5 |
| Example 107 | 112.0 |
| Example 108 | 26.6 |
| Example 109 | 191.7 |
| Example 110 | 383 |
| Example 111 | 23 |
| Example 112 | 164.9 |
| Example 113 | 46.2 |
| Example 114 | 66.3 |
| Example 122 | 5.80 |
| Example 123 | 38.9 |
| Example 124 | 28.74 |
| Example 125 | 16.16 |
| Example 126 | 9.37 |
| Example 127 | 7.14 |
| Example 128 | 9.15 |
| Example 129 | 5.65 |
| Example 130 | 8.1 |

Experimental Example 2: Mouse Pharmacokinetic Study

Experimental Method:

The mice were randomly divided into two groups (one intravenous group and one oral group) or only oral group, 3 males in each group. The compounds were formulated into the designated preparations. The intravenous preparations should be filtered to provide clear solutions, and the oral preparations can be clear or can be uniform suspensions. All animals in the intravenous group were intravenously injected with the given doses of the compound preparations through tail veins. The oral group was administrated with the given doses of the preparations by gavage.

Whole blood samples were collected from the other side of the tail vein at 8 time points (2 min, 5 min, 15 min, 30 min, 1 h, 2 h, 4 h and 8 h after administration) in the intravenous group, about 25 µL for each sample; whole blood samples were collected from the tail vein at 8 time points (2 min, 5 min, 15 min, 30 min, 1 h, 2 h, 4 h and 8 h after administration) in the oral group, about 25 µL for each sample.

The plasma samples were added to a centrifuge tube containing anticoagulants, and centrifuged at 4° C., 3000 g for 15 min. The supernatant plasma was quickly frozen on dry ice and stored in a • refrigerator at −70° C.±10° C. until LC-MS/MS analysis was performed.

Data Processing:

The concentration data of plasma drug for the compounds were processed with the non-compartmental model using WinNonlin™ Version 6.3.0 (Pharsight, Mountain View, Calif.) pharmacokinetic software. The peak concentration ($C_{max}$), time to peak concentration ($T_{max}$) and last time for quantitative were obtained directly from the blood concentration-time chart.

The following pharmacokinetic parameters were calculated by using Log-linear Trapezoidal method: elimination phase half-life ($T_{1/2}$); apparent volume of distribution ($V_{dss}$) and clearance rate (CL); the average residence time of the drug in vivo from 0 to the last time point ($MRT_{0-last}$); the average residence time of the drug in vivo from zero time to infinity ($MRT_{0-inf}$); the area under time-plasma concentration curve from 0 to the last time point ($AUC_{0-last}$); the area under time-plasma concentration curve from zero time to infinity ($AUC_{0-inf}$); initial concentration ($C_0$).

For individual plasma concentrations of less than BQL, the concentrations appeared before $T_{max}$ were calculated as 0, and the concentrations appeared after $T_{max}$ were directly excluded. All parameters and ratios were reported in the forms of three significant digits.

The pharmacokinetic parameters of this experiment were calculated according to the theoretical blood collection times and the theoretical dose concentrations as described in the protocol. The deviations between the actual dose concentrations and the theoretical concentrations were within the range of ±20%. The deviations between the actual blood collection times and the theoretical blood collection times were in conformity with the relevant SOP (the point within 1 hour after administration was within the range of ±1 min, and the others were within 5% of the theoretical time).

Experimental Results:

The experimental results of the test compounds were shown in Table 2.

TABLE 2

Pharmacokinetic study of the test compounds

| | | Test Compounds | | | |
|---|---|---|---|---|---|
| | | IDN-6556 | Example 7 | Example 49 | Example 69 |
| Intravenous injection (1 mpk) | Half-life (h) | 0.25 | N/A | 0.87 | N/A |
| | Apparent volume of distribution (L/kg) | 0.82 | | 0.653 | |
| | Clearance rate (mL/min/kg) | 106 | | 38.6 | |
| | Area under the concentration-time curve (nM · h) | 446 | | 852 | |
| Oral administration (10 mpk) | Time to peak concentration (h) | 0.25 | 0.833 | 1 | 0.5 |
| | Peak concentration (nM) | 227 | 1636 | 405 | 1993 |
| | Area under the concentration-time curve (nM · h) | 197 | 3657 | 1708 | 4180 |
| | Bioavailability (%) | 4.4% | N/A | 20.1 | N/A |

Experimental Results:

As can be seen from the above Table 2, the reference compound IDN-6556 had a relatively short half-life, low in vivo exposure, and oral bioavailability of no more than 4%. The in vivo exposures of the compounds shown in Examples 7, 49 and 69 were significantly improved compared to the reference compound IDN-6556. The oral bioavailability and half-life of the compound shown in Example 7 were also significantly improved, which gives the possibility for reducing the frequency of clinical dosing, such as reducing the twice-daily dosing of IDN-6556 to once-a-day dosing.

What is claimed is:

1. A compound represented by formula (I), or a pharmaceutically acceptable salt or tautomer thereof:

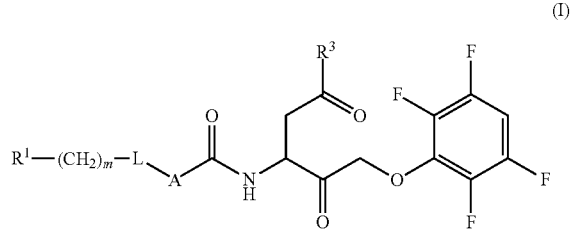

(I)

wherein,
R¹ is selected from $C_{1-6}$ alkyl, $C_{3-12}$ cycloalkyl, 3- to 12-membered heterocycloalkyl, 6- to 12-membered aryl or 5- to 12-membered heteroaryl, which is optionally substituted with 1, or 3 R;
m is 0, 1, or 3;
L is selected from a bond, C(=O), S(=O), S(=O)₂,

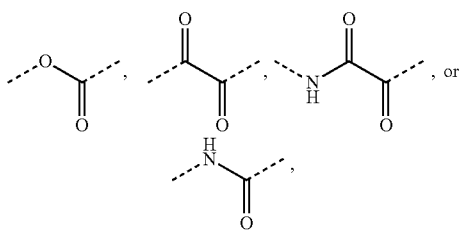, or

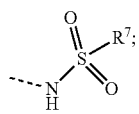, which is optionally substituted with R;
A is selected from the following groups optionally substituted with R: —NHR²—, wherein R² is selected from phenylene, cyclohexylidene;

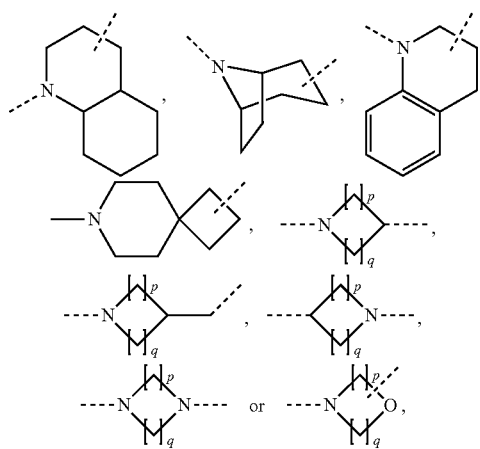

wherein p, q are independently selected from 1, 2, 3, 4, or 5;
R³ is selected from OH, OR⁷, or

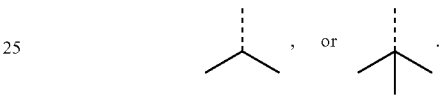

R⁷ is selected from $C_{1-6}$ alkyl or $C_{3-6}$ cycloalkyl, which is optionally substituted with 1, 2, or 3 R;
R is selected from halogen, CN, OH, NH₂, COOH, $C_{1-6}$ alkyl, $C_{1-6}$ alkoxy, $C_{3-6}$ cycloalkyl, 3- to 6-membered heterocycloalkyl, phenyl or 5- to 6-membered heteroaryl, and said $C_{1-6}$ alkyl, $C_{1-6}$ alkoxy, $C_{3-6}$ cycloalkyl, 3- to 6-membered heterocycloalkyl, phenyl, or 5- to 6-membered heteroaryl is optionally substituted with 1, 2 or 3 R'; and
R' is selected from halogen, OH, CN, NH₂, COOH, Me, Et, CF₃, CHF₂, CH₂F, NHCH₃, or N(CH₃)₂.

2. The compound of claim 1, when R is present, wherein R is selected from halogen, CN, OH, NH₂, COOH, $C_{1-4}$ alkyl, $C_{1-4}$ alkoxy, or phenyl, and said $C_{1-4}$ alkyl, $C_{1-4}$ alkoxy, or phenyl is optionally substituted with 1, 2, or 3 R'.

3. The compound of claim 1, when R is present, wherein R is selected from F, Cl, CN, OH, NH₂, COOH, methyl, ethyl, propyl, isopropyl, tert-butyl, methoxy, ethoxy or phenyl, and said methyl, ethyl, propyl, isopropyl, tert-butyl, methoxy, ethoxy, or phenyl optionally substituted with 1, 2, or 3 R'.

4. The compound of claim 1, when R is present, wherein R is selected from F, Cl, CN, OH, NH₂, COOH, Me, MeO, Et, CF₃, CHF₂, CH₂F,

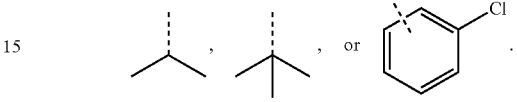

5. The compound of claim 1, when R is present, wherein R is selected from F, Cl, CN, OH, NH₂, COOH, Me, MeO, Et, CF₃, CHF₂, CH₂F, 6. The compound of claim 1, when R' is present, wherein R' is selected from F or Cl.

7. The compound of claim 1, wherein R¹ is selected from $C_1$-6 alkyl, $C_{3-10}$ cycloalkyl, 4- to 7-membered heterocycloalkyl, phenyl, naphthyl or 5- to 12-membered heteroaryl containing 1, 2 or 3 atoms independently selected from N, O or S, which is optionally substituted with 1, 2 or 3 R.

8. The compound of claim 1, wherein R¹ is selected from $C_{1-5}$ alkyl, $C_{3-10}$ cycloalkyl, azetidinyl, pyrrolidinyl, piperidinyl, tetrahydropyranyl, morpholinyl, oxazolyl, isoxazolyl, thiazolyl, isothiazolyl, thienyl, furyl, imidazolyl, pyrazolyl, pyrrolyl, phenyl, pyridyl, pyrimidinyl, pyrazinyl, naphthyl, quinolyl, isoquinolyl, indolyl, benzimidazolyl, benzothiazolyl, benzisothiazolyl, benzoxazolyl, benzisoxazolyl, benzothienyl or quinazolinyl, which is optionally substituted with 1, 2 or 3 R.

9. The compound of claim 1, wherein R¹ is selected from Me, Et,

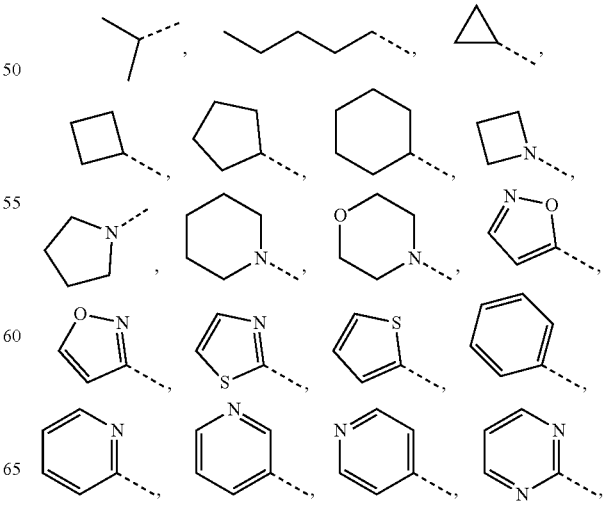

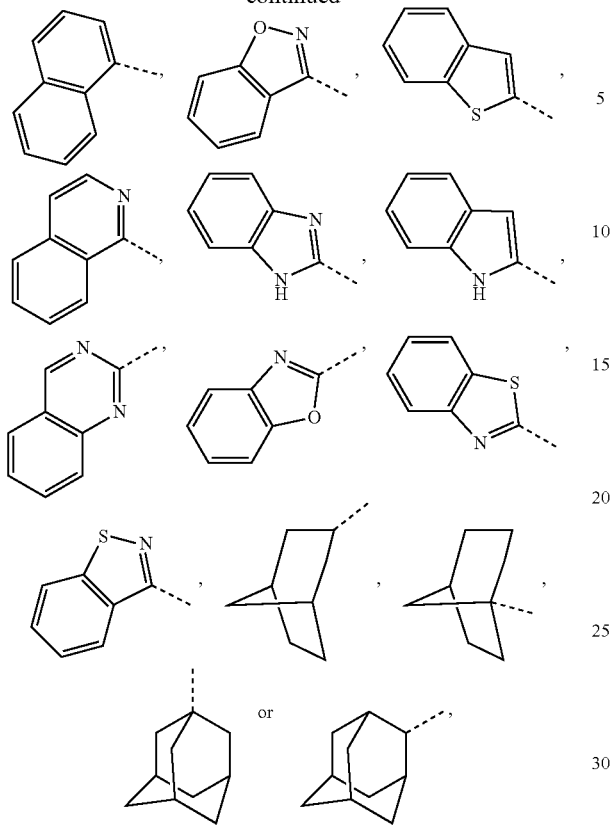
which is optionally substituted with 1, 2 or 3 R.
10. The compound of claim 1, wherein R¹ is selected from Me,
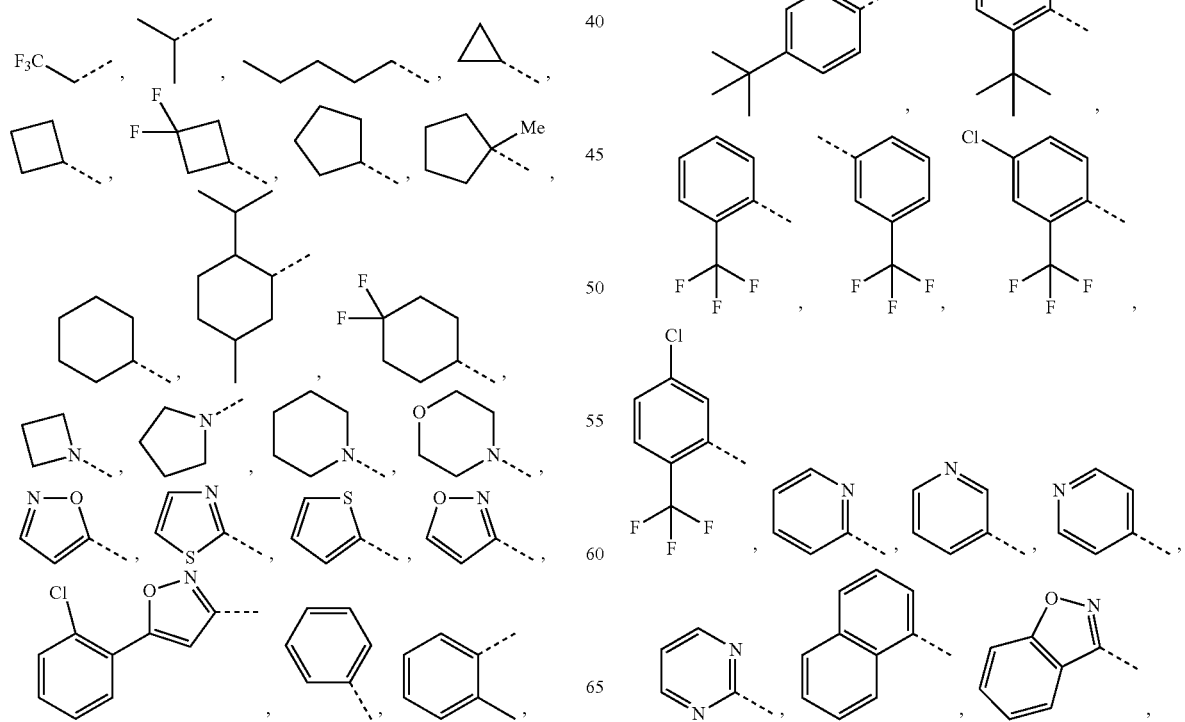
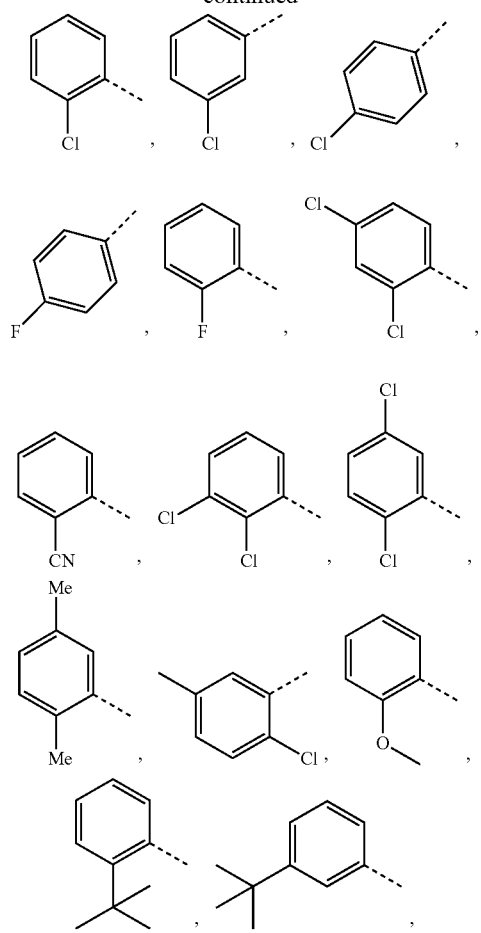

-continued

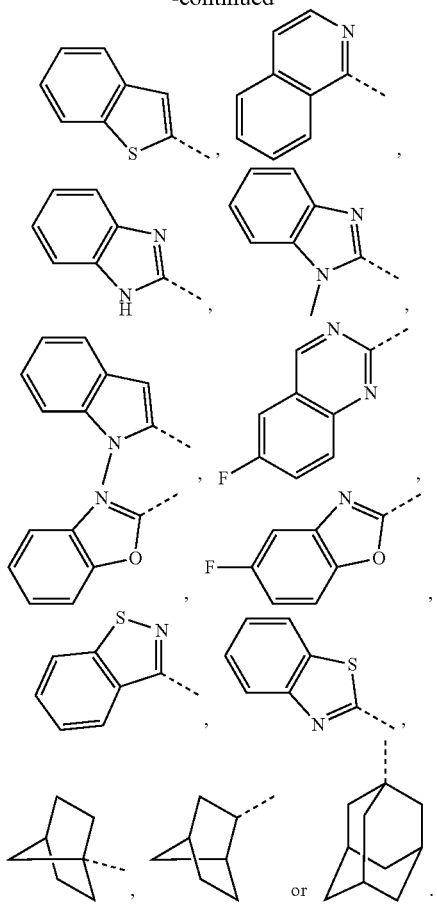

11. The compound of claim 1, wherein L is selected from a bond, C(=O), S(=O)$_2$,

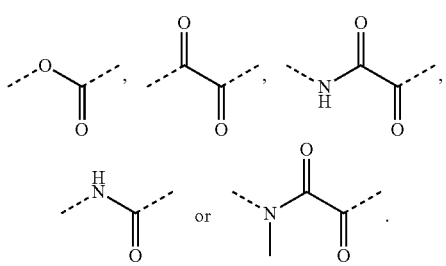

12. The compound of claim 1, wherein A is selected from the following groups optionally substituted with R:

—NHR$^2$—, wherein R$^2$ is selected from phenylene or cyclohexylidene;

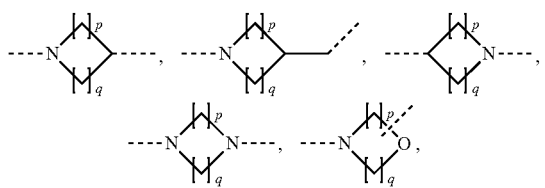

wherein p, q are independently selected from 1, 2, 3, 4 or 5;

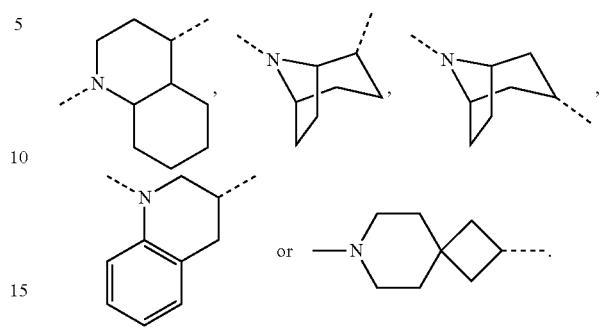

13. The compound of claim 1, wherein A is selected from the following groups optionally substituted with R:

—NHR$^2$—, wherein R$^2$ is selected from phenylene or cyclohexylidene;

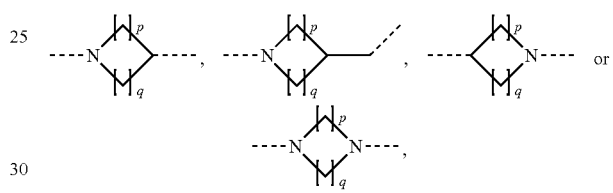

wherein p, q are independently selected from 1, 2, 3 or 4;

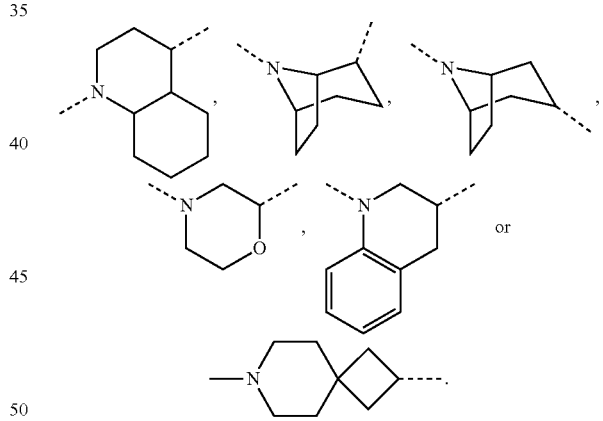

14. The compound of claim 1, wherein A is selected from the following groups optionally substituted with R:

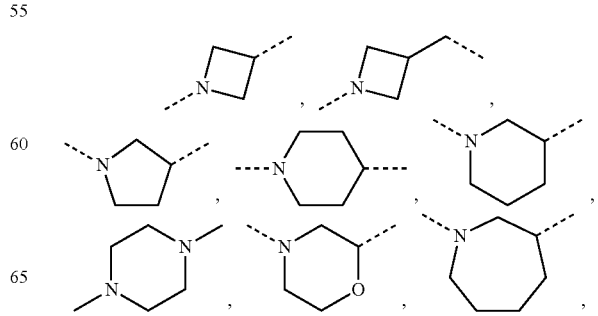

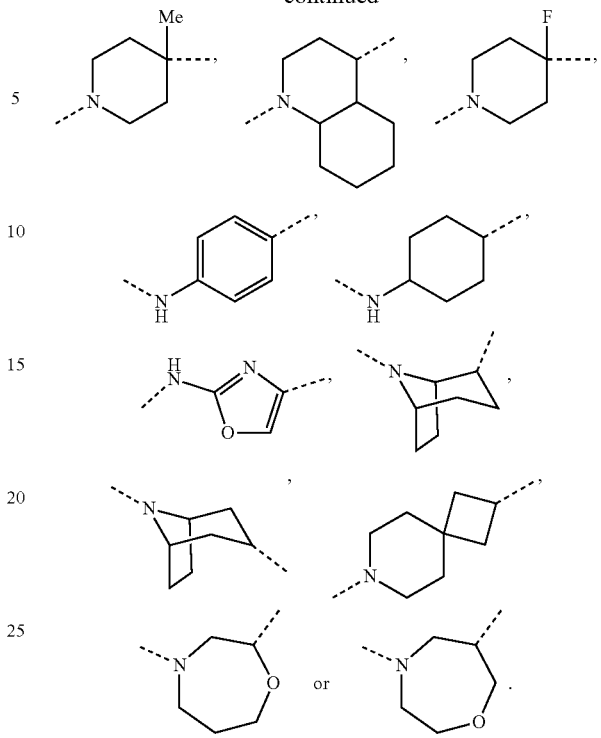
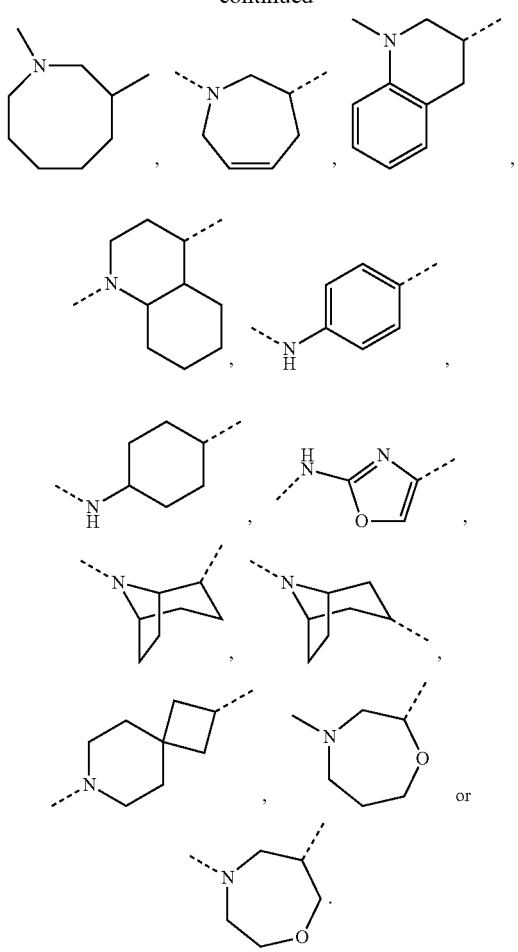
15. The compound of claim 1, wherein A is selected from
16. The compound of claim 1, wherein $R^3$ is OH.
17. The compound of claim 1, wherein the compound of formula (I) is selected from:
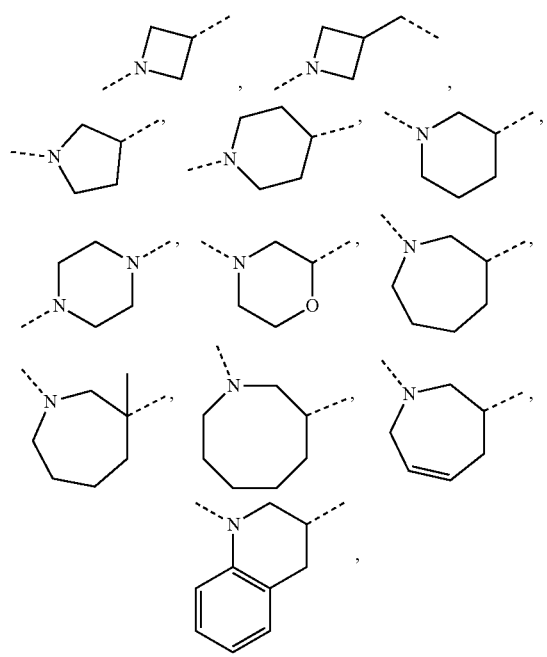
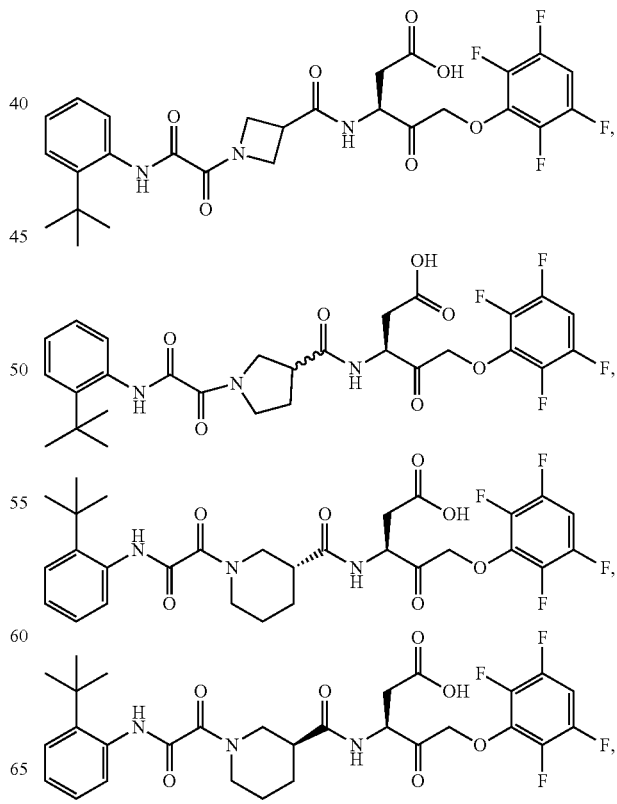

-continued
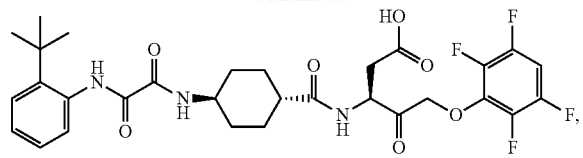
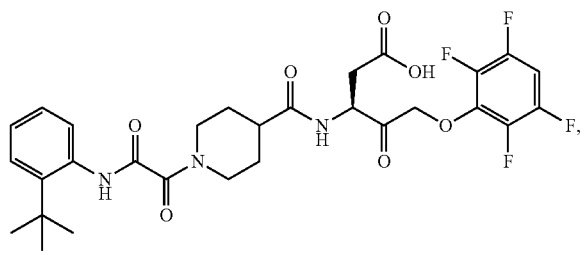
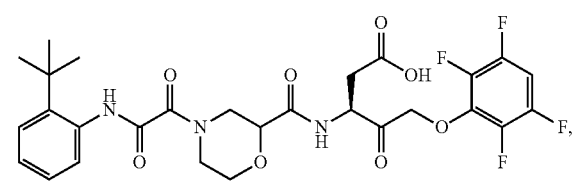
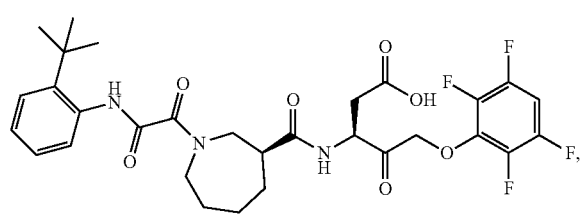
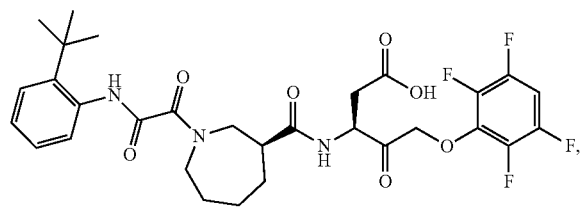
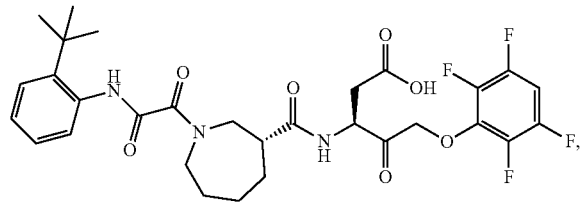
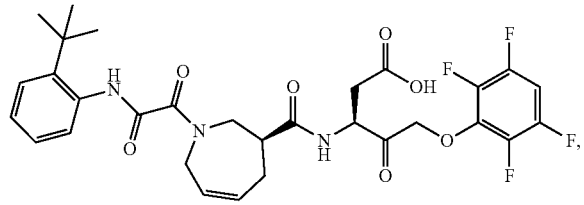
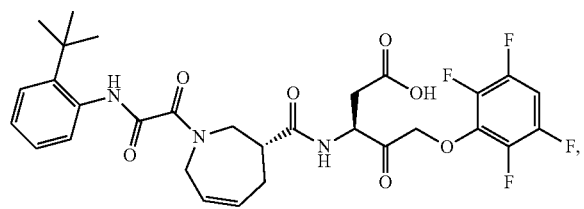
-continued
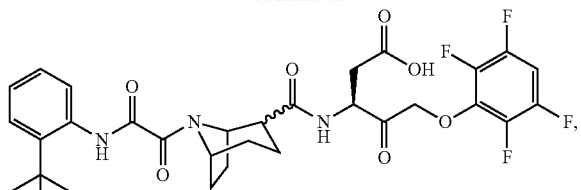
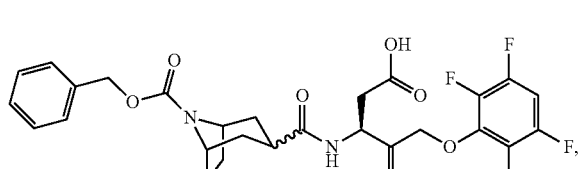
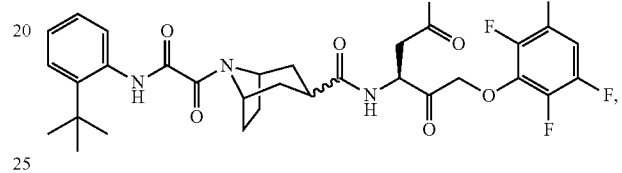
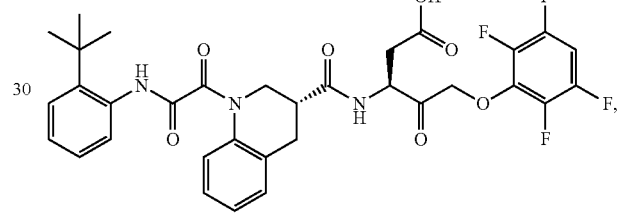
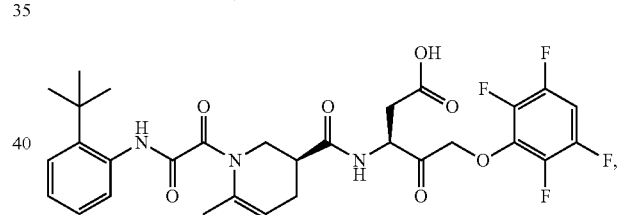
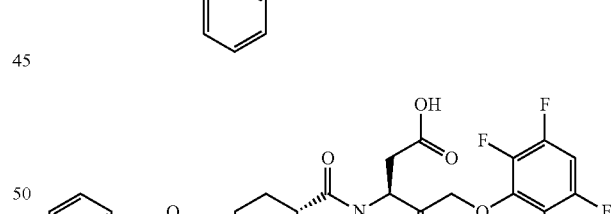
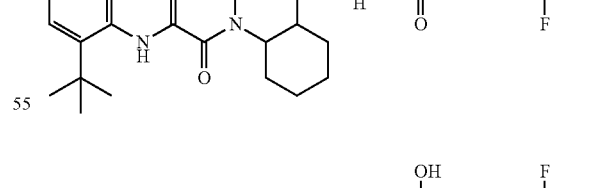
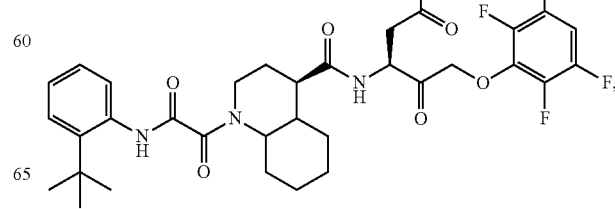

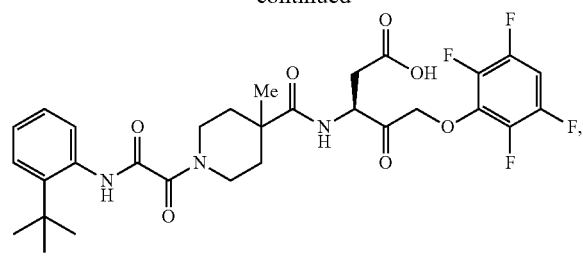
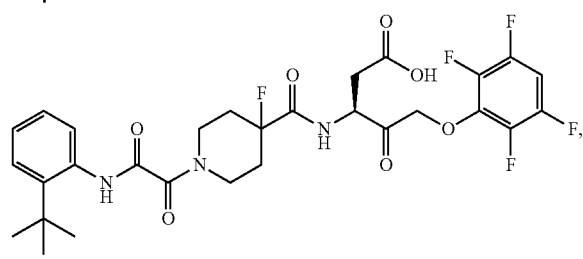
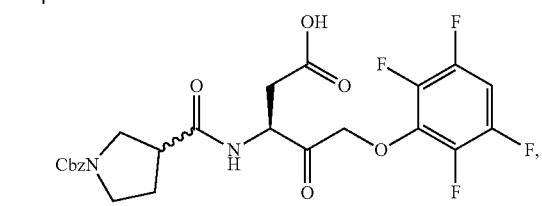
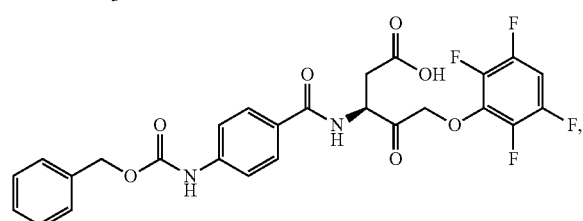
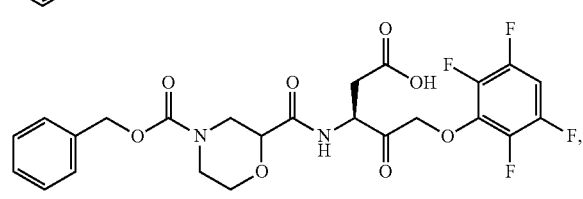
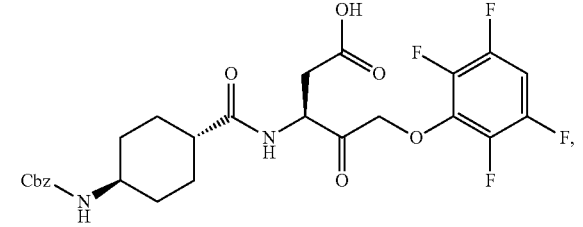
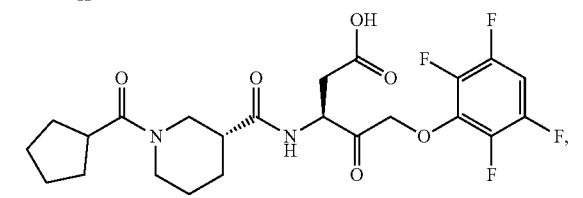
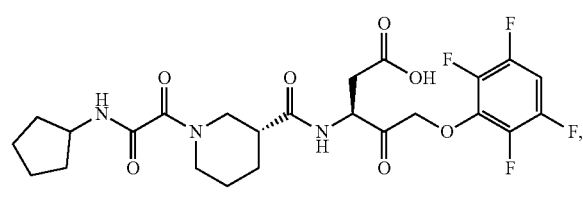
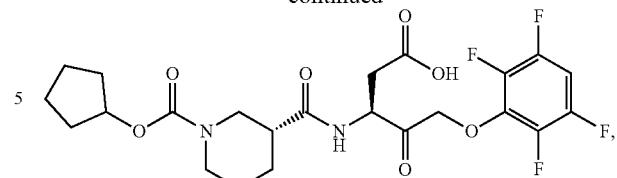
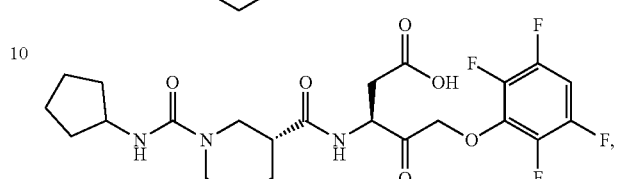
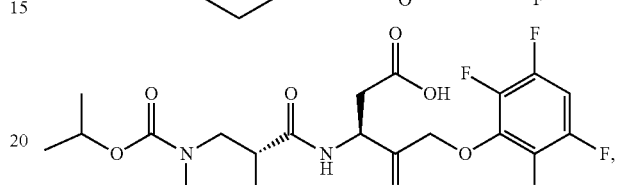
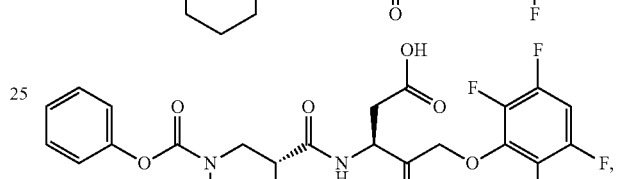
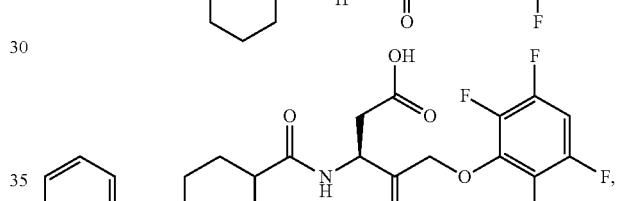
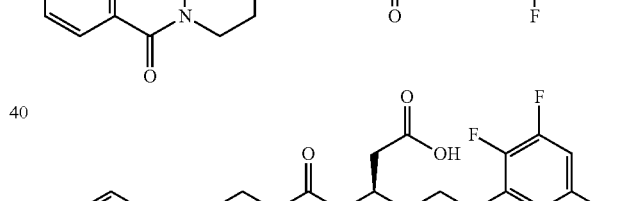
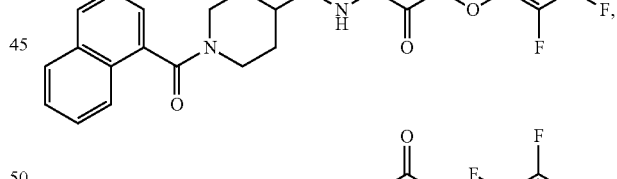
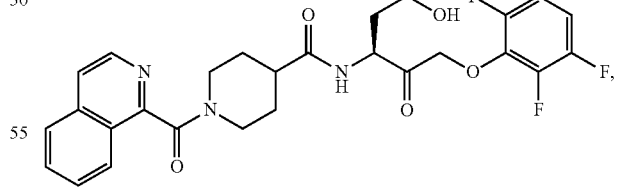
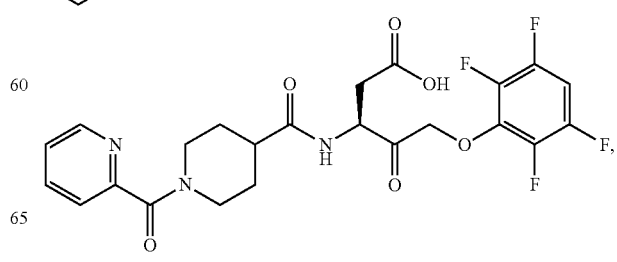

383
-continued
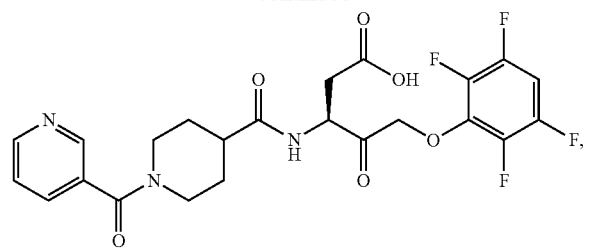
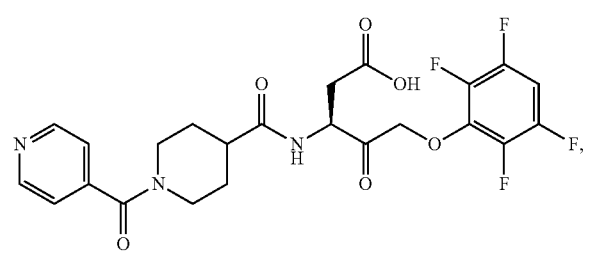
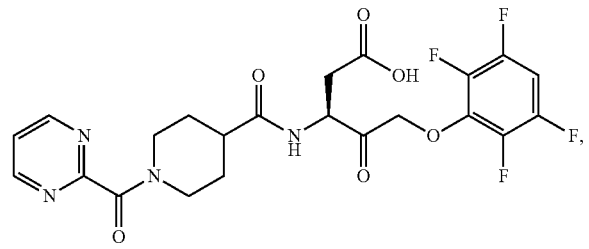
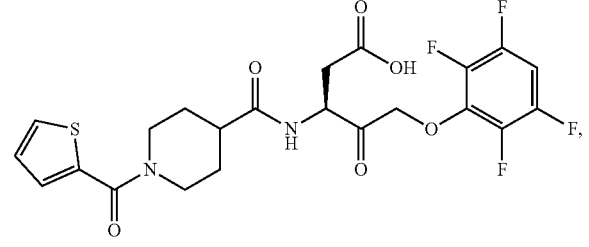
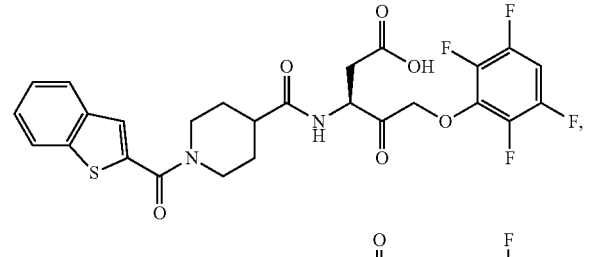
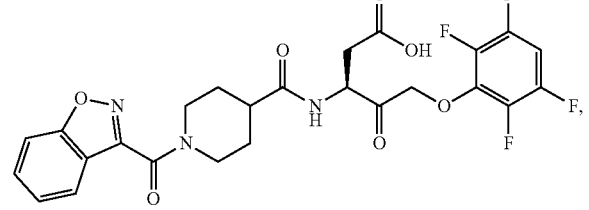
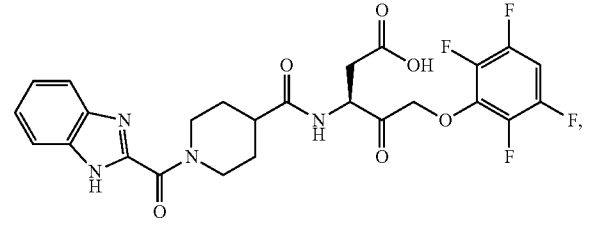
384
-continued
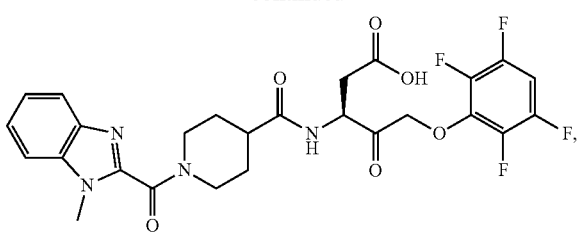
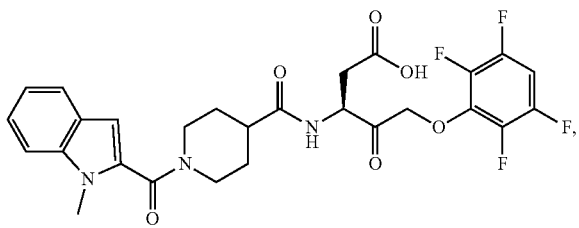
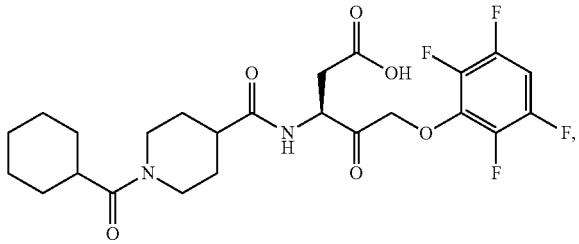
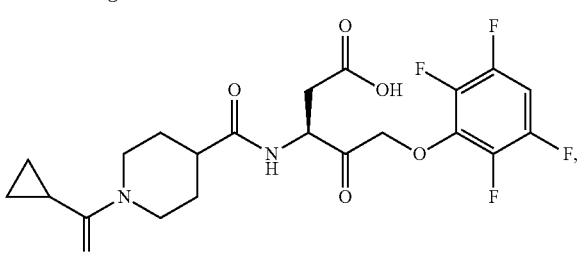
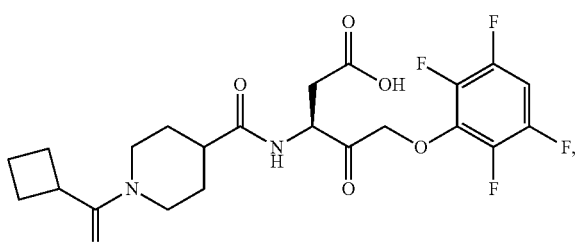
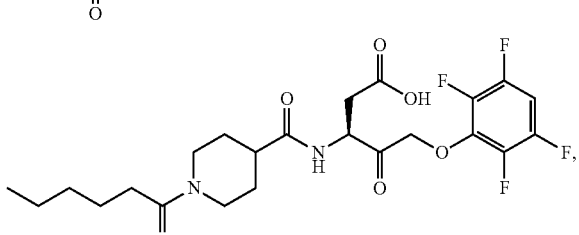
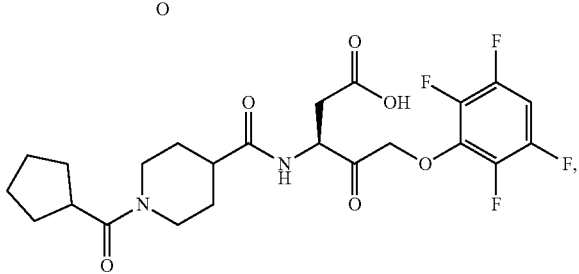

385
-continued
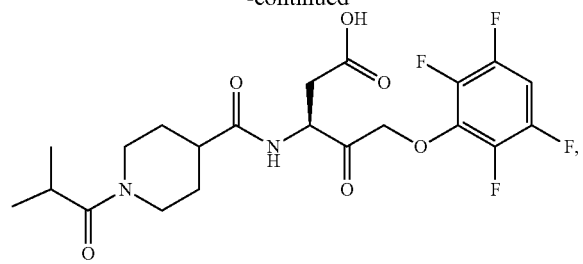
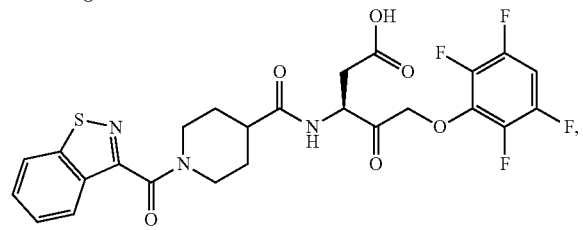
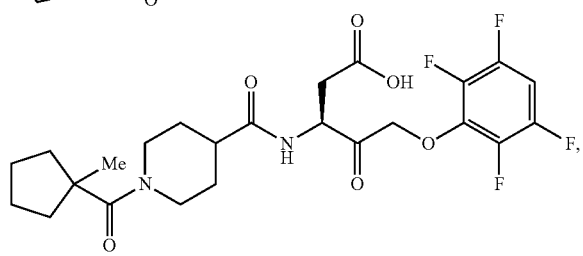
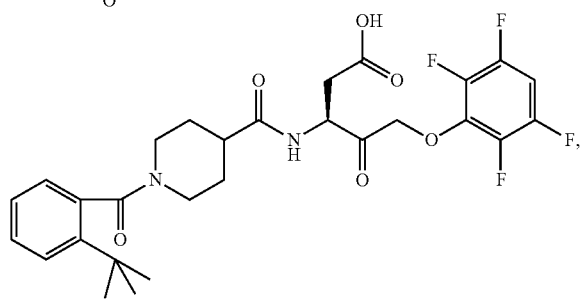
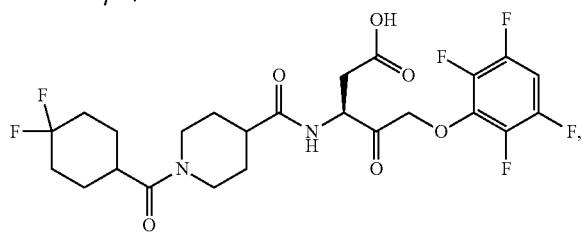
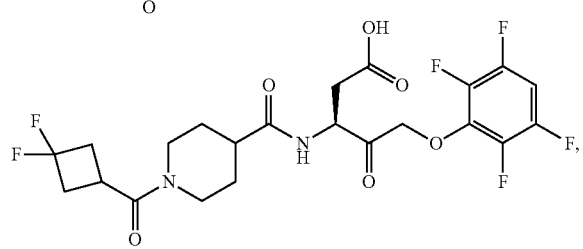
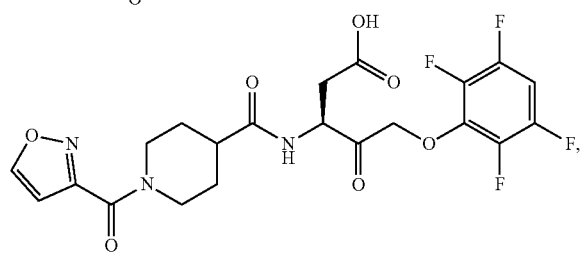
386
-continued
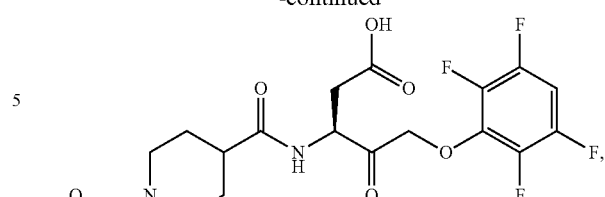
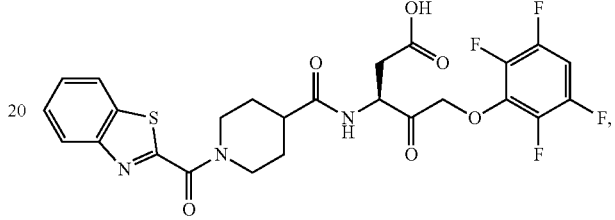
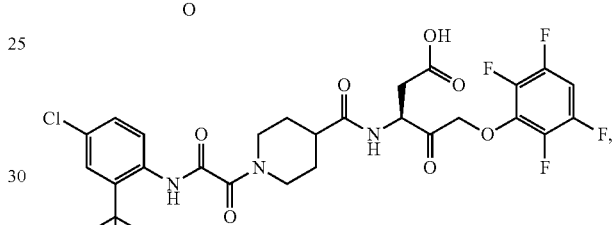
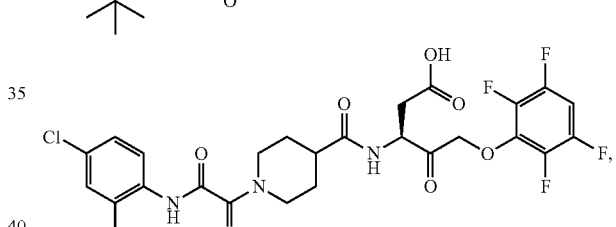
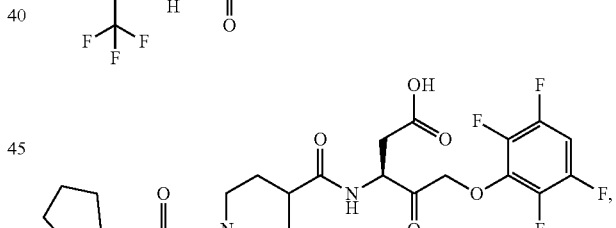
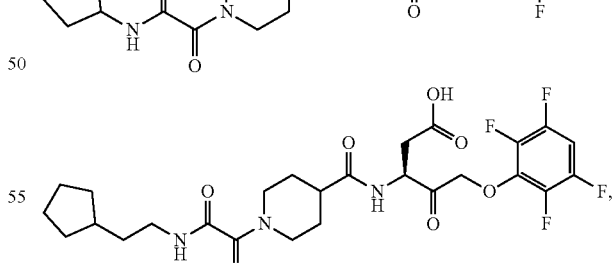

387
-continued
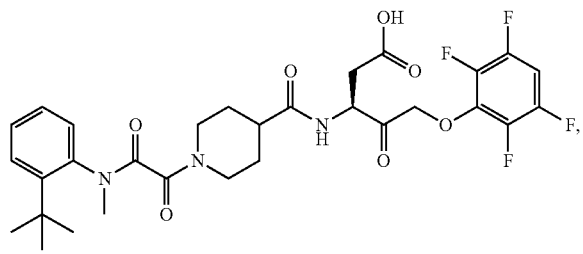
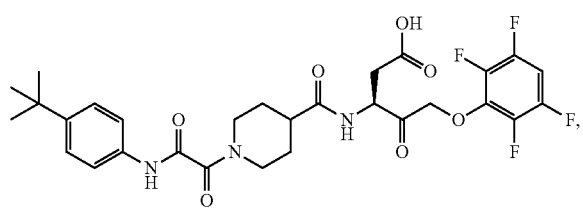
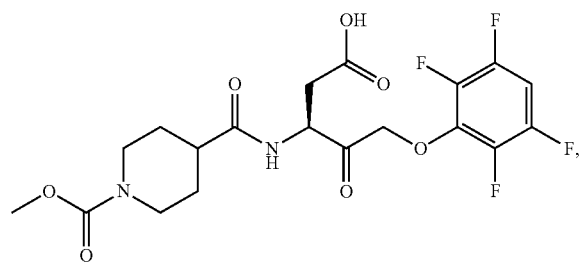
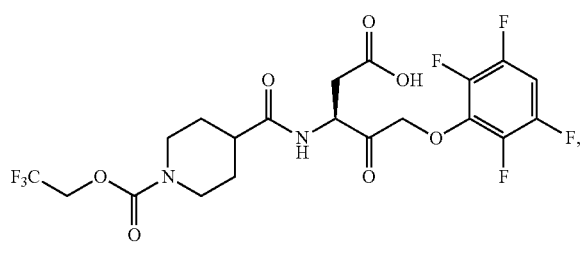
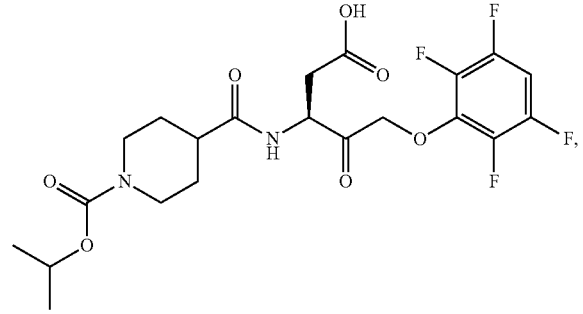
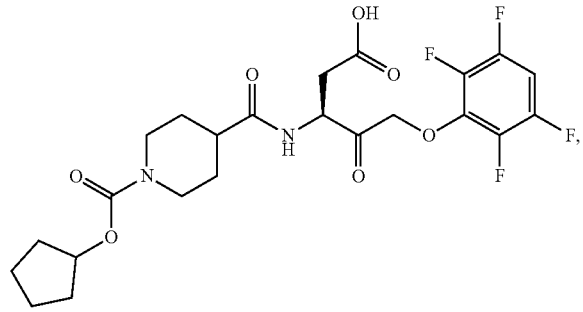
388
-continued
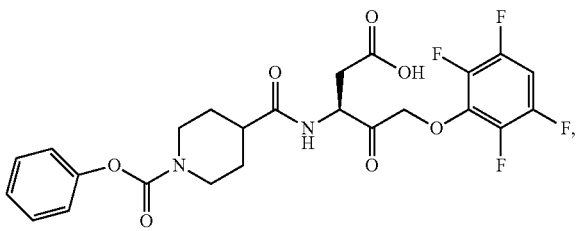
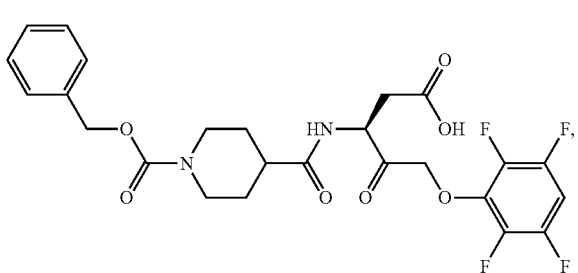
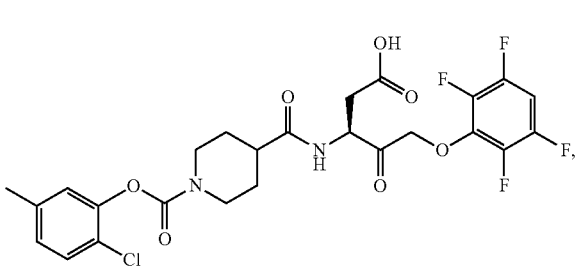
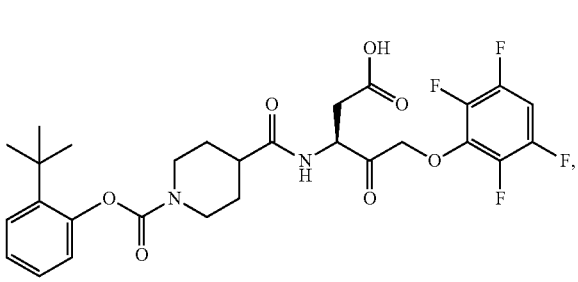
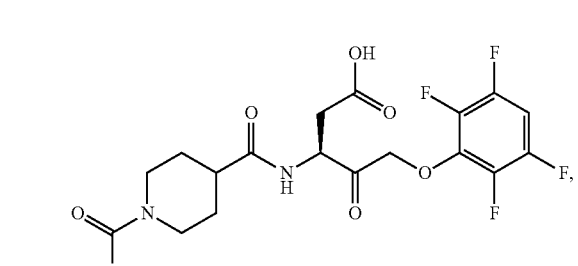
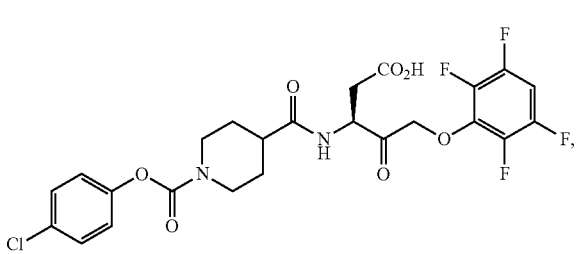

-continued
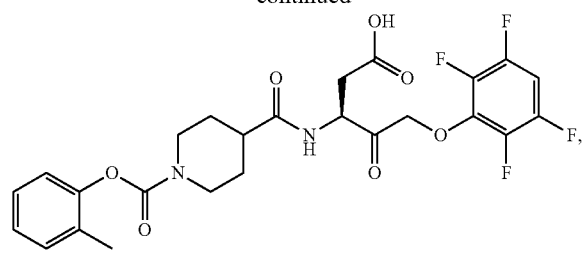
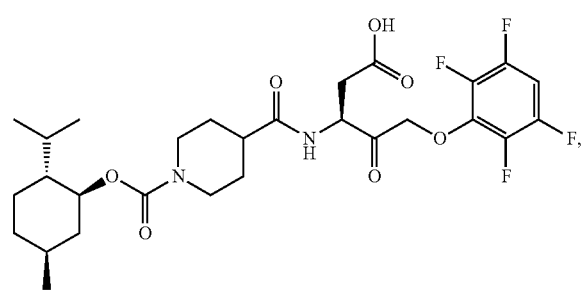
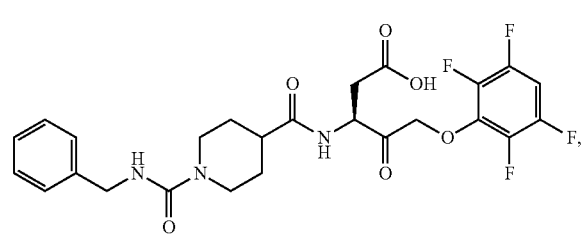
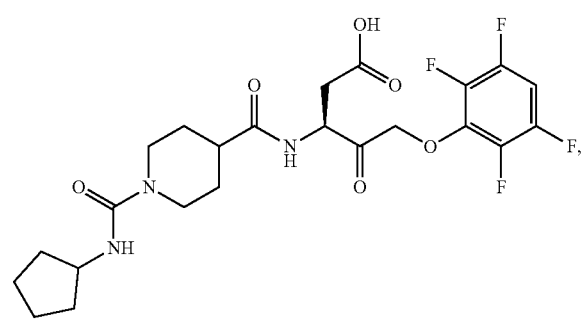
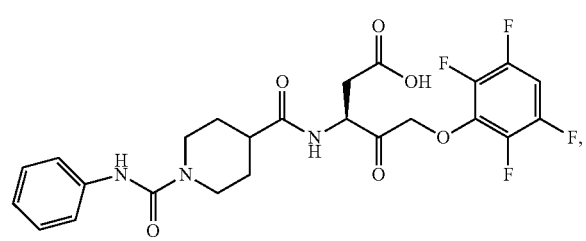
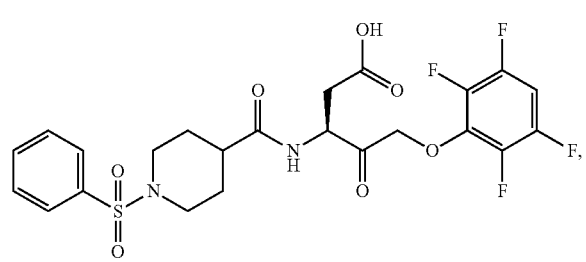
-continued
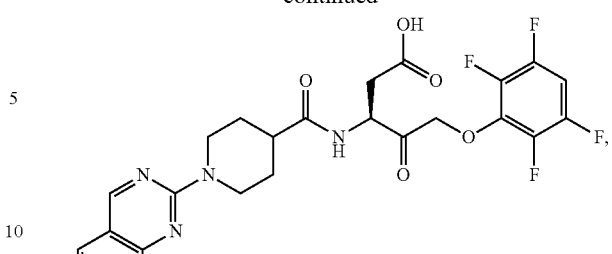
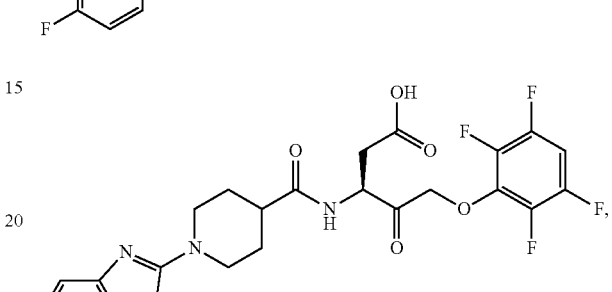
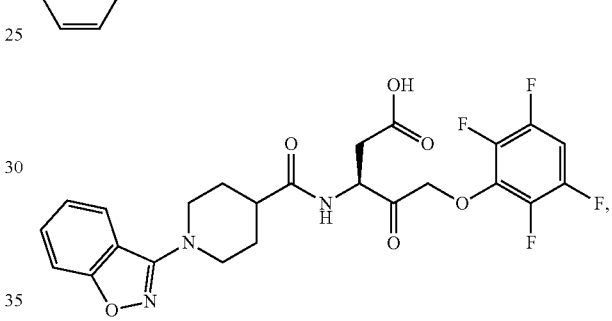
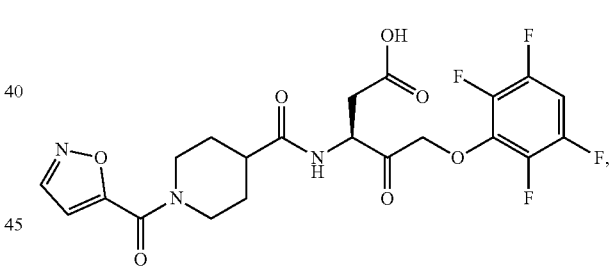
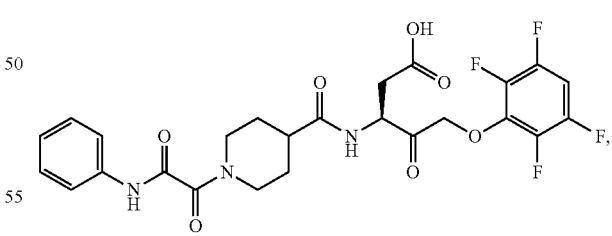
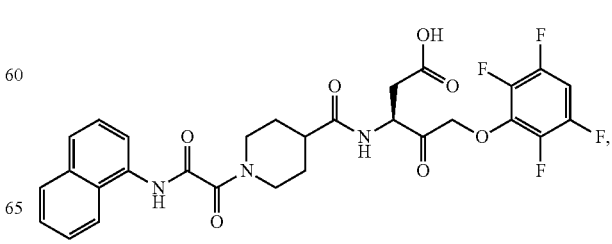

391
-continued
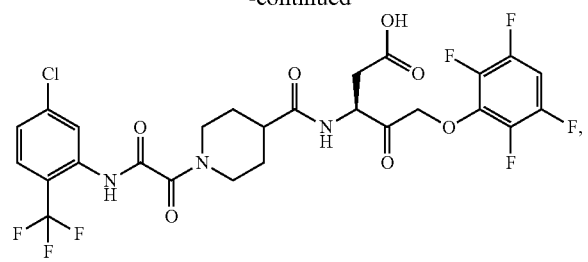
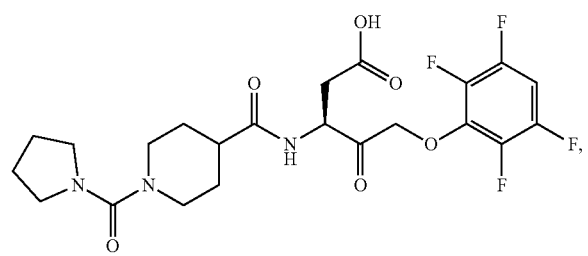
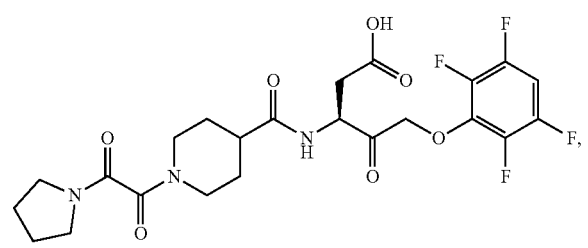
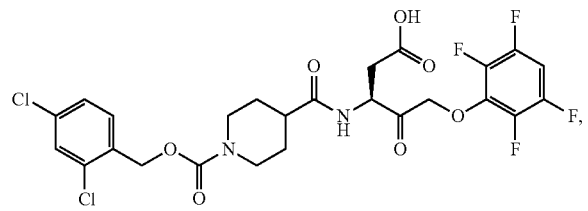
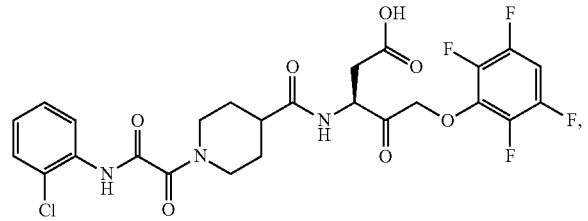
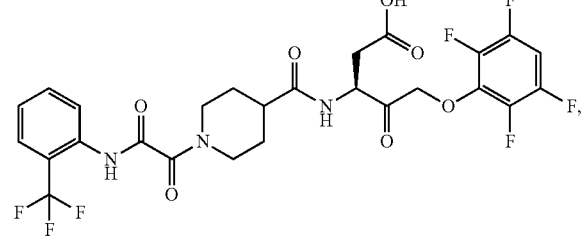
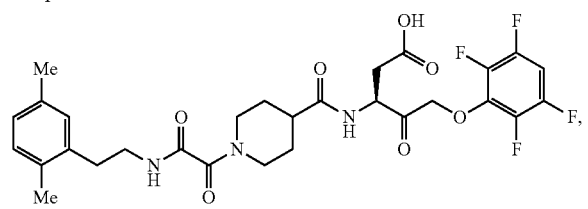
392
-continued
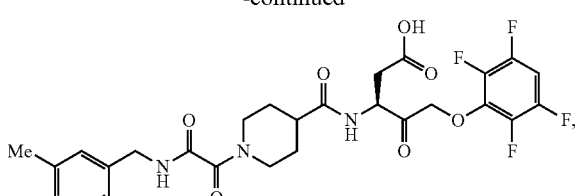
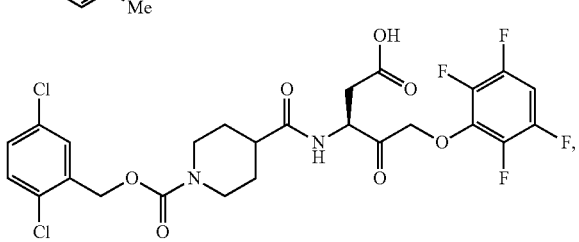
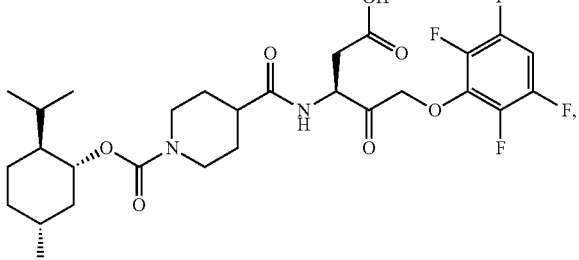
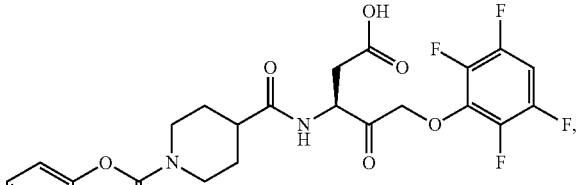
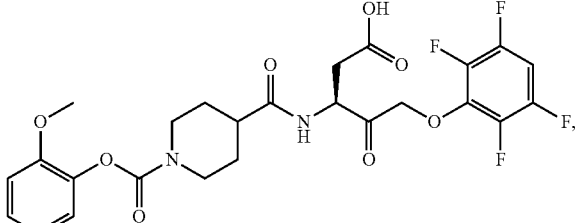
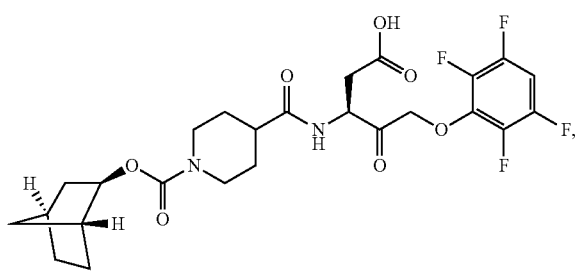
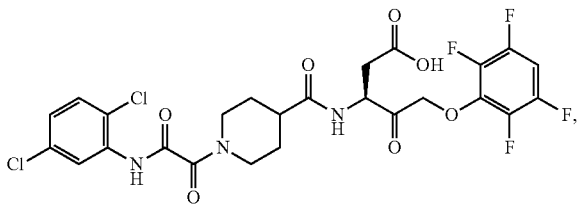

393
-continued
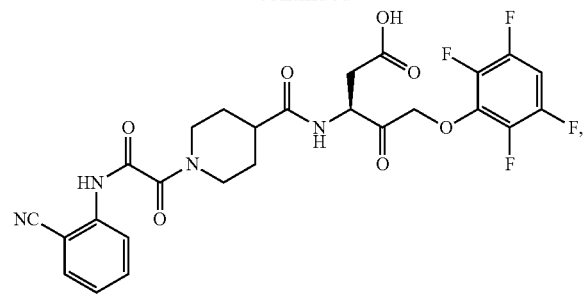
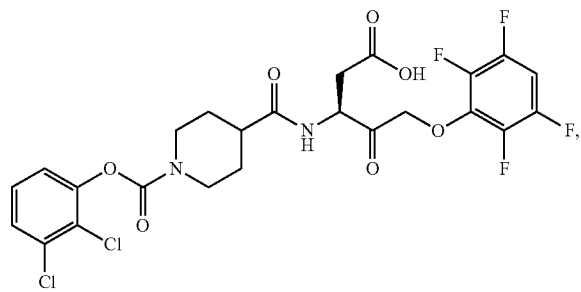
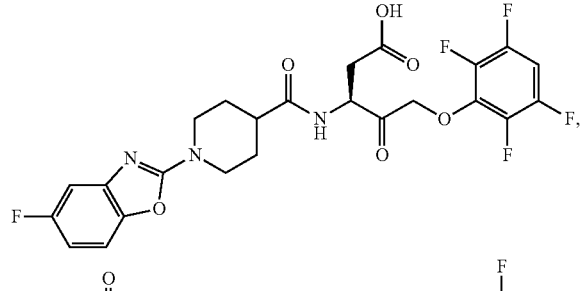
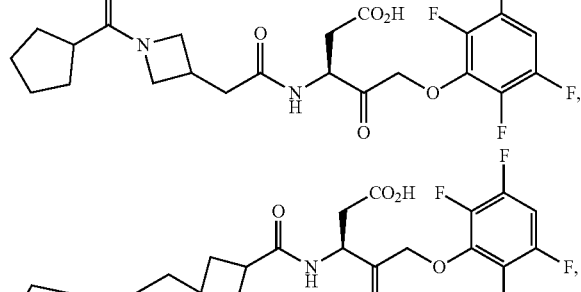
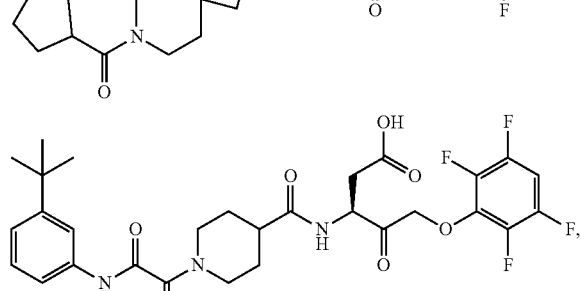
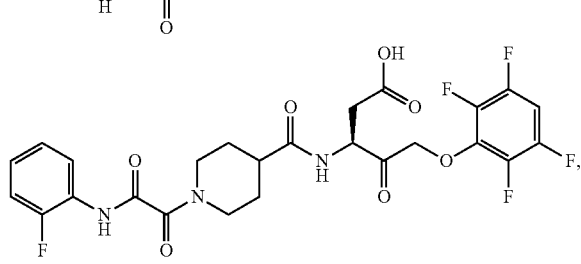
394
-continued
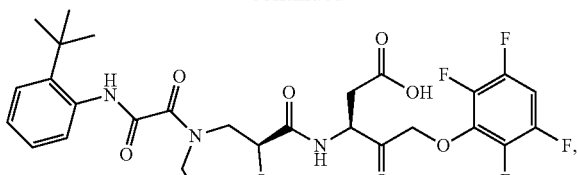
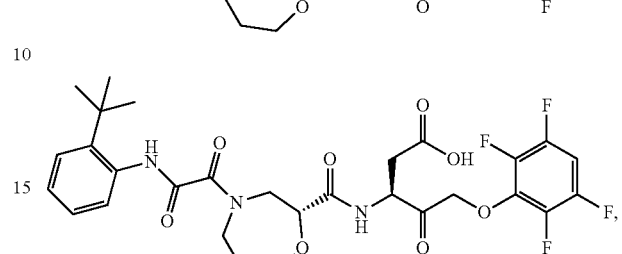
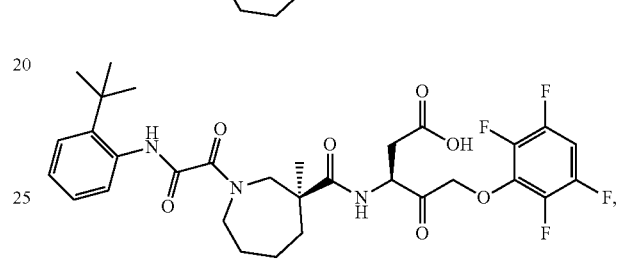
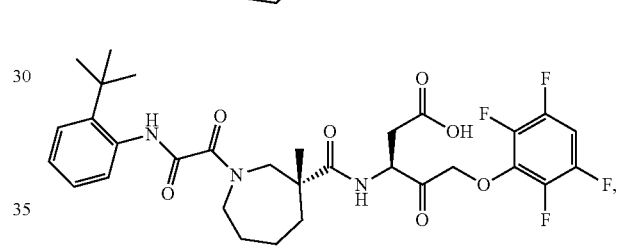
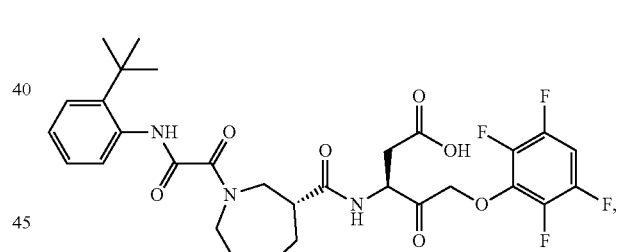
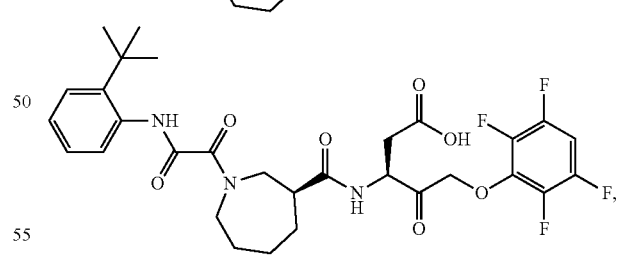
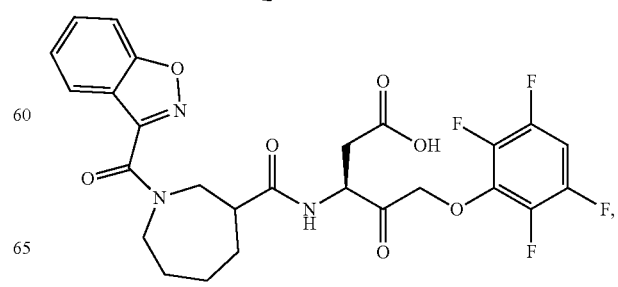

395
-continued
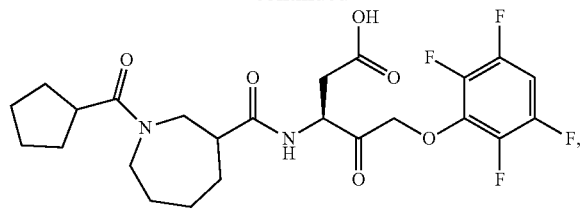
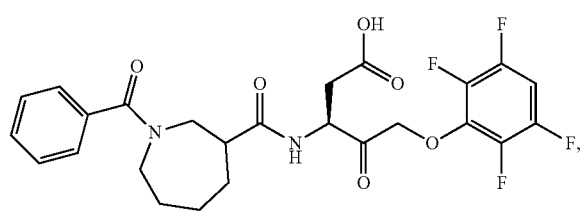
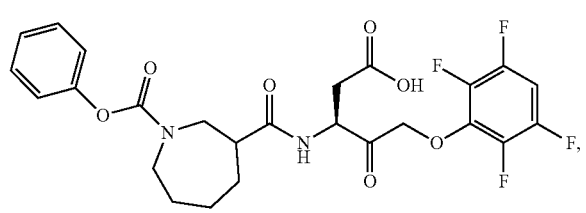
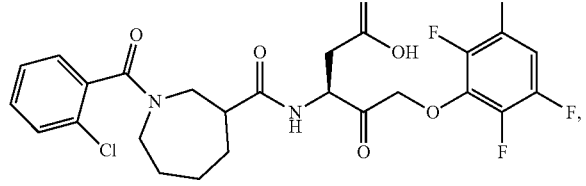
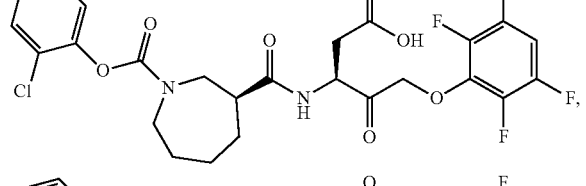
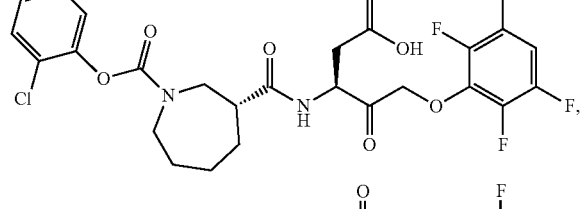
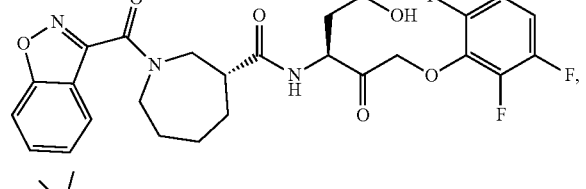
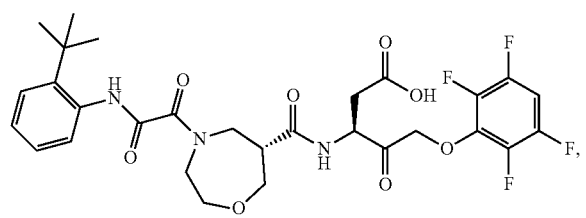
396
-continued
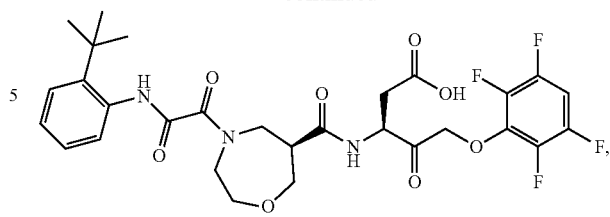
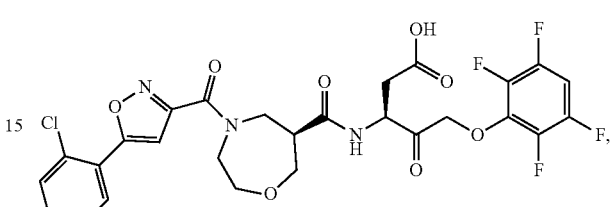
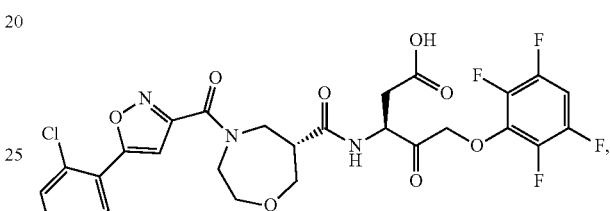
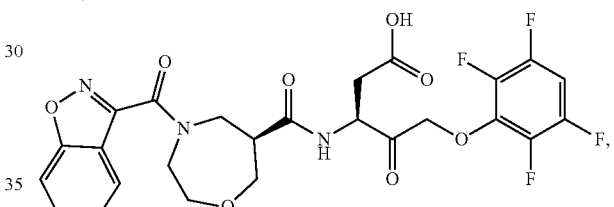
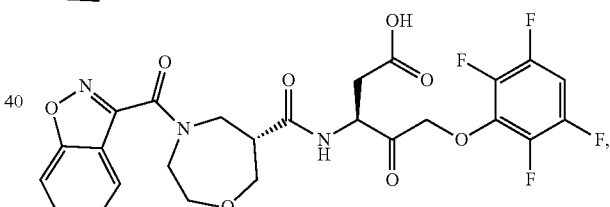
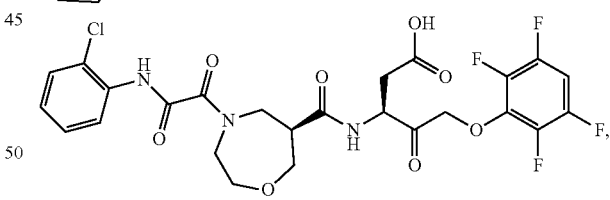
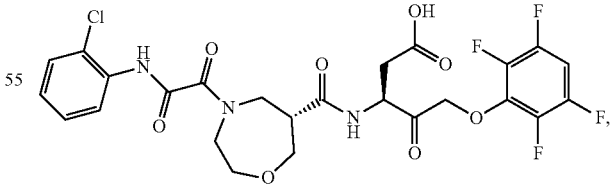
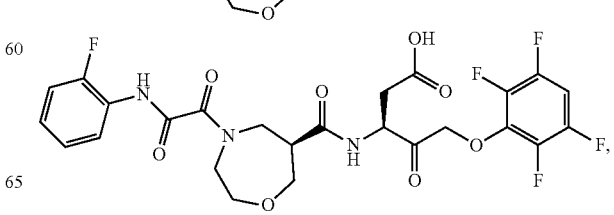

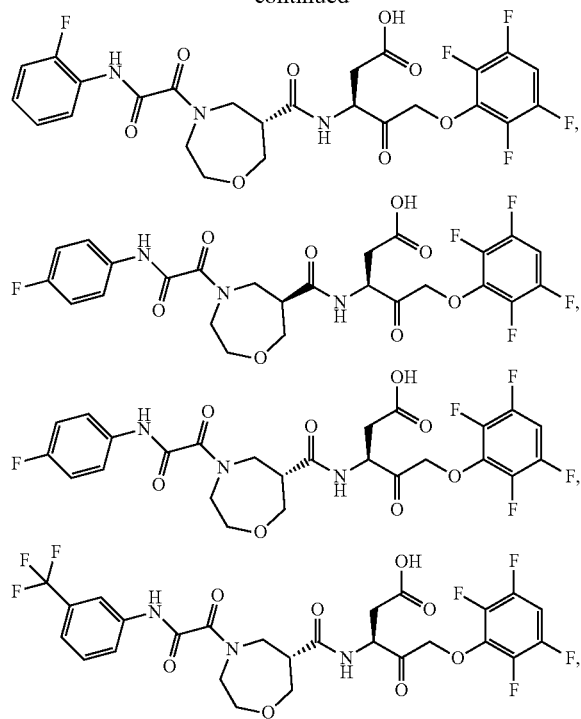
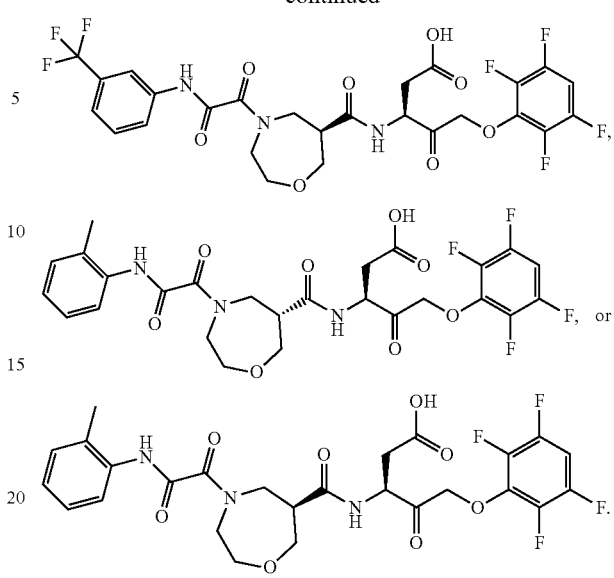
18. A pharmaceutical composition comprising a therapeutically effective amount of the compound of claim 1, and a pharmaceutically acceptable carrier or excipient.
* * * * *

UNITED STATES PATENT AND TRADEMARK OFFICE
CERTIFICATE OF CORRECTION

Page 1 of 3

PATENT NO. : 10,981,860 B2
APPLICATION NO. : 16/099989
DATED : April 20, 2021
INVENTOR(S) : Haiying He et al.

It is certified that error appears in the above-identified patent and that said Letters Patent is hereby corrected as shown below:

In the Claims

In Column 371, Line 4, Claim 1, delete "aryl" and insert --aryl,--.

In Column 371, Line 5, Claim 1, delete "1," and insert --1, 2,--.

In Column 371, Line 6, Claim 1, delete "1," and insert --1, 2,--.

In Column 371, Lines 26-32, Claim 1, after " 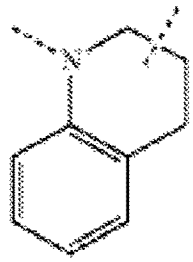 " insert --,--.

In Column 371, Lines 33-35, Claim 1, delete " 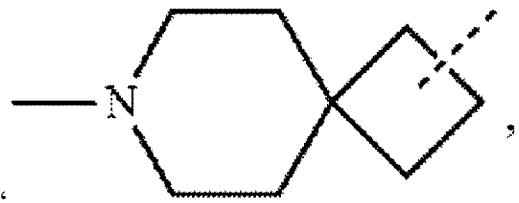 " and insert 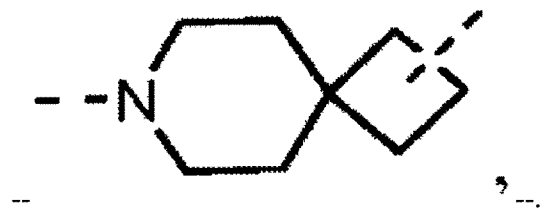 --.

Signed and Sealed this
Twenty-first Day of December, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,981,860 B2

In Column 371, Line 59, Claim 1, delete "phenyl" and insert --phenyl,--.

In Column 372, Line 5, Claim 3, delete "ethoxy" and insert --ethoxy,--.

In Column 372, Line 7, Claim 3, after "phenyl" insert --is--.

In Column 372, Line 32, Claim 7, delete "$C_1$-6 alkyl" insert --$C_{1-6}$ alkyl--.

In Column 376, Lines 12-15, Claim 12, delete "  " and insert --  --.

In Column 376, Lines 48-50, Claim 13, delete " 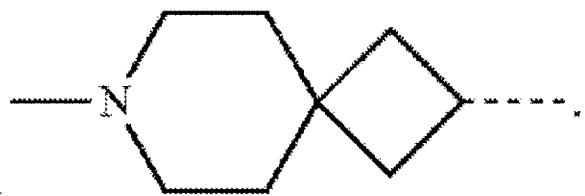 " and insert -- 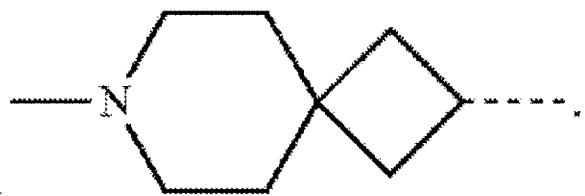 --.

In Column 376, Lines 63-66 (approx.), Claim 14, delete " 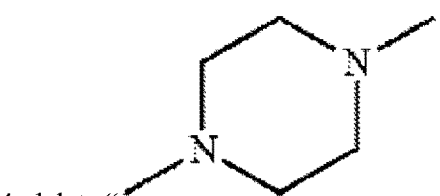 " and insert -- 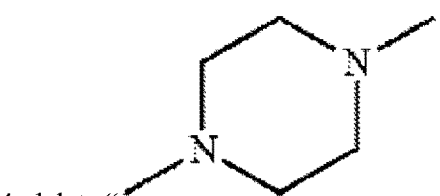 --.

CERTIFICATE OF CORRECTION (continued)
U.S. Pat. No. 10,981,860 B2

Page 3 of 3

In Column 377, Lines 1-8 (approx.), Claim 14, delete " 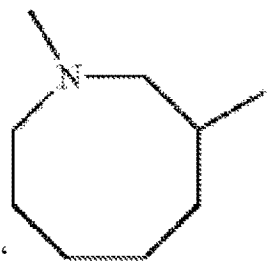 " and insert

-- , --.

In Column 377, Lines 1-8 (approx.), Claim 14, delete " 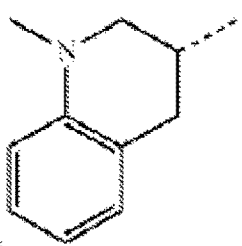 " and insert

-- , --.

In Column 379, Lines 35-43, Claim 14, below

" 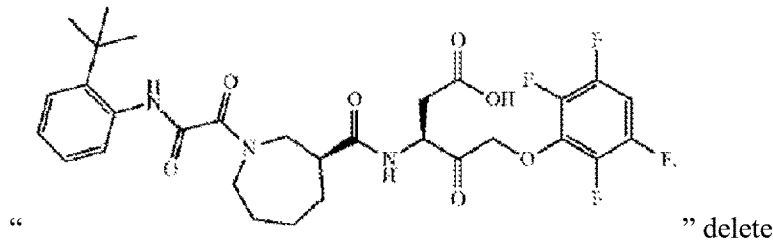 " delete

" 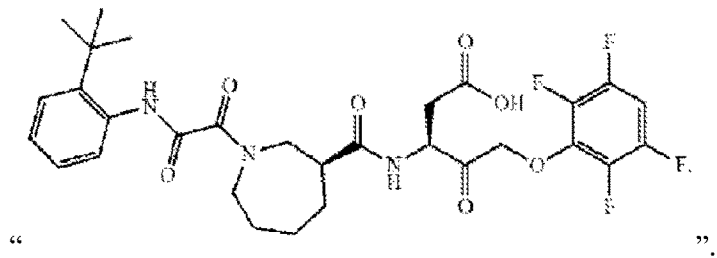 ".